US011732038B2

(12) United States Patent
Fishkin et al.

(10) Patent No.: US 11,732,038 B2
(45) Date of Patent: Aug. 22, 2023

(54) CONJUGATES COMPRISING CELL-BINDING AGENTS AND CYTOTOXIC AGENTS

(71) Applicant: IMMUNOGEN, INC., Waltham, MA (US)

(72) Inventors: Nathan Elliott Fishkin, Weymouth, MA (US); Daniel J. Tavares, Natick, MA (US); Lingyun Rui, Weston, MA (US); Luke B. Harris, Boston, MA (US); Manami Shizuka, Belmont, MA (US); Michael Louis Miller, Framingham, MA (US); Ravi V. J. Chari, Newton, MA (US)

(73) Assignee: IMMUNOGEN, INC., Waltham, MA (US)

( * ) Notice: Subject to any disclaimer, the term of this patent is extended or adjusted under 35 U.S.C. 154(b) by 182 days.

(21) Appl. No.: 17/174,911

(22) Filed: Feb. 12, 2021

(65) Prior Publication Data
US 2021/0299271 A1    Sep. 30, 2021

Related U.S. Application Data

(62) Division of application No. 14/843,429, filed on Sep. 2, 2015, now Pat. No. 10,988,531.
(Continued)

(51) Int. Cl.
*A61K 47/68* (2017.01)
*C07K 16/28* (2006.01)
(Continued)

(52) U.S. Cl.
CPC .......... *C07K 16/28* (2013.01); *A61K 31/5517* (2013.01); *A61K 47/6803* (2017.08);
(Continued)

(58) Field of Classification Search
None
See application file for complete search history.

(56) References Cited

U.S. PATENT DOCUMENTS

| 5,362,852 A | 11/1994 | Geoghegan |
| 8,197,793 B2 | 6/2012 | Cuthbertson et al. |

(Continued)

FOREIGN PATENT DOCUMENTS

| CN | 101918027 A | 12/2010 |
| WO | 1993/006132 A1 | 4/1993 |

(Continued)

OTHER PUBLICATIONS

Database Registry, Chemical Abstracts Service, Columbus, Ohio, US; Registry No. 1401203-61-9, Entered STN: Oct. 17, 2012 (Registry No. 1401203-61-9 (Year: 2012).*

(Continued)

*Primary Examiner* — Karl J Puttlitz
(74) *Attorney, Agent, or Firm* — McCarter & English, LLP; Xin Zhang; Daniel R. Jones

(57) ABSTRACT

The invention relates to novel cell-binding agent-cytotoxic agent conjugates, wherein the cell-binding agent (CBA) is covalently linked to the cytotoxic agent through an aldehyde group obtained from oxidation of a 2-hydroxyethylamine moiety on the CBA. The invention also provides methods of preparing the conjugates of the present invention. The invention further provides composition and methods useful for inhibiting abnormal cell growth or treating a proliferative disorder in a mammal using the conjugates of the invention.

6 Claims, 41 Drawing Sheets
Specification includes a Sequence Listing.

Related U.S. Application Data

(60) Provisional application No. 62/186,235, filed on Jun. 29, 2015, provisional application No. 62/149,379, filed on Apr. 17, 2015, provisional application No. 62/086,986, filed on Dec. 3, 2014, provisional application No. 62/045,264, filed on Sep. 3, 2014.

(51) Int. Cl.
*A61K 31/5517* (2006.01)
*A61K 39/00* (2006.01)

(52) U.S. Cl.
CPC ...... *A61K 47/6849* (2017.08); *A61K 47/6851* (2017.08); *C07K 16/2866* (2013.01); *A61K 2039/505* (2013.01); *C07K 2317/21* (2013.01); *C07K 2317/24* (2013.01); *C07K 2317/515* (2013.01); *C07K 2317/56* (2013.01); *C07K 2317/73* (2013.01)

(56) References Cited

U.S. PATENT DOCUMENTS

| | | |
|---|---|---|
| 8,258,258 B2 | 9/2012 | Kolmar et al. |
| 8,557,966 B2 | 10/2013 | Ab et al. |
| 8,889,669 B2 | 11/2014 | Li et al. |
| 10,988,531 B2 | 4/2021 | Fishkin et al. |
| 2003/0162185 A1 | 8/2003 | Melnyk et al. |
| 2004/0126361 A1 | 7/2004 | Saifer et al. |
| 2006/0173160 A1 | 8/2006 | Dumy et al. |
| 2007/0122408 A1 | 5/2007 | Barbas |
| 2008/0187956 A1 | 8/2008 | Carrico et al. |
| 2008/0206151 A1 | 8/2008 | Cuthbertson |
| 2009/0181037 A1* | 7/2009 | Heavner .......... A61K 38/26 530/391.1 |
| 2009/0221449 A1 | 9/2009 | Defrancq et al. |
| 2010/0129314 A1 | 5/2010 | Singh et al. |
| 2013/0295007 A1* | 11/2013 | Chen .......... G01N 33/60 424/1.49 |
| 2013/0302359 A1 | 11/2013 | Li et al. |
| 2014/0335018 A1 | 11/2014 | Wong et al. |
| 2015/0150998 A1 | 6/2015 | Hu et al. |

FOREIGN PATENT DOCUMENTS

| | | | |
|---|---|---|---|
| WO | 9306132 | * | 4/1993 |
| WO | 2005/117986 A2 | | 12/2005 |
| WO | 2006/042848 A2 | | 4/2006 |
| WO | 2007/020965 A1 | | 2/2007 |
| WO | 2009/012268 A1 | | 1/2009 |
| WO | 2009/052431 A2 | | 4/2009 |
| WO | 2009/059278 A1 | | 5/2009 |
| WO | 2012/112687 A1 | | 8/2012 |
| WO | 2012112687 | * | 8/2012 |
| WO | 2013/165940 A1 | | 11/2013 |
| WO | 2013/174003 A1 | | 11/2013 |
| WO | 2013/182661 A1 | | 12/2013 |
| WO | 2014/047357 A1 | | 3/2014 |
| WO | 2015/031815 A2 | | 3/2015 |

OTHER PUBLICATIONS

Axup et al., Synthesis of site-specific antibody-drug conjugates using unnatural amino acids. Proc Natl Acad Sci U S A. Oct. 2, 2012;109(40):16101-6.

Geoghegan et al., Site-directed conjugation of nonpeptide groups to peptides and proteins via periodate oxidation of a 2-amino alcohol. Application to modification at N-terminal serine. Bioconjug Chem. Mar.-Apr. 1992;3(2):138-46.

Kalia et al., Hydrolytic stability of hydrazones and oximes. Angew Chem Int Ed Engl. 2008;47(39):7523-6.

Kawakami et.al., Peptide bond formation mediated by 4,5-dimethoxy-2-mercaptobenzylamine after periodate oxidation of the N-terminal serine residue. Org Lett. May 3, 2001;3(9):1403-5.

Kumaresan et al., Evaluation of ketone-oxime method for developing therapeutic on-demand cleavable immunoconjugates. Bioconjug Chem. Jun. 2008;19(6):1313-8.

Rodwell et al., Site-specific covalent modification of monoclonal antibodies: in vitro and in vivo evaluations. Proc Natl Acad Sci U S A. Apr. 1986;83(8):2632-6.

Thygesen et.al., Nucleophilic catalysis of carbohydrate oxime formation by anilines. J Org Chem. Mar. 5, 2010;75(5):1752-5.

Wendeler et al., Enhanced catalysis of oxime-based bioconjugations by substituted anilines. Bioconjug Chem. Jan. 15, 2014;25(1):93-101.

Zuberbühler et.al., Fucose-specific conjugation of hydrazide derivatives to a vascular-targeting monoclonal antibody in IgG format. Chem Commun (Camb). Jul. 18, 2012;48(56):7100-2.

\* cited by examiner

Scheme 2

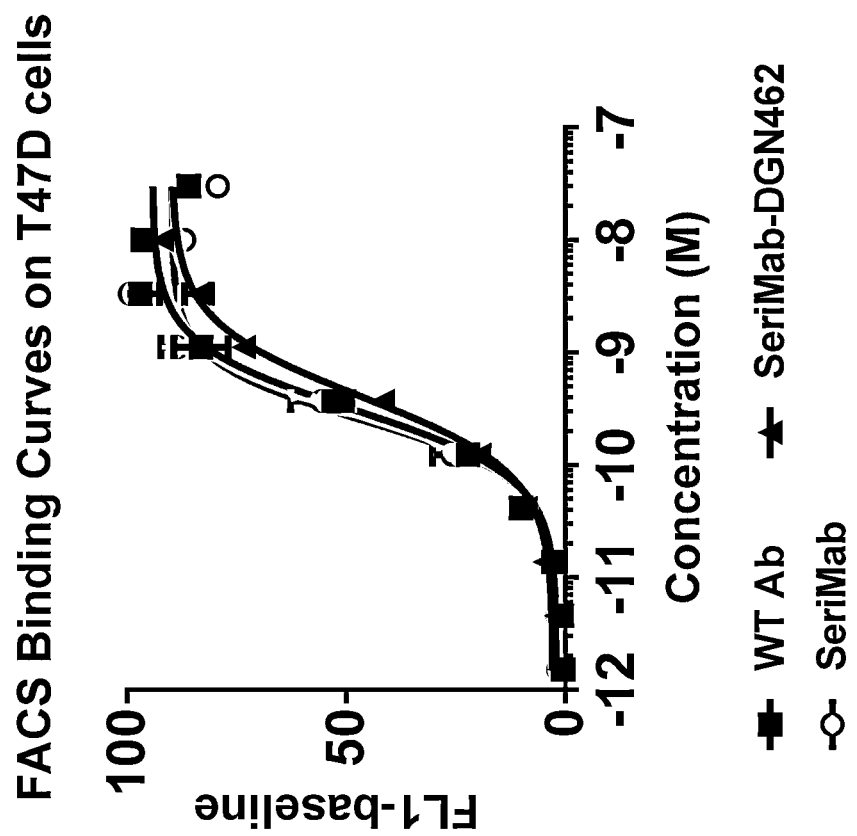

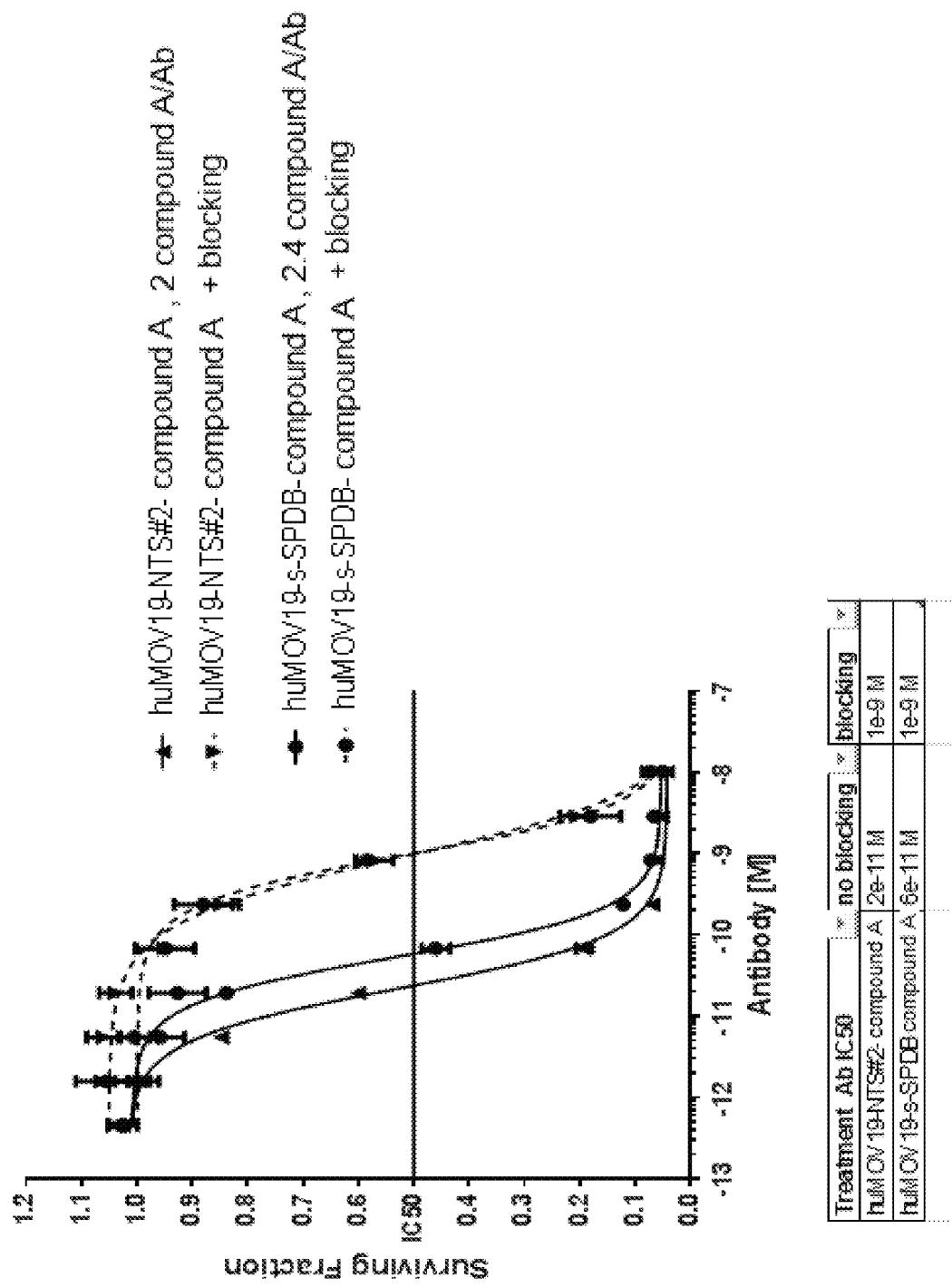

Scheme 4

Scheme 5

Scheme 6

Scheme 7

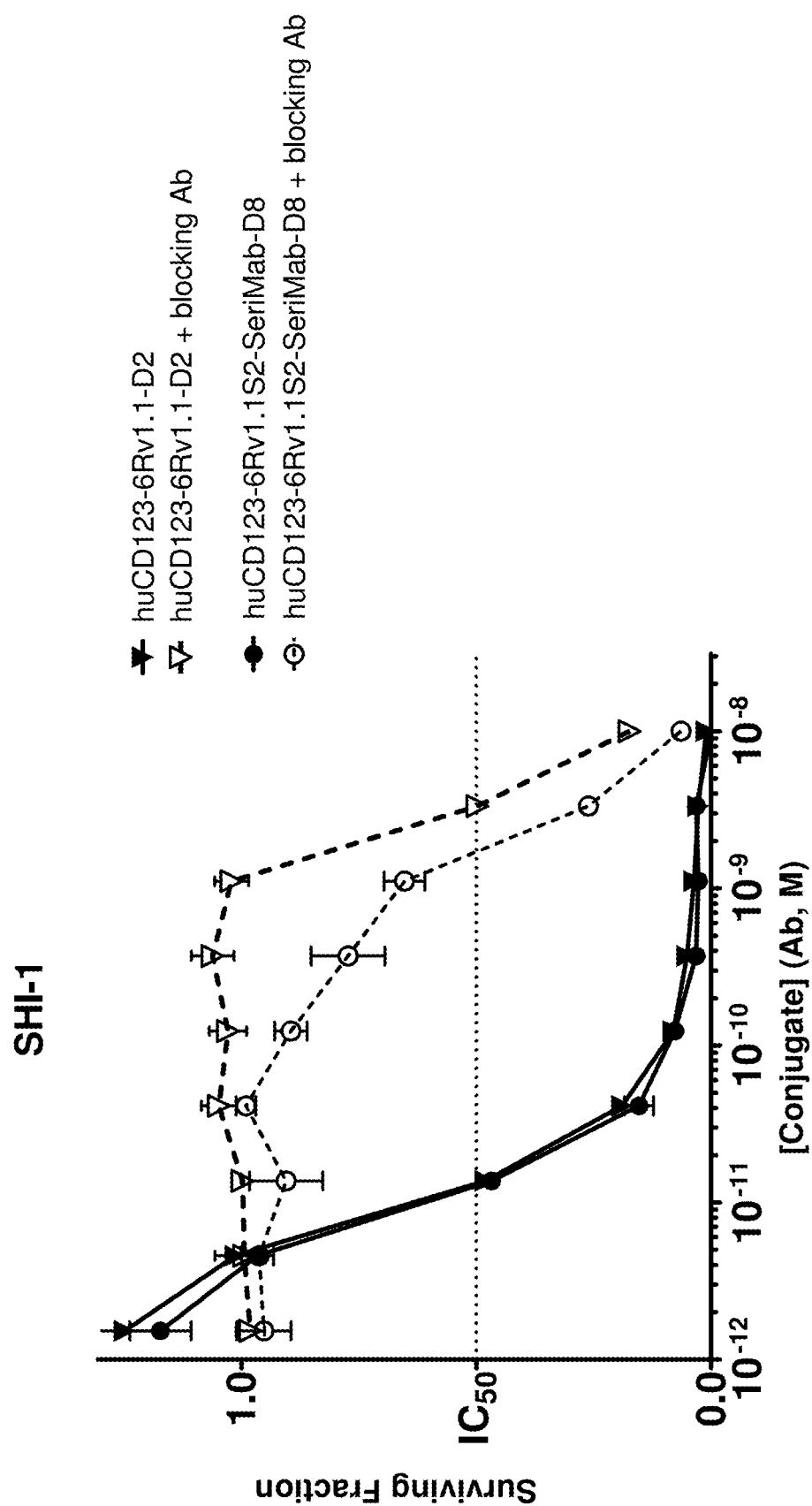

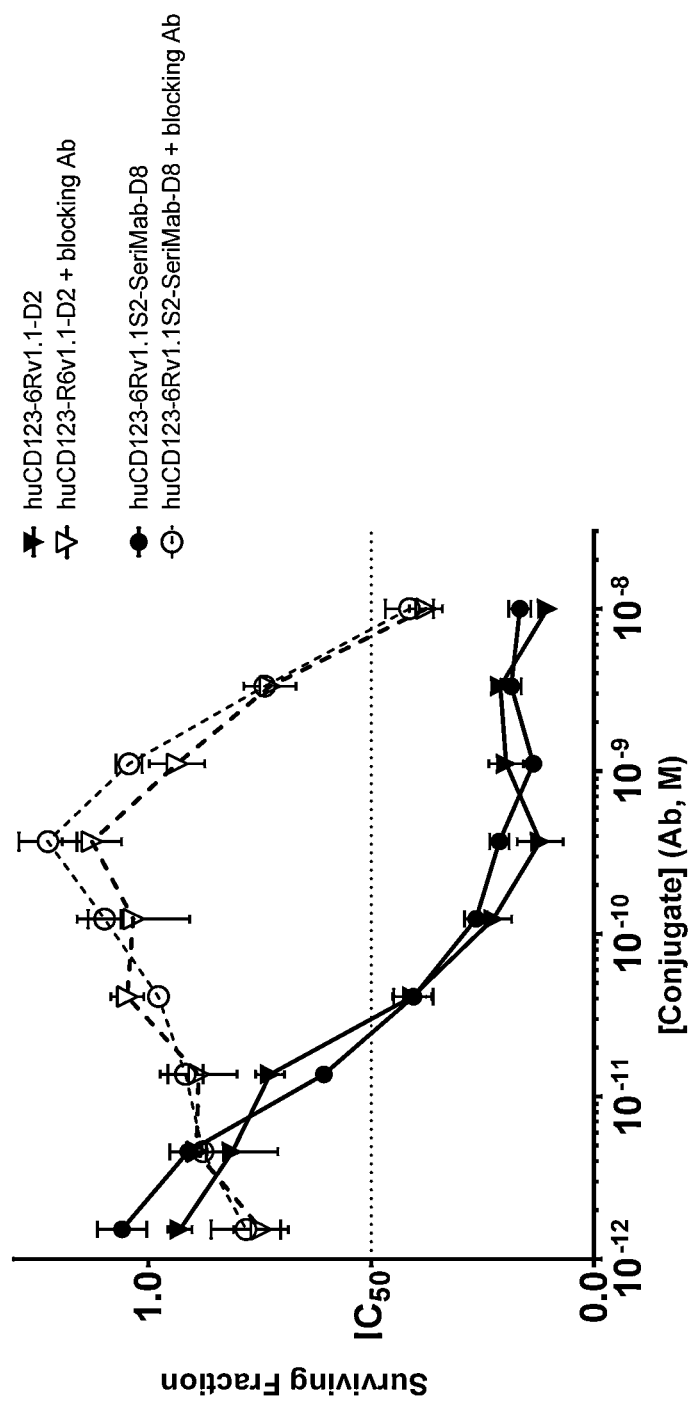

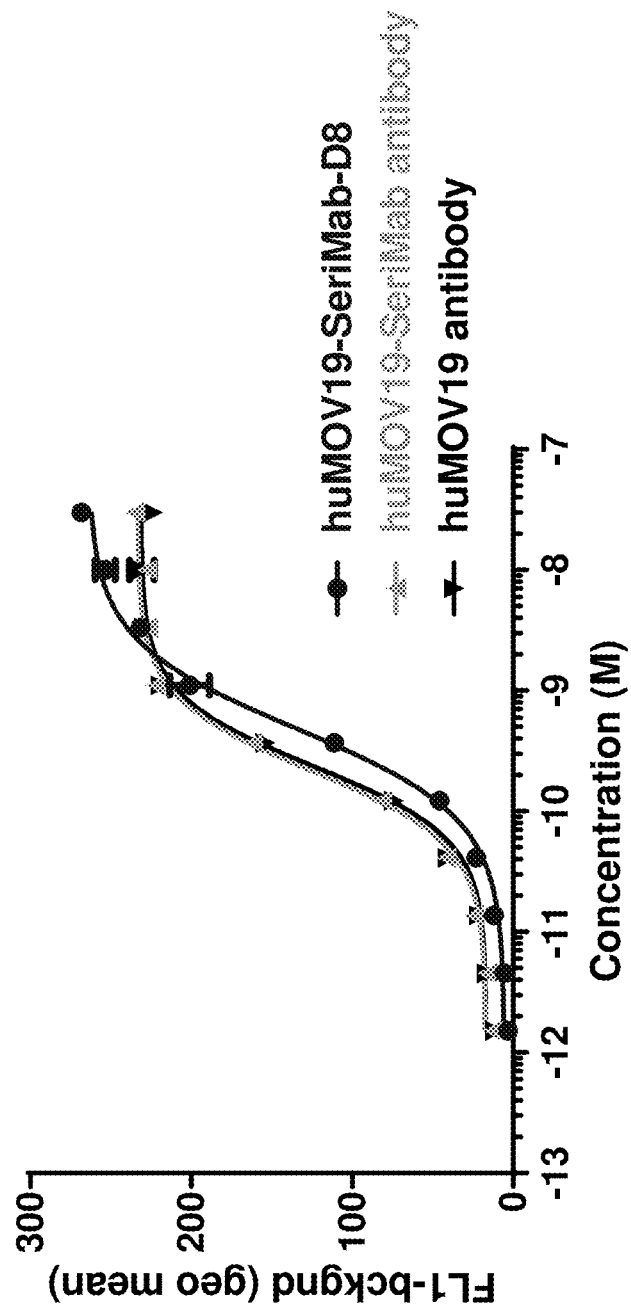

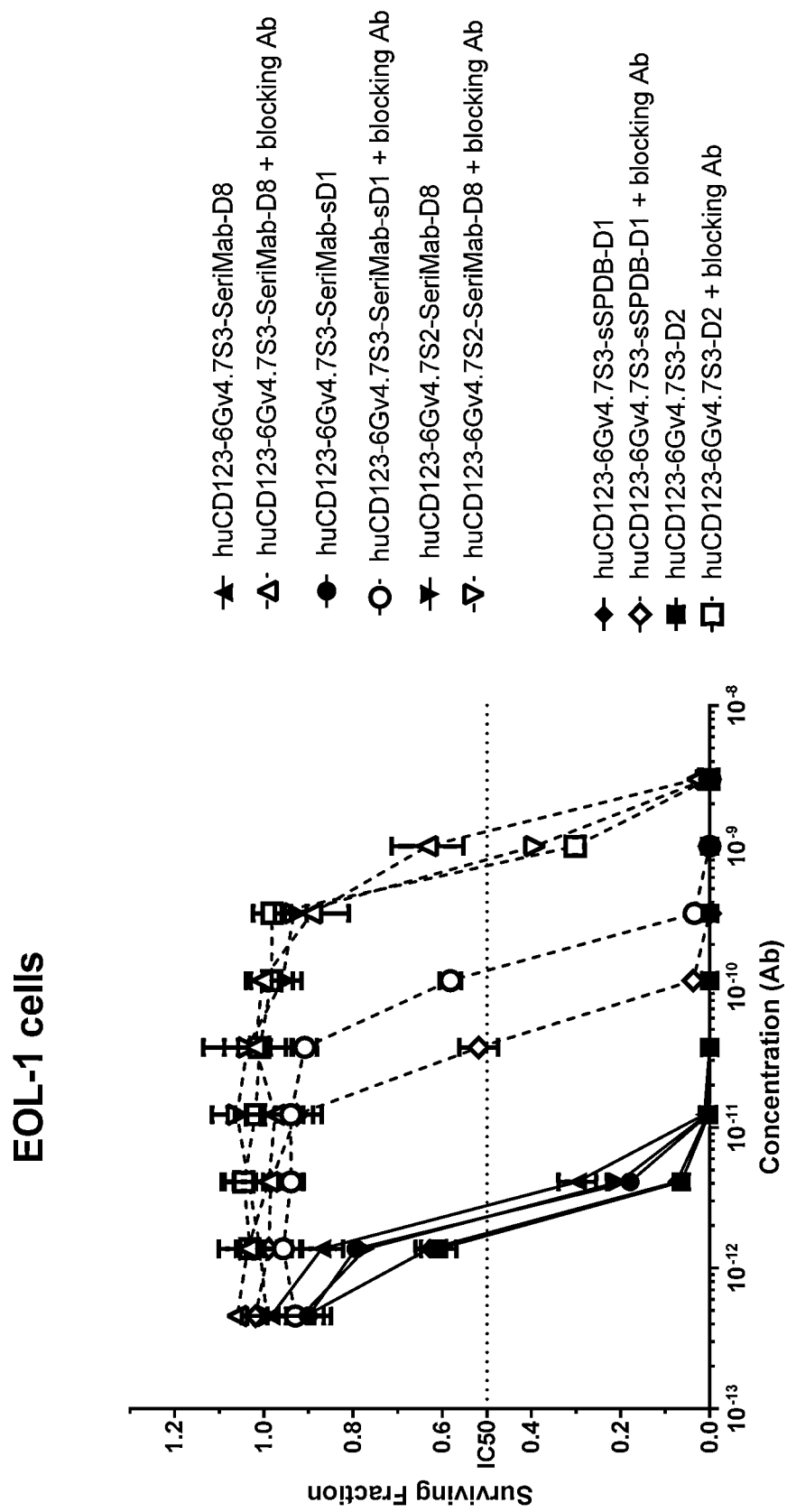

SEQUENCE LISTING

```
<160> NUMBER OF SEQ ID NOS: 71

<210> SEQ ID NO 1
<211> LENGTH: 20
<212> TYPE: PRT
<213> ORGANISM: Artificial
<220> FEATURE:
<223> OTHER INFORMATION: FR1-2.1 antibody light chain signal peptide
      (NCBI CAB46122)

<400> SEQUENCE: 1

Met Lys Leu Pro Val Leu Leu Val Val Leu Leu Leu Phe Thr Ser Pro
1               5                   10                  15

Ala Ser Ser Ser
            20

<210> SEQ ID NO 2
<211> LENGTH: 120
<212> TYPE: PRT
<213> ORGANISM: Artificial
<220> FEATURE:
<223> OTHER INFORMATION: IGKV1-99*01 Accession CAB46122

<400> SEQUENCE: 2
```

```
Met Lys Leu Pro Val Leu Leu Val Val Leu Leu Phe Thr Ser Pro
1               5                   10                  15

Ala Ser Ser Ser Asp Val Val Leu Thr Gln Thr Pro Leu Ser Leu Pro
            20                  25                  30

Val Asn Ile Gly Asp Gln Ala Ser Ile Ser Cys Lys Ser Thr Lys Ser
            35                  40                  45

Leu Leu Asn Ser Asp Gly Phe Thr Tyr Leu Asp Trp Tyr Leu Gln Lys
    50                  55                  60

Pro Gly Gln Ser Pro Gln Leu Leu Ile Tyr Leu Val Ser Asn Arg Phe
65                  70                  75                  80

Ser Gly Val Pro Asp Arg Phe Ser Gly Ser Gly Ser Gly Thr Asp Phe
            85                  90                  95

Thr Leu Lys Ile Ser Arg Val Glu Ala Glu Asp Leu Gly Val Tyr Tyr
            100                 105                 110

Cys Phe Gln Ser Asn Tyr Leu Pro
            115                 120
```

<210> SEQ ID NO 3
<211> LENGTH: 220
<212> TYPE: PRT
<213> ORGANISM: Artificial
<220> FEATURE:
<223> OTHER INFORMATION: FR1-2.1 light chain (as expressed)

<400> SEQUENCE: 3

```
Ser Asp Val Val Leu Thr Gln Thr Pro Leu Ser Leu Pro Val Asn Ile
1               5                   10                  15

Gly Asp Gln Ala Ser Ile Ser Cys Lys Ser Ser Lys Ser Leu Leu Asn
            20                  25                  30

Ser Asp Gly Phe Thr Tyr Leu Asp Trp Tyr Leu Gln Lys Pro Gly Gln
            35                  40                  45

Ser Pro Gln Leu Leu Ile Tyr Leu Val Ser Asn His Phe Ser Gly Val
    50                  55                  60

Pro Asp Arg Phe Ser Gly Ser Gly Ser Gly Thr Asp Phe Thr Leu Lys
65                  70                  75                  80

Ile Ser Arg Val Glu Ala Glu Asp Leu Gly Val Tyr Tyr Cys Phe Gln
            85                  90                  95

Ser Asn Tyr Leu Pro Leu Thr Phe Gly Gly Gly Thr Lys Leu Glu Ile
            100                 105                 110

Lys Arg Ala Asp Ala Ala Pro Thr Val Ser Ile Phe Pro Pro Ser Ser
            115                 120                 125

Glu Gln Leu Thr Ser Gly Gly Ala Ser Val Val Cys Phe Leu Asn Asn
    130                 135                 140

Phe Tyr Pro Lys Asp Ile Asn Val Lys Trp Lys Ile Asp Gly Ser Glu
145                 150                 155                 160

Arg Gln Asn Gly Val Leu Asn Ser Trp Thr Asp Gln Asp Ser Lys Asp
            165                 170                 175

Ser Thr Tyr Ser Met Ser Ser Thr Leu Thr Leu Thr Lys Asp Glu Tyr
            180                 185                 190

Glu Arg His Asn Ser Tyr Thr Cys Glu Ala Thr His Lys Thr Ser Thr
            195                 200                 205

Ser Pro Ile Val Lys Ser Phe Asn Arg Asn Glu Cys
    210                 215                 220
```

<210> SEQ ID NO 4
<211> LENGTH: 239

```
<212> TYPE: PRT
<213> ORGANISM: Artificial
<220> FEATURE:
<223> OTHER INFORMATION: FR1-2.1 light chain full length, with signal
      peptide

<400> SEQUENCE: 4

Met Lys Leu Pro Val Leu Leu Val Val Leu Leu Phe Thr Ser Pro
1               5                   10                  15

Ala Ser Ser Ser Asp Val Val Leu Thr Gln Thr Pro Leu Ser Leu Pro
            20                  25                  30

Val Asn Ile Gly Asp Gln Ala Ser Ile Ser Cys Lys Ser Ser Lys Ser
            35                  40                  45

Leu Leu Asn Ser Asp Gly Phe Thr Tyr Leu Asp Trp Tyr Leu Gln Lys
    50                  55                  60

Pro Gly Gln Ser Pro Gln Leu Leu Ile Tyr Leu Val Ser Asn His Phe
65                  70                  75                  80

Ser Gly Val Pro Asp Arg Phe Ser Gly Ser Gly Ser Gly Thr Asp Phe
                85                  90                  95

Thr Leu Lys Ile Ser Arg Val Glu Ala Glu Asp Leu Gly Val Tyr Tyr
            100                 105                 110

Cys Phe Gln Ser Asn Tyr Leu Pro Leu Thr Phe Gly Gly Gly Thr Lys
            115                 120                 125

Leu Glu Ile Lys Arg Ala Asp Ala Ala Pro Thr Val Ser Ile Phe Pro
    130                 135                 140

Pro Ser Glu Gln Leu Thr Ser Gly Gly Ala Ser Val Val Cys Phe
145                 150                 155                 160

Leu Asn Asn Phe Tyr Pro Lys Asp Ile Asn Val Lys Trp Lys Ile Asp
                165                 170                 175

Gly Ser Glu Arg Gln Asn Gly Val Leu Asn Ser Trp Thr Asp Gln Asp
            180                 185                 190

Ser Lys Asp Ser Thr Tyr Ser Met Ser Ser Thr Leu Thr Leu Thr Lys
            195                 200                 205

Asp Glu Tyr Glu Arg His Asn Ser Tyr Thr Cys Glu Ala Thr His Lys
    210                 215                 220

Thr Ser Thr Ser Pro Ile Val Lys Ser Phe Asn Arg Asn Glu Cys
225                 230                 235

<210> SEQ ID NO 5
<211> LENGTH: 446
<212> TYPE: PRT
<213> ORGANISM: Artificial
<220> FEATURE:
<223> OTHER INFORMATION: FR1-2.1 heavy chain

<400> SEQUENCE: 5

Gln Val Gln Leu Gln Gln Ser Gly Pro Glu Leu Val Lys Pro Gly Ala
1               5                   10                  15

Ser Val Arg Ile Ser Cys Lys Ala Ser Gly Tyr Thr Phe Thr Asn Ser
            20                  25                  30

Tyr Ile His Trp Val Lys Lys Arg Pro Gly Gln Gly Leu Glu Trp Ile
            35                  40                  45

Gly Trp Ile Tyr Pro Glu Ser Leu Asn Thr Gln Tyr Asn Glu Lys Phe
    50                  55                  60

Lys Ala Lys Ala Thr Leu Thr Ala Asp Lys Ser Ser Ser Thr Ser Tyr
65                  70                  75                  80

Met Gln Leu Ser Ser Leu Thr Ser Glu Asp Ser Ala Val Tyr Phe Cys
```

```
                      85                  90                  95

Ala Arg Arg Gly Ile Tyr Tyr Tyr Ser Pro Tyr Ala Leu Asp His Trp
            100                 105                 110

Gly Gln Gly Ala Ser Val Thr Val Ser Ser Ala Lys Thr Thr Pro Pro
            115                 120                 125

Ser Val Tyr Pro Leu Ala Pro Gly Ser Ala Ala Gln Thr Asn Ser Met
            130                 135                 140

Val Thr Leu Gly Cys Leu Val Lys Gly Tyr Phe Pro Glu Pro Val Thr
145                 150                 155                 160

Val Thr Trp Asn Ser Gly Ser Leu Ser Ser Gly Val His Thr Phe Pro
            165                 170                 175

Ala Val Leu Glu Ser Asp Leu Tyr Thr Leu Ser Ser Ser Val Thr Val
            180                 185                 190

Pro Ser Ser Met Arg Pro Ser Glu Thr Val Thr Cys Asn Val Ala His
            195                 200                 205

Pro Ala Ser Ser Thr Lys Val Asp Lys Lys Ile Val Pro Arg Asp Cys
            210                 215                 220

Gly Cys Lys Pro Cys Ile Cys Thr Val Pro Glu Val Ser Ser Val Phe
225                 230                 235                 240

Ile Phe Pro Pro Lys Pro Lys Asp Val Leu Thr Ile Thr Leu Thr Pro
            245                 250                 255

Lys Val Thr Cys Val Val Val Asp Ile Ser Lys Asp Asp Pro Glu Val
            260                 265                 270

Gln Phe Ser Trp Phe Val Asp Asp Val Glu Val His Thr Ala Gln Thr
            275                 280                 285

Gln Pro Arg Glu Glu Gln Phe Asn Ser Thr Phe Arg Ser Val Ser Glu
            290                 295                 300

Leu Pro Ile Met His Gln Asp Trp Leu Asn Gly Lys Glu Phe Lys Cys
305                 310                 315                 320

Arg Val Asn Ser Ala Ala Phe Pro Ala Pro Ile Glu Lys Thr Ile Ser
            325                 330                 335

Lys Thr Lys Gly Arg Pro Lys Ala Pro Gln Val Tyr Thr Ile Pro Pro
            340                 345                 350

Pro Lys Glu Gln Met Ala Lys Asp Lys Val Ser Leu Thr Cys Met Ile
            355                 360                 365

Thr Asp Phe Phe Pro Glu Asp Ile Thr Val Glu Trp Gln Trp Asn Gly
            370                 375                 380

Gln Pro Ala Glu Asn Tyr Lys Asn Thr Gln Pro Ile Met Asn Thr Asn
385                 390                 395                 400

Gly Ser Tyr Phe Val Tyr Ser Lys Leu Asn Val Gln Lys Ser Asn Trp
            405                 410                 415

Glu Ala Gly Asn Thr Phe Thr Cys Ser Val Leu His Glu Gly Leu His
            420                 425                 430

Asn His His Thr Glu Lys Ser Leu Ser His Ser Pro Gly Lys
            435                 440                 445

<210> SEQ ID NO 6
<211> LENGTH: 19
<212> TYPE: PRT
<213> ORGANISM: Artificial
<220> FEATURE:
<223> OTHER INFORMATION: huMov19 LC and HC signal peptide

<400> SEQUENCE: 6

Met Gly Trp Ser Cys Ile Ile Leu Phe Leu Val Ala Thr Ala Thr Gly
```

Val His Ser

<210> SEQ ID NO 7
<211> LENGTH: 218
<212> TYPE: PRT
<213> ORGANISM: Artificial
<220> FEATURE:
<223> OTHER INFORMATION: huMov19 LC

<400> SEQUENCE: 7

Asp Ile Val Leu Thr Gln Ser Pro Leu Ser Leu Ala Val Ser Leu Gly
1               5                   10                  15

Gln Pro Ala Ile Ile Ser Cys Lys Ala Ser Gln Ser Val Ser Phe Ala
            20                  25                  30

Gly Thr Ser Leu Met His Trp Tyr His Gln Lys Pro Gly Gln Gln Pro
        35                  40                  45

Arg Leu Leu Ile Tyr Arg Ala Ser Asn Leu Glu Ala Gly Val Pro Asp
    50                  55                  60

Arg Phe Ser Gly Ser Gly Ser Lys Thr Asp Phe Thr Leu Thr Ile Ser
65                  70                  75                  80

Pro Val Glu Ala Glu Asp Ala Ala Thr Tyr Tyr Cys Gln Gln Ser Arg
                85                  90                  95

Glu Tyr Pro Tyr Thr Phe Gly Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 8
<211> LENGTH: 447
<212> TYPE: PRT
<213> ORGANISM: Artificial
<220> FEATURE:
<223> OTHER INFORMATION: huMov19 HC

<400> SEQUENCE: 8

Gln Val Gln Leu Val Gln Ser Gly Ala Glu Val Val Lys Pro Gly Ala
1               5                   10                  15

Ser Val Lys Ile Ser Cys Lys Ala Ser Gly Tyr Thr Phe Thr Gly Tyr
            20                  25                  30

Phe Met Asn Trp Val Lys Gln Ser Pro Gly Gln Ser Leu Glu Trp Ile
        35                  40                  45

Gly Arg Ile His Pro Tyr Asp Gly Asp Thr Phe Tyr Asn Gln Lys Phe
    50                  55                  60

Gln Gly Lys Ala Thr Leu Thr Val Asp Lys Ser Ser Asn Thr Ala His

```
            65                   70                  75                  80
        Met Glu Leu Leu Ser Leu Thr Ser Glu Asp Phe Ala Val Tyr Tyr Cys
                            85                  90                  95

Thr Arg Tyr Asp Gly Ser Arg Ala Met Asp Tyr Trp Gly Gln Gly Thr
                            100                 105                 110

Thr Val Thr Val Ser Ser Ala Ser Thr Lys Gly Pro Ser Val Phe Pro
                        115                 120                 125

Leu Ala Pro Ser Ser Lys Ser Thr Ser Gly Gly Thr Ala Ala Leu Gly
                    130                 135                 140

Cys Leu Val Lys Asp Tyr Phe Pro Glu Pro Val Thr Val Ser Trp Asn
        145                 150                 155                 160

Ser Gly Ala Leu Thr Ser Gly Val His Thr Phe Pro Ala Val Leu Gln
                            165                 170                 175

Ser Ser Gly Leu Tyr Ser Leu Ser Val Val Thr Val Pro Ser Ser
                        180                 185                 190

Ser Leu Gly Thr Gln Thr Tyr Ile Cys Asn Val Asn His Lys Pro Ser
                    195                 200                 205

Asn Thr Lys Val Asp Lys Lys Val Glu Pro Lys Ser Cys Asp Lys Thr
                210                 215                 220

His Thr Cys Pro Pro Cys Pro Ala Pro Glu Leu Leu Gly Gly Pro Ser
        225                 230                 235                 240

Val Phe Leu Phe Pro Pro Lys Pro Lys Asp Thr Leu Met Ile Ser Arg
                            245                 250                 255

Thr Pro Glu Val Thr Cys Val Val Val Asp Val Ser His Glu Asp Pro
                        260                 265                 270

Glu Val Lys Phe Asn Trp Tyr Val Asp Gly Val Glu Val His Asn Ala
                    275                 280                 285

Lys Thr Lys Pro Arg Glu Glu Gln Tyr Asn Ser Thr Tyr Arg Val Val
                290                 295                 300

Ser Val Leu Thr Val Leu His Gln Asp Trp Leu Asn Gly Lys Glu Tyr
        305                 310                 315                 320

Lys Cys Lys Val Ser Asn Lys Ala Leu Pro Ala Pro Ile Glu Lys Thr
                            325                 330                 335

Ile Ser Lys Ala Lys Gly Gln Pro Arg Glu Pro Gln Val Tyr Thr Leu
                        340                 345                 350

Pro Pro Ser Arg Asp Glu Leu Thr Lys Asn Gln Val Ser Leu Thr Cys
                    355                 360                 365

Leu Val Lys Gly Phe Tyr Pro Ser Asp Ile Ala Val Glu Trp Glu Ser
                370                 375                 380

Asn Gly Gln Pro Glu Asn Asn Tyr Lys Thr Thr Pro Pro Val Leu Asp
        385                 390                 395                 400

Ser Asp Gly Ser Phe Phe Leu Tyr Ser Lys Leu Thr Val Asp Lys Ser
                            405                 410                 415

Arg Trp Gln Gln Gly Asn Val Phe Ser Cys Ser Val Met His Glu Ala
                        420                 425                 430

Leu His Asn His Tyr Thr Gln Lys Ser Leu Ser Leu Ser Pro Gly
                    435                 440                 445

<210> SEQ ID NO 9
<211> LENGTH: 219
<212> TYPE: PRT
<213> ORGANISM: Artificial
<220> FEATURE:
<223> OTHER INFORMATION: huMov19 LC NTS1 (as expressed)
```

<400> SEQUENCE: 9

Ser Asp Ile Val Leu Thr Gln Ser Pro Leu Ser Leu Ala Val Ser Leu
1               5                   10                  15

Gly Gln Pro Ala Ile Ile Ser Cys Lys Ala Ser Gln Ser Val Ser Phe
            20                  25                  30

Ala Gly Thr Ser Leu Met His Trp Tyr His Gln Lys Pro Gly Gln Gln
        35                  40                  45

Pro Arg Leu Leu Ile Tyr Arg Ala Ser Asn Leu Glu Ala Gly Val Pro
    50                  55                  60

Asp Arg Phe Ser Gly Ser Gly Ser Lys Thr Asp Phe Thr Leu Thr Ile
65                  70                  75                  80

Ser Pro Val Glu Ala Glu Asp Ala Ala Thr Tyr Tyr Cys Gln Gln Ser
                85                  90                  95

Arg Glu Tyr Pro Tyr Thr Phe Gly Gly Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 10
<211> LENGTH: 238
<212> TYPE: PRT
<213> ORGANISM: Artificial
<220> FEATURE:
<223> OTHER INFORMATION: huMov19 LC NTS1 with FR1-2.1 light chain signal
      peptide

<400> SEQUENCE: 10

Met Lys Leu Pro Val Leu Leu Val Val Leu Leu Phe Thr Ser Pro
1               5                   10                  15

Ala Ser Ser Ser Asp Ile Val Leu Thr Gln Ser Pro Leu Ser Leu Ala
            20                  25                  30

Val Ser Leu Gly Gln Pro Ala Ile Ile Ser Cys Lys Ala Ser Gln Ser
        35                  40                  45

Val Ser Phe Ala Gly Thr Ser Leu Met His Trp Tyr His Gln Lys Pro
    50                  55                  60

Gly Gln Gln Pro Arg Leu Leu Ile Tyr Arg Ala Ser Asn Leu Glu Ala
65                  70                  75                  80

Gly Val Pro Asp Arg Phe Ser Gly Ser Gly Ser Lys Thr Asp Phe Thr
                85                  90                  95

Leu Thr Ile Ser Pro Val Glu Ala Glu Asp Ala Ala Thr Tyr Tyr Cys
            100                 105                 110

Gln Gln Ser Arg Glu Tyr Pro Tyr Thr Phe Gly Gly Gly Thr Lys Leu
        115                 120                 125

```
Glu Ile Lys Arg Thr Val Ala Ala Pro Ser Val Phe Ile Phe Pro Pro
    130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala
        195                 200                 205

Asp Tyr Glu Lys His Lys Val Tyr Ala Cys Glu Val Thr His Gln Gly
210                 215                 220

Leu Ser Ser Pro Val Thr Lys Ser Phe Asn Arg Gly Glu Cys
225                 230                 235
```

<210> SEQ ID NO 11
<211> LENGTH: 447
<212> TYPE: PRT
<213> ORGANISM: Artificial
<220> FEATURE:
<223> OTHER INFORMATION: huMov19 HC NTS2

<400> SEQUENCE: 11

```
Ser Val Gln Leu Val Gln Ser Gly Ala Glu Val Lys Pro Gly Ala
1               5                   10                  15

Ser Val Lys Ile Ser Cys Lys Ala Ser Gly Tyr Thr Phe Thr Gly Tyr
                20                  25                  30

Phe Met Asn Trp Val Lys Gln Ser Pro Gly Gln Ser Leu Glu Trp Ile
            35                  40                  45

Gly Arg Ile His Pro Tyr Asp Gly Asp Thr Phe Tyr Asn Gln Lys Phe
        50                  55                  60

Gln Gly Lys Ala Thr Leu Thr Val Asp Lys Ser Ser Asn Thr Ala His
65                  70                  75                  80

Met Glu Leu Leu Ser Leu Thr Ser Glu Asp Phe Ala Val Tyr Tyr Cys
                85                  90                  95

Thr Arg Tyr Asp Gly Ser Arg Ala Met Asp Tyr Trp Gly Gln Gly Thr
            100                 105                 110

Thr Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255
```

```
Thr Pro Glu Val Thr Cys Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
            325                 330                 335

Ile Ser Lys Ala Lys Gly Gln Pro Arg Glu Pro Gln Val Tyr Thr Leu
        340                 345                 350

Pro Pro Ser Arg Asp Glu Leu Thr Lys Asn Gln Val Ser Leu Thr Cys
    355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
            405                 410                 415

Arg Trp Gln Gln Gly Asn Val Phe Ser Cys Ser Val Met His Glu Ala
        420                 425                 430

Leu His Asn His Tyr Thr Gln Lys Ser Leu Ser Leu Ser Pro Gly
    435                 440                 445
```

<210> SEQ ID NO 12
<211> LENGTH: 218
<212> TYPE: PRT
<213> ORGANISM: Artificial
<220> FEATURE:
<223> OTHER INFORMATION: huMov19 LC NTS3

<400> SEQUENCE: 12

```
Ser Ile Val Leu Thr Gln Ser Pro Leu Ser Leu Ala Val Ser Leu Gly
1               5                   10                  15

Gln Pro Ala Ile Ile Ser Cys Lys Ala Ser Gln Ser Val Ser Phe Ala
            20                  25                  30

Gly Thr Ser Leu Met His Trp Tyr His Gln Lys Pro Gly Gln Gln Pro
        35                  40                  45

Arg Leu Leu Ile Tyr Arg Ala Ser Asn Leu Glu Ala Gly Val Pro Asp
50                  55                  60

Arg Phe Ser Gly Ser Gly Ser Lys Thr Asp Phe Thr Leu Thr Ile Ser
65                  70                  75                  80

Pro Val Glu Ala Glu Asp Ala Ala Thr Tyr Tyr Cys Gln Gln Ser Arg
            85                  90                  95

Glu Tyr Pro Tyr Thr Phe Gly Gly Gly Thr Lys Leu Glu Ile Lys Arg
        100                 105                 110

Thr Val Ala Ala Pro Ser Val Phe Ile Phe Pro Pro Ser Asp Glu Gln
    115                 120                 125

Leu Lys Ser Gly Thr Ala Ser Val Val Cys Leu Leu Asn Asn Phe Tyr
130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
            165                 170                 175
```

```
Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
        210                 215

<210> SEQ ID NO 13
<211> LENGTH: 448
<212> TYPE: PRT
<213> ORGANISM: Artificial
<220> FEATURE:
<223> OTHER INFORMATION: huMov19 HC NTS4 (as expressed)

<400> SEQUENCE: 13

Ser Gln Val Gln Leu Val Gln Ser Gly Ala Glu Val Val Lys Pro Gly
1               5                   10                  15

Ala Ser Val Lys Ile Ser Cys Lys Ala Ser Gly Tyr Thr Phe Thr Gly
            20                  25                  30

Tyr Phe Met Asn Trp Val Lys Gln Ser Pro Gly Gln Ser Leu Glu Trp
        35                  40                  45

Ile Gly Arg Ile His Pro Tyr Asp Gly Asp Thr Phe Tyr Asn Gln Lys
    50                  55                  60

Phe Gln Gly Lys Ala Thr Leu Thr Val Asp Lys Ser Ser Asn Thr Ala
65                  70                  75                  80

His Met Glu Leu Leu Ser Leu Thr Ser Glu Asp Phe Ala Val Tyr Tyr
                85                  90                  95

Cys Thr Arg Tyr Asp Gly Ser Arg Ala Met Asp Tyr Trp Gly Gln Gly
            100                 105                 110

Thr Thr Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320
```

```
Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

<210> SEQ ID NO 14
<211> LENGTH: 467
<212> TYPE: PRT
<213> ORGANISM: Artificial
<220> FEATURE:
<223> OTHER INFORMATION: huMov19 HC NTS4 with FR1-2.1 light chain signal
      peptide

<400> SEQUENCE: 14

Met Lys Leu Pro Val Leu Leu Val Val Leu Leu Phe Thr Ser Pro
1               5                   10                  15

Ala Ser Ser Ser Gln Val Gln Leu Val Gln Ser Gly Ala Glu Val Val
                20                  25                  30

Lys Pro Gly Ala Ser Val Lys Ile Ser Cys Lys Ala Ser Gly Tyr Thr
            35                  40                  45

Phe Thr Gly Tyr Phe Met Asn Trp Val Lys Gln Ser Pro Gly Gln Ser
        50                  55                  60

Leu Glu Trp Ile Gly Arg Ile His Pro Tyr Asp Gly Asp Thr Phe Tyr
65                  70                  75                  80

Asn Gln Lys Phe Gln Gly Lys Ala Thr Leu Thr Val Asp Lys Ser Ser
                85                  90                  95

Asn Thr Ala His Met Glu Leu Leu Ser Leu Thr Ser Glu Asp Phe Ala
            100                 105                 110

Val Tyr Tyr Cys Thr Arg Tyr Asp Gly Ser Arg Ala Met Asp Tyr Trp
        115                 120                 125

Gly Gln Gly Thr Thr Val Thr Val Ser Ser Ala Ser Thr Lys Gly Pro
130                 135                 140

Ser Val Phe Pro Leu Ala Pro Ser Ser Lys Ser Thr Ser Gly Gly Thr
145                 150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
            180                 185                 190

Ala Val Leu Gln Ser Ser Gly Leu Tyr Ser Leu Ser Ser Val Val Thr
        195                 200                 205

Val Pro Ser Ser Ser Leu Gly Thr Gln Thr Tyr Ile Cys Asn Val Asn
    210                 215                 220

His Lys Pro Ser Asn Thr Lys Val Asp Lys Lys Val Glu Pro Lys Ser
225                 230                 235                 240
```

```
Cys Asp Lys Thr His Thr Cys Pro Pro Cys Pro Ala Pro Glu Leu Leu
                245                 250                 255

Gly Gly Pro Ser Val Phe Leu Phe Pro Pro Lys Pro Lys Asp Thr Leu
            260                 265                 270

Met Ile Ser Arg Thr Pro Glu Val Thr Cys Val Val Val Asp Val Ser
        275                 280                 285

His Glu Asp Pro Glu Val Lys Phe Asn Trp Tyr Val Asp Gly Val Glu
    290                 295                 300

Val His Asn Ala Lys Thr Lys Pro Arg Glu Glu Gln Tyr Asn Ser Thr
305                 310                 315                 320

Tyr Arg Val Val Ser Val Leu Thr Val Leu His Gln Asp Trp Leu Asn
                325                 330                 335

Gly Lys Glu Tyr Lys Cys Lys Val Ser Asn Lys Ala Leu Pro Ala Pro
            340                 345                 350

Ile Glu Lys Thr Ile Ser Lys Ala Lys Gly Gln Pro Arg Glu Pro Gln
        355                 360                 365

Val Tyr Thr Leu Pro Pro Ser Arg Asp Glu Leu Thr Lys Asn Gln Val
    370                 375                 380

Ser Leu Thr Cys Leu Val Lys Gly Phe Tyr Pro Ser Asp Ile Ala Val
385                 390                 395                 400

Glu Trp Glu Ser Asn Gly Gln Pro Glu Asn Asn Tyr Lys Thr Thr Pro
                405                 410                 415

Pro Val Leu Asp Ser Asp Gly Ser Phe Phe Leu Tyr Ser Lys Leu Thr
            420                 425                 430

Val Asp Lys Ser Arg Trp Gln Gln Gly Asn Val Phe Ser Cys Ser Val
        435                 440                 445

Met His Glu Ala Leu His Asn His Tyr Thr Gln Lys Ser Leu Ser Leu
    450                 455                 460

Ser Pro Gly
465

<210> SEQ ID NO 15
<211> LENGTH: 218
<212> TYPE: PRT
<213> ORGANISM: Artificial
<220> FEATURE:
<223> OTHER INFORMATION: huMov19 LC NTT1

<400> SEQUENCE: 15

Thr Ile Val Leu Thr Gln Ser Pro Leu Ser Leu Ala Val Ser Leu Gly
1               5                   10                  15

Gln Pro Ala Ile Ile Ser Cys Lys Ala Ser Gln Ser Val Ser Phe Ala
            20                  25                  30

Gly Thr Ser Leu Met His Trp Tyr His Gln Lys Pro Gly Gln Gln Pro
        35                  40                  45

Arg Leu Leu Ile Tyr Arg Ala Ser Asn Leu Glu Ala Gly Val Pro Asp
    50                  55                  60

Arg Phe Ser Gly Ser Gly Ser Lys Thr Asp Phe Thr Leu Thr Ile Ser
65                  70                  75                  80

Pro Val Glu Ala Glu Asp Ala Ala Thr Tyr Tyr Cys Gln Gln Ser Arg
                85                  90                  95

Glu Tyr Pro Tyr Thr Phe Gly Gly Gly Thr Lys Leu Glu Ile Lys Arg
            100                 105                 110

Thr Val Ala Ala Pro Ser Val Phe Ile Phe Pro Pro Ser Asp Glu Gln
        115                 120                 125
```

```
Leu Lys Ser Gly Thr Ala Ser Val Val Cys Leu Leu Asn Asn Phe Tyr
            130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
        210                 215

<210> SEQ ID NO 16
<211> LENGTH: 447
<212> TYPE: PRT
<213> ORGANISM: Artificial
<220> FEATURE:
<223> OTHER INFORMATION: huMov19 HC NTT2

<400> SEQUENCE: 16

Thr Val Gln Leu Val Gln Ser Gly Ala Glu Val Val Lys Pro Gly Ala
1               5                   10                  15

Ser Val Lys Ile Ser Cys Lys Ala Ser Gly Tyr Thr Phe Thr Gly Tyr
            20                  25                  30

Phe Met Asn Trp Val Lys Gln Ser Pro Gly Gln Ser Leu Glu Trp Ile
        35                  40                  45

Gly Arg Ile His Pro Tyr Asp Gly Asp Thr Phe Tyr Asn Gln Lys Phe
    50                  55                  60

Gln Gly Lys Ala Thr Leu Thr Val Asp Lys Ser Ser Asn Thr Ala His
65                  70                  75                  80

Met Glu Leu Leu Ser Leu Thr Ser Glu Asp Phe Ala Val Tyr Tyr Cys
                85                  90                  95

Thr Arg Tyr Asp Gly Ser Arg Ala Met Asp Tyr Trp Gly Gln Gly Thr
            100                 105                 110

Thr Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270
```

-continued

```
Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly
        435                 440                 445

<210> SEQ ID NO 17
<211> LENGTH: 4
<212> TYPE: PRT
<213> ORGANISM: Artificial
<220> FEATURE:
<223> OTHER INFORMATION: Peptide

<400> SEQUENCE: 17

Ala Leu Ala Leu
1

<210> SEQ ID NO 18
<211> LENGTH: 4
<212> TYPE: PRT
<213> ORGANISM: Artificial
<220> FEATURE:
<223> OTHER INFORMATION: Peptide
<220> FEATURE:
<221> NAME/KEY: X
<222> LOCATION: (1)..(1)
<223> OTHER INFORMATION: beta-ala

<400> SEQUENCE: 18

Xaa Leu Ala Leu
1

<210> SEQ ID NO 19
<211> LENGTH: 4
<212> TYPE: PRT
<213> ORGANISM: Artificial
<220> FEATURE:
<223> OTHER INFORMATION: Peptide

<400> SEQUENCE: 19

Gly Phe Leu Gly
1

<210> SEQ ID NO 20
```

```
<211> LENGTH: 95
<212> TYPE: PRT
<213> ORGANISM: Artificial
<220> FEATURE:
<223> OTHER INFORMATION: light chain sequence derived from the murine
      IGKV6-32*01 sequence

<400> SEQUENCE: 20

Ser Ile Val Met Thr Gln Thr Pro Lys Phe Leu Leu Val Ser Ala Gly
1               5                   10                  15

Asp Arg Val Thr Ile Thr Cys Lys Ala Ser Gln Ser Val Ser Asn Asp
            20                  25                  30

Val Ala Trp Tyr Gln Gln Lys Pro Gly Gln Ser Pro Lys Leu Leu Ile
        35                  40                  45

Tyr Tyr Ala Ser Asn Arg Tyr Thr Gly Val Pro Asp Arg Phe Thr Gly
    50                  55                  60

Ser Gly Tyr Gly Thr Asp Phe Thr Phe Thr Ile Ser Thr Val Gln Ala
65                  70                  75                  80

Glu Asp Leu Ala Val Tyr Phe Cys Gln Gln Asp Tyr Ser Ser Pro
                85                  90                  95

<210> SEQ ID NO 21
<211> LENGTH: 95
<212> TYPE: PRT
<213> ORGANISM: Artificial
<220> FEATURE:
<223> OTHER INFORMATION: Human Lambda V3 family of V gene sequence
      IGLV3-1*01

<400> SEQUENCE: 21

Ser Tyr Glu Leu Thr Gln Pro Pro Ser Val Ser Val Ser Pro Gly Gln
1               5                   10                  15

Thr Ala Ser Ile Thr Cys Ser Gly Asp Lys Leu Gly Asp Lys Tyr Ala
            20                  25                  30

Cys Trp Tyr Gln Gln Lys Pro Gly Gln Ser Pro Val Leu Val Ile Tyr
        35                  40                  45

Gln Asp Ser Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Ala Trp Asp Ser Ser Thr Ala
                85                  90                  95

<210> SEQ ID NO 22
<211> LENGTH: 97
<212> TYPE: PRT
<213> ORGANISM: Artificial
<220> FEATURE:
<223> OTHER INFORMATION: Human Lambda V3 family of V gene sequence
      IGLV3-10*01
<220> FEATURE:
<221> NAME/KEY: X
<222> LOCATION: (97)..(97)
<223> OTHER INFORMATION: Any amino acid

<400> SEQUENCE: 22

Ser Tyr Glu Leu Thr Gln Pro Pro Ser Val Ser Val Ser Pro Gly Gln
1               5                   10                  15

Thr Ala Arg Ile Thr Cys Ser Gly Asp Ala Leu Pro Lys Lys Tyr Ala
            20                  25                  30

Tyr Trp Tyr Gln Gln Lys Ser Gly Gln Ala Pro Val Leu Val Ile Tyr
        35                  40                  45
```

```
Glu Asp Ser Lys Arg Pro Ser Gly Ile Pro Glu Arg Phe Ser Gly Ser
        50                  55                  60

Ser Ser Gly Thr Met Ala Thr Leu Thr Ile Ser Gly Ala Gln Val Glu
 65                  70                  75                  80

Asp Glu Ala Asp Tyr Tyr Cys Tyr Ser Thr Asp Ser Ser Gly Asn His
                85                  90                  95

Xaa

<210> SEQ ID NO 23
<211> LENGTH: 95
<212> TYPE: PRT
<213> ORGANISM: Artificial
<220> FEATURE:
<223> OTHER INFORMATION: Human Lambda V3 family of V gene sequence
      IGLV3-10*02

<400> SEQUENCE: 23

Ser Tyr Glu Leu Thr Gln Pro Pro Ser Val Ser Val Ser Pro Gly Gln
 1               5                  10                  15

Thr Ala Arg Ile Thr Cys Ser Gly Asp Ala Leu Pro Lys Lys Tyr Ala
                20                  25                  30

Tyr Trp Tyr Gln Gln Lys Ser Gly Gln Ala Pro Val Leu Val Ile Tyr
                35                  40                  45

Lys Asp Ser Lys Arg Pro Ser Gly Ile Pro Glu Arg Phe Ser Gly Ser
        50                  55                  60

Ser Ser Gly Thr Met Ala Thr Leu Thr Ile Ser Gly Ala Gln Val Glu
 65                  70                  75                  80

Asp Glu Asp Asp Tyr Tyr Cys Tyr Ser Ala Asp Tyr Ser Gly Asn
                85                  90                  95

<210> SEQ ID NO 24
<211> LENGTH: 97
<212> TYPE: PRT
<213> ORGANISM: Artificial
<220> FEATURE:
<223> OTHER INFORMATION: Human Lambda V3 family of V gene sequence
      IGLV3-12*01

<400> SEQUENCE: 24

Ser Tyr Glu Leu Thr Gln Pro His Ser Val Ser Val Ala Thr Ala Gln
 1               5                  10                  15

Met Ala Arg Ile Thr Cys Gly Gly Asn Asn Ile Gly Ser Lys Ala Val
                20                  25                  30

His Trp Tyr Gln Gln Lys Pro Gly Gln Asp Pro Val Leu Val Ile Tyr
                35                  40                  45

Ser Asp Ser Asn Arg Pro Ser Gly Ile Pro Glu Arg Phe Ser Gly Ser
        50                  55                  60

Asn Pro Gly Asn Thr Thr Thr Leu Thr Ile Ser Arg Ile Glu Ala Gly
 65                  70                  75                  80

Asp Glu Ala Asp Tyr Tyr Cys Gln Val Trp Asp Ser Ser Ser Asp His
                85                  90                  95

Pro

<210> SEQ ID NO 25
<211> LENGTH: 97
<212> TYPE: PRT
<213> ORGANISM: Artificial
<220> FEATURE:
<223> OTHER INFORMATION: Human Lambda V3 family of V gene sequence
```

```
    IGLV3-12*02

<400> SEQUENCE: 25

Ser Tyr Glu Leu Thr Gln Pro His Ser Val Ser Val Ala Thr Ala Gln
1               5                   10                  15

Met Ala Arg Ile Thr Cys Gly Gly Asn Asn Ile Gly Ser Lys Ala Val
            20                  25                  30

His Trp Tyr Gln Gln Lys Pro Gly Gln Asp Pro Val Leu Val Ile Tyr
        35                  40                  45

Ser Asp Ser Asn Arg Pro Ser Gly Ile Pro Glu Arg Phe Ser Gly Ser
    50                  55                  60

Asn Pro Gly Asn Thr Ala Thr Leu Thr Ile Ser Arg Ile Glu Ala Gly
65                  70                  75                  80

Asp Glu Ala Asp Tyr Tyr Cys Gln Val Trp Asp Ser Ser Ser Asp His
                85                  90                  95

Pro

<210> SEQ ID NO 26
<211> LENGTH: 95
<212> TYPE: PRT
<213> ORGANISM: Artificial
<220> FEATURE:
<223> OTHER INFORMATION: Human Lambda V3 family of V gene sequence
      IGLV3-13*01
<220> FEATURE:
<221> NAME/KEY: X
<222> LOCATION: (92)..(92)
<223> OTHER INFORMATION: Any amino acid

<400> SEQUENCE: 26

Ser Tyr Glu Leu Thr Gln Pro Pro Ala Val Ser Val Ser Pro Gly Gln
1               5                   10                  15

Thr Ala Arg Ile Ser Cys Ser Gly Asp Val Leu Arg Asp Asn Tyr Ala
            20                  25                  30

Asp Trp Tyr Pro Gln Lys Pro Gly Gln Ala Pro Val Leu Val Ile Tyr
        35                  40                  45

Lys Asp Gly Glu Arg Pro Ser Gly Ile Pro Glu Arg Phe Ser Gly Ser
    50                  55                  60

Thr Ser Gly Asn Thr Thr Ala Leu Thr Ile Ser Arg Val Leu Thr Lys
65                  70                  75                  80

Gly Gly Ala Asp Tyr Tyr Cys Phe Ser Gly Asp Xaa Asn Asn Leu
                85                  90                  95

<210> SEQ ID NO 27
<211> LENGTH: 97
<212> TYPE: PRT
<213> ORGANISM: Artificial
<220> FEATURE:
<223> OTHER INFORMATION: Human Lambda V3 family of V gene sequence
      IGLV3-16*01

<400> SEQUENCE: 27

Ser Tyr Glu Leu Thr Gln Pro Pro Ser Val Ser Val Ser Leu Gly Gln
1               5                   10                  15

Met Ala Arg Ile Thr Cys Ser Gly Glu Ala Leu Pro Lys Lys Tyr Ala
            20                  25                  30

Tyr Trp Tyr Gln Gln Lys Pro Gly Gln Phe Pro Val Leu Val Ile Tyr
        35                  40                  45

Lys Asp Ser Glu Arg Pro Ser Gly Ile Pro Glu Arg Phe Ser Gly Ser
    50                  55                  60
```

```
Ser Ser Gly Thr Ile Val Thr Leu Thr Ile Ser Gly Val Gln Ala Glu
 65                  70                  75                  80

Asp Glu Ala Asp Tyr Tyr Cys Leu Ser Ala Asp Ser Ser Gly Thr Tyr
                 85                  90                  95

Pro

<210> SEQ ID NO 28
<211> LENGTH: 97
<212> TYPE: PRT
<213> ORGANISM: Artificial
<220> FEATURE:
<223> OTHER INFORMATION: Human Lambda V3 family of V gene sequence
      IGLV3-19*01

<400> SEQUENCE: 28

Ser Ser Glu Leu Thr Gln Asp Pro Ala Val Ser Val Ala Leu Gly Gln
 1               5                  10                  15

Thr Val Arg Ile Thr Cys Gln Gly Asp Ser Leu Arg Ser Tyr Tyr Ala
             20                  25                  30

Ser Trp Tyr Gln Gln Lys Pro Gly Gln Ala Pro Val Leu Val Ile Tyr
         35                  40                  45

Gly Lys Asn Asn Arg Pro Ser Gly Ile Pro Asp Arg Phe Ser Gly Ser
 50                  55                  60

Ser Ser Gly Asn Thr Ala Ser Leu Thr Ile Thr Gly Ala Gln Ala Glu
 65                  70                  75                  80

Asp Glu Ala Asp Tyr Tyr Cys Asn Ser Arg Asp Ser Ser Gly Asn His
                 85                  90                  95

Leu

<210> SEQ ID NO 29
<211> LENGTH: 97
<212> TYPE: PRT
<213> ORGANISM: Artificial
<220> FEATURE:
<223> OTHER INFORMATION: Human Lambda V3 family of V gene sequence
      IGLV3-21*01

<400> SEQUENCE: 29

Ser Tyr Val Leu Thr Gln Pro Pro Ser Val Ser Val Ala Pro Gly Lys
 1               5                  10                  15

Thr Ala Arg Ile Thr Cys Gly Gly Asn Asn Ile Gly Ser Lys Ser Val
             20                  25                  30

His Trp Tyr Gln Gln Lys Pro Gly Gln Ala Pro Val Leu Val Ile Tyr
         35                  40                  45

Tyr Asp Ser Asp Arg Pro Ser Gly Ile Pro Glu Arg Phe Ser Gly Ser
 50                  55                  60

Asn Ser Gly Asn Thr Ala Thr Leu Thr Ile Ser Arg Val Glu Ala Gly
 65                  70                  75                  80

Asp Glu Ala Asp Tyr Tyr Cys Gln Val Trp Asp Ser Ser Ser Asp His
                 85                  90                  95

Pro

<210> SEQ ID NO 30
<211> LENGTH: 97
<212> TYPE: PRT
<213> ORGANISM: Artificial
<220> FEATURE:
<223> OTHER INFORMATION: Human Lambda V3 family of V gene sequence
      IGLV3-21*02
```

```
<400> SEQUENCE: 30

Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Val Tyr
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Pro

<210> SEQ ID NO 31
<211> LENGTH: 97
<212> TYPE: PRT
<213> ORGANISM: Artificial
<220> FEATURE:
<223> OTHER INFORMATION: Human Lambda V3 family of V gene sequence
      IGLV3-21*03

<400> SEQUENCE: 31

Ser Tyr Val Leu Thr Gln Pro Pro Ser Val Ser Val Ala Pro Gly Lys
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Val Tyr
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Pro

<210> SEQ ID NO 32
<211> LENGTH: 95
<212> TYPE: PRT
<213> ORGANISM: Artificial
<220> FEATURE:
<223> OTHER INFORMATION: Human Lambda V3 family of V gene sequence
      IGLV3-22*01

<400> SEQUENCE: 32

Ser Tyr Glu Leu Thr Gln Leu Pro Ser Val Ser Val Ser Pro Gly Gln
1               5                   10                  15

Thr Ala Arg Ile Thr Cys Ser Gly Asp Val Leu Gly Glu Asn Tyr Ala
            20                  25                  30

Asp Trp Tyr Gln Gln Lys Pro Gly Gln Ala Pro Glu Leu Val Ile Tyr
        35                  40                  45

Glu Asp Ser Glu Arg Tyr Pro Gly Ile Pro Glu Arg Phe Ser Gly Ser
    50                  55                  60

Thr Ser Gly Asn Thr Thr Thr Leu Thr Ile Ser Arg Val Leu Thr Glu
65                  70                  75                  80
```

Asp Glu Ala Asp Tyr Tyr Cys Leu Ser Gly Asp Glu Asp Asn Pro
                85                  90                  95

<210> SEQ ID NO 33
<211> LENGTH: 97
<212> TYPE: PRT
<213> ORGANISM: Artificial
<220> FEATURE:
<223> OTHER INFORMATION: Human Lambda V3 family of V gene sequence
      IGLV3-25*01

<400> SEQUENCE: 33

Ser Tyr Glu Leu Met Gln Pro Pro Ser Val Ser Val Ser Pro Gly Gln
1               5                   10                  15

Thr Ala Arg Ile Thr Cys Ser Gly Asp Ala Leu Pro Lys Gln Tyr Ala
                20                  25                  30

Tyr Trp Tyr Gln Gln Lys Pro Gly Gln Ala Pro Val Leu Val Ile Tyr
            35                  40                  45

Lys Asp Ser Glu Arg Pro Ser Gly Ile Pro Glu Arg Phe Ser Gly Ser
        50                  55                  60

Ser Ser Gly Thr Thr Val Thr Leu Thr Ile Ser Gly Val Gln Ala Glu
65                  70                  75                  80

Asp Glu Ala Asp Tyr Tyr Cys Gln Ser Ala Asp Ser Ser Gly Thr Tyr
                85                  90                  95

Pro

<210> SEQ ID NO 34
<211> LENGTH: 97
<212> TYPE: PRT
<213> ORGANISM: Artificial
<220> FEATURE:
<223> OTHER INFORMATION: Human Lambda V3 family of V gene sequence
      IGLV3-25*02

<400> SEQUENCE: 34

Ser Tyr Glu Leu Thr Gln Pro Pro Ser Val Ser Val Ser Pro Gly Gln
1               5                   10                  15

Thr Ala Arg Ile Thr Cys Ser Gly Asp Ala Leu Pro Lys Gln Tyr Ala
                20                  25                  30

Tyr Trp Tyr Gln Gln Lys Pro Gly Gln Ala Pro Val Leu Val Ile Tyr
            35                  40                  45

Lys Asp Ser Glu Arg Pro Ser Gly Ile Pro Glu Arg Phe Ser Gly Ser
        50                  55                  60

Ser Ser Gly Thr Thr Val Thr Leu Thr Ile Ser Gly Val Gln Ala Glu
65                  70                  75                  80

Asp Glu Ala Asp Tyr Tyr Cys Gln Ser Ala Asp Ser Ser Gly Thr Tyr
                85                  90                  95

Pro

<210> SEQ ID NO 35
<211> LENGTH: 94
<212> TYPE: PRT
<213> ORGANISM: Artificial
<220> FEATURE:
<223> OTHER INFORMATION: Human Lambda V3 family of V gene sequence
      IGLV3-25*03

<400> SEQUENCE: 35

Ser Tyr Glu Leu Thr Gln Pro Pro Ser Val Ser Val Ser Pro Gly Gln
1               5                   10                  15

```
Thr Ala Arg Ile Thr Cys Ser Gly Asp Ala Leu Pro Lys Gln Tyr Ala
                20                  25                  30

Tyr Trp Tyr Gln Gln Lys Pro Gly Gln Ala Pro Val Leu Val Ile Tyr
        35                  40                  45

Lys Asp Ser Glu Arg Pro Ser Gly Ile Pro Glu Arg Phe Ser Gly Ser
 50                  55                  60

Ser Ser Gly Thr Thr Val Thr Leu Thr Ile Ser Gly Val Gln Ala Glu
 65                  70                  75                  80

Asp Glu Ala Asp Tyr Tyr Cys Gln Ser Ala Asp Ser Ser Gly
                85                  90
```

<210> SEQ ID NO 36
<211> LENGTH: 95
<212> TYPE: PRT
<213> ORGANISM: Artificial
<220> FEATURE:
<223> OTHER INFORMATION: Human Lambda V3 family of V gene sequence IGLV3-27*01

<400> SEQUENCE: 36

```
Ser Tyr Glu Leu Thr Gln Pro Ser Ser Val Ser Val Ser Pro Gly Gln
 1               5                  10                  15

Thr Ala Arg Ile Thr Cys Ser Gly Asp Val Leu Ala Lys Lys Tyr Ala
                20                  25                  30

Arg Trp Phe Gln Gln Lys Pro Gly Gln Ala Pro Val Leu Val Ile Tyr
        35                  40                  45

Lys Asp Ser Glu Arg Pro Ser Gly Ile Pro Glu Arg Phe Ser Gly Ser
 50                  55                  60

Ser Ser Gly Thr Thr Val Thr Leu Thr Ile Ser Gly Ala Gln Val Glu
 65                  70                  75                  80

Asp Glu Ala Asp Tyr Tyr Cys Tyr Ser Ala Ala Asp Asn Asn Leu
                85                  90                  95
```

<210> SEQ ID NO 37
<211> LENGTH: 95
<212> TYPE: PRT
<213> ORGANISM: Artificial
<220> FEATURE:
<223> OTHER INFORMATION: Human Lambda V3 family of V gene sequence IGLV3-31*01

<400> SEQUENCE: 37

```
Ser Ser Glu Leu Ser Gln Glu Pro Ala Val Ser Val Ala Leu Gly Thr
 1               5                  10                  15

Ala Arg Ile Thr Cys Gln Gly Asp Ser Ile Glu Asp Ser Val Val Asn
                20                  25                  30

Trp Tyr Lys Gln Lys Pro Ser Gln Ala Pro Gly Leu Val Ile Leu Asn
        35                  40                  45

Ser Val Gln Ser Ser Gly Ile Pro Lys Lys Phe Ser Gly Ser Ser Ser
 50                  55                  60

Gly Asn Met Ala Thr Leu Thr Ile Thr Gly Ile Gln Val Glu Asp Lys
 65                  70                  75                  80

Ala Asp Tyr Tyr Cys Gln Ser Trp Asp Ser Ser Arg Thr His Ser
                85                  90                  95
```

<210> SEQ ID NO 38
<211> LENGTH: 95
<212> TYPE: PRT
<213> ORGANISM: Artificial

```
<220> FEATURE:
<223> OTHER INFORMATION: Human Lambda V3 family of V gene sequence
      IGLV3-31*02

<400> SEQUENCE: 38

Ser Ser Glu Leu Ser Gln Glu Pro Ala Val Ser Val Ser Leu Gly Thr
1               5                   10                  15

Ala Arg Ile Thr Cys Gln Gly Asp Ser Ile Glu Asp Ser Val Val Asn
            20                  25                  30

Trp Tyr Lys Gln Lys Pro Ser Gln Ala Pro Gly Leu Val Ile Leu Asn
        35                  40                  45

Ser Val Gln Ser Ser Gly Ile Pro Lys Lys Phe Ser Gly Ser Ser Ser
    50                  55                  60

Gly Asn Met Ala Thr Leu Thr Ile Thr Gly Ile Gln Val Glu Asp Lys
65                  70                  75                  80

Ala Asp Tyr Tyr Cys Gln Ser Trp Asp Ser Ser Arg Thr His Ser
                85                  90                  95

<210> SEQ ID NO 39
<211> LENGTH: 95
<212> TYPE: PRT
<213> ORGANISM: Artificial
<220> FEATURE:
<223> OTHER INFORMATION: Human Lambda V3 family of V gene sequence
      IGLV3-32*01

<400> SEQUENCE: 39

Ser Ser Gly Pro Thr Gln Val Pro Ala Val Ser Val Ala Leu Gly Gln
1               5                   10                  15

Met Ala Arg Ile Thr Cys Gln Gly Asp Ser Met Glu Gly Ser Tyr Glu
            20                  25                  30

His Trp Tyr Gln Gln Lys Pro Gly Gln Ala Pro Val Leu Val Ile Tyr
        35                  40                  45

Asp Ser Ser Asp Arg Pro Ser Arg Ile Pro Glu Arg Phe Ser Gly Ser
    50                  55                  60

Lys Ser Gly Asn Thr Thr Thr Leu Thr Ile Thr Gly Ala Gln Ala Glu
65                  70                  75                  80

Asp Glu Ala Asp Tyr Tyr Tyr Gln Leu Ile Asp Asn His Ala Thr
                85                  90                  95

<210> SEQ ID NO 40
<211> LENGTH: 95
<212> TYPE: PRT
<213> ORGANISM: Artificial
<220> FEATURE:
<223> OTHER INFORMATION: Human Lambda V3 family of V gene sequence
      IGLV3-9*01

<400> SEQUENCE: 40

Ser Tyr Glu Leu Thr Gln Pro Leu Ser Val Ser Val Ala Leu Gly Gln
1               5                   10                  15

Thr Ala Arg Ile Thr Cys Gly Gly Asn Asn Ile Gly Ser Lys Asn Val
            20                  25                  30

His Trp Tyr Gln Gln Lys Pro Gly Gln Ala Pro Val Leu Val Ile Tyr
        35                  40                  45

Arg Asp Ser Asn Arg Pro Ser Gly Ile Pro Glu Arg Phe Ser Gly Ser
    50                  55                  60

Asn Ser Gly Asn Thr Ala Thr Leu Thr Ile Ser Arg Ala Gln Ala Gly
65                  70                  75                  80
```

```
Asp Glu Ala Asp Tyr Tyr Cys Gln Val Trp Asp Ser Ser Thr Ala
             85                  90                  95

<210> SEQ ID NO 41
<211> LENGTH: 97
<212> TYPE: PRT
<213> ORGANISM: Artificial
<220> FEATURE:
<223> OTHER INFORMATION: Human Lambda V3 family of V gene sequence
      IGLV3-9*02

<400> SEQUENCE: 41

Ser Tyr Glu Leu Thr Gln Pro Leu Ser Val Ser Val Ala Leu Gly Gln
1               5                   10                  15

Ala Ala Arg Ile Thr Cys Gly Gly Asn Asn Leu Gly Tyr Lys Ser Val
            20                  25                  30

His Trp Tyr Gln Gln Lys Pro Gly Gln Ala Pro Val Leu Val Ile Tyr
        35                  40                  45

Arg Asp Asn Asn Arg Pro Ser Gly Ile Pro Glu Arg Phe Ser Gly Ser
    50                  55                  60

Asn Ser Gly Asn Thr Ala Thr Leu Thr Ile Ser Arg Ala Gln Ala Gly
65                  70                  75                  80

Asp Glu Ala Asp Tyr Tyr Cys Gln Val Trp Asp Ser Ser Thr Ala His
                85                  90                  95

Pro

<210> SEQ ID NO 42
<211> LENGTH: 20
<212> TYPE: PRT
<213> ORGANISM: Artificial
<220> FEATURE:
<223> OTHER INFORMATION: Modified huMov19 light chain or heavy chain
      signal peptide

<400> SEQUENCE: 42

Met Gly Trp Ser Cys Ile Ile Leu Phe Leu Val Ala Thr Ala Thr Gly
1               5                   10                  15

Val His Ser Ser
            20

<210> SEQ ID NO 43
<211> LENGTH: 447
<212> TYPE: PRT
<213> ORGANISM: Artificial
<220> FEATURE:
<223> OTHER INFORMATION: anti-CD33 antibody heavy chain

<400> SEQUENCE: 43

Gln Val Gln Leu Gln Gln Pro Gly Ala Glu Val Val Lys Pro Gly Ala
1               5                   10                  15

Ser Val Lys Met Ser Cys Lys Ala Ser Gly Tyr Thr Phe Thr Ser Tyr
            20                  25                  30

Tyr Ile His Trp Ile Lys Gln Thr Pro Gly Gln Gly Leu Glu Trp Val
        35                  40                  45

Gly Val Ile Tyr Pro Gly Asn Asp Asp Ile Ser Tyr Asn Gln Lys Phe
    50                  55                  60

Gln Gly Lys Ala Thr Leu Thr Ala Asp Lys Ser Ser Thr Thr Ala Tyr
65                  70                  75                  80

Met Gln Leu Ser Ser Leu Thr Ser Glu Asp Ser Ala Val Tyr Tyr Cys
                85                  90                  95
```

Ala Arg Glu Val Arg Leu Arg Tyr Phe Asp Val Trp Gly Gln Gly Thr
                100                 105                 110

Thr Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
        180                 185                 190

Ser Leu Gly Thr Gln Thr Tyr Ile Cys Asn Val Asn His Lys Pro Ser
    195                 200                 205

Asn Thr Lys Val Asp Lys Lys Val Glu Pro Lys Ser Cys Asp Lys Thr
210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
        260                 265                 270

Glu Val Lys Phe Asn Trp Tyr Val Asp Gly Val Glu Val His Asn Ala
    275                 280                 285

Lys Thr Lys Pro Arg Glu Glu Gln Tyr Asn Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
        340                 345                 350

Pro Pro Ser Arg Asp Glu Leu Thr Lys Asn Gln Val Ser Leu Thr Cys
    355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
        420                 425                 430

Leu His Asn His Tyr Thr Gln Lys Ser Leu Ser Leu Ser Pro Gly
    435                 440                 445

<210> SEQ ID NO 44
<211> LENGTH: 219
<212> TYPE: PRT
<213> ORGANISM: Artificial
<220> FEATURE:
<223> OTHER INFORMATION: anti-CD33 antibody light chain

<400> SEQUENCE: 44

Glu Ile Val Leu Thr Gln Ser Pro Gly Ser Leu Ala Val Ser Pro Gly
1               5                   10                  15

```
Glu Arg Val Thr Met Ser Cys Lys Ser Ser Gln Ser Val Phe Phe Ser
                20                  25                  30

Ser Ser Gln Lys Asn Tyr Leu Ala Trp Tyr Gln Gln Ile Pro Gly Gln
            35                  40                  45

Ser Pro Arg Leu Leu Ile Tyr Trp Ala Ser Thr Arg Glu Ser Gly Val
        50                  55                  60

Pro Asp Arg Phe Thr Gly Ser Gly Ser Gly Thr Asp Phe Thr Leu Thr
65                  70                  75                  80

Ile Ser Ser Val Gln Pro Glu Asp Leu Ala Ile Tyr Tyr Cys His Gln
                85                  90                  95

Tyr Leu Ser Ser Arg Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
210                 215
```

<210> SEQ ID NO 45
<211> LENGTH: 5
<212> TYPE: PRT
<213> ORGANISM: Artificial
<220> FEATURE:
<223> OTHER INFORMATION: FOLR1 antibody heavy chain CDR1

<400> SEQUENCE: 45

```
Gly Tyr Phe Met Asn
1               5
```

<210> SEQ ID NO 46
<211> LENGTH: 17
<212> TYPE: PRT
<213> ORGANISM: Artificial
<220> FEATURE:
<223> OTHER INFORMATION: FOLR1 antibody heavy chain CDR2
<220> FEATURE:
<221> NAME/KEY: X
<222> LOCATION: (14)..(14)
<223> OTHER INFORMATION: Lys, Gln, His, or Arg
<220> FEATURE:
<221> NAME/KEY: X
<222> LOCATION: (16)..(16)
<223> OTHER INFORMATION: Gln, His, Asn, or Arg
<220> FEATURE:
<221> NAME/KEY: X
<222> LOCATION: (17)..(17)
<223> OTHER INFORMATION: Gly, Glu, Thr, Ser, Ala, or Val

<400> SEQUENCE: 46

```
Arg Ile His Pro Tyr Asp Gly Asp Thr Phe Tyr Asn Gln Xaa Phe Xaa
1               5                   10                  15

Xaa
```

```
<210> SEQ ID NO 47
<211> LENGTH: 9
<212> TYPE: PRT
<213> ORGANISM: Artificial
<220> FEATURE:
<223> OTHER INFORMATION: FOLR1 antibody heavy chain CDR3

<400> SEQUENCE: 47

Tyr Asp Gly Ser Arg Ala Met Asp Tyr
1               5

<210> SEQ ID NO 48
<211> LENGTH: 15
<212> TYPE: PRT
<213> ORGANISM: Artificial
<220> FEATURE:
<223> OTHER INFORMATION: FOLR1 antibody light chain CDR1

<400> SEQUENCE: 48

Lys Ala Ser Gln Ser Val Ser Phe Ala Gly Thr Ser Leu Met His
1               5                   10                  15

<210> SEQ ID NO 49
<211> LENGTH: 7
<212> TYPE: PRT
<213> ORGANISM: Artificial
<220> FEATURE:
<223> OTHER INFORMATION: FOLR1 antibody light chain CDR2

<400> SEQUENCE: 49

Arg Ala Ser Asn Leu Glu Ala
1               5

<210> SEQ ID NO 50
<211> LENGTH: 9
<212> TYPE: PRT
<213> ORGANISM: Artificial
<220> FEATURE:
<223> OTHER INFORMATION: FOLR1 antibody light chain CDR2

<400> SEQUENCE: 50

Gln Gln Ser Arg Glu Tyr Pro Tyr Thr
1               5

<210> SEQ ID NO 51
<211> LENGTH: 17
<212> TYPE: PRT
<213> ORGANISM: Artificial
<220> FEATURE:
<223> OTHER INFORMATION: FOLR1 antibody heavy chain CDR2

<400> SEQUENCE: 51

Arg Ile His Pro Tyr Asp Gly Asp Thr Phe Tyr Asn Gln Lys Phe Gln
1               5                   10                  15

Gly

<210> SEQ ID NO 52
<211> LENGTH: 448
<212> TYPE: PRT
<213> ORGANISM: Artificial
<220> FEATURE:
<223> OTHER INFORMATION: FOLR1 antibody heavy chain

<400> SEQUENCE: 52

Gln Val Gln Leu Val Gln Ser Gly Ala Glu Val Val Lys Pro Gly Ala
1               5                   10                  15
```

Ser Val Lys Ile Ser Cys Lys Ala Ser Gly Tyr Thr Phe Thr Gly Tyr
            20                  25                  30

Phe Met Asn Trp Val Lys Gln Ser Pro Gly Gln Ser Leu Glu Trp Ile
        35                  40                  45

Gly Arg Ile His Pro Tyr Asp Gly Asp Thr Phe Tyr Asn Gln Lys Phe
50                  55                  60

Gln Gly Lys Ala Thr Leu Thr Val Asp Lys Ser Ser Asn Thr Ala His
65                  70                  75                  80

Met Glu Leu Leu Ser Leu Thr Ser Glu Asp Phe Ala Val Tyr Tyr Cys
                85                  90                  95

Thr Arg Tyr Asp Gly Ser Arg Ala Met Asp Tyr Trp Gly Gln Gly Thr
            100                 105                 110

Thr Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

```
Leu His Asn His Tyr Thr Gln Lys Ser Leu Ser Leu Ser Pro Gly Lys
            435                 440                 445
```

<210> SEQ ID NO 53
<211> LENGTH: 218
<212> TYPE: PRT
<213> ORGANISM: Artificial
<220> FEATURE:
<223> OTHER INFORMATION: FOLR1 antibody light chain

<400> SEQUENCE: 53

```
Asp Ile Val Leu Thr Gln Ser Pro Leu Ser Leu Ala Val Ser Leu Gly
1               5                   10                  15

Gln Pro Ala Ile Ile Ser Cys Lys Ala Ser Gln Ser Val Ser Phe Ala
            20                  25                  30

Gly Thr Ser Leu Met His Trp Tyr His Gln Lys Pro Gly Gln Gln Pro
        35                  40                  45

Arg Leu Leu Ile Tyr Arg Ala Ser Asn Leu Glu Ala Gly Val Pro Asp
    50                  55                  60

Arg Phe Ser Gly Ser Gly Ser Lys Thr Asp Phe Thr Leu Asn Ile Ser
65                  70                  75                  80

Pro Val Glu Ala Glu Asp Ala Thr Tyr Tyr Cys Gln Gln Ser Arg
                85                  90                  95

Glu Tyr Pro Tyr Thr Phe Gly Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215
```

<210> SEQ ID NO 54
<211> LENGTH: 218
<212> TYPE: PRT
<213> ORGANISM: Artificial
<220> FEATURE:
<223> OTHER INFORMATION: FOLR1 antibody light chain

<400> SEQUENCE: 54

```
Asp Ile Val Leu Thr Gln Ser Pro Leu Ser Leu Ala Val Ser Leu Gly
1               5                   10                  15

Gln Pro Ala Ile Ile Ser Cys Lys Ala Ser Gln Ser Val Ser Phe Ala
            20                  25                  30

Gly Thr Ser Leu Met His Trp Tyr His Gln Lys Pro Gly Gln Gln Pro
        35                  40                  45

Arg Leu Leu Ile Tyr Arg Ala Ser Asn Leu Glu Ala Gly Val Pro Asp
    50                  55                  60

Arg Phe Ser Gly Ser Gly Ser Lys Thr Asp Phe Thr Leu Thr Ile Ser
65                  70                  75                  80
```

```
Pro Val Glu Ala Glu Asp Ala Ala Thr Tyr Tyr Cys Gln Gln Ser Arg
                85                  90                  95

Glu Tyr Pro Tyr Thr Phe Gly Gly Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 55
<211> LENGTH: 118
<212> TYPE: PRT
<213> ORGANISM: Artificial
<220> FEATURE:
<223> OTHER INFORMATION: FOLR1 antibody heavy chain variable domain

<400> SEQUENCE: 55

Gln Val Gln Leu Val Gln Ser Gly Ala Glu Val Val Lys Pro Gly Ala
1               5                   10                  15

Ser Val Lys Ile Ser Cys Lys Ala Ser Gly Tyr Thr Phe Thr Gly Tyr
            20                  25                  30

Phe Met Asn Trp Val Lys Gln Ser Pro Gly Gln Ser Leu Glu Trp Ile
        35                  40                  45

Gly Arg Ile His Pro Tyr Asp Gly Asp Thr Phe Tyr Asn Gln Lys Phe
    50                  55                  60

Gln Gly Lys Ala Thr Leu Thr Val Asp Lys Ser Ser Asn Thr Ala His
65                  70                  75                  80

Met Glu Leu Leu Ser Leu Thr Ser Glu Asp Phe Ala Val Tyr Tyr Cys
                85                  90                  95

Thr Arg Tyr Asp Gly Ser Arg Ala Met Asp Tyr Trp Gly Gln Gly Thr
            100                 105                 110

Thr Val Thr Val Ser Ser
        115

<210> SEQ ID NO 56
<211> LENGTH: 112
<212> TYPE: PRT
<213> ORGANISM: Artificial
<220> FEATURE:
<223> OTHER INFORMATION: FOLR1 antibody light chain variable domain

<400> SEQUENCE: 56

Asp Ile Val Leu Thr Gln Ser Pro Leu Ser Leu Ala Val Ser Leu Gly
1               5                   10                  15

Gln Pro Ala Ile Ile Ser Cys Lys Ala Ser Gln Ser Val Ser Phe Ala
            20                  25                  30

Gly Thr Ser Leu Met His Trp Tyr His Gln Lys Pro Gly Gln Gln Pro
```

```
                35                  40                  45

Arg Leu Leu Ile Tyr Arg Ala Ser Asn Leu Glu Ala Gly Val Pro Asp
         50                  55                  60

Arg Phe Ser Gly Ser Gly Ser Lys Thr Asp Phe Thr Leu Asn Ile Ser
 65                  70                  75                  80

Pro Val Glu Ala Glu Asp Ala Ala Thr Tyr Tyr Cys Gln Gln Ser Arg
                 85                  90                  95

Glu Tyr Pro Tyr Thr Phe Gly Gly Gly Thr Lys Leu Glu Ile Lys Arg
                100                 105                 110

<210> SEQ ID NO 57
<211> LENGTH: 112
<212> TYPE: PRT
<213> ORGANISM: Artificial
<220> FEATURE:
<223> OTHER INFORMATION: FOLR1 antibody light chain variable domain

<400> SEQUENCE: 57

Asp Ile Val Leu Thr Gln Ser Pro Leu Ser Leu Ala Val Ser Leu Gly
  1               5                  10                  15

Gln Pro Ala Ile Ile Ser Cys Lys Ala Ser Gln Ser Val Ser Phe Ala
                 20                  25                  30

Gly Thr Ser Leu Met His Trp Tyr His Gln Lys Pro Gly Gln Gln Pro
             35                  40                  45

Arg Leu Leu Ile Tyr Arg Ala Ser Asn Leu Glu Ala Gly Val Pro Asp
         50                  55                  60

Arg Phe Ser Gly Ser Gly Ser Lys Thr Asp Phe Thr Leu Thr Ile Ser
 65                  70                  75                  80

Pro Val Glu Ala Glu Asp Ala Ala Thr Tyr Tyr Cys Gln Gln Ser Arg
                 85                  90                  95

Glu Tyr Pro Tyr Thr Phe Gly Gly Gly Thr Lys Leu Glu Ile Lys Arg
                100                 105                 110

<210> SEQ ID NO 58
<211> LENGTH: 214
<212> TYPE: PRT
<213> ORGANISM: Artificial
<220> FEATURE:
<223> OTHER INFORMATION: anti-CD37 antibody immunoglobulin light chain

<400> SEQUENCE: 58

Asp Ile Gln Met Thr Gln Ser Pro Ser Ser Leu Ser Val Ser Val Gly
  1               5                  10                  15

Glu Arg Val Thr Ile Thr Cys Arg Ala Ser Glu Asn Ile Arg Ser Asn
                 20                  25                  30

Leu Ala Trp Tyr Gln Gln Lys Pro Gly Lys Ser Pro Lys Leu Leu Val
             35                  40                  45

Asn Val Ala Thr Asn Leu Ala Asp Gly Val Pro Ser Arg Phe Ser Gly
         50                  55                  60

Ser Gly Ser Gly Thr Asp Tyr Ser Leu Lys Ile Asn Ser Leu Gln Pro
 65                  70                  75                  80

Glu Asp Phe Gly Thr Tyr Tyr Cys Gln His Tyr Trp Gly Thr Thr Trp
                 85                  90                  95

Thr Phe Gly Gln Gly Thr Lys Leu Glu Ile Lys Arg Thr Val Ala Ala
                100                 105                 110

Pro Ser Val Phe Ile Phe Pro Pro Ser Asp Glu Gln Leu Lys Ser Gly
                115                 120                 125
```

```
Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
                195                 200                 205

Phe Asn Arg Gly Glu Cys
    210
```

<210> SEQ ID NO 59
<211> LENGTH: 444
<212> TYPE: PRT
<213> ORGANISM: Artificial
<220> FEATURE:
<223> OTHER INFORMATION: anti-CD37 antibody immunoglobulin heavy chain

<400> SEQUENCE: 59

```
Gln Val Gln Val Gln Glu Ser Gly Pro Gly Leu Val Ala Pro Ser Gln
1               5                   10                  15

Thr Leu Ser Ile Thr Cys Thr Val Ser Gly Phe Ser Leu Thr Thr Ser
            20                  25                  30

Gly Val Ser Trp Val Arg Gln Pro Pro Gly Lys Gly Leu Glu Trp Leu
        35                  40                  45

Gly Val Ile Trp Gly Asp Gly Ser Thr Asn Tyr His Pro Ser Leu Lys
    50                  55                  60

Ser Arg Leu Ser Ile Lys Lys Asp His Ser Lys Ser Gln Val Phe Leu
65                  70                  75                  80

Lys Leu Asn Ser Leu Thr Ala Ala Asp Thr Ala Thr Tyr Tyr Cys Ala
                85                  90                  95

Lys Gly Gly Tyr Ser Leu Ala His Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
    210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270
```

```
Phe Asn Trp Tyr Val Asp Gly Val Glu Val His Asn Ala Lys Thr Lys
            275                 280                 285

Pro Arg Glu Glu Gln Tyr Asn Ser Thr Tyr Arg Val Val Ser Val Leu
290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Asp Glu Leu Thr Lys Asn Gln Val Ser Leu Thr Cys Leu Val Lys
355                 360                 365

Gly Phe Tyr Pro Ser Asp Ile Ala Val Glu Trp Glu Ser Asn Gly Gln
370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly
            435                 440

<210> SEQ ID NO 60
<211> LENGTH: 444
<212> TYPE: PRT
<213> ORGANISM: Artificial
<220> FEATURE:
<223> OTHER INFORMATION: anti-CD37 antibody immunoglobulin heavy chain

<400> SEQUENCE: 60

Gln Val Gln Val Gln Glu Ser Gly Pro Gly Leu Val Ala Pro Ser Gln
1               5                   10                  15

Thr Leu Ser Ile Thr Cys Thr Val Ser Gly Phe Ser Leu Thr Thr Ser
            20                  25                  30

Gly Val Ser Trp Val Arg Gln Pro Pro Gly Lys Gly Leu Glu Trp Leu
        35                  40                  45

Gly Val Ile Trp Gly Asp Gly Ser Thr Asn Tyr His Ser Ser Leu Lys
    50                  55                  60

Ser Arg Leu Ser Ile Lys Lys Asp His Ser Lys Ser Gln Val Phe Leu
65                  70                  75                  80

Lys Leu Asn Ser Leu Thr Ala Ala Asp Thr Ala Thr Tyr Tyr Cys Ala
                85                  90                  95

Lys Gly Gly Tyr Ser Leu Ala His Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190
```

Thr Gln Thr Tyr Ile Cys Asn Val Asn His Lys Pro Ser Asn Thr Lys
                195                 200                 205

Val Asp Lys Lys Val Glu Pro Lys Ser Cys Asp Lys Thr His Thr Cys
210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Asp Glu Leu Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly
        435                 440

<210> SEQ ID NO 61
<211> LENGTH: 213
<212> TYPE: PRT
<213> ORGANISM: Artificial
<220> FEATURE:
<223> OTHER INFORMATION: anti-CD37 antibody immunoglobulin light chain
      region

<400> SEQUENCE: 61

Glu Ile Val Leu Thr Gln Ser Pro Ala Thr Met Ser Ala Ser Pro Gly
1               5                   10                  15

Glu Arg Val Thr Met Thr Cys Ser Ala Thr Ser Ser Val Thr Tyr Met
                20                  25                  30

His Trp Tyr Gln Gln Lys Pro Gly Gln Ser Pro Lys Arg Trp Ile Tyr
            35                  40                  45

Asp Thr Ser Asn Leu Pro Tyr Gly Val Pro Ala Arg Phe Ser Gly Ser
        50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Asp Asn Pro Pro Thr
                85                  90                  95

Phe Gly Gln Gly Thr Lys Leu Glu Ile Lys Arg Thr Val Ala Ala Pro
            100                 105                 110

```
Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
        210

<210> SEQ ID NO 62
<211> LENGTH: 449
<212> TYPE: PRT
<213> ORGANISM: Artificial
<220> FEATURE:
<223> OTHER INFORMATION: anti-CD37 antibody immunoglobulin heavy chain
      region

<400> SEQUENCE: 62

Gln Val Gln Leu Gln Glu Ser Gly Pro Gly Leu Leu Lys Pro Ser Gln
1               5                   10                  15

Ser Leu Ser Leu Thr Cys Thr Val Ser Gly Tyr Ser Ile Thr Ser Gly
            20                  25                  30

Phe Ala Trp His Trp Ile Arg Gln His Pro Gly Asn Lys Leu Glu Trp
        35                  40                  45

Met Gly Tyr Ile Leu Tyr Ser Gly Ser Thr Val Tyr Ser Pro Ser Leu
    50                  55                  60

Lys Ser Arg Ile Ser Ile Thr Arg Asp Thr Ser Lys Asn His Phe Phe
65                  70                  75                  80

Leu Gln Leu Asn Ser Val Thr Ala Ala Asp Thr Ala Thr Tyr Tyr Cys
                85                  90                  95

Ala Arg Gly Tyr Tyr Gly Tyr Gly Ala Trp Phe Ala Tyr Trp Gly Gln
            100                 105                 110

Gly Thr Leu Val Thr Val Ser Ala Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
```

```
                    245                 250                 255
Ser Arg Thr Pro Glu Val Thr Cys Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
            325                 330                 335

Lys Thr Ile Ser Lys Ala Lys Gly Gln Pro Arg Glu Pro Gln Val Tyr
        340                 345                 350

Thr Leu Pro Pro Ser Arg Asp Glu Leu Thr Lys Asn Gln Val Ser Leu
    355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
            405                 410                 415

Lys Ser Arg Trp Gln Gln Gly Asn Val Phe Ser Cys Ser Val Met His
        420                 425                 430

Glu Ala Leu His Asn His Tyr Thr Gln Lys Ser Leu Ser Leu Ser Pro
    435                 440                 445

Gly

<210> SEQ ID NO 63
<211> LENGTH: 445
<212> TYPE: PRT
<213> ORGANISM: Artificial
<220> FEATURE:
<223> OTHER INFORMATION: huML66HC Full-Length Heavy Chain

<400> SEQUENCE: 63

Gln Val Gln Leu Gln Glu Ser Gly Pro Gly Leu Val Lys Pro Ser Glu
1               5                   10                  15

Thr Leu Ser Leu Thr Cys Thr Val Ser Gly Leu Ser Leu Ala Ser Asn
            20                  25                  30

Ser Val Ser Trp Ile Arg Gln Pro Pro Gly Lys Gly Leu Glu Trp Met
        35                  40                  45

Gly Val Ile Trp Asn His Gly Gly Thr Asp Tyr Asn Pro Ser Ile Lys
    50                  55                  60

Ser Arg Leu Ser Ile Ser Arg Asp Thr Ser Lys Ser Gln Val Phe Leu
65                  70                  75                  80

Lys Met Asn Ser Leu Thr Ala Ala Asp Thr Ala Met Tyr Phe Cys Val
                85                  90                  95

Arg Lys Gly Gly Ile Tyr Phe Asp Tyr Trp Gly Gln Gly Val Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160
```

```
Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly
        435                 440                 445

<210> SEQ ID NO 64
<211> LENGTH: 213
<212> TYPE: PRT
<213> ORGANISM: Artificial
<220> FEATURE:
<223> OTHER INFORMATION: huML66LC Full-Length Light Chain

<400> SEQUENCE: 64

Asp Thr Val Leu Thr Gln Ser Pro Ser Leu Ala Val Ser Pro Gly Glu
1               5                   10                  15

Arg Ala Thr Ile Ser Cys Arg Ala Ser Glu Ser Val Ser Thr Leu Met
            20                  25                  30

His Trp Tyr Gln Gln Lys Pro Gly Gln Gln Pro Lys Leu Leu Ile Tyr
        35                  40                  45

Leu Ala Ser His Arg Glu Ser Gly Val Pro Ala Arg Phe Ser Gly Ser
    50                  55                  60

Gly Ser Gly Thr Asp Phe Thr Leu Thr Ile Asp Pro Met Glu Ala Glu
65                  70                  75                  80
```

```
Asp Thr Ala Thr Tyr Tyr Cys Gln Gln Ser Arg Asn Asp Pro Trp Thr
                85                  90                  95

Phe Gly Gln Gly Thr Lys Leu Glu Leu Lys Arg Thr Val Ala Ala Pro
            100                 105                 110

Ser Val Phe Ile Phe Pro Pro Ser Asp Glu Gln Leu Lys Ser Gly Thr
            115                 120                 125

Ala Ser Val Val Cys Leu Leu Asn Asn Phe Tyr Pro Arg Glu Ala Lys
            130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
            195                 200                 205

Asn Arg Gly Glu Cys
        210

<210> SEQ ID NO 65
<211> LENGTH: 448
<212> TYPE: PRT
<213> ORGANISM: Artificial
<220> FEATURE:
<223> OTHER INFORMATION: anti-EGFR antibody immunoglobulin heavy chain

<400> SEQUENCE: 65

Gln Val Gln Leu Val Gln Ser Gly Ala Glu Val Ala Lys Pro Gly Ala
1               5                   10                  15

Ser Val Lys Leu Ser Cys Lys Ala Ser Gly Tyr Thr Phe Thr Ser Tyr
            20                  25                  30

Trp Met Gln Trp Val Lys Gln Arg Pro Gly Gln Gly Leu Glu Cys Ile
        35                  40                  45

Gly Thr Ile Tyr Pro Gly Asp Gly Asp Thr Thr Tyr Thr Gln Lys Phe
    50                  55                  60

Gln Gly Lys Ala Thr Leu Thr Ala Asp Lys Ser Ser Ser Thr Ala Tyr
65                  70                  75                  80

Met Gln Leu Ser Ser Leu Arg Ser Glu Asp Ser Ala Val Tyr Tyr Cys
                85                  90                  95

Ala Arg Tyr Asp Ala Pro Gly Tyr Ala Met Asp Tyr Trp Gly Gln Gly
            100                 105                 110

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
            130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
210                 215                 220
```

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
            245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
            325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
            405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

<210> SEQ ID NO 66
<211> LENGTH: 214
<212> TYPE: PRT
<213> ORGANISM: artificial
<220> FEATURE:
<223> OTHER INFORMATION: anti-EGFR antibody immunoglobulin light chain

<400> SEQUENCE: 66

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Asn Asn Tyr
            20                  25                  30

Leu Ala Trp Tyr Gln His Lys Pro Gly Lys Gly Pro Lys Leu Leu Ile
        35                  40                  45

His Tyr Thr Ser Thr Leu His Pro Gly Ile Pro Ser Arg Phe Ser Gly
    50                  55                  60

Ser Gly Ser Gly Arg Asp Tyr Ser Phe Ser Ile Ser Ser Leu Glu Pro
65                  70                  75                  80

Glu Asp Ile Ala Thr Tyr Tyr Cys Leu Gln Tyr Asp Asn Leu Leu Tyr
            85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Lys His Lys Val Tyr
        180                 185                 190

Ala Cys Glu Val Thr His Gln Gly Leu Ser Ser Pro Val Thr Lys Ser
            195                 200                 205

Phe Asn Arg Gly Glu Cys
        210

<210> SEQ ID NO 67
<211> LENGTH: 214
<212> TYPE: PRT
<213> ORGANISM: artificial
<220> FEATURE:
<223> OTHER INFORMATION: anti-EGFR antibody immunoglobulin light chain

<400> SEQUENCE: 67

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Asn Asn Tyr
            20                  25                  30

Leu Ala Trp Tyr Gln His Lys Pro Gly Lys Pro Lys Leu Leu Ile
        35                  40                  45

His Tyr Thr Ser Thr Leu His Pro Gly Ile Pro Ser Arg Phe Ser Gly
    50                  55                  60

Ser Gly Ser Gly Arg Asp Tyr Ser Phe Ser Ile Ser Ser Leu Glu Pro
65                  70                  75                  80

Glu Asp Ile Ala Thr Tyr Tyr Cys Leu Gln Tyr Asp Asn Leu Leu Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Lys His Lys Val Tyr
        180                 185                 190

Ala Cys Glu Val Thr His Gln Gly Leu Ser Ser Pro Val Thr Lys Ser
            195                 200                 205

Phe Asn Arg Gly Glu Cys
        210

<210> SEQ ID NO 68
<211> LENGTH: 450
<212> TYPE: PRT
<213> ORGANISM: Artificial
<220> FEATURE:
<223> OTHER INFORMATION: anti-CD19 antibody immunoglobulin heavy chain

<400> SEQUENCE: 68

Gln Val Gln Leu Val Gln Pro Gly Ala Glu Val Val Lys Pro Gly Ala

-continued

```
 1               5                   10                  15
Ser Val Lys Leu Ser Cys Lys Thr Ser Gly Tyr Thr Phe Thr Ser Asn
                20                  25                  30

Trp Met His Trp Val Lys Gln Ala Pro Gly Gln Gly Leu Glu Trp Ile
                35                  40                  45

Gly Glu Ile Asp Pro Ser Asp Ser Tyr Thr Asn Tyr Asn Gln Asn Phe
 50                  55                  60

Gln Gly Lys Ala Lys Leu Thr Val Asp Lys Ser Thr Ser Thr Ala Tyr
 65                  70                  75                  80

Met Glu Val Ser Ser Leu Arg Ser Asp Asp Thr Ala Val Tyr Tyr Cys
                85                  90                  95

Ala Arg Gly Ser Asn Pro Tyr Tyr Ala Met Asp Tyr Trp Gly Gln Gly
                100                 105                 110

Thr Ser Val Thr Val Ser Ser Ala Ser Thr Lys Gly Pro Ser Val
                115                 120                 125

Phe Pro Leu Ala Pro Ser Ser Lys Ser Thr Ser Gly Gly Thr Ala Ala
 130                 135                 140

Leu Gly Cys Leu Val Lys Asp Tyr Phe Pro Glu Pro Val Thr Val Ser
 145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
                180                 185                 190

Ser Ser Ser Leu Gly Thr Gln Thr Tyr Ile Cys Asn Val Asn His Lys
                195                 200                 205

Pro Ser Asn Thr Lys Val Asp Lys Lys Val Glu Pro Lys Ser Cys Asp
 210                 215                 220

Lys Thr His Thr Cys Pro Pro Cys Pro Ala Pro Glu Leu Leu Gly Gly
 225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
                260                 265                 270

Asp Pro Glu Val Lys Phe Asn Trp Tyr Val Asp Gly Val Glu Val His
                275                 280                 285

Asn Ala Lys Thr Lys Pro Arg Glu Glu Gln Tyr Asn Ser Thr Tyr Arg
 290                 295                 300

Val Val Ser Val Leu Thr Val Leu His Gln Asp Trp Leu Asn Gly Lys
 305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
                340                 345                 350

Thr Leu Pro Pro Ser Arg Asp Glu Leu Thr Lys Asn Gln Val Ser Leu
                355                 360                 365

Thr Cys Leu Val Lys Gly Phe Tyr Pro Ser Asp Ile Ala Val Glu Trp
 370                 375                 380

Glu Ser Asn Gly Gln Pro Glu Asn Asn Tyr Lys Thr Thr Pro Pro Val
 385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
                420                 425                 430
```

```
Glu Ala Leu His Asn His Tyr Thr Gln Lys Ser Leu Ser Leu Ser Pro
        435                 440                 445

Gly Lys
    450

<210> SEQ ID NO 69
<211> LENGTH: 211
<212> TYPE: PRT
<213> ORGANISM: artificial
<220> FEATURE:
<223> OTHER INFORMATION: anti-CD19 antibody immunoglobulin light chain

<400> SEQUENCE: 69

Glu Ile Val Leu Thr Gln Ser Pro Ala Ile Met Ser Ala Ser Pro Gly
1               5                   10                  15

Glu Arg Val Thr Met Thr Cys Ser Ala Ser Ser Gly Val Asn Tyr Met
            20                  25                  30

His Trp Tyr Gln Gln Lys Pro Gly Thr Ser Pro Arg Arg Trp Ile Tyr
        35                  40                  45

Asp Thr Ser Lys Leu Ala Ser Gly Val Pro Ala Arg Phe Ser Gly Ser
    50                  55                  60

Gly Ser Gly Thr Asp Tyr Ser Leu Thr Ile Ser Ser Met Glu Pro Glu
65                  70                  75                  80

Asp Ala Ala Thr Tyr Tyr Cys His Gln Arg Gly Ser Tyr Thr Phe Gly
                85                  90                  95

Gly Gly Thr Lys Leu Glu Ile Lys Arg Thr Val Ala Ala Pro Ser Val
            100                 105                 110

Phe Ile Phe Pro Pro Ser Asp Glu Gln Leu Lys Ser Gly Thr Ala Ser
        115                 120                 125

Val Val Cys Leu Leu Asn Asn Phe Tyr Pro Arg Glu Ala Lys Val Gln
    130                 135                 140

Trp Lys Val Asp Asn Ala Leu Gln Ser Gly Asn Ser Gln Glu Ser Val
145                 150                 155                 160

Thr Glu Gln Asp Ser Lys Asp Ser Thr Tyr Ser Leu Ser Ser Thr Leu
                165                 170                 175

Thr Leu Ser Lys Ala Asp Tyr Glu Lys His Lys Val Tyr Ala Cys Glu
            180                 185                 190

Val Thr His Gln Gly Leu Ser Ser Pro Val Thr Lys Ser Phe Asn Arg
        195                 200                 205

Gly Glu Cys
    210

<210> SEQ ID NO 70
<211> LENGTH: 447
<212> TYPE: PRT
<213> ORGANISM: Artificial
<220> FEATURE:
<223> OTHER INFORMATION: anti-Muc1 antibody immunoglobulin heavy chain

<400> SEQUENCE: 70

Gln Ala Gln Leu Val Gln Ser Gly Ala Glu Val Val Lys Pro Gly Ala
1               5                   10                  15

Ser Val Lys Met Ser Cys Lys Ala Ser Gly Tyr Thr Phe Thr Ser Tyr
            20                  25                  30

Asn Met His Trp Val Lys Gln Thr Pro Gly Gln Gly Leu Glu Trp Ile
        35                  40                  45

Gly Tyr Ile Tyr Pro Gly Asn Gly Ala Thr Asn Tyr Asn Gln Lys Phe
```

```
                50                  55                  60
Gln Gly Lys Ala Thr Leu Thr Ala Asp Thr Ser Ser Thr Ala Tyr
 65                  70                  75                  80

Met Gln Ile Ser Ser Leu Thr Ser Glu Asp Ser Ala Val Tyr Phe Cys
                 85                  90                  95

Ala Arg Gly Asp Ser Val Pro Phe Ala Tyr Trp Gly Gln Gly Thr Leu
                100                 105                 110

Val Thr Val Ser Ala Ala Ser Thr Lys Gly Pro Ser Val Phe Pro Leu
                115                 120                 125

Ala Pro Ser Ser Lys Ser Thr Ser Gly Gly Thr Ala Ala Leu Gly Cys
                130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
                180                 185                 190

Leu Gly Thr Gln Thr Tyr Ile Cys Asn Val Asn His Lys Pro Ser Asn
                195                 200                 205

Thr Lys Val Asp Lys Lys Val Glu Pro Lys Ser Cys Asp Lys Thr His
                210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
                260                 265                 270

Val Lys Phe Asn Trp Tyr Val Asp Gly Val Glu Val His Asn Ala Lys
                275                 280                 285

Thr Lys Pro Arg Glu Glu Gln Tyr Asn Ser Thr Tyr Arg Val Val Ser
                290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
                340                 345                 350

Pro Ser Arg Asp Glu Leu Thr Lys Asn Gln Val Ser Leu Thr Cys Leu
                355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
                420                 425                 430

His Asn His Tyr Thr Gln Lys Ser Leu Ser Leu Ser Pro Gly Lys
                435                 440                 445

<210> SEQ ID NO 71
<211> LENGTH: 213
<212> TYPE: PRT
<213> ORGANISM: Artificial
```

```
<220> FEATURE:
<223> OTHER INFORMATION: anti-Muc1 antibody immunoglobulin light chain

<400> SEQUENCE: 71

Glu Ile Val Leu Thr Gln Ser Pro Ala Thr Met Ser Ala Ser Pro Gly
1               5                   10                  15

Glu Arg Val Thr Ile Thr Cys Ser Ala His Ser Ser Val Ser Phe Met
            20                  25                  30

His Trp Phe Gln Gln Lys Pro Gly Thr Ser Pro Lys Leu Trp Ile Tyr
        35                  40                  45

Ser Thr Ser Ser Leu Ala Ser Gly Val Pro Ala Arg Phe Gly Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Arg Ser Ser Phe Pro Leu Thr
                85                  90                  95

Phe Gly Ala Gly Thr Lys Leu Glu Leu Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
            195                 200                 205

Asn Arg Gly Glu Cys
        210
```

CONJUGATES COMPRISING CELL-BINDING AGENTS AND CYTOTOXIC AGENTS

REFERENCE TO RELATED APPLICATIONS

This application is a divisional application of U.S. patent application Ser. No. 14/843,429 filed on Sep. 2, 2015, which claims the benefit of the filing date under 35 U.S.C. § 119(e), of U.S. Provisional Application No. 62/045,264 filed on Sep. 3, 2014, U.S. Provisional Application No. 62/086,986 filed on Dec. 3, 2014, U.S. Provisional Application No. 62/149,379 filed on Apr. 17, 2015, and U.S. Provisional Application No. 62/186,235 filed on Jun. 29, 2015, the entire contents of each of which, including all drawings, formulae, specifications, and claims, are incorporated herein by reference.

BACKGROUND OF THE INVENTION

Antibody-drug conjugates (ADC) and cell binding agent-drug conjugates are emerging as a powerful class of anti-tumor agents with efficacy across a range of cancers. Cell binding agent-drug conjugates (such as ADCs) are commonly composed of three distinct elements: a cell-binding agent (e.g., an antibody); a linker; and a cytotoxic moiety. Conventionally, the cytotoxic drug moiety is covalently attached to lysines on the antibody, resulting in conjugates that are heterogeneous mixtures of ADCs bearing varying numbers of drugs attached at different positions on the antibody molecule.

SUMMARY OF THE INVENTION

It is surprisingly found that the 2-hydroxyethylamine moiety of a N-terminal serine residue on a cell binding agent, such as an antibody, can be selectively oxidized to an aldehyde group without over-oxidation of the antibody. The resulting antibody having an aldehyde group allows site-specific conjugation with a cytotoxic drug having an aldehyde reactive group or through a linker compound having an aldehyde reactive group. The resulting antibody-drug conjugates surprisingly retain antigen binding affinity similar to the unconjugated antibody, despite the fact that the conjugation site is located at the N-terminus of the antibody. In addition, the resulting conjugates unexpectedly exhibit high potency despite having a drug load of only two molecules linked per antibody and are better tolerated as compared to lysine-linked conjugates.

In certain embodiments, the cell binding agent, such as an antibody, is covalently linked to a cytotoxic agent through an oxime linkage (—C=N—O—). Surprisingly, in contrast to recent published findings (see Agarwal et al., Proc. Natl. Acad. Sci. USA 110:46-51, 2013), the oxime linkage is highly stable in vivo.

The present invention provides a cell-binding agent-cytotoxic agent conjugate represented by the following structural formula:

or a pharmaceutically acceptable salt thereof, wherein:

CBA is a cell-binding agent covalently linked to the $J_{CB}'$ group;

$J_{CB}'$ is a moiety formed by reacting an aldehyde group on the CBA and an aldehyde reactive group connected to the group L, wherein the aldehyde group is derived from oxidation of a 2-hydroxyethylamine moiety represented by the following structural formula:

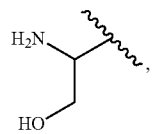

wherein the 2-hydroxyethylamine moiety being part of a serine, threonine, hydroxylysine, 4-hydroxyornithine or 2,4-diamino-5-hydroxy valeric acid residue;

L is a spacer or a bond;

$J_D'$ is a linking moiety connecting the cytotoxic agent D with the group L or absent when L is a bond;

D is a cytotoxic agent covalently linked to L through the linking moiety $J_D'$ or to CBA through $J_{CB}'$ when L is a bond; and w is 1, 2, 3 or 4.

The present invention also provides a recombinant antibody heavy chain (HC), light chain (LC), or an antigen-binding portion thereof, comprising a heterologous signal peptide having an amino acid sequence of SEQ ID NO: 1.

The present invention further provides a recombinant antibody heavy chain (HC), light chain (LC), or an antigen-binding portion thereof, comprising a Ser or Thr residue immediately C-terminal to the last residue of the signal peptide of the heavy chain (HC), light chain (LC), or antigen-binding portion thereof.

Also provided is a modified antibody oxidized from an antibody having an N-terminal Ser or Thr on a mature processed sequence of the heavy chain, light chain, or antigen-binding portion thereof, wherein the N-terminal Ser or Thr has been oxidized to an aldehyde group in the modified antibody.

The present invention also includes a polynucleotide encoding the recombinant antibody heavy chain (HC), light chain (LC), or antigen-binding portion thereof described herein and a method of producing a recombinant antibody heavy chain (HC), light chain (LC), or an antigen-binding portion thereof described herein.

In one embodiment, the present invention is directed to a method of preparing a cell-binding agent-cytotoxic agent conjugate, comprising the steps of:

(a) oxidizing a 2-hydroxyethylamine moiety of a cell-binding agent with an oxidizing agent to form an oxidized cell-binding agent having an aldehyde group; wherein the 2-hydroxyethylamine moiety is part of a serine, threonine, hydroxylysine, 4-hydroxyornithine or 2,4-diamino-5-hydroxy valeric acid residue, and is represented by the following structural formula:

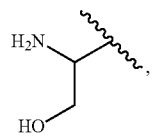

and (b) contacting the oxidized cell-binding agent with:
(i) a cytotoxic agent-linker compound having an aldehyde reactive group or a cytotoxic agent having an aldehyde reactive group to form the cell-binding agent-cytotoxic agent conjugate; or
(ii) a linker compound having an aldehyde reactive group to form a modified antibody or a modified antigen-binding portion thereof having a linker bound thereto, followed by reacting the modified antibody or the modified antigen-binding portion thereof with a cytotoxic agent to form the cell-binding agent-cytotoxic agent conjugate; or (iii) a cytotoxic agent followed by the addition of a linker compound having an aldehyde reactive group and a reactive group that can form a covalent bond with the cytotoxic agent to form the cell-binding agent-cytotoxic agent conjugate.

In one embodiment, the present invention is directed to a cytotoxic compound represented by the following formula:

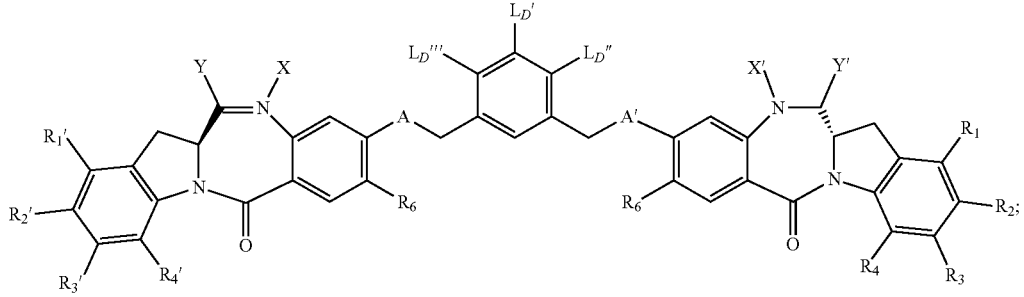

(D18')

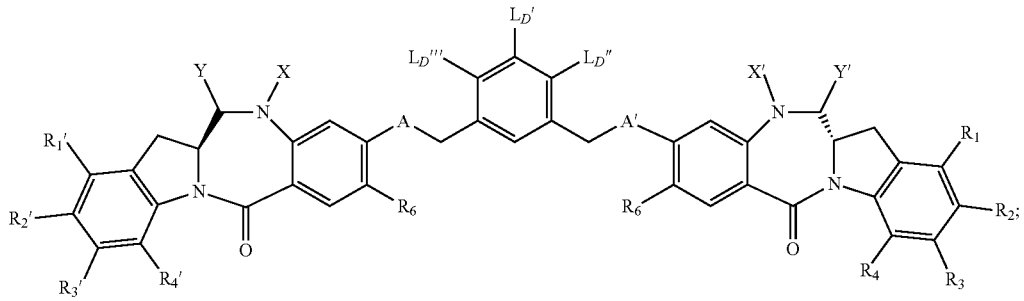

(D19')

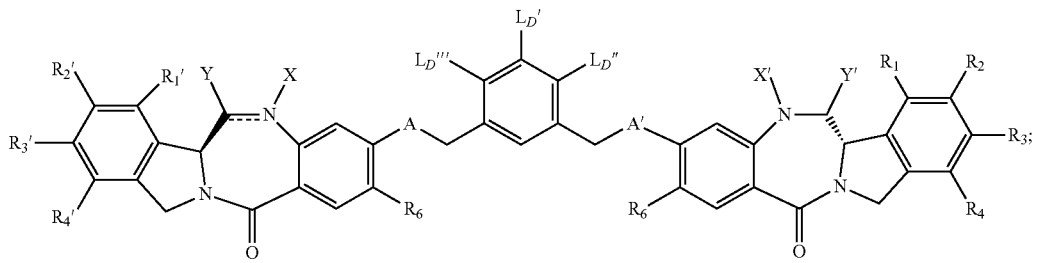

(D20')

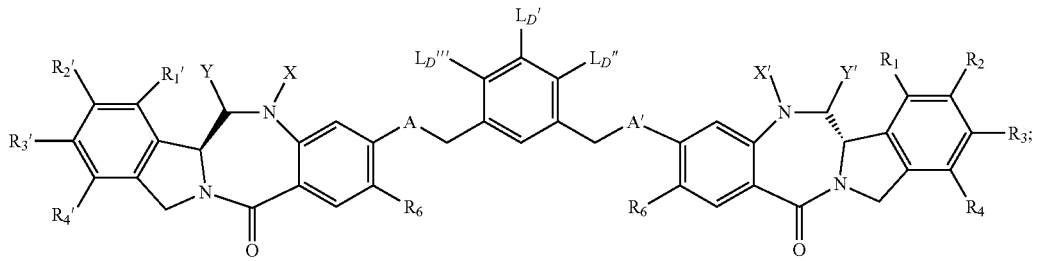

(D21')

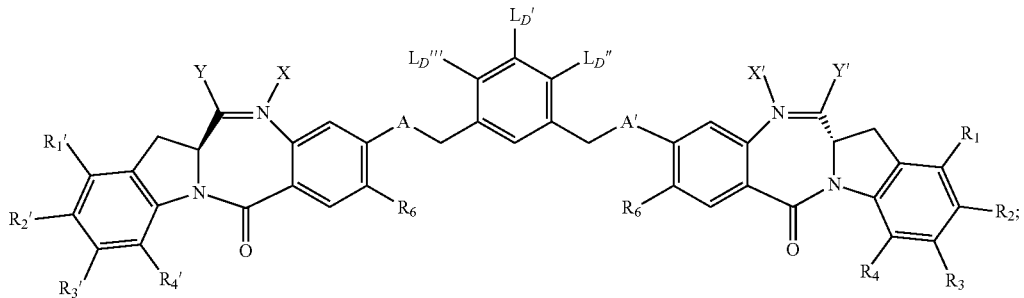

(D22')

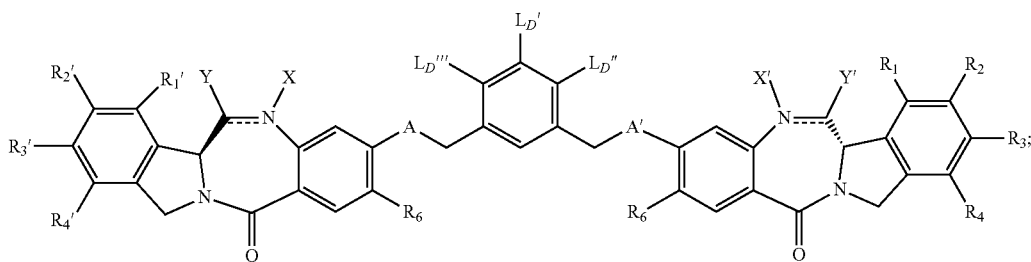

(D23')

or a pharmaceutically acceptable salt thereof, wherein:
one of LD', LD", and LD'" is represented by the following formula:

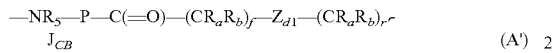

(A')

and the other two are the same or different, and are independently selected from —H, an optionally substituted linear, branched or cyclic alkyl, alkenyl or alkynyl having from 1 to 10 carbon atoms, a polyethylene glycol unit —(OCH$_2$CH$_2$)$_n$—R$^c$, halogen, guanidinium [—NH(C=NH)NH$_2$], —OR, —NR'R", —NO$_2$, —NR'COR", —SR, —SOR', —SO$_2$R', —SO$_3$H, —OSO$_3$H, —SO$_2$NR'R", cyano, an azido, —COR', —OCOR', and —OCONR'R";

$Z_{d1}$ is absent, —C(=O)—NR$_9$— or —NR$_9$—C(=O)—;
P is an amino acid residue or a peptide containing between 2 to 20 amino acid residues;
$R_a$ and $R_b$, for each occurrence, are independently —H, (C$_1$-C$_3$)alkyl or a charged substituent or an ionizable group Q;
r and r' are independently an integer from 1 to 6;
the double line ═ between N and C represents a single bond or a double bond, provided that when it is a double bond X is absent and Y is —H, or a linear or branched alkyl having 1 to 4 carbon atoms, and when it is a single bond, X is —H or an amine protecting moiety;
Y is a leaving group selected from —OR, —OCOR', —OCOOR', —OCONR'R", —NR'R", —NR'COR", —NR'NR'R", an optionally substituted 5- or 6-membered nitrogen-containing heterocycle (e.g., piperidine, tetrahydropyrrole, pyrazole, morpholine, etc. attached through the nitrogen atom), a guanidinum represented by —NR'(C=NH)NR'R", an amino acid, or a peptide represented by —NRCOP', —SR, —SOR', halogen, cyano, azido, —OSO$_3$H, sulfite (—SO$_3$H or —SO$_2$H), metabisulfite (H$_2$S$_2$O$_5$), mono-, di-, tri-, and tetra-thiophosphate (PO$_3$SH$_3$, PO$_2$S$_2$H$_2$, POS$_3$H$_2$, PS$_4$H$_2$), thio phosphate ester (R$^i$O)$_2$PS(OR$^i$), R$^i$SO, R$^i$SO$_2$, R$^i$SO$_3$, thiosulfate (HS$_2$O$_3$), dithionite (HS$_2$O$_4$), phosphorodithioate (P(=S)(OR$^{k'}$)(S)(OH)), hydroxamic acid (R$^{k'}$C(=O)NOH), and formaldehyde sulfoxylate (HOCH$_2$SO$_2$") or a mixture thereof, wherein R$^i$ is a linear or branched alkyl having 1 to 10 carbon atoms and is substituted with at least one substituent selected from —N(R$^j$)$_2$, —CO$_2$H, —SO$_3$H, and —PO$_3$H; can be further optionally substituted with a substituent for an alkyl described herein; R$^j$ is a linear or branched alkyl having 1 to 6 carbon atoms; R$^{k'}$ is a linear, branched or cyclic alkyl, alkenyl or alkynyl having 1 to 10 carbon atoms, aryl, heterocyclyl or heteroaryl;
P' is an amino acid residue or a polypeptide containing between 2 to 20 amino acid residue, R, for each occurrence, is independently selected from the group consisting of —H, an optionally substituted linear, branched or cyclic alkyl, alkenyl or alkynyl having from 1 to 10 carbon atoms, a polyethylene glycol unit —(CH$_2$CH$_2$O)$_n$—R$^c$, an optionally substituted aryl having 6 to 18 carbon atoms, an optionally substituted 5- to 18-membered heteroaryl ring containing one or more heteroatoms independently selected from nitrogen, oxygen, and sulfur, or an optionally substituted 3- to 18-membered heterocyclic ring containing 1 to 6 heteroatoms independently selected from O, S, N and P;

R$^i$ and R$^j$ are each independently selected from —H, —OH, —OR, —NHR, —NR$_2$, —COR, an optionally substituted linear, branched or cyclic alkyl, alkenyl or alkynyl having from 1 to 10 carbon atoms, a polyethylene glycol unit —(CH$_2$CH$_2$O)$_n$—R$^c$, and an optionally substituted 3- to 18-membered heterocyclic ring having 1 to 6 heteroatoms independently selected from O, S, N and P;

R$^c$ is —H or an optionally substituted linear or branched alkyl having 1 to 4 carbon atoms;

n is an integer from 1 to 24;

X' is selected from —H, an amine-protecting group, an optionally substituted linear, branched or cyclic alkyl, alkenyl or alkynyl having from 1 to 10 carbon atoms, a polyethylene glycol unit —(CH$_2$CH$_2$O)$_n$—R$^c$, an optionally substituted aryl having 6 to 18 carbon atoms, an optionally substituted 5- to 18-membered heteroaryl ring containing one or more heteroatoms independently selected from nitrogen, oxygen, and sulfur, and an optionally substituted 3- to 18-membered heterocyclic ring containing 1 to 6 heteroatoms independently selected from O, S, N and P;

Y' is selected from —H, an oxo group, an optionally substituted linear, branched or cyclic alkyl, alkenyl or alkynyl having from 1 to 10 carbon atoms, an optionally substituted 6- to 18-membered aryl, an optionally substituted 5- to 18-membered heteroaryl ring containing one or more heteroatoms independently selected from nitrogen, oxygen, and sulfur, an optionally substituted 3- to 18-membered heterocyclic ring having 1 to 6 heteroatoms;

$R_1$, $R_2$, $R_3$, $R_4$, $R_1'$, $R_2'$, $R_3'$ and $R_4'$ are each independently selected from the group consisting of —H, an optionally substituted linear, branched or cyclic alkyl, alkenyl or alkynyl having from 1 to 10 carbon atoms, a polyethylene glycol unit —(OCH$_2$CH$_2$)$_n$—R$^c$, halogen, guanidinium [—NH(C=NH)NH$_2$], —OR, —NR'R", —NO$_2$, —NCO, —NR'COR", —SR, —SOR', —SO$_2$R', —SO$_3$$^-$H, —OSO$_3$H, —SO$_2$NR'R", cyano, an azido, —COR', —OCOR', and —OCONR'R";

$R_6$ is —H, —R, —OR, —SR, —NR'R", —NO$_2$, or halogen;

A and A' are the same or different, and are independently selected from —O—, oxo (—C(=O)—), —CRR' O—, —CRR'—, —S—, —CRR'S—, —NR$_5$ and —CRR'N(R$_5$)—;

$R_5$ and $R_9$ are each independently —H or an optionally substituted linear or branched alkyl having 1 to 10 carbon atoms;

$J_{CB}$ is an aldehyde reactive group.

Also included in the present invention is a pharmaceutical composition comprising a conjugate of formula (I) or a cytotoxic compound of formulas (D18')-(D23') or a pharmaceutically acceptable salt thereof and a pharmaceutically acceptable carrier.

The pharmaceutical composition can further include a second therapeutic (e.g., chemotherapeutic) agent.

The present invention also includes a method of inhibiting abnormal cell growth or treating a proliferative disorder, a destructive bone disorder, an autoimmune disorder, a graft versus host disease, a transplant rejection, an immune deficiency, an inflammatory diseases, an infectious disease, a viral disease, a fibrotic disease, a neurodegenerative disorder, pancreatitis, or a kidney disease in a mammal (e.g., human), comprising administering to said mammal a therapeutically effective amount of a conjugate formula (I) or, a cytotoxic compound represented of formulas (D18')-(D23') or a pharmaceutically acceptable salt thereof.

In a related embodiment, the method described above further comprises administering to said mammal sequentially or consecutively a second therapeutic (e.g., chemotherapeutic) agent.

BRIEF DESCRIPTION OF THE DRAWINGS

As shown in FIGS. 7A and 7B above, wildtype anti-FRα antibody huMOV19, its N-terminal Ser modified version huMOV19-NTS #2 ("SeriMab"), and their respective conjugates to maytansinoid—Ab-SMCC-DM1 (wild-type huMOV19 linked through Lys residues to DM1 via SMCC linkers) and SeriMab-May (huMOV19-NTS #2 linked through the engineered N-terminal Ser to maytansinoid)—all have essentially the same binding affinity to the FRα-bearing T47D cells, as measured by FACS.

FIG. 8B shows that N-terminal Ser-specific modification or conjugation does not noticeably affect antibody binding to antigen. As shown in FIGS. 7A and 7B above, wildtype anti-FRα antibody huMOV19, its N-terminal Ser modified version huMOV19-NTS #2 ("SeriMab") and its conjugate to the cytotoxic Compound A (SeriMab-sDGN462) all have essentially the same binding affinity to the FRα-bearing T47D cells, as measured by FACS.

FIG. 9A shows the result of cytotoxic evaluation of the ADC conjugate MOV19-NTS #2-Linker1-Compound A on the KB cervical cancer cell line. The data shows that the subject site-specific N-terminal Ser linked SERIMab-Compound A conjugate is about 3-fold more potent than the lysine-conjugated sSPDB-Compound A on the basis of antibody concentration, and about 5-fold more potent based on Compound A concentration. Both conjugates have identical antigen-independent activity, since potency for the two tested conjugates, in the presence of 1 μM unconjugated huMOV19 to block antigen binding sites on the KB cells, are nearly identical.

FIGS. 22A-22C show that SeriMab of huCD123-6 (huCD123-6Rv1.1S2-SeriMab-D8, filled black circle) is at least as active as the lysine-linked conjugate (huCD123-6Rv1.1-D2, filled downward black triangle) of the same antibody in AML cell lines SHI-1 (FIG. 22A) and HNT-34 (FIG. 22B), as well as the CML cell line MOLM-1 (FIG. 22C). The dotted curves connecting open data points in each figure represent activity of the respective conjugates (i.e., open circle for huCD123-6Rv1.1S2-SeriMab-D8, and open downward triangle for huCD123-6Rv1.1-D2) in the presence of blocking concentration (500 nM) of the unconjugated huCD123-6 antibody. See Example 28 for structure of Lys-linked antibody-D2 conjugate (shown is the huMOV19-D2 structure, but huCD123-6Rv1.1-D2 conjugate has the same structure).

FIG. 23 shows N-terminal Ser-specific modification or conjugation does not noticeably affect antibody binding to antigen. Wild-type anti-FRα huMOV19 antibody, its N-terminal Ser modified version huMOV19-NTS2 ("huMOV19-SeriMab antibody") and its conjugate to the cytotoxic compound D8 (huMOV19-SeriMab-D8) all have essentially the same binding affinity to the FRα-bearing T47D cells, as measured by FACS.

FIG. 24 shows that huCD123-6Gv4.7S3-SeriMab-sD1 conjugate (see FIG. 18) shows similar potency as the huCD123-6Gv4.7S2 (or S3)-SeriMab-D8 conjugate in EOL-1 cells. Results for the Lys-linked huCD123-6Gv4.7S3-sSPDB-D1 and huCD123-6Gv4.7S3-D2 conjugates are also shown.

DETAILED DESCRIPTION OF THE INVENTION

Figure 1:
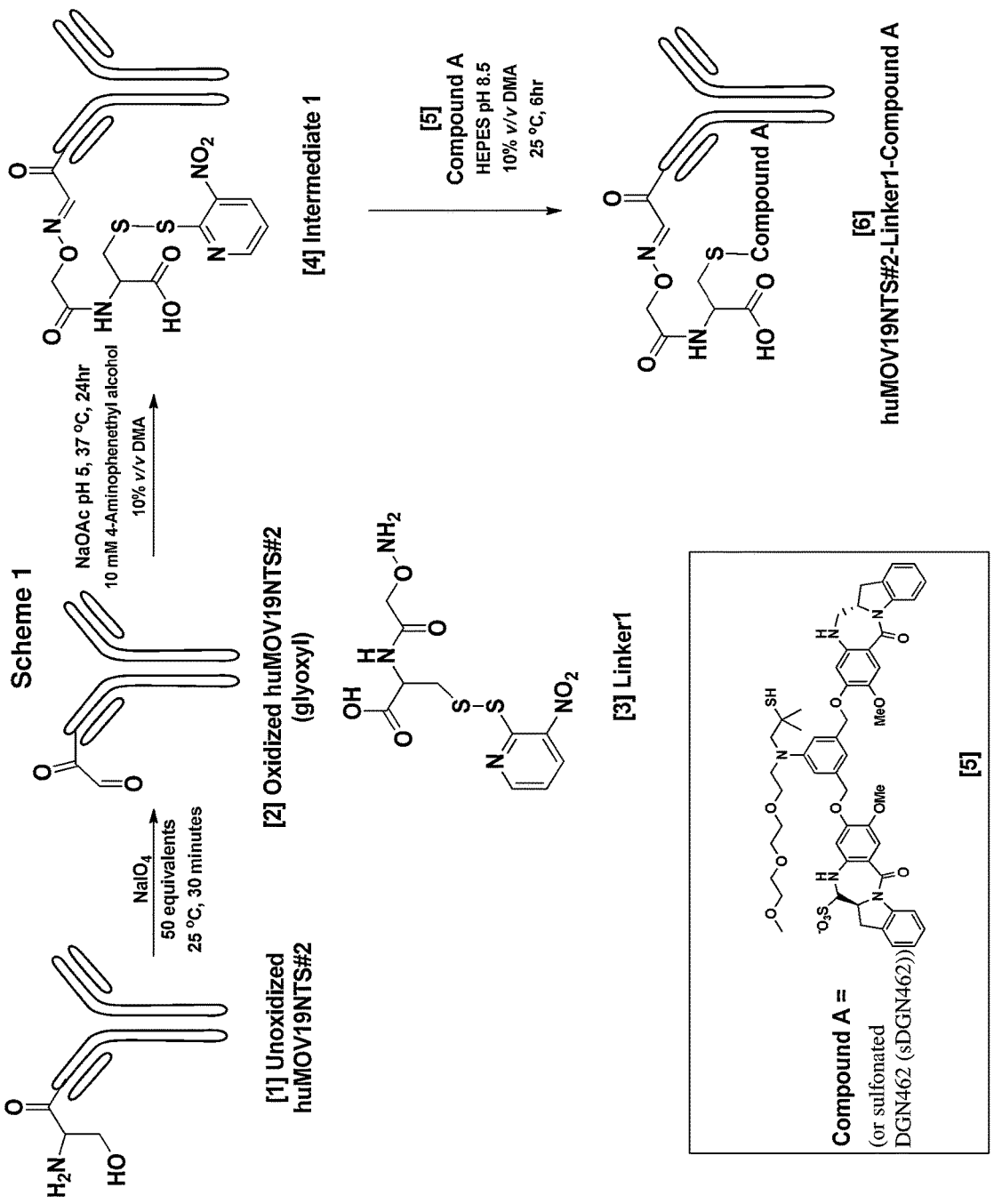
FIG. 1 shows Scheme 1 for synthesizing the huMOV19-NTS #2-Linker1-Compound A ADC using engineered N-terminal Ser-containing humanized monoclonal antibody huMOV19-NTS #2.

Reference will now be made in detail to certain embodiments of the invention, examples of which are illustrated in the accompanying structures and formulae. While the invention will be described in conjunction with the enumerated embodiments, it will be understood that they are not intended to limit the invention to those embodiments. On the contrary, the invention is intended to cover all alternatives, modifications, and equivalents which may be included within the scope of the present invention as defined by the claims. One skilled in the art will recognize many methods and materials similar or equivalent to those described herein, which could be used in the practice of the present invention.

It should be understood that any of the embodiments described herein, including those described under different aspects of the invention (e.g., compounds, conjugates, compositions, methods of making and using) and different parts of the specification (including embodiments described only in the Examples) can be combined with one or more other embodiments of the invention, unless explicitly disclaimed or improper. Combination of embodiments are not limited to those specific combinations claimed via the multiple dependent claims.

Definitions

"Linear or branched alkyl" as used herein refers to a saturated linear or branched-chain monovalent hydrocarbon radical of one to twenty carbon atoms. Examples of alkyl include, but are not limited to, methyl, ethyl, 1-propyl, 2-propyl, 1-butyl, 2-methyl-1-propyl, —$CH_2CH(CH_3)_2$), 2-butyl, 2-methyl-2-propyl, 1-pentyl, 2-pentyl 3-pentyl, 2-methyl-2-butyl, 3-methyl-2-butyl, 3-methyl-1-butyl, 2-methyl-1-butyl, 1-hexyl), 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, 3,3-dimethyl-2-butyl, 1-heptyl, 1-octyl, and the like. Preferably, the alkyl has one to ten carbon atoms. More preferably, the alkyl has one to four carbon atoms.

"Linear or branched alkenyl" refers to linear or branched-chain monovalent hydrocarbon radical of two to twenty carbon atoms with at least one site of unsaturation, i.e., a carbon-carbon, double bond, wherein the alkenyl radical includes radicals having "cis" and "trans" orientations, or alternatively, "E" and "Z" orientations. Examples include, but are not limited to, ethylenyl or vinyl (—$CH=CH_2$), allyl (—$CH_2CH=CH_2$), and the like. Preferably, the alkenyl has two to ten carbon atoms. More preferably, the alkyl has two to four carbon atoms.

"Linear or branched alkynyl" refers to a linear or branched monovalent hydrocarbon radical of two to twenty carbon atoms with at least one site of unsaturation, i.e., a carbon-carbon, triple bond. Examples include, but are not limited to, ethynyl, propynyl, 1-butynyl, 2-butynyl, 1-pentynyl, 2-pentynyl, 3-pentynyl, hexynyl, and the like. Preferably, the alkynyl has two to ten carbon atoms. More preferably, the alkynyl has two to four carbon atoms.

The term "carbocycle," "carbocyclyl" and "carbocyclic ring" refer to a monovalent non-aromatic, saturated or partially unsaturated ring having 3 to 12 carbon atoms as a monocyclic ring or 7 to 12 carbon atoms as a bicyclic ring. Bicyclic carbocycles having 7 to 12 atoms can be arranged, for example, as a bicyclo [4,5], [5,5], [5,6], or [6,6] system, and bicyclic carbocycles having 9 or 10 ring atoms can be arranged as a bicyclo [5,6] or [6,6] system, or as bridged systems such as bicyclo[2.2.1]heptane, bicyclo[2.2.2]octane and bicyclo[3.2.2]nonane. Examples of monocyclic carbocycles include, but are not limited to, cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl, cyclododecyl, and the like.

The terms "cyclic alkyl" and "cycloalkyl" can be used interchangeably. They refer to a monovalent saturated carbocyclic ring radical. Preferably, the cyclic alkyl is 3 to 7 membered monocyclic ring radical. More preferably, the cyclic alkyl is cyclohexyl.

The term "cyclic alkenyl" refers to a carbocyclic ring radical having at least one double bond in the ring structure.

The term "cyclic alkynyl" refers to a carbocyclic ring radical having at least one triple bond in the ring structure.

"Aryl" means a monovalent aromatic hydrocarbon radical of 6-18 carbon atoms derived by the removal of one hydrogen atom from a single carbon atom of a parent aromatic ring system. Some aryl groups are represented in the exemplary structures as "Ar." Aryl includes bicyclic radicals comprising an aromatic ring fused to a saturated, partially unsaturated ring, or aromatic carbocyclic or heterocyclic ring. Typical aryl groups include, but are not limited to, radicals derived from benzene (phenyl), substituted benzenes, naphthalene, anthracene, indenyl, indanyl, 1,2-dihydronapthalene, 1,2,3,4-tetrahydronapthyl, and the like. Preferably, aryl is phenyl group.

The terms "heterocycle," "heterocyclyl," and "heterocyclic ring" are used interchangeably herein and refer to a saturated or a partially unsaturated (i.e., having one or more double and/or triple bonds within the ring) carbocyclic radical of 3 to 18 ring atoms in which at least one ring atom is a heteroatom selected from nitrogen, oxygen, phosphorus, and sulfur, the remaining ring atoms being C, where one or more ring atoms is optionally substituted independently with one or more substituents described below. A heterocycle may be a monocycle having 3 to 7 ring members (2 to 6 carbon atoms and 1 to 4 heteroatoms selected from N, O, P, and S) or a bicycle having 7 to 10 ring members (4 to 9 carbon atoms and 1 to 6 heteroatoms selected from N, O, P, and S), for example: a bicyclo [4,5], [5,5], [5,6], or [6,6] system. Heterocycles are described in Paquette, Leo A.; "Principles of Modern Heterocyclic Chemistry" (W. A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; and J. Am. Chem. Soc. (1960) 82:5566. "Heterocyclyl" also includes radicals where heterocycle radicals are fused with a saturated, partially unsaturated ring, or aromatic carbocyclic or heterocyclic ring. Examples of heterocyclic rings include, but are not limited to, pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, homopiperazinyl, azetidinyl, oxetanyl, thietanyl, homopiperidinyl, oxepanyl, thiepanyl, oxazepinyl, diazepinyl, thiazepinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinylimidazolinyl, imidazolidinyl, 3-azabicyco[3.1.0]hexanyl, 3-azabicyclo[4.1.0]heptanyl, and azabicyclo[2.2.2]hexanyl. Spiro moieties are also included within the scope of this definition. Examples of a heterocyclic group wherein ring atoms are substituted with oxo (=O) moieties are pyrimidinonyl and 1,1-dioxo-thiomorpholinyl.

The term "heteroaryl" refers to a monovalent aromatic radical of 5- or 6-membered rings, and includes fused ring systems (at least one of which is aromatic) of 5-18 atoms, containing one or more heteroatoms independently selected from nitrogen, oxygen, and sulfur. Examples of heteroaryl groups are pyridinyl (including, for example, 2-hydroxypyridinyl), imidazolyl, imidazopyridinyl, pyrimidinyl (including, for example, 4-hydroxypyrimidinyl), pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, triazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl.

The heterocycle or heteroaryl groups may be carbon (carbon-linked) or nitrogen (nitrogen-linked) attached where such is possible. By way of example and not limitation, carbon bonded heterocycles or heteroaryls are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline.

By way of example and not limitation, nitrogen bonded heterocycles or heteroaryls are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or O-carboline.

The heteroatoms present in heteroaryl or heterocycicyl include the oxidized forms such as NO, SO, and $SO_2$.

The term "halo" or "halogen" refers to F, Cl, Br or I.

The alkyl, alkenyl, alkynyl, cyclic alkyl, cyclic alkenyl, cyclic alkynyl, carbocyclyl, aryl, heterocyclyl and heteroaryl described above can be optionally substituted with one more (e.g., 2, 3, 4, 5, 6 or more) substituents.

If a substituent is described as being "substituted," a non-hydrogen substituent is in the place of a hydrogen substituent on a carbon, oxygen, sulfur or nitrogen of the substituent. Thus, for example, a substituted alkyl substituent is an alkyl substituent wherein at least one non-hydrogen substituent is in the place of a hydrogen substituent on the alkyl substituent. To illustrate, monofluoroalkyl is alkyl substituted with a fluoro substituent, and difluoroalkyl is alkyl substituted with two fluoro substituents. It should be recognized that if there is more than one substitution on a substituent, each non-hydrogen substituent may be identical or different (unless otherwise stated).

If a substituent is described as being "optionally substituted," the substituent may be either (1) not substituted, or (2) substituted. If a carbon of a substituent is described as being optionally substituted with one or more of a list of substituents, one or more of the hydrogens on the carbon (to the extent there are any) may separately and/or together be replaced with an independently selected optional substituent. If a nitrogen of a substituent is described as being optionally substituted with one or more of a list of substituents, one or more of the hydrogens on the nitrogen (to the extent there are any) may each be replaced with an independently selected optional substituent. One exemplary substituent may be depicted as —NR'R", wherein $R^i$ and $R^j$ together with the nitrogen atom to which they are attached, may form a heterocyclic ring. The heterocyclic ring formed from $R^i$ and $R^j$ together with the nitrogen atom to which they are attached may be partially or fully saturated. In one embodiment, the heterocyclic ring consists of 3 to 7 atoms. In another embodiment, the heterocyclic ring is selected from the group consisting of pyrrolyl, imidazolyl, pyrazolyl, triazolyl, tetrazolyl, isoxazolyl, pyridyl and thiazolyl.

This specification uses the terms "substituent," "radical," and "group" interchangeably.

If a group of substituents are collectively described as being optionally substituted by one or more of a list of substituents, the group may include: (1) unsubstitutable substituents, (2) substitutable substituents that are not substituted by the optional substituents, and/or (3) substitutable substituents that are substituted by one or more of the optional substituents.

If a substituent is described as being optionally substituted with up to a particular number of non-hydrogen substituents, that substituent may be either (1) not substituted; or (2) substituted by up to that particular number of non-hydrogen substituents or by up to the maximum number of substitutable positions on the substituent, whichever is less. Thus, for example, if a substituent is described as a heteroaryl optionally substituted with up to 3 non-hydrogen substituents, then any heteroaryl with less than 3 substitutable positions would be optionally substituted by up to only as many non-hydrogen substituents as the heteroaryl has substitutable positions. Such substituents, in non-limiting examples, can be selected from a linear, branched or cyclic alkyl, alkenyl or alkynyl having from 1 to 10 carbon atoms, aryl, heteroaryl, heterocycyclyl, halogen, guanidinium [—NH(C=NH)NH$_2$], —OR$^{100}$, NR$^{101}$R$^{102}$, —NO$_2$, —NR$^{101}$COR$^{102}$, —SR$^{100}$, a sulfoxide represented by —SOR$^{101}$, a sulfone represented by —SO$_2$R$^{101}$, a sulfonate —SO$_3$M, a sulfate —OSO$_3$M, a sulfonamide represented by —SO$_2$NR$^{101}$R$^{102}$, cyano, an azido, —COR$^{101}$, —OCOR$^{101}$, —OCONR$^{101}$R$^{102}$ and a polyethylene glycol unit (—OCH$_2$CH$_2$)$_n$R$^{101}$ wherein M is H or a cation (such as Na$^+$ or K$^+$); R$^{101}$, R$^{102}$ and R$^{103}$ are each independently selected from H, linear, branched or cyclic alkyl, alkenyl or alkynyl having from 1 to 10 carbon atoms, a polyethylene glycol unit (—OCH$_2$CH$_2$)$_n$—R$^{104}$, wherein n is an integer from 1 to 24, an aryl having from 6 to 10 carbon atoms, a heterocyclic ring having from 3 to 10 carbon atoms and a heteroaryl having 5 to 10 carbon atoms; and R$^{104}$ is H or a linear or branched alkyl having 1 to 4 carbon atoms, wherein the alkyl, alkenyl, alkynyl, aryl, heteroaryl and heterocyclcyl in the groups represented by R$^{100}$, R$^{101}$, R$^{102}$, R$^{103}$ and R$^{104}$ are optionally substituted with one or more (e.g., 2, 3, 4, 5, 6 or more) substituents independently selected from halogen, —OH, —CN, —NO$_2$ and unsubstituted linear or branched alkyl having 1 to 4 carbon atoms. Preferably, the substituents for the optionally substituted alkyl, alkenyl, alkynyl, cyclic alkyl, cyclic alkenyl, cyclic alkynyl, carbocyclyl, aryl, heterocyclyl and heteroaryl described above include halogen, —CN, —NR$^{102}$R$^{103}$, —CF$_3$, —OR$^{101}$, aryl, heteroaryl, heterocycycl, —SR$^{101}$, —SOR$^{101}$, —SO$_2$R$^{101}$ and —SO$_3$M.

The term "compound" or "cytotoxic compound," "cytotoxic dimer" and "cytotoxic dimer compound" are used interchangeably. They are intended to include compounds for which a structure or formula or any derivative thereof has been disclosed in the present invention or a structure or formula or any derivative thereof that has been incorporated by reference. The term also includes, stereoisomers, geometric isomers, tautomers, solvates, metabolites, salts (e.g., pharmaceutically acceptable salts) and prodrugs, and prodrug salts of a compound of all the formulae disclosed in the present invention. The term also includes any solvates, hydrates, and polymorphs of any of the foregoing. The specific recitation of "stereoisomers," "geometric isomers," "tautomers," "solvates," "metabolites," "salt" "prodrug," "prodrug salt," "conjugates," "conjugates salt," "solvate," "hydrate," or "polymorph" in certain aspects of the invention described in this application shall not be interpreted as an intended omission of these forms in other aspects of the invention where the term "compound" is used without recitation of these other forms.

The term "immunoconjugate" or "conjugate" as used herein refers to a compound or a derivative thereof that is linked to a cell binding agent (i.e., an anti-CD123/IL-3Rα antibody or an anti-FRα antibody, or fragments thereof) and is defined by a generic formula: A-L-C, wherein C=cytotoxin, L=linker, and A=cell binding agent (CBA), such as anti-CD123/IL-3Rα or an anti-FRα antibody or antibody fragment. Immunoconjugates can also be defined by the generic formula in reverse order: C-L-A.

The term "linkable to a cell binding agent" as used herein refers to the compounds described herein or derivates thereof comprising at least one linking group or a precursor thereof suitable to bond these compounds or derivatives thereof to a cell binding agent.

The term "precursor" of a given group refers to any group which may lead to that group by any deprotection, a chemical modification, or a coupling reaction.

The term "linked to a cell binding agent" refers to a conjugate molecule comprising at least one of the cytotoxic agent compounds or cytotoxic agent-linker compounds described herein (e.g., compounds of formulas (D1')-(D29') and cytotoxic agent-linker compounds of formula (II)), or derivative thereof bound to a cell binding agent via a suitable linking group or a precursor thereof.

The term "chiral" refers to molecules which have the property of non-superimposability of the mirror image partner, while the term "achiral" refers to molecules which are superimposable on their mirror image partner.

The term "stereoisomer" refers to compounds which have identical chemical constitution and connectivity, but different orientations of their atoms in space that cannot be interconverted by rotation about single bonds.

"Diastereomer" refers to a stereoisomer with two or more centers of chirality and whose molecules are not mirror images of one another. Diastereomers have different physical properties, e.g. melting points, boiling points, spectral properties, and reactivities. Mixtures of diastereomers may separate under high resolution analytical procedures such as crystallization, electrophoresis and chromatography.

"Enantiomers" refer to two stereoisomers of a compound which are non-superimposable mirror images of one another.

Stereochemical definitions and conventions used herein generally follow S. P. Parker, Ed., McGraw-Hill Dictionary of Chemical Terms (1984) McGraw-Hill Book Company, New York; and Eliel, E. and Wilen, S., "Stereochemistry of Organic Compounds," John Wiley & Sons, Inc., New York, 1994. The compounds of the invention may contain asymmetric or chiral centers, and therefore exist in different stereoisomeric forms. It is intended that all stereoisomeric forms of the compounds of the invention, including but not limited to, diastereomers, enantiomers and atropisomers, as well as mixtures thereof such as racemic mixtures, form part of the present invention. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

The term "prodrug" as used in this application refers to a precursor or derivative form of a compound of the invention that is capable of being enzymatically or hydrolytically activated or converted into the more active parent form. See, e.g., Wilman, "Prodrugs in Cancer Chemotherapy," *Biochemical Society Transactions*, 14:375-382, 615th Meeting Belfast (1986); and Stella et al., "Prodrugs: A Chemical Approach to Targeted Drug Delivery," *Directed Drug Delivery*, Borchardt et al., (eds.), pp. 247-267, Humana Press (1985). The prodrugs of this invention include, but are not limited to, ester-containing prodrugs, phosphate-containing prodrugs, thiophosphate-containing prodrugs, sulfate-containing prodrugs, peptide-containing prodrugs, D-amino acid-modified prodrugs, glycosylated prodrugs, β-lactam-containing prodrugs, optionally substituted phenoxyacetamide-containing prodrugs, optionally substituted phenylacetamide-containing prodrugs, 5-fluorocytosine and other 5-fluorouridine prodrugs which can be converted into the more active cytotoxic free drug. Examples of cytotoxic drugs that can be derivatized into a prodrug form for use in this invention include, but are not limited to, compounds of the invention and chemotherapeutic agents such as described above.

The term "prodrug" is also meant to include a derivative of a compound that can hydrolyze, oxidize, or otherwise react under biological conditions (in vitro or in vivo) to provide a compound of this invention. Prodrugs may only become active upon such reaction under biological conditions, or they may have activity in their unreacted forms. Examples of prodrugs contemplated in this invention include, but are not limited to, analogs or derivatives of compounds of any one of the formulae disclosed herein that comprise biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. Other examples of prodrugs include derivatives of compounds of any one of the formulae disclosed herein that comprise —NO, —NO$_2$, —ONO, or —ONO$_2$ moieties. Prodrugs can typically be prepared using well-known methods, such as those described by *Burger's Medicinal Chemistry and Drug Discovery* (1995) 172-178, 949-982 (Manfred E. Wolff ed., 5th ed.); see also Goodman and Gilman's, *The Pharmacological basis of Therapeutics*, 8th ed., McGraw-Hill, Int. Ed. 1992, "Biotransformation of Drugs."

One preferred form of prodrug of the invention includes compounds (with or without any linker groups) and conjugates of the invention comprising an adduct formed between an imine bond of the compounds/conjugates and an imine reactive reagent. Another preferred form of prodrug of the invention includes compounds such as those of formula (I)-(IV), wherein when the double line between N and C represents a single bond, X is H or an amine protecting group, and the compound becomes a prodrug. A prodrug of the invention may contain one or both forms of prodrugs described herein (e.g., containing an adduct formed between an imine bond of the compounds/conjugates and an imine reactive reagent, and/or containing a Y leaving group when X is —H).

The term "imine reactive reagent" refers to a reagent that is capable of reacting with an imine group. Examples of imine reactive reagent includes, but is not limited to, sulfites (H$_2$SO$_3$, H$_2$SO$_2$ or a salt of HSO$_3^-$, SO$_3^{2-}$ or HSO$_2^-$ formed with a cation), metabisulfite (H$_2$S$_2$O$_5$ or a salt of S$_2$O$_5^{2-}$ formed with a cation), mono, di, tri, and tetra-thiophosphates (PO$_3$SH$_3$, PO$_2$S$_2$H$_3$, POS$_3$H$_3$, PS$_4$H$_3$ or a salt of PO$_3$S$^{3-}$, PO$_2$S$_2^{3-}$, POS$_3^{3-}$ or PS$_4^{3-}$ formed with a cation), thio phosphate esters ((R$^i$O)$_2$PS(OR$^i$), R$^i$SH, R$^i$SOH, R$^i$SO$_2$H, R$^i$SO$_3$H), various amines (hydroxyl amine (e.g., NH$_2$OH), hydrazine (e.g., NH$_2$NH$_2$), NH$_2$O—R$^i$, R$^i$NH—R$^i$, NH$_2$—R$^i$), NH$_2$—CO—NH$_2$, NH$_2$—C(=S)—NH$_2$, thiosulfate (H$_2$S$_2$O$_3$ or a salt of S$_2$O$_3^{2-}$ formed with a cation), dithionite (H$_2$S$_2$O$_4$ or a salt of S$_2$O$_4^{2-}$ formed with a cation), phosphorodithioate (P(=S)(OR$^k$)(SH)(OH) or a salt thereof formed with a cation), hydroxamic acid (R$^k$C(=O)NHOH or a salt formed with a cation), hydrazide (R$^k$CONHNH$_2$), formaldehyde sulfoxylate (HOCH$_2$SO$_2$H or a salt of HOCH$_2$SO$_2^-$ formed with a cation, such as HOCH$_2$SO$_2^-$Na$^+$) glycated nucleotide (such as GDP-mannose), fludarabine or a mixture thereof, wherein R$^i$ and R$^{i'}$ are each independently a linear or branched alkyl having 1 to 10 carbon atoms and are substituted with at least one substituent selected from —N(R$^j$)$_2$, —CO$_2$H, —SO$_3$H, and —PO$_3$H; R$^i$ and R$^{i'}$ can be further optionally substituted with a substituent for an alkyl described herein; R$^j$ is a linear or branched alkyl having 1 to 6 carbon atoms; and R$^k$ is a linear, branched or cyclic alkyl, alkenyl or alkynyl having 1 to 10 carbon atoms, aryl, heterocyclyl or heteroaryl (preferably, R$^k$ is a linear or branched alkyl having 1 to 4 carbon atoms; more preferably, R$^k$ is methyl, ethyl or propyl). Preferably, the cation is a monovalent cation, such as Na$^+$ or K$^+$. Preferably, the imine reactive reagent is selected from sulfites, hydroxyl amine, urea and hydrazine. More preferably, the imine reactive reagent is NaHSO$_3$ or KHSO$_3$.

As used herein and unless otherwise indicated, the terms "biohydrolyzable amide," "biohydrolyzable ester," "biohydrolyzable carbamate," "biohydrolyzable carbonate," "biohydrolyzable ureide" and "biohydrolyzable phosphate analogue" mean an amide, ester, carbamate, carbonate, ureide, or phosphate analogue, respectively, that either: 1) does not destroy the biological activity of the compound and confers upon that compound advantageous properties in vivo, such as uptake, duration of action, or onset of action; or 2) is itself biologically inactive but is converted in vivo to a biologically active compound. Examples of biohydrolyzable amides include, but are not limited to, lower alkyl amides, α-amino acid amides, alkoxyacyl amides, and alkylaminoalkylcarbonyl amides. Examples of biohydrolyzable esters include, but are not limited to, lower alkyl esters, alkoxyacyloxy esters, alkyl acylamino alkyl esters, and choline esters. Examples of biohydrolyzable carbamates include, but are not limited to, lower alkylamines, substituted ethylenediamines, amino acids, hydroxyalkylamines, heterocyclic and heteroaromatic amines, and polyether amines. Particularly favored prodrugs and prodrug salts are those that increase the bioavailability of the compounds of this invention when such compounds are administered to a mammal.

The phrase "pharmaceutically acceptable salt" as used herein, refers to pharmaceutically acceptable organic or inorganic salts of a compound of the invention. Exemplary salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate "mesylate," ethanesulfonate, benzenesulfonate, p-toluenesulfonate, pamoate (i.e., 1,1'-methylenebis-(2-hydroxy-3-naphthoate)) salts, alkali metal (e.g., sodium and potassium) salts, alkaline earth metal (e.g., magnesium) salts, and ammonium salts. A pharmaceutically acceptable salt may involve the inclusion of another molecule such as an acetate ion, a succinate ion or other counter ion. The counter ion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counter ion.

If the compound of the invention is a base, the desired pharmaceutically acceptable salt may be prepared by any suitable method available in the art, for example, treatment of the free base with an inorganic acid, such as hydrochloric acid, hydrobromic acid, sulfuric acid, nitric acid, methanesulfonic acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alpha hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like.

If the compound of the invention is an acid, the desired pharmaceutically acceptable salt may be prepared by any suitable method, for example, treatment of the free acid with an inorganic or organic base, such as an amine (primary, secondary or tertiary), an alkali metal hydroxide or alkaline earth metal hydroxide, or the like. Illustrative examples of suitable salts include, but are not limited to, organic salts derived from amino acids, such as glycine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum and lithium.

As used herein, the term "solvate" means a compound which further includes a stoichiometric or non-stoichiometric amount of solvent such as water, isopropanol, acetone, ethanol, methanol, DMSO, ethyl acetate, acetic acid, and ethanolamine dichloromethane, 2-propanol, or the like, bound by non-covalent intermolecular forces. Solvates or hydrates of the compounds are readily prepared by addition of at least one molar equivalent of a hydroxylic solvent such as methanol, ethanol, 1-propanol, 2-propanol or water to the compound to result in solvation or hydration of the imine moiety.

The terms "abnormal cell growth" and "proliferative disorder" are used interchangeably in this application. "Abnormal cell growth," as used herein, unless otherwise indicated, refers to cell growth that is independent of normal regulatory mechanisms (e.g., loss of contact inhibition). This includes, for example, the abnormal growth of: (1) tumor cells (tumors) that proliferate by expressing a mutated tyrosine kinase or overexpression of a receptor tyrosine kinase; (2) benign and malignant cells of other proliferative diseases in which aberrant tyrosine kinase activation occurs; (3) any tumors that proliferate by receptor tyrosine kinases; (4) any tumors that proliferate by aberrant serine/threonine kinase activation; and (5) benign and malignant cells of other proliferative diseases in which aberrant serine/threonine kinase activation occurs.

The terms "cancer" and "cancerous" refer to or describe the physiological condition in mammals that is typically characterized by unregulated cell growth. A "tumor" comprises one or more cancerous cells, and/or benign or pre-cancerous cells.

A "therapeutic agent" encompasses both a biological agent such as an antibody, a peptide, a protein, an enzyme or a chemotherapeutic agent.

A "chemotherapeutic agent" is a chemical compound useful in the treatment of cancer.

A "metabolite" is a product produced through metabolism in the body of a specified compound, a derivative thereof, or a conjugate thereof, or salt thereof. Metabolites of a compound, a derivative thereof, or a conjugate thereof, may be identified using routine techniques known in the art and their activities determined using tests such as those described herein. Such products may result for example from the oxidation, hydroxylation, reduction, hydrolysis, amidation, deamidation, esterification, deesterification, enzymatic cleavage, and the like, of the administered compound. Accordingly, the invention includes metabolites of compounds, a derivative thereof, or a conjugate thereof, of the invention, including compounds, a derivative thereof, or a conjugate thereof, produced by a process comprising contacting a compound, a derivative thereof, or a conjugate thereof, of this invention with a mammal for a period of time sufficient to yield a metabolic product thereof.

The phrase "pharmaceutically acceptable" indicates that the substance or composition must be compatible chemically and/or toxicologically, with the other ingredients comprising a formulation, and/or the mammal being treated therewith.

The term "protecting group" or "protecting moiety" refers to a substituent that is commonly employed to block or protect a particular functionality while reacting other functional groups on the compound, a derivative thereof, or a conjugate thereof. For example, an "amine-protecting group" or an "amino-protecting moiety" is a substituent attached to an amino group that blocks or protects the amino functionality in the compound. Such groups are well known in the art (see for example P. Wuts and T. Greene, 2007, Protective Groups in Organic Synthesis, Chapter 7, J. Wiley & Sons, NJ) and exemplified by carbamates such as methyl and ethyl carbamate, FMOC, substituted ethyl carbamates, carbamates cleaved by 1,6-β-elimination (also termed "self immolative"), ureas, amides, peptides, alkyl and aryl derivatives. Suitable amino-protecting groups include acetyl, trifluoroacetyl, t-butoxycarbonyl (BOC), benzyloxycarbonyl (CBZ) and 9-fluorenylmethylenoxycarbonyl (Fmoc). For a general description of protecting groups and their use, see P. G. M. Wuts & T. W. Greene, Protective Groups in Organic Synthesis, John Wiley & Sons, New York, 2007.

The term "leaving group" refers to an group of charged or uncharged moiety that departs during a substitution or displacement. Such leaving groups are well known in the art and include, but not limited to, halogens, esters, alkoxy, hydroxyl, tosylates, triflates, mesylates, nitriles, azide, carbamate, disulfides, thioesters, thioethers and diazonium compounds.

The term "bifunctional crosslinking agent," "bifunctional linker" "crosslinking agents" or "linker compound" refers to modifying agents that possess two reactive groups; one of which is capable of reacting with a cell binding agent while the other one reacts with the cytotoxic compound to link the two moieties together. Such bifunctional crosslinkers are well known in the art (see, for example, Isalm and Dent in *Bioconjugation*, chapter 5, p 218-363, Groves Dictionaries Inc. New York, 1999). For example, bifunctional crosslinking agents that enable linkage via a thioether bond include N-succinimidyl-4-(N-maleimidomethyl)-cyclohexane-1-carboxylate (SMCC) to introduce maleimido groups, or with N-succinimidyl-4-(iodoacetyl)-aminobenzoate (SIAB) to introduce iodoacetyl groups. Other bifunctional crosslinking agents that introduce maleimido groups or haloacetyl groups on to a cell binding agent are well known in the art (see US Patent Applications 2008/0050310, 20050169933, available from Pierce Biotechnology Inc. P.O. Box 117, Rockland, Ill. 61105, USA) and include, but not limited to, bis-maleimidopolyethyleneglycol (BMPEO), BM(PEO)$_2$, BM(PEO)$_3$, N—(β-maleimidopropyloxy)succinimide ester (BMPS), γ-maleimidobutyric acid N-succinimidyl ester (GMBS), ε-maleimidocaproic acid N-hydroxysuccinimide ester (EMCS), 5-maleimidovaleric acid NHS, HBVS, N-succinimidyl-4-(N-maleimidomethyl)-cyclohexane-1-carboxy-(6-amidocaproate), which is a "long chain" analog of SMCC (LC-SMCC), m-maleimidobenzoyl-N-hydroxysuccinimide ester (MBS), 4-(4-N-maleimidophenyl)-butyric acid hydrazide or HCl salt (MPBH), N-succinimidyl 3-(bromoacetamido)propionate (SBAP), N-succinimidyl iodoacetate (SIA), maleimidoundecanoic acid N-succinimidyl ester (KMUA), N-succinimidyl 4-(p-maleimidophenyl)-butyrate (SMPB), succinimidyl-6-(β-maleimidopropionamido) hexanoate (SMPH), succinimidyl-(4-vinylsulfonyl)benzoate (SVSB), dithiobis-maleimidoethane (DTME), 1,4-bis-maleimidobutane (BMB), 1,4 bismaleimidyl-2,3-dihydroxybutane (BMDB), bis-maleimidohexane (BMH), bis-maleimidoethane (BMOE), sulfosuccinimidyl 4-(N-maleimidomethyl)cyclohexane-1-carboxylate (sulfo-SMCC), sulfosuccinimidyl(4-iodo-acetyl)aminobenzoate (sulfo-SIAB), m-maleimidobenzoyl-N-hydroxysulfosuccinimide ester (sulfo-MBS), N-(γ-maleimidobutryloxy)sulfosuccinimde ester (sulfo-GMBS), N-(ε-maleimidocaproyloxy) sulfosuccimido ester (sulfo-EMCS), N-(κ-maleimidoundecanoyloxy)sulfosuccinimide ester (sulfo-KMUS), and sulfosuccinimidyl 4-(p-maleimidophenyl)butyrate (sulfo-SMPB).

Heterobifunctional crosslinking agents are bifunctional crosslinking agents having two different reactive groups. Heterobifunctional crosslinking agents containing both an amine-reactive N-hydroxysuccinimide group (NHS group) and a carbonyl-reactive hydrazine group can also be used to link the cytotoxic compounds described herein with a cell-binding agent (e.g., antibody). Examples of such commercially available heterobifunctional crosslinking agents include succinimidyl 6-hydrazinonicotinamide acetone hydrazone (SANH), succinimidyl 4-hydrazidoterephthalate hydrochloride (SHTH) and succinimidyl hydrazinium nicotinate hydrochloride (SHNH). Conjugates bearing an acid-labile linkage can also be prepared using a hydrazine-bearing benzodiazepine derivative of the present invention. Examples of bifunctional crosslinking agents that can be used include succinimidyl-p-formyl benzoate (SFB) and succinimidyl-p-formylphenoxyacetate (SFPA).

Bifunctional crosslinking agents that enable the linkage of cell binding agent with cytotoxic compounds via disulfide bonds are known in the art and include N-succinimidyl-3-(2-pyridyldithio)propionate (SPDP), N-succinimidyl-4-(2-pyridyldithio)pentanoate (SPP), N-succinimidyl-4-(2-pyridyldithio)butanoate (SPDB), N-succinimidyl-4-(2-pyridyldithio)2-sulfo butanoate (sulfo-SPDB) to introduce dithiopyridyl groups. Other bifunctional crosslinking agents that can be used to introduce disulfide groups are known in the art and are disclosed in U.S. Pat. Nos. 6,913,748, 6,716,821 and US Patent Publications 20090274713 and 20100129314, all of which are incorporated herein by reference. Alternatively, crosslinking agents such as 2-iminothiolane, homocysteine thiolactone or S-acetylsuccinic anhydride that introduce thiol groups can also be used.

A "linker," "linker moiety," or "linking group" as defined herein refers to a moiety that connects two groups, such as a cell binding agent and a cytotoxic compound, together. Typically, the linker is substantially inert under conditions for which the two groups it is connecting are linked. A bifunctional crosslinking agent may comprise two reactive groups, one at each ends of a linker moiety, such that one reactive group can be first reacted with the cytotoxic compound to provide a compound bearing the linker moiety and a second reactive group, which can then react with a cell binding agent. Alternatively, one end of the bifunctional crosslinking agent can be first reacted with the cell binding agent to provide a cell binding agent bearing a linker moiety and a second reactive group, which can then react with a cytotoxic compound. The linking moiety may contain a chemical bond that allows for the release of the cytotoxic moiety at a particular site. Suitable chemical bonds are well known in the art and include disulfide bonds, thioether bonds, acid labile bonds, photolabile bonds, peptidase labile bonds and esterase labile bonds (see for example U.S. Pat. Nos. 5,208,020; 5,475,092; 6,441,163; 6,716,821; 6,913, 748; 7,276,497; 7,276,499; 7,368,565; 7,388,026 and 7,414, 073). Preferred are disulfide bonds, thioether and peptidase labile bonds. Other linkers that can be used in the present invention include non-cleavable linkers, such as those described in are described in detail in U.S. publication number 20050169933, or charged linkers or hydrophilic linkers and are described in US 2009/0274713, US 2010/01293140 and WO 2009/134976, each of which is expressly incorporated herein by reference, each of which is expressly incorporated herein by reference.

The term "amino acid" refers to naturally occurring amino acids or non-naturally occurring amino acid. They may be represented by $NH_2—C(R^{aa}R^{aa'})—C(=O)OH$, wherein $R^{aa}$ and $R^{aa'}$ are each independently H, an optionally substituted linear, branched or cyclic alkyl, alkenyl or alkynyl having 1 to 10 carbon atoms, aryl, heteroaryl or heterocyclyl, or $R^{aa}$ and the N-terminal nitrogen atom, can together form a heterocyclic ring (e.g., in proline). The term "amino acid residue" refers to the corresponding residue when one hydrogen atom is removed from the amine and/or carboxy end of the amino acid, such as —NH—C($R^{aa'}R^{aa}$)—C(=O)O—.

The term "cation" refers to an ion with positive charge. The cation can be monovalent (e.g., $Na^+$, $K^+$, etc.), bi-valent (e.g., $Ca^{2+}$, $Mg^{2+}$, etc.) or multi-valent (e.g., $Al^{3+}$ etc.). Preferably, the cation is monovalent.

The term "therapeutically effective amount" means that amount of active compound or conjugate that elicits the desired biological response in a subject. Such response includes alleviation of the symptoms of the disease or disorder being treated, prevention, inhibition or a delay in the recurrence of symptom of the disease or of the disease itself, an increase in the longevity of the subject compared with the absence of the treatment, or prevention, inhibition or delay in the progression of symptom of the disease or of the disease itself. Determination of the effective amount is well within the capability of those skilled in the art, especially in light of the detailed disclosure provided herein. Toxicity and therapeutic efficacy of compound I can be determined by standard pharmaceutical procedures in cell cultures and in experimental animals. The effective amount of compound or conjugate of the present invention or other therapeutic agent to be administered to a subject will depend on the stage, category and status of the multiple myeloma and characteristics of the subject, such as general health, age, sex, body weight and drug tolerance. The effective amount of compound or conjugate of the present invention or other therapeutic agent to be administered will also depend on administration route and dosage form. Dosage amount and interval can be adjusted individually to provide plasma levels of the active compound that are sufficient to maintain desired therapeutic effects.

The term "humanized antibody" refers to forms of non-human (e.g., murine) antibodies that are specific immunoglobulin chains, chimeric immunoglobulins, or fragments thereof that contain minimal non-human (e.g., murine) sequences. Typically, humanized antibodies are human immunoglobulins in which residues from the complementary determining region (CDR) are replaced by residues from the CDR of a non-human species (e.g., mouse, rat, rabbit, hamster) that have the desired specificity, affinity, and capability (Jones et al, Nature 321:522-525, 1986; Riechmann et al, Nature 332:323-327, 1988; Verhoeyen et al, Science 239:1534-1536, 1988).

In some instances, the $F_v$ framework region (FR) residues of a human immunoglobulin are replaced with the corresponding residues in an antibody from a non-human species that has the desired specificity, affinity, and capability. The humanized antibody can be further modified by the substitution of additional residues either in the $F_v$ framework region and/or within the replaced non-human residues to refine and optimize antibody specificity, affinity, and/or capability. In general, the humanized antibody will comprise substantially all of at least one, and typically two or three, variable domains containing all or substantially all of the CDR regions that correspond to the non-human immunoglobulin whereas all or substantially all of the FR regions are those of a human immunoglobulin consensus sequence. The humanized antibody can also comprise at least a portion of an immunoglobulin constant region or domain ($F_c$), typically that of a human immunoglobulin. Examples of methods used to generate humanized antibodies are described in U.S. Pat. Nos. 5,225,539 and 5,639,641, Roguska et al, Proc. Natl. Acad. Sci. USA 91(3):969-973, 1994; and Roguska et al, Protein Eng. 9(10):895-904, 1996 (all incorporated herein by reference). In some embodiments, a "humanized antibody" is a resurfaced antibody. In some embodiments, a "humanized antibody" is a CDR-grafted antibody.

Cell-Binding Agent-Cytotoxic Agent Conjugates

The present invention provides cell-binding agent-cytotoxic agent conjugates comprising a cell-binding agent described herein covalently linked to one or more molecules of the cytotoxic agent of the present invention via a variety of linkers, including, but not limited to, disulfide linkers, thioether linkers, amide bonded linkers, acid-labile linkers, and esterase-labile linkers.

In a first embodiment, the present invention provides a cell-binding agent-cytotoxic agent conjugate of structural formula (I):

or a pharmaceutically acceptable salt thereof, wherein:

CBA is a cell-binding agent covalently linked to the $J_{CB'}$ group;

$J_{CB'}$ is a moiety formed by reacting an aldehyde group on the CBA and an aldehyde reactive group connected to the group L, wherein the aldehyde is derived from oxidation of a 2-hydroxyethylamine moiety represented by the following structural formula:

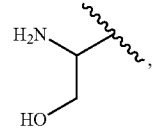

wherein the 2-hydroxyethylamine moiety being part of a serine, threonine, hydroxylysine, 4-hydroxyornithine or 2,4-diamino-5-hydroxy valeric acid residue;

L is a spacer or a bond;

$J_D'$ is a linking moiety connecting the cytotoxic agent D with the group L;

D is a cytotoxic agent covalently linked to L through the linking moiety $J_D'$ or to CBA through $J_{CB'}$ when L is a bond; and w is 1, 2, 3 or 4.

Any aldehyde reactive group can be used in the present invention. Exemplary aldehyde reactive groups include, but are not limited to, those described in R. C. Larock, 1999, *Comprehensive Organic Transformations*, $2^{nd}$ Ed. Wiley-VCH.

In one embodiment, the aldehyde reactive group is a hydrazine, a hydrazide or a hydroxylamine.

In another embodiment, the aldehyde reactive group is selected from:

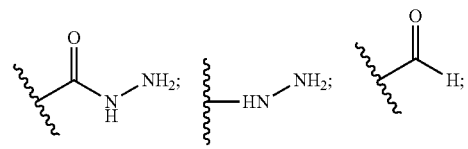

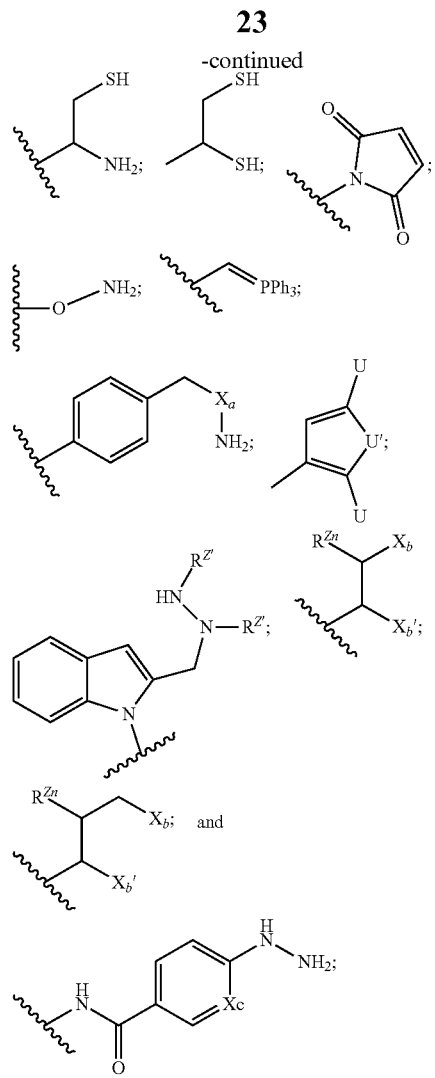

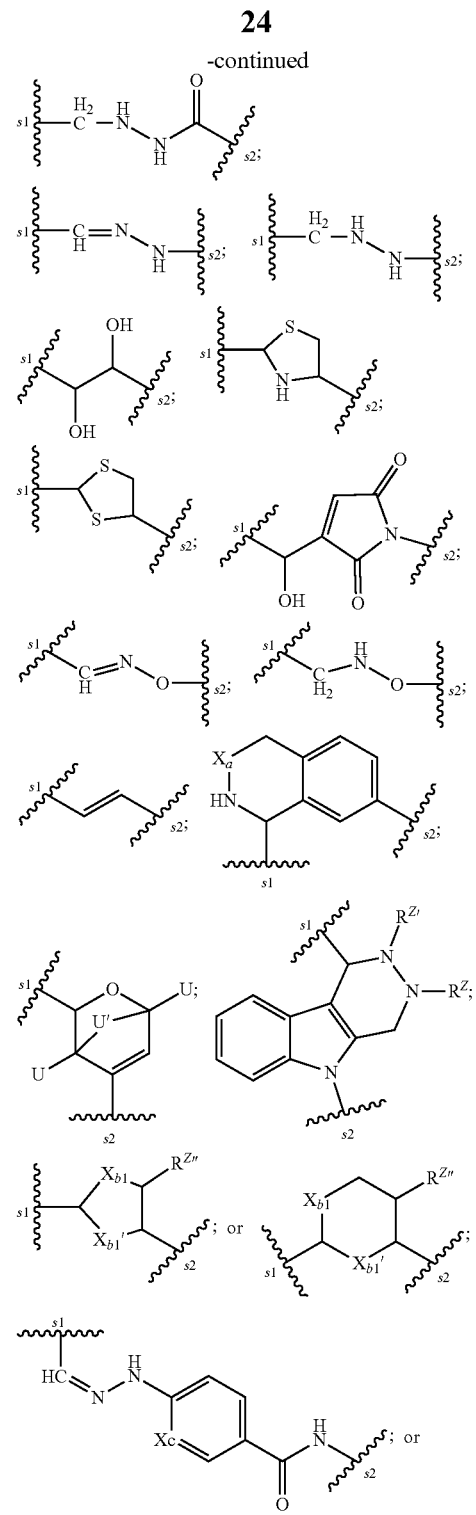

wherein: $X_a$ is $CH_2$, O or $NCH_3$; U' is NH, O, S or $CH_2$; U is H or an electron donating group; $X_b$ and $X_b'$ are each independently —OH, —SH or —$NH_2$; $R^Z$ and $R^{Z'}$ are each independently H or an alkyl (preferably -Me); $R^{Z''}$ is H or an alkyl; and $X_c$ is N or CH. More specifically, the aldehyde reactive group

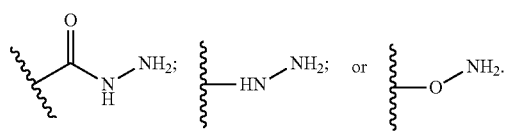

In a 1st specific embodiment, for conjugates of structural formula (I) or a pharmaceutically acceptable salt thereof, $J_{CB}'$ is represented by one of the following structural formulas:

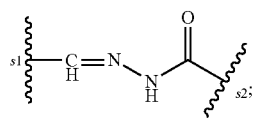

wherein: $X_a$ is $CH_2$, O or $NCH_3$; U' is NH, O, S or $CH_2$; U is H or an electron donating group; $X_{b1}$ and $X_{b1'}$ are each independently —O—, —S— or —NH—; $R^Z$ and $R^{Z'}$ are each independently H or an alkyl (preferably -Me); and $R^{Z''}$ is H or an alkyl; s1 is the site covalently linked to the cell-binding agent; and s2 is the site covalently linked to the group L. More specifically, $J_{CB'}$ is

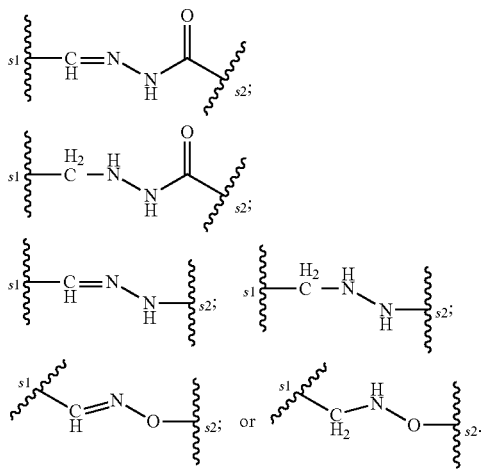

In a $2^{nd}$ specific embodiment, for conjugates of formula (I) or a pharmaceutically acceptable salt thereof, -L-$J_D$'- is represented by the following structural formula:

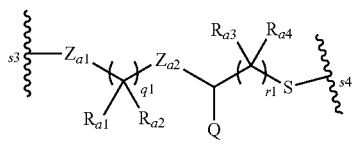

(L1)

wherein:
s3 is the site covalently linked to the group $J_{CB}$';
s4 is the site covalently linked to the group D; $Z_{a1}$ is absent, —SO$_2$NR$_9$—, —NR$_9$SO$_2$—, —C(=O)—NR$_9$—, —NR$_9$—C(=O)—, —(CH$_2$CH$_2$)$_p$' NR$_9$—C(=O)—, —C(=O)—NR$_9$(CH$_2$CH$_2$)$_p$', —(CH$_2$CH$_2$)$_p$—C(=O) NR$_9$—, —NR$_9$C(=O)(CH$_2$CH$_2$)$_p$'—, —C(=O)—O—, or —O—C(=O)—;
$Z_a2$ is absent, —SO$_2$NR$_9$—, —NR$_9$SO$_2$—, —C(=O)—NR$_9$—, —NR$_9$—C(=O)—, —C(=O)—O—, —O—C(=O)—, —C(=O)—NR$_9$—(CH$_2$CH$_2$O)$_p$—, —NR$_9$—C(=O)—(CH$_2$CH$_2$O)$_p$—, —(OCH$_2$CH$_2$)$_p$—C(=O)NR$_9$—, or —(OCH$_2$CH$_2$)$_p$—NR$_9$—C(=O)—;
$R_9$ is H or an optionally substituted alkyl;
p and p' are each independently an integer from 1 to 10;
Q is H, a charged substituent or an ionizable group;
$R_{a1}$, $R_{a2}$, $R_{a3}$, $R_{a4}$, for each occurrence, are independently H or an optionally substituted alkyl;
q1 and r1 are each independently an integer from 0 to 10, provided that q1 and r1 are not both 0; and the remaining variables are as described above in the first embodiment or the $1^{st}$ specific embodiment or any more specific embodiments described therein.
In one embodiment, Q is i) H; ii) —SO$_3$H, —Z'—SO$_3$H, —OPO$_3$H$_2$, —Z'—OPO$_3$H$_2$, —PO$_3$H$_2$, —Z'—PO$_3$H$_2$, —CO$_2$H, —Z'—CO$_2$H, —NR$_{11}$R$_{12}$, or —Z'—NR$_{11}$R$_{12}$, or a pharmaceutically acceptable salt thereof; or, iii) —N$^+$R$_{14}$R$_{15}$R$_{16}$X$^-$ or —Z'—N$^+$R$_{14}$R$_{15}$R$_{16}$X$^-$; Z' is an optionally substituted alkylene, an optionally substituted cycloalkylene or an optionally substituted phenylene; $R_{14}$ to $R_{16}$ are each independently an optionally substituted alkyl; X$^-$ is a pharmaceutically acceptable anion; and the remaining variables are as described above in the $2^{nd}$ specific embodiment. More specifically, Q is —SO$_3$H or —CO$_2$H or a pharmaceutically acceptable salt thereof.

In another embodiment, $Z_{a1}$ is absent; $Z_{a2}$ is —C(=O)—NR$_9$— or —NR$_9$—C(=O)—; and the remaining variables are as described above in any embodiments of the $2^{nd}$ specific embodiment. More specifically, $R_9$ is H.

In yet another embodiment, $Z_{a1}$ and $Z_a2$ are both absent; and the remaining variables are as described above in any embodiments of the $2^{nd}$ specific embodiment.

In another embodiment, $R_{a1}$, $R_{a2}$, $R_{a3}$ and $R_{a4}$ are all —H; q and r are each independently an integer from 0 to 4; and the remaining variables are as described above in any embodiments of the $2^{nd}$ specific embodiment.

In yet another embodiment, for conjugates of formula (I) or a pharmaceutically acceptable salt thereof, -L-$J_D$'- is represented by the following structural formula:

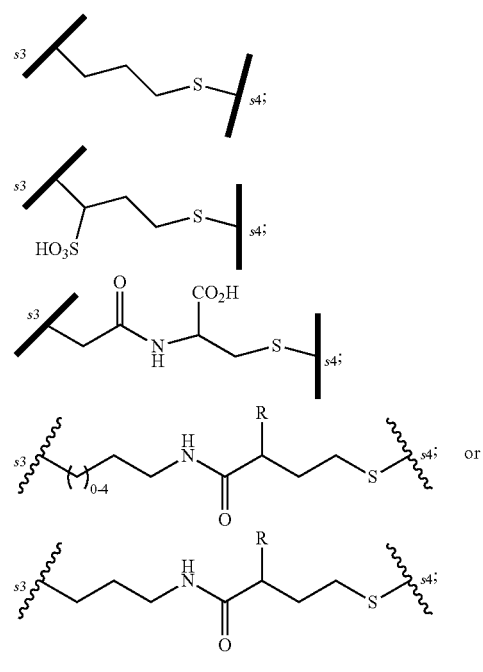

or a pharmaceutically acceptable salt thereof and the remaining variables are as described above in the first embodiment or the $1^{st}$ specific embodiment or any more specific embodiments described therein.

In a $3^{rd}$ specific embodiment, for conjugates of formula (I) or a pharmaceutically acceptable salt thereof, -L-$J_D$'- is represented by the following structural formula:

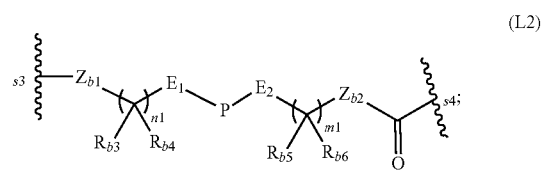

(L2)

-continued

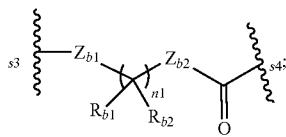 (L3)

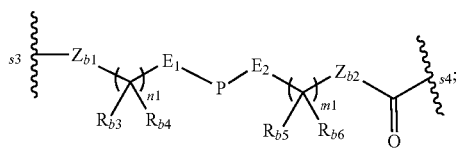 (L2)

wherein:
s3 is the site covalently linked to the group $J_{CB}'$ group;
s4 is the site covalently linked to the group D;
$Z_{b1}$ and $Z_{b2}$ are each independently absent, $-SO_2NR_9-$, $-NR_9SO_2-$, $-C(=O)-NR_9-$, $-NR_9-C(=O)-$, $-C(=O)-O-$, $-O-C(=O)-$, $-CH_2-O-$, $-O-CH_2-$, $-(CH_2CH_2O)_p-$ or $-(OCH_2CH_2)_{p'}-$, $-NR_9-C(=O)-CH_2-$, or $-CH_2-C(=O)-NR_9-$ wherein p and p' are independently an integer from 1 to 1000;
one of $E_1$ and $E_2$ is $-C(=O)-$, and the other is $-NR_9-$; or one of $E_1$ and $E_2$ is $-C(=O)-$ or $-NR_9-$, and the other is absent;
$R_9$ is H or an optionally substituted alkyl;
P is $[XX]_{1-10}$, in which each XX is a residue of an independently selected amino acid, or P is $-(NR^m-CH_2CH_2)_s-$;
s is an integer from 1 to 5;
$R^m$ is H, or alkyl optionally substituted with a charged substituent or an ionizable group;
$R_{b1}$, $R_{b2}$, $R_{b3}$, $R_{b4}$, $R_{b5}$ and $R_{b6}$, for each occurrence, are each independently H or an optionally substituted alkyl;
m1 and n1, for each occurrence, are independently an integer from 0 to 10; and the remaining variables are as described above in the first embodiment or the 1$^{st}$ specific embodiment or any more specific embodiments described therein.

In one embodiment, for conjugates of formula (I) or a pharmaceutically acceptable salt thereof, -L-$J_D'$- is represented by the following structural formula:

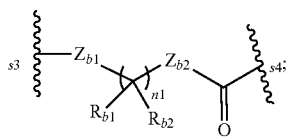 (L3)

wherein:
$Z_{b1}$ and $Z_{b2}$ are both absent, or one of $Z_{b1}$ and $Z_{b2}$ is absent and the other is $-CH_2-O-$ or $-O-CH_2-$;
n1 is an integer from 1 to 6; and the remaining variables are as described above in the first embodiment or the 1$^{st}$ specific embodiment or any more specific embodiments described therein. More specifically, $R_{b1}$ and $R_{b2}$ are both H.

In another embodiment, for conjugates of formula (I) or a pharmaceutically acceptable salt thereof, -L-$J_D'$- is represented by the following structural formula:

wherein:
$Z_{b1}$ and $Z_{b2}$ are each independently absent, $-CH_2-O-$, $-O-CH_2-$, $-NR_9-C(=O)-CH_2-$, or $-CH_2-C(=O)-NR_9-$;
n1 and m1 are each independently an integer from 1 to 6; and
the remaining variables are as described above in the first embodiment or the 1$^{st}$ specific embodiment or any more specific embodiments described therein.

In a more specific embodiment, for formula (L2) described in any embodiments above, $Z_{b1}$ and $Z_{b2}$ are both absent. In yet another more specific embodiment, for formula (L2) described above, $Z_{b1}$ is $-CH_2-O-$; and $Z_{b2}$ is absent. Alternatively, for formula (L2) described above, $Z_{b1}$ is $-CH_2-C(=O)-NR_9-$; and $Z_{b2}$ is $-O-CH_2-$ or absent. Even more specifically, $R_9$ is $-H$.

In one embodiment, for formula (L2) described in any embodiments above, P is $[XX]_{2-4}$. In yet another specific embodiment, for formula (L2) described in any embodiments above, P is $[XX]_2$ or $[XX]_3$. Each XX as used herein is a residue of an independently selected amino acid.

In another embodiment, for formula (L2) described in any embodiments above, P is a peptide cleavable by a protease. More specifically, P is a peptide cleavable by a protease expressed in tumor tissue. In yet another more specific embodiment, P is a peptide cleavable by a lysosomal protease.

In yet another embodiment, for formula (L2) described in any embodiments above, P is selected from the group consisting of: Val-Cit, Val-Lys, Phe-Lys, Lys-Lys, Ala-Lys, Phe-Cit, Leu-Cit, Lle-Cit, Trp, Cit, Phe-Ala, Phe-$N^9$-tosyl-Arg, Phe-$N^9$-nitro-Arg, Phe-Phe-Lys, D-Phe-Phe-Lys, Gly-Phe-Lys, Leu-Ala-Leu, Ile-Ala-Leu, Val-Ala-Val, Ala-Leu-Ala-Leu (SEQ ID NO: 17), β-Ala-Leu-Ala-Leu (SEQ ID NO: 18), Gly-Phe-Leu-Gly (SEQ ID NO: 19), Val-Arg, Arg-Val, Arg-Arg, Val-D-Cit, Val-D-Lys, Val-D-Arg, D-Val-Cit, D-Val-Lys, D-Val-Arg, D-Val-D-Cit, D-Val-D-Lys, D-Val-D-Arg, D-Arg-D-Arg, Ala-Ala, Ala-D-Ala, D-Ala-Ala, and D-Ala-D-Ala., Gly-Gly-Gly, Ala-Ala-Ala, d-Ala-Ala-Ala, Ala-d-Ala-Ala, Ala-Ala-d-Ala, Ala-Val-Cit, and Ala-Val-Ala. More specifically, P is Gly-Gly-Gly, Ala-Ala-Ala, d-Ala-Ala-Ala, Ala-d-Ala-Ala, Ala-Val-Ala, Gly-Gly or Ala-Ala.

In another embodiment, for conjugates of formula (I) or a pharmaceutically acceptable salt thereof, -L-$J_D'$- is represented by the following structural formula:

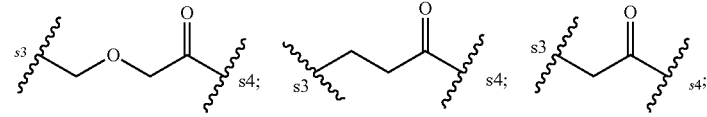

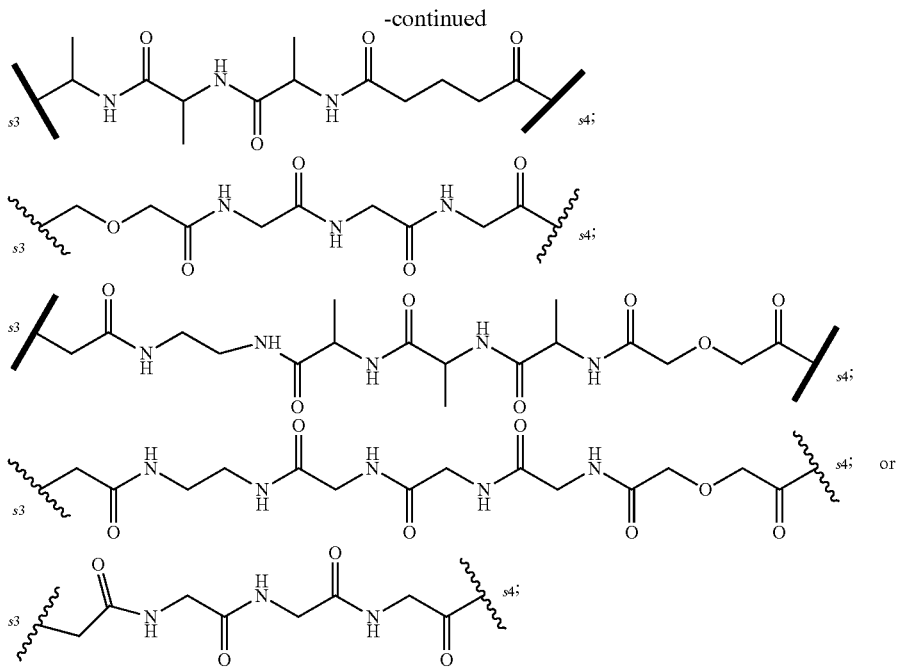

and the remaining variables are as described in the first embodiment or the 1$^{st}$ specific embodiment or any more specific embodiments described therein.

In a 4$^{th}$ specific embodiment, for conjugates of formula (I) or a pharmaceutically acceptable salt thereof, -L-J$_D$'- is represented by the following structural formula:

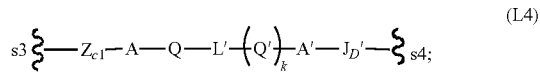
(L4)

s3 is the site covalently linked to the group J$_{CB}$';
s4 is the site covalently linked to the group D;
Z$_{c1}$ is absent, —SO$_2$NR$_9$—, —NR$_9$SO$_2$—, —C(=O)—NR$_9$—, —NR$_9$—C(=O)—, —C(=O)—O—, —O—C(=O)—, —CH$_2$—O—, —O—CH$_2$—, —(CH$_2$CH$_2$O)$_p$— or —(OCH$_2$CH$_2$)$_{p'}$—, wherein p and p' are independently an integer from 1 to 1000;

J$_{D'}$ is

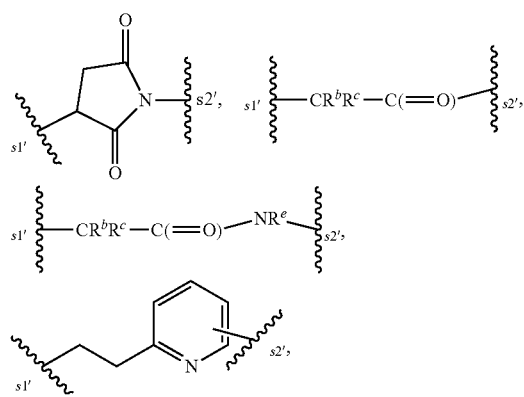

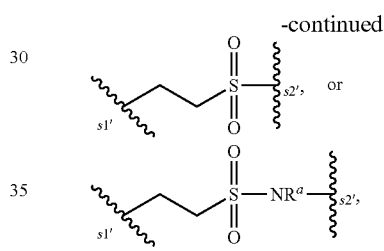

in which s1' is the site covalently linked to the cytotoxic agent D, s2' is the site covalently linked to the group A';

A and A' are each independently an optionally substituted alkylene, an optionally substituted alkenylene, an optionally substituted alkynylene, an optionally substituted cycloalkylene, an optionally substituted cycloalkenylene or an optionally substituted cycloalkynylene;

Q is —Z$_1$—P—Z$_2$—;
Q' is —Z$_1$'—P'—Z$_2$'—;
one of Z$_1$ and Z$_2$ is —C(=O)—, and the other is —NR$^h$—;
one of Z$_1$' and Z$_2$' is —C(=O)—, and the other is —NR$^{h'}$—;
P and P' are each independently absent, an optionally substituted alkylene, —(CH$_2$—CH$_2$—O)$_j$, —(O—CH$_2$—CH$_2$)$_j$—, or [XX]$_{1-10}$, in which each XX is a residue of an independently selected amino acid;
j is an integer between 1 and 500;
k is 0 or 1;
L is —(CR$_5$R$_6$)$_v$—, —(CR$_7$R$_8$)$_q$—N(R$^g$)—(CR$_9$R$_{10}$)$_r$—, —(CR$_7$R$_8$)$_q$—C(R$^a$)(R$^g$)—(CR$_9$R$_{10}$)$_r$, or —(CR$_{11}$R$_{12}$)$_s$—N(R$^g$)—(CR$_{13}$R$_{14}$)$_t$—N(R$^{g'}$)—(CR$_{15}$R$_{16}$)$_u$—;
R$^g$ and R$^{g'}$ are each independently —(CR$_{17}$R$_{18}$)$_p$—Z—V;
p is an integer between 1 and 5;
V is H, a charged substituent or an ionizable group;
Z is absent, —C(=O)NR$^h$-alkylene- or —NR$^h$—C(=O)-alkylene-;
R$^h$ and R$^{h'}$, for each occurrence, are independently H or an optionally substituted alkyl;

$R_5$ to $R_{18}$, for each occurrence, are independently H or an optionally substituted alkyl;

q, r, s, t, u and v are each independently an integer between 0 and 10; and the remaining variables are as described above in the first embodiment or the 1$^{st}$ specific embodiment or any more specific embodiments described therein.

In one embodiment, for conjugates of formula (I) or a pharmaceutically acceptable salt thereof, -L-$J_D$'- is represented by the following structural formula:

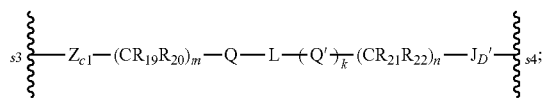
(L5)

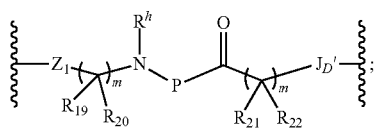
(L6)

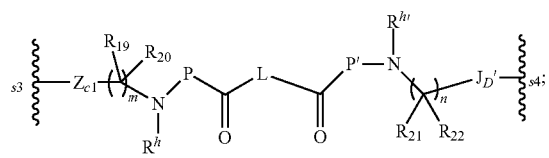
(L7)

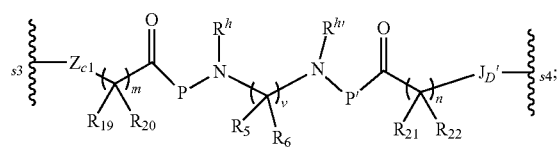
(L8)

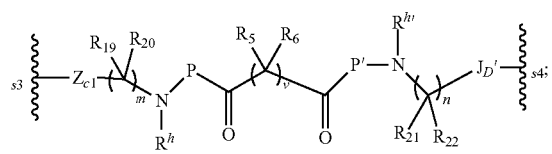
(L9)

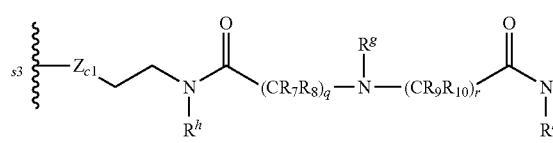
(L10)

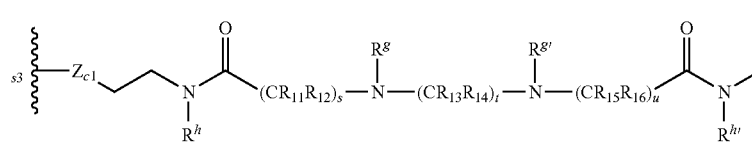
(L11)

wherein:

$R_{19}$ to $R_{22}$, for each occurrence, are independently H or an optionally substituted alkyl;

m and n are each independently 0 to 10; and the remaining variables are as described above in the first embodiment or the 1$^{st}$ specific embodiment. More specifically, $R_{19}$ to $R_{22}$ are each H; $R_5$ and $R_6$ are each H; $R_7$ to $R_{10}$ are each H; and $R_{11}$ to $R_{16}$ are each H.

In one embodiment, for formulas (L4)-(L11), P and P', for each occurrence, are independently [XX]$_{1-10}$. More specifically, P and P', for each occurrence, are independently [XX]$_{2-5}$; and the remaining variables are as described above.

In another embodiment, for formulas (L4)-(L11), P and P' are each a peptide cleavable by a protease. In yet another embodiment, P and P' are each a peptide cleavable by a protease expressed in tumor tissue. Alternatively, P and P' are each a peptide cleavable by a lysosomal protease.

In yet another embodiment, for formulas (L4)-(L11), P and P' are each selected from the group consisting of: Val-Cit, Val-Lys, Phe-Lys, Lys-Lys, Ala-Lys, Phe-Cit, Leu-Cit, Lle-Cit, Trp, Cit, Phe-Ala, Phe-N$^9$-tosyl-Arg, Phe-N$^9$-nitro-Arg, Phe-Phe-Lys, D-Phe-Phe-Lys, Gly-Phe-Lys, Leu-Ala-Leu, Ile-Ala-Leu, Val-Ala-Val, Ala-Leu-Ala-Leu (SEQ ID NO: 17), β-Ala-Leu-Ala-Leu (SEQ ID NO: 18), Gly-Phe-Leu-Gly (SEQ ID NO: 19), Val-Arg, Arg-Val, Arg-Arg, Val-D-Cit, Val-D-Lys, Val-D-Arg, D-Val-Cit, D-Val-Lys, D-Val-Arg, D-Val-D-Cit, D-Val-D-Lys, D-Val-D-Arg, D-Arg-D-Arg, Ala-Ala, Ala-D-Ala, D-Ala-Ala, and D-Ala-D-Ala., Gly-Gly-Gly, Ala-Ala-Ala, D-Ala-Ala-Ala, Ala-D-Ala-Ala, Ala-Ala-D-Ala, Ala-Val-Cit, Ala-Val-Ala, and β-Ala-Gly-Gly-Gly. More specifically, P and P' are each Gly-Gly-Gly, Ala-Ala-Ala, D-Ala-Ala-Ala, Ala-D-Ala-Ala, Ala-Val-Ala, or β-Ala-Gly-Gly-Gly.

In certain embodiments, [XX] in any embodiments described above, for each occurrence, is the residue of an independently selected amino acid selected from: a naturally occurring amino acid, a synthetic amino acid, an amino acid analog, or an amino acid mimetic that functions in a manner similar to the naturally occurring amino acids.

In certain embodiments, [XX] in any embodiments described above, for each occurrence, is the residue of an independently selected amino acid selected from the group consisting of: Histidine, Alanine, Isoleucine, Arginine, Leucine, Asparagine, Lysine, Aspartic acid, Methionine, Cysteine, Phenylalanine, Glutamic acid, Threonine, Glutamine, Tryptophan, Glycine, Valine, Proline, Serine, Tyrosine, N-methyl-Histidine, N-methyl-Alanine, N-methyl-Isoleucine, N-methyl-Arginine, N-methyl-Leucine, N-methyl-Asparagine, N-methyl-Lysine, N-methyl-Aspartic acid, N-methyl-Methionine, N-methyl-Cysteine, N-methyl-Phenylalanine, N-methyl-Glutamic acid, N-methyl-Threonine, N-methyl-Glutamine, N-methyl-Tryptophan, N-methyl-Glycine, N-methyl-Valine, N-methyl-Proline, N-methyl-Serine, N-methyl-Tyrosine, hydroxyproline, γ-carboxyglutamate, selinocysteine, O-phosphoserine, homoserine, norleucine, methionine sulfoxide, methionine methyl sulfonium, citrulline, Ornithine, cysteine sulfonic acid, cysteine sulfinic acid, 3-aminoalanine, 3-dimethylaminoalanine, 2-amino-4-(dimethylamino)butanoic acid, 2,4-diaminobutanoic acid, 2-amino-6-(dimethylamino)hexanoic acid, 2-amino-5-(dimethylamino)pentanoic acid, and β-alanine, each independently as an L or D isomer. More specifically, each XX is independently the residue of a glycine or an alanine.

In a $5^{th}$ specific embodiment, for conjugates of formula (I), D is a maytansinoid; and the remaining variables are as described above in the first embodiment or the $1^{st}$, $2^{nd}$, $3^{rd}$ or $4^{th}$ embodiment or any more specific embodiments describe therein.

In a more specific embodiment, D is a maytansinoid represented by the following structural formula:

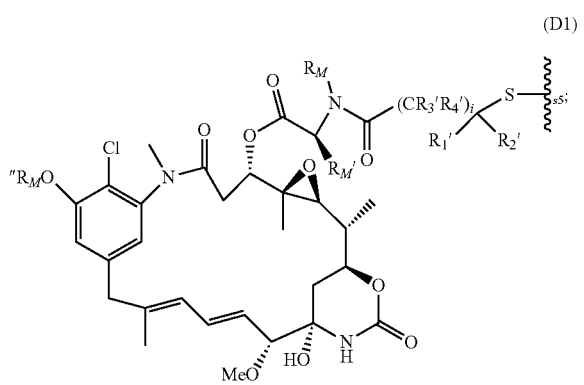

(D1)

wherein:

$R_M$, $R_M'$, and $R_M''$, for each occurrence, are independently H or an optionally substituted alkyl;

$R_1'$, $R_2'$, $R_3'$ and $R_4'$ for each occurrence, are independently H, an optionally substituted an optionally substituted alkyl, an optionally substituted alkenyl, an optionally substituted cycloalkyl, an optionally substituted heterocyclyl, an optionally substituted aryl, or an optionally substituted heteroaryl;

i is an integer between 0 and 15; and s5 is the site covalently linked to the group $J_D'$;

-L-$J_D'$- are as described above in the first embodiment, or the $2^{nd}$ or $4^{th}$ specific embodiment or more specific embodiments described therein.

More specifically, D is represented by the following structural formula:

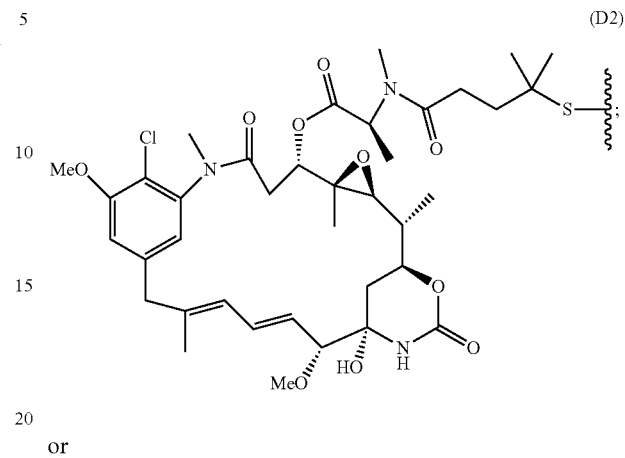

(D2)

or

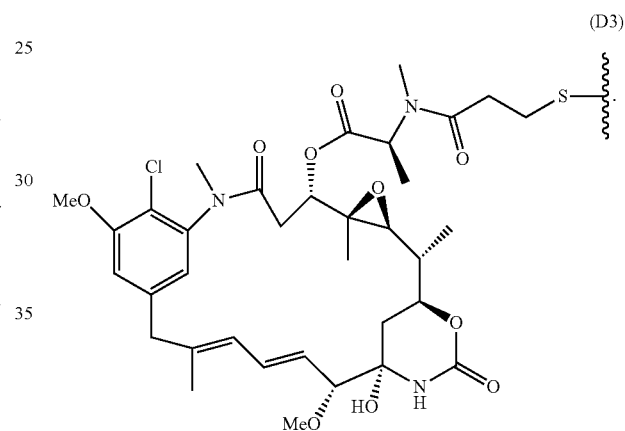

(D3)

In yet another specific embodiment, D is a represented by the following structural formula:

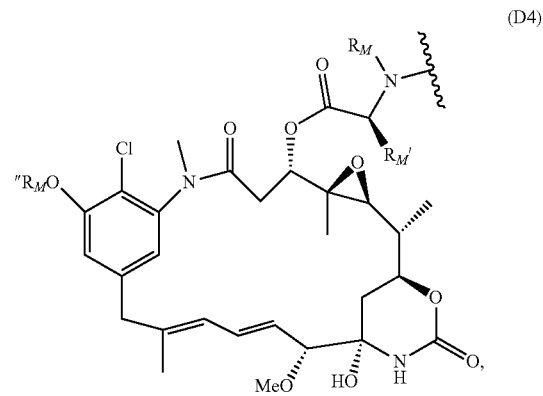

(D4)

wherein: $R_M$, $R_M'$, and $R_M''$, for each occurrence, are independently H or an optionally substituted alkyl; s5 is the site covalently linked to the group $J_D'$; and -L-$J_D'$- are as described above in the first embodiment, or the 3' specific embodiment or any more specific embodiments described therein.

More specifically, D is represented by the following structural formula:

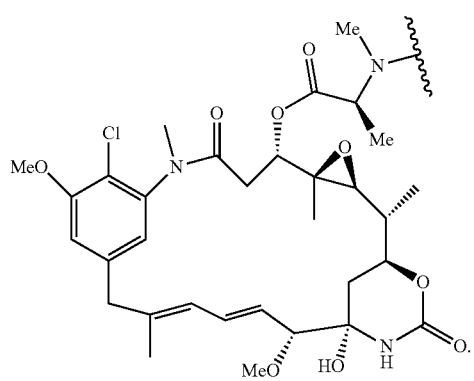

(D5)

In a 6$^{th}$ specific embodiment, D is a benzodiazepine compound; and the remaining variables are as described above in the first embodiment or the 1$^{st}$, 2$^{nd}$, 3$^{rd}$ or 4$^{th}$ embodiment or any more specific embodiments describe therein. Exemplary benzodiazepine compounds include, but are not limited those described in U.S. Pat. Nos. 8,765,740, 8,426,402, US2014/0088089, WO2011/130613, WO2011/130616, WO2010/091150, and WO2009/016516. The entire teachings of these references are incorporated herein by reference.

In a more specific embodiment, D is a benzodiazepine compound represented by the following structural formula:

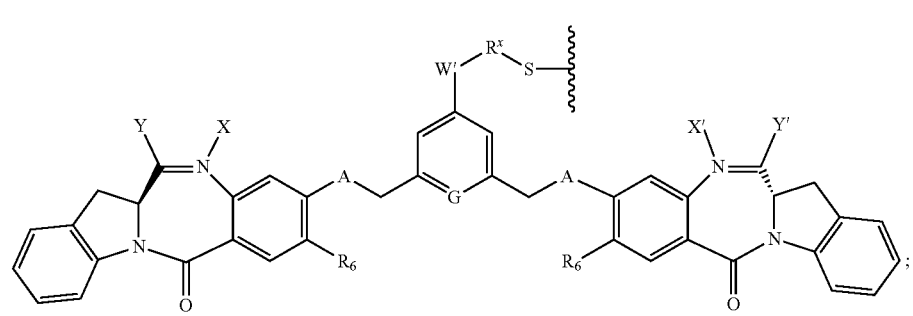

(D6)

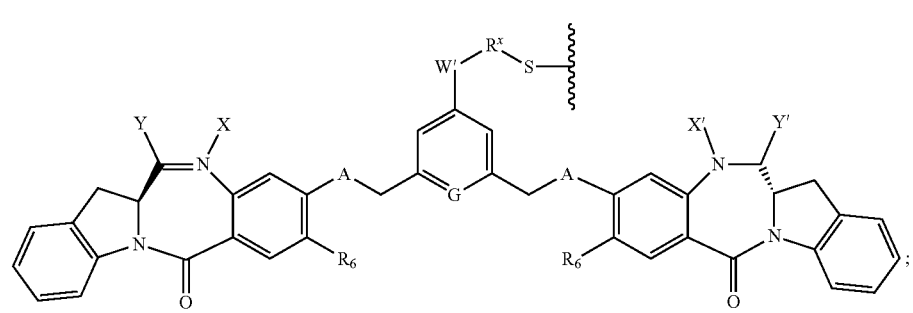

(D7)

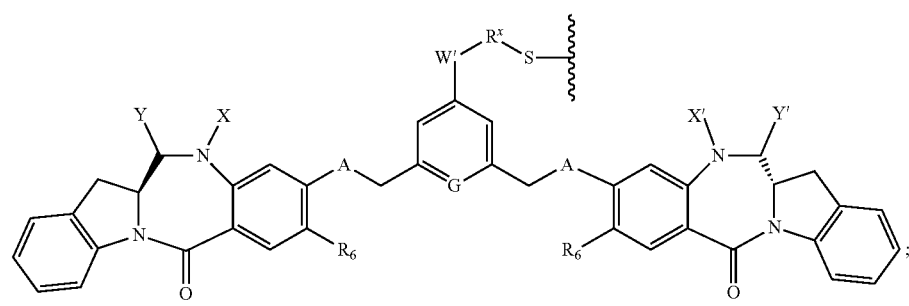

(D8)

-continued
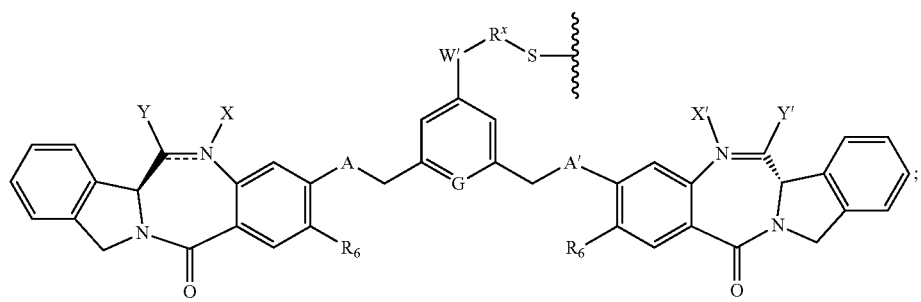
(D9)
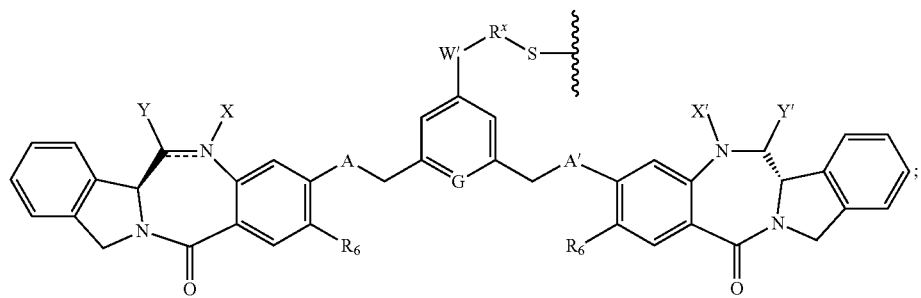
(D10)
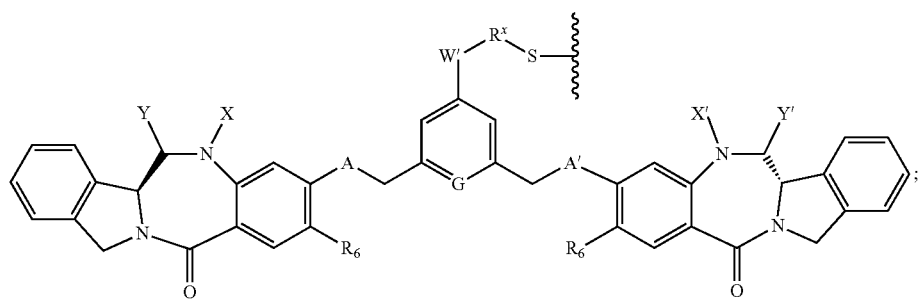
(D11)
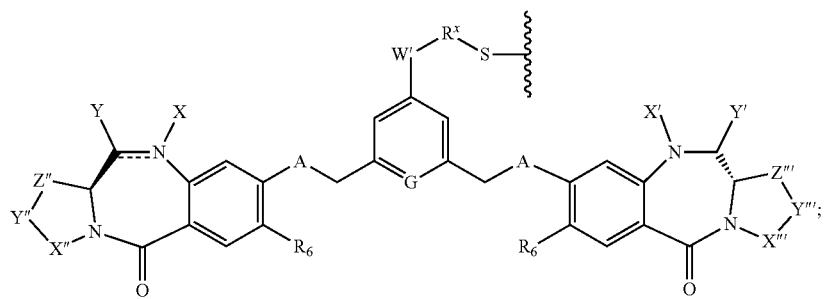
(D12)
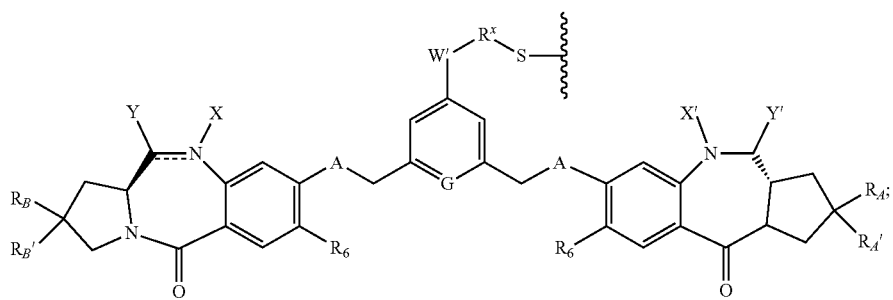
(D13)

(D14)

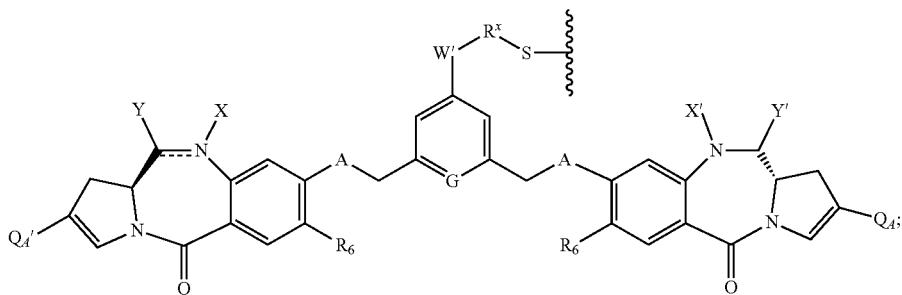

wherein:

the double line == between N and C represents a single bond or a double bond, provided that when it is a double bond, X is absent and Y is —H, and when it is a single bond, X is selected from —H, the linking group with the reactive group bonded thereto, or an amine protecting group (preferably X is —H);

Y is selected from —H, —OR, —OCOR', —SR, —NR'R," —SO₃M, —SO₂M or —OSO₃M, wherein M is —H or a cation such as Na⁺ or K⁺;

R is —H, an optionally substituted linear, branched or cyclic alkyl, alkenyl or alkynyl having from 1 to 10 carbon atoms or a PEG group —(CH₂CH₂O)$_n$—R$^c$, wherein n is an integer from 1 to 24, and R$^c$ is a linear or branched alkyl having 1 to 4 carbon atoms;

R' and R" are the same or different, and are selected from —H, —OH, —OR, —NRR$^{g'}$, —COR, an optionally substituted linear, branched or cyclic alkyl, alkenyl or alkynyl having from 1 to 10 carbon atoms, an optionally substituted aryl having from 6 to 18 carbon atoms, an optionally substituted 3- to 18-membered heterocyclic ring having 1 to 6 heteroatoms selected from O, S, N and P, a PEG group —(CH₂CH₂O)$_n$—R$^c$, wherein n is an integer from 1 to 24, preferably n is 2, 4 or 8; and R$^{g'}$ is —H, an optionally substituted linear, branched or cyclic alkyl, alkenyl or alkynyl having from 1 to 10 carbon atoms or a PEG group —(CH₂CH₂O)$_n$—R$^c$;

X' is selected from the group consisting of —H, —OH, a substituted or unsubstituted linear, branched or cyclic alkyl, alkenyl or alkynyl having from 1 to 10 carbon atoms, phenyl, and an amine-protecting group;

Y' is selected from the group consisting of —H, an oxo group, a substituted or unsubstituted linear, branched or cyclic alkyl, alkenyl or alkynyl having from 1 to 10 carbon atoms;

A and A' are selected from —O— and —S—;

W' is absent, or selected from —O—, —N(R$^e$)—, —N(R$^e$)—C(=O)—, —N(C(=O)R$^e$)—, —S—, or —CH₂—S—, —CH₂NR$^e$—;

R$^x$ is absent or selected from a linear, branched or cyclic alkyl having 1 to 10 carbon atoms;

R$^e$ is —H, a linear, branched or cyclic alkyl, alkenyl or alkynyl having 1 to 10 carbon atoms or —(CH₂—CH₂—O)$_n$—R$^k$, wherein R$^k$ is a —H, a linear, branched cyclic alkyl having 1 to 6 carbon atoms, optionally bearing a secondary amino (e.g., —NHR$^{101}$) or tertiary amino (—NR$^{101}$R$^{102}$) group or a 5- or 6-membered nitrogen containing heterocycle, such as piperidine or morpholine, wherein R$^{101}$ and R$^{102}$ are each independently a linear, branched, or cyclic alkyl, alkenyl or alkynyl having 1 to 10 carbon atoms; and G is selected from —CH— or —N—;

X" and X''' are the same or different, and are independently selected from —(CH₂)$_{n'}$—, —NR'—, —CO—, —BH—, —SO— or —SO₂—;

Y" and Y''' are the same or different, and are independently selected from —O—, —NR'— or —S—;

Z" and Z''' are the same or different, and are independently selected from —(CH₂)$_{n'}$—, —NR$_9$'—, —O—, and —S—;

n' is selected from 0, 1, 2 and 3;

R$_7$' and R$_8$' are the same or different, and are each independently selected from —H, —OH, —SH, —COOH, —NHR', a polyethylene glycol unit —(OCH₂CH₂)$_n$—, an amino acid, a peptide unit bearing 2 to 6 amino acids, an optionally substituted linear, branched or cyclic alkyl having from 1 to 10 carbon atoms;

R$_9$' is independently selected from —H, an optionally substituted linear, branched or cyclic alkyl having from 1 to 10 carbon atoms, a polyethylene glycol unit —(OCH₂CH₂)$_n$ —;

R$_A$, R$_{A'}$, R$_B$ and R$_{B'}$ are the same or different, and are independently selected from the group consisting of —H, halide, or an optionally substituted branched, linear or cyclic alkyl having 1 to 10 carbon atoms; or R$_A$ and R$_{A'}$ and/or R$_B$ and R$_{B'}$ together form a double bond containing group =B and =B' respectively;

=B and =B' are the same or different and independently selected from an optionally substituted branched or linear alkenyl or a carbonyl group;

Q$_A$ is Q$_{A1}$-Ar-Q$_{A2}$;

Q$_A$' is Q$_{A1'}$-Ar'-Q$_{A2}$';

Q$_{A1}$ and Q$_{A2}$' are each independently absent, a linear, branched or cyclic alkyl from 1 to 6 carbon atoms or a —CH=CH unit;

Ar and Ar' are each independently absent, or represent an aryl group;

Q$_{A2}$ and Q$_{A2}$' are each independently selected from —H, the linking group with the reactive group bonded thereto, a substituted or unsubstituted linear, branched or cyclic alkyl, alkenyl or alkynyl having from 1 to 10 carbon atoms, a polyethylene glycol unit —R$^{c_1}$—(OCH₂CH₂)$_n$—R$^c$, or a substituent selected from a halogen, guanidinium [—NH(C=NH)NH₂], —OR, —NR'R", —NO₂, —NCO, —NR'COR", —SR, a sulfoxide represented by —SOR', a sulfone represented by —SO₂R', a sulfonate —SO₃M, a sulfate —OSO₃M, a sulfonamide represented by SO₂NR'R", cyano, an azido, —COR', —OCOR' or —OCONR'R"; and R$^{c_1}$ is absent or selected from linear or branched alkyl, alkenyl or alkynyl having 1 to 5 carbon atoms.

In yet another more specific embodiment, D is represented by the following structural formula:

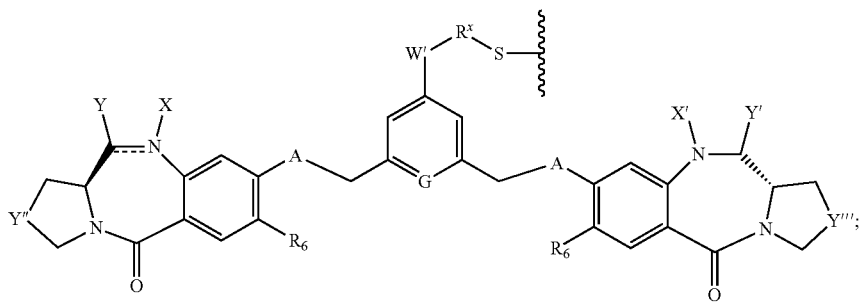

(D15)

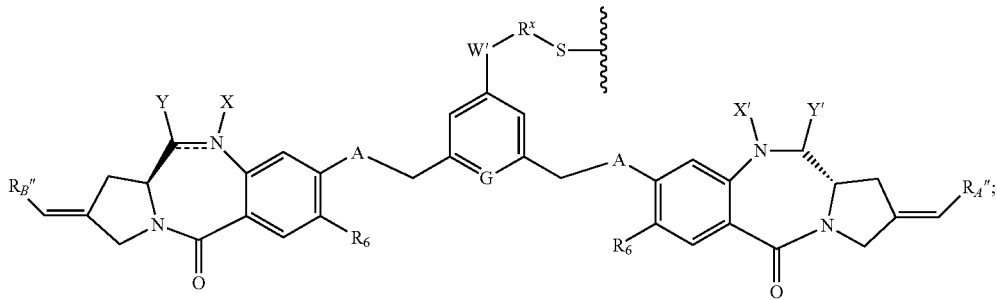

(D16)

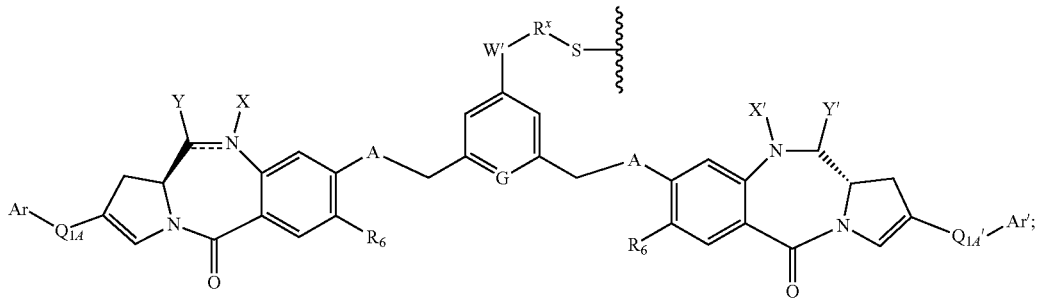

(D17)

or a pharmaceutically acceptable salt thereof, wherein $R_A''$ and $R_B''$ are the same or different, and are selected from —H and -Me; and the remaining variables are as described above.

In certain embodiments, for formulas (D6)-(D17), the double line ═ between N and C represents a single bond or a double bond, provided that when it is a double bond X is absent and Y is —H, and when it is a single bond, X is —H; Y is —OH or —SO$_3$M;

M is —H or a pharmaceutically acceptable cation (e.g., Na$^+$);

X' and Y' are both —H;

A and A' are both —O—;

R$_6$ is —OMe; and

R$^x$ is a linear or branched alkyl having 1 to 6 carbon atoms.

In a more specific embodiment, D is represented by the following structural formula:

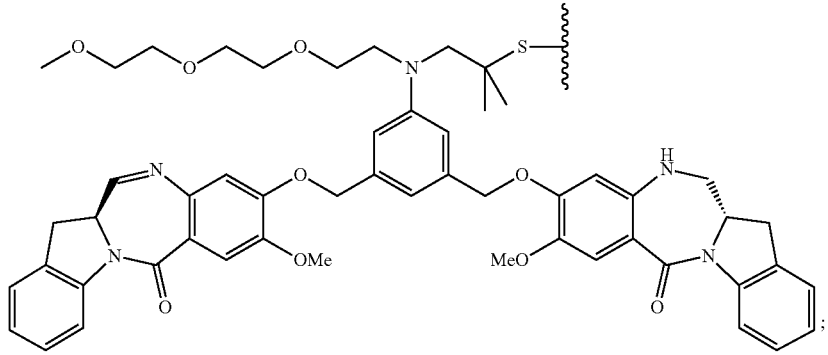

-continued
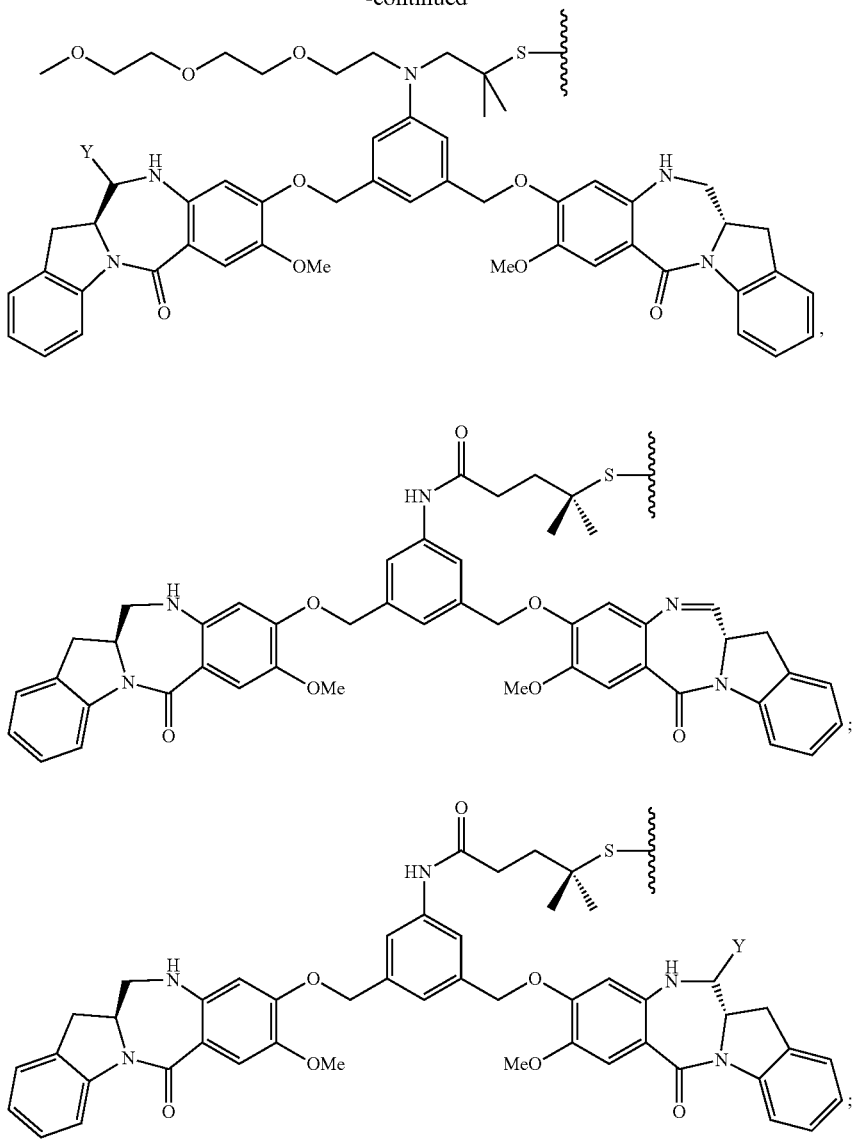
or a pharmaceutically acceptable salt thereof, wherein Y is —H or —SO$_3$M, and M is H$^+$ or a cation. Even more specifically, Y is —SO$_3$M, and M is H$^+$, Na$^+$ or K$^+$.
In a 7$^{th}$ specific embodiment, for the conjugates of formula (I), -L-J$_D$'- is a bond; and D is represented by the following structural formula:
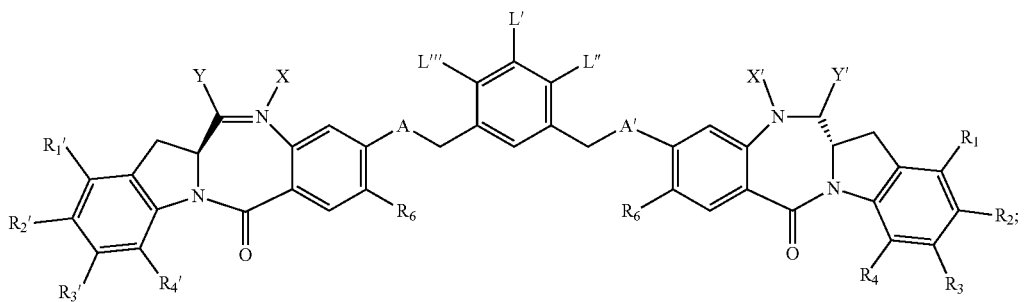

-continued
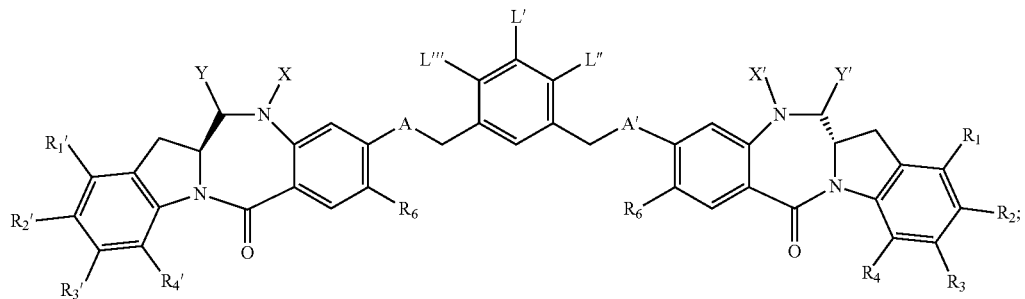
(D19)
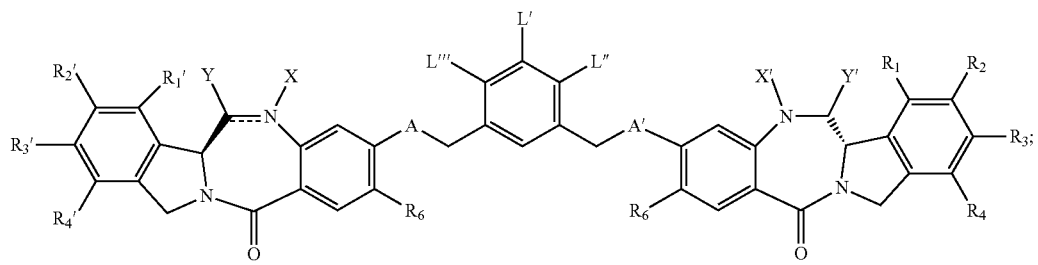
(D20)
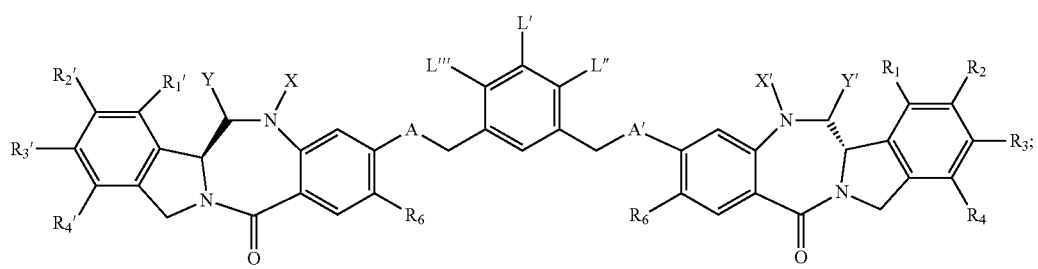
(D21)
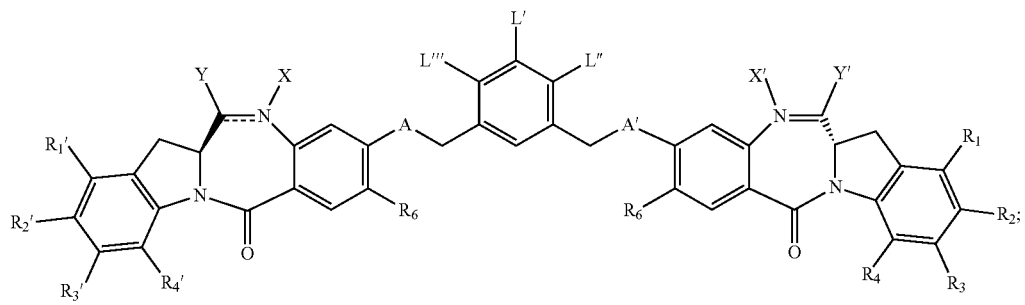
(D22)
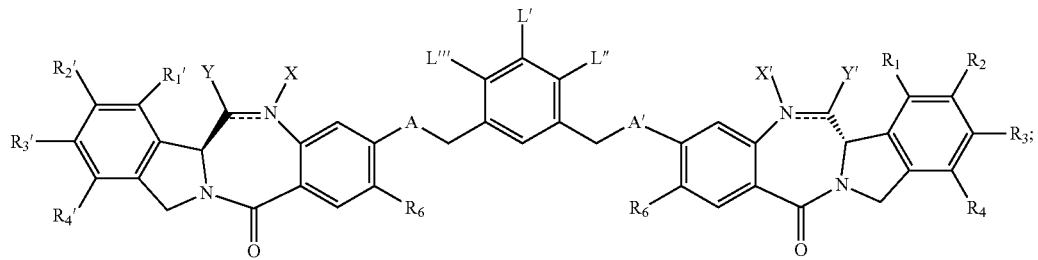
(D23)
or a pharmaceutically acceptable salt thereof, wherein:

one of L', L", and L'" is represented by the following formula:

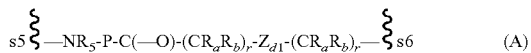

(A)

and the other two are the same or different, and are independently selected from —H, an optionally substituted linear, branched or cyclic alkyl, alkenyl or alkynyl having from 1 to 10 carbon atoms, a polyethylene glycol unit —(OCH$_2$CH$_2$)$_n$—R$^c$, halogen, guanidinium [—NH(C=NH)NH$_2$], —OR, —NR'R", —NO$_2$, —NR'COR", —SR, —SOR', —SO$_2$R', —SO$_3$H, —OSO$_3$H, —SO$_2$NR'R", cyano, an azido, —COR', —OCOR', and —OCONR'R";

$Z_{d1}$ is absent, —C(=O)—NR$_9$— or —NR$_9$—C(=O)—;

P is an amino acid residue or a peptide containing between 2 to 20 amino acid residues;

R$_a$ and R$_b$, for each occurrence, are independently —H, (C$_1$-C$_3$)alkyl or a charged substituent or an ionizable group Q;

r and r' are independently an integer from 1 to 6;

the double line == between N and C represents a single bond or a double bond, provided that when it is a double bond X is absent and Y is —H, or a linear or branched alkyl having 1 to 4 carbon atoms, and when it is a single bond, X is —H or an amine protecting moiety;

Y is a leaving group selected from —OR, —OCOR', —OCOOR', —OCONR'R", —NR'R", —NR'COR", —NR'NR'R", an optionally substituted 5- or 6-membered nitrogen-containing heterocycle (e.g., piperidine, tetrahydropyrrole, pyrazole, morpholine, etc. attached through the nitrogen atom), a guanidinum represented by —NR'(C=NH)NR'R", an amino acid, or a peptide represented by —NR-COP', —SR, —SOR', halogen, cyano, azido, —OSO$_3$H, sulfite (—SO$_3$H or —SO$_2$H), metabisulfite (H$_2$S$_2$O$_5$), mono-, di-, tri-, and tetra-thiophosphate (PO$_3$SH$_3$, PO$_2$S$_2$H$_2$, POS$_3$H$_2$, PS$_4$H$_2$), thio phosphate ester (R$^i$O)$_2$PS(OR$^i$), R$^i$S—, R$^i$SO, R$^i$S$_{02}$, R$^1$SO$_3$, thiosulfate (HS$_2$O$_3$), dithionite (HS$_2$O$_4$), phosphorodithioate (P(=S)(OR$^{k'}$)(S)(OH)), hydroxamic acid (R$^k$C(=O)NOH), and formaldehyde sulfoxylate (HOCH$_2$SO$_2$") or a mixture thereof, wherein R$^i$ is a linear or branched alkyl having 1 to 10 carbon atoms and is substituted with at least one substituent selected from —N(R$^j$)$_2$, —CO$_2$H, —SO$_3$H, and —PO$_3$H; R$^i$ can be further optionally substituted with a substituent for an alkyl described herein; R$^j$ is a linear or branched alkyl having 1 to 6 carbon atoms; R$^{k'}$ is a linear, branched or cyclic alkyl, alkenyl or alkynyl having 1 to 10 carbon atoms, aryl, heterocyclyl or heteroaryl;

P' is an amino acid residue or a polypeptide containing between 2 to 20 amino acid residue, R, for each occurrence, is independently selected from the group consisting of —H, an optionally substituted linear, branched or cyclic alkyl, alkenyl or alkynyl having from 1 to 10 carbon atoms, a polyethylene glycol unit —(CH$_2$CH$_2$O)$_n$—R$^c$, an optionally substituted aryl having 6 to 18 carbon atoms, an optionally substituted 5- to 18-membered heteroaryl ring containing one or more heteroatoms independently selected from nitrogen, oxygen, and sulfur, or an optionally substituted 3- to 18-membered heterocyclic ring containing 1 to 6 heteroatoms independently selected from O, S, N and P;

R' and R" are each independently selected from —H, —OH, —OR, —NHR, —NR$_2$, —COR, an optionally substituted linear, branched or cyclic alkyl, alkenyl or alkynyl having from 1 to 10 carbon atoms, a polyethylene glycol unit —(CH$_2$CH$_2$O)$_n$—R$^c$, and an optionally substituted 3- to 18-membered heterocyclic ring having 1 to 6 heteroatoms independently selected from O, S, N and P;

R$^c$ is —H or an optionally substituted linear or branched alkyl having 1 to 4 carbon atoms;

n is an integer from 1 to 24;

X' is selected from —H, an amine-protecting group, an optionally substituted linear, branched or cyclic alkyl, alkenyl or alkynyl having from 1 to 10 carbon atoms, a polyethylene glycol unit —(CH$_2$CH$_2$O)$_n$—R$^c$, an optionally substituted aryl having 6 to 18 carbon atoms, an optionally substituted 5- to 18-membered heteroaryl ring containing one or more heteroatoms independently selected from nitrogen, oxygen, and sulfur, and an optionally substituted 3- to 18-membered heterocyclic ring containing 1 to 6 heteroatoms independently selected from O, S, N and P;

Y' is selected from —H, an oxo group, an optionally substituted linear, branched or cyclic alkyl, alkenyl or alkynyl having from 1 to 10 carbon atoms, an optionally substituted 6- to 18-membered aryl, an optionally substituted 5- to 18-membered heteroaryl ring containing one or more heteroatoms independently selected from nitrogen, oxygen, and sulfur, an optionally substituted 3- to 18-membered heterocyclic ring having 1 to 6 heteroatoms;

R$_1$, R$_2$, R$_3$, R$_4$, R$_1$', R$_2$', R$_3$' and R$_4$' are each independently selected from the group consisting of —H, an optionally substituted linear, branched or cyclic alkyl, alkenyl or alkynyl having from 1 to 10 carbon atoms, a polyethylene glycol unit —(OCH$_2$CH$_2$)$_n$—R$^c$, halogen, guanidinium [—NH(C=NH)NH$_2$], —OR, —NR'R", —NO$_2$, —NCO, —NR'COR", —SR, —SOR', —SO$_2$R', —SO$_3$$^-$H, —OSO$_3$H, —SO$_2$NR'R", cyano, an azido, —COR', —OCOR', and —OCONR'R";

R$_6$ is —H, —R, —OR, —SR, —NR'R", —NO$_2$, or halogen;

A and A' are the same or different, and are independently selected from —O—, oxo (—C(=O)—), —CRR' O—, —CRR'—, —S—, —CRR'S—, —NR$_5$ and —CRR'N(R$_5$)—; and R$_5$ and R$_9$ are each independently —H or an optionally substituted linear or branched alkyl having 1 to 10 carbon atoms; and the remaining variables are as described above in the first embodiment or the 1$^{st}$ specific embodiment or any more specific embodiments described therein.

In a more specific embodiment, for formulas (D18)-(D23), L' is represented by formula (A) and L" and L'" are both —H.

In another more specific embodiment, for formulas (D18)-(D23):

the double line == between N and C represents a single bond or double bond, provided that when it is a double bond X is absent and Y is —H, and when it is a single bond, X is —H, Y is —OH or —SO$_3$M;

R$_1$, R$_2$, R$_3$, R$_4$, R$_1$', R$_2$', R$_3$' and R$_4$' are all —H;

R$_6$ is —OMe;

X' and Y' are both —H;

A and A' are —O—; and

M is H$^+$, Na$^+$ or K$^+$; and the remaining variables are as described above in the 7$^{th}$ specific embodiment or any more specific embodiments described above.

In yet another more specific embodiment, for formulas (D18)-(D23), R$_a$ and R$_b$ are both H; and the remaining variables are as described above in the 7$^{th}$ specific embodiment or any more specific embodiments described above.

In another more specific embodiment, for formulas (D18)-(D23), R$_5$ and R$_9$ are each independently H or Me; and the remaining variables are as described above in the 7$^{th}$ specific embodiment or any more specific embodiments described above. More specifically, $R_5$ and $R_9$ are both H.

In another more specific embodiment, for formulas (D18)-(D23), P is a peptide containing 2 to 10 amino acid residues; and the remaining variables are as described above in the 7$^{th}$ specific embodiment or any more specific embodiments described above. More specifically, P is a peptide containing 2 to 5 amino acid residues. Even more specifically, P is elected from Gly-Gly-Gly, Ala-Val, Val-Ala, Val-Cit, Val-Lys, Phe-Lys, Lys-Lys, Ala-Lys, Phe-Cit, Leu-Cit, Ile-Cit, Trp, Cit, Phe-Ala, Phe-N$^9$-tosyl-Arg, Phe-N$^9$-nitro-Arg, Phe-Phe-Lys, D-Phe-Phe-Lys, Gly-Phe-Lys, Leu-Ala-Leu, Ile-Ala-Leu, Val-Ala-Val, Ala-Leu-Ala-Leu (SEQ ID NO: 17), β-Ala-Leu-Ala-Leu (SEQ ID NO: 18) and Gly-Phe-Leu-Gly (SEQ ID NO: 19), Val-Arg, Arg-Val, Arg-Arg, Val-D-Cit, Val-D-Lys, Val-D-Arg, D-Val-Cit, D-Val-Lys, D-Val-Arg, D-Val-D-Cit, D-Val-D-Lys, D-Val-D-Arg, D-Arg-D-Arg, Ala-Ala, Ala-D-Ala, D-Ala-Ala, and D-Ala-D-Ala.

In another more specific embodiment, for the conjugates of formula (I), -L-J$_D$'-D is represented by the following structural formula:

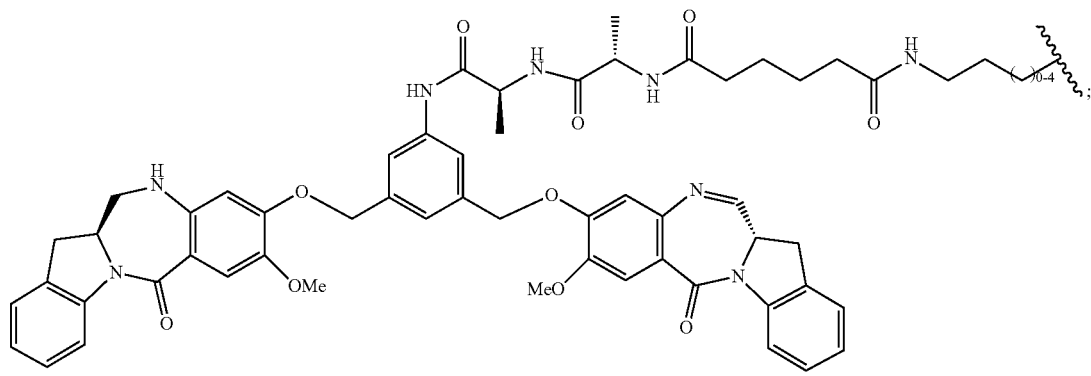

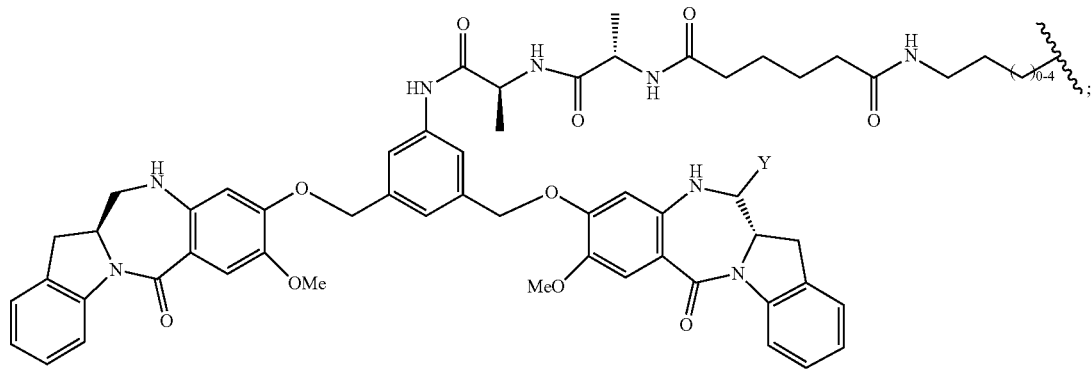

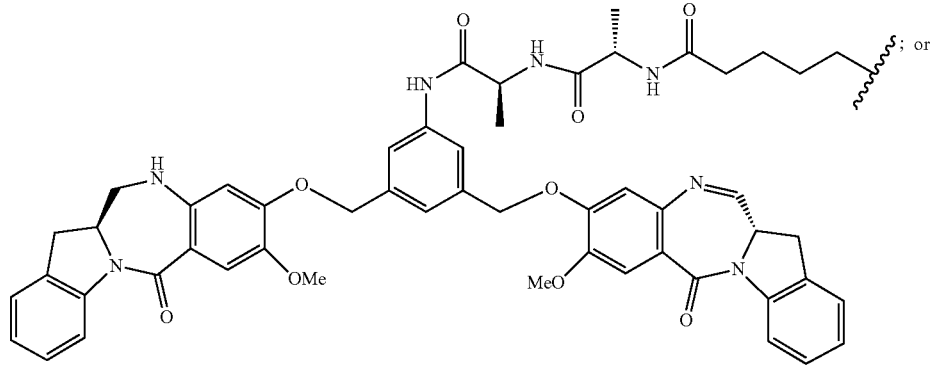

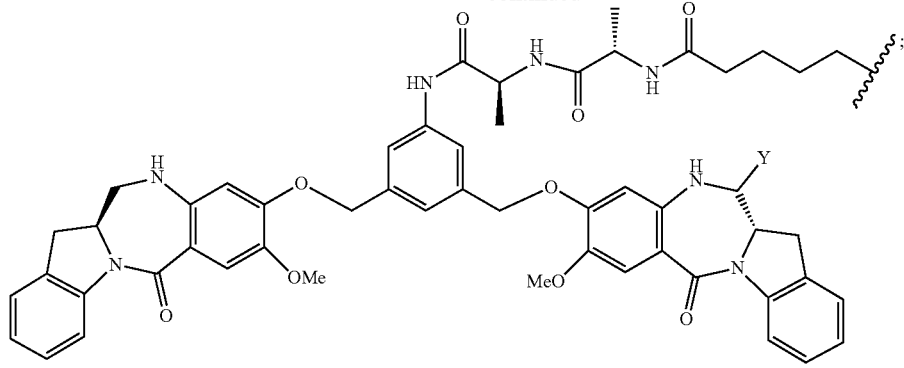
or a pharmaceutically acceptable salt thereof, wherein Y is H or —$SO_3M$ and M is $H^+$, $Na^+$ or $K^+$.
In a 8$^{th}$ specific embodiment, the conjugates of formula (I) is represented by the following structural formulas:
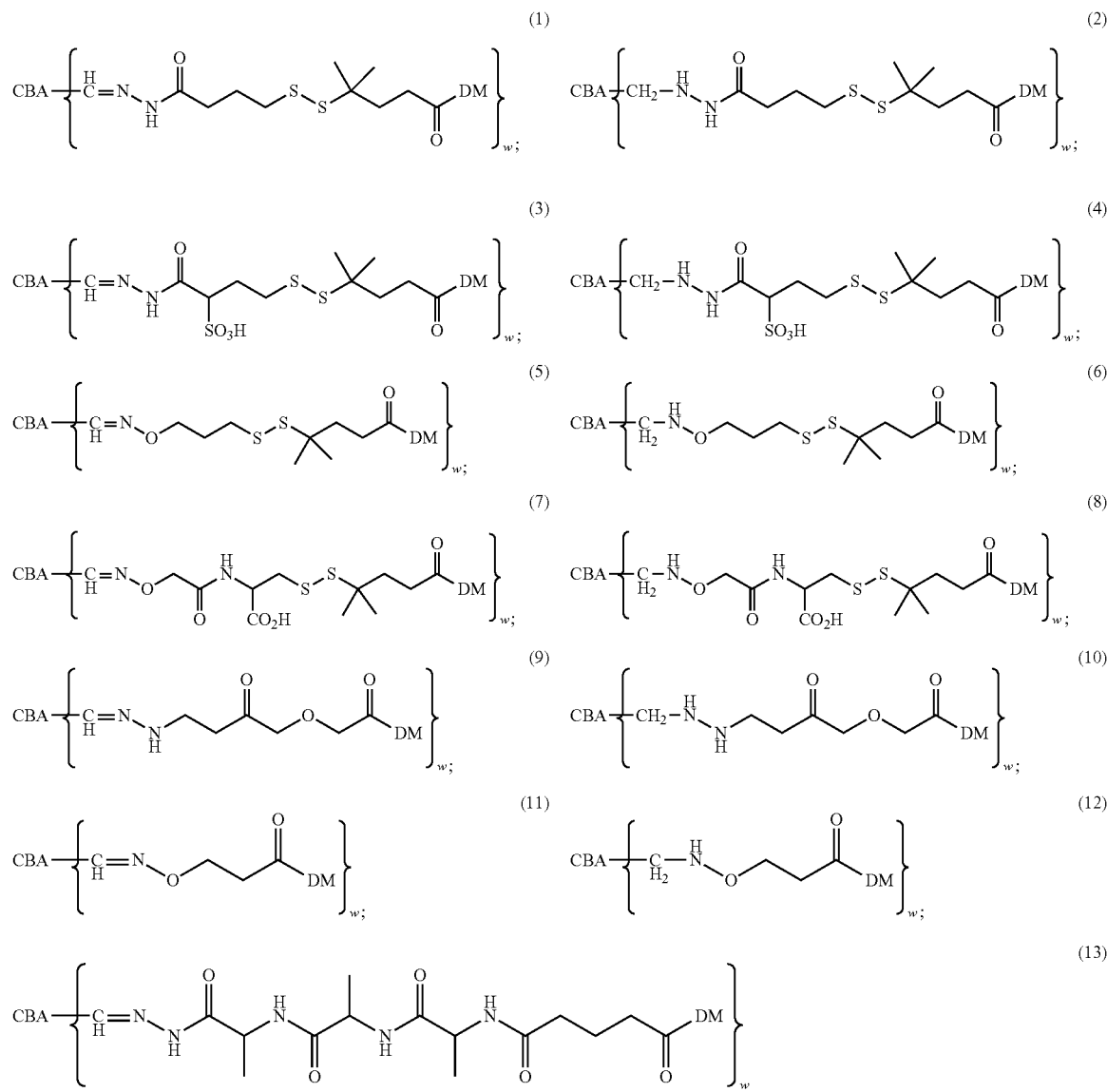

-continued
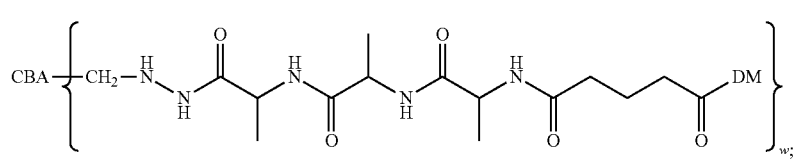
(14)
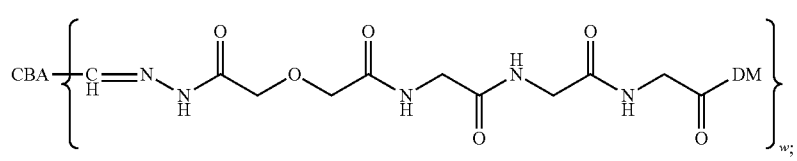
(15)
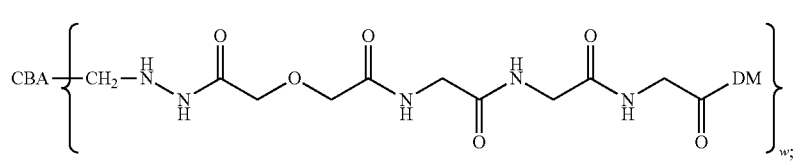
(16)
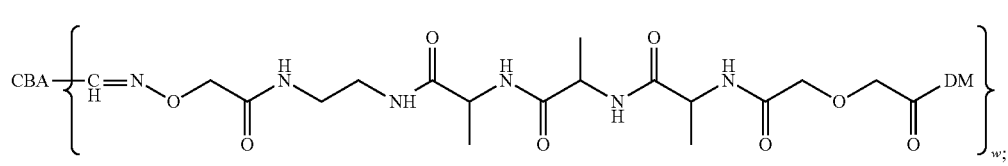
(17)
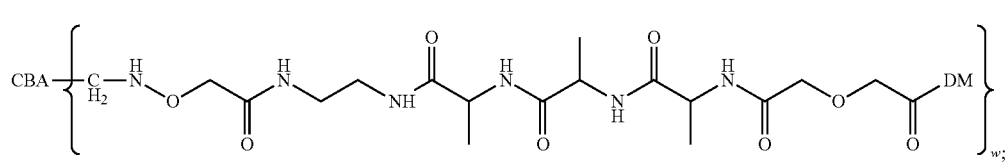
(18)
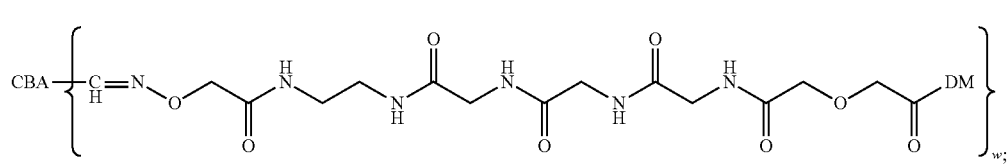
(19)
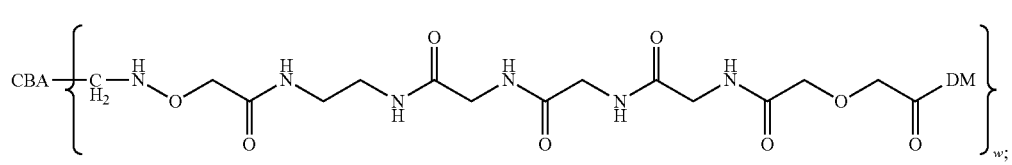
(20)
(21)
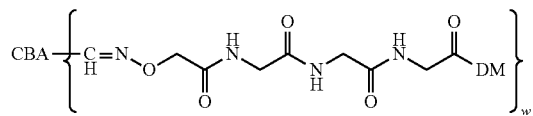
(22)
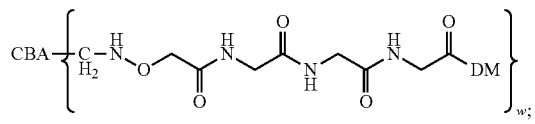
(23)
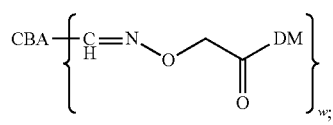
(24)
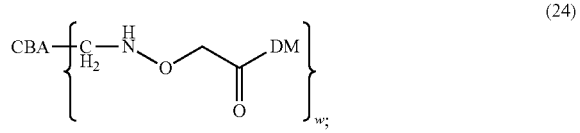

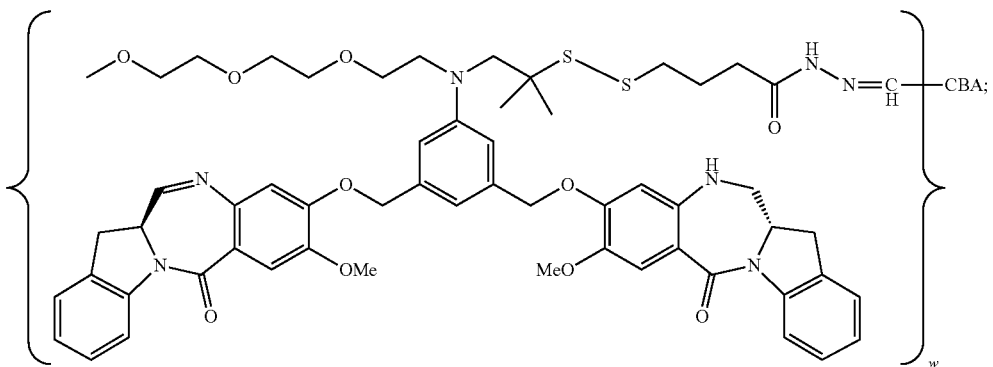
(25)
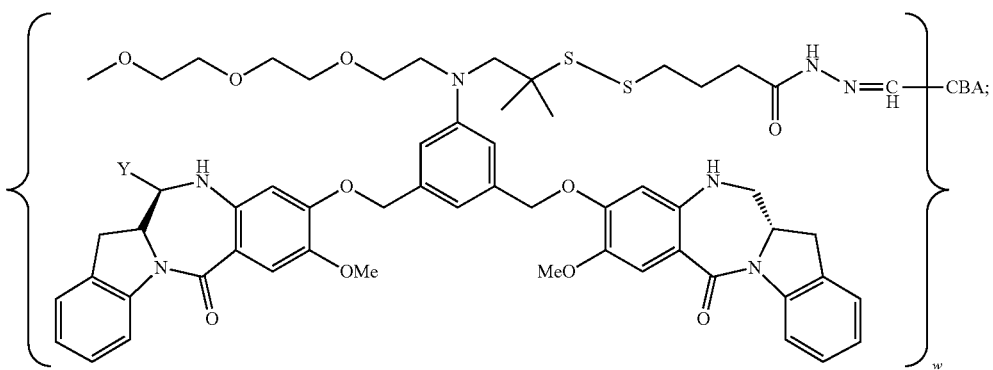
(26)
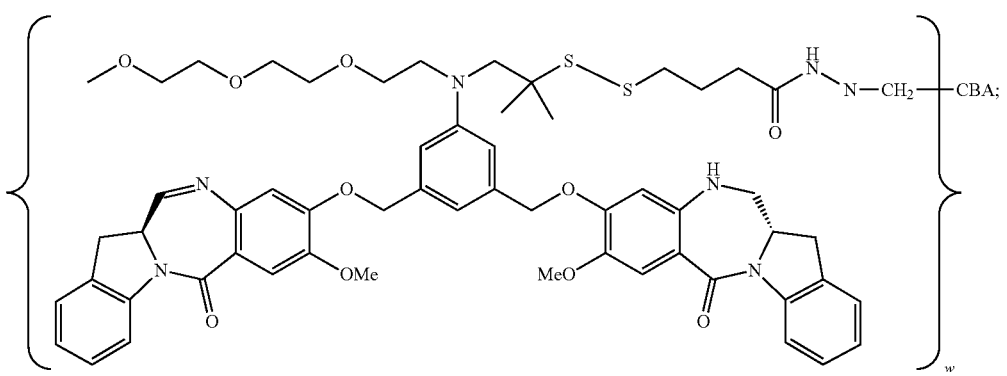
(27)
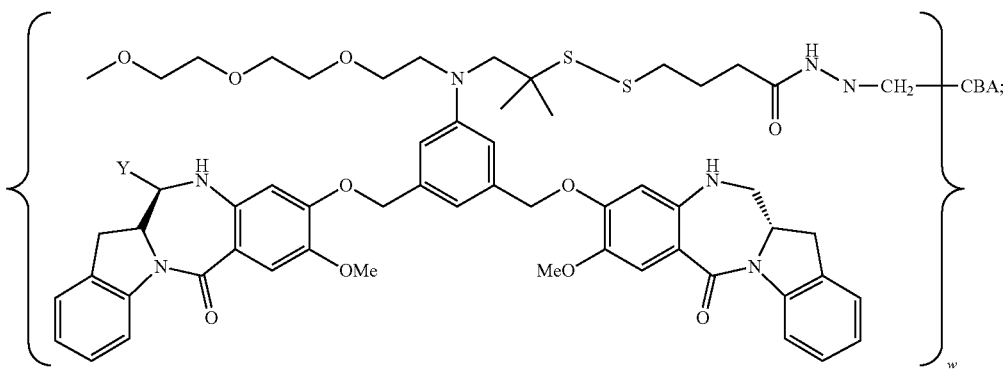
(28)

-continued
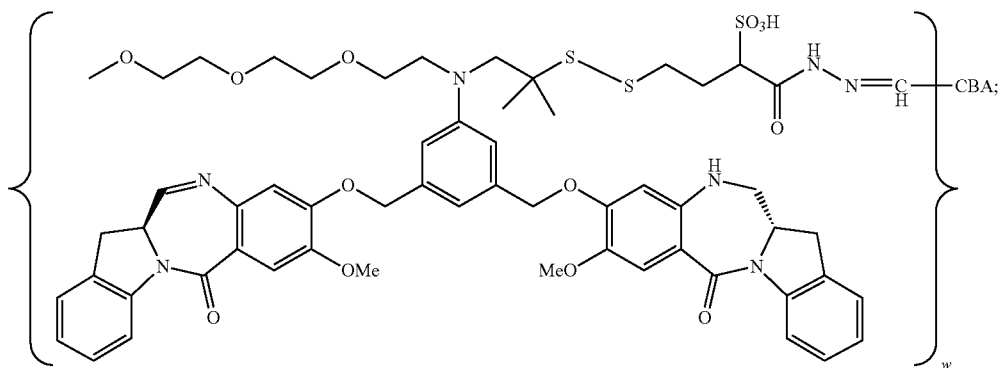
(29)
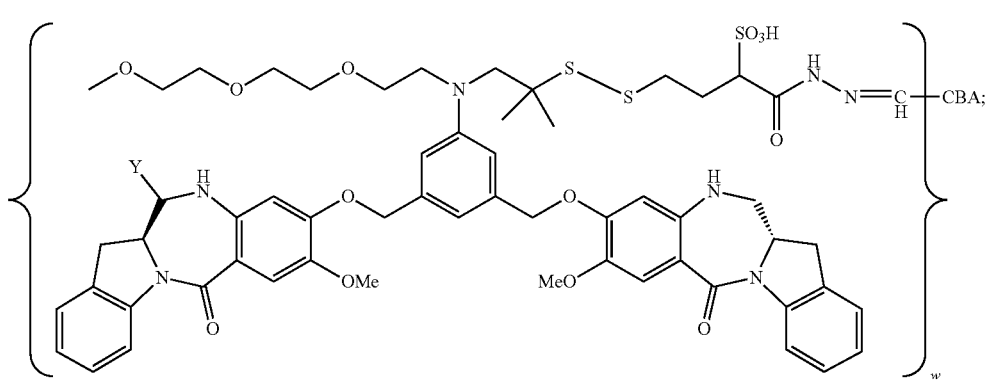
(30)
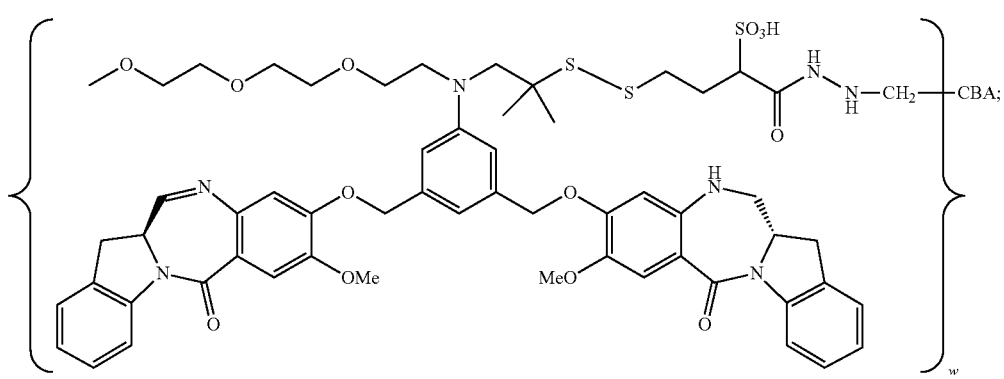
(31)
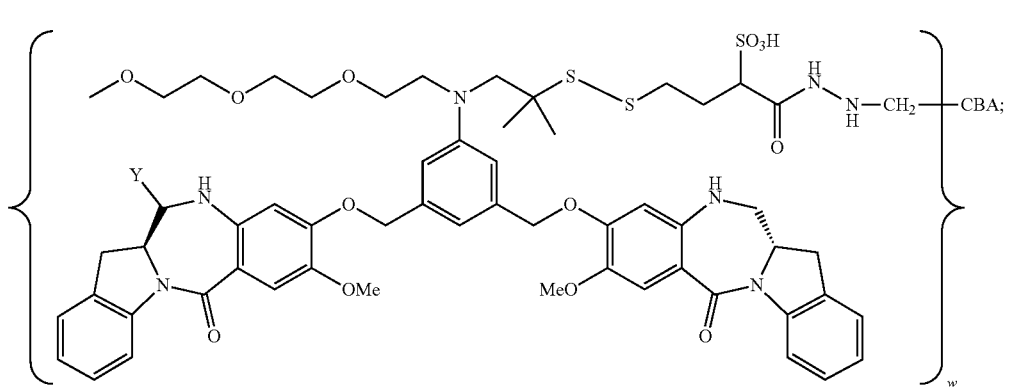
(32)

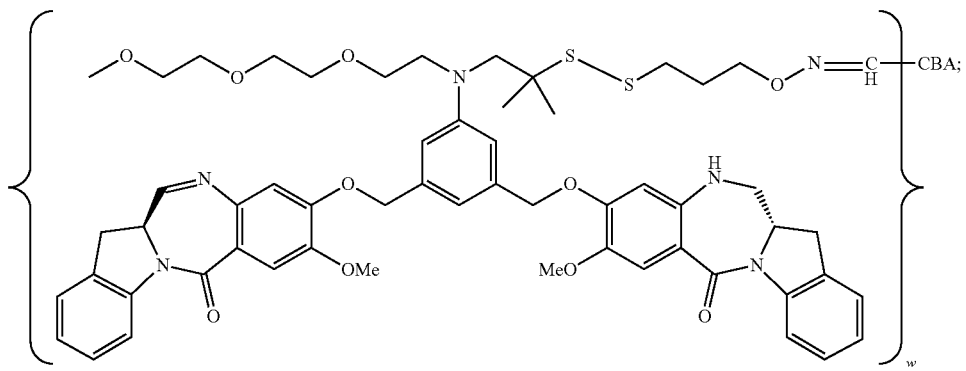
(33)
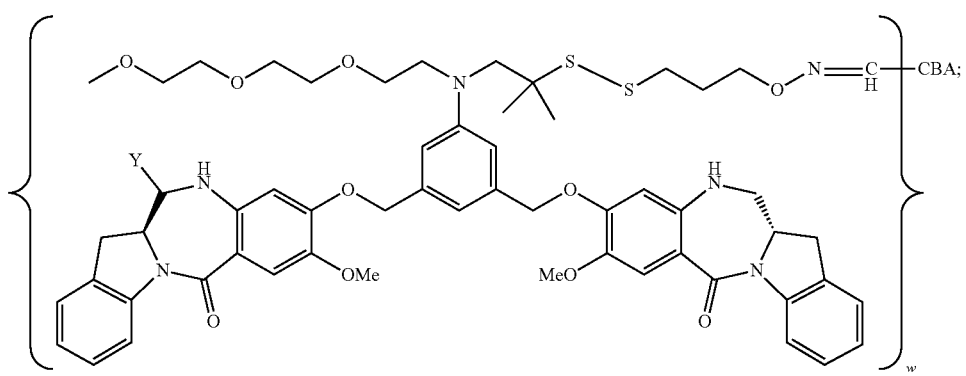
(34)
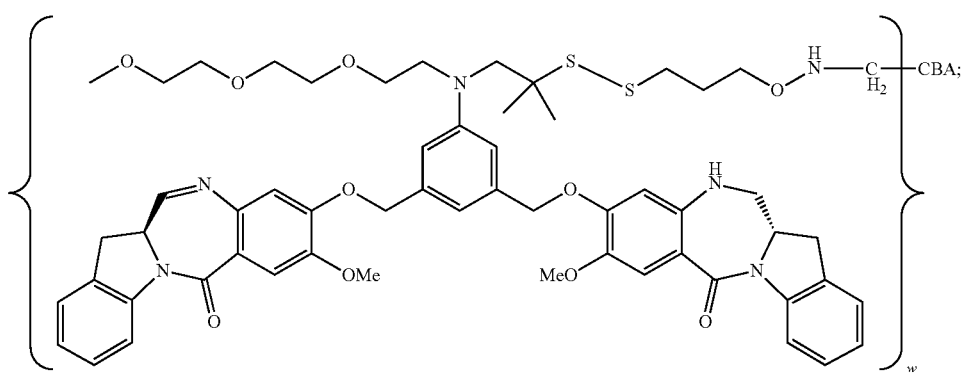
(35)
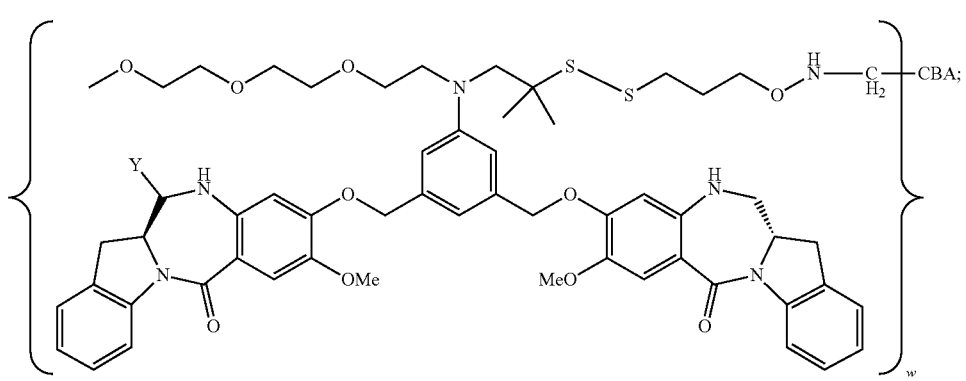
(36)

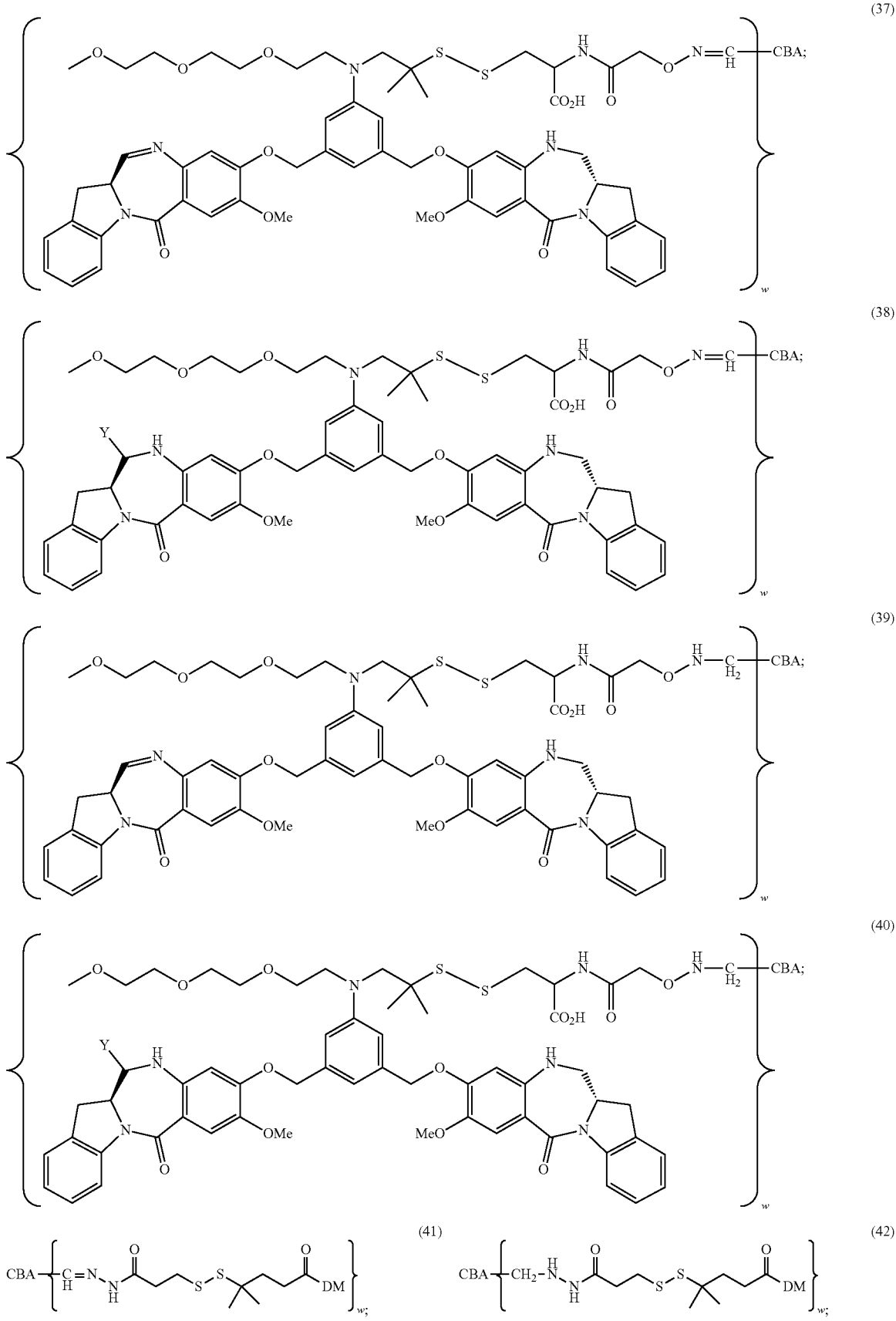

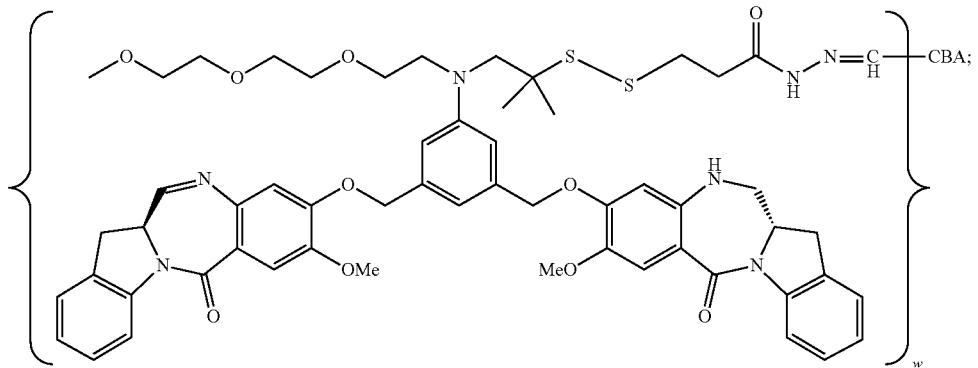
(43)
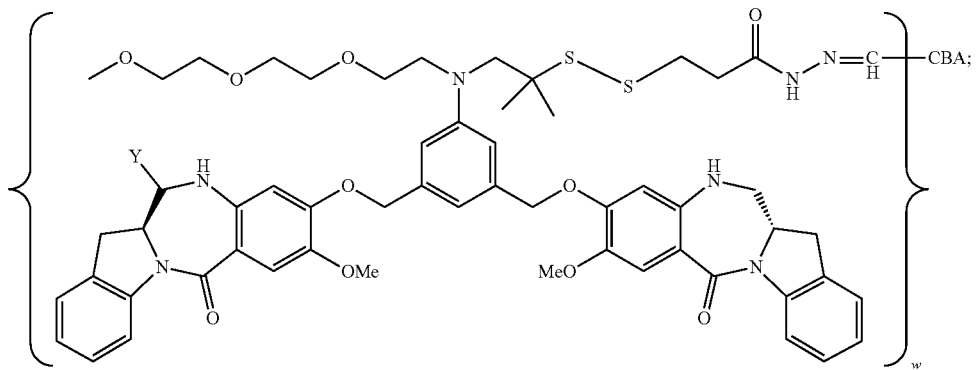
(44)
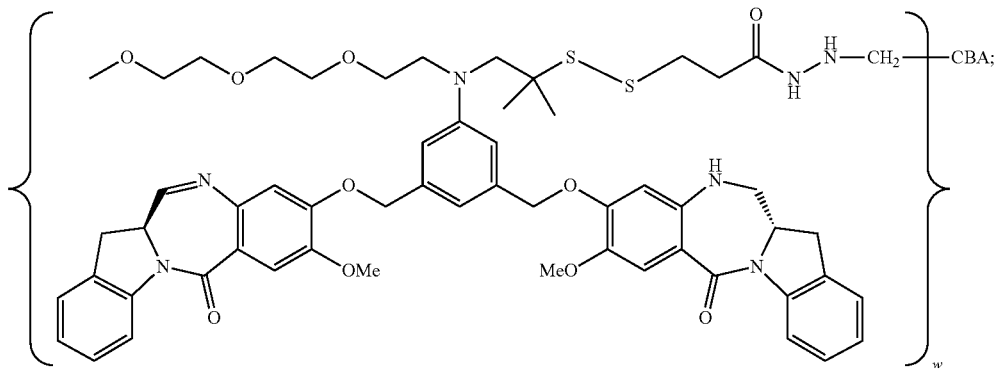
(45)
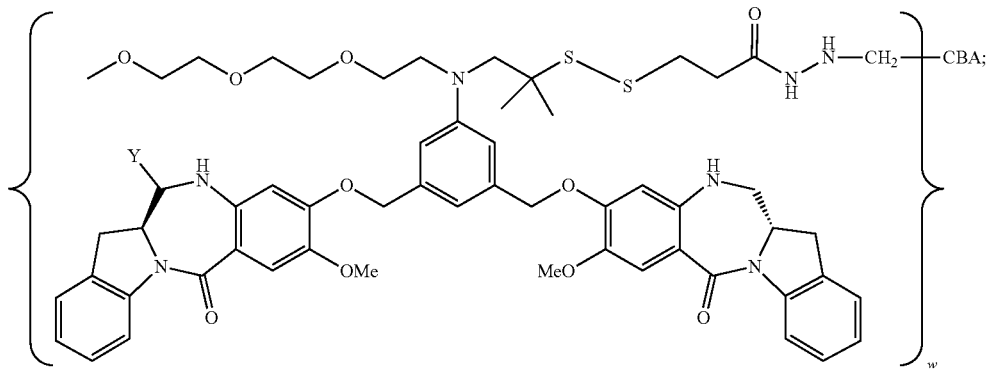
(46)

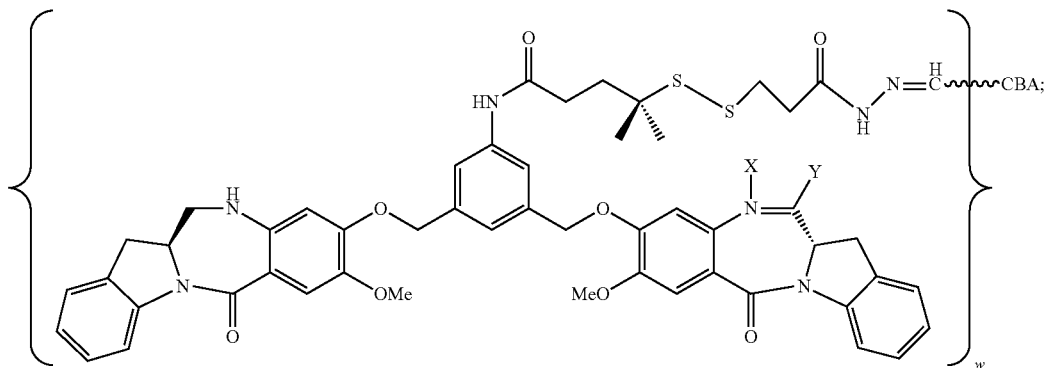
(47a)
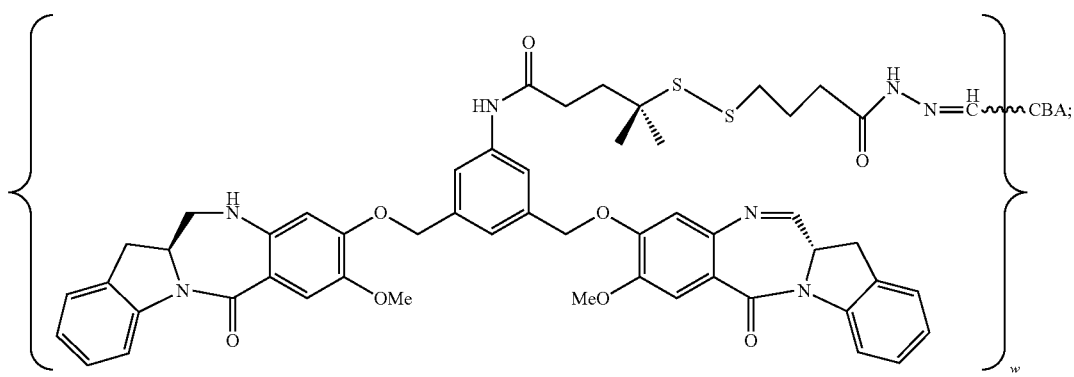
(47)
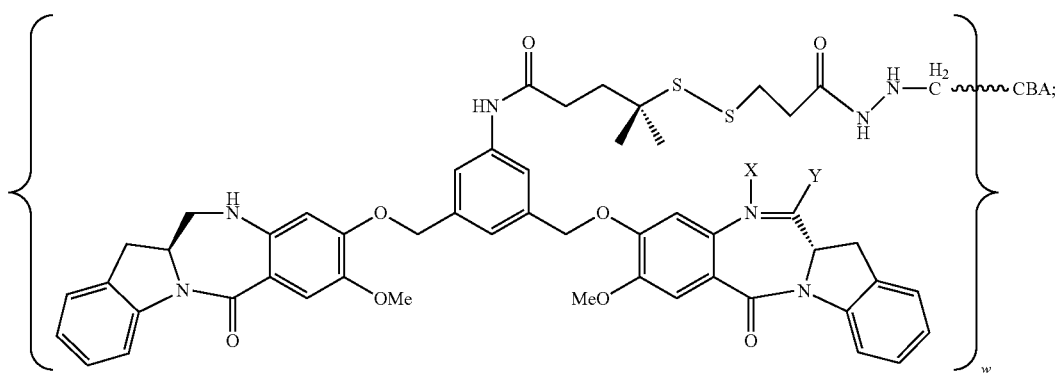
(48a)
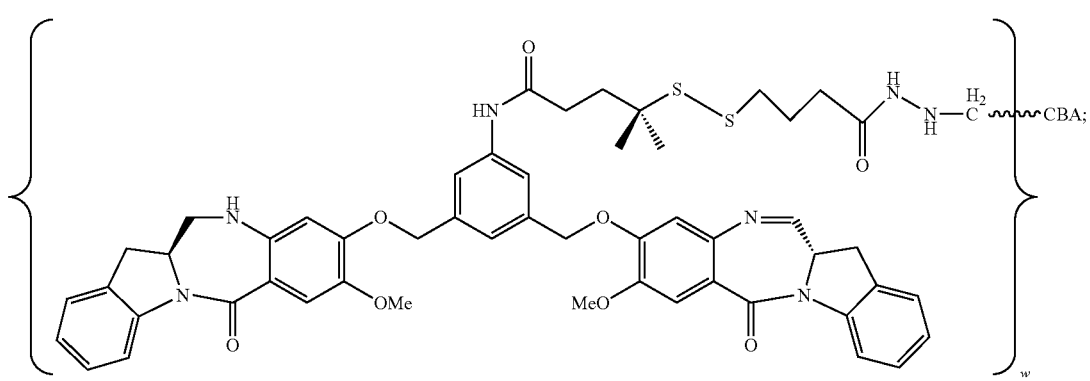
(48)

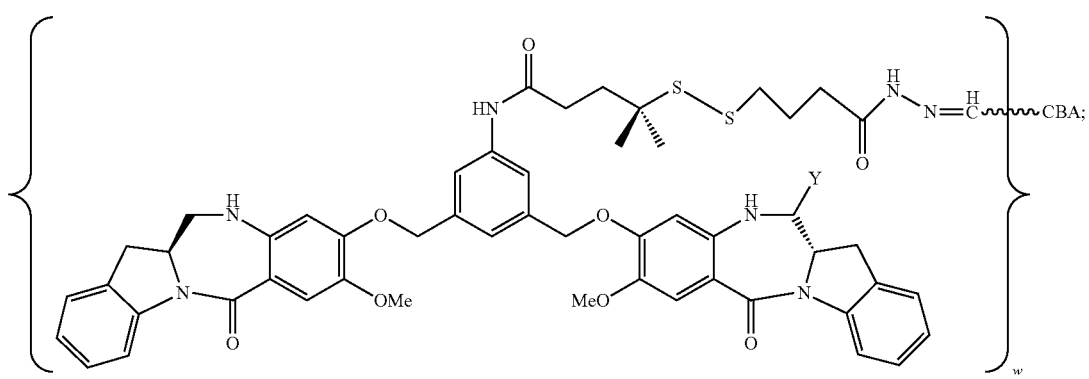
(49)
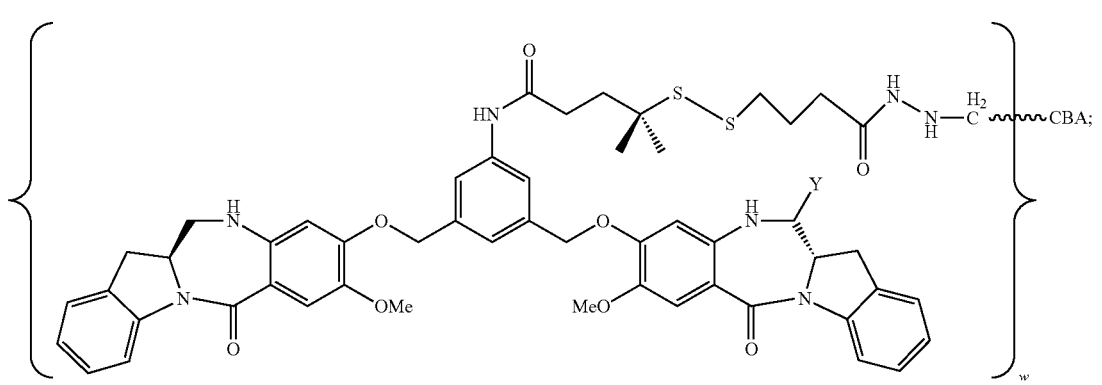
(50)
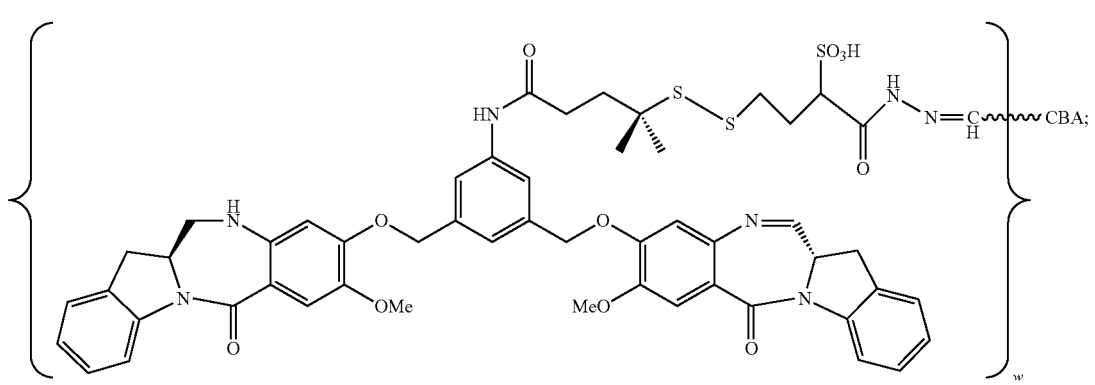
(51)
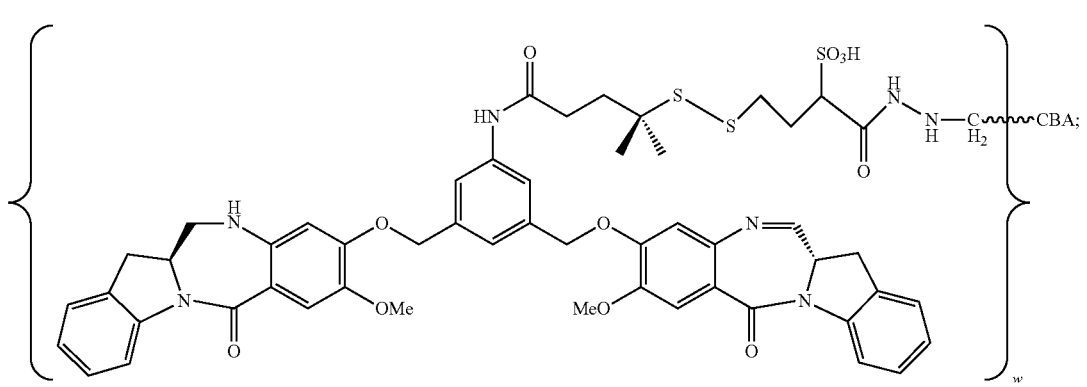
(52)

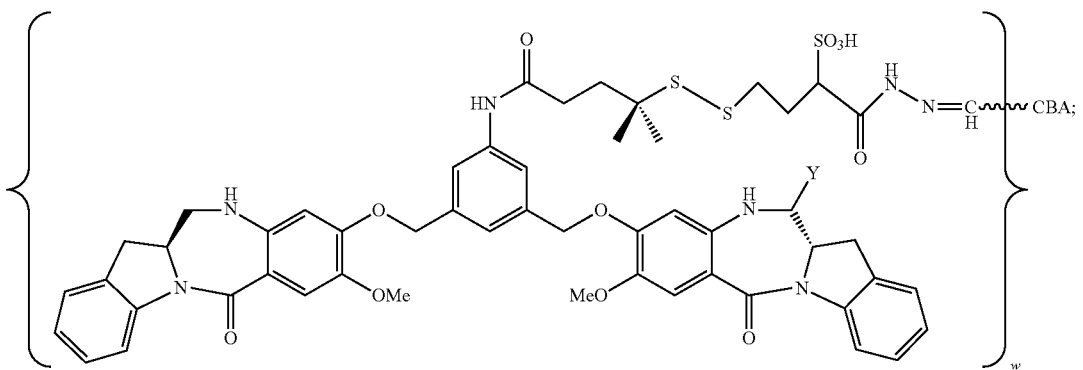
(53)
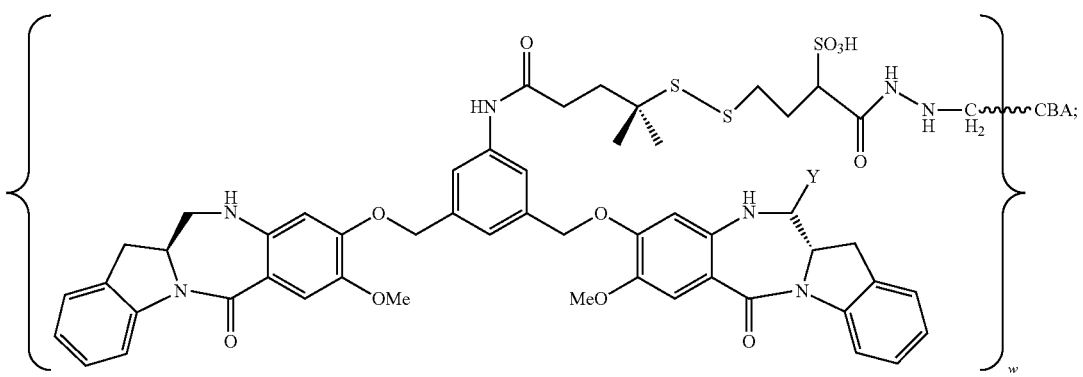
(54)
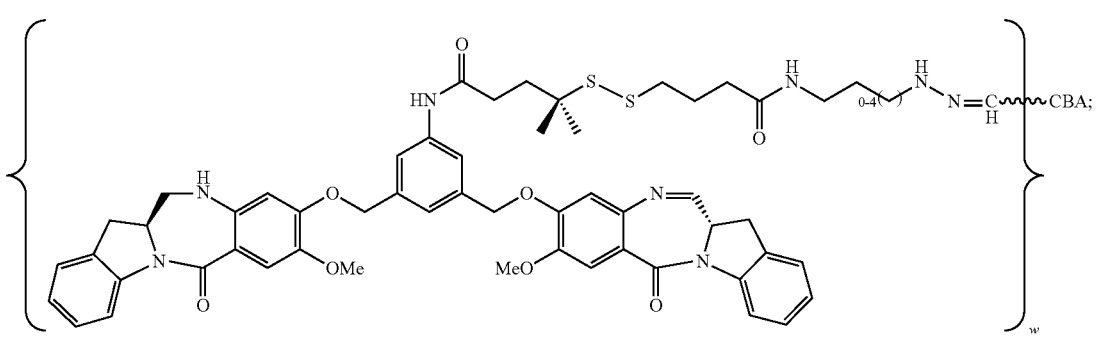
(55)
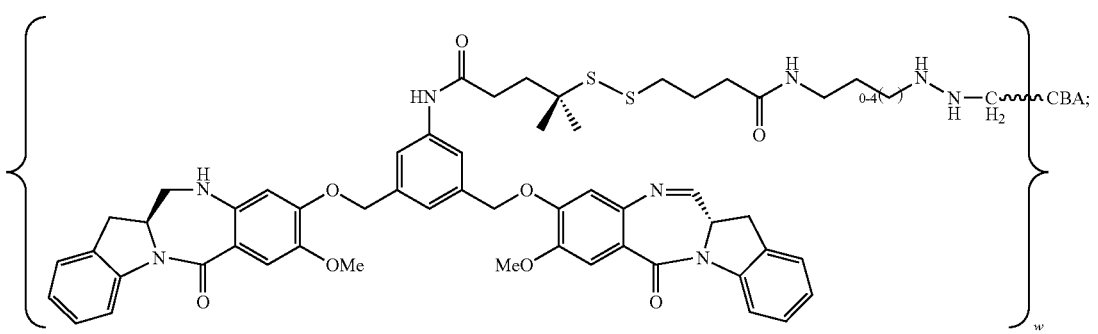
(56)

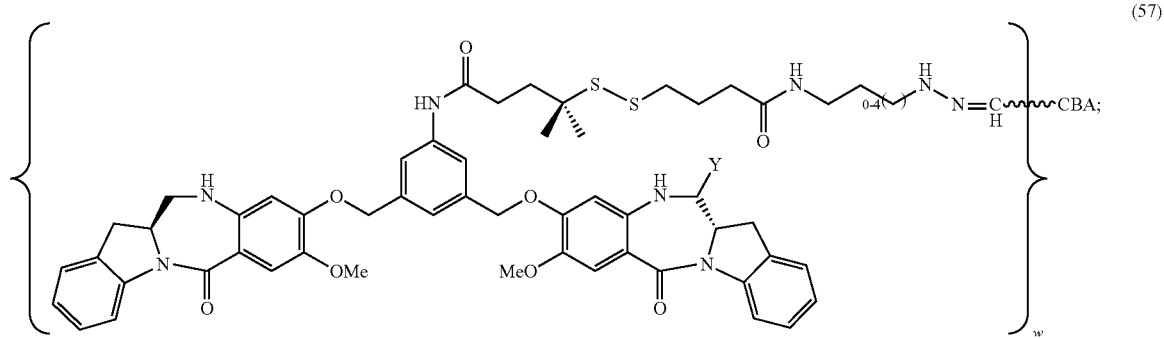
(57)
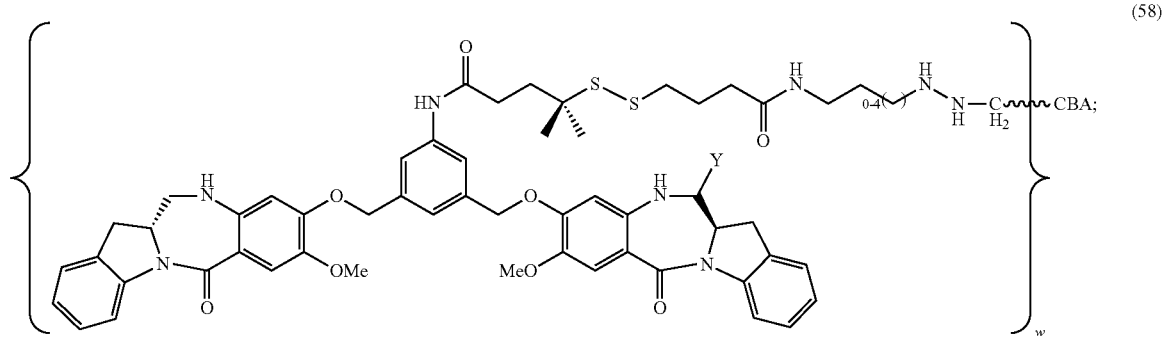
(58)
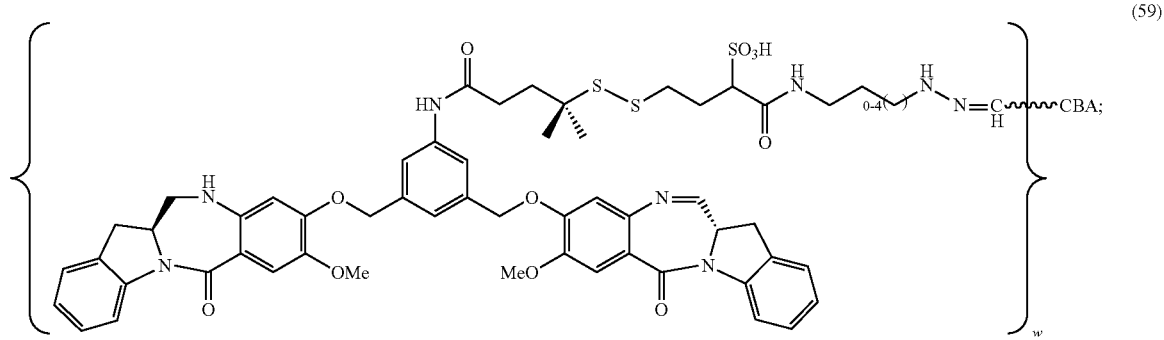
(59)
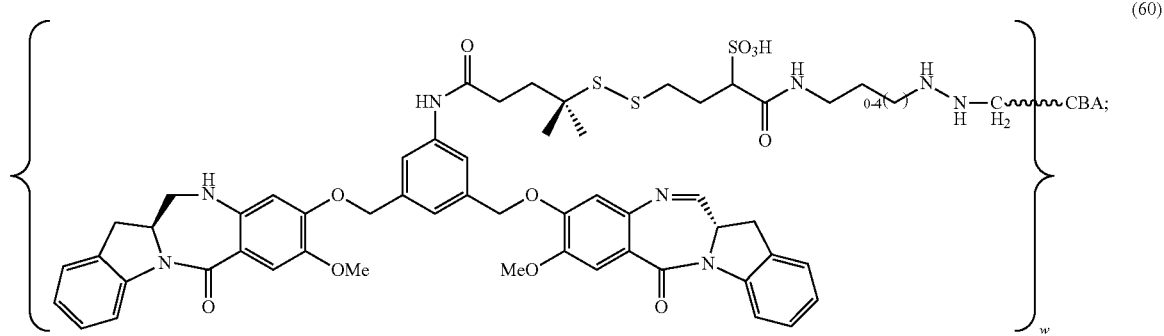
(60)
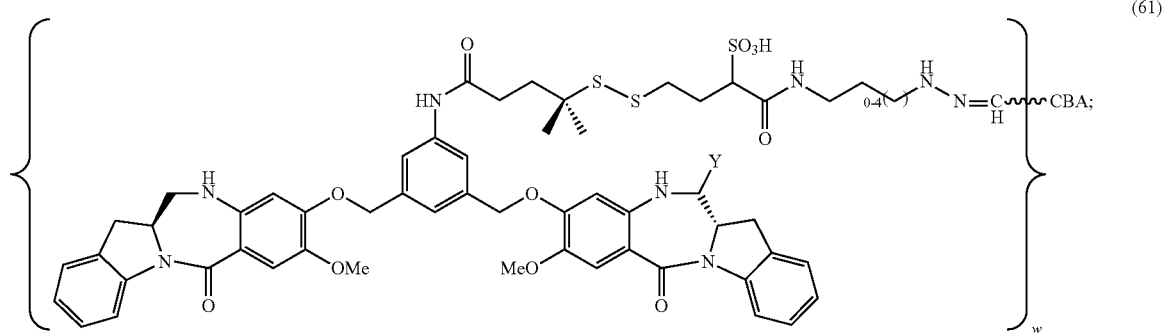
(61)

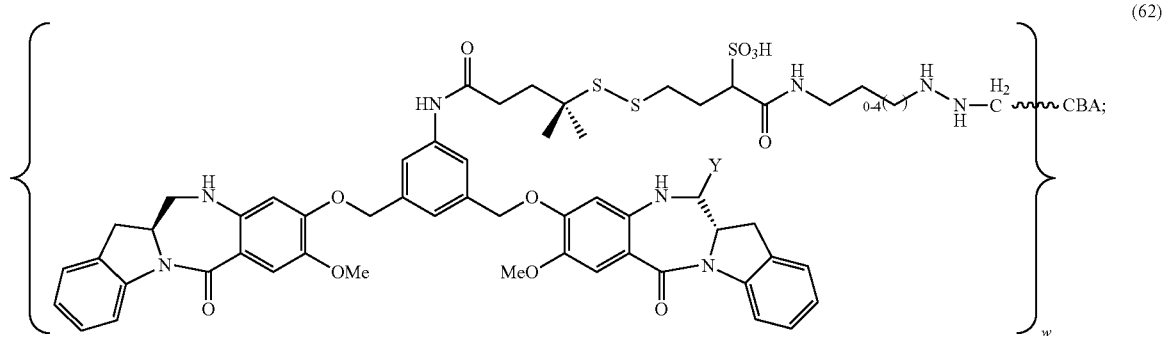
(62)
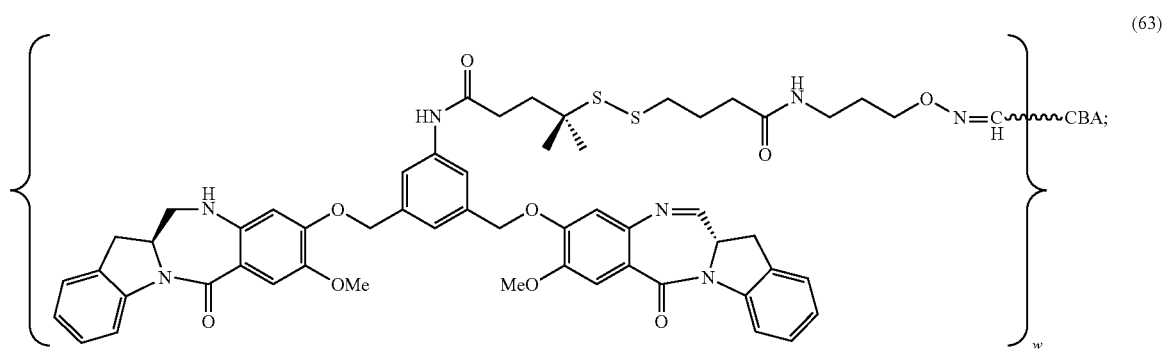
(63)
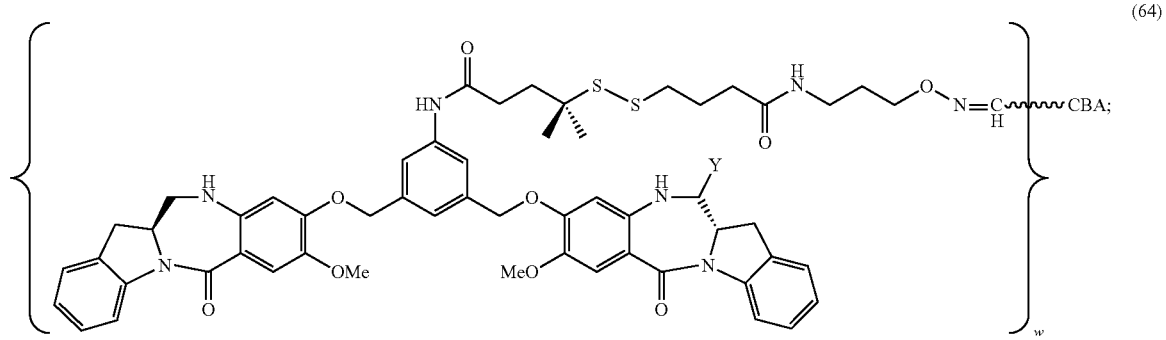
(64)
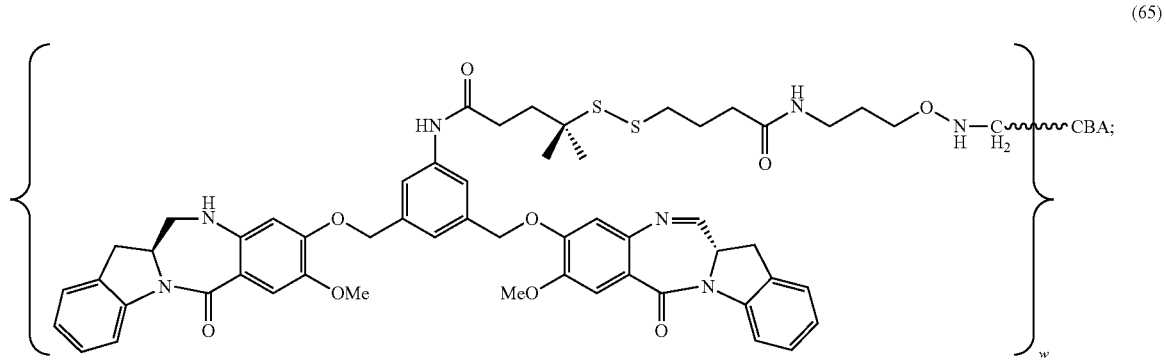
(65)

-continued
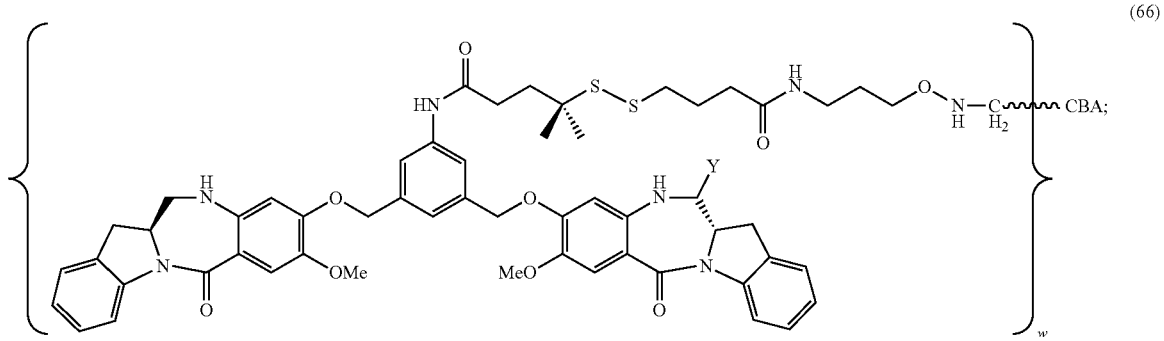
(66)
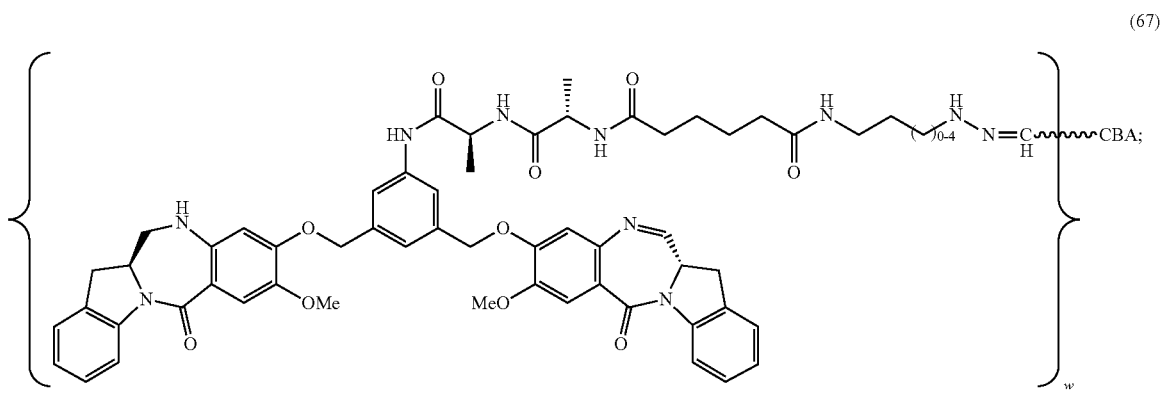
(67)
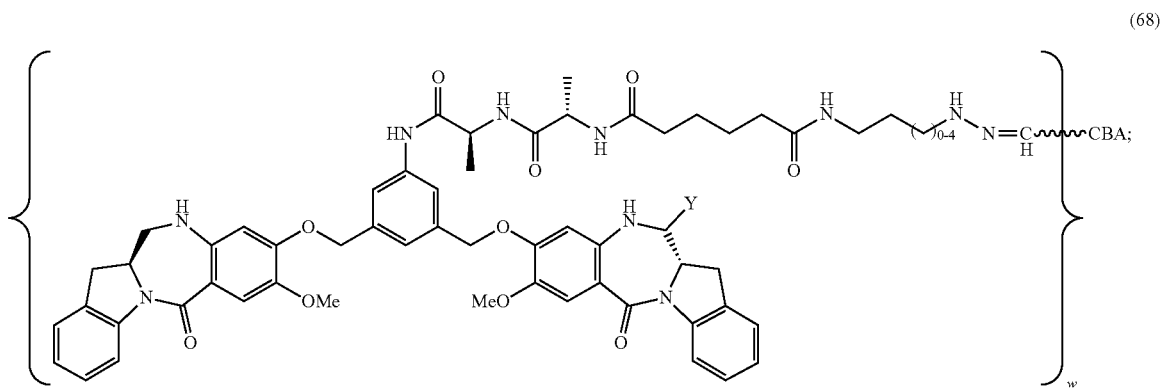
(68)
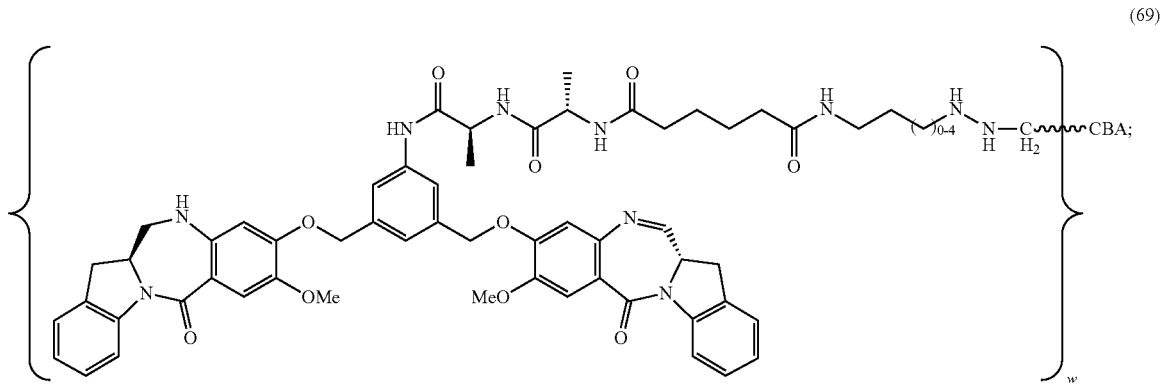
(69)

(70)
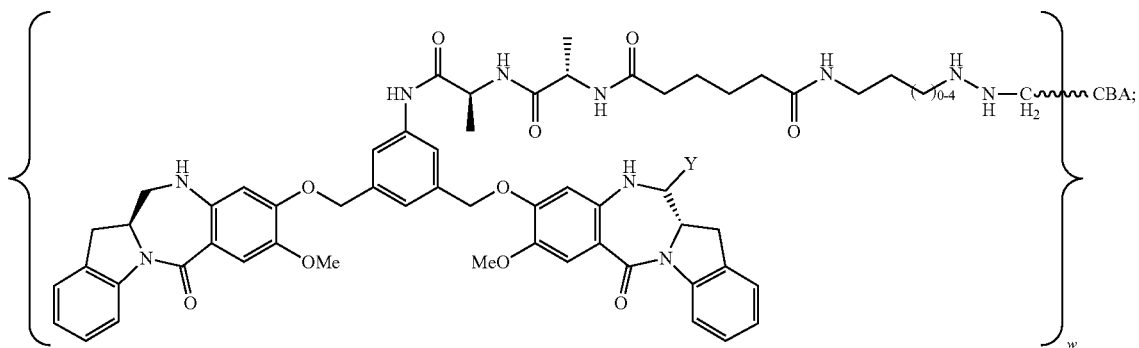
(71)
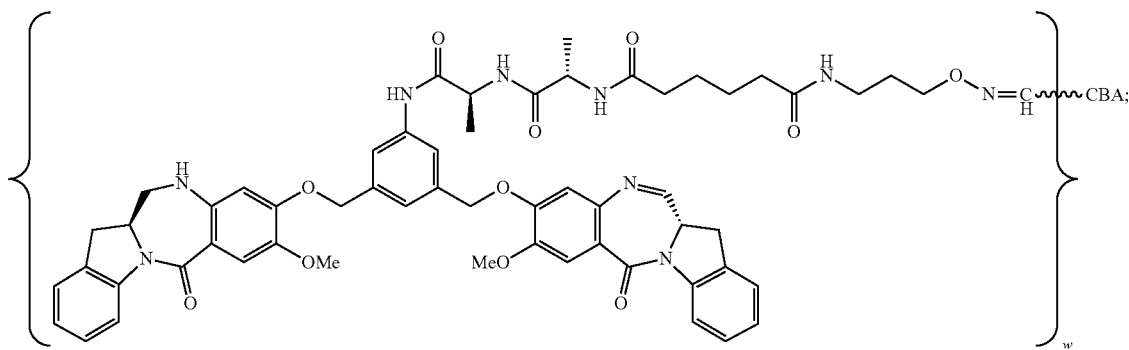
(72)
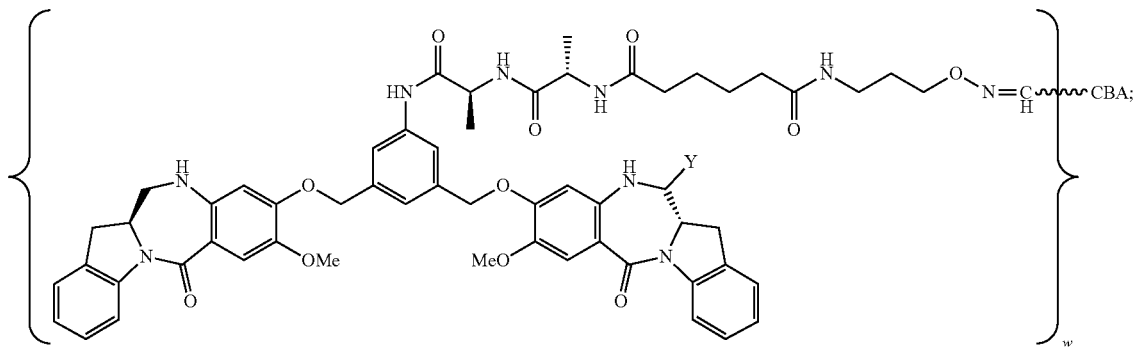
(73)
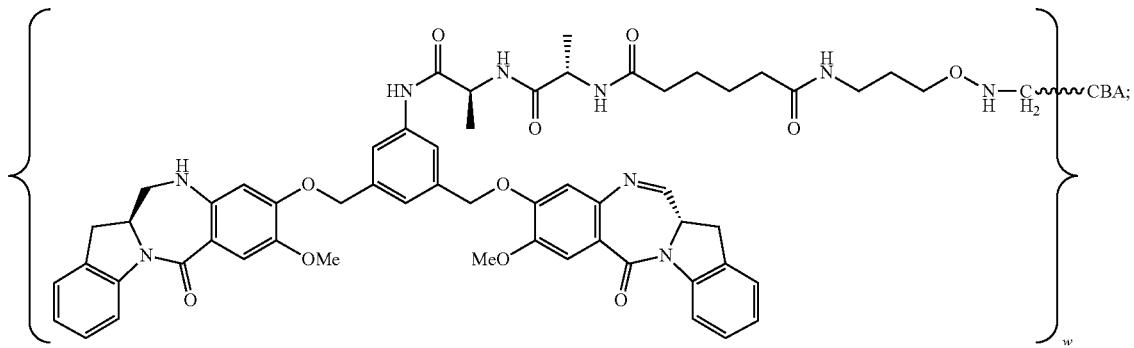

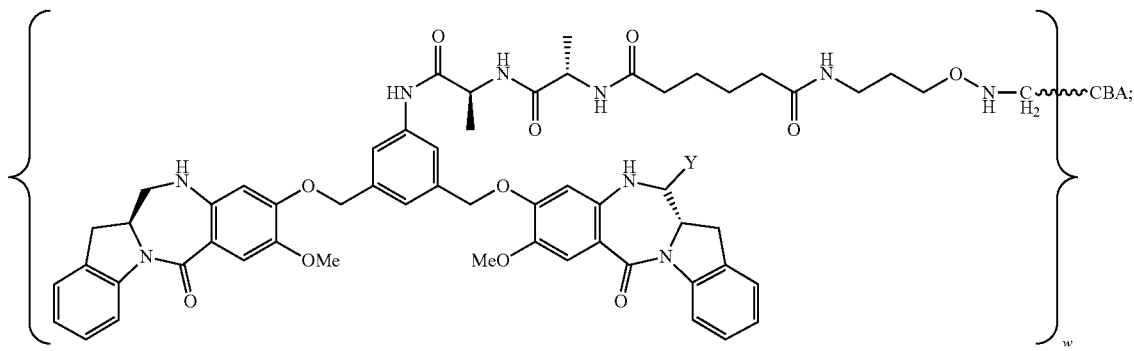
(74)
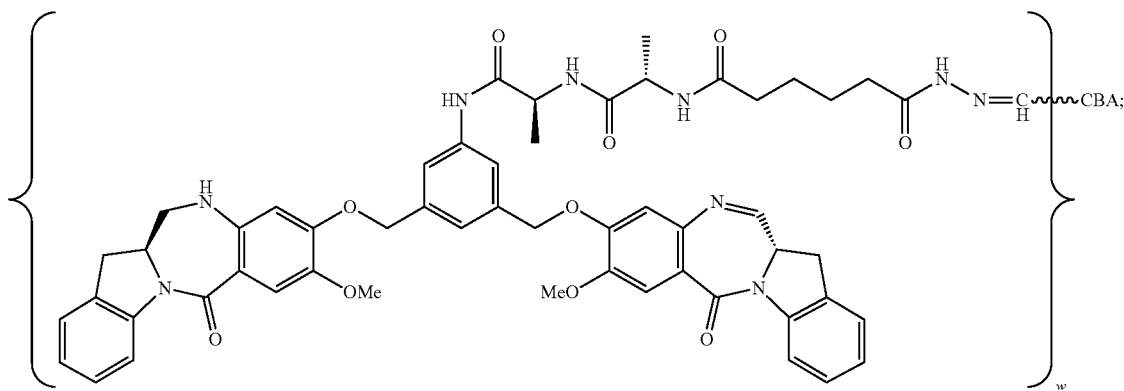
(75)
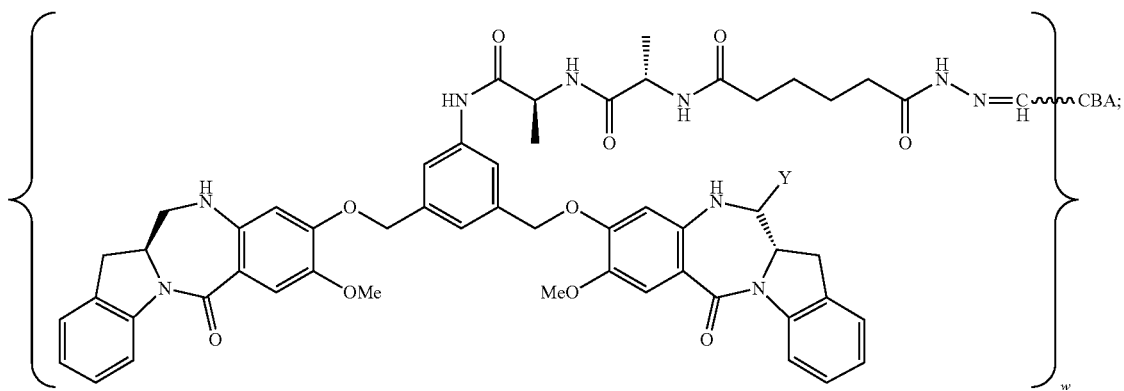
(76)
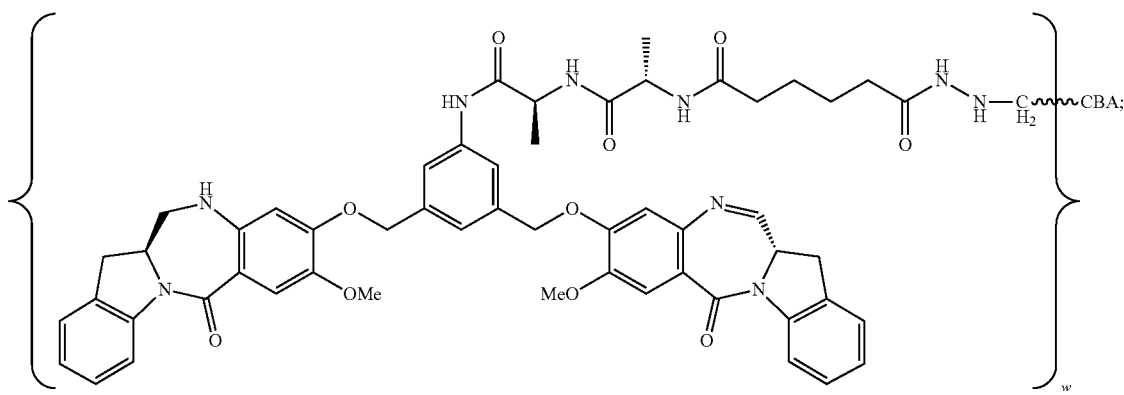
(77)

(78)
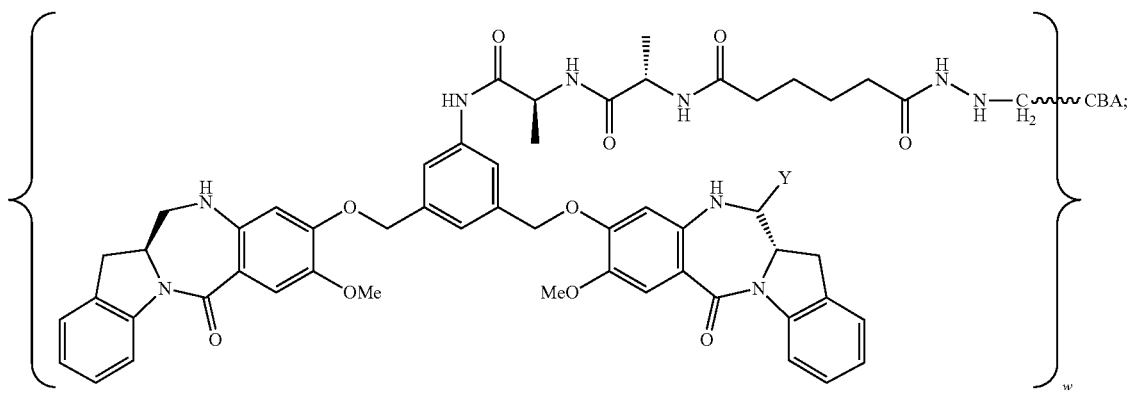
(79)
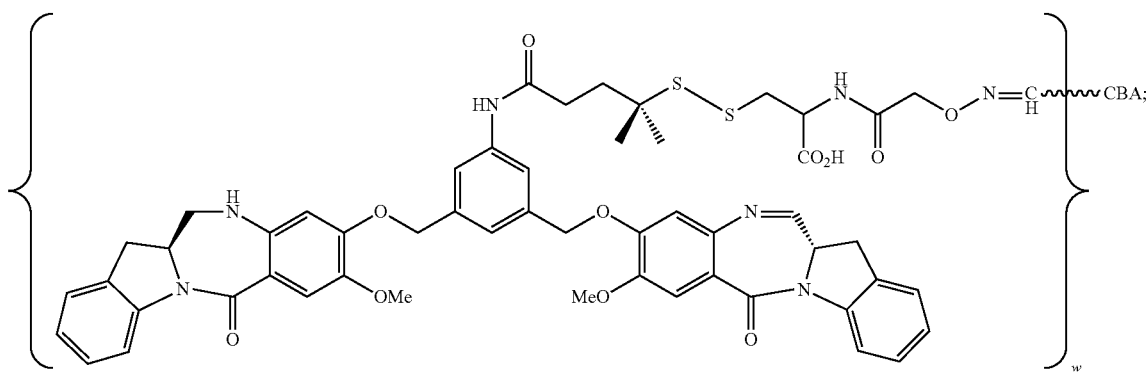
(80)
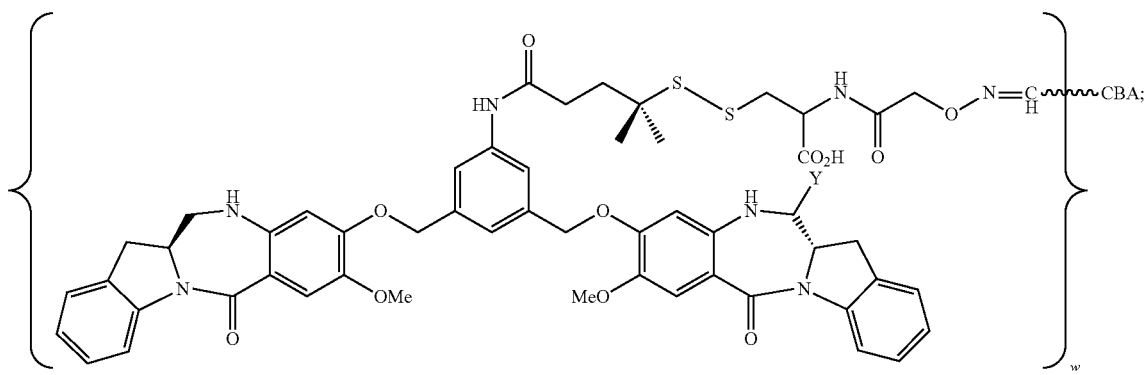
(81)
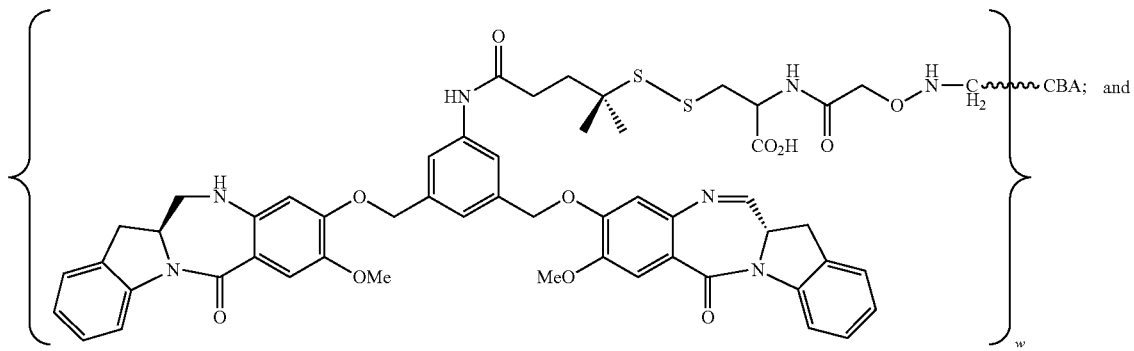

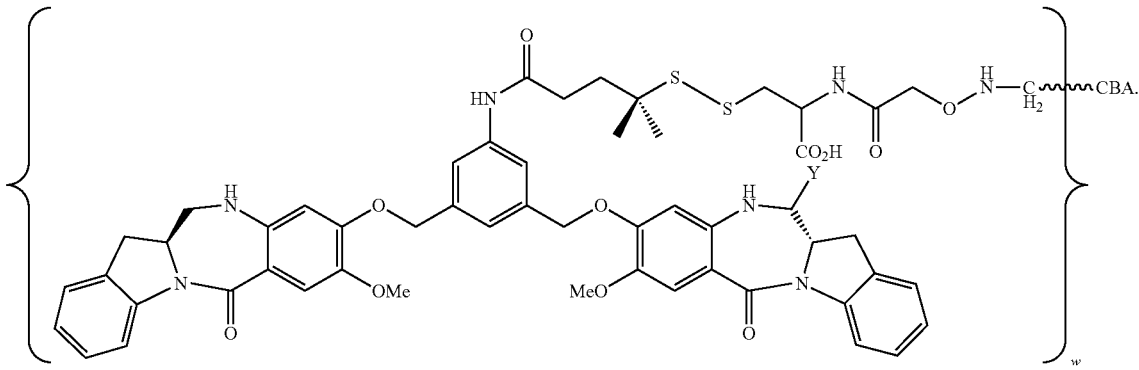

(82)

The CBA in the conjugates of any one of the embodiments described above, such as the first embodiment or the $1^{st}$ to $8^{th}$ specific embodiments or any more specific embodiments described therein, may be any cell-binding agents described herein, such as those described in the second embodiment below.

In certain embodiment, the conjugates of any one of the embodiments described above, such as the first embodiment or the $1^{st}$ to $8^{th}$ specific embodiments or any more specific embodiments described therein, may comprise 1-4 cytotoxic agent molecules bound per cell-binding agent (e.g., antibody) molecule. In certain embodiment, the conjugates may comprise 2 or 4 cytotoxic agent molecules per cell-binding agent molecule. The number of cytotoxic agent molecules bound per cell-binding agent (e.g., antibody) molecule can be determined spectroscopically by measuring the ratio of the absorbance at 280 nm and 252 nm for maytansinoid compounds, and the ratio of the absorbance at 280 nm and 330 nm for benzodiazepine compounds. Alternatively, the number of cytotoxic agent molecule bound per cell-binding agent (e.g., antibody) molecule can be determined by mass spectrometry.

The present invention further provides a composition comprising the conjugates of any one of the embodiments described above, such as the first embodiment or the $1^{st}$ to $8^{th}$ specific embodiments or any more specific embodiments described therein. In certain embodiments, at least about 50%, 60%, 70%, 80%, 90%, 95%, 99%, 99.5%, 99.9% or more of the conjugates in the composition have 2 or 4 cytotoxic agents covalently linked to each CBA. In certain embodiments, in the composition described above, no more than about 20%, 15%, 10%, 9%, 8%, 7%, 6%, 5%, 4%, 3%, 2%, 1%, 0.5% or 0.1% of the conjugates have only 1 cytotoxic agent covalently linked to each CBA.

Cell Binding Agent

In a second embodiment, the invention provides a cell-binding agent (CBA) for preparing the cell-binding agent-cytotoxic agent conjugates described herein. Such CBA may be a protein (e.g., a protein found in nature, or an engineered or recombinant protein), such as an antibody, an antigen-binding portion thereof (which may include an antibody derivative), or an antibody mimetic protein. The N-terminus of such proteinaceous CBA may comprise a 2-hydroxyethylamine moiety that may be part of a serine, threonine, hydroxylysine, 4-hydroxyornithine or 2,4-diamino-5-hydroxy valeric acid residue. The 2-hydroxyethylamine moiety can be oxidized using the methods of the invention to become an aldehyde group, which can then react with an aldehyde reactive group to form the subject conjugates.

In a related aspect, the invention also provides certain engineered proteinaceous CBA, such as engineered antibody, antigen-binding portion thereof (or antibody derivative), or antibody mimetic protein, which may have a Ser or Thr as the N-terminal residue, as opposed to a non-Ser, non-Thr natural sequence of such antibody, antigen-binding portion thereof (or antibody derivative), or antibody mimetic protein.

The N-terminal Ser/Thr can be added by inserting a Ser/Thr codon immediately after a signal peptide sequence. Such signal peptide sequence may be the natural signal peptide for the antibody, antigen-binding portion thereof (or antibody derivative), or antibody mimetic protein, or may be a heterologous signal peptide fused N-terminal to the mature processed sequence of the antibody, antigen-binding portion thereof (or antibody derivative), or antibody mimetic protein.

Here, "mature processed sequence (e.g., of recombinant antibody heavy chain (HC), light chain (LC), or antigen-binding portion thereof)" refers to the processed sequence of certain secreted proteins—such as the recombinant antibody heavy chain (HC), light chain (LC), or antigen-binding portion thereof—which secreted proteins are synthesized with an N-terminal signal peptide (either a naturally occurring one, or a heterologous one fused N-terminal using recombinant technology). After the normal maturation process, including cleavage of the signal peptide, the resulting mature processed sequence generally lacks all signal peptide sequences.

SEQ ID NOs: 1 and 6 may be used as such natural or heterologous signal peptides. Additional sequence changes to the N-terminal residues in the mature processed sequence of the antibody, antigen-binding portion thereof (or antibody derivative), or antibody mimetic protein may be present, so long as the N-terminal residue, after signal peptide cleavage, is Ser/Thr.

Specifically, the N-terminal Ser/Thr can be added by using a specific signal peptide sequence obtained from the light chain signal peptide of a murine anti-FOLR1 antibody FR1-2.1 (produced by the hybridoma deposited with the ATCC on Apr. 16, 2013 and having ATCC deposit no. PTA-120197), which signal peptide is represented by SEQ ID NO: 1. It was surprisingly found that this signal peptide sequence is uniquely processed to leave behind its last Ser as the N-terminal residue of the mature processed sequence of the protein.

Regardless of whether the N-terminal Ser/Thr is naturally existing in the CBA, or is engineered using any of the recombinant technology described herein, another aspect of the invention further provides a modified CBA (e.g., a modified antibody, antigen-binding portion thereof (or antibody derivative), or antibody mimetic protein) in which its N-terminal Ser/Thr has been oxidized to an aldehyde group. In certain embodiments, the aldehyde is derived from the oxidation of N-terminal Ser/Thr on the heavy chain of an antibody or an antigen-binding portion thereof. The oxidation can be done using any of the methods of the invention described herein. Such modified CBA can react with a linker bearing an aldehyde reactive group (such as those described herein) to form the conjugates of the invention.

Thus the invention also provides a method of making a conjugate of the invention described herein, using a modified CBA of the invention (e.g., an antibody, antigen-binding portion thereof (or antibody derivative), or antibody mimetic protein). The invention further provides a polynucleotide encoding any of the engineered CBA (e.g., an antibody, antigen-binding portion thereof (or antibody derivative), or antibody mimetic protein) that produces a mature processed sequence of the CBA with an N-terminal Ser/Thr.

In certain embodiments, the aldehyde group is located at the N-terminus of the proteinaceous CBA (e.g., antibody or antigen-binding portion thereof). For example, the N-terminal aldehyde group can be derived from oxidation of an N-terminal serine or threonine.

In one embodiment, the N-terminal serine or threonine may be naturally existing in the proteinaceous CBA (e.g., antibody or antigen-binding portion thereof). For example, the antibody or antigen-binding portion thereof may comprise a light chain sequence of SEQ ID NO: 3, or a light chain sequence derived from the same mouse germ line sequence that encodes the signal peptide of SEQ ID NO: 1. In a related embodiment, the antibody or antigen-binding portion thereof is a chimeric, humanized, or human antibody or antigen-binding portion thereof of a murine antibody or antigen-binding portion thereof comprising a light chain sequence of SEQ ID NO: 3, or a light chain sequence derived from the same mouse germ line sequence that encodes the signal peptide of SEQ ID NO: 1.

Similarly, the antibody or antigen-binding portion thereof may comprise a light chain sequence derived from the murine IGKV6-32*01 sequence (i.e., SIVMTQTPKFLLVS AGDRVTITCKASQSVSNDVAWYQQKPGQ- SPKLLI YYASNRYTGVPDRFTGSGYGTDFTFTIS TVQAED-LAVYFCQQDYSSP, SEQ ID NO: 20). In a related embodiment, the antibody or antigen-binding portion thereof is a chimeric, humanized, or human antibody or antigen-binding portion thereof of a murine antibody or antigen-binding portion thereof comprising a light chain sequence derived from the murine IGKV6-32*01 sequence of SEQ ID NO: 20.

In addition, the antibody or antigen-binding portion thereof may comprise a light chain sequence derived from any one of the human Lambda V3 family of V gene sequences listed below (i.e., SEQ ID NOs: 21-41). In a related embodiment, the antibody or antigen-binding portion thereof is a chimeric, humanized, or human antibody or antigen-binding portion thereof of a murine antibody or antigen-binding portion thereof comprising a light chain sequence derived from any one of the human Lambda V3 family of V gene sequences listed below.

Human Lambda V3 Family of V Gene Sequences
IGLV3-1*01
SYELTQPPSVSVSPGQTASITCSGDKLGDKYACWYQ QKPGQSPVLVIYQDSKRPSGIPERFS GSNSGNTATL TISGTQAMDEADYYCQAWDSSTA (SEQ ID NO: 21)
IGLV3-10*01
SYELTQPPSVSVSPGQTARITCSGDALPKKYAYWYQ QKSGQAPVLVIYEDSKRPSGIPERFS GSSSGTMAIL-TISGAQVEDEADYYCYSTDSSGNHX (SEQ ID NO: 22)
IGLV3-10*02
SYELTQPPSVSVSPGQTARITCSGDALPKKYAYWYQQ KSGQAPVLVIYKDSKRPSGIPERFS GSSSGTMAIL-TISGAQVEDEDDYYCYSADYSGN (SEQ ID NO: 23)
IGLV3-12*01
SYELTQPHSVSVATAQMARITCGGNNIGSKAVHWY QQKPGQDPVLVIYSDSNRPSGIPERFS GSNPGNTTILT-ISRIEAGDEADYYCQVWDSSSDHP (SEQ ID NO: 24)
IGLV3-12*02
SYELTQPHSVSVATAQMARITCGGNNIGSKAVHWY QQKPGQDPVLVIYSDSNRPSGIPERFS GSNPGNTATL TISRIEAGDEADYYCQVWDSSSDHP (SEQ ID NO: 25)
IGLV3-13*01
SYELTQPPAVSVSPGQTARISCSGDVLRDNYADWYP QKPGQAPVLVIYKDGERPSGIPERFS GSTSGN TTALT ISRVLTKGGADYYCFSGD*NNL (SEQ ID NO: 26)
IGLV3-16*01
SYELTQPPSVSVSLGQMARITCSGEALPKKYAYWY QQKPGQFPVLVIYKDSERPSGIPERFS GSSSGTIVTL TISGVQAEDEADYYCLSADSSGTYP (SEQ ID NO: 27)
IGLV3-19*01
SSELTQDPAVSVALGQTVRITCQGDSLRSYYASWYQ QKPGQAPVLVIYGKNNRPSGIPDRFS GSSSGNTAS LTITGAQAEDEADYYCNSRDSSGNHL (SEQ ID NO: 28)
IGLV3-21*01
SYVLIQPPSVSVAPGKTARITCGGNNIGSKSVHWY QQKP GQAPVLVIYYDSDRPSGIPERFS GSNSGN-TATLTISRVEAGDEADYYCQVWDSSSDHP (SEQ ID NO: 29)
IGLV3-21*02
SYVLTQPPSVSVAPGQTARITCGGNNIGSKSVHWYQ QKPGQAPVLVVYDDSDRPSGIPERFS GSNSGNTAT LTISRVEAGDEADYYCQVWDSSSDHP (SEQ ID NO: 30)
IGLV3-21*03
SYVLTQPPSVSVAPGKTARITCGGNNIGSKSVHWY QQKPGQAPVLVVYDDSDRPSGIPERFS GSNSGNTA TLTISRVEAGDEADYYCQVWDSSSDHP (SEQ ID NO: 31)
IGLV3-22*01
SYELTQLPSVSVSPGQTARITCSGDVLGENYADWYQ QKPGQAPELVIYEDSERYPGIPERFS GSTSGNTT-TLTISRVLTEDEADYYCLSGDEDNP (SEQ ID NO: 32)
IGLV3-25*01
SYELMQPPSVSVSPGQTARITCSGDALPKQYAYW YQQKPGQAPVLVIYKDSERPSGIPERFS GSSS GTTVTLTISGVQAEDEADYYCQSADSSGTYP (SEQ ID NO: 33)
IGLV3-25*02
SYELTQPPSVSVSPGQTARITCSGDALPKQYAYWYQ QKPGQAPVLVIYKDSERPSGIPERFS GSSSGTTVTLTISGVQAEDEADYYCQSADSSGTYP (SEQ ID NO: 34)

IGLV3-25*03
SYELTQPPSVSVSPGQTARITCSGDALPKQYAY-WYQ
QKPGQAPVLVIYKDSERPSGIPERFS GSSSGTTVT
LTISGVQAEDEADYYCQSADSSG (SEQ ID NO: 35)
IGLV3-27*01
SYELTQPSSVSVSPGQTARITCSGDVLAKKYARWF
QQKPGQAPVLVIYKDSERPSGIPERFS GSSSGTTV
TLTISGAQVEDEADYYCYSAADNNL (SEQ ID NO: 36)
IGLV3-31*01
SSELSQEPAVSVALG*TARITCQGDSIEDSVVNWY
KQKPSQAPGLVI*LNSVQSSGIPKKFS GSSSGN-
MATLTITGIQVEDKADYYCQSWDSSRTHS (SEQ ID NO: 37)
IGLV3-31*02
SSELSQEPAVSVSLG*TARITCQGDSIEDSVVNWY-
KQKPSQAPGLVI*LNSVQSSGIPKKFS GSSSGN-
MATLTITGIQVEDKADYYCQSWDSSRTHS (SEQ ID NO: 38)
IGLV3-32*01
SSGPTQVPAVSVALGQMARITCQGDSMEGSYEHW-
YQQKPGQAPVLVIYDSSDRPSRIPERFS GSKSGNTT-
TLTITGAQAEDEADYYYQLIDNHAT (SEQ ID NO: 39)
IGLV3-9*01
SYELTQPLSVSVALGQTARITCGGNNIGSKNVHW-
YQQKPGQAPVLVIYRDSNRPSGIPERFS GSNSGN-
TATLTISRAQAGDEADYYCQVWDSSTA (SEQ ID NO: 40)
IGLV3-9*02
SYELTQPLSVSVALGQAARITCGGNNLGYKSVH-
WYQQKPGQAPVLVIYRDNNRPSGIPERFS GSNSGN-
TATLTISRAQAGDEADYYCQVWDSSTAHP (SEQ ID NO: 41)

The humanized antibody or antigen-binding portion thereof may be resurfaced or CDR grafted antibody or antigen-binding portion thereof.

In another embodiment, the N-terminal serine or threonine may be engineered into the proteinaceous CBA (e.g., antibody or antigen-binding portion thereof). For example, the antibody or antibody-binding portion thereof may be any one of the recombinant antibody of the invention described herein (see below).

In certain embodiments, the N-terminal aldehyde group is located on one or both heavy chains of the antibody or antigen-binding portion thereof, or on one or both light chains of the antibody or antigen-binding portion thereof, or a combination thereof.

In certain embodiments, the CBA is an antibody or an antigen-binding portion thereof. In certain embodiments, the antigen-binding portion may be Fab, F(ab)$_2$, F(ab'), F(ab')$_2$, F(ab')$_3$, Fd, Fv, disulfide linked Fv, dAb or sdAb (or nanobody), CDR, scFv, (scFv)$_2$, di-scFv, bi-scFv, tascFv (tandem scFv), AVIBODY (e.g., diabody, triabody, tetrabody), T-cell engager (BiTE), scFv-Fc, Fcab, mAb2, small modular immunopharmaceutical (SMIP), Genmab/unibody or duobody, V-NAR domain, IgNAR, minibody, IgGΔCH2, DVD-Ig, probody, intrabody, or a multispecificity antibody. In certain specific embodiments, the antigen-binding portion may be a single domain antibody (sdAb) or a nanobody.

In certain embodiments, the CBA is an antibody mimetic, such as a DARPin, a Centyrin, an affibody, an affilin, an affitin, an anticalin, an avimer, a Fynomer, a Kunitz domain peptide, a monobody (or adnectin), a tribody, or a nanofitin. In certain specific embodiments, the CBA is a DARPin. In other specific embodiments, the CBA is a Centyrin. In yet another specific embodiments, the CBA is a monobody or adnectin. In certain embodiments, the CBA is a dual receptor retargeting (DART) molecule (P. A. Moore et al., *Blood*, 2011; 117(17):4542-4551; Veri M C et al., *Arthritis Rheum.*, 2010 Mar. 30; 62(7):1933-43; Johnson, S et al., *J. Mol. Biol.*, 2010 Apr. 9; 399(3):436-49) or a cell penetrating supercharged proteins (*Methods in Enzymol.* 502, 293-319 (2012).

In another aspect, the invention provides a recombinant antibody heavy chain (HC), light chain (LC), or an antigen-binding portion thereof, comprising a heterologous signal peptide having an amino acid sequence of SEQ ID NO: 1.

This aspect of the invention is partly based on the surprising finding that, SEQ ID NO: 1, the light chain signal peptide of antibody FR1-2.1, can be cleaved naturally just before the last Ser in SEQ ID NO: 1, thus leaving an N-terminal serine in the resulting processed polypeptide (e.g., recombinant antibody heavy chain (HC), light chain (LC), or an antigen-binding portion thereof expressed with SEQ ID NO: 1 as the signal peptide). Thus the signal peptide of SEQ ID NO: 1 can be recombinantly fused to a heterologous polypeptide (e.g., recombinant antibody heavy chain (HC), light chain (LC), or an antigen-binding portion thereof), and used in a general approach to produce polypeptides having an N-terminal Ser.

In certain embodiments, the heterologous signal peptide is fused to the N-terminus of the mature processed sequence of the recombinant antibody heavy chain (HC), light chain (LC), or antigen-binding portion thereof.

In certain embodiments, the heterologous signal peptide is fused to the $2^{nd}$ amino acid residue of the N-terminus of the mature processed sequence of the recombinant antibody heavy chain (HC), light chain (LC), or antigen-binding portion thereof. Thus in this embodiment, the processed polypeptide does not have one extra amino acid residue due to the N-terminal Ser from SEQ ID NO: 1. In other related embodiments, the heterologous signal peptide is fused to the any residue (e.g., the $3^{rd}$, $4^{th}$, $5^{th}$, etc.) of the N-terminal portion of the mature processed sequence of the recombinant antibody heavy chain (HC), light chain (LC), or antigen-binding portion thereof, resulting in "deletion" of one or more N-terminal residues, so long as the binding ability of the antibody or antigen-binding portion thereof is not substantially affected. Alternatively or in addition, one or more additional residues can be added after the N-terminal Ser, so long as the N-terminal residue is a Ser, such as the Ser from the last residue of SEQ ID NO: 1.

In a related aspect, the invention provides a recombinant antibody heavy chain (HC), light chain (LC), or an antigen-binding portion thereof, comprising a Ser or Thr residue immediately C-terminal to the last residue of the (natural) signal peptide of the heavy chain (HC), light chain (LC), or antigen-binding portion thereof. This can be accomplished by inserting a codon for Ser or Thr immediately after the coding sequence for the natural signal peptide. For example, a Ser residue can be inserted immediately after the natural signal peptide sequence of the monoclonal antibody huMov19 light chain or heavy chain, to create the sequence MGWSCIILFLVATATGVHSS (SEQ ID NO: 42). After natural processing (cleavage) of the natural signal peptide sequence, the resulting N-terminal residue is expected to be Ser.

For example, in certain embodiments, the Ser or Thr residue may be immediately N-terminal to the first residue of the mature processed sequence of the recombinant antibody heavy chain (HC), light chain (LC), or antigen-binding portion thereof.

In another embodiment, the Ser or Thr residue replaces one or more N-terminal amino acid residue(s) of the mature processed sequence of the recombinant antibody heavy chain (HC), light chain (LC), or antigen-binding portion thereof. Alternatively or in addition, additional amino acid residues can be added, deleted, or replaced, so long as the 1st residue of the resulting polypeptide after signal peptide processing is Ser/Thr.

Exemplary recombinant antibody heavy chain (HC), light chain (LC), or an antigen-binding portion thereof, may have a sequence of: SEQ ID NOs: 10 or 14. Others may include those comprising SEQ ID NO: 42.

Yet another aspect of the invention provide a recombinant antibody comprising a mature processed sequence of the heavy chain, light chain, or antigen-binding portion thereof, derived from any one of the subject recombinant antibody heavy chain (HC), light chain (LC), or antigen-binding portion thereof described herein.

For example, the recombinant antibody may be or may comprise an Fab, F(ab)$_2$, F(ab'), F(ab')$_2$, F(ab')$_3$, Fd, Fv, disulfide linked Fv, dAb or sdAb (or nanobody), CDR, scFv, (scFv)$_2$, di-scFv, bi-scFv, tascFv (tandem scFv), AVIBODY (e.g., diabody, triabody, tetrabody), T-cell engager (BiTE), scFv-Fc, Fcab, mAb2, small modular immunopharmaceutical (SMIP), Genmab/unibody or duobody, V-NAR domain, IgNAR, minibody, IgGΔCH2, DVD-Ig, probody, intrabody, or a multispecificity antibody. In certain specific embodiments, the antigen-binding portion may be a single domain antibody (sdAb) or a nanobody.

In certain embodiments, the recombinant antibody may comprise 1, 2, 3, or 4 of the mature processed sequence of the heavy chain, light chain, or antigen-binding portion thereof, each derived from any one of the subject recombinant antibody heavy chain (HC), light chain (LC), or antigen-binding portion thereof described herein.

In certain embodiments, the recombinant antibody may be a heterodimeric antibody comprising a first heavy chain polypeptide and a second heavy chain polypeptide, wherein the Fc region of the first heavy chain polypeptide and the Fc region of the second heavy chain polypeptide meet at an interface, and the interface of the Fc region of the second heavy chain polypeptide comprises a protuberance which is positionable in a cavity in the interface of the Fc region of the first heavy chain polypeptide. In certain embodiments, the knob-into-hole technology to promote specific pairing of heavy chains in the bi-specific antibody may be further improved based on, for example, the CrossMab technology of Genentech/Roche, e.g., by swapping CH1 and Kappa constant regions to further reduce or eliminate light chain mis-pairing.

Alternatively, similar results can also be achieved using LC heterodimers, such as Zymeworks AZYMETRIC™ heterodimeric IgG$_1$ light chain platform technology that fully complements multiple other biologics approaches, including common light chain, domain antibody, and single chain formats, in the development of fully bi-specific antibodies.

In certain embodiments, the Fc region of the second heavy chain polypeptide has been altered from a template/original polypeptide to encode the protuberance, or the Fc region of the first heavy chain polypeptide has been altered from a template/original polypeptide to encode the cavity, or both.

In certain embodiments, the protuberance and the cavity each comprises a naturally occurring amino acid residue.

In certain embodiments, the Fc region of the second heavy chain polypeptide comprising the protuberance is generated by replacing an original residue from the interface of a template/original polypeptide with an import residue having a larger side chain volume than the original residue.

In certain embodiments, the Fc region of the second heavy chain polypeptide comprising the protuberance is generated by a method comprising a step wherein nucleic acids encoding an original residue from the interface of said polypeptide is replaced with nucleic acids encoding an import residue having a larger side chain volume than the original.

Yet another aspect of the invention provides a modified antibody oxidized from an antibody having an N-terminal Ser or Thr on a mature processed sequence of the heavy chain, light chain, or antigen-binding portion thereof, wherein the N-terminal Ser or Thr has been oxidized to an aldehyde group in the modified antibody.

In certain embodiments, the antibody is derived from a recombinant antibody heavy chain (HC), light chain (LC), or antigen-binding portion thereof comprising: (1) a heterologous signal peptide having an amino acid sequence of SEQ ID NO: 1; (2) a Ser or Thr residue immediately N-terminal to the first residue of the mature processed sequence of the recombinant antibody heavy chain (HC), light chain (LC), or antigen-binding portion thereof; or (3) a Ser or Thr residue replacing one or more N-terminal amino acid residue(s) of the mature processed sequence of the recombinant antibody heavy chain (HC), light chain (LC), or antigen-binding portion thereof.

In certain embodiments, the antibody is a murine antibody or antigen-binding portion thereof comprising a light chain sequence of SEQ ID NO: 3.

In certain embodiments, the antibody is a chimeric, humanized, or human antibody or antigen-binding portion thereof of a murine antibody or antigen-binding portion thereof comprising a light chain sequence of SEQ ID NO: 3. The humanized antibody or antigen-binding portion thereof may be resurfaced or CDR grafted antibody or antigen-binding portion thereof.

Another aspect of the invention provides a polynucleotide encoding a subject recombinant antibody heavy chain (HC), light chain (LC), or antigen-binding portion thereof described herein.

In certain embodiments, the polynucleotide is codon-optimized for expression in a mammalian expression system.

Another aspect of the invention provides a method of producing a subject recombinant antibody heavy chain (HC), light chain (LC), or an antigen-binding portion thereof, the method comprising expressing the subject polynucleotide described herein in an expression system, such as a mammalian expression system.

As used herein, the term "cell-binding agent" or "CBA" refers to a compound that can bind a cell (e.g., on a cell-surface ligand) or bind a ligand associated with or proximate to the cell, preferably in a specific manner. In certain embodiments, binding to the cell or a ligand on or near the cell is specific. The CBA may include peptides and non-peptides. For CBA of proteinaceous nature, if the natural N-terminal residue is not Ser or Thr, the N-terminal residue can be engineered using any of the recombinant methods described herein, e.g., by using a heterologous signal peptide of SEQ ID NO: 1, or by inserting a Ser/Thr codon to code for the N-terminal residue.

Selection of the appropriate cell-binding agent is a matter of choice that partly depends upon the particular cell population that is to be targeted, but in many (but not all) cases, humanized monoclonal antibodies are a good choice if an appropriate one is available. For example, the monoclonal antibody MY9 is a murine IgG$_1$ antibody that binds specifically to the CD33 Antigen (J. D. Griffin et al., *Leukemia Res.*, 8:521 (1984)), and can be used if the target cells express CD33 as in the disease of acute myelogenous leukemia (AML).

In certain embodiments, the cell-binding agent is not a protein. For example, in certain embodiments, the cell binding agent may be a vitamin that binds to a vitamin receptor, such as a cell-surface receptor. In this regard, vitamin A binds to retinol-binding protein (RBP) to form a complex, which complex in turn binds the STRA6 receptor with high affinity and increases vitamin A in-take. In another example, folic acid/folate/vitamin B9 binds the cell-surface folate receptor (FR), for example, FRα, with high affinity. Folic acid or antibodies that bind to FRα can be used to target the folate receptor expressed on ovarian and other tumors, including solid tumors that over-express FRα, including non-small cell lung cancer (NSCLC). In addition, vitamin D and its analog bind to vitamin D receptor.

In other embodiments, the cell-binding agent is a protein or a polypeptide, or a compound comprising a protein or polypeptide, including antibody, non-antibody protein, or polypeptide.

For instance, GM-CSF, a ligand/growth factor which binds to myeloid cells can be used as a cell-binding agent to diseased cells from acute myelogenous leukemia. IL-2 which binds to activated T-cells can be used for prevention of transplant graft rejection, for therapy and prevention of graft-versus-host disease, and for treatment of acute T-cell leukemia. MSH, which binds to melanocytes, can be used for the treatment of melanoma, as can antibodies directed towards melanomas. Epidermal growth factor can be used to target squamous cancers, such as lung and head and neck. Somatostatin can be used to target neuroblastomas and other tumor types. Estrogen (or estrogen analogues) can be used to target breast cancer. Androgen (or androgen analogues) can be used to target testes.

Thus in certain embodiments, the cell-binding agent can be a lymphokine, a hormone, a growth factor, a colony stimulating factor, or a nutrient-transport molecule.

In certain embodiments, the cell-binding agent is an antibody mimetic, such as an ankyrin repeat protein, a Centyrin, or an adnectin/monobody.

In other embodiments, the cell-binding agent is an antibody, a single chain antibody, an antibody fragment that specifically binds to the target cell, a monoclonal antibody, a single chain monoclonal antibody, a monoclonal antibody fragment (or "antigen-binding portion") that specifically binds to a target cell, a chimeric antibody, a chimeric antibody fragment (or "antigen-binding portion") that specifically binds to the target cell, a domain antibody (e.g., sdAb), or a domain antibody fragment that specifically binds to the target cell. In certain embodiments, the cell-binding agent is a humanized antibody, a humanized single chain antibody, or a humanized antibody fragment (or "antigen-binding portion").

In another embodiment, the cell-binding agent is an anti-CD33 antibody or fragement thereof, such as the antibodies or fragements thereof described in U.S. Pat. Nos. 7,557,189, 7,342,110, 8,119,787 and 8,337,855 and WO2004/043344, herein incorporated by reference. In a specific embodiment, the humanized antibody is huMy9-6 or another related antibody, which is described in U.S. Pat. Nos. 7,342,110 and 7,557,189. In another embodiment, the anti-CD33 antibody is huMy9-6 antibody.

As used herein, double underlined sequences represent the variable regions (i.e., heavy chain variable region or HCVR, and light chain variable region or LCVR) of the heavy or light chain sequences, while bold sequences represent the CDR regions (i.e., from N-terminal to C-terminal, CDR1, CDR2, and CDR3, respectively, of the heavy chain or light chain sequences).

In one embodiment, the anti-CD33 antibody comprises an immunoglobulin heavy chain region having the amino acid sequence of QVQLQQPGAEVVKPGASVKMSCKAS GYTFTSYYIHWIKQTPGQGLEWVGVIYPGNDDISY NQKFQGKATLTADKSSTTAYMQLSSLTSEDSAVYY CAREVRLRYFDVWGQGTTVTVSSASTKGPSVFPLA-PSSKSTSGGTAALGCLVKDYFPEPVTVSWNSGALT-SGV HTFPAVLQSSGLYSLSSVVTVPSSSLGTQ TYICN-VNHKPSNTKVDKKVEPKSCDKTHTCPPCPAPELL G-G PSVFLFPPKPKDTLMISRTPEVTCVVVDVSHEDPE-VKFNWYVDGV EVHNAKTKPREEQYNSTYRVVSV-LTVLHQDWLNGKEYKCKVSNKALPAPIEKTISK AKGQPREPQVYTLPPSRDELTKNQVSLTCLVKGF-YPSDIAVEWESNGQPENNYKTTP PVLDSDGSFFLY-SKLTVDKSRWQQGNVFSCSVMHEALHNHYTQKSL-SLSPG (SEQ ID NO:43), and an immunoglobulin light chain region having the amino acid sequence of EIVLTQSPGSLAVSPGERVTMS CKSSQSVFFSSSQKNYLAWYQQIPGQSPRLLIYWAST RESGVPDRFTGSGSGTDFTLTISSVQPEDLAIYY CHQYLSSRTFGQGTKLEIKRTVA APSVFIFPPSDEQL-KSGTASVVCLLNNFYPREAKVQWKVDNALQS-GNSQESVTEQDS KDSTYSLSSTLTLSKADYEKHKVY-ACEVTHQGLSSPVTKSFNRGEC (SEQ ID NO:44).

In yet another embodiment, the anti-CD33 antibody comprises the heavy chain CDR1-CDR3 of SEQ ID NO: 43, and/or the light chain CDR1-CDR3 of SEQ ID NO: 44, and preferably specifically binds CD33.

In yet another embodiment, the anti-CD33 antibody comprises a heavy chain variable region (HCVR) sequence at least about 90%, 95%, 97%, 99%, or 100% identical to SEQ ID NO: 43, and/or a light chain variable region (LCVR) sequence at least about 90%, 95%, 97%, 99%, or 100% identical to SEQ ID NO: 44, and preferably specifically binds CD33.

In another specific embodiment, the humanized antibody is an anti-folate receptor antibody described herein. In another specific embodiment the antibody is an anti-folate receptor antibody described in U.S. Pat. No. 8,577,966). More specifically, the anti-folate receptor antibody is a humanized antibody or antigen binding fragment thereof that specifically binds a human folate receptor 1. The terms "human folate receptor 1," "FOLR1," or "folate receptor alpha (FR-α)", as used herein, refers to any native human FOLR1, unless otherwise indicated. Thus, all of these terms can refer to either a protein or nucleic acid sequence as indicated herein. The term "FOLR1" encompasses "full-length," unprocessed FOLR1 as well as any form of FOLR1 that results from processing within the cell. The FOLR1 antibody comprises: (a) a heavy chain CDR1 comprising GYFMN (SEQ ID NO: 45); a heavy chain CDR2 comprising RIHPYDGDTFYNQXaaiFXaa2Xaa3 (SEQ ID NO: 46); and a heavy chain CDR3 comprising YDGSRAMDY (SEQ ID NO: 47); and (b) a light chain CDR1 comprising KASQSVSFAGTSLMH (SEQ ID NO: 48); a light chain CDR2 comprising RASNLEA (SEQ ID NO: 49); and a light chain CDR3 comprising QQSREYPYT (SEQ ID NO: 50); wherein $Xaa_1$ is selected from K, Q, H, and R; Xaa2 is selected from Q, H, N, and R; and Xaa3 is selected from G, E, T, S, A, and V. Preferably, the heavy chain CDR2 sequence comprises RIHPYDGDTFYNQKFQG (SEQ ID NO: 51).

In another embodiment, the anti-folate receptor antibody is a humanized antibody or antigen binding fragment thereof that specifically binds the human folate receptor 1 comprising the heavy chain having the amino acid sequence of QVQLVQSGAEVVKPGASVKISCK- ASGYTFTGYFMNWVKQSPGQSLEWIGRIHPYD GDTFYNQKFQGKATLTVDKSSNTAHMELLSLTSEDFAV YYCTRYDGSRAMDYWG QGTTVTVSSASTKGPSVFPLAPSSKSTSGGTAALGCLVKDYFPEPVTVS WNSGA LTSG VHTFPAVLQSSGLYSLSSVVTVPSSSL GTQTYIC NVNHKPSNTKVDKKVEPKSCDKT HTCPPCPAPELL GGPSVFLFPPKPKDTLMISRTPEVTCVVVDVSHEDPEVKFNWYVD GVEVHNAKTKPREEQYNSTYRVVSV LTVLHQDWLNGKEYKCKVSNKALPAPIEKTI SKAKGQ PREPQVYTLPPSRDELTKNQVSLTCLVK GFYPSDIAVEWESNGQPENNYKT TPPVLDSDGSFFLYSKLTVDKSRWQQGNVFSCSVMHEALHNHYTQK SLSLSPGK (SEQ ID NO: 52).

In another embodiment, the anti-folate receptor antibody is a humanized antibody or antigen binding fragment thereof encoded by the plasmid DNA deposited with the ATCC on Apr. 7, 2010 and having ATCC deposit nos. PTA-10772 and PTA-10773 or PTA-10774.

In another embodiment, the anti-folate receptor antibody is a humanized antibody or antigen binding fragment thereof that specifically binds the human folate receptor 1 comprising the light chain having the amino acid sequence of DIVLTQSPLSLAVSLGQPAIISCKASQSVSFAGTSLMH WYHQKPGQQPRLLIYRASN LEAGVPDRFSGSGSKT DFTLNISPVEAEDAATYYCQQSREYPYTFGGG TKLE IKRTV AAPSVFIFPPSDEQLKSGTASVVCLLNNFYPREAKVQWKVDNALQSGNSQESVTEQD SKDSTYSLSSTLTLSKADYEKHKVYACEVTHQGLSSP VTKSF NRGEC (SEQ ID NO: 53); or DIVLTQSPLSLA VSLGQPAIISCKASQSVSFAGTSLMHWYHQKPG QQPRLLIYRASN LEAGVPDRFSGSGSKTDFTLTISP VEAEDAATYYCQQSREYPYTFGGGTKLEIKRTV AAP SVFIFPPSDEQLKSGTASVVCLLNNFYPREAKVQ WK VDNALQSGNSQESVTEQD SKDSTYSLSSTLTLSK ADYEKHKVYACEVTHQGLSSPVTKSFNRGEC (SEQ ID NO: 54).

In another embodiment the anti-folate receptor antibody is a humanized antibody or antigen binding fragment thereof that specifically binds the human folate receptor 1 comprising the heavy chain having the amino acid sequence of SEQ ID NO: 52, and the light chain having the amino acid sequence of SEQ ID NO: 53 or SEQ ID NO: 54. Preferably, the antibody comprises the heavy chain having the amino acid sequence of SEQ ID NO: 52 and the light chain having the amino acid sequence of SEQ ID NO: 54 (hu FOLR1).

In another embodiment, the anti-folate receptor antibody is a humanized antibody or antigen binding fragment thereof encoded by the plasmid DNA deposited with the ATCC on Apr. 7, 2010 and having ATCC deposit nos. PTA-10772 and PTA-10773 or 10774.

In another embodiment, the anti-folate receptor antibody is a humanized antibody or antigen binding fragment thereof that specifically binds the human folate receptor 1, and comprising a heavy chain variable domain at least about 90%, 95%, 99% or 100% identical to QVQLVQSGAEVVKPGASVKISCKASGYTFTGYFMNWVKQSP GQSLEWIGRIHPYDG DTFYNQKFQGKATLTVD KS SNTAHMELLSLTSEDFAVYYCTRYDGSRAMDY WG QG TTVTVSS (SEQ ID NO: 55), and a light chain variable domain at least about 90%, 95%, 99% or 100% identical to DIVLTQSPLSLAVSLGQPAIISCKASQSVSFAGTSLMEIWYHQKPGQQPRLLIYRASNL EAGVPDRFSGSGSK TDFTLNISPVEAEDAATYYCQQSREYPYTFGGGTK LEIKR (SEQ ID NO: 56); or DIVLTQSPLSLAVSLGQPAIISCKASQSVSFAGTSLMEIWYHQKPG QQPRLL IYRASNL EAGVPDRFSGSGSKTDFTLTISPV EAEDAATYYCQQSREYPYTFGGGTKLEIKR (SEQ ID NO: 57).

In another embodiment, the anti-folated receptor antibody is huMov19 or M9346A (see, for example, U.S. Pat. Nos. 8,709,432, 8,557,966, and WO2011106528, all incorporated herein by reference).

In certain embodiments the humanized antibody is an anti-CD37 antibody (e.g., anti-CD37-3) described in U.S. Pat. No. 8,765,917. In another embodiment, the cell-binding agent is an anti-CD37 antibody or an antibody fragment thereof, such as those described in U.S. Pat. No. 8,765,917 and WO 2011/112978, herein incorporated by reference. In one embodiment, the anti-CD37 antibody is huCD37-3 antibody.

In one embodiment, the anti-CD37 antibody comprises an immunoglobulin light chain region having the amino acid sequence of <u>DIQMTQSPSSLSVSVGERVTIT CRASENIRSNLAWYQQKPGKSPKLLVNVATNLA DGVPSRFSGSGSGTDYSLKINSLQPEDFGTYYCQHY WGTTWTFGQGTKLEIKR</u>TVAAPS VFIFPPSDEQLKSGTASVVCLLNNFYPREAKVQWKVDNALQSGNSQESVTEQDSKDS TYSLSSTLTLSKADYEKHKVYACEVTHQGLSSPVTKSFNRGEC (SEQ ID NO: 58) and an immunoglobulin heavy chain region having the amino acid sequence of <u>QVQVQESGPGLVAPSQTLSITCTVS GFSLTTSGVSWVRQPPGKGLEWLGVIWGDGSTNY HPSLKSRLSIKKDHSKSQVFLKNSLTAADTATYYCAL KGGYSLAHWGQGTLVTVSS</u>ASTKGPSVFPLAPSSKSTSGGTAALGCLVKDYFPEPVTVSWNSGALTSGVHTFPA VLQSSGLYSLSSVVTVPSSSLGTQTYICNVNHKPSNTKVDKKVEPKSCDKTHTCPPCP APELLGGPSVFLFPPKPKDTLMISRTPEVTCVVVDVSHEDPEVKFNWYVDGVEVHNA KTKPREEQYNSTYRVVSVLTVLHQDWLNGKEYKCKVSNKALPAPIEKTISKAKGQP REPQVYTLPPSRDELTKNQVSLTCLVKGFYPSDIAVEWESNGQPENNYKTTPPVLDS DGSFFLYSKLTVDKSRWQQGNVFSCSVMHEALHNHYTQKSLSLSPG (SEQ ID NO: 59), or an immunoglobulin heavy chain region having the amino acid sequence of <u>QVQVQESGPGLVAPSQTLSITCTVSGFSLTTSGVSW VRQPPGKGLEWLGVIWGDGSTNYHSSLKSRLSI KKDHSKSQVFLKNSLTAADTATYYCAKGGYSLA HWGQGTLVTVSS</u>ASTKGPSVFPLAPSSKSTSGGTAALGCLVKDYFPEPVTVSWNSGALTSGVHTFPA VLQS SGLYSLSSVVTVPSSSLGTQTYICNVNHKPS NTKVDK KVEPKSCDKTHTCPPCP APELLGGPSVFLFPPK PKD TLMISRTPEVTCVVVDVSHEDPEVKFNWYVDG VEV HNA KTKPREEQYNSTYRVVSVLTVLHQDWLNGKE YKCKVSNKALPAPIEKTISKAKGQP REPQVYTLP PSRDELTKNQVSLTCLVKGFYPSDIAVEWESNGQPENNYKTTPPVLDS DGSFFLYSKLTVDKSRW QQG NVFSCSVMHEALHNHYTQKSLSLSPG (SEQ ID NO: 60)

In another embodiment, the anti-CD37 antibody comprises an immunoglobulin light chain region having the amino acid sequence set forth in SEQ ID NO: 58 and an immunoglobulin heavy chain region having the amino acid sequence set forth in SEQ ID NO: 59.

In yet another embodiment, the anti-CD37 antibody comprises an immunoglobulin light chain region having the amino acid sequence set forth in SEQ ID NO: 58 and an immunoglobulin heavy chain region having the amino acid sequence set forth in SEQ ID NO: 60.

In yet another embodiment, the anti-CD37 antibody comprises the heavy chain CDR1-CDR3 of SEQ ID NO: 59 or 60, and/or the light chain CDR1-CDR3 of SEQ ID NO: 58, and preferably specifically binds CD37.

In yet another embodiment, the anti-CD37 antibody comprises a heavy chain variable region (HCVR) sequence at least about 90%, 95%, 97%, 99%, or 100% identical to SEQ ID NO: 59 or 60, and/or a light chain variable region (LCVR) sequence at least about 90%, 95%, 97%, 99%, or 100% identical to SEQ ID NO: 58, and preferably specifically binds CD37.

In yet another embodiment, the anti-CD37 antibody comprises an immunoglobulin light chain region having the amino acid sequence of EIVLTQSPATMSASPGERVT MTCSATSSVTYMHWYQQKPGQSPKRWIYDTSNLP TYGVPARFSGSGSGTSYSLTISSMEAEDAATYY CQQWSDNPPTFGQGTKLEIKRTVAAPSVFIFPPSDEQ-LKSGTASVVCLLNNFYPREAKVQWKVDNALQSG-NSQESVTEQDSKDS TYSLSSTLTLSKADYEKHKVY-ACEVTHQGLSSPVTKSFNRGEC (SEQ ID NO: 61) and an immunoglobulin heavy chain region having the amino acid sequence of QVQLQESGPGLLKPSQSLSLTCTVSG YSITSGFAWHWIRQHPGNKLEWMGYILYSGSTVYS PSLKSRISITRDTSKNHFFLQLNSVTAADTATYYCAR GYYGYGAWFAYWGQGTLVTVSAASTKGPSVFPLAP SSKSTSGGTAALGCLVKDYFPEPVTVSWNSGALT-SGV HTFPAVLQSSGLYSLSSVVTVPSSSLGTQ- TYIC-NVNHKPSNTKVDKKVEPKSCDKTHTCPPCPAPEL-LGGPSVFLFPPKPKDTLMISRTPEVTCVVVDVSHE-DPEVKFNWYVDGVEVHNAKTKPREEQYNSTYRV-VSVLTVLHQDWLNGKEYKCKVSNKALPAPIEKTISK-AKGQPREPQVYTLPPSRDELTKNQVSLTCLVKGF-YPSDIAVEWESNGQPENNYKTTPPVLDSDGSFFLY-SKLTVDKSRWQQGNVFSCSVMHEALHNHYTQKS-LSLSPG (SEQ ID NO: 62).

In yet another embodiment, the anti-CD37 antibody comprises the heavy chain CDR1-CDR3 of SEQ ID NO: 62, and/or the light chain CDR1-CDR3 of SEQ ID NO: 61, and preferably specifically binds CD37.

In yet another embodiment, the anti-CD37 antibody comprises a heavy chain variable region (HCVR) sequence at least about 90%, 95%, 97%, 99%, or 100% identical to SEQ ID NO: 62, and/or a light chain variable region (LCVR) sequence at least about 90%, 95%, 97%, 99%, or 100% identical to SEQ ID NO: 61, and preferably specifically binds CD37.

In yet another embodiment, the anti-CD37 antibody is huCD37-50 antibody.

In certain embodiments, the humanized antibody is an anti-EGFR antibody described in U.S. Pat. No. 8,790,649. In another embodiment, the antibody is an anti-EGFR antibody. In one embodiment, the anti-EGFR antibody is a non-antagonist antibody, including, for example, the antibodies described in WO2012058592, herein incorporated by reference. In another embodiment, the anti-EGFR antibody is a non-functional antibody, for example, humanized ML66 or EGFR-8. More specifically, the anti-EGFR antibody is huML66. The teachings of all these applications are incorporated herein by reference in its entirety.

In yet another embodiment, the anti-EGFR antibody comprising the heavy chain having the amino acid sequence of SEQ ID NO: 63, and the light chain having the amino acid sequence of SEQ ID NO: 64.

| Antibody | Full-Length Heavy/Light Chain Amino Acid Sequence |
|---|---|
| huML66HC | QVQLQESGPGLVKPSETLSLTCTVSGLSLASNSVSWIRQPPGKGLEWMGVIWNH GGTDYNPSIKSRLSISRDTSKSQVFLKMNSLTAADTAMYFCVRKGGIYFDYWG QGVLVTVSSASTKGPSVFPLAPSSKSTSGGTAALGCLVKDYFPEPVTVSWNSGA LTSGVHTFPAVLQSSGLYSLSSVVTVPSSSLGTQTYICNVNHKPSNTKVDKKVEP KSCDKTHTCPPCPAPELLGGPSVFLFPPKPKDTLMISRTPEVTCVVVDVSHEDPE VKFNWYVDGVEVHNAKTKPREEQYNSTYRVVSVLTVLHQDWLNGKEYKCKV SNKALPAPIEKTISKAKGQPREPQVYTLPPSRDELTKNQVSLTCLVKGFYPSDIAV EWESNGQPENNYKTTPPVLDSDGSFFLYSKLTVDKSRWQQGNVFSCSVMHEAL HNHYTQKSLSLSPG (SEQ ID NO: 63) |
| huML66LC | DTVLTQSPSLAVSPGERATISCRASESVSTLMHWYQQKPGQQPKLLIYLASHRE SGVPARFSGSGSGTDFTLTIDPMEAEDTATYYCQQSRNDPWTFGQGTKLELKRT VAAPSVFIFPPSDEQLKSGTASVVCLLNNFYPREAKVQWKVDNALQSGNSQESV TEQDSKDSTYSLSSTLTLSKADYEKHKVYACEVTHQGLSSPVTKSFNRGEC (SEQ ID NO: 64) |

In yet another embodiment, the anti-EGFR antibody comprises the heavy chain CDR1-CDR3 of SEQ ID NO: 63, and/or the light chain CDR1-CDR3 of SEQ ID NO: 64, and preferably specifically binds EGFR.

In yet another embodiment, the anti-EGFR antibody comprises a heavy chain variable region (HCVR) sequence at least about 90%, 95%, 97%, 99%, or 100% identical to SEQ ID NO: 63, and/or a light chain variable region (LCVR) sequence at least about 90%, 95%, 97%, 99%, or 100% identical to SEQ ID NO: 64, and preferably specifically binds EGFR.

In another embodiment, the anti-EGFR antibody are antibodies described in 8,790,649 and WO 2012/058588, herein incorporated by reference. In one embodiment, the anti-EGFR antibody is huEGFR-7R antibody.

In one embodiment, the anti-EGFR antibody comprises an immunoglobulin heavy chain region having the amino acid sequence of QVQLVQSGAEVAKPGASVKLSC KASGYTFTSYWMQWVKQRPGQGLECIGTIYPGD GDTTYTQKFQGKATLTADKSSSTAYMQLSSLRSED SAVYYCARYDAPGYAMDYWGQGTLVTVSSASTKG-PSVFPLAPSSKSTSGGTAALGCLVKDYFPEPVTVSW-NSGALTS GVHTFPAVLQSSGLYSLSSVVTVPSSSLG-TQTYICNVNHKPSNTKVDKKVEPKSCDKTHTCPPC-PAPELLGGPSVFLFPPKPKDTLMISRTPEVTCVVV-DVSHEDPEVKFNWYVD GVEVHNAKTKPREEQYN-STYRVVSVLTVLHQDWLNGKEYKCKVSNKALPA-PIEKTI SKAKGQPREPQVYTLPPSRDELTKNQVSLT-CLVKGFYPSDIAVEWESNGQPENNYKT TPPVLDSD-GSFFLYSKLTVDKSRWQQGNVFSCSVMHEALHN-HYTQKSLSLSPG (SEQ ID NO: 65) and an immunoglobulin light chain region having the amino acid sequence of DIQMTQSPSSLSASVGDRVTITCRASQDINNYLAWY QHKPGKTGPKLLIHYTSTLHPGIPSRFSGSGSGRDY SFSISSLEPEDIATYYCLQYDNLLYTFGQGTKLEIKRT-VAAPSVFI FPPSDEQLKSGTASVVCLLNNFYPREA-KVQWKVDNALQSGNSQESVTEQDSKDSTY SLSST- LTLSKADYEKHKVYACEVTHQGLSSPVTKSFNRGEC (SEQ ID NO: 66), or an immunoglobulin light chain region having the amino acid sequence of DIQMTQSPSSLSASVGDRVTITCKASQDINNYLAWY QHKPGKGPKLLIHYTSTLHPGIPSRFSGSGSGRDYS FSISSLEPEDIATYYCLQYDNLLYTFGQGTKLEIKRT-VAAPSVFI FPPSDEQLKSGTASVVCLLNNFYPREA KV QWKVDNALQSGNSQESVTEQDSKDSTY SLSSTLTL-SKADYEKHKVYACEVTHQGLSSPVTKSFNRGEC (SEQ ID NO: 67).

In another embodiment, the anti-EGFR antibody comprises an immunoglobulin heavy chain region having the amino acid sequence set forth in SEQ ID NO: 65 and an immunoglobulin light chain region having the amino acid sequence set forth in SEQ ID NO: 66.

In another embodiment, the anti-EGFR antibody comprises an immunoglobulin heavy chain region having the amino acid sequence set forth in SEQ ID NO: 65 and an immunoglobulin light chain region having the amino acid sequence set forth in SEQ ID NO: 67.

In yet another embodiment, the anti-EGFR antibody comprises the heavy chain CDR1-CDR3 of SEQ ID NO: 65, and/or the light chain CDR1-CDR3 of SEQ ID NO: 66 or 67, and preferably specifically binds EGFR.

In yet another embodiment, the anti-EGFR antibody comprises a heavy chain variable region (HCVR) sequence at least about 90%, 95%, 97%, 99%, or 100% identical to SEQ ID NO: 65, and/or a light chain variable region (LCVR) sequence at least about 90%, 95%, 97%, 99%, or 100% identical to SEQ ID NO: 66 or 67, and preferably specifically binds EGFR.

In another embodiment, the cell-binding agent is an anti-CD19 antibody, such as those described in U.S. Pat. No. 8,435,528 and WO2004/103272, herein incorporated by reference. In one embodiment, the anti-CD19 antibody comprises an immunoglobulin heavy chain region having the amino acid sequence of QVQLVQPGAEVVKP-GASVKLSCKTGYTFTSNWMHWVKQAPGQGLE WIGEIDPSD SYTNYNQNFQGKAKLTVDKSTSTAYM EVSSLRSDDTAVYYCARGSNPYYYAMDY WGQGTS VT VSSASTKGPSVFPLAPSSKSTSGGTAALGCLVK DYFPEPVTVSWNSGAL TSGVHTFPAVLQSSGLYS-LSSVVTVPSSSLGTQTYICNVNHKPSNTKVDKKVE-PKSCD KTHTCPPCPAPELLGGPSVFLFPPKPKD TLM IS RTPEVTCVVVDVSHEDPEVKFNWYV DGVEV HNAKTKPREEQYNSTYRVVSVLTVLHQDWL NGKE YKCKVSNKALPAPIEK TISKAKGQPREPQVYT LPPSR DELTKNQVSLTCLVKGFYPSDIAVEWESNGQPENNY KTTPPVLDSDGSFFLYSKLTVDKSRWQQGNVFS CSVMHEALHNHYTQKSLSLSPGK (SEQ ID NO: 68) and an immunoglobulin light chain region having the amino acid sequence of EIVLTQSPAIMSASPGERVTM TCSASSGVNYMHWYQQKPGTSPRRWIYDTSKLASG VPARFSGSGSGTDYSLTISSMEPEDAATYYCHQRG-SYTFGGGTKLEIKRTVAAPSVFI FPPSDEQLKSGTAS VVCLLNNFYPREAKVQWKVDNALQSGNSQESVTE-QDSKDSTY SLSSTLTLSKADYEKHKVYACEVTH QGLSSPVTKSFNRGEC (SEQ ID NO: 69).

In another embodiment, the anti-CD19 antibody is huB4 antibody.

In yet another embodiment, the anti-CD19 antibody comprises the heavy chain CDR1-CDR3 of SEQ ID NO: 68, and/or the light chain CDR1-CDR3 of SEQ ID NO: 69, and preferably specifically binds CD19.

In yet another embodiment, the anti-CD19 antibody comprises a heavy chain variable region (HCVR) sequence at least about 90%, 95%, 97%, 99%, or 100% identical to SEQ ID NO: 68, and/or a light chain variable region (LCVR) sequence at least about 90%, 95%, 97%, 99%, or 100% identical to SEQ ID NO: 69, and preferably specifically binds CD19.

In yet another embodiment, the cell-binding agent is an anti-Muc1 antibody, such as those described in U.S. Pat. No. 7,834,155, WO 2005/009369 and WO 2007/024222, herein incorporated by reference. In one embodiment, the anti-Muc1 antibody comprises an immunoglobulin heavy chain region having the amino acid sequence of QAQLVQSGAEVVKPGASVKMSCKASGYTFTSYNMH WVKQTPGQGLEWIGYIYPGNGATNYNQKFQGKA TLTADTSSSTAYMQISSLTSEDSAVYFCARGDSVPFAY WGQGTLVTVSAASTKGPSVFPLAPSSKSTSGGTAAL-GCLVKDYFPEPVTVSWNSGALTSG VHTFPAVLQSSG-LYSLSSVVTVPSSSLGTQTYICNVNHKPSNTKVD KKVEPKSCDKT HTCPPCPAPELLGGPSVFLFP PKPK DTLMISRTPEVTCVVVDVSHEDPEVKFNWYVD GVEVHNAKTKPREEQYNSTYRVVSVLTVLHQD WLN GKEYKCKVSNKALPAPIEKTI SKAKGQPRE PQVY TLPPSRDELTKNQVSLTCLVKGFYPSDIAVEWESNGQ-PENNYKT TPPVLDSDGSFFLYSKLTVDKSRWQ QGN VFSCSVMHEALHNHYTQKSLSLSPGK (SEQ ID NO: 70) and an immunoglobulin light chain region having the amino acid sequence of EIVLTQSPATMSAS PGERVTITCSAHSSVSFMHWFQQKPGTSPKLWIYST SSLASGVPARFGGSGSGTSYSLTISSMEAEDAATYY CQQRSSFPLTFGAGTKLELKRTVAAPSVFI FPPSDEQ LKSGTASVVCLLNNFYPREAKVQWKVDNALQSG NSQESVTEQDSKDSTY SLSSTLTLSKADYEKHKVYA CEVTHQGLSSPVTKSFNRGEC (SEQ ID NO:71).

In another embodiment, the anti-Muc1 antibody is huDS6 antibody.

In yet another embodiment, the anti-Muc1 antibody comprises the heavy chain CDR1-CDR3 of SEQ ID NO: 70, and/or the light chain CDR1-CDR3 of SEQ ID NO: 71, and preferably specifically binds Muc1.

In yet another embodiment, the anti-Muc1 antibody comprises a heavy chain variable region (HCVR) sequence at least about 90%, 95%, 97%, 99%, or 100% identical to SEQ ID NO: 70, and/or a light chain variable region (LCVR) sequence at least about 90%, 95%, 97%, 99%, or 100% identical to SEQ ID NO: 71, and preferably specifically binds Muc1.

In certain embodiments, the cell-binding agent is a resurfaced antibody, a resurfaced single chain antibody, a resurfaced antibody fragment (or "antigen-binding portion"), or a bispecific antibody.

In certain embodiments, the cell-binding agent is a minibody, an avibody, a diabody, a tribody, a tetrabody, a nanobody, a probody, a domain antibody, or an unibody.

In other words, an exemplary cell binding agent may include an antibody, a single chain antibody, an antibody fragment that specifically binds to the target cell, a monoclonal antibody, a single chain monoclonal antibody, a monoclonal antibody fragment that specifically binds to a target cell, a chimeric antibody, a chimeric antibody fragment that specifically binds to the target cell, a bispecific antibody, a domain antibody, a domain antibody fragment that specifically binds to the target cell, an interferon, a lymphokine (e.g., IL-2, IL-3, IL-4, and IL-6), a hormone (e.g., insulin, thyrotropin releasing hormone, melanocyte-stimulating hormone, and a steroid hormone (e.g., androgen and estrogen)), a vitamin (e.g., folate), a growth factor (e.g., EGF, TGF-alpha, FGF, VEGF), a colony stimulating factor, a nutrient-transport molecule (e.g., transferrin; see O'Keefe et al. (1985) *J. Biol. Chem.* 260:932-937, incorporated herein by reference), a Centyrin (a protein scaffold based on a consensus sequence of fibronectin type III (FN3) repeats; see U.S. Patent Publication 2010/0255056, 2010/0216708 and 2011/0274623 incorporated herein by reference), an Ankyrin Repeat Protein (e.g., a designed ankyrin repeat protein, known as DARPin; see U.S. Patent Publication Nos. 2004/0132028, 2009/0082274, 2011/0118146, and 2011/0224100, incorporated herein by reference, and also see C. Zahnd et al., *Cancer Res.* (2010) 70:1595-1605; Zahnd et al., J. Biol. Chem. (2006) 281(46):35167-35175; and Binz, H. K., Amstutz, P. & Pluckthun, A., *Nature Biotechnology* (2005) 23:1257-1268, incorporated herein by reference), an ankyrin-like repeats protein or synthetic peptide (see e.g., U.S. Patent Publication No. 2007/0238667; U.S. Pat. No. 7,101,675; WO 2007/147213; and WO 2007/062466, incorporated herein by reference), an Adnectin (a fibronectin domain scaffold protein; see US Patent Publication Nos. 2007/0082365; 2008/0139791, incorporated herein by reference), Avibody (including diabodies, triabodies, and tetrabodies; see U.S. Publication Nos. 2008/0152586 and 2012/0171115), and other cell-binding molecules or substances.

In certain embodiments, the cell-binding agent may be a ligand that binds to a moiety on the target cell, such as a cell-surface receptor. For example, the ligand may be a growth factor or a fragment thereof that binds to a growth factor receptor; or may be a cytokine or a fragment thereof that binds to a cytokine receptor. In certain embodiments, the growth factor receptor or cytokine receptor is a cell-surface receptor.

In certain embodiments, wherein the cell-binding agent is an antibody or an antigen-binding portion thereof (including antibody derivatives), or certain antibody mimetics, the CBA may bind to a ligand on the target cell, such as a cell-surface ligand, including cell-surface receptors.

Specific exemplary antigens or ligands may include renin; a growth hormone (e.g., human growth hormone and bovine growth hormone); a growth hormone releasing factor; a parathyroid hormone; a thyroid stimulating hormone; a lipoprotein; alpha-1-antitrypsin; insulin A-chain; insulin B-chain; proinsulin; a follicle stimulating hormone; calcitonin; a luteinizing hormone; glucagon; a clotting factor (e.g., factor vmc, factor IX, tissue factor, and von Willebrands factor); an anti-clotting factor (e.g., Protein C); an atrial natriuretic factor; a lung surfactant; a plasminogen activator (e.g., a urokinase, a human urine or tissue-type plasminogen activator); bombesin; a thrombin; hemopoietic growth factor; tumor necrosis factor-alpha and -beta; an enkephalinase; RANTES (i.e., the regulated on activation normally T-cell expressed and secreted); human macrophage inflammatory protein-1-alpha; a serum albumin (human serum albumin); Muellerian-inhibiting substance; relaxin A-chain; relaxin B-chain; prorelaxin; a mouse gonadotropin-associated peptide; a microbial protein (beta-lactamase); DNase; IgE; a cytotoxic T-lymphocyte associated antigen (e.g., CTLA-4); inhibin; activin; a vascular endothelial growth factor; a receptor for hormones or growth factors; protein A or D; a rheumatoid factor; a neurotrophic factor (e.g., bone-derived neurotrophic factor, neurotrophin-3, -4, -5, or -6), a nerve growth factor (e.g., NGF-β); a platelet-derived growth factor; a fibroblast growth factor (e.g., aFGF and bFGF); fibroblast growth factor receptor 2; an epidermal growth factor; a transforming growth factor (e.g., TGF-alpha, TGF-β1, TGF-β2, TGF-β3, TGF-β4, and TGF-β5); insulin-like growth factor-I and —II; des(1-3)-IGF-I (brain IGF-I); an insulin-like growth factor binding protein; melanotransferrin; EpCAM; GD3; FLT3; PSMA; PSCA; MUC1; MUC16; STEAP; CEA; TENB2; an EphA receptor; an EphB receptor; a folate receptor; FOLR1; mesothelin; cripto; an alpha$_v$beta$_6$; integrins; VEGF; VEGFR; EGFR; transferrin receptor; IRTA1; IRTA2; IRTA3; IRTA4; IRTA5; CD proteins (e.g., CD2, CD3, CD4, CD5, CD6, CD8, CD11, CD14, CD19, CD20, CD21, CD22, CD25, CD26, CD28, CD30, CD33, CD36, CD37, CD38, CD40, CD44, CD52, CD55, CD56, CD59, CD70, CD79, CD80. CD81, CD103, CD105, CD123, CD134, CD137, CD138, and CD152), one or more tumor-associated antigens or cell-surface receptors (see US Publication No. 20080171040 or US Publication No. 20080305044, incorporated in their entirety by reference); erythropoietin; an osteoinductive factor; an immunotoxin; a bone morphogenetic protein; an interferon (e.g., interferon-alpha, -beta, and -gamma); a colony stimulating factor (e.g., M-CSF, GM-CSF, and G-CSF); interleukins (e.g., IL-1 to IL-10); a superoxide dismutase; a T-cell receptor; a surface membrane protein; a decay accelerating factor; a viral antigen s (e.g., a portion of the HIV envelope); a transport protein, a homing receptor; an addressin; a regulatory protein; an integrin (e.g., CD11a, CD11b, CD11c, CD18, an ICAM, VLA-4, and VCAM;) a tumor associated antigen (e.g., HER2, HER3 and HER4 receptor); endoglin; c-Met; c-kit; 1GF1R; PSGR; NGEP; PSMA; PSCA; TMEFF2; LGRS; B7H4; and fragments of any of the above-listed polypeptides.

As used herein, the term "antibody" includes immunoglobulin (Ig) molecules. In certain embodiments, the antibody is a full-length antibody that comprises four polypeptide chains, namely two heavy chains (HC) and two light chains (LC) inter-connected by disulfide bonds. Each heavy chain is comprised of a heavy chain variable region (HCVR or VH) and a heavy chain constant region (CH). The heavy chain constant region is comprised of three domains, CH1, CH2, and CH3. Each light chain is comprised of a light chain variable region (LCVR or VL) and a light chain constant region, which is comprised of one domain, CL. The VH and VL regions can be further subdivided into regions of hypervariability, termed complementarity determining regions (CDRs). Interspersed with such regions are the more conserved framework regions (FRs). Each VH and VL is composed of three CDRs and four FRs, arranged from amino-terminus to carboxy-terminus in the following order: FR1, CDR1, FR2, CDR2, FR3, CDR3, and FR4.

In certain embodiments, the antibody is IgG, IgA, IgE, IgD, or IgM. In certain embodiments, the antibody is IgG1, IgG2, IgG3, or IgG4; or IgA1 or IgA2.

In certain embodiments, the cell-binding agent is an "antigen-binding portion" of a monoclonal antibody, sharing sequences critical for antigen-binding with an antibody (such as huMy9-6 or its related antibodies described in U.S. Pat. Nos. 7,342,110 and 7,557,189, incorporated herein by reference).

As used herein, the term "antigen-binding portion" of an antibody (or sometimes interchangeably referred to as "antibody fragments"), include one or more fragments of an antibody that retain the ability to specifically bind to an antigen. It has been shown that the antigen-binding function of an antibody can be performed by certain fragments of a full-length antibody. Examples of binding fragments encompassed within the term "antigen-binding portion" of an antibody include (without limitation): (i) a Fab fragment, a monovalent fragment consisting of the VL, VH, CL and CH1 domains (e.g., an antibody digested by papain yields three fragments: two antigen-binding Fab fragments, and one Fc fragment that does not bind antigen); (ii) a F(ab')$_2$ fragment, a bivalent fragment comprising two Fab fragments linked by a disulfide bridge at the hinge region (e.g., an antibody digested by pepsin yields two fragments: a bivalent antigen-binding F(ab')$_2$ fragment, and a pFc' fragment that does not bind antigen) and its related F(ab') monovalent unit; (iii) a Fd fragment consisting of the VH and CH1 domains (i.e., that portion of the heavy chain which is included in the Fab); (iv) a Fv fragment consisting of the VL and VH domains of a single arm of an antibody, and the related disulfide linked Fv; (v) a dAb (domain antibody) or sdAb (single domain antibody) fragment (Ward et al., Nature 341:544-546, 1989), which consists of a VH domain; and (vi) an isolated complementarity determining region (CDR). In certain embodiments, the antigen-binding portion is a sdAb (single domain antibody).

In certain embodiments, antigen-binding portion also include certain engineered or recombinant derivatives (or "derivative antibodies") that also include one or more fragments of an antibody that retain the ability to specifically bind to an antigen, in addition to elements or sequences that may not be found in naturally existing antibodies.

For example, although the two domains of the Fv fragment, VL and VH, are coded for by separate genes, they can be joined, using standard recombinant methods, by a synthetic linker that enables them to be made as a single protein chain in which the VL and VH regions pair to form monovalent molecules (known as single chain Fv (scFv); see, e.g., Bird et al. Science 242:423-426, 1988: and Huston et al., Proc. Natl. Acad. Sci. USA 85:5879-5883, 1988).

In all embodiments described herein, the N-terminum of an scFv may be a VH domain (i.e., N—VH—VL-C), or a VL domain (i.e., N-VL-VH—C).

Divalent (or bivalent) single-chain variable fragments (di-scFvs, bi-scFvs) can be engineered by linking two scFvs. This produces a single peptide chain with two VH and two VL regions, yielding a tandem scFvs (tascFv). More tandem repeats, such as tri-scFv, may be similarly produced by linking three or more scFv in a head-to-tail fashion.

In certain embodiments, scFvs may be linked through linker peptides that are too short (about five amino acids) for the two variable regions to fold together, forcing scFvs to dimerize, and form diabodies (see, e.g., Holliger et al., Proc. Natl. Acad. Sci. USA 90:6444-6448, 1993; Poljak et al., Structure 2:1121-1123, 1994). Diabodies may be bi-specific or monospecific. Diabodies have been shown to have dissociation constants up to 40-fold lower than corresponding scFvs, i.e., having a much higher affinity to the target.

Still shorter linkers (one or two amino acids) lead to the formation of trimers, or so-called triabodies or tribodies. Tetrabodies have also been produced similarly. They exhibit an even higher affinity to their targets than diabodies. Diabodies, triabodies, and tetrabodies are sometimes collectively called "AVIBODY™" cell binding agents (or "AVIBODY" in short). That is, AVIBODY having two, three, or four Target Binding Regions (TBRs) are commonly known as Dia-, Tria- and Tetra-bodies. See, for example, U.S. Publication Nos. 2008/0152586 and 2012/0171115 for details, the entire teachings of which are incorporated herein by reference.

All of these formats can be composed from variable fragments with specificity for two or more different antigens, in which case they are types of bi- or multi-specific antibodies. For example, certain bispecific tandem di-scFvs, are known as bi-specific T-cell engagers (BiTEs).

In certain embodiments, each scFv in the tandem scFv or diabody/triabody/tetrabody may have the same or different binding specificity, and each may independently have an N-terminal VH or N-terminal VL.

Single chain Fv (scFv) can also be fused to an Fc moiety, such as the human IgG Fc moiety to obtain IgG-like properties, but nevertheless they are still encoded by a single gene. As transient production of such scFv-Fc proteins in mammalians can easily achieve milligram amounts, this derivative antibody format is particularly suitable for many research applications.

Fcabs are antibody fragments engineered from the Fc constant region of an antibody. Fcabs can be expressed as soluble proteins, or they can be engineered back into a full-length antibody, such as IgG, to create mAb2. A mAb2 is a full-length antibody with an Fcab in place of the normal Fc region. With these additional binding sites, mAb2 bispecific monoclonal antibodies can bind two different targets at the same time.

In certain embodiments, the engineered antibody derivatives have reduced size of the antigen-binding Ig-derived recombinant proteins ("miniaturized" full-size mAbs), produced by removing domains deemed non-essential for function. One of the best examples is SMIPs.

A Small modular immunopharmaceutical, or SMIP, is an artificial protein largely built from parts of antibodies (immunoglobulins), and is intended for use as a pharmaceutical drug. SMIPs have similar biological half-life as antibodies, but are smaller than antibodies and hence may have better tissue penetration properties. SMIPs are single-chain proteins that comprise one binding region, one hinge region as a connector, and one effector domain. The binding region comprises a modified single-chain variable fragment (scFv), and the rest of the protein can be constructed from the Fc (such as CH2, and CH3 as the effector domain) and the hinge region of an antibody, such as IgG1. Genetically modified cells produce SMIPs as antibody-like dimers that are about 30% smaller than real antibodies.

Another example of such engineered miniaturized antibody is "unibody," in which the hinge region has been removed from IgG4 molecules. IgG4 molecules are unstable and can exchange light-heavy chain heterodimers with one another. Deletion of the hinge region prevents heavy chain-heavy chain pairing entirely, leaving highly specific monovalent light/heavy heterodimers, while retaining the Fc region to ensure stability and half-life in vivo.

A single-domain antibody (sdAb, including but not limited to those called nanobody by Ablynx) is an antibody fragment consisting of a single monomeric variable antibody domain. Like a whole antibody, it is able to bind selectively to a specific antigen, but is much smaller due to its molecular weight of only 12-15 kDa. In certain embodiments, the single-domain antibody is engineered from heavy-chain antibodies (hcIgG). The first such sdAb was engineered based on an hcIgG found in camelids, called $V_HH$ fragments. In certain embodiments, the single-domain antibody is engineered from IgNAR ("immunoglobulin new antigen receptor," see below) using a VNAR fragment. Cartilaginous fishes (such as shark) have such heavy-chain IgNAR antibodies. In certain embodiments, the sdAb is engineered by splitting the dimeric variable domains from common immunoglobulin G (IgG), such as those from humans or mice, into monomers. In certain embodiments, a nanobody is derived from a heavy chain variable domain. In certain embodiments, a nanobody is derived from light chain variable domain. In certain embodiments, the sdAb is obtained by screening libraries of single domain heavy chain sequences (e.g., human single domain HCs) for binders to a target antigen.

The single variable new antigen receptor domain antibody fragments (VNARs, or VNAR domains) are derived from cartilaginous fish (e.g., shark) immunoglobulin new antigen receptor antibodies (IgNARs). Being one of the smallest known immunoglobulin-based protein scaffolds, such single domain proteins demonstrate favorable size and cryptic epitope recognition properties. Mature IgNAR antibodies consist of homodimers of one variable new antigen receptor (VNAR) domain and five constant new antigen receptor (CNAR) domains. This molecule is highly stable, and possesses efficient binding characteristics. Its inherent stability can likely be attributed to both (i) the underlying Ig scaffold, which presents a considerable number of charged and hydrophilic surface exposed residues compared to the conventional antibody VH and VL domains found in murine antibodies; and (ii) stabilizing structural features in the complementary determining region (CDR) loops including inter-loop disulphide bridges, and patterns of intra-loop hydrogen bonds.

A minibody is an engineered antibody fragment comprising an scFv linked to a CH domain, such as the CH3γ1 (CH3 domain of IgG1) or CH4ε (CH4 domain of IgE). For example, an scFv specific for carcinoembryonic antigen (CEA) has been linked to the CH3γ1 to create a minibody, which has previously been demonstrated to possess excellent tumor targeting coupled with rapid clearance in vivo (Hu et al., *Cancer Res.* 56:3055-3061, 1996). The scFv may have a N-terminal VH or VL. The linkage may be a short peptide (e.g., two amino acid linker, such as ValGlu) that results in a non-covalent, hingeless minibody. Alternatively, the linkage may be an IgG1 hinge and a GlySer linker peptide that produces a covalent, hinge-minibody.

Natural antibodies are mono-specific, but bivalent, in that they express two identical antigen-binding domains. In contrast, in certain embodiments, certain engineered antibody derivatives are bi- or multi-specific molecules possess two or more different antigen-binding domains, each with different target specificity. Bispecific antibodies can be generated by fusing two antibody-producing cells, each with distinct specificity. These "quadromas" produced multiple molecular species, as the two distinct light chains and two distinct heavy chains were free to recombine in the quadromas in multiple configurations. Since then, bispecific Fabs, scFvs and full-size mAbs have been generated using a variety of technologies (see above).

The dual variable domain immunoglobulin (DVD-Ig) protein is a type of dual-specific IgG that simultaneously target two antigens/epitopes (DiGiammarino et al., *Methods Mol Biol.* 899:145-56, 2012). The molecule contains an Fc region and constant regions in a configuration similar to a conventional IgG. However, the DVD-Ig protein is unique in that each arm of the molecule contains two variable domains (VDs). The VDs within an arm are linked in tandem and can possess different binding specificities.

A DuoBody® is a bispecific modified IgG1 antibody heterodimer. IgG1 hinge region that generally includes (i) a stable hinge region that contains a CPPC sequence and is non-permissive for Fab arm exchange in vivo and (ii) an IgG4-like CH3 domain that is modified to contain F405L and K409R residues, which renders it permissive for Fab arm exchange in vivo. (See, for example, WO2008119353 and WO2011131746).

Trispecific antibody derivative molecules can also been generated by, for example, expressing bispecific antibodies with two distinct Fabs and an Fc. One example is a mouse IgG2a anti-Ep-CAM, rat IgG2b anti-CD3 quadroma, called BiUII, which is thought to permit the co-localization of tumor cells expressing Ep-CAM, T cells expressing CD3, and macrophages expressing FCγRI, thus potentiating the costimulatory and anti-tumor functions of the immune cells.

Probodies are fully recombinant, masked monoclonal antibodies that remain inert in healthy tissue, but are activated specifically in the disease microenvironment (e.g., through protease cleavage by a protease enriched or specific in a disease microenvironment). See Desnoyers et al., *Sci. Transl. Med.*, 5:207ra144, 2013. Similar masking techniques can be used for any of the antibodies or antigen-binding portions thereof described herein.

An intrabody is an antibody that has been modified for intracellular localization, for working within the cell to bind to an intracellular antigen. The intrabody may remain in the cytoplasm, or may have a nuclear localization signal, or may have a KDEL sequence for ER targeting. The intrabody may be a single-chain antibody (scFv), modified immunoglobulin VL domains with hyperstability, selected antibody resistant to the more reducing intracellular environment, or expressed as a fusion protein with maltose binding protein or other stable intracellular proteins. Such optimizations have improved the stability and structure of intrabodies, and may have general applicability to any of the antibodies or antigen-binding portions thereof described herein.

The antigen-binding portions or derivative antibodies of the invention may have substantially the same or identical (1) light chain and/or heavy chain CDR3 regions; (2) light chain and/or heavy chain CDR1, CDR2, and CDR3 regions; or (3) light chain and/or heavy chain regions, compared to an antibody from which they are derived/engineered. Sequences within these regions may contain conservative amino acid substitutions, including substitutions within the CDR regions. In certain embodiments, there is no more than 1, 2, 3, 4, or 5 conservative substitutions. In an alternative, the antigen-binding portions or derivative antibodies have a light chain region and/or a heavy chain region that is at least about 90%, 95%, 99% or 100% identical to an antibody from which they are derived/engineered. These antigen-binding portions or derivative antibodies may have substantially the same binding specificity and/or affinity to the target antigen compared to the antibody. In certain embodiments, the $K_d$ and/or $k_{off}$ values of the antigen-binding portions or derivative antibodies are within 10-fold (either higher or lower), 5-fold (either higher or lower), 3-fold (either higher or lower), or 2-fold (either higher or lower) of an antibody described herein.

In certain embodiments, the antigen-binding portions or derivative antibodies may be derived/engineered from fully human antibodies, humanized antibodies, or chimeric antibodies, and may be produced according to any art-recognized methods.

Monoclonal antibody techniques allow for the production of extremely specific cell-binding agents in the form of specific monoclonal antibodies. Particularly well known in the art are techniques for creating monoclonal antibodies produced by immunizing mice, rats, hamsters or any other mammal with the antigen of interest such as the intact target cell, antigens isolated from the target cell, whole virus, attenuated whole virus, and viral proteins such as viral coat proteins. Sensitized human cells can also be used. Another method of creating monoclonal antibodies is the use of phage libraries of scFv (single chain variable region), specifically human scFv (see e.g., Griffiths et al., U.S. Pat. Nos. 5,885,793 and 5,969,108; McCafferty et al., WO 92/01047; Liming et al., WO 99/06587). In addition, resurfaced antibodies disclosed in U.S. Pat. No. 5,639,641 may also be used, as may chimeric antibodies and humanized antibodies.

Cell-binding agent can also be peptides derived from phage display (see, for example, Wang et al., *Proc. Natl. Acad. Sci. USA* (2011) 108(17), 6909-6914) or peptide library techniques (see, for example, Dane et al., *Mol. Cancer. Ther.* (2009) 8(5):1312-1318).

In certain embodiments, the CBA of the invention also includes an antibody mimetic, such as a DARPin, an affibody, an affilin, an affitin, an anticalin, an avimer, a Fynomer, a Kunitz domain peptide, a monobody, or a nanofitin.

As used herein, the terms "DARPin" and "(designed) ankyrin repeat protein" are used interchangeably to refer to certain genetically engineered antibody mimetic proteins typically exhibiting preferential (sometimes specific) target binding. The target may be protein, carbohydrate, or other chemical entities, and the binding affinity can be quite high. The DARPins may be derived from natural ankyrin repeat-containing proteins, and preferably consist of at least three, usually four or five ankyrin repeat motifs (typically about 33 residues in each ankyrin repeat motif) of these proteins. In certain embodiments, a DARPin contains about four- or five-repeats, and may have a molecular mass of about 14 or 18 kDa, respectively. Libraries of DARPins with randomized potential target interaction residues with diversities of over $10^{12}$ variants can be generated at the DNA level, for use in selecting DARPins that bind desired targets (e.g., acting as receptor agonists or antagonists, inverse agonists, enzyme inhibitors, or simple target protein binders) with picomolar affinity and specificity, using a variety of technologies such as ribosome display or signal recognition particle (SRP) phage display. See, for example, U.S. Patent Publication Nos. 2004/0132028, 2009/0082274, 2011/0118146, and 2011/0224100, WO 02/20565 and WO 06/083275 for DARPin preparation (the entire teachings of which are incorporated herein by reference), and also see C. Zahnd et al. (2010) *Cancer Res.*, 70:1595-1605; Zahnd et al. (2006) *J. Biol. Chem.*, 281(46):35167-35175; and Binz, H. K., Amstutz, P. & Pluckthun, A. (2005) *Nature Biotechnology*, 23:1257-1268 (all incorporated herein by reference). Also see U.S. Patent Publication No. 2007/0238667; U.S. Pat. No. 7,101,675; WO 2007/147213; and WO 2007/062466 (the entire teachings of which are incorporated herein by reference), for the related ankyrin-like repeats protein or synthetic peptide.

Affibody molecules are small proteins engineered to bind to a large number of target proteins or peptides with high affinity, thus imitating monoclonal antibodies. An Affibody consists of three alpha helices with 58 amino acids and has a molar mass of about 6 kDa. They have been shown to withstand high temperatures (90° C.) or acidic and alkaline conditions (pH 2.5 or pH 11), and binders with an affinity of down to sub-nanomolar range have been obtained from naïve library selections, and binders with picomolar affinity have been obtained following affinity maturation. In certain embodiments, affibodies are conjugated to weak electrophiles for binding to targets covalently.

Monobodies (also known as Adnectins), are genetically engineered antibody mimetic proteins capable of binding to antigens. In certain embodiments, monobodies consist of 94 amino acids and have a molecular mass of about 10 kDa. They are based on the structure of human fibronectin, more specifically on its tenth extracellular type III domain, which has a structure similar to antibody variable domains, with seven beta sheets forming a barrel and three exposed loops on each side corresponding to the three complementarity determining regions. Monobodies with specificity for different proteins can be tailored by modifying the loops BC (between the second and third beta sheets) and FG (between the sixth and seventh sheets).

A tribody is a self-assembly antibody mimetic designed based on the C-terminal coiled-coil region of mouse and human cartilage matrix protein (CMP), which self-assembles into a parallel trimeric complex. It is a highly stable trimeric targeting ligand created by fusing a specific target-binding moiety with the trimerization domain derived from CMP. The resulting fusion proteins can efficiently self-assemble into a well-defined parallel homotrimer with high stability. Surface plasmon resonance (SPR) analysis of the trimeric targeting ligands demonstrated significantly enhanced target-binding strength compared with the corresponding monomers. Cellular-binding studies confirmed that such tribodies have superior binding strength toward their respective receptors.

A Centyrin is another antibody mimetic that can be obtained using a library built upon the framework of a consensus FN3 domain sequence (Diem et al., *Protein Eng. Des. Sel.*, 2014). This library employs diversified positions within the C-strand, CD-loop, F-strand and FG-loop of the FN3 domain, and high-affinity Centyrin variants can be selected against specific targets.

All methods for introducing N-terminal Ser/Thr and the subsequent oxidation to aldehyde group for reacting with aldehyde reacting groups are applicable for cell-binding agents that are antibodies and that are not antibodies, including, for example, centyrin, Darpin, Avibody, adnectin, antibody fragment, minibody, diabody, tribody, tetrabody, nanobody, probody, duobody, domain body or unibody, etc.

Certain examples below refer to various humanized anti-CD123 antibodies, the nomenclature of such antibodies are briefly described here. One class of huCD123-6 antibodies are humanized by grafting the 6 CDRs from the heavy and light chains of the murine anti-CD123 antibody muCD123-6. In those antibodies, the letter "G" immediately follows the clone designation (i.e., huCD123-6), which is in turn followed by a version number that designates the origin of the human light chain and heavy chain variable region sequences. Thus huCD123-6Gv4.6 refers to the humanized CD123 antibody based on grafting ("G") the 6 CDR regions from the corresponding muCDR123-6 antibody, onto the human light chain variable region Gv4 and the heavy chain variable region Gv6. Similarly, -Gv4.7 comprises human light chain variable region Gv4 and heavy chain variable region Gv7.

Another class of huCD123-6 antibodies are humanized by way of resurfacing. The resurfaced antibody having the resurfaced heavy chain sequence huCD123-6rhv1.1 and the resurfaced light chain sequence huCD123-6rlv1.0 is huCD123-6Rv1.1.

As used herein, NTS #2 or "S2" for short refers to an antibody having an engineered Ser at the N-terminus of heavy chain. Thus the S2 variant of the huCD123-6Gv4.7 antibody is designated huCD123-6Gv4.7S2. Likewise, NTS #3 or "S3" for short refers to an antibody having an engineered Ser at the N-terminus of light chain. The S3 variant of the huCD123-6Gv4.7 antibody is designated huCD123-6Gv4.7S3.

Figure 17:
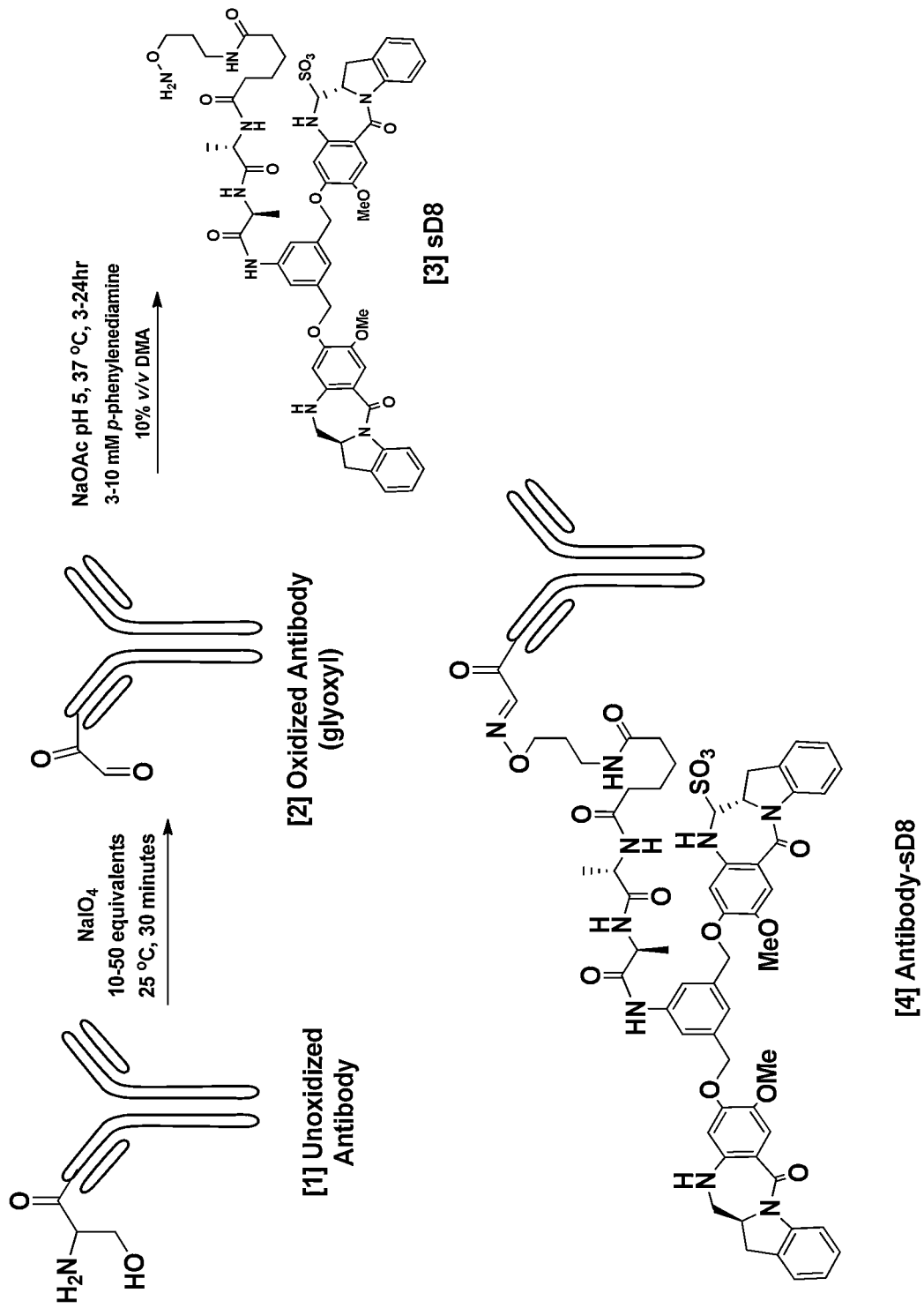
FIG. 17 shows an exemplary scheme for synthesizing the huCD123-sD8 conjugate using engineered N-terminal Ser-containing humanized monoclonal antibody.
Figure 18:
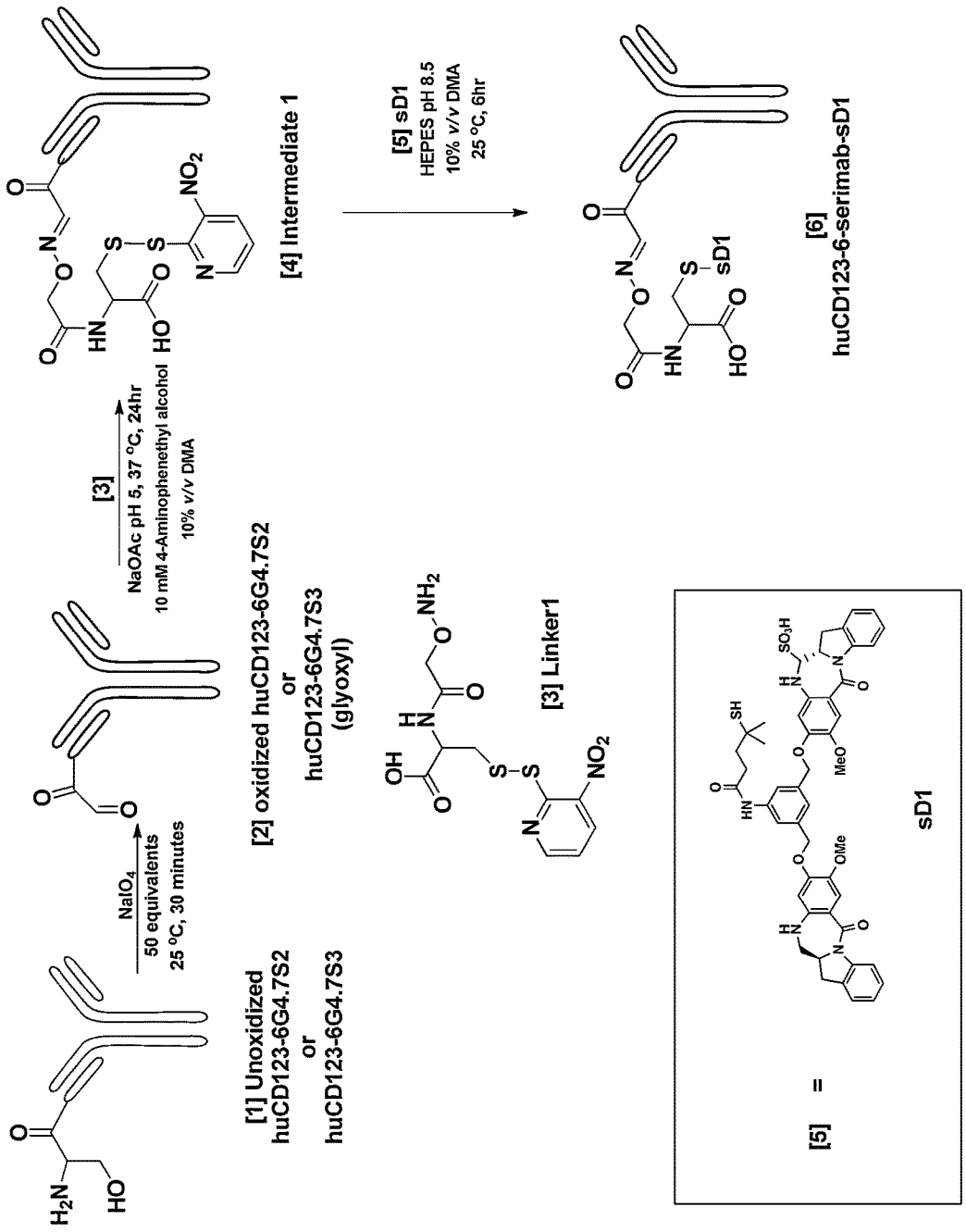
FIG. 18 shows an exemplary scheme for synthesizing the huCD123-6-SeriMab-sD1 conjugate bearing a Linker 1 residue.

When an antibody comprising an engineered N-terminal Ser (either S2 or S3) is conjugated with a cytotoxic drug/agent through the oxidized N-terminal Ser, the conjugate name may contain a "SeriMab" designation. For example, huCD123-6Gv4.7S3-SeriMab-D8 refers to conjugate between D8 (see FIG. 17 for D8 or sD8 structure) and the humanized CD123 antibody huCD123-6Gv4.7S3, through the oxidized N-terminal Ser on the light chain.

Note that the cytotoxic agents used in Examples 23-30, and FIGS. 17, 18, 22A-24, 26A-26C, and 29, such as "D8" and its sulfonated version "sD8" and related "D2," "D1" and its sulfonated version "sD1," may not follow the general formula of drug molecule "D" in the subject conjugates, but the structures of these cytotoxic agents are depicted in the associated figures and text.

Certain humanized anti-CD123 antibodies are described in U.S. Provisional Application No. 62/186,161, filed on Jun. 29, 2015, entitled "ANTI-CD123 ANTIBODIES AND CONJUGATES AND DERIVATIVES THEREOF," the entire teaching of the 62/186,161 application, including all protein (e.g., antibody and CDRs, HCVRs, LCVRs, full-length HC and LC sequences thereof) and nucleic acid sequences and the associated SEQ ID NOs, particularly those of CD123-SeriMab having one or more engineered N-terminal Ser/Thr residues, are incorporated herein by reference in its entirety.

Cytotoxic Agents

In a third embodiment, the present invention provides cytotoxic agents (represented by D') that can be covalently linked to the cell-binding agents described herein to form the conjugates of the present invention.

In one embodiment, the cytotoxic agent is a maytansinoid. More specifically, the cytotoxic agent D' is represented by the following structural formula:

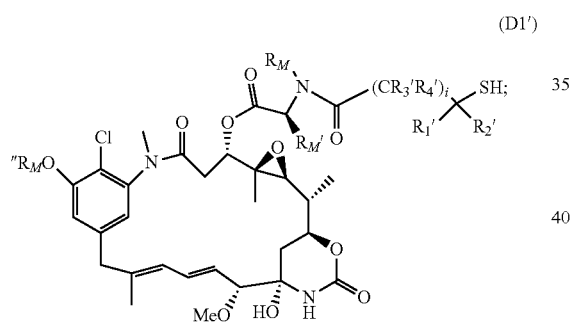

(D1')

wherein the variables are as described for formula (D1) in the $5^{th}$ specific embodiment of the first embodiment. More specifically, the cytotoxic agent D' is DM1 (D2') or DM4 (D3'):

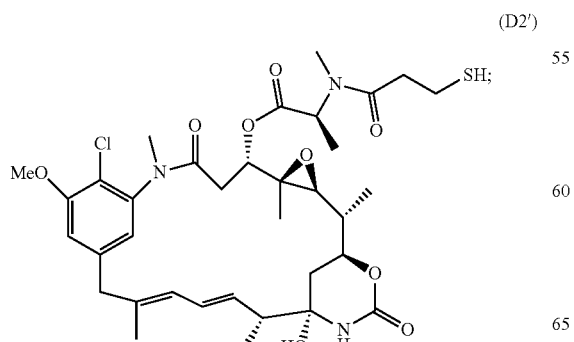

(D2')

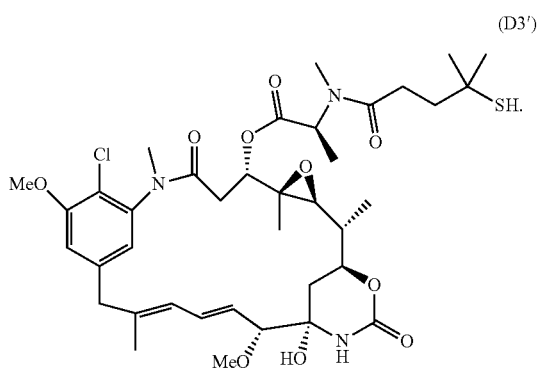

(D3')

In another more specific embodiment, the cytotoxic agent D' is represented by the following formula:

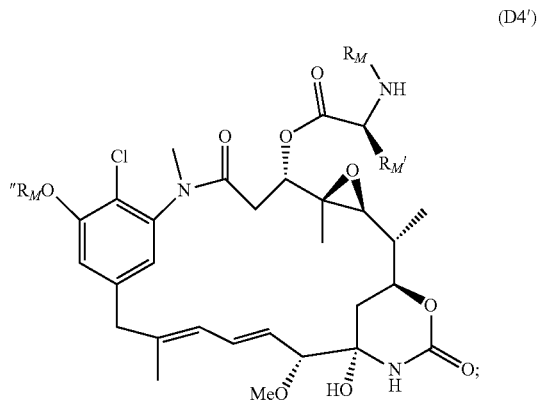

(D4')

wherein the variables as described above for formula (D4) in the $5^{th}$ specific embodiment of the first embodiment.

In yet another specific embodiment, the cytotoxic agent D' is represented by the following formula:

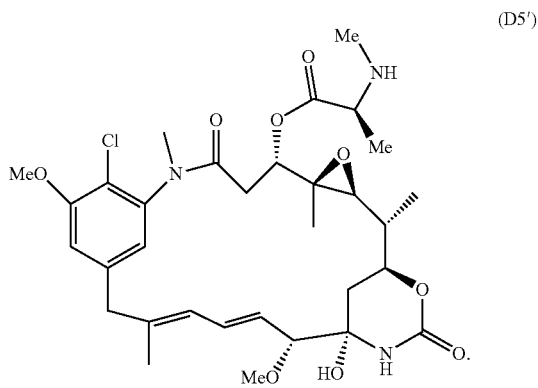 [SMILES: CN[C@@H](C)C(=O)O[C@H]1CC(=O)N(C)c2cc(cc(OC)c2Cl)C/C(C)=C/C=C/[C@@H](OC)[C@@]2(O)C[C@H](OC(=O)N2)[C@@H](C)[C@@H]2O[C@@]12C]

(D5')

In another specific embodiment, the cytotoxic agent D' is a maytansinoid compound comprising an aldehyde reactive group, which can be directly linked to the cell-binding agent. More specifically, the maytansinoid compound is represented by the following formula:

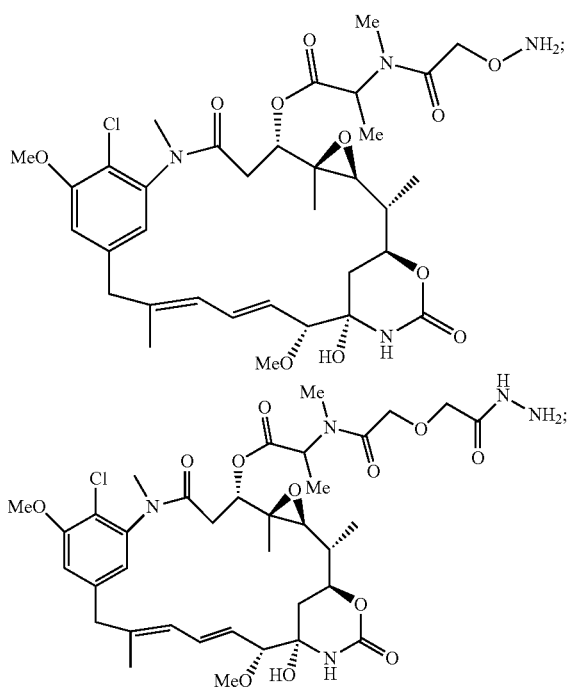
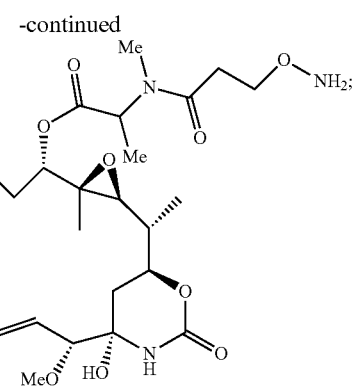
In another embodiment, the cytotoxic agent is a benzodiazepine compound. Exemplary benzodiazepine compounds include, but are not limited those described in U.S. Pat. Nos. 8,765,740, 8,426,402, US2014/0088089, WO2011/130613, WO2011/130616, WO2010/091150, and WO2009/016516.
In a more specific embodiment, the cytotoxic agent D' is a benzodiazepine compound represented by the following structural formula:
(D6')
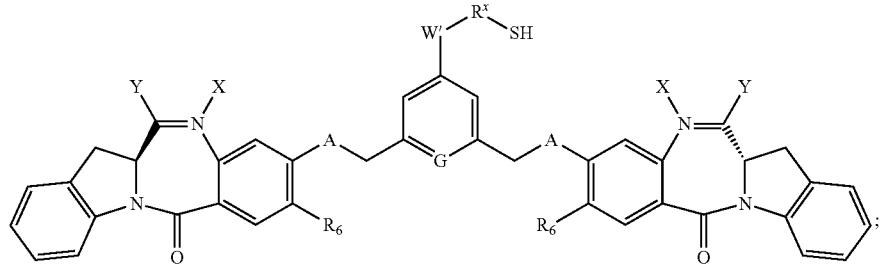
(D7')
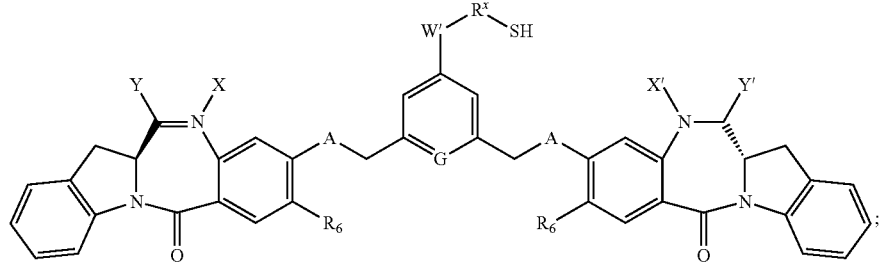
(D8')
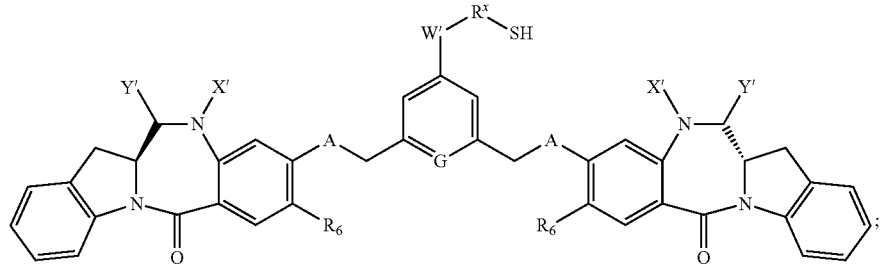

-continued
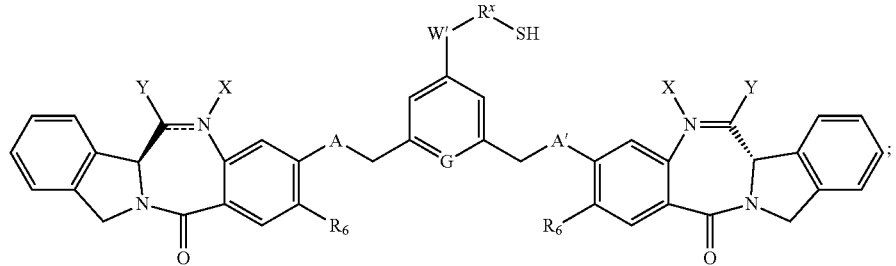
(D9′)
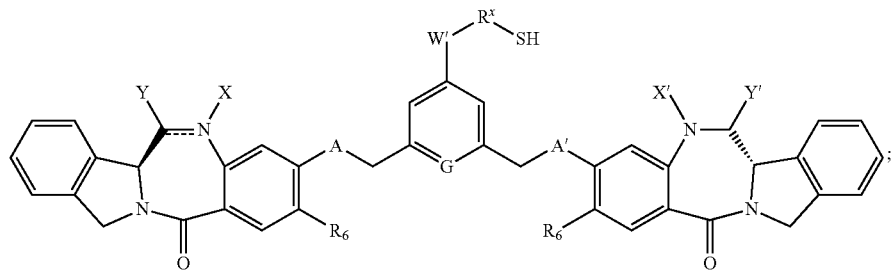
(D10′)
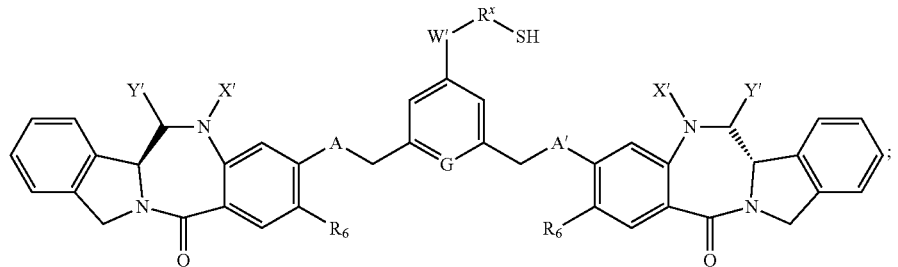
(D11′)
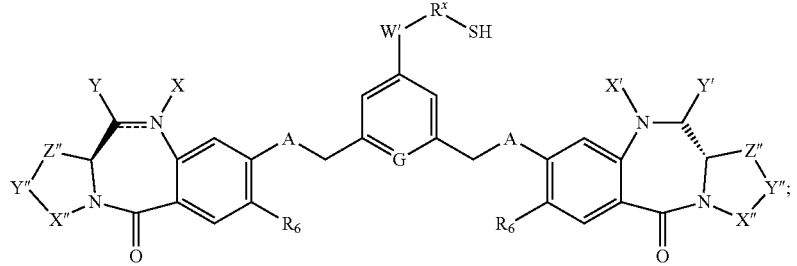
(D12′)
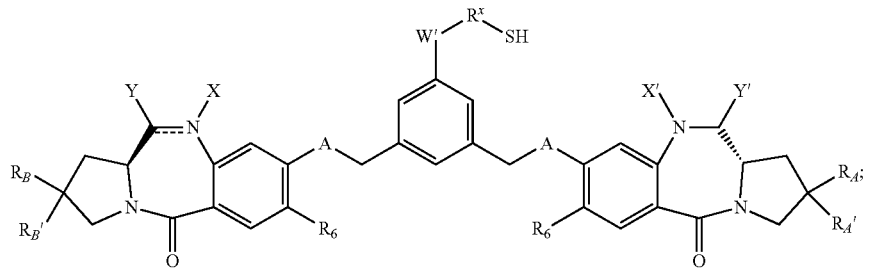
(D13′)

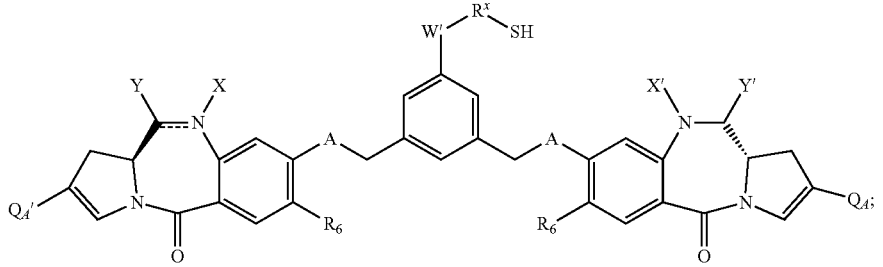
(D14')
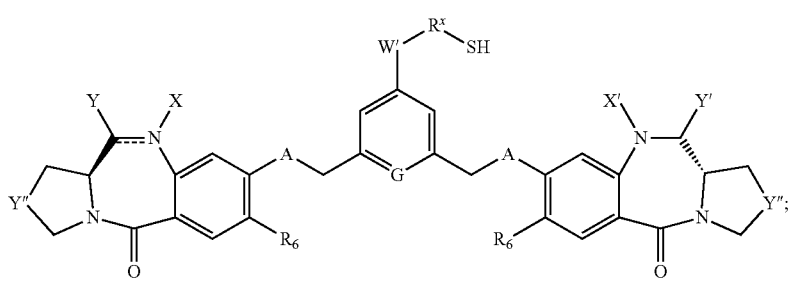
(D15')
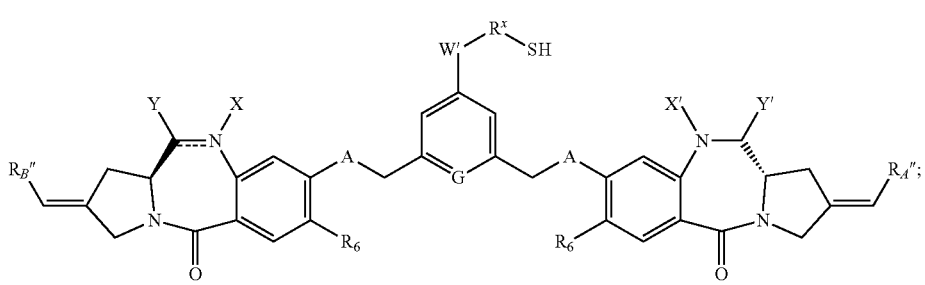
(D16')
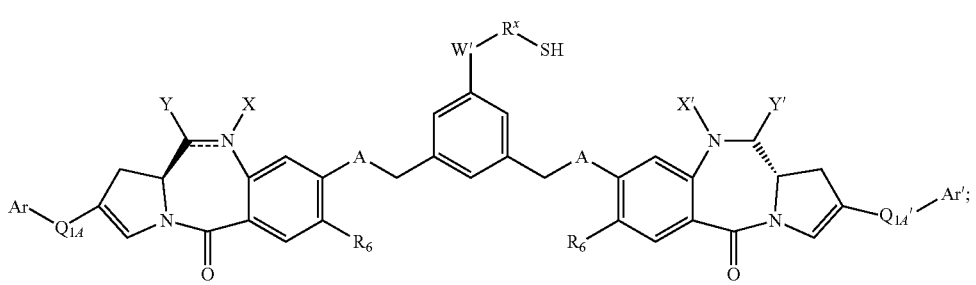
(D17')
or a pharmaceutically acceptable salt thereof, wherein the variables are as described above for formulas (D6)-(D17) in the 6$^{th}$ specific embodiment of the first embodiment.
In a more specific embodiment, D' is represented by the following structural formula:
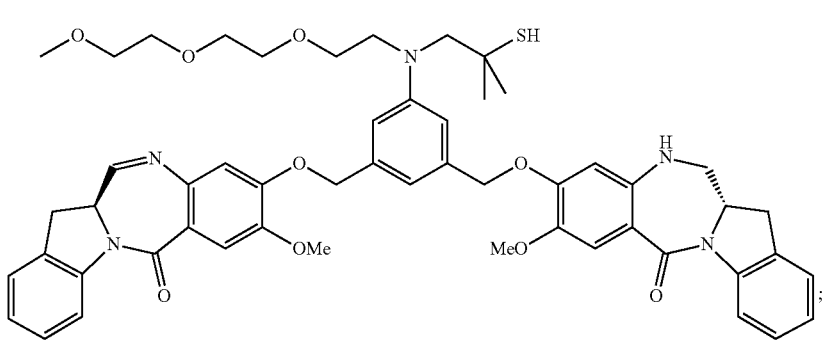
(D30')

(D31')

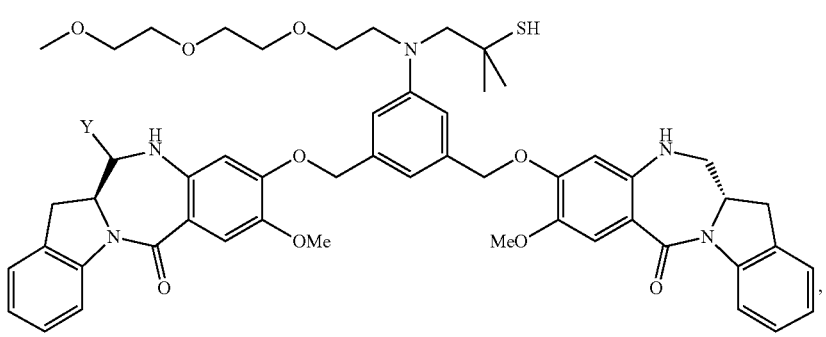

(D32')

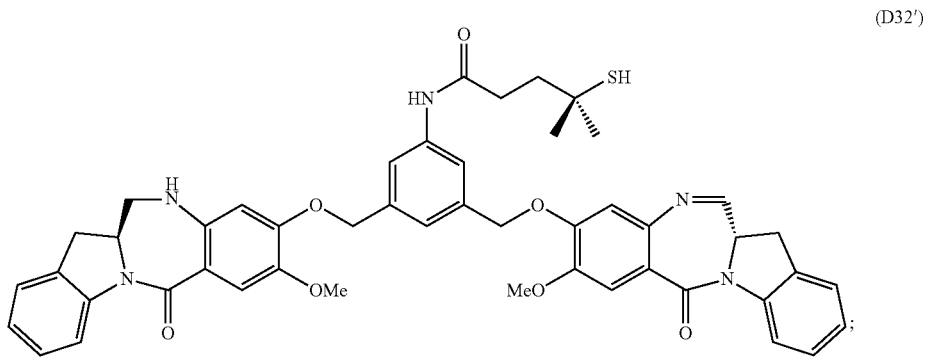

(D33')

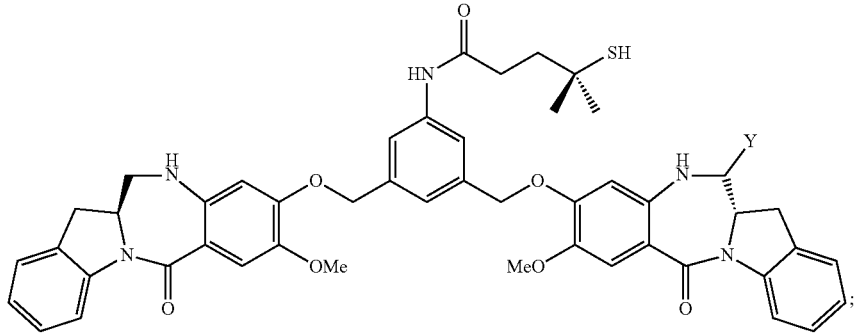

or a pharmaceutically acceptable salt thereof, wherein Y is —H or —SO$_3$M, and M is H$^+$ or a cation. Even more specifically, Y is —SO$_3$M, and M is H$^+$, Na$^+$ or K$^+$.

In another more specific embodiment, the cytotoxic agent D' is a benzodiazepine compound comprising an aldehyde reactive group, which can be directly linked to the cell-binding agent. More specifically, the benzodiazepine compound is represented by the following structural formula:

(D18')

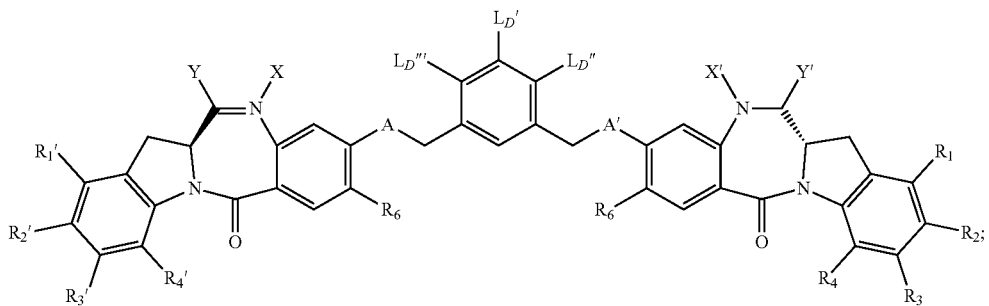

-continued (D19′)
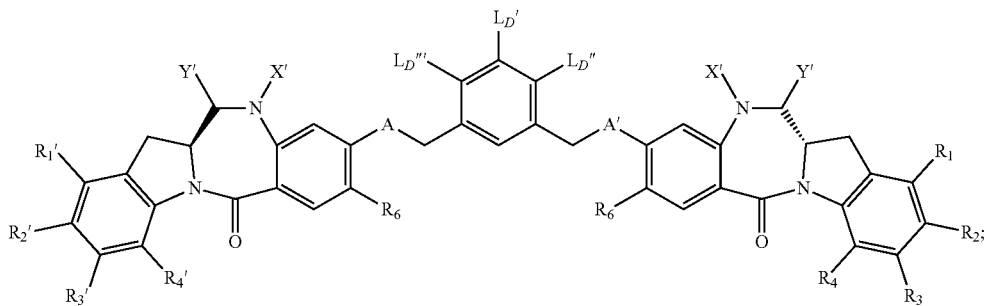

(D20′)
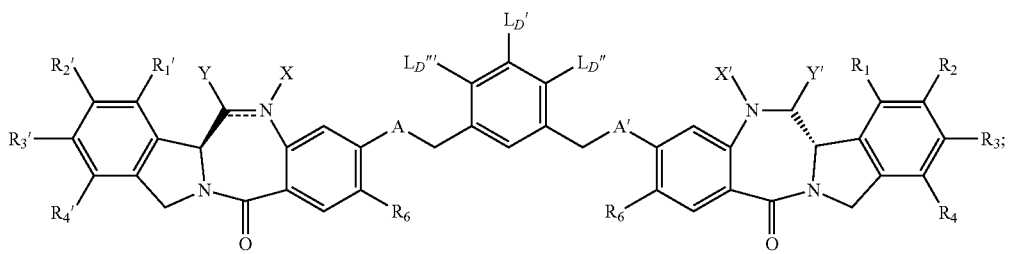

(D21′)
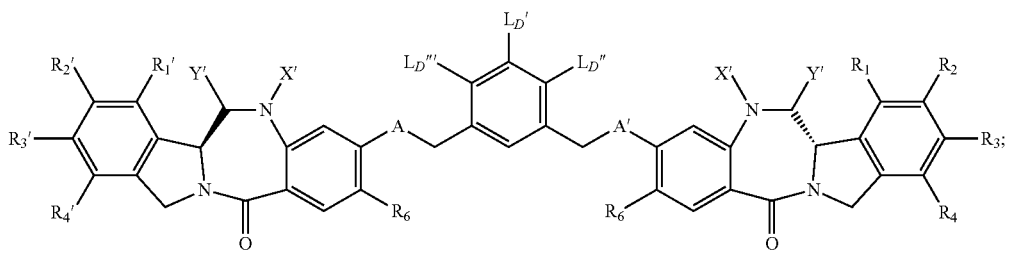

(D22′)
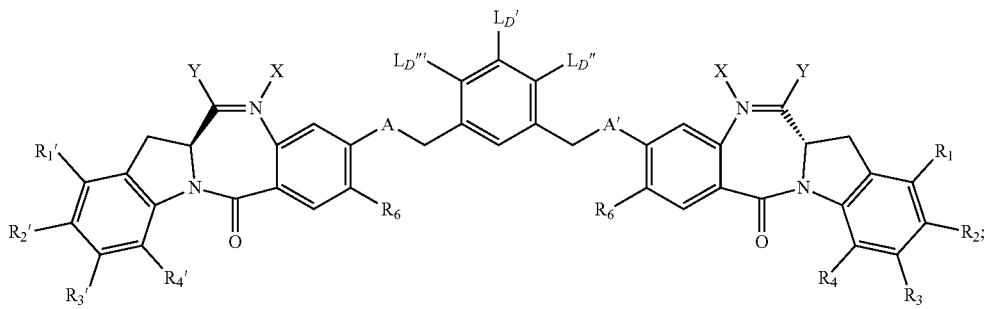

(D23′)
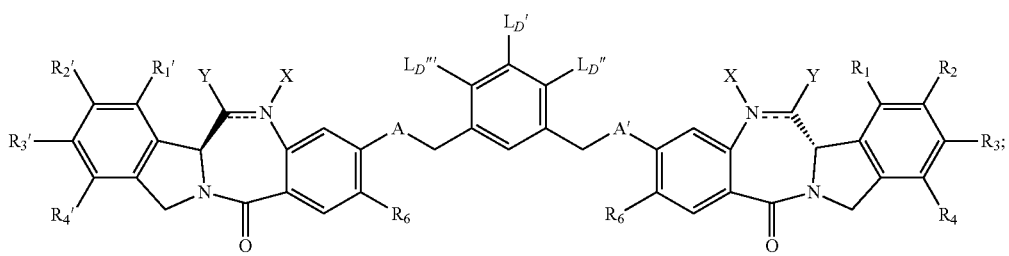

or a pharmaceutically acceptable salt thereof, wherein:
one of $L_D'$, $L_D''$, and $L_D'''$ is represented by the following formula:

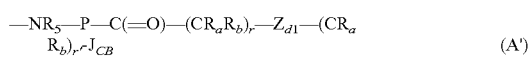

(A′)

and the other two are the same or different, and are independently selected from —H, an optionally substituted linear, branched or cyclic alkyl, alkenyl or alkynyl having from 1 to 10 carbon atoms, a polyethylene glycol unit —(OCH$_2$CH2)$_n$—R$^c$, halogen, guanidinium [—NH(C=NH)NH$_2$], —OR, —NR'R", —NO$_2$, —NR'COR", —SR, —SOR', —SO$_2$R', —SO$_3$H, —OSO$_3$H, —SO$_2$NR'R", cyano, an azido, —COR', —OCOR', and —OCONR'R";

$J_{CB}$ is an aldehyde reactive group as described above in the first embodiment; and the remaining variables are as described above for structural formulas (D18)-(D23) in the 7th specific embodiment of the first embodiment and any more specific embodiments described therein.

More specifically, for formulas (D18')-(D23'), $J_{CB}$ is

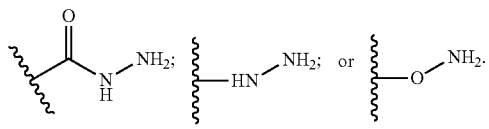

In another more specific embodiment, for formulas (D18')-(D23'), L' is represented by formula (A) and L" and L'" are both —H; and remaining variables are as describe in any embodiments above.

In another more specific embodiment, for formulas (D18')-(D23'):
the double line == between N and C represents a single bond or double bond, provided that when it is a double bond X is absent and Y is —H, and when it is a single bond, X is —H, Y is —OH or —SO$_3$M;
$R_1$, $R_2$, $R_3$, $R_4$, $R_1'$, $R_2'$, $R_3'$ and $R_4'$ are all —H;
$R_6$ is —OMe;
X' and Y' are both —H;
A and A' are —O—; and
M is H$^+$, Na$^+$ or K$^+$ and the remaining variables are as described in any embodiments above.

In yet another more specific embodiment, for formulas (D18')-(D23'), $R_a$ and $R_b$ are both H; and the remaining variables are as described in any embodiments above.

In another more specific embodiment, for formulas (D18')-(D23'), $R_5$ and $R_9$ are each independently H or Me; and the remaining variables are as described any embodiments above. More specifically, $R_5$ and $R_9$ are both H.

In another more specific embodiment, for formulas (D18')-(D23'), P is a peptide containing 2 to 10 amino acid residues; and the remaining variables are as described in any embodiments above. More specifically, P is a peptide containing 2 to 5 amino acid residues. Even more specifically, P is elected from Gly-Gly-Gly, Ala-Val, Val-Ala, Val-Cit, Val-Lys, Phe-Lys, Lys-Lys, Ala-Lys, Phe-Cit, Leu-Cit, Lle-Cit, Trp, Cit, Phe-Ala, Phe-N$^9$-tosyl-Arg, Phe-N$^9$-nitro-Arg, Phe-Phe-Lys, D-Phe-Phe-Lys, Gly-Phe-Lys, Leu-Ala-Leu, Ile-Ala-Leu, Val-Ala-Val, Ala-Leu-Ala-Leu (SEQ ID NO: 17), β-Ala-Leu-Ala-Leu (SEQ ID NO: 18) and Gly-Phe-Leu-Gly (SEQ ID NO: 19), Val-Arg, Arg-Val, Arg-Arg, Val-D-Cit, Val-D-Lys, Val-D-Arg, D-Val-Cit, D-Val-Lys, D-Val-Arg, D-Val-D-Cit, D-Val-D-Lys, D-Val-D-Arg, D-Arg-D-Arg, Ala-Ala, Ala-D-Ala, D-Ala-Ala, and D-Ala-D-Ala.

In another more specific embodiment, the cytotoxic agent D' is represented by the following structural formula:

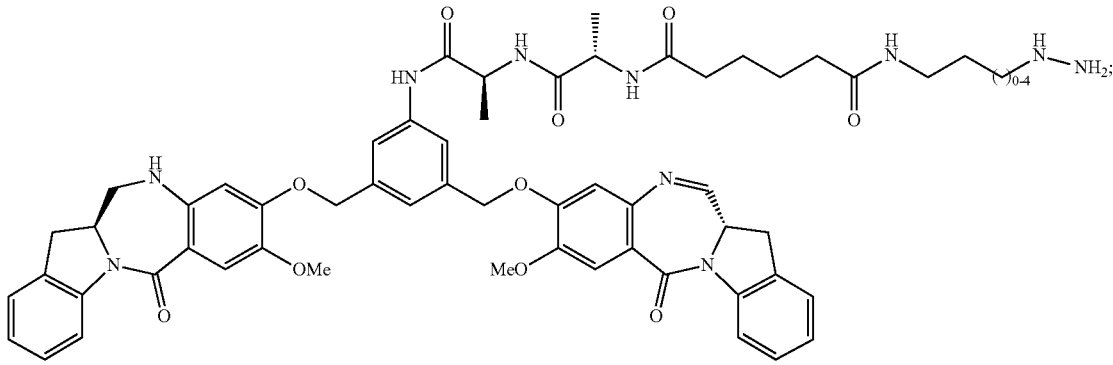

(D24')

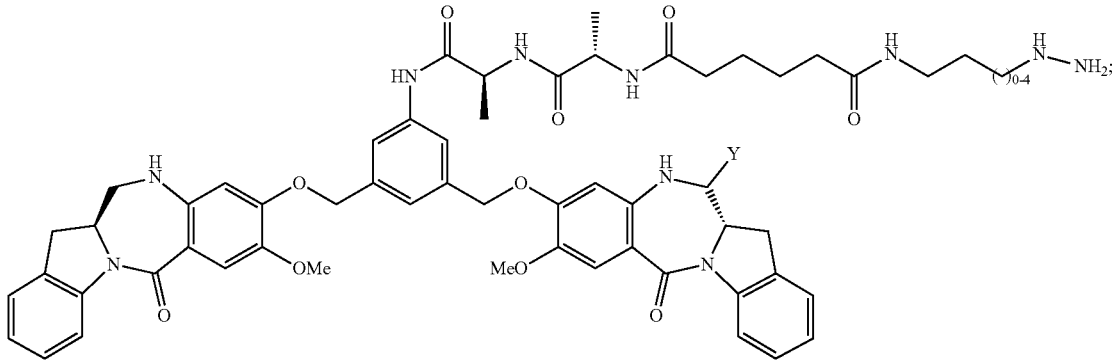

(D25')

-continued
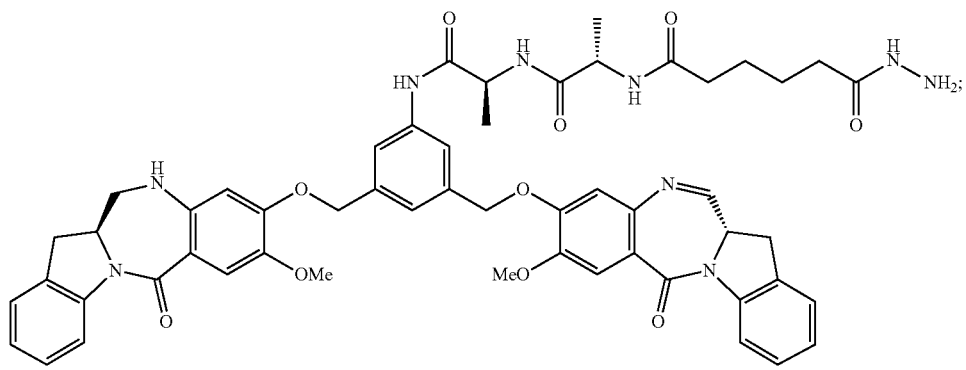
(D26′)
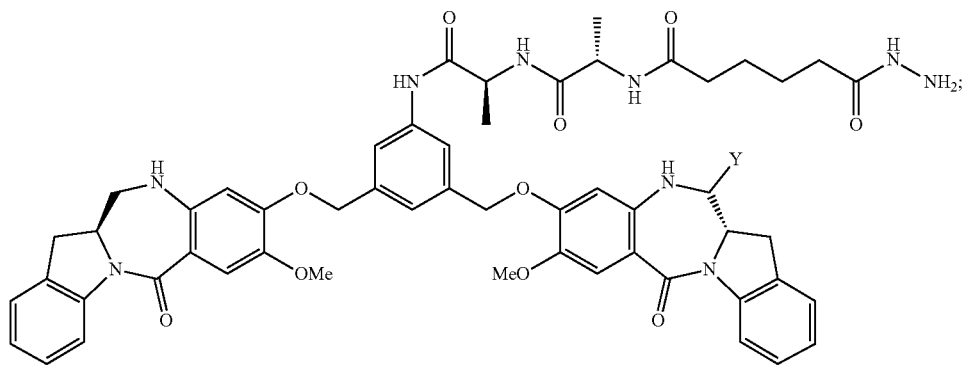
(D27′)
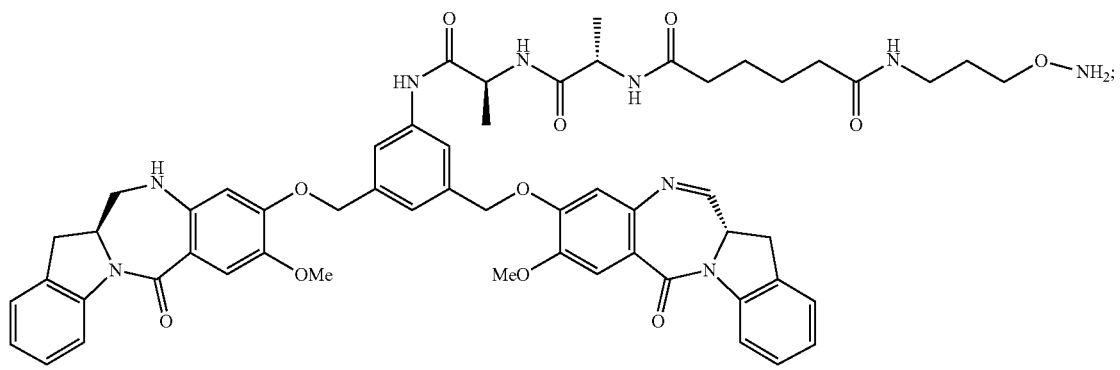
(D28′)
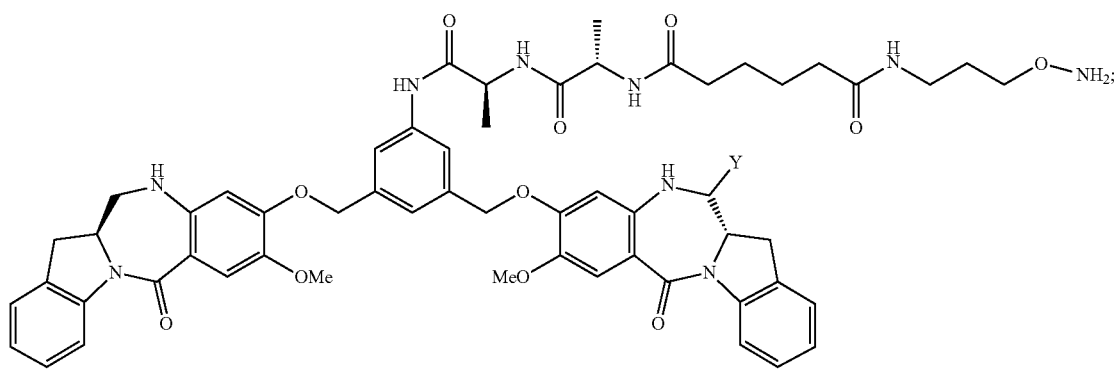
(D29′)
or a pharmaceutically acceptable salt thereof, wherein Y is H or —SO$_3$M and M is H$^+$, Na$^+$ or K$^+$.

Cytotoxic Agent-Linker Compounds

In a fourth embodiment, the present invention provides cytotoxic agent-linker compounds having an aldehyde reactive group, which can be covalently linked to the cell-binding agents describe herein.

In certain embodiments, the cytotoxic agent-linker compounds are represented by the following formula:

$$J_{CB}\text{-}L\text{-}J_{D}\text{-}D \qquad (II),$$

wherein $J_{CB}$ is an aldehyde reactive group described in the first embodiment; and the remaining variables are as describe above in the first embodiment or the $2^{nd}$ to $6^{th}$ specific embodiment of the first embodiment or any more specific embodiments described therein.

More specifically, $J_{CB}$ is a hydrazine, a hydrazide or a hydroxylamine.

In another embodiment, $J_{CB}$ is selected from:

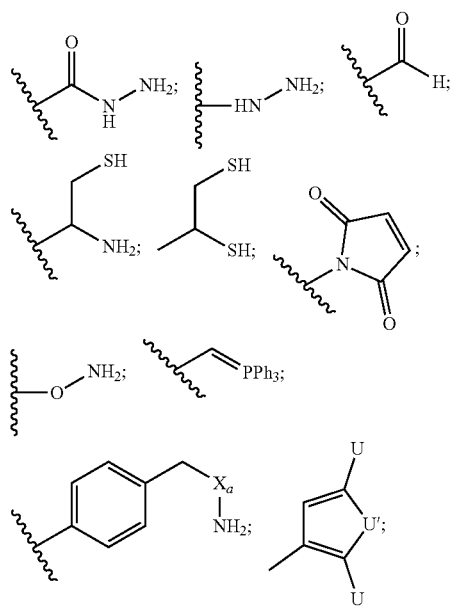

-continued

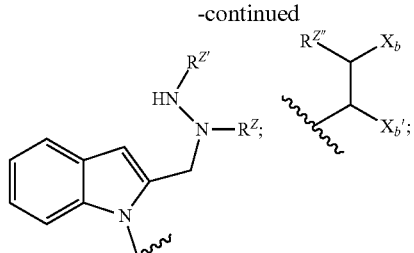

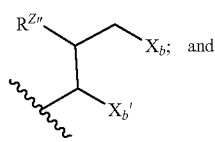

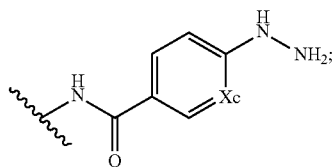

wherein: $X_a$ is CH2, O or NCH$_3$; U' is NH, O, S or CH$_2$; U is H or an electron donating group; $X_b$ and $X_b'$ are each independently —OH, —SH or —NH$_2$; $R^Z$ and $R^{Z'}$ are each independently H or an alkyl (preferably -Me); $R^{Z''}$ is H or an alkyl; and $X_c$ is N or CH. More specifically, the aldehyde reactive group

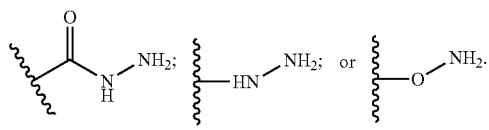

In one embodiment, the cytotoxic agent-linker compound is represented by the following structural formula:

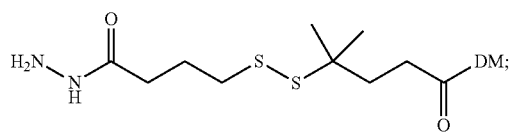

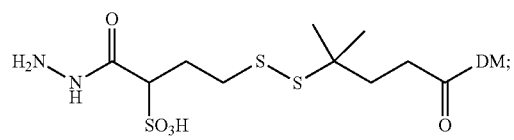

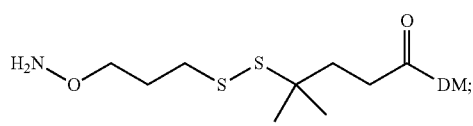

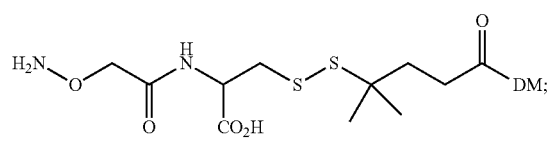

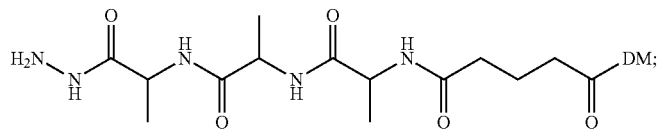

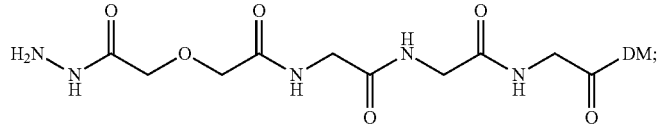

-continued
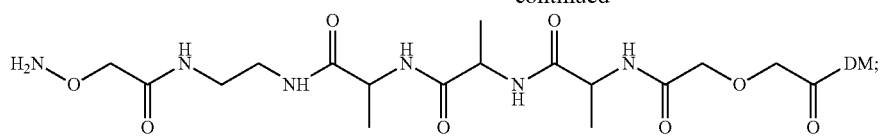
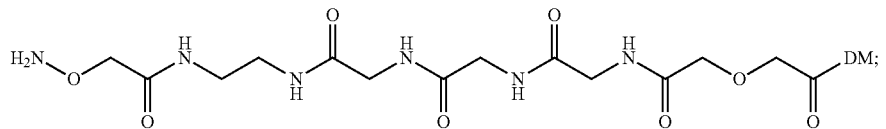
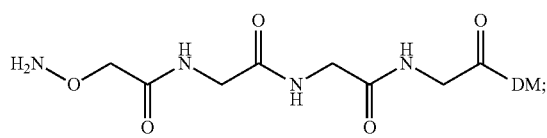
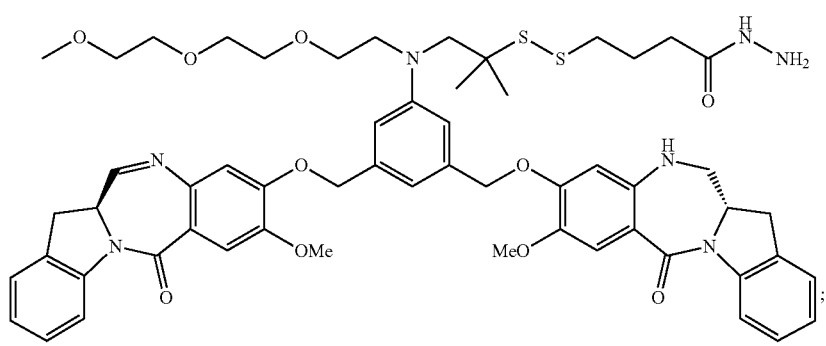
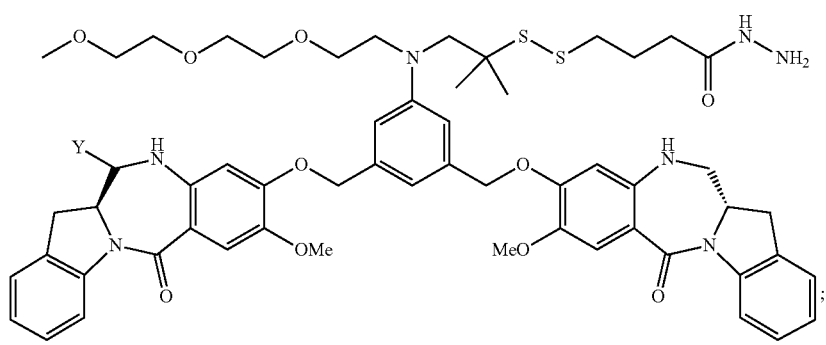
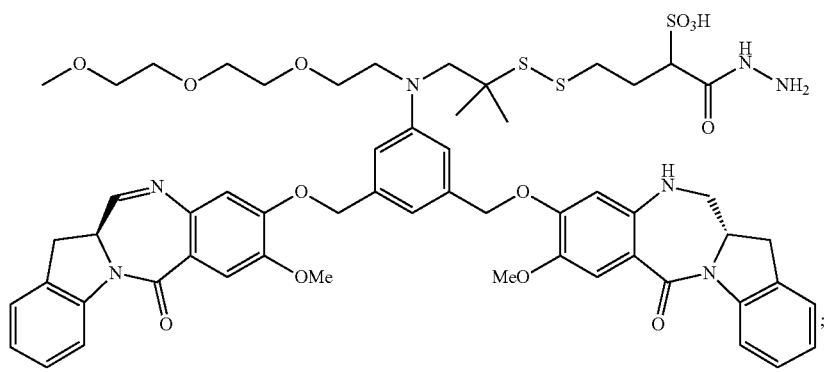

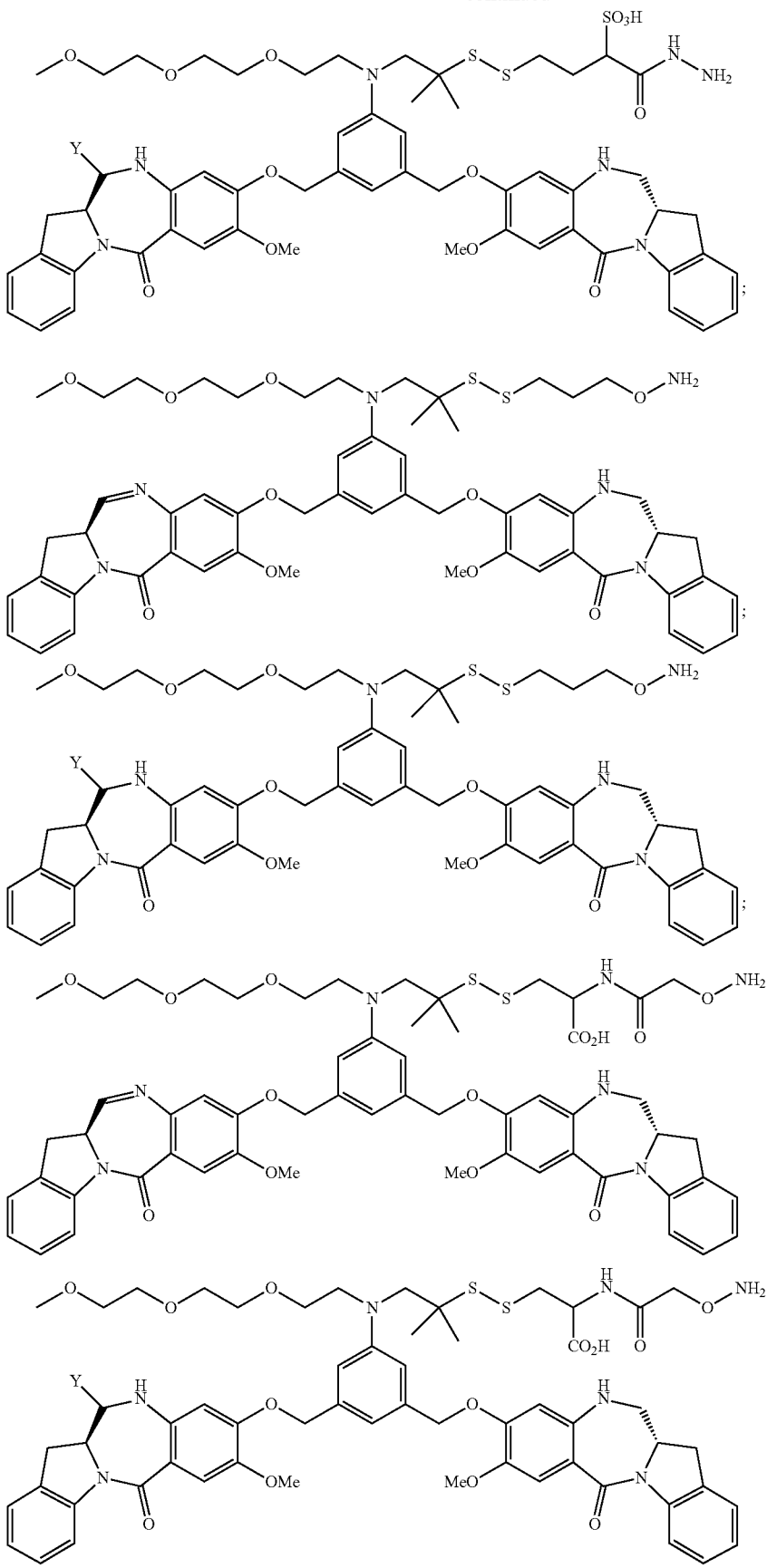

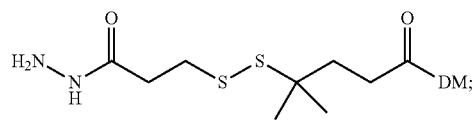
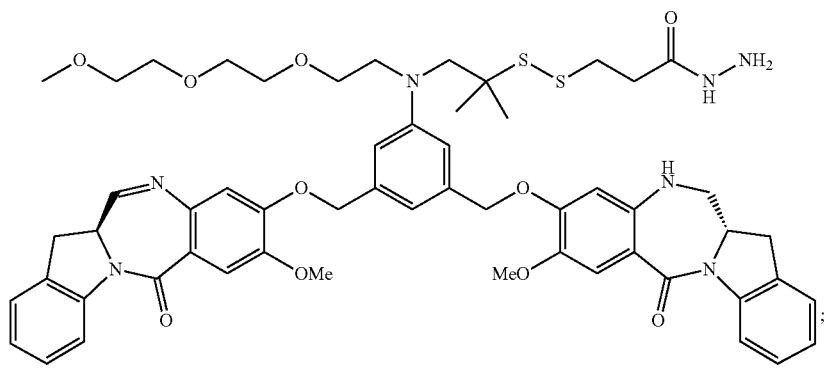
(44)
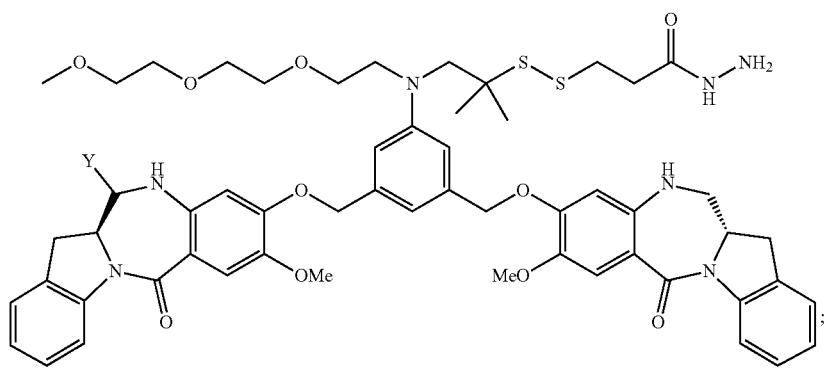
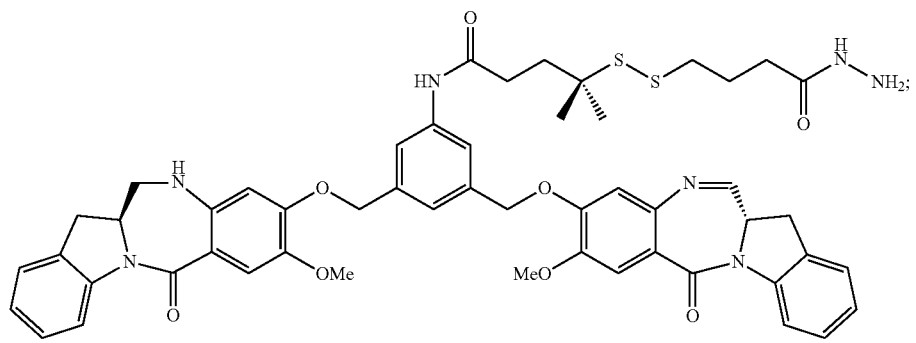
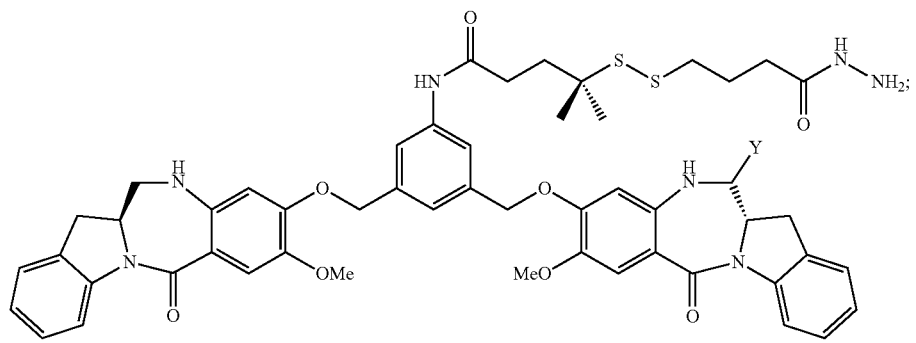

-continued
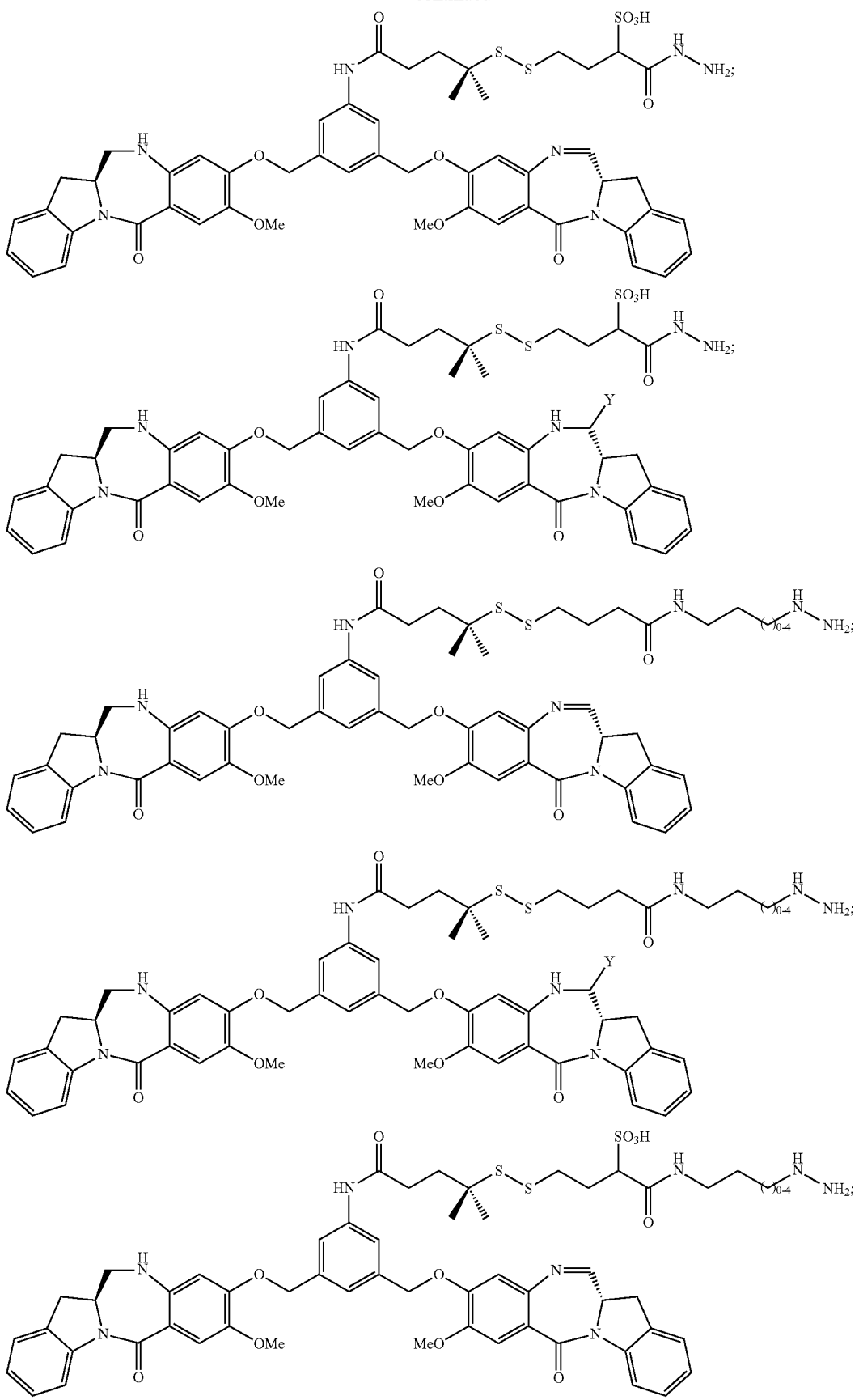

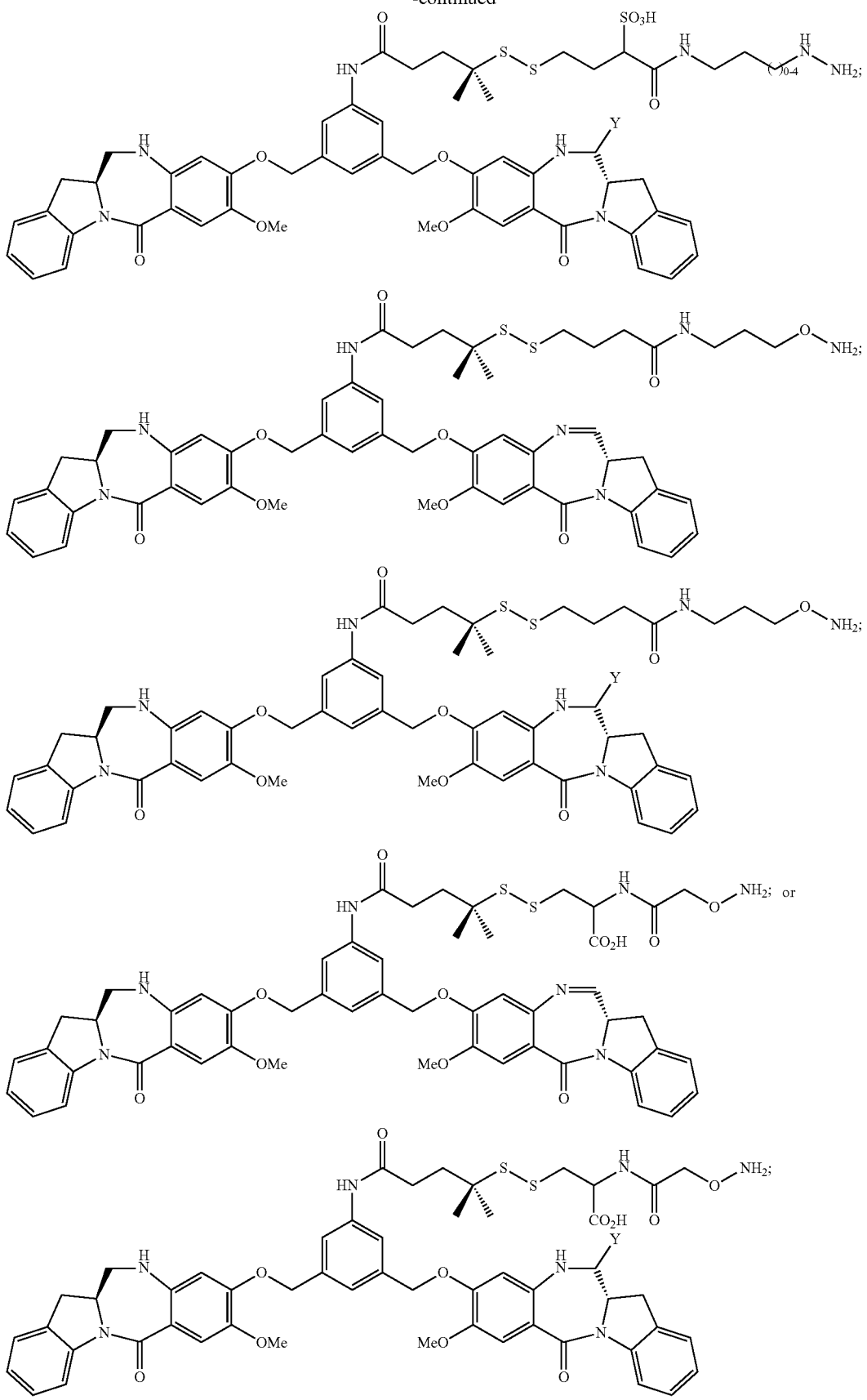

or a pharmaceutically acceptable salt thereof, and Y is H or —SO₃M and M is H⁺, Na⁺ or K⁺.

Modified Cell-Binding Agent

In a fifth embodiment, the present invention provides modified cell-binding agents formed by reacting cell-binding agents described herein with a linker compound having an aldehyde reactive group.

In certain embodiment, the modified cell-binding agent is represented by the following formula:

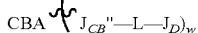     (III)

wherein $J_D$ is a reactive group that can form a covalent bond with the cytotoxic agent D'; and the remaining variables are as described above in the first embodiment or any specific embodiments described therein.

In a 1st specific embodiment, for modified cell-binding agent of structural formula (III) or a pharmaceutically acceptable salt thereof, $J_{CB'}$ is represented by one of the following structural formulas:

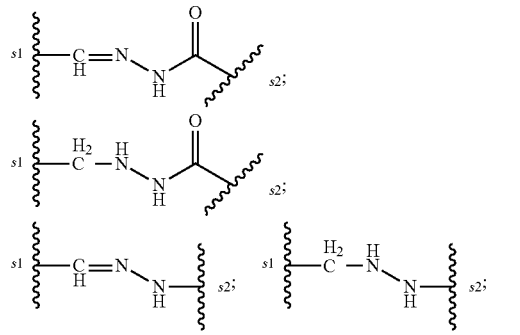

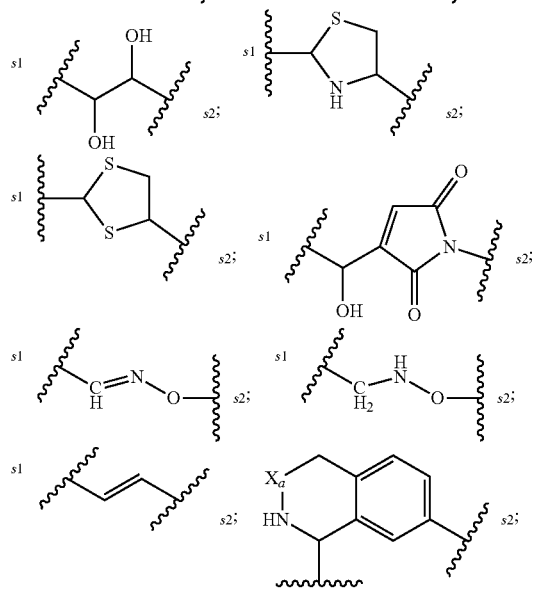

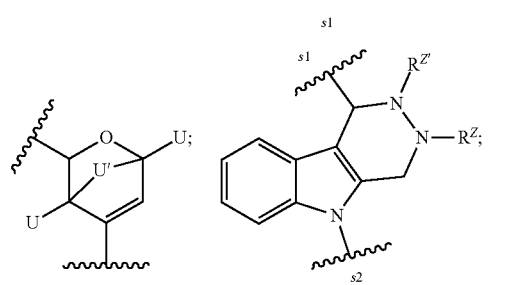

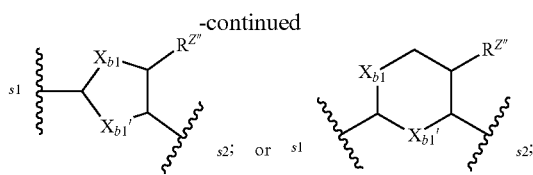

wherein: $X_a$ is $CH_2$, O or $NCH_3$; U' is NH, O, S or $CH_2$; U is H or an electron donating group; $X_{b1}$ and $X_{b2}$ are each independently —O—, —S— or —NH—; $R^Z$ and $R^{Z'}$ are each independently H or an alkyl (preferably -Me); and $R^{Z''}$ is H or an alkyl; s1 is the site covalently linked to the cell-binding agent; and s2 is the site covalently linked to the group L. More specifically, $J_{CB'}$ is

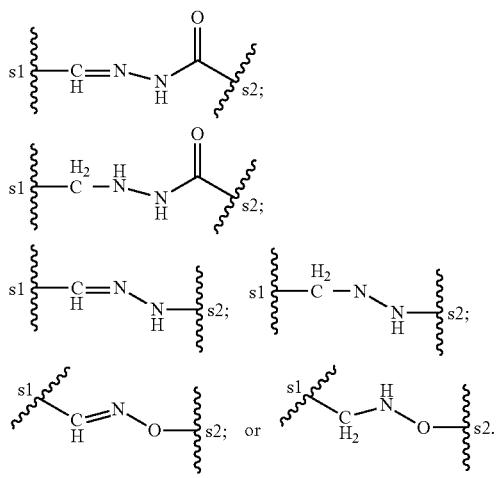

In a 2nd specific embodiment, for formula (III), -L-$J_D$ is represented by the following formula:

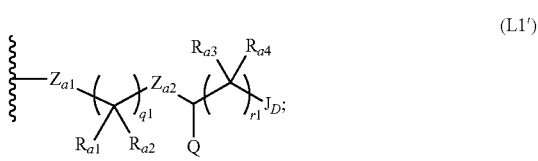     (L1')

wherein $J_D$ is —SH, —SSR$^d$ or —SC(=O)R$^g$, wherein R$^d$ is phenyl, nitrophenyl, dinitrophenyl, carboxynitrophenyl, pyridyl or nitropyridyl; and R$^g$ is alkyl; $J_{CB'}$ is as described above in the 1st specific embodiment; and the remaining variables are as described above for formula (L1) in the 2nd specific embodiment of the first embodiment and any more specific embodiments described therein. More specifically, $J_D$ is -SH or —SSR$^d$.

In a more specific embodiment, -L-$J_D$ is represented by the following structural formula:

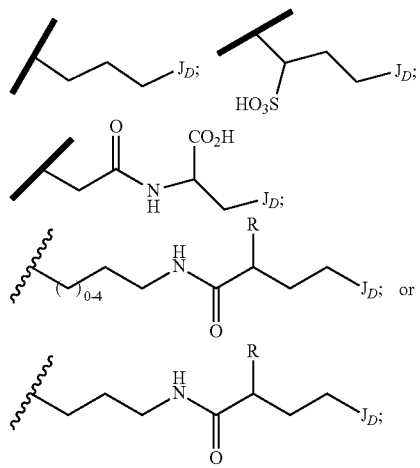

or a pharmaceutically acceptable salt thereof, wherein $J_{CB}'$ and $J_D$ are as described above in the 2nd specific embodiment. More specifically, $J_D$ is -SH or —SSR$^d$.

In a 3rd specific embodiment, for formula (III), -L-$J_D$ is represented by the following formula:

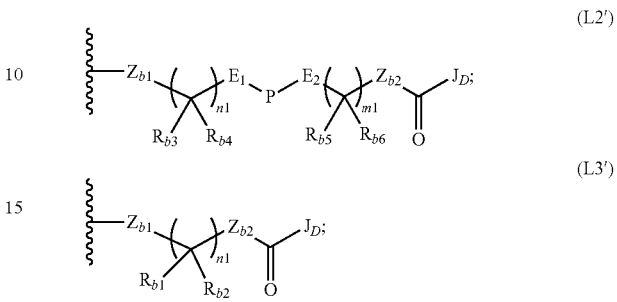

wherein $J_D$ is —OH or halogen; or —C(=O)-$J_D$ is a reactive ester; $J_{CB}'$ is as described above in the 1" specific embodiment; and the remaining variables are as described above for formulas (L2) and (L3) in the 3' specific embodiment of the first embodiment or any more specific embodiments described therein. More specifically, —C(=O)-$J_D$ is N-hydroxysuccinimide ester.

In a more specific embodiment, -L-$J_D$ is represented by the following structural formula:

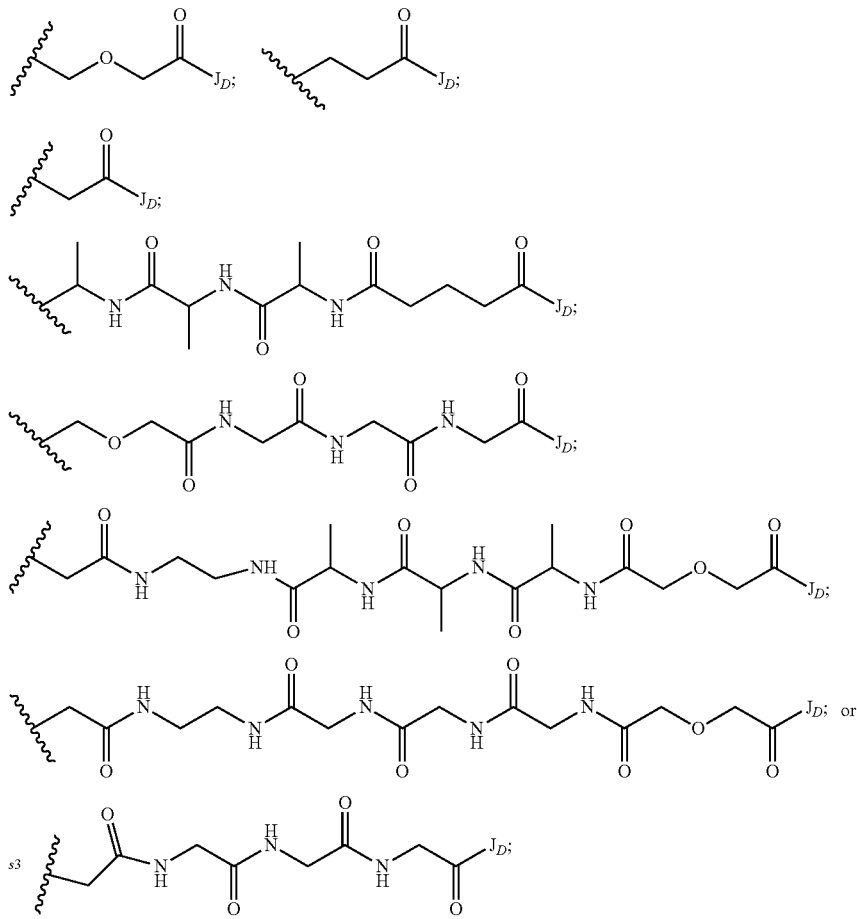

wherein $J_{CB}'$ and $J_D$ are as described above in the 3rd specific embodiment. More specifically, —C(=O)-$J_D$ is N-hydroxysuccinimide ester.

In a 4$^{th}$ specific embodiment, for formula (III), -L-$J_D$ is represented by the following formula:

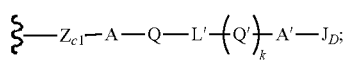
(L4')

wherein $J_D$ is a maleimide, X'—CR$^b$R$^c$—C(=O)—, X'—CR$^b$R$^c$—C(=O)—NR$^e$—,

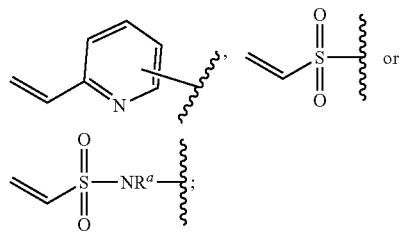

X' is a halogen; $J_{CB}'$ is as described above in the 1$^{st}$ specific embodiment; and the remaining variables are as described above for structural formula (L4) in the 4$^{th}$ specific embodiment of the first embodiment and any more specific embodiments described therein.

In certain embodiments, for formula (III) described in any one of embodiments above, such as in the fifth embodiment or the 1$^{st}$ to 4$^{th}$ specific embodiments of the fifth embodiment, or any more specific embodiments described therein, CBA can be any cell-binding agents described in the second embodiment.

Bifunctional Crosslinking Agent (or Linker Compound)

In a sixth embodiment, the present invention provides bifunctional crosslinking agents (i.e., linker compounds) having an aldehyde group and a reactive group that can form a covalent bond with the cytotoxic agents described herein.

In one embodiment, the linker compound is represented by the following formula:

(IV), wherein the variables are as described above formulas (I), (II) and (III).

In one embodiment, the linker compound is represented by the following formula:

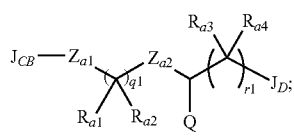
(IV1)

or a pharmaceutically acceptable salt thereof, wherein $J_{CB}$ is an aldehyde reactive group described in the first embodiment; and the remaining variables are as described above for structural formula (L1'). More specifically, $J_D$ is-SH or —SSR$^d$. Even more specifically, $J_{CB}$ is

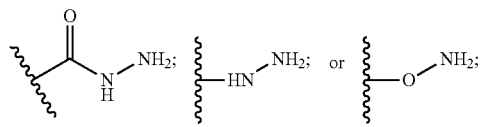

In a more specific embodiment, the bifunctional cross-linking agent is represented by the following structural formula:

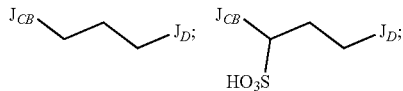

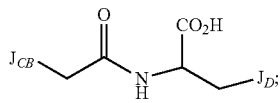

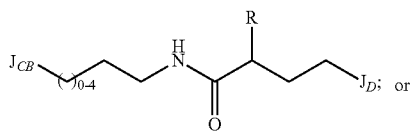

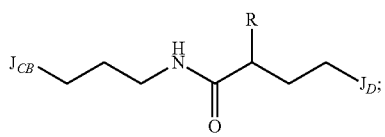

or a pharmaceutically acceptable salt thereof, wherein $J_{CB}$ and $J_D$ are as described above. More specifically, $J_D$ is-SH or —SSR$^d$. Even more specifically, $J_{CB}$ is

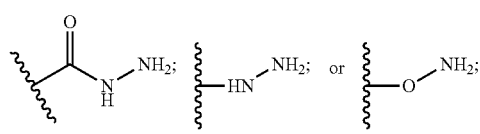

In another embodiment, the linker compound is represented by the following structural formula:

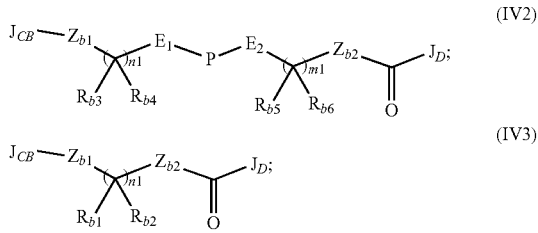
(IV2)

(IV3)

wherein $J_{CB}$ is an aldehyde reactive group described in the first embodiment; and the remaining variables are as described above for structural formulas (L2') and (L3'). More specifically, —C(=O)-$J_D$ is N-hydroxysuccinimide ester. Even more specifically, $J_{CB}$ is

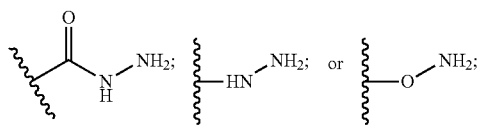 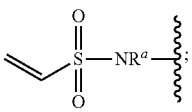

In a more specific embodiment, the bifunctional crosslinking agent is represented by the following structural formula:

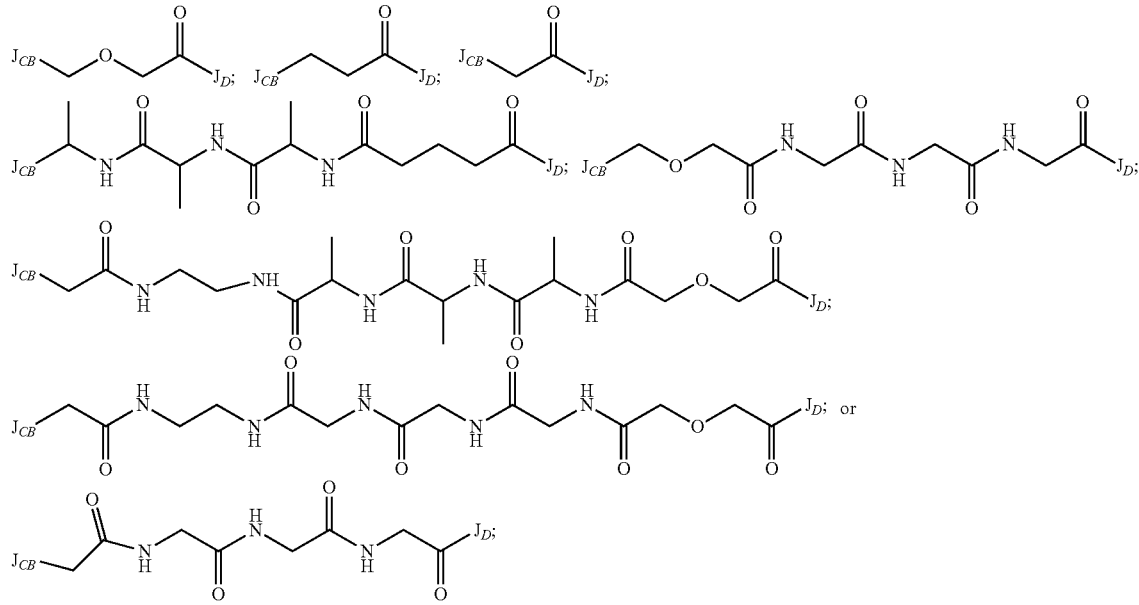

wherein $J_{CB}$ and $J_D$ are as described above. More specifically, —C(=O)-$J_D$ is N-hydroxysuccinimide ester. Even more specifically, $J_{CB}$ is

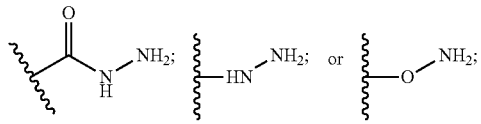

In another embodiment, the bifunctional crosslinking agent is represented by the following structural formula:

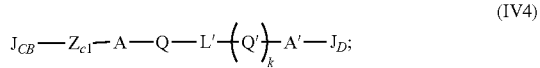
(IV4)

wherein $J_D$ is a maleimide, X'—CR$^b$R$^c$—C(=O)—, X'—CR$^b$R$^c$—C(=O)—NR$^e$—,

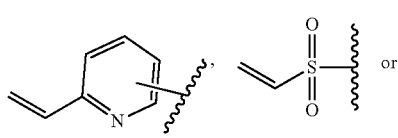

X' is a halogen; and the remaining variables are as described above for structural formula (L4'). More specifically, $J_D$ is a maleimide. Even more specifically, $J_{CB}$ is

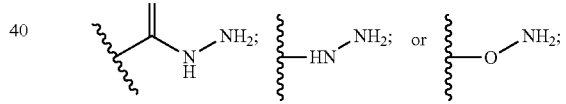

Production of Cell-Binding Agent-Drug Conjugates

In a seventh embodiment, the present invention provides methods for preparing the cell-binding agent-cytotoxic agent conjugates described herein.

In one embodiment, the present invention provides a method of preparing the cell-binding agent-cytotoxic agent conjugates described herein comprising the steps of:

(a) oxidizing a 2-hydroxyethylamine moiety of a cell-binding agent with an oxidizing agent to form an oxidized cell-binding agent having an aldehyde group; wherein the 2-hydroxyethylamine moiety is part of a serine, threonine, hydroxylysine, 4-hydroxyornithine or 2,4-diamino-5-hydroxy valeric acid residue, and is represented by the following structural formula:

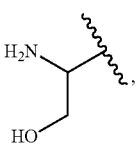

and (b) contacting the oxidized cell-binding agent with:

(i) a cytotoxic agent-linker compound having an aldehyde reactive group or a cytotoxic agent having an aldehyde reactive group to form the cell-binding agent-cytotoxic agent conjugate; or (ii) a linker compound having an aldehyde reactive group to form a modified antibody or a modified antigen-binding portion thereof having a linker bound thereto, followed by reacting the modified antibody or the modified antigen-binding portion thereof with a cytotoxic agent to form the cell-binding agent-cytotoxic agent conjugate; or (iii) a cytotoxic agent followed by the addition of a linker compound having an aldehyde reactive group and a reactive group that can form a covalent bond with the cytotoxic agent to form the cell-binding agent-cytotoxic agent conjugate.

In a $1^{st}$ specific embodiment, the cell binding-agent is an antibody or an antigen binding portion thereof and the method comprises the steps of:

(a) oxidizing an 2-hydroxyethylamine moiety of an antibody or an antigen-binding portion thereof with an oxidizing agent to form an oxidized antibody or an oxidized antigen-binding portion thereof having an aldehyde group,

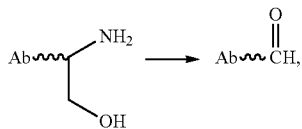

wherein the 2-hydroxyethylamine moiety is part of an N-terminal serine, threonine, hydroxylysine, 4-hydroxyornithine or 2,4-diamino-5-hydroxy valeric acid residue; and (b) reacting the oxidized antibody or the oxidized antigen-binding portion thereof with a cytotoxic agent-linker compound having an aldehyde reactive group or a cytotoxic agent having an aldehyde reactive group to form the antibody-cytotoxic agent conjugate

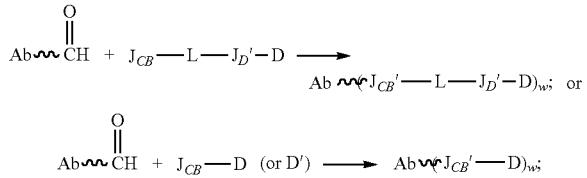

wherein:

Ab is an antibody or an antigen binding portion thereof described herein;

$J_{CB}$ is an aldehyde reactive group as described above;

L is a spacer or a bond as described above;

$J_D'$ is a linking moiety connecting cytotoxic agent D with the group L or absent when L is a bond;

D is a cytotoxic agent covalently linked to L through the linking moiety $J_D'$; and w is 1, 2, 3 or 4.

In certain embodiments, for the methods described in the $1^{st}$ specific embodiment above, any cytotoxic agent-linker compounds described in the fourth embodiment above or cytotoxic agent described in the third embodiment can be used.

In certain embodiments, for the methods described in the $1^{st}$ specific embodiment above, the cytotoxic agent-linker compound or the cytotoxic agent having an imine functional group (—C=N—) is reacted with an imine-reactive reagent to form a modified cytotoxic agent-linker compound or a modified cytotoxic agent before reacting with the oxidized antibody or the oxidized antigen-binding portion thereof in step (b). In one embodiment, the modified cytotoxic agent-linker compound or a modified cytotoxic agent is generated in situ and reacted with the oxidized antibody or the oxidized antigen-binding portion thereof without purification.

In a $2^{nd}$ specific embodiment, the cell binding-agent is an antibody or an antigen binding portion thereof and the method comprises the steps of:

(a) oxidizing an N-terminal 2-hydroxyethylamine moiety of an antibody or an antigen-binding portion thereof with an oxidizing agent to form an oxidized antibody or an oxidized antigen-binding portion thereof having a N-terminal aldehyde group,

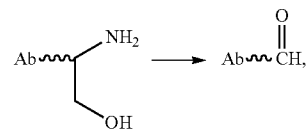

wherein the 2-hydroxyethylamine moiety is part of an N-terminal serine, threonine, hydroxylysine, 4-hydroxyornithine or 2,4-diamino-5-hydroxy valeric acid residue; and (b) reacting the oxidized antibody or the oxidized antigen-binding portion thereof with a linker compound having an aldehyde reactive group to form a modified antibody or a modified antigen-binding portion thereof having a linker bound thereto, followed by reacting the modified antibody or the modified antigen-binding portion thereof with a cytotoxic agent to form the antibody-cytotoxic agent conjugate

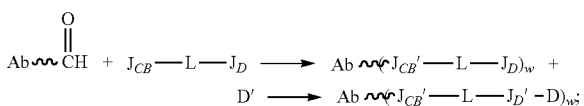

wherein D' is a cytotoxic agent; $J_D$ is a reactive group that can form a covalent bond with the cytotoxic agent D'; and the remaining variables are as described in the $1^{st}$ specific embodiment.

In certain embodiments, for methods described in the $2^{nd}$ specific embodiment above, any linker compounds described in the sixth embodiment above can be used.

In certain embodiments, for methods described in the $2^{nd}$ specific embodiment, the cytotoxic agent having an imine functional imine functional group (—C=N—) is reacted with an imine-reactive reagent to form a modified cytotoxic agent before reacting with the modified antibody or the modified antigen-binding portion thereof having a linker bound thereto in step (b). In one embodiment, the modified cytotoxic agent is generated in situ and not purified before reacting with the modified antibody or the modified antigen-binding portion thereof having a linker bound thereto.

In a $3^{rd}$ specific embodiment, the cell binding-agent is an antibody or an antigen binding portion thereof and the method comprises the steps of:

(a) oxidizing an N-terminal 2-hydroxyethylamine moiety of an antibody or an antigen-binding portion thereof with an oxidizing agent to form an oxidized antibody or an oxidized antigen-binding portion thereof having a N-terminal aldehyde group,

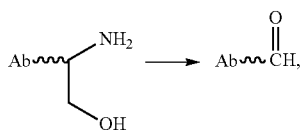

wherein the 2-hydroxyethylamine moiety is part of an N-terminal serine, threonine, hydroxylysine, 4-hydroxyornithine or 2,4-diamino-5-hydroxy valeric acid residue; and (b) contacting the oxidized antibody or the oxidized antigen-binding portion thereof with a cytotoxic agent followed by addition of a linker compound having an aldehyde reactive group to form the antibody-cytotoxic agent conjugate

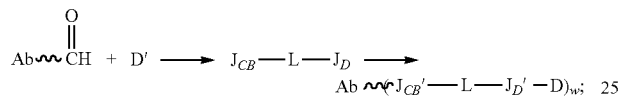

wherein the variables are as described above in the $1^{st}$ and $2^{nd}$ specific embodiments.

In certain embodiments, for the methods described in the $3^{rd}$ specific embodiment above, any linker compounds described in the sixth embodiment and cytotoxic agent described in the third embodiment can be used.

Any suitable oxidizing agent can be used in step (a) of the methods described above. In certain embodiments, the oxidizing agent is a periodate. More specifically, the oxidizing agent is sodium periodate.

Excess molar equivalents of the oxidizing agent relative to the cell-binding agent (e.g., antibody) can be used. In certain embodiments, about 2-100, 5-80, 10-50, 1-10 or 5-10 molar equivalents of the oxidizing agent can be used. In certain embodiment, about 10 or about 50 equivalents of the oxidizing agent can be used. When large amount of the oxidizing agent is used, short reaction time is used to avoid over-oxidation. For example, when 50 equivalents of the oxidizing agent is used, the oxidation reaction is carried out for about 5 to about 60 minutes. Alternatively, when 10 equivalents of the oxidizing agent is used, the reaction is carried out for about 30 minutes to about 24 hours. In one embodiment, 5-10 molar equivalents of the oxidizing agent is used and the oxidation reaction is carried out for about 5 to about 60 minutes (e.g., about 10 to about 30 minutes, about 20 to about 30 minutes).

In certain embodiments, the oxidation reaction does not lead to significant non-targeted oxidation. For example, no signification amount (e.g., less than 20%, less than 10%, less than 5%, less than 3%, less than 2% or less than 1%) of methionine and/or glycans are oxidized during the oxidation process of N-terminal serine to generate the oxidized CD123/IL-3Rα-binding agent having a N-terminal aldehyde group.

In certain embodiments, a catalyst is present in the reaction of step (b) in the methods described above. Any suitable catalyst in the art can be used. In one embodiment, the catalyst is an aniline or substituted aniline. Exemplary aniline catalyst include, but are not limited to, aniline, o-phenylenediamine, m-phenylenediamine, 3,5-diamino-benzoic acid, p-phenylenediamine, 2-methyl-p-phenylenediamine, N-methyl-p-phenylenediamine, o-aminophenol, m-aminophenol, p-aminophenol, p-methoxyaniline, 5-methoxy-anthranilic acid, o-aminobenzoid acid, and 4-aminophenethylalcohol. In one embodiment, the catalyst is 4-aminophenethylalcohol. In certain embodiments, the reaction of step (b) is carried out at pH about 5.0 to about 6.5. In certain embodiments, the reaction of step (b) is carried out at pH about 5.0.

In certain embodiments, for step (b) of the methods described herein, the compound having an aldehyde reactive group (e.g., cytotoxic agent-linker compound, cytotoxic agent, or the linker compound described herein) is used in molar excess relative to the oxidized cell-binding agent (e.g., oxidized antibody or oxidized antigen binding portion). In certain embodiments, the ratio for the compound having an aldehyde reactive group to oxidized cell-binding agent is between about 10:1 to about 1.1:1, between about 5:1 to about 2:1. In one embodiment, the ratio is about 4:1.

In certain embodiments, for the methods described above, such as those in the third or the $1^{st}$ to $3^{rd}$ specific embodiments, the cell-binding agent, such as the antibody or antigen binding portion thereof, can be obtained by any methods described herein.

In a $4^{th}$ specific embodiment, the present invention provides a method of preparing an antibody-cytotoxic agent conjugate, comprising the steps of:

(a) oxidizing a 2-hydroxyethylamine moiety of an N-terminal serine or threonine residue of an antibody or an antigen-binding portion thereof, with an oxidizing agent to form an oxidized antibody or an oxidized antigen-binding portion thereof having a N-terminal aldehyde group, wherein the 2-hydroxyethylamine moiety is represented by the following structural formula:

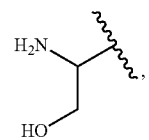

and (b) contacting the oxidized antibody or the oxidized antigen-binding portion thereof with: (i) a cytotoxic agent-linker compound having an aldehyde reactive group to form the antibody-cytotoxic agent conjugate; or (ii) a linker compound having an aldehyde reactive group to form a modified antibody or a modified antigen-binding portion thereof having a linker bound thereto, followed by reacting the modified antibody or the modified antigen-binding portion thereof with a cytotoxic agent to form the antibody-cytotoxic agent conjugate; or (iii) a cytotoxic agent followed by the addition of a linker compound having an aldehyde reactive group and a reactive group that can form a covalent bond with the cytotoxic agent to form the antibody-cytotoxic agent conjugate.

In certain embodiments, for any methods described above, such as those in the seventh embodiment or the $1^{st}$ to $4^{th}$ specific embodiment or any more specific embodiment, the antibody or antigen-binding portion thereof is obtained by expressing a polynucleotide encoding a recombinant antibody heavy chain (HC), light chain (LC), or antigen-binding portion thereof comprising: (1) a heterologous signal peptide having an amino acid sequence of SEQ ID NO: 1; (2) a Ser or Thr residue immediately N-terminal to the first residue of the mature processed sequence of the recombinant antibody heavy chain (HC), light chain (LC), or antigen-binding portion thereof; or (3) a Ser or Thr residue replacing one or more N-terminal amino acid residue(s) of the mature processed sequence of the recombinant antibody heavy chain (HC), light chain (LC), or antigen-binding portion thereof.

In certain embodiments, for any methods described above, such as those in the seventh embodiment or the $1^{st}$ to $4^{th}$ specific embodiment or any more specific embodiment, the antibody or antigen-binding portion thereof comprises a light chain sequence of SEQ ID NO: 3.

In certain embodiments, for any methods described above, such as those in the seventh embodiment or the $1^{st}$ to $4^{th}$ specific embodiment or any more specific embodiment, the antibody or antigen-binding portion thereof is a chimeric, humanized, or human antibody or antigen-binding portion thereof of a murine antibody or antigen-binding portion thereof comprising a light chain sequence of SEQ ID NO: 3. The humanized antibody or antigen-binding portion thereof may be a resurfaced or CDR grafted antibody or antigen-binding portion thereof.

In certain embodiments, the conjugate prepared according to any methods described above can then be purified. Any purification methods known in the art can be used to purify the conjugates of the present invention (See, for example, Bioconjugate Techniques, 2nd Edition by Greg T. Hermanson, published by Academic Press, Inc., 2008). In one embodiment, the conjugates of the present invention can be purified using tangential flow filtration (TFF), non-adsorptive chromatography, adsorptive chromatography, adsorptive filtration, selective precipitation, high performance liquid chromatography (HPLC), dialysis or any other suitable purification process, as well as combinations thereof.

Any suitable TFF systems may be utilized for purification, including a Pellicon type system (Millipore, Billerica, Mass.), a Sartocon Cassette system (Sartorius AG, Edgewood, N.Y.), and a Centrasette type system (Pall Corp., East Hills, N.Y.).

Any suitable adsorptive chromatography resin may be utilized for purification. Preferred adsorptive chromatography resins include hydroxyapatite chromatography, hydrophobic charge induction chromatography (HCIC), hydrophobic interaction chromatography (HIC), ion exchange chromatography, mixed mode ion exchange chromatography, immobilized metal affinity chromatography (IMAC), dye ligand chromatography, affinity chromatography, reversed phase chromatography, and combinations thereof. Examples of suitable hydroxyapatite resins include ceramic hydroxyapatite (CHT Type I and Type II, Bio-Rad Laboratories, Hercules, Calif.), HA Ultrogel hydroxyapatite (Pall Corp., East Hills, N.Y.), and ceramic fluoroapatite (CFT Type I and Type II, Bio-Rad Laboratories, Hercules, Calif.). An example of a suitable HCIC resin is MEP Hypercel resin (Pall Corp., East Hills, N.Y.). Examples of suitable HIC resins include Butyl-Sepharose, Hexyl-Sepaharose, Phenyl-Sepharose, and Octyl Sepharose resins (all from GE Healthcare, Piscataway, N.J.), as well as Macro-prep Methyl and Macro-Prep t-Butyl resins (Biorad Laboratories, Hercules, Calif.). Examples of suitable ion exchange resins include SP-Sepharose, CM-Sepharose, and Q-Sepharose resins (all from GE Healthcare, Piscataway, N.J.), and Unosphere S resin (Bio-Rad Laboratories, Hercules, Calif.). Examples of suitable mixed mode ion exchangers include Bakerbond ABx resin (JT Baker, Phillipsburg N.J.). Examples of suitable IMAC resins include Chelating Sepharose resin (GE Healthcare, Piscataway, N.J.) and Profinity IMAC resin (Bio-Rad Laboratories, Hercules, Calif.). Examples of suitable dye ligand resins include Blue Sepharose resin (GE Healthcare, Piscataway, N.J.) and Affi-gel Blue resin (Bio-Rad Laboratories, Hercules, Calif.). Examples of suitable affinity resins include Protein A Sepharose resin (e.g., MabSelect, GE Healthcare, Piscataway, N.J.), His-Tag metal affinity resins, anti-FLAG affinity resins, and lectin affinity resins, e.g. Lentil Lectin Sepharose resin (GE Healthcare, Piscataway, N.J.), where the antibody bears appropriate lectin binding sites. Examples of suitable reversed phase resins include C4, C8, and C18 resins (Grace Vydac, Hesperia, Calif.).

Any suitable non-adsorptive chromatography resin may be utilized for purification. For example, size-exclusion chromatography can be used for purifying the conjugates of the invention. Examples of suitable non-adsorptive chromatography resins include, but are not limited to, SEPHADEX™ G-10, G-25, G-50, G-100, SEPHACRYL™ resins (e.g., S-200 and S-300), SUPERDEX™ resins (e.g., SUPERDEX™ 75 and SUPERDEX™ 200), BIO-GEL® resins (e.g., P-6, P-10, P-30, P-60, and P-100), and others known to those of ordinary skill in the art.

In one embodiment, when the cell-binding agent is an epitope-tagged Avibody, the conjugate can be purified using hydroxyl apatite chromatography, size-exclusion chromatography, tangential flow filtration, gel electrophoresis, dialysis, and affinity chromatography, preferably affinity chromatography, more preferably His-tag metal affinity chromatography and anti-FLAG M2 affinity chromatography (see, for example, US 2008/0152586 and US 2012/0171115).

In another embodiment, when the cell-binding agent is a centyrin, the conjugate can be purified using protein A purification, ammonium sulfate or ethanol precipitation, acid extraction, anion or cation exchange chromatography, phosphocellulose chromatography, hydrophobic interaction chromatography, size-exclusion chromatography, tangential flow filtration, affinity chromatography, hydroxylapatite chromatography and lectin chromatography. Alternatively, the conjugate can be purified using HPLC. Preferably, the conjugate can be purified by using affinity chromatography, more preferably His-tag metal affinity chromatography. See, for example, US Patent Publication Nos. US 2010/0255056, US 2010/0216708 and US 2011/0274623.

In another embodiment, when the cell-binding agent is a DARPin, the conjugate can be purified by affinity chromatography, size exclusion chromatography, hydroxylapatite chromatography, tangential flow filtration, preferably affinity chromatography, more preferably His-Tag affinity chromatography. See, for example, U.S. Patent Publication Nos. 20040132028, 2009/0082274, 2011/0118146, and 2011/0224100, WO 02/20565 and WO 06/083275.

In Vitro Evaluation of Cytotoxicity

The cytotoxic compounds and cell-binding agent-drug conjugates of the invention can be evaluated for their ability to suppress proliferation of various cancer cell lines in vitro. Cells to be evaluated can be exposed to the compounds or conjugates for 1-5 days and the surviving fractions of cells measured in direct assays by known methods. IC$_{50}$ values can then be calculated from the results of the assays. Alternatively or in addition, an in vitro cell line sensitivity screen, such as the one described by the U.S. National Cancer Institute (see Voskoglou-Nomikos et al., 2003, *Clinical Cancer Res.* 9: 42227-4239, incorporated herein by reference) can be used as one of the guides to determine the types of cancers that may be sensitive to treatment with the compounds or conjugates of the invention.

Compositions and Methods of Use

The present invention includes a composition (e.g., a pharmaceutical composition) comprising novel benzodiazepine compounds described herein (e.g., indolinobenzodiazepine or oxazolidinobenzodiazepine), derivatives thereof, or conjugates thereof, (and/or solvates, hydrates and/or salts thereof) and a carrier (a pharmaceutically acceptable carrier). The present invention also includes a composition (e.g., a pharmaceutical composition) comprising novel benzodiazepine compounds described herein, derivatives thereof, or conjugates thereof, (and/or solvates, hydrates and/or salts thereof) and a carrier (a pharmaceutically acceptable carrier), further comprising a second therapeutic agent. The present compositions are useful for inhibiting abnormal cell growth or treating a proliferative disorder in a mammal (e.g., human). The present compositions are also useful for treating depression, anxiety, stress, phobias, panic, dysphoria, psychiatric disorders, pain, and inflammatory diseases in a mammal (e.g., human).

The present invention includes a method of inhibiting abnormal cell growth or treating a proliferative disorder in a mammal (e.g., human) comprising administering to said mammal a therapeutically effective amount of novel benzodiazepine compounds described herein (e.g., indolinobenzodiazepine or oxazolidinobenzodiazepine), derivatives thereof, or conjugates thereof, (and/or solvates and salts thereof) or a composition thereof, alone or in combination with a second therapeutic agent.

In one embodiment, the proliferative disorder is cancer. Cancer can include a hematological cancer or a solid tumor. More specifically, the cancer is leukemia (e.g., acute myeloid leukemia (AML), acute monocytic leukemia, promyelocytic leukemia, eosinophilic leukemia, acute lymphoblastic leukemia (ALL) such as acute B lymphoblastic leukemia (B-ALL), chronic myelogenous leukemia (CML), chronic lymphocytic leukemia (CLL)) or lymphoma (e.g., non-Hodgkin lymphoma), myelodysplastic syndrome (MDS), melanoma, lung cancer (e.g., non-small cell lung cancer (NSCLC)), ovarian cancer, endometrial cancer, peritoneal cancer, pancreatic cancer, breast cancer, prostate cancer, squamous cell carcinoma of the head and neck, and cervical cancer.

The present invention also provides methods of treatment comprising administering to a subject in need of treatment an effective amount of any of the conjugates described above. Similarly, the present invention provides a method for inducing cell death in selected cell populations comprising contacting target cells or tissue containing target cells with an effective amount of a cytotoxic agent comprising any of the cytotoxic compound-cell-binding agents (e.g., indolinobenzodiazepine or oxazolidinobenzodiazepine dimer linked to a cell binding agent) of the present invention, a salt or solvate thereof. The target cells are cells to which the cell-binding agent can bind.

If desired, other active agents, such as other anti-tumor agents, may be administered along with the conjugate.

Suitable pharmaceutically acceptable carriers, diluents, and excipients are well known and can be determined by those of ordinary skill in the art as the clinical situation warrants. Examples of suitable carriers, diluents and/or excipients include: (1) Dulbecco's phosphate buffered saline, pH about 7.4, containing or not containing about 1 mg/mL to 25 mg/mL human serum albumin, (2) 0.9% saline (0.9% w/v NaCl), and (3) 5% (w/v) dextrose; and may also contain an antioxidant such as tryptamine and a stabilizing agent such as Tween 20.

The method for inducing cell death in selected cell populations can be practiced in vitro, in vivo, or ex vivo.

Examples of in vitro uses include treatments of autologous bone marrow prior to their transplant into the same patient in order to kill diseased or malignant cells; treatments of bone marrow prior to their transplantation in order to kill competent T cells and prevent graft-versus-host-disease (GVHD); treatments of cell cultures in order to kill all cells except for desired variants that do not express the target antigen; or to kill variants that express undesired antigen. The conditions of non-clinical in vitro use are readily determined by one of ordinary skill in the art.

Examples of clinical ex vivo use are to remove tumor cells or lymphoid cells from bone marrow prior to autologous transplantation in cancer treatment or in treatment of autoimmune disease, or to remove T cells and other lymphoid cells from autologous or allogenic bone marrow or tissue prior to transplant in order to prevent GVHD. Treatment can be carried out as follows. Bone marrow is harvested from the patient or other individual and then incubated in medium containing serum to which is added the cytotoxic agent of the invention, concentrations range from about 10 μM to 1 pM, for about 30 minutes to about 48 hours at about 37° C. The exact conditions of concentration and time of incubation, i.e., the dose, are readily determined by one of ordinary skill in the art. After incubation the bone marrow cells are washed with medium containing serum and returned to the patient intravenously according to known methods. In circumstances where the patient receives other treatment such as a course of ablative chemotherapy or total-body irradiation between the time of harvest of the marrow and reinfusion of the treated cells, the treated marrow cells are stored frozen in liquid nitrogen using standard medical equipment.

For clinical in vivo use, the cytotoxic agent of the invention will be supplied as a solution or a lyophilized powder that are tested for sterility and for endotoxin levels. Examples of suitable protocols of conjugate administration are as follows. Conjugates are given weekly for 4 weeks as an intravenous bolus each week. Bolus doses are given in 50 to 1000 mL of normal saline to which 5 to 10 mL of human serum albumin can be added. Dosages will be 10 μg to 2000 mg per administration, intravenously (range of 100 ng to 20 mg/kg per day). After four weeks of treatment, the patient can continue to receive treatment on a weekly basis. Specific clinical protocols with regard to route of administration, excipients, diluents, dosages, times, etc., can be determined by one of ordinary skill in the art as the clinical situation warrants.

Examples of medical conditions that can be treated according to the in vivo or ex vivo methods of inducing cell death in selected cell populations include malignancy of any type including, for example, cancer; autoimmune diseases, such as systemic lupus, rheumatoid arthritis, and multiple sclerosis; graft rejections, such as renal transplant rejection, liver transplant rejection, lung transplant rejection, cardiac transplant rejection, and bone marrow transplant rejection; graft versus host disease; viral infections, such as CMV infection, HIV infection, AIDS, etc.; and parasite infections, such as giardiasis, amoebiasis, schistosomiasis, and others as determined by one of ordinary skill in the art.

Cancer therapies and their dosages, routes of administration and recommended usage are known in the art and have been described in such literature as the Physician's Desk Reference (PDR). The PDR discloses dosages of the agents that have been used in treatment of various cancers. The dosing regimen and dosages of these aforementioned chemotherapeutic drugs that are therapeutically effective will depend on the particular cancer being treated, the extent of the disease and other factors familiar to the physician of skill in the art and can be determined by the physician. The contents of the PDR are expressly incorporated herein in its entirety by reference. One of skill in the art can review the PDR, using one or more of the following parameters, to determine dosing regimen and dosages of the chemotherapeutic agents and conjugates that can be used in accordance with the teachings of this invention. These parameters include:

Comprehensive index
By Manufacturer
Products (by company's or trademarked drug name)
Category index
Generic/chemical index (non-trademark common drug names)
Color images of medications
Product information, consistent with FDA labeling
Chemical information
Function/action
Indications & Contraindications
Trial research, side effects, warnings
Analogues and Derivatives One skilled in the art of cytotoxic agents will readily understand that each of the cytotoxic agents described herein can be modified in such a manner that the resulting compound still retains the specificity and/or activity of the starting compound. The skilled artisan will also understand that many of these compounds can be used in place of the cytotoxic agents described herein. Thus, the cytotoxic agents of the present invention include analogues and derivatives of the compounds described herein.

All references cited herein and in the examples that follow are expressly incorporated by reference in their entireties.

EXAMPLES

Example 1 Construction of Recombinant Antibodies with N-Terminal Ser/Thr

The sequence of the murine anti-folate receptor alpha antibody FR1-2.1 light chain (LC) was previously described with an N-terminal Serine (U.S. patent application No. 61/872,407, filed on Aug. 30, 2013; 61/875,475, filed on Sep. 9, 2013; and 61/940,184, filed on Feb. 14, 2014; and WO 2015/031815 claiming priority thereto, all incorporated by reference). This N-terminal Ser is the result of signal peptidase utilizing an usual cleavage site in the signal peptide of the IGKV1-99*01 murine germline sequence (accession number CAB46122; SEQ ID NO: 2) from which the FR1-2.1 light chain is derived. Unlike typical antibody signal peptides that are completely removed upon cleavage during antibody expression, the final serine of the IGKV1-99* signal peptide (Kabat position −1) remains at the N terminus of the FR1-2.1 light chain. The FR1-2.1 antibody proved to be a useful tool for evaluating the serine oxidation modification methods described herein, and, in addition, the FR1-2.1 signal peptide (Table 1; SEQ ID NO: 1) provides a possible mechanism for generating recombinant antibodies with serines at their light or heavy chain N termini. The use of a native antibody signal peptide to incorporate the N-terminal serine allows for the avoidance of potential negative consequences of antibody engineering, including but not limited to expression problems and cleavage site heterogeneity that could come from non-natural constructs.

To demonstrate that the FR1-2.1 signal peptide leaves a serine residue at the N-terminus of recombinant antibodies expressed in transfected mammalian cell lines, new antibody expression constructs were synthesized utilizing the FR1-2.1 light chain signal peptide. The variable region amino acid sequence for humanized Mov19 light chain (LC), previously described in U.S. Pat. No. 8,557,966 (Table 1: SEQ ID NO: 3), was combined with the FR1-2.1 signal peptide in place of the standard antibody signal peptide (SEQ ID NO: 6) to generate the huMov19 LC NTS1 sequence (SEQ ID NO: 10). The light chain sequence was then provided to Blue Heron Biotechnology where it was codon-optimized, synthesized, and cloned into the EcoRI and BsiWI sites of the pAbKZeo mammalian expression plasmid containing the human Kappa constant region sequence.

An alternative approach to generate recombinant antibodies with serine/threonione residues at the N termini is to replace the N-terminal residue (Kabat position+1) with a serine or a threonine. To demonstrate this methodology, the humanized Mov19 heavy chain (HC) (SEQ ID NO: 8) N-terminal residue (glutamine) was replaced with a serine to generate the huMov19 HC NTS2 sequence (SEQ ID NO: 11). The heavy chain sequence was then codon-optimized, synthesized, and cloned by Blue Heron Biotechnology in frame with the human IgG1 constant region at the HindIII and Apa1 sites of the pAbG1Neo plasmid.

Various combinations of the N-terminal serine addition and N-terminal serine replacement schemes described above are used to generate additional recombinant antibodies with up to 4 N-terminal serines (e.g., 2 on the heavy chains and 2 on the light chains). The reverse of the constructs described above are synthesized such that the humanized Mov19 light chain (LC) has its N-terminal aspartate replaced with serine (huMov19LC NTS3, SEQ ID NO: 12) or conversely, the humanized Mov19 heavy chain is synthesized with the FR1-2.1 signal peptide to add the N terminal serine (huMov19HC NTS4; SEQ ID NO: 14). In addition, these light and heavy chain constructs can be mixed together to generate recombinant antibodies with serines at both N-termini for a total of 4 N-terminal serines per antibody (e.g., huMov19LC NTS3 with huMov19HC NTS4). These constructs are limited to either 2 (single chain N terminal serines) or 4 (both chains with N terminal serines) incorporation sites but with heterodimeric antibody technologies, such as "Knob in the Hole" mutations (WO 2005/063816 A2, incorporated by reference). Construction of antibodies with either 1 or 3 N terminal serines is also possible.

Finally, although additional approaches to generate recombinant antibodies with N-terminal serines could be followed, such as multi-amino acid N-terminal appendages or N-terminal truncations, the described methods provide the added advantage that they are less likely to impact critical antibody attributes such as binding specificity or structural integrity.

In addition to serines, recombinant antibodies can be generated with threonine residues at their N-termini by simply replacing the N terminal residue (Kabat position+1) with a threonine in order to conjugate these antibodies by the methods described herein. For example, the humanized Mov19 light chain (LC) N terminal aspartate is replaced with threonine (huMov19 LC NTT1, SEQ ID NO: 15) or the humanized Mov19 heavy chain (HC) N-terminal glutamine is replaced with a threonine (huMov19 HC NTT2, SEQ ID NO: 16). These constructs are then cloned into the respective mammalian expression plasmids as described above.

TABLE 1

Selected Sequences

| Antibody | Sequence |
| --- | --- |
| FR1-2.1 light chain signal peptide (NCBI CAB46122) | MKLPVLLVVLLLFTSPASSS (SEQ ID NO: 1) |
| IGKV1-99*01 Accession CAB46122 | MKLPVLLVVLLLFTSPASSSDVVLTQTPLSLPVNIGDQASISCKSTKSL LNSDGFTYLDWYLQKPGQSPQLLIYLVSNRFSGVPDRFSGSGSGTDFTL KISRVEAEDLGVYYCFQSNYLP (SEQ ID NO: 2) |
| IGKV1-99*01 Accession CAB46122 | MKLPVLLVVLLLFTSPASSSDVVLTQTPLSLPVNIGDQASISCKSTKSL LNSDGFTYLDWYLQKPGQSPQLLIYLVSNRFSGVPDRFSGSGSGTDFTL KISRVEAEDLGVYYCFQSNYLP (SEQ ID NO: 2) |
| FR1-2.1 light chain (as expressed) | SDVVLTQTPLSLPVNIGDQASISCKSSKSLLNSDGFTYLDWYLQKPGQS PQLLIYLVSNHFSGVPDRFSGSGSGTDFTLKISRVEAEDLGVYYCFQSN YLPLTFGGGTKLEIKRADAAPTVSIFPPSSEQLTSGGASVVCFLNNFYP KDINVKWKIDGSERQNGVLNSWTDQDSKDSTYSMSSTLTLTKDEYERHN SYTCEATHKTSTSPIVKSFNRNEC (SEQ ID NO: 3) |
| FR1-2.1 light chain full length, with signal peptide | MKLPVLLVVLLLFTSPASSSDVVLTQTPLSLPVNIGDQASISCKSSKSL LNSDGFTYLDWYLQKPGQSPQLLIYLVSNHFSGVPDRFSGSGSGTDFTL KISRVEAEDLGVYYCFQSNYLPLTFGGGTKLEIKRADAAPTVSIFPPSS EQLTSGGASVVCFLNNFYPKDINVKWKIDGSERQNGVLNSWTDQDSKDS TYSMSSTLTLTKDEYERHNSYTCEATHKTSTSPIVKSFNRNEC (SEQ ID NO: 4) |
| FR1-2.1 heavy chain | QVQLQQSGPELVKPGASVRISCKASGYTFTNSYIHWVKKRPGQGLEWIG WIYPESLNTQYNEKFKAKATLTADKSSSTSYMQLSSLTSEDSAVYFCAR RGIYYYSPYALDHWGQGASVTVSSAKTTPPSVYPLAPGSAAQTNSMVTL GCLVKGYFPEPVTVTWNSGSLSSGVHTFPAVLESDLYTLSSSVTVPSSM RPSETVTCNVAHPASSTKVDKKIVPRDCGCKPCICTVPEVSSVFIFPPK PKDVLTITLTPKVTCVVVDISKDDPEVQFSWFVDDVEVHTAQTQPREEQ FNSTFRSVSELPIMHQDWLNGKEFKCRVNSAAFPAPIEKTISKTKGRPK APQVYTIPPPKEQMAKDKVSLTCMITDFFPEDITVEWQWNGQPAENYKN TQPIMNTNGSYFVYSKLNVQKSNWEAGNTFTCSVLHEGLHNHHTEKSLS HSPGK (SEQ ID NO: 5) |
| huMov19 LC and HC signal peptide | MGWSCIILFLVATATGVHS (SEQ ID NO: 6) |
| huMov19 LC | DIVLTQSPLSLAVSLGQPAIISCKASQSVSFAGTSLMHWYHQKPGQQPR LLIYRASNLEAGVPDRFSGSGSKTDFTLTISPVEAEDAATYYCQQSREY PYTFGGGTKLEIKRTVAAPSVFIFPPSDEQLKSGTASVVCLLNNFYPRE AKVQWKVDNALQSGNSQESVTEQDSKDSTYSLSSTLTLSKADYEKHKVY ACEVTHQGLSSPVTKSFNRGEC (SEQ ID NO: 7) |
| huMov19 HC | QVQLVQSGAEVVKPGASVKISCKASGYTFTGYFMNWVKQSPGQSLEWIG RIHPYDGDTFYNQKFQGKATLTVDKSSNTAHMELLSLTSEDFAVYYCTR YDGSRAMDYWGQGTTVTVSSASTKGPSVFPLAPSSKSTSGGTAALGCLV KDYFPEPVTVSWNSGALTSGVHTFPAVLQSSGLYSLSSVVTVPSSSLGT QTYICNVNHKPSNTKVDKKVEPKSCDKTHTCPPCPAPELLGGPSVFLFP PKPKDTLMISRTPEVTCVVVDVSHEDPEVKFNWYVDGVEVHNAKTKPRE EQYNSTYRVVSVLTVLHQDWLNGKEYKCKVSNKALPAPIEKTISKAKGQ PREPQVYTLPPSRDELTKNQVSLTCLVKGFYPSDIAVEWESNGQPENNY KTTPPVLDSDGSFFLYSKLTVDKSRWQQGNVFSCSVMHEALHNHYTQKS LSLSPG (SEQ ID NO: 8) |
| huMov19 LC NTS1 (as expressed) | SDIVLTQSPLSLAVSLGQPAIISCKASQSVSFAGTSLMHWYHQKPGQQP RLLIYRASNLEAGVPDRFSGSGSKTDFTLTISPVEAEDAATYYCQQSRE YPYTFGGGTKLEIKRTVAAPSVFIFPPSDEQLKSGTASVVCLLNNFYPR EAKVQWKVDNALQSGNSQESVTEQDSKDSTYSLSSTLTLSKADYEKHKV YACEVTHQGLSSPVTKSFNRGEC (SEQ ID NO: 9) |
| huMov19 LC NTS1 with FR1-2.1 light chain signal peptide | MKLPVLLVVLLLFTSPASSSDIVLTQSPLSLAVSLGQPAIISCKASQSV SFAGTSLMHWYHQKPGQQPRLLIYRASNLEAGVPDRFSGSGSKTDFTLT ISPVEAEDAATYYCQQSREYPYTFGGGTKLEIKRTVAAPSVFIFPPSDE QLKSGTASVVCLLNNFYPREAKVQWKVDNALQSGNSQESVTEQDSKDST YSLSSTLTLSKADYEKHKVYACEVTHQGLSSPVTKSFNRGEC (SEQ ID NO: 10) |
| huMov19 HC NTS2 | SVQLVQSGAEVVKPGASVKISCKASGYTFTGYFMNWVKQSPGQSLEWIG RIHPYDGDTFYNQKFQGKATLTVDKSSNTAHMELLSLTSEDFAVYYCTR YDGSRAMDYWGQGTTVTVSSASTKGPSVFPLAPSSKSTSGGTAALGCLV KDYFPEPVTVSWNSGALTSGVHTFPAVLQSSGLYSLSSVVTVPSSSLGT QTYICNVNHKPSNTKVDKKVEPKSCDKTHTCPPCPAPELLGGPSVFLFP PKPKDTLMISRTPEVTCVVVDVSHEDPEVKFNWYVDGVEVHNAKTKPRE EQYNSTYRVVSVLTVLHQDWLNGKEYKCKVSNKALPAPIEKTISKAKGQ PREPQVYTLPPSRDELTKNQVSLTCLVKGFYPSDIAVEWESNGQPENNY KTTPPVLDSDGSFFLYSKLTVDKSRWQQGNVFSCSVMHEALHNHYTQKS LSLSPG (SEQ ID NO: 11) |
| huMov19 LC NTS3 | SIVLTQSPLSLAVSLGQPAIISCKASQSVSFAGTSLMHWYHQKPGQQPR LLIYRASNLEAGVPDRFSGSGSKTDFTLTISPVEAEDAATYYCQQSREY PYTFGGGTKLEIKRTVAAPSVFIFPPSDEQLKSGTASVVCLLNNFYPRE AKVQWKVDNALQSGNSQESVTEQDSKDSTYSLSSTLTLSKADYEKHKVY ACEVTHQGLSSPVTKSFNRGEC (SEQ ID NO: 12) |
| huMov19 HC NTS4 (as expressed) | SQVQLVQSGAEWKPGASVKISCKASGYTFTGYFMNWVKQSPGQSLEWI GRIHPYDGDTFYNQKFQGKATLTVDKSSNTAHMELLSLTSEDFAVYYCT RYDGSRAMDYWGQGTTVTVSSASTKGPSVFPLAPSSKSTSGGTAALGCL |

TABLE 1-continued

Selected Sequences

| Antibody | Sequence |
|---|---|
| | VKDYFPEPVTVSWNSGALTSGVHTFPAVLQSSGLYSLSSVVTVPSSSLG TQTYICNVNHKPSNTKVDKKVEPKSCDKTHTCPPCPAPELLGGPSVFLF PPKPKDTLMISRTPEVTCVVVDVSHEDPEVKFNWYVDGVEVHNAKTKPR EEQYNSTYRVVSVLTVLHQDWLNGKEYKCKVSNKALPAPIEKTISKAKG QPREPQVYTLPPSRDELTKNQVSLTCLVKGFYPSDIAVEWESNGQPENN YKTTPPVLDSDGSFFLYSKLTVDKSRWQQGNVFSCSVMHEALHNHYTQK SLSLSPG (SEQ ID NO: 13) |
| huMov19 HC NTS4 with FR1-2.1 light chain signal peptide | MKLPVLLVVLLLFTSPASSSQVQLVQSGAEVVKPGASVKISCKASGYTF TGYFMNWVKQSPGQSLEWIGRIHPYDGDTFYNQKFQGKATLTVDKSSNT AHMELLSLTSEDFAVYYCTRYDGSRAMDYWGQGTTVTVSSASTKGPSVF PLAPSSKSTSGGTAALGCLVKDYFPEPVTVSWNSGALTSGVHTFPAVLQ SSGLYSLSSVVTVPSSSLGTQTYICNVNHKPSNTKVDKKVEPKSCDKTH TCPPCPAPELLGGPSVFLFPPKPKDTLMISRTPEVTCVVVDVSHEDPEV KFNWYVDGVEVHNAKTKPREEQYNSTYRVVSVLTVLHQDWLNGKEYKCK VSNKALPAPIEKTISKAKGQPREPQVYTLPPSRDELTKNQVSLTCLVKG FYPSDIAVEWESNGQPENNYKTTPPVLDSDGSFFLYSKLTVDKSRWQQG NVFSCSVMHEALHNHYTQKSLSLSPG (SEQ ID NO: 14) |
| huMov19 LC NTT1 | TIVLTQSPLSLAVSLGQPAIISCKASQSVSFAGTSLMHWYHQKPGQQPR LLIYRASNLEAGVPDRFSGSGSKTDFTLTISPVEAEDAATYYCQQSREY PYTFGGGTKLEIKRTVAAPSVFIFPPSDEQLKSGTASVVCLLNNFYPRE AKVQWKVDNALQSGNSQESVTEQDSKDSTYSLSSTLTLSKADYEKHKVY ACEVTHQGLSSPVTKSFNRGEC (SEQ ID NO: 15) |
| huMov19 HC NTT2 | TVQLVQSGAEVVKPGASVKISCKASGYTFTGYFMNWVKQSPGQSLEWIG RIHPYDGDTFYNQKFQGKATLTVDKSSNTAHMELLSLTSEDFAVYYCTR YDGSRAMDYWGQGTTVTVSSASTKGPSVFPLAPSSKSTSGGTAALGCLV KDYFPEPVTVSWNSGALTSGVHTFPAVLQSSGLYSLSSVVTVPSSSLGT QTYICNVNHKPSNTKVDKKVEPKSCDKTHTCPPCPAPELLGGPSVFLFP PKPKDTLMISRTPEVTCVVVDVSHEDPEVKFNWYVDGVEVHNAKTKPRE EQYNSTYRVVSVLTVLHQDWLNGKEYKCKVSNKALPAPIEKTISKAKGQ PREPQVYTLPPSRDELTKNQVSLTCLVKGFYPSDIAVEWESNGQPENNY KTTPPVLDSDGSFFLYSKLTVDKSRWQQGNVFSCSVMHEALHNHYTQKS LSLSPG (SEQ ID NO: 16) |

Example 1A Construction of Recombinant Antibodies with N-Terminal Ser/Thr

Using substantially the same methods described in Example 1 above, SEQ ID NO: 6 is used as a signal peptide for its natural huMov19 LC and HC, or as a signal peptide for a heterologous LC or HC, with the modification that a Ser or Thr residue is inserted immediately after SEQ ID NO: 6 such that, after processing a cleavage of the signal peptide, the inserted Ser/Thr becomes the first (N-terminal) residue in the mature processed sequence of the LC or HC.

Example 2 Recombinant Antibody Expression

The chimeric and humanized antibody constructs were transiently produced in suspension-adapted HEK-293T cells, using a modified PEI procedure (Durocher Y, Perret S, & Kamen A High-level and high-throughput recombinant protein production by transient transfection of suspension-growing human 293-EBNA1 cells. *Nucleic Acids Res.* 2002 Jan. 15; 30(2):E$_9$) in shake flasks. The PEI transient transfections were performed as previously described (Durocher, supra), except that the HEK-293T cells were grown in Freestyle 293 (Invitrogen), and the culture volume was left undiluted after the addition of the PEI-DNA complexes. Both the adherent and suspension transient transfections were incubated for a week, and then the cleared supernatant was purified by a Protein A column followed by a CM column ion exchange chromatography as described below.

Example 3 Recombinant Antibody Purification

Antibodies were purified from cleared cell culture supernatants using standard methods, such as, for example, Protein A or G chromatography (HiTrap Protein A or G HP, 1 mL, Amersham Biosciences). Briefly, supernatant was prepared for chromatography by the addition of 1/10 volume of 1 M Tris/HCl buffer, pH 8.0. The pH-adjusted supernatant was filtered through a 0.22 μm filter membrane and loaded onto column equilibrated with binding buffer (PBS, pH 7.3). The column was washed with binding buffer until a stable baseline was obtained with no absorbance at 280 nm. Antibody was eluted with 0.1 M acetic acid buffer containing 0.15 M NaCl, pH 2.8, using a flow rate of 0.5 mL/min. Fractions of approximately 0.25 mL were collected and neutralized by the addition of 1/10 volume of 1M Tris/HCl, pH 8.0. The peak fraction(s) was dialyzed overnight twice against 1×PBS, and sterilized by filtering through a 0.2 μm filter membrane. Purified antibody was quantified by absorbance at A280.

Protein A purified fractions were further purified using ion exchange chromatography (IEX) with carboxymethyl (CM) chromatography. Briefly, samples from protein A purification were buffer exchanged into the start buffer (10 mM potassium phosphate, 10 mM sodium chloride, pH 7.5) and filtered through 0.22 μm filer. The prepared sample was then loaded onto a CM fast flow resin (GE Lifesciences) that was equilibrated with the start buffer at a flow rate of 120 cm/hr. Column size was chosen to have sufficient capacity to bind all the antibody in the sample. The column was then washed with binding buffer until a stable baseline was obtained with no absorbance at 280 nm. Antibody was eluted by initiating a gradient from 10 mM to 500 mM sodium chloride in 20 column volume (CV). Fractions with the UV reading above 50 mAu of the major peak were collected. The purity (the percentage of monomer and soluble high molecular weight aggregates) was assessed with size exclusion chromatography (SEC) on a TSK gel G3000SWXL, 7.8×300 mm with a SWXL guard column, 6.0×40 mm (Tosoh Bioscience, Montgomeryville, Pa.) using an Agilent HPLC 1100 system (Agilent, Santa Clara, Calif.). Fractions with desired purity (>95%) were pooled, buffer exchanged to PBS (pH 7.4) using TFF system, and sterilized by filtering through a 0.2 µm filter membrane. Purified antibody was further tested for its purity by SEC and the IgG concentration was determined by absorbance measurement at 280 nm using an extinction coefficient of 1.47. Dilution was made, if necessary. Alternatively, ceramic hydroxyapatite (CHT) can be used to polish both murine and humanized antibodies with improved selectivity. Type II CHT resin with 40 µm particle size (Bio-Rad Laboratories) was applied to the polishing of antibodies with similar protocol as IEX chromatography. The start buffer for CHT was 20 mM sodium phosphate, pH 7.0 and antibody was eluted with a gradient of 20-160 mM sodium phosphate over 20 CV.

Example 4 N-Terminal Antibody Conjugation—a Two-Step Approach huMOV19-NTS #2 antibody engineered with an N-terminal serine on the heavy chain ([1], in Scheme 1 as shown in FIG. 1; 3 mg/mL in PBS, pH7.4) was treated with 5 mM aqueous sodium periodate (50 equivalents, 25° C., 30 minutes). The mixture was then buffer exchanged through a NAP desalting column (Illustra Sephadex G-25 DNA Grade, GE Healthcare) into sodium acetate buffer, pH5.0.

The resulting solution was treated with 4-Aminophenethyl alcohol (100 mM in DMA [N,N-Dimethylacetamide]) to a 10 mM concentration in the reaction vessel, which contained 10% v/v DMA (N,N-Dimethylacetamide) cosolvent. Linker1 ([3] in Scheme 1; 4 or 5 equivalents) was subsequently introduced, and the reaction vessel was sealed and incubated at 37° C. for 24 hours.

The mixture was then buffer exchanged through a NAP desalting column (Illustra Sephadex G-25 DNA Grade, GE Healthcare) into HEPES (4-(2-hydroxyethyl)-1-piperazine ethanesulfonic acid), pH8.5 buffer. The solution was then adjusted with DMA (N,N-Dimethylacetamide) cosolvent (10% v/v), and treated with Compound A (or sulfonated DGN462 (sDGN462) or sulfonated D1 (or sD1)) ([5], Scheme 1; free thiol; 5 equivalents), at 25° C. for 6 hours.

The resulting conjugate was buffer exchanged into 250 mM Glycine, 10 mM Histidine, 1% sucrose, 0.01% Tween-20, 50 µM sodium bisulfite formulation buffer at pH 6.2 using a NAP filtration column (Illustra Sephadex G-25 DNA Grade, GE Healthcare). Dialysis was performed in the same buffer for 4 hours at 25° C. utilizing Slide-a-Lyzer dialysis cassettes (ThermoScientific 10,000 MWCO).

Figure 2:
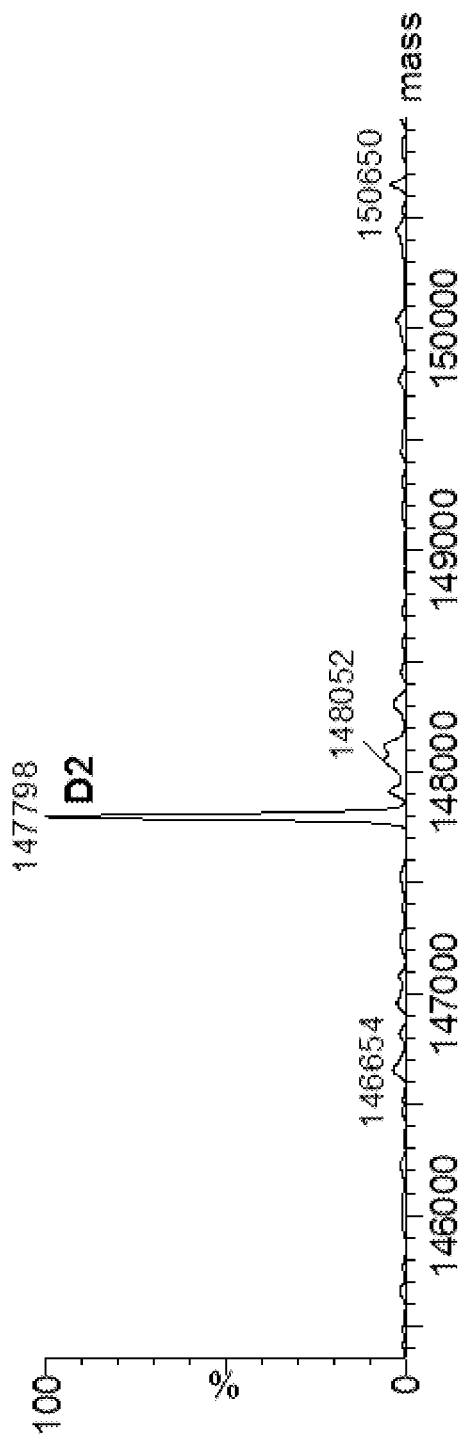
FIG. 2 is Q-ToF Mass Spectrometry (MS) data of intact huMOV19-NTS #2-Linker1-Compound A. It is apparent that the reaction product is a homogeneous ADC with two incorporated Compound A molecules per antibody.

The purified conjugate ([6], Scheme 1) was found to have a homogenous average of two Compound A molecules linked per antibody (via Q-ToF Mass Spectrometry, FIG. 2), >98% monomer (via Size Exclusion Chromatography), <2% free drug (via acetone precipitated reverse-phase HPLC analysis), and a final protein concentration of 0.14 mg/mL (via UV-Vis using molar extinction coefficients $\varepsilon_{280}=201400$ $M^{-1}$ $cm^{-1}$ for the huMOV19-NTS #2 antibody).

Example 5 N-Terminal Antibody Conjugation—DMx Direct Link

Figure 3:
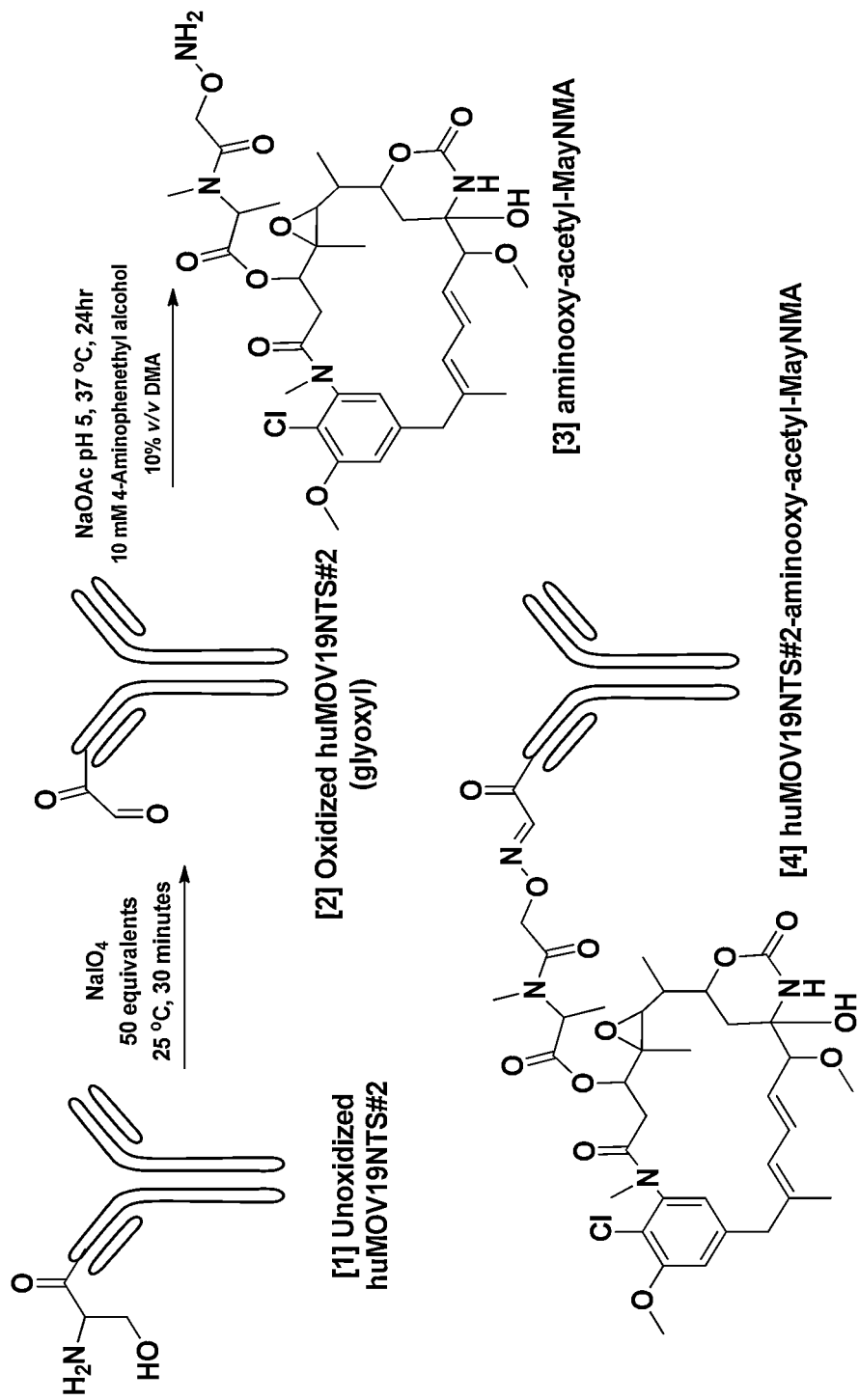
FIG. 3 shows Scheme 2 for synthesizing the huMOV19-NTS #2-aminooxy-acetyl-MayNMA ADC using engineered N-terminal Ser-containing humanized monoclonal antibody huMOV19-NTS #2.

The engineered N-terminal Ser-containing huMOV19-NTS #2 antibody ([1] in Scheme 2, FIG. 3; 3 mg/mL in PBS, pH7.4) was treated with 5 mM aqueous sodium periodate (50 molar equivalents) at 25° C. for 30 minutes. The mixture was then buffer exchanged through a NAP desalting column (Illustra Sephadex G-25 DNA Grade, GE Healthcare) into sodium acetate buffer, pH5.0.

The resulting solution was treated with 4-Aminophenethyl alcohol (100 mM in DMA [N,N-Dimethylacetamide]) to a 10 mM concentration in the reaction vessel, which contained 10% v/v DMA (N,N-Dimethylacetamide) cosolvent. Then, aminooxy-acetyl-MayNMA ([3], Scheme2; 4 or 5 molar equivalents) was subsequently introduced, and the reaction vessel was sealed and incubated at 37° C. for 24 hours.

The mixture was then buffer exchanged through a NAP desalting column (Illustra Sephadex G-25 DNA Grade, GE Healthcare) into 250 mM Glycine, 10 mM Histidine, 1% sucrose buffer at pH 6.2. Dialysis was performed in the same buffer for 4 hours at 25° C., utilizing Slide-a-Lyzer dialysis cassettes (ThermoScientific 10,000 MWCO).

Figure 4:
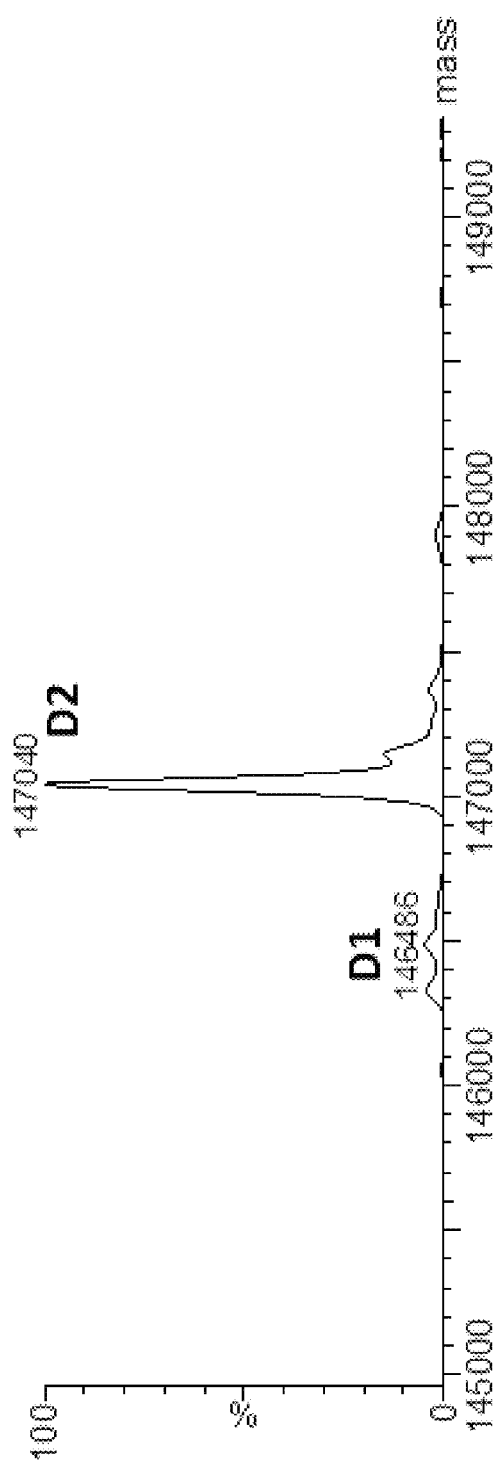
FIG. 4 is Q-ToF Mass Spectrometry (MS) data of intact huMOV19-NTS #2-aminooxy-acetyl-MayNMA. It is apparent that the reaction product is a homogeneous ADC with two incorporated MayNMA molecules per antibody.

The purified conjugate ([4], Scheme 2) was found to have a homogenous average of two MayNMA molecules linked per antibody (via Q-ToF Mass Spectrometry, FIG. 4), >98% monomer (via Size Exclusion Chromatography), <2% free drug (via HISEP reverse-phase HPLC analysis), and a final protein concentration of 0.31 mg/mL (via UV-Vis using molar extinction coefficients $\varepsilon_{280}=201400$ $M^{-1}$ $cm^{-1}$ for the huMov19-NTS #2 antibody).

Example 6 N-Terminal Antibody Conjugation—Two-Step Protocol for MOV19-NTS #1 huMov19-NTS #1 antibody engineered with an N-terminal serine on the light chain through a leader peptide sequence ([1] in Scheme 3, FIG. 5; 3 mg/mL in PBS, pH7.4) was treated with 5 mM aqueous sodium periodate (50 molar equivalents) at 25° C. for 30 minutes. The mixture was then buffer exchanged through a NAP desalting column (Illustra Sephadex G-25 DNA Grade, GE Healthcare) into sodium acetate buffer, pH5.0.

The resulting solution was treated with 4-Aminophenethyl alcohol (100 mM in DMA [N,N-Dimethylacetamide]) to a 10 mM concentration in the reaction vessel, which contained 10% v/v DMA (N,N-Dimethylacetamide) cosolvent. Linker1 ([3], Scheme 3; 4 or 5 molar equivalents) was subsequently introduced, and the reaction vessel was sealed and incubated at 37° C. for 24 hours.

The mixture was then buffer exchanged through a NAP desalting column (Illustra Sephadex G-25 DNA Grade, GE Healthcare) into HEPES (4-(2-hydroxyethyl)-1-piperazine ethanesulfonic acid) pH8.5 buffer. The solution was then adjusted with DMA (N,N-Dimethylacetamide) cosolvent (10% v/v), and treated with Compound A ([5], Scheme 3; free thiol; 5 molar equivalents) at 25° C. for 6 hours.

The resulting conjugate was buffer exchanged into 250 mM Glycine, 10 mM Histidine, 1% sucrose, 0.01% Tween-20, 50 µM sodium bisulfite formulation buffer at pH 6.2, using a NAP filtration column (Illustra Sephadex G-25 DNA Grade, GE Healthcare). Dialysis was performed in the same buffer for 4 hours at 25° C., utilizing Slide-a-Lyzer dialysis cassettes (ThermoScientific 10,000 MWCO).

Figure 6:
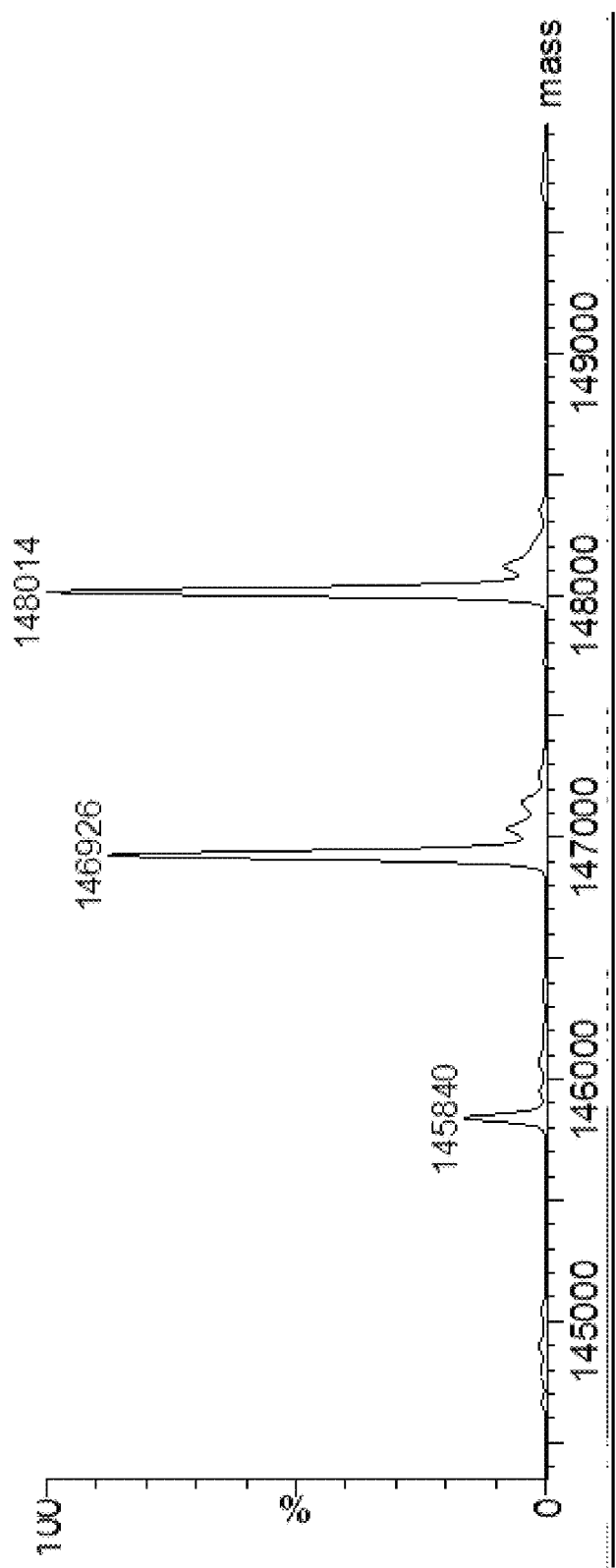
FIG. 6 shows Q-ToF Mass Spectrometry (MS) data of intact huMOV19-NTS #1-Linker1-Compound A.

The purified conjugate ([6], Scheme 3) was found to have an average of 1.4 molecules of Compound A linked per antibody (via Q-ToF Mass Spectrometry, FIG. 6), >98% monomer (via Size Exclusion Chromatography), <2% free drug (via acetone precipitated reverse-phase HPLC analysis), and a final protein concentration of 0.14 mg/mL (via UV-Vis using molar extinction coefficients $\varepsilon_{280}=201400$ $M^{-1}$ $cm^{-1}$ for the huMov19-NTS #1 antibody).

Example 7 Binding of N-Terminal Ser Conjugates on T47D Cells is Comparable to Control The binding affinity of an N-terminal Ser-drug conjugate (SERIMab ADC) was analyzed using T47D cells, which have been previously shown to have ~$1\times10^5$ folate receptor alpha (FR-α) antigens bound per cell. The humanized monoclonal antibody huMOV19 specifically binds FRα.

To evaluate the binding affinity, about 100 μl/well of ADC or control antibody (e.g., unconjugated native huMOV19, or M9346A) were diluted in FACS buffer (1% BSA, 1×PBS) in a 96-well plate (Falcon, round bottom), at a starting concentration of about $3\times10^{-8}$ M in duplicate, and followed by serial 3-fold dilution in FACS buffer at 4° C. The human breast cancer cell line T47D cells were grown in RPMI-1640 (Life Technologies) supplemented with heat-inactivated 10% FBS (Life Technologies), 0.1 mg/mL gentamycin (Life Technologies) and 0.2 IU bovine insulin/mL (Sigma), and were washed once in PBS before being removed with Versene (Life Technologies). T47D cells were then resuspended in growth media (see above) to neutralize trypsin, and were counted on a Coulter counter. Cells were then washed twice in cold FACS buffer, centrifuging in between washes at 1200 rpm for 5 min.

About 100 μl/mL of $2\times10^4$ cells/well were added to wells containing ADC, antibody or FACS buffer only, and incubated at 4° C. for 2 hr. After incubation, cells were centrifuged as before and washed once in 200 μL/well cold FACS buffer. Cells were then stained with 200 μL/well FITC-conjugated Goat Anti-Human-IgG-Fcγ secondary antibody (controls included were unstained cells and those stained with secondary antibody only) for 40 min at 4° C., centrifuged and washed once in 200 μL/well cold PBS-D. Cells were fixed in 200 μL/well 1% formaldehyde/PBS-D and stored at 4° C.

Figure 8A:
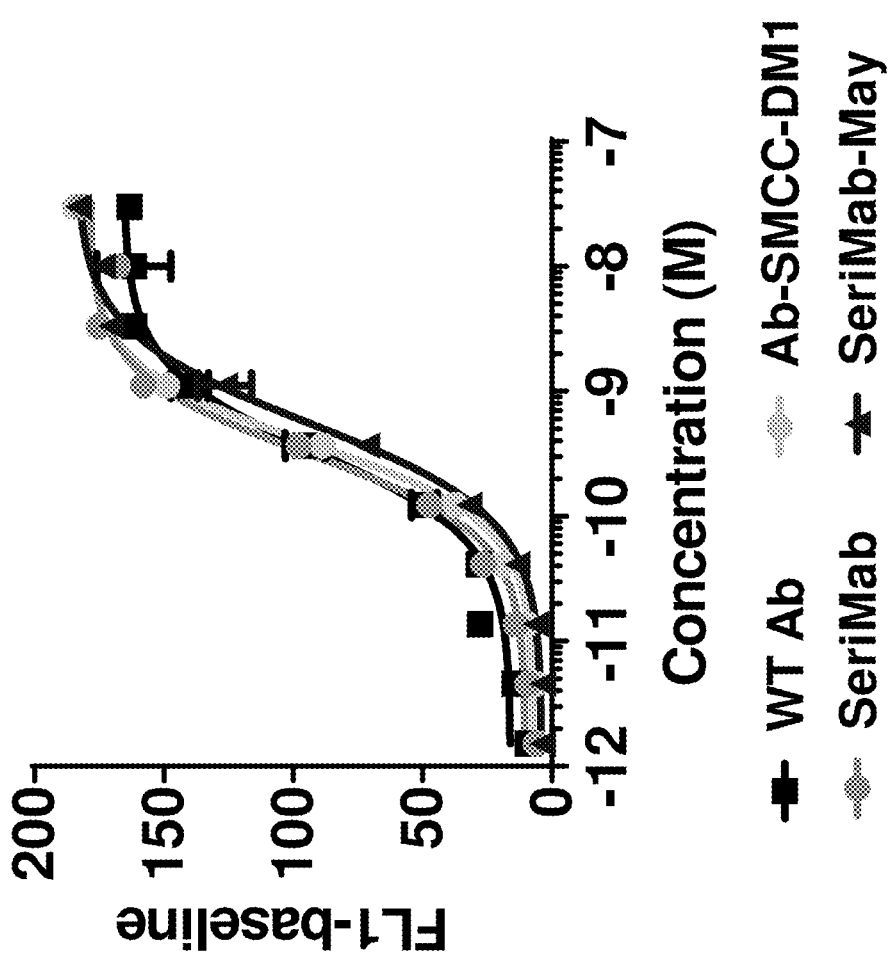
FIG. 8A shows that N-terminal Ser-specific modification or conjugation does not noticeably affect antibody binding to antigen.

After storage, cellular surface staining of conjugate or antibody was detected using flow cytometry on a FACS Calibur (BD Biosciences). The geometric means were plotted against the log concentration of ADC or antibody using GraphPad Prism and the $EC_{50}$ was calculated via non-linear 4-parameter logistic regression analysis. See FIG. 8.

A similar experiment was also conducted using (1) huMOV19-NTS #2-Linker1-Compound A (also known as "SeriMab-sDGN462") having on average two molecules of Compound A per Ab; (2) huMOV19-sSPDB-Compound A linked through a sulfo-SPDB linker to the ε-amino groups of lysine residues on huMOV-19, with an average of 2.4 molecules of Compound A per huMOV19); (3) unconjugated native huMOV19 antibody (M9346A); and (4) the unconjugated engineered huMOV19-NTS #2 antibody having the engineered N-terminal Ser. See FIG. 7A.

Figure 7A:
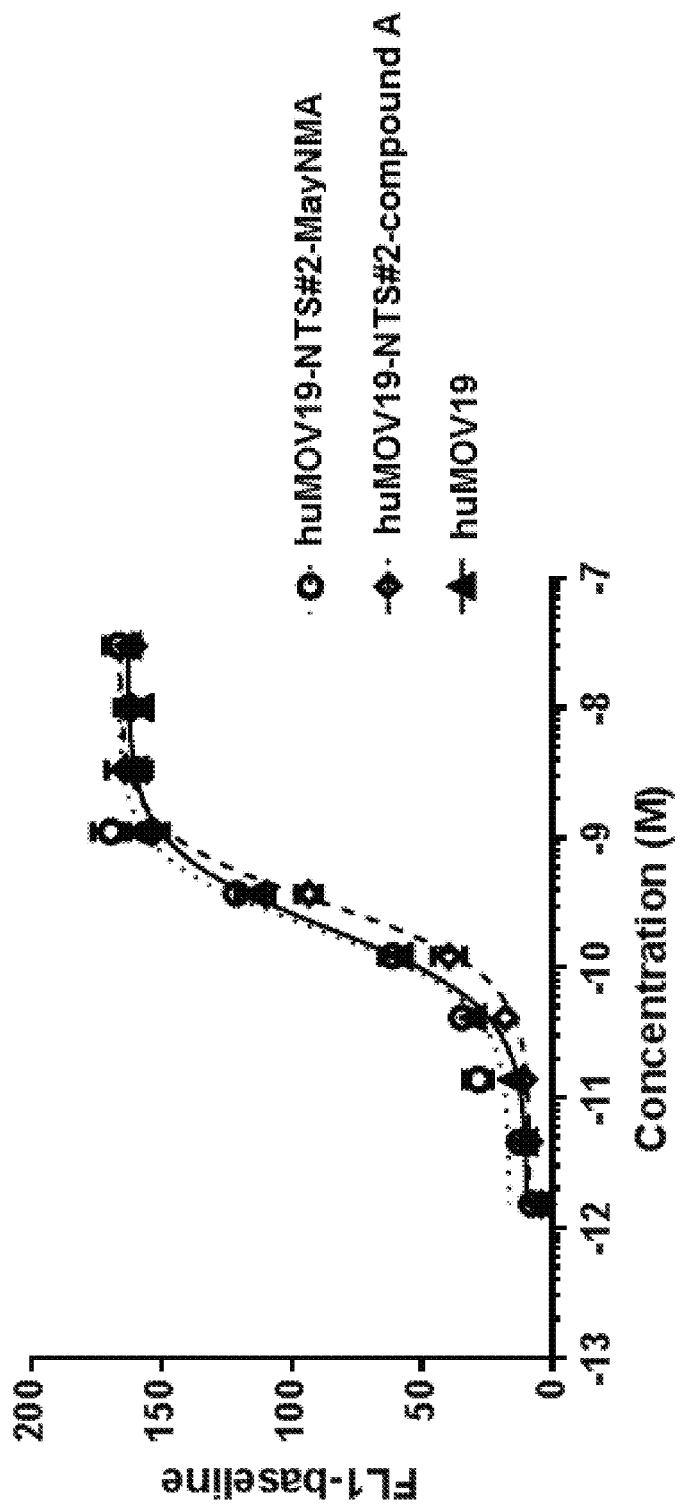
FIG. 7A demonstrates that N-terminal Ser-specific conjugation does not noticeably affect antibody binding to antigen. huMOV19-NTS #2-MayNMA (or SeriMab-May) and huMOV19-NTS #2-Compound A (or SeriMab-sDGN462) are both ADCs comprising the humanized IgG monoclonal antibody huMOV19, linked through an engineered N-terminal Ser residue to Maytansinoid and cytotoxic Compound A (or sulfonated DGN462 (sDGN462)), respectively. Binding between T47D (i.e., the FRα antigen on the surface) and the ADCs (or the control antibody or the FACS buffer control) was measured by FACS detection of FITC-conjugated Goat Anti-Human-IgG-Fcγ secondary antibody bound to any ADC (or control Ab) on T47D surface.
Figure 7B:
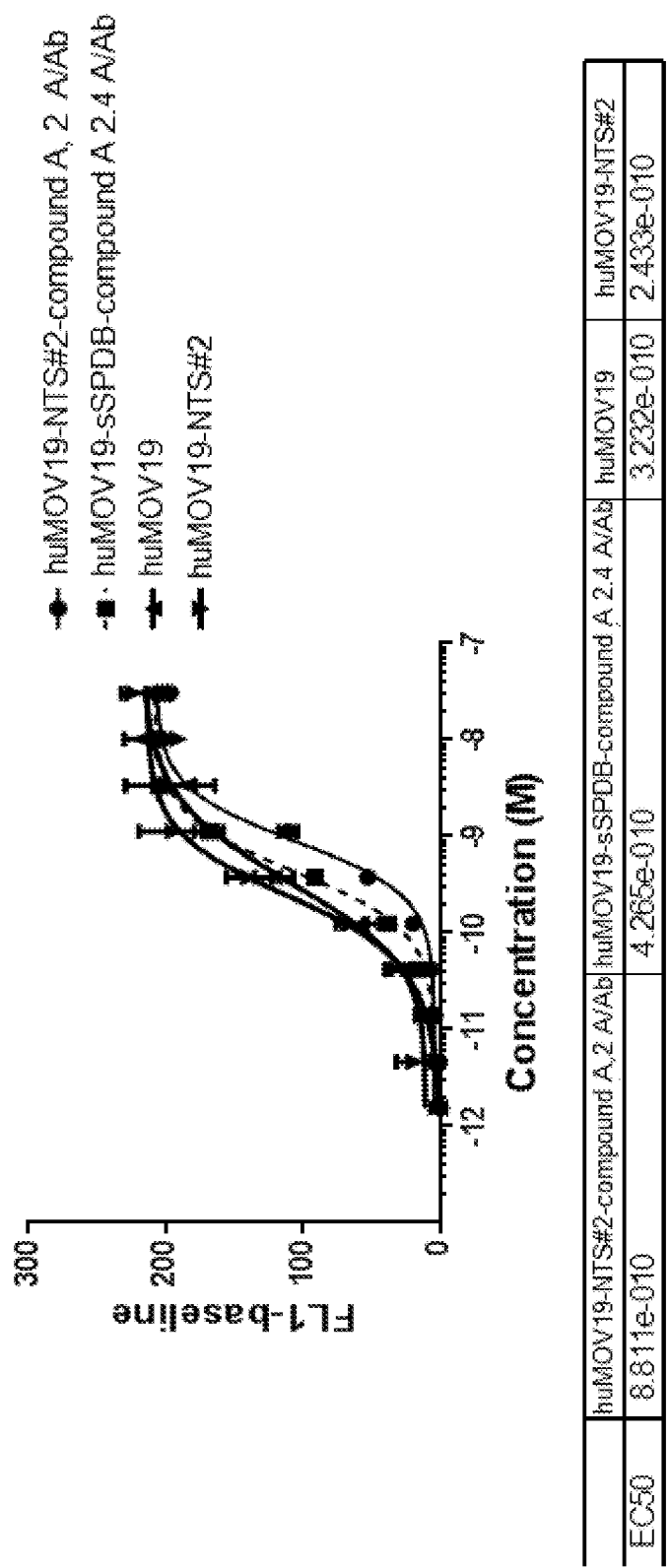
FIG. 7B shows FACS binding data for huMOV19-NTS #2-Linker1-Compound A to T47D cells expressing the FRα- antigen. Both lysine-loaded huMOV19-sSPDB-Compound A and N-terminal modified huMOV19-NTS #2-Linker1-Compound A have comparable cell binding, which is also similar to that of unconjugated native huMOV19 and engineered huMOV19-NTS #2 (see $EC_{50}$ values in the table).

As shown in FIGS. 7A and 7B, the SERIMAb ADC(s) bound similarly to the surface of T47D cells expressing the target antigen as the unconjugated antibody (M9346A) control. See, for example, $EC_{50}$ values in FIG. 7B. Substantially the same results were obtained in a similar experiment show in FIGS. 8A and 8B. These experiments demonstrate that antigen binding is not affected by the conjugation process at the N-terminal Serine residue.

Similar results were also observed for huMOV19-NTS #2-D8 conjugate. The conjugate bound similarly to the surface of T47D cells expressing the target antigen as the unconjugated control (M9346A antibody) and unconjugated engineered huMOV19-NTS #2 antibody (or SeriMab). See FIG. 23.

Example 8 Cytotoxic Evaluation of huMOV19NTS #2-Linker1-Compound A of KB Cervical Cancer Cell Line This experiment demonstrates that site-specific antibody conjugation to the engineered N-terminal Ser not only provides predictable and reliable drug load per antibody, but also surprisingly confers the resulting ADC conjugate higher potency compared to conjugates with antibody linkage to Lys sidechains.

100 μl/well of each ADC was diluted in RPMI-1640 (Life Technologies) supplemented with heat-inactivated 10% FBS (Life Technologies) and 0.1 mg/ml gentamycin (Life Technologies) in a 96-well plate (Corning, flat bottom) at starting concentrations of $3.5\times10^{-9}$ M to $3.5\times10^{-8}$ M in triplicate and serially diluted 3-fold in media above at ambient temperature. KB cells (buccal epithelial tumor), grown in EMEM (ATCC) supplemented with heat-inactivated 10% FBS (Life Technologies) and 0.1 mg/ml gentamycin (Life Technologies), were washed once in PBS and removed with 0.05% trypsin-EDTA (Life Technologies). Other cells tested were NCI-H2110 (NSCLC) and T47D (breast epithelial) grown in RPMI-1640 (LifeTechnologies) supplemented with heat-inactivated 10% FBS (Life Technologies) and 0.1 mg/ml gentamycin (Life Technologies). T47D media also was supplemented with 0.2 IU/ml bovine insulin. All cells were resuspended in growth media (see above) to neutralize trypsin and counted on a Coulter counter. 100 μl/ml of 1000-2000 cells/well were added to wells containing ADC or media only and incubated in a 37° C. incubator with 5% $CO_2$ for 5 days with and without 1 μM blocking huMOV19 antibody. Total volume is 200 μl/well. After incubation, cell viability was analyzed by addition of 20 μl/well WST-8 (Dojindo) and allowed to develop for 2 hr. Absorbance was read on a plate reader at 450 and 620 nm. Absorbances at 620 nm were subtracted from absorbances at 450 nm. Background in wells containing media only was further subtracted from corrected absorbances and surviving fraction (SF) of untreated cells was calculated in Excel. An XY graph of ADC concentration (M) vs. SF was created using Graph Pad Prism.

Figure 9B:
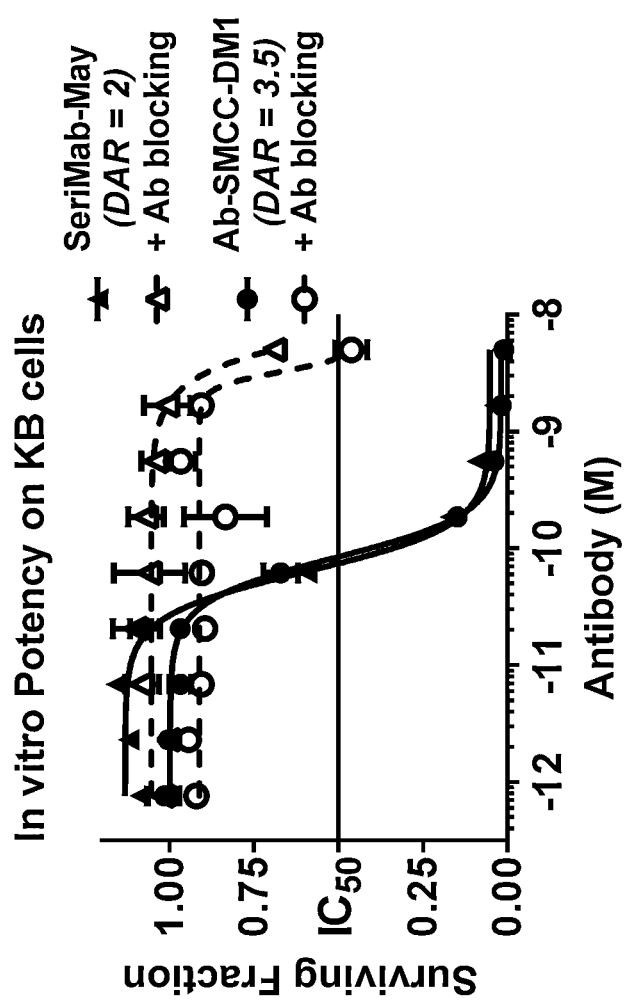
FIG. 9B shows the result of cytotoxic evaluation of the ADC conjugate SeriMab-May on KB cervical cancer cell line. The data shows that SeriMab-May conjugate has the same potency as the lysine-conjugate Ab-SMCC-DM1 with higher DAR (cytotoxic compound to antibody ratio).
Figure 10:
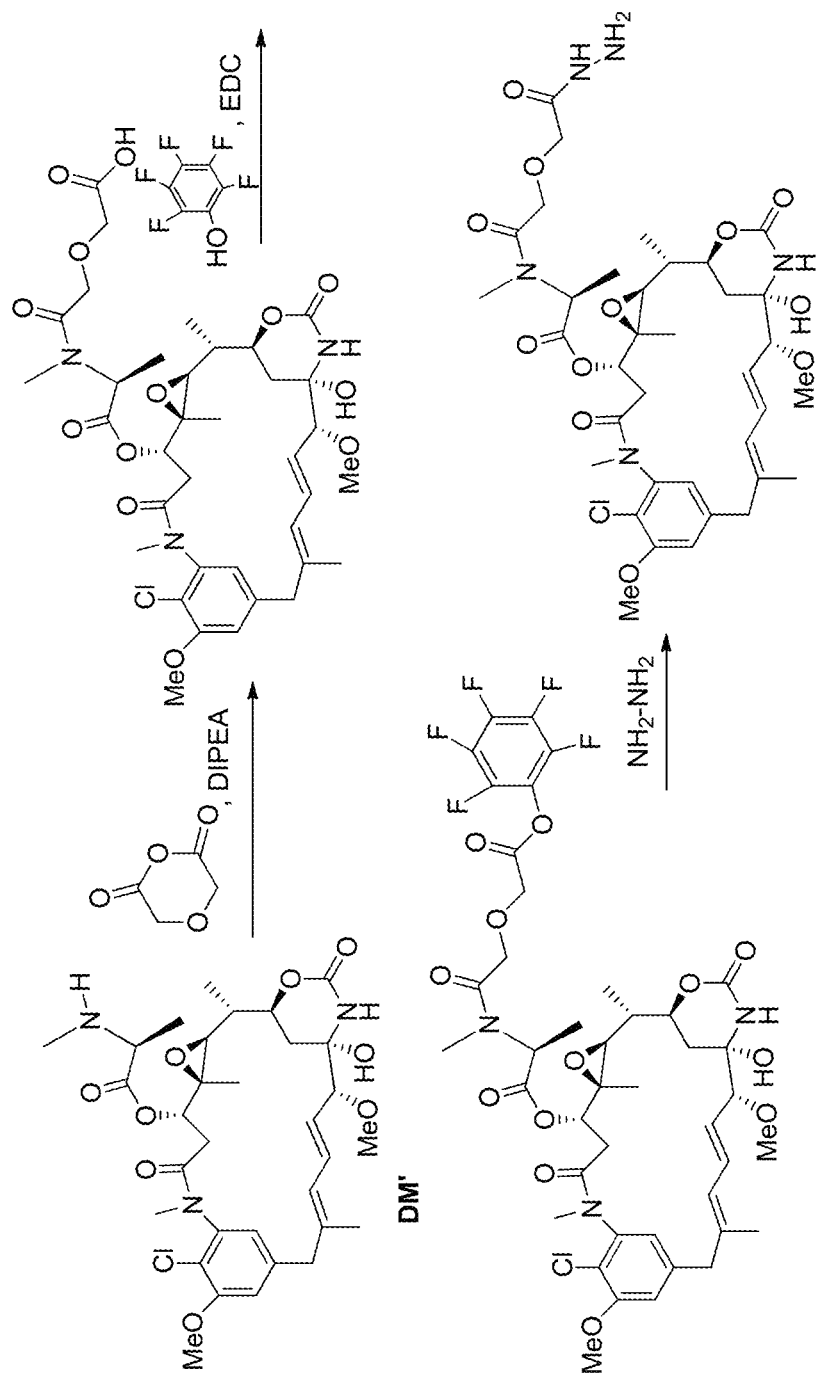
FIGS. 10 and 11 show exemplary cytotoxic compounds that can be used in preparing the conjugates of the present invention.
Figure 11:
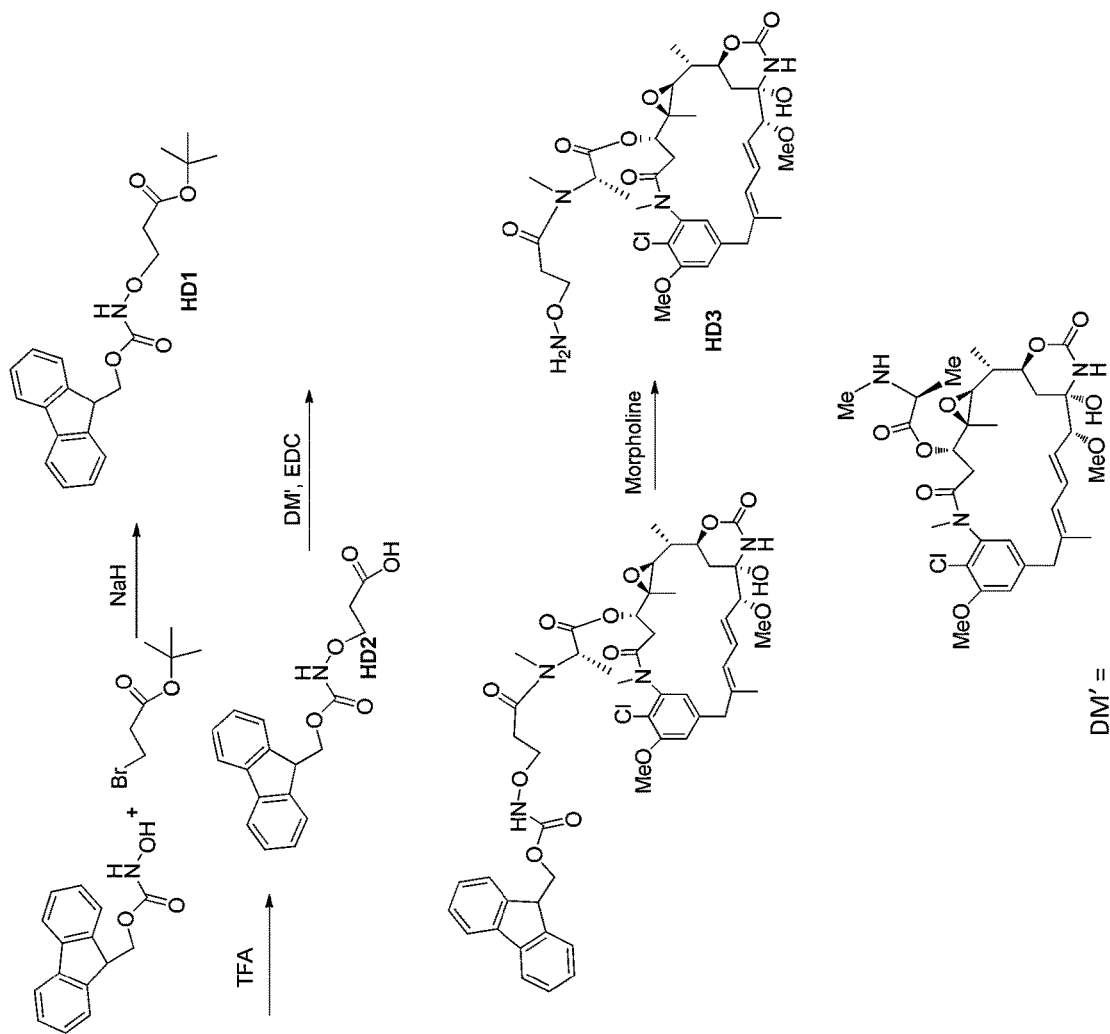
Figure 12A:
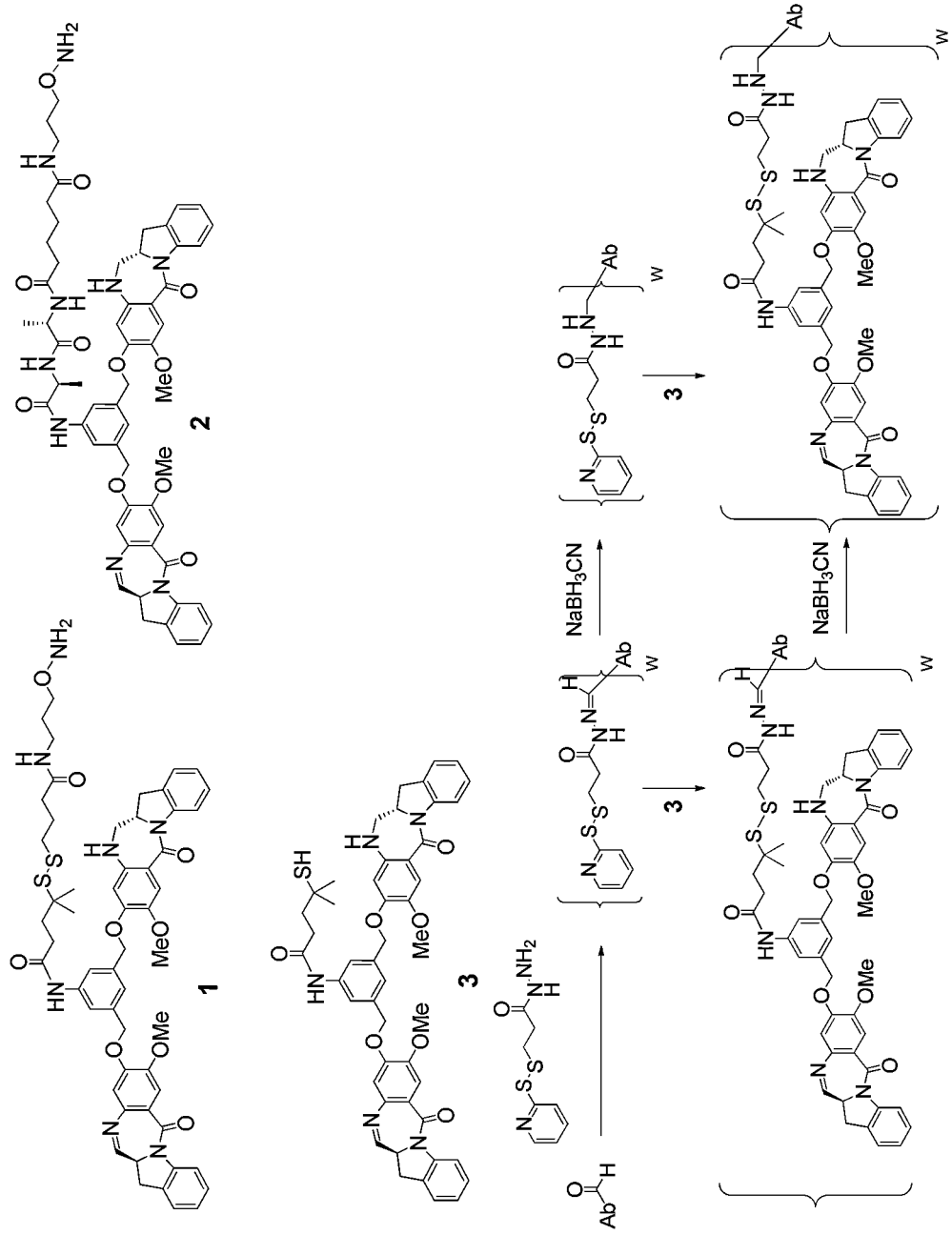
FIGS. 12A-12D show exemplary schemes for preparing the conjugates of the present invention.
Figure 12B:
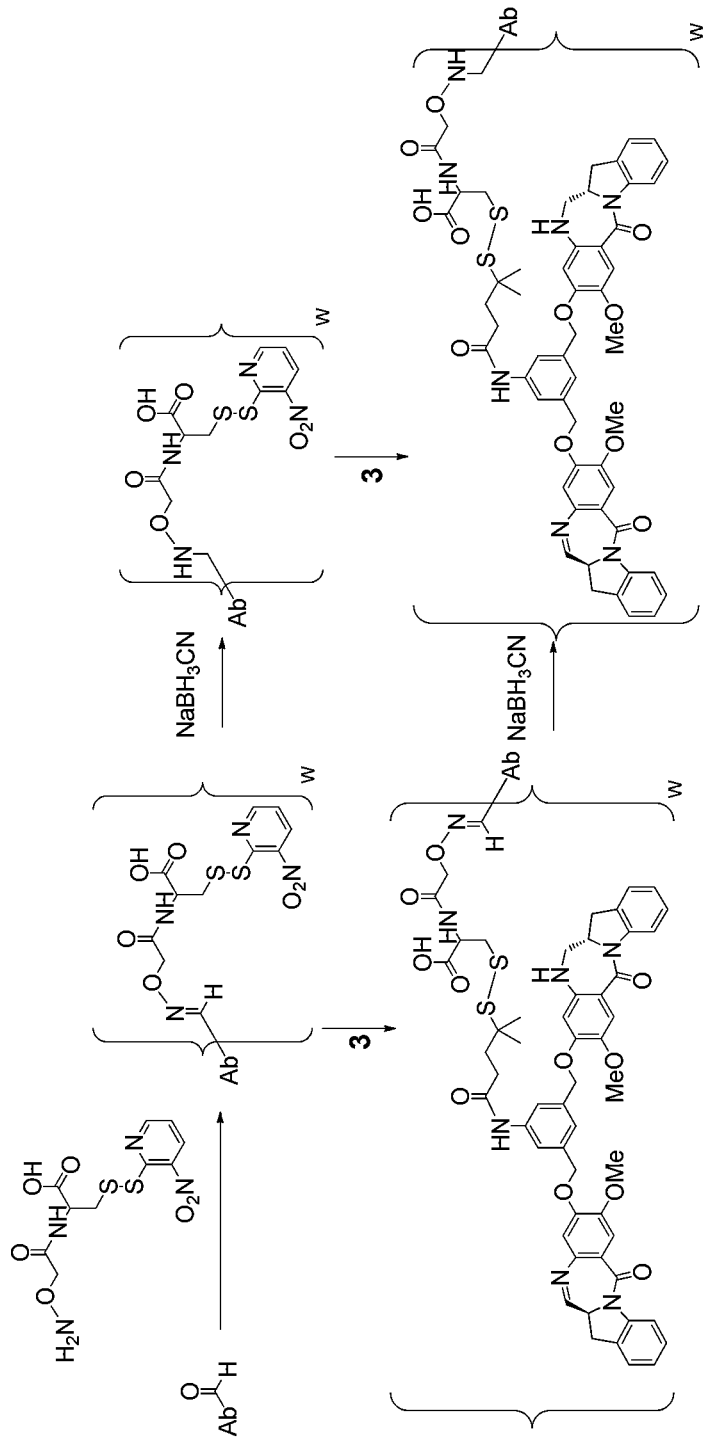
Figure 12C:
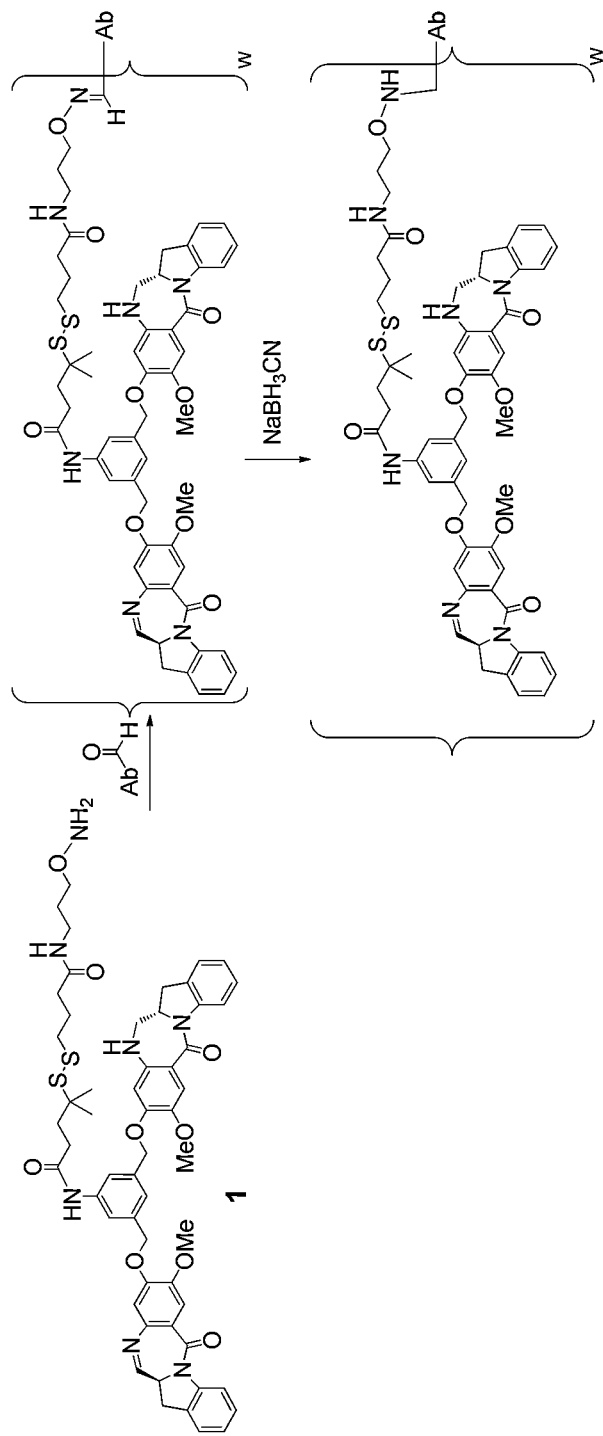
Figure 12D:
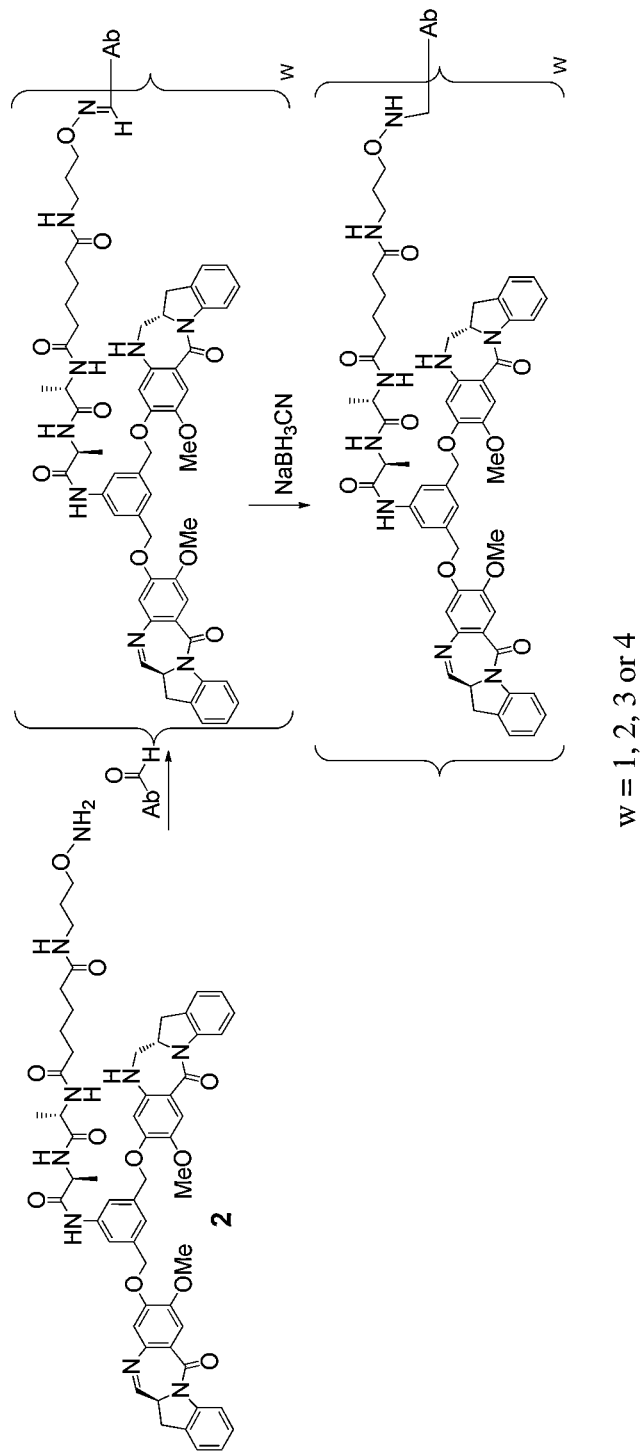

The data in FIG. 9A shows that Compound A can be linked to the engineered N-terminal Ser, and yield an ADC with precisely two molecules of Compound A per antibody molecule. In contrast, Compound A linked to the same huMOV19 antibody through Lys side chains yields ADC with an average of 2.4 molecules of Compound A per antibody, suggesting a relatively heterogeneous population of ADCs with different numbers of linked Compound A.

FIGS. 7A and 7B have previously shown that, regardless of the linkage used (either through the engineered N-terminal Ser, or through the natural Lys side chains), the resulting ADCs have essentially the same binding affinity to the antigen, compared to the unconjugated antibody.

However, despite a higher drug load in the Lys-conjugated ADCs (i.e., 2.4 vs. 2.0 Compound A), the ADC with the N-terminal Ser linkage is about 3-fold more potent than the lysine-conjugated ADC on the basis of antibody concentration, and about 5-fold more potent based on Compound A concentration. See measured $IC_{50}$ values in FIG. 9A.

Furthermore, adding excess (1 μM) unconjugated huMOV19 can block the observed killing effect, suggesting not only that the observed cytotoxicity is specific and depends on huMOV19 binding to its antigen on the target cell, but also that both ADCs have identical antigen-independent activity against the target cell.

Similar results were also obtained for a different cytotoxin conjugated to huMOV19 and its engineered version with N-terminal Ser conjugation. See the maytansinoid conjugates in FIG. 9B. The ADC with the N-terminal Ser linkage has similar potency as the Lys-conjugated ADC despite the fact that the Lys-conjugated ADC has a higher drug load (3.5 v. 2).

Similar results as described above for huMOV19 were also observed for an unrelated antibody.

Example 9

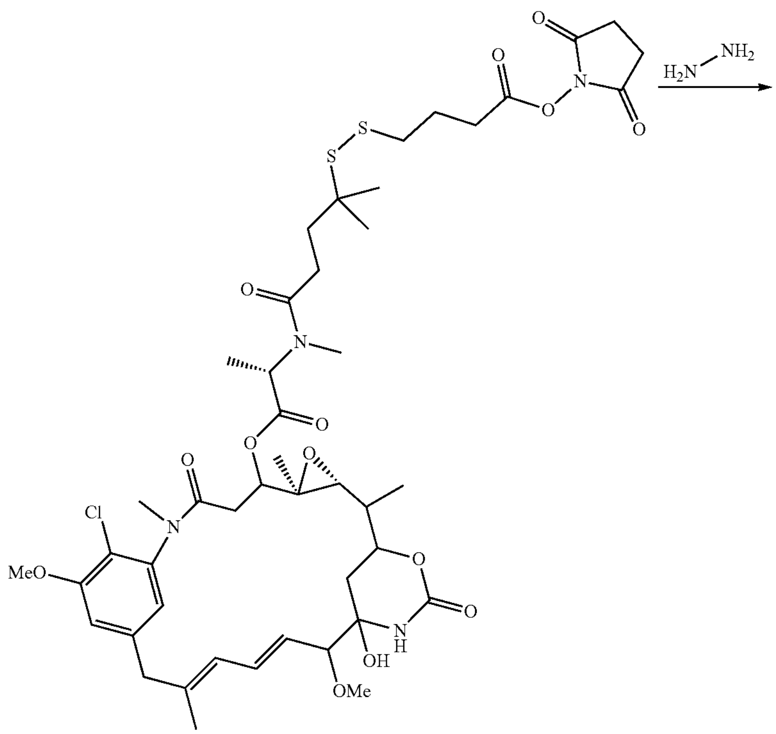

DM4-SPDB

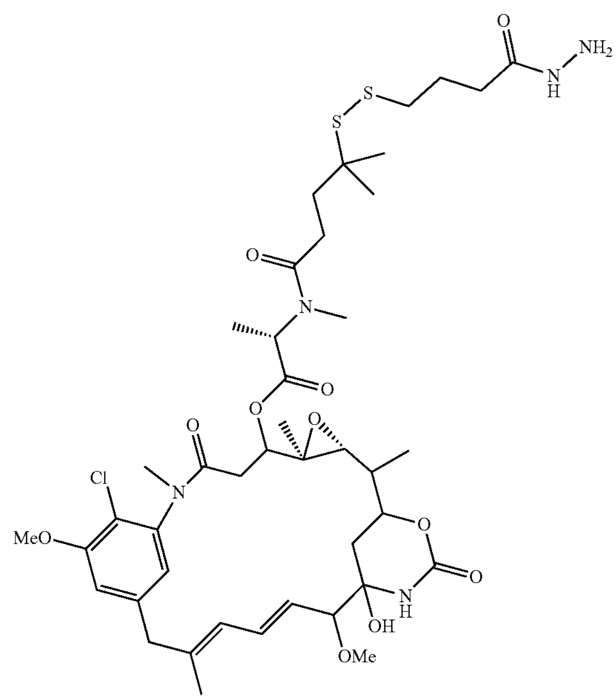

DM4-SPDB-hydrazide

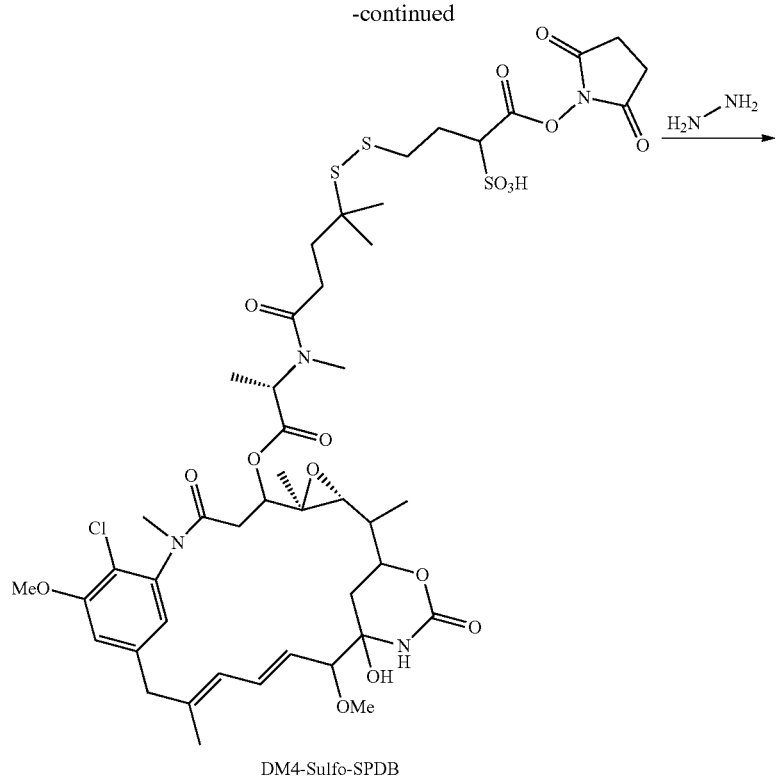
DM4-Sulfo-SPDB
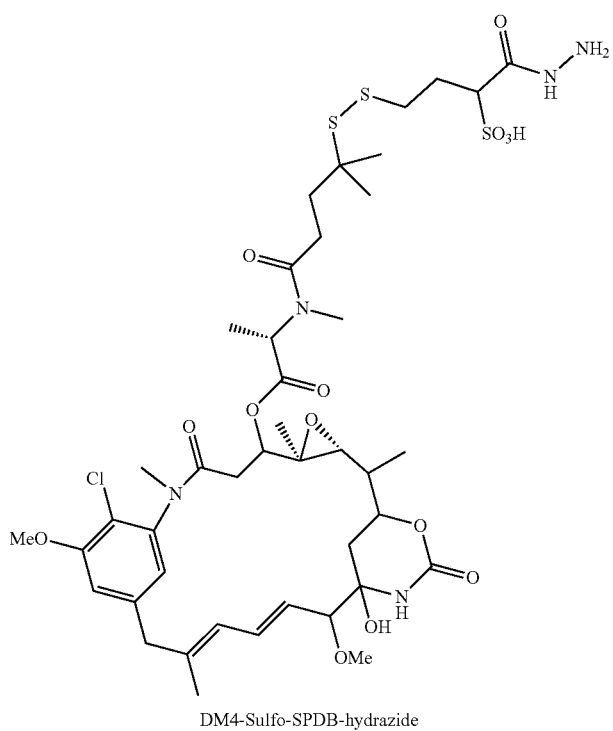
DM4-Sulfo-SPDB-hydrazide
DM4-SPDB-hydrazide and DM4-Sulfo-SPDB-hydrazide will be prepared by reacting DM4-SPDB or DM4-Sulfo-SPDB with hydrazine as shown above.

Example 10

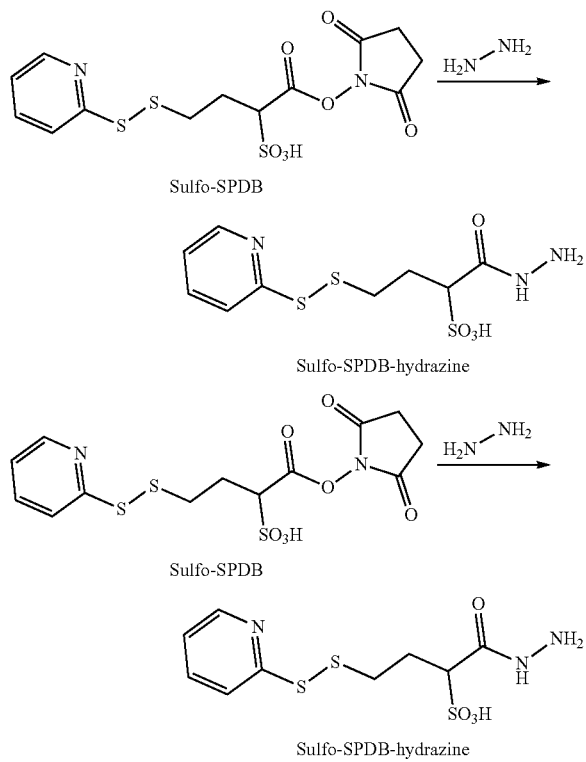

Previously described sulfo-SPDB (U.S. Pat. No. 8,236,319) can be reacted with hydrazine to yield sulfo-SPDB-hydrozine linker.

To a 0.24M solution of hydrazine (0.015 ml, 0.242 mmol) in DMA was added a 0.06M solution of 1-((2,5-dioxopyrrolidin-1-yl)oxy)-1-oxo-4-(pyridin-2-yldisulfanyl)butane-2-sulfonic acid (25.9 mg, 0.0635 mmol) in DMA, dropwise with rapid stirring at room temperature. After stirring for 40 min under argon at 50° C., the crude reaction mixture was purified by reverse-phase HPLC (C18, 21.2×250 mm) eluting with deionized water containing 0.1% formic acid using an acetonitrile gradient 5-25% over 30 min. Fractions containing desired product were combined, frozen and lyophilized give 3.1 mg (15% yield) of desired product as a white solid. MS $(M+1)^+$ found: 324.05, calculated: 324.01. $^1$H NMR (400 MHz, DMSO-d6) δ 2.13-2.26 (m, 2H), 2.82-2.91 (m, 2H), 3.52 (t, J=7.8, 6.1 Hz, 1H), 7.24 (t, J=7.3, 4.7 Hz, 1H), 7.76 (d, J=8.0 Hz, 1H), 7.83 (t, 1H), 8.45 (d, J=3.5, 2.0 Hz, 1H).

The resulting compound can be reacted with an aldehyde or ketone-bearing cell binding agent then the hydrazide linkage can be optionally reduced. The resulting linker can be reacted with an aldehyde or ketone-bearing cell binding agent then reacted with a thiol bearing maytansinoid such as DM1 or DM4 to give conjugate.

Alternatively once the linker is reacted with the cell binding agent the reactive disulfide of the resulting molecule can be reduced using reagents such as dithiothreitol or TCEP to give a thiol which can be reacted with a maytansinoid-bearing a reactive disulfide such as PyS-DM1 or PyS-DM4.

Example 11

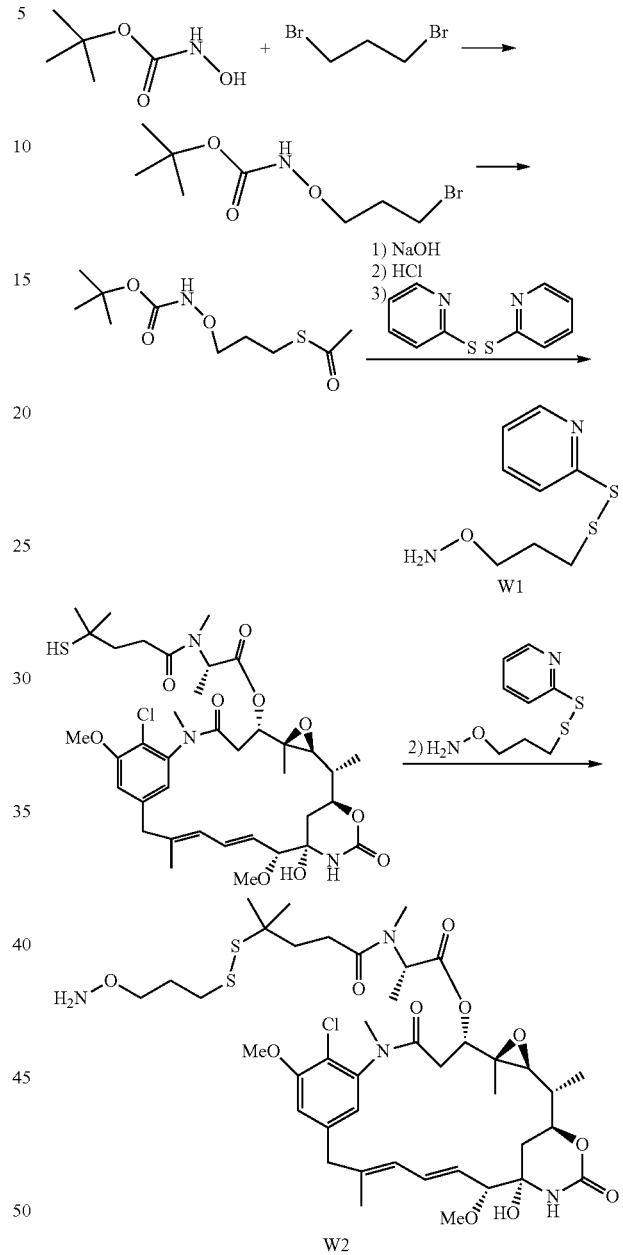

Boc-hydroxyl amine will be reacted with 1,3-dibromopropane then with thioacetic acid. The thiol and amine will be deprotected by treatment with NaOH followed by HCl then the thiol moiety will be reacted with 2,2'-dipyridyldisulfide to give W1. DM4 will be reacted with W1 to give W2. 1,3-dibromopropane can be replaced by other symmetric dibromides to give spacers of other lengths between the DM and disulfide moieties.

The linker W1 can also be used to derivatize a ketone or aldehyde-bearing cell binding agent to introduce a reactive disulfide. The oxime can also be optionally reduced. Either method will allow the addition of a thiol bearing maytansinoid such as DM1 or DM4 to complete the conjugation.

Example 12

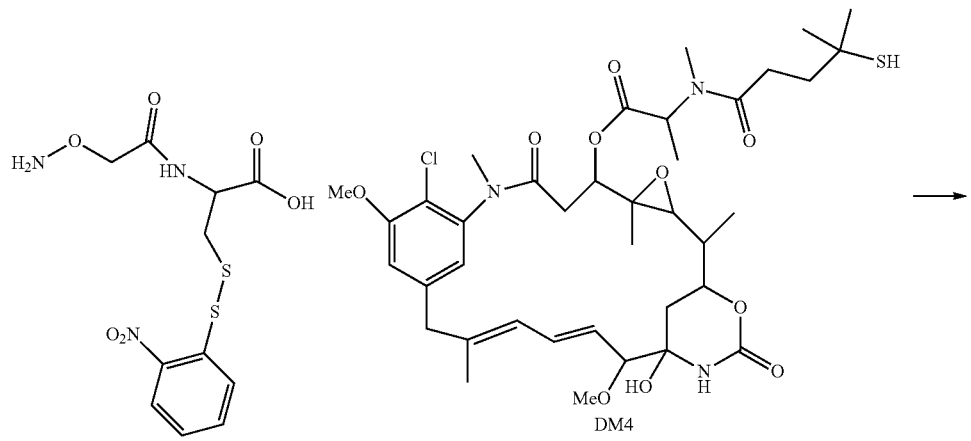

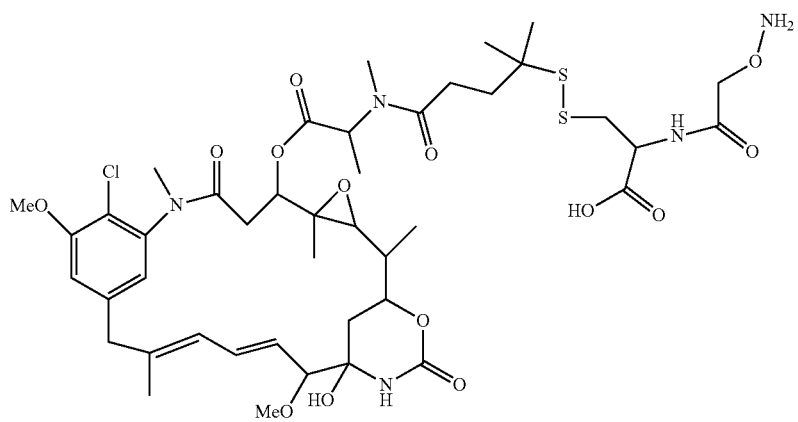

Alkoxaminoacetyl-Cys(S-2-NO₂-Phenyl)-OH (1 mg, 2.88 prepared as previously described in *Org. Biomol. Biochem.* 2006, 4:1313-1419) and DM4 (6 mg, 7.7 μmol) were dissolved in DMF (250 μL) and deionized water (25 μL) and magnetically stirred for 1 h. The reaction mixture was HPLC purified using a 21×150 mm C18 column eluting at 20 mL/min with 95% deionized water containing 0.1% formic acid and an acetonitrile gradient of 5%-95% over 30 min. Desired product was collected, frozen and lyophilized to give approximately 0.25 mg (9% yield) of desired product as a white solid. MS (M+H)⁺ found 972.5; calcd. 972.3; MS (M-1) found 970.4; calcd. 970.3.

Example 13

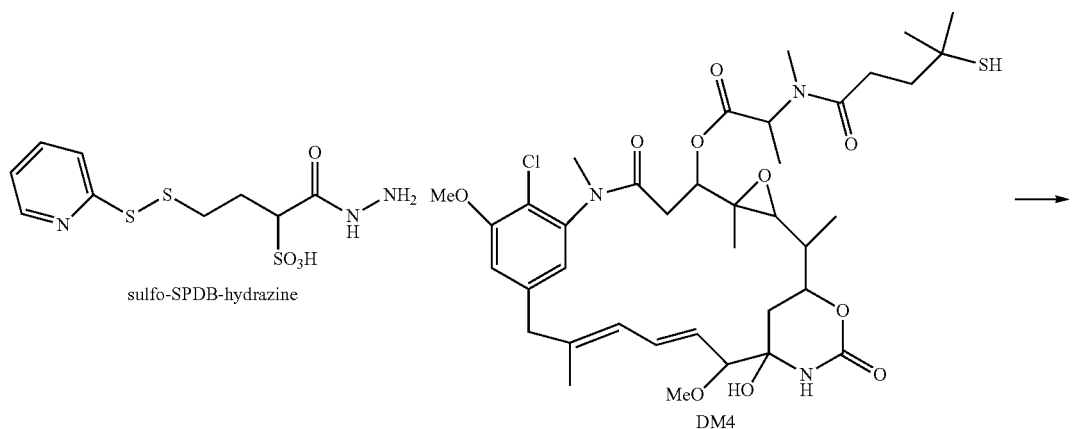

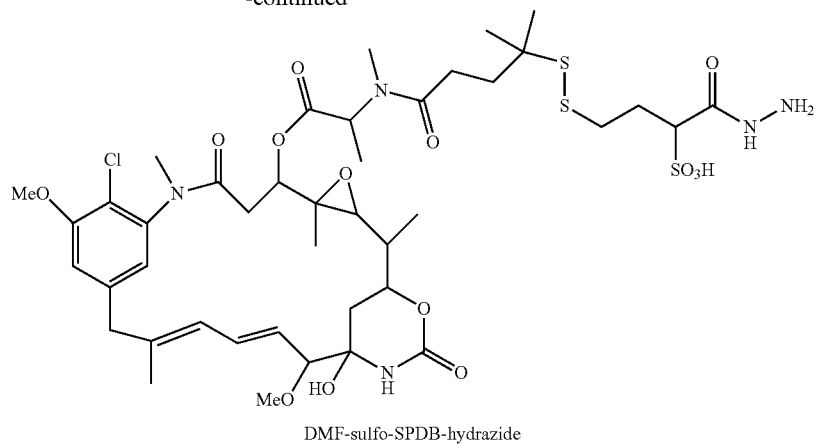

DMF-sulfo-SPDB-hydrazide

Sulfo-SPDB-hydrazine (1 mg, 3.1 µmol) and DM4 (4 mg, 5.1 µmol) were dissolved in DMF (300 µL) and ¼th saturated aqueous sodium bicarbonate (100 µL) and magnetically stirred for 1 hour. The reaction mixture was HPLC purified using a 21×150 mm C18 column eluting at 20 mL/min with 95% deionized water containing 0.1% formic acid and an acetonitrile gradient of 5%-95% over 30 min. Desired product was collected, frozen and lyophilized to give approximately 1 mg (19% yield) of desired product as a white solid. MS (M+H)⁺ found 992.6, calcd. 992.3; MS (M-1) found 990.5, calcd. 990.3.

Example 14

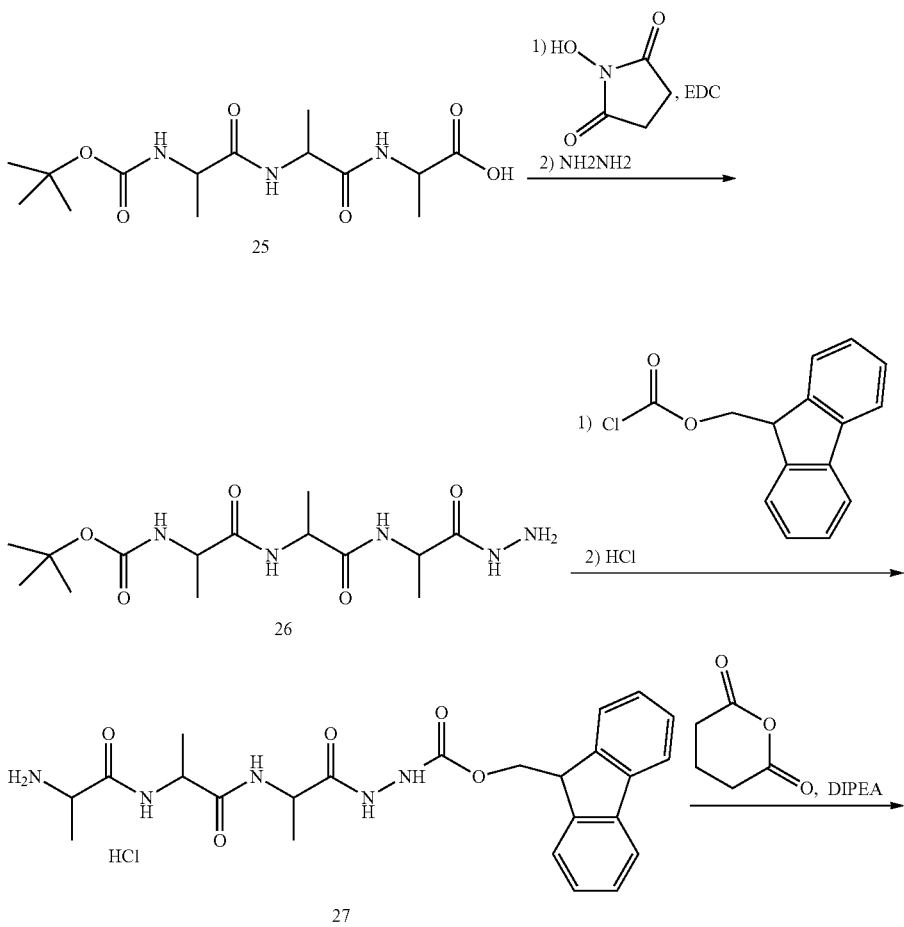

-continued

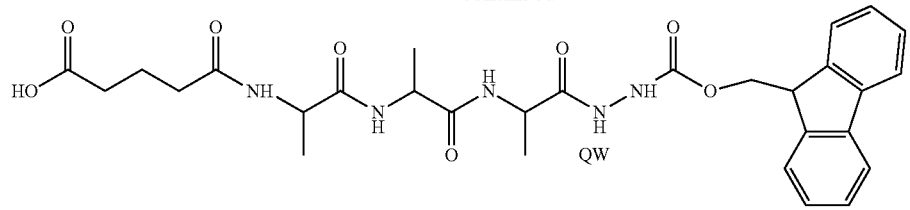

28

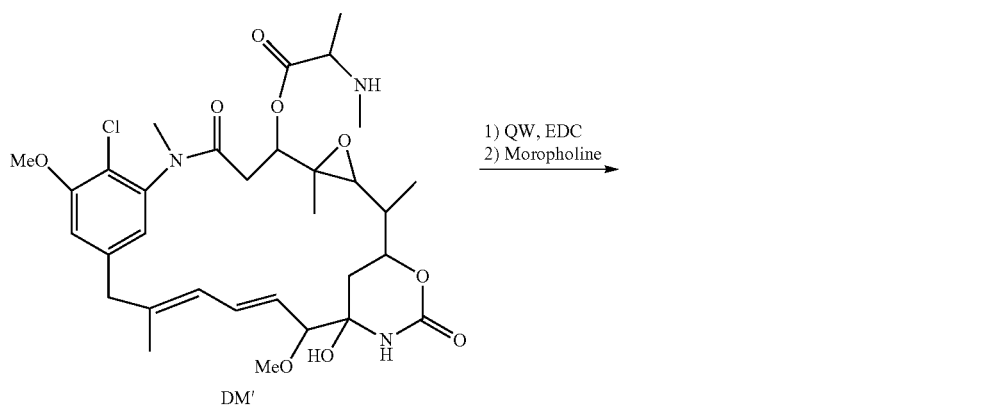

DM'

1) QW, EDC
2) Moropholine
→

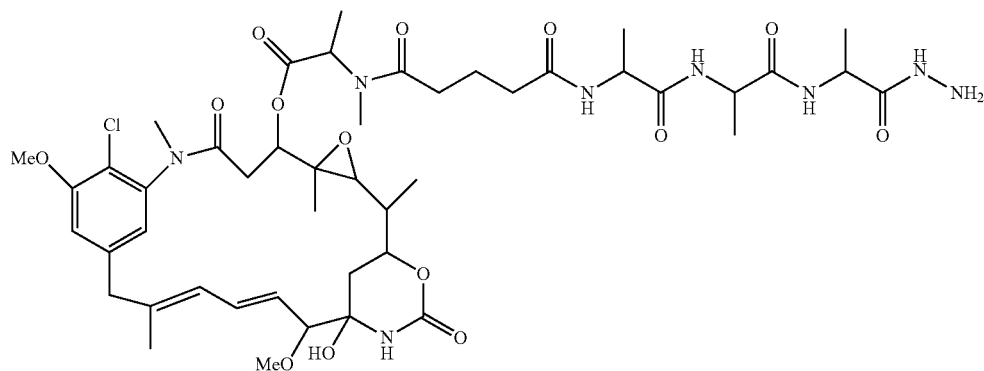

29

The Boc protected Ala-Ala-Ala-OH (compound 25) can be activated by reaction with N-hydroxysuccinimde and EDC coupling agent followed by reaction with hydrazine. The resulting hydrazide (compound 26) can be FMoc protected by reaction with FMoc-Cl and the Boc protecting group can be removed by reaction with dilute HCl. The resulting compound 27 can react with 1,4-Dioxane-2,6-dione in the presence of DIPEA to give compound 28. DM' can be coupled to compound 28 using EDC and the FMoc protecting group can be removed by reaction with morpholine to give desired compound 29.

The scheme can be generalized by replacing Boc-Ala-Ala-Ala-OH (compound 25) with a Boc protected amino acid or peptide and the glutaric anhydride can also be replaced by a different cyclic anhydride or with a mono protected diacid to give other spacers between the DM' and peptide moieties.

Example 15
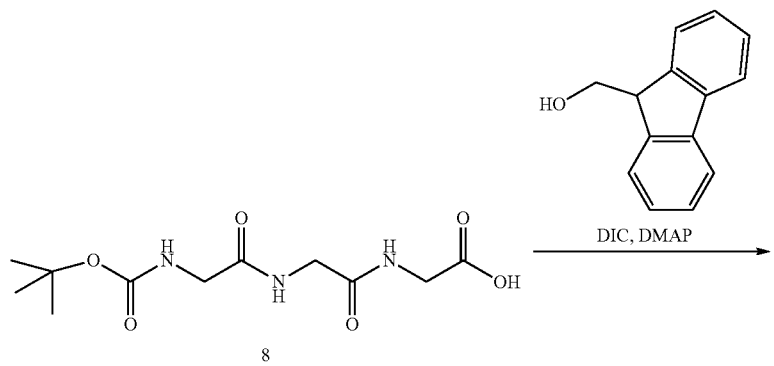
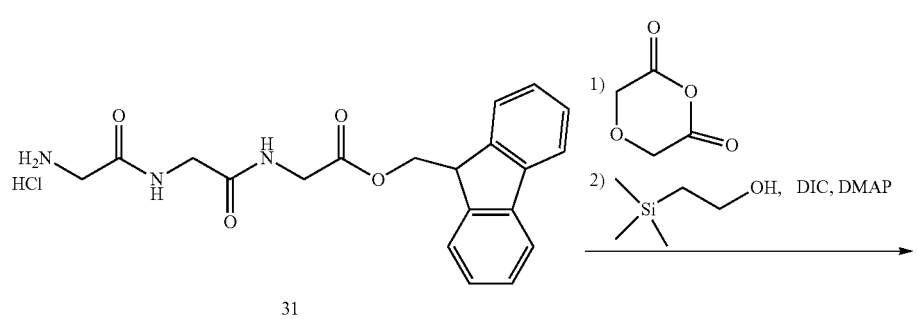
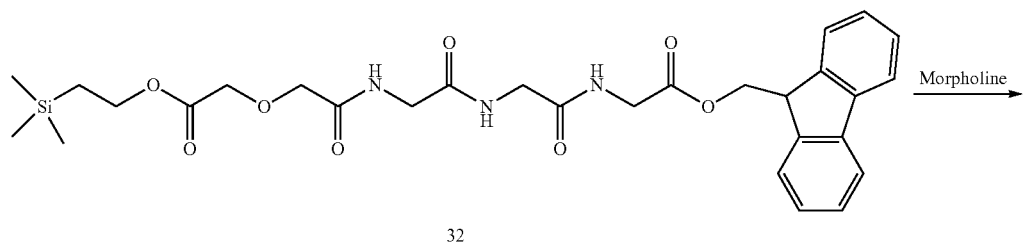
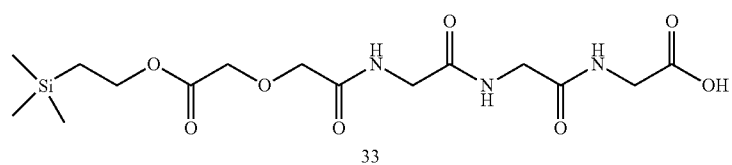

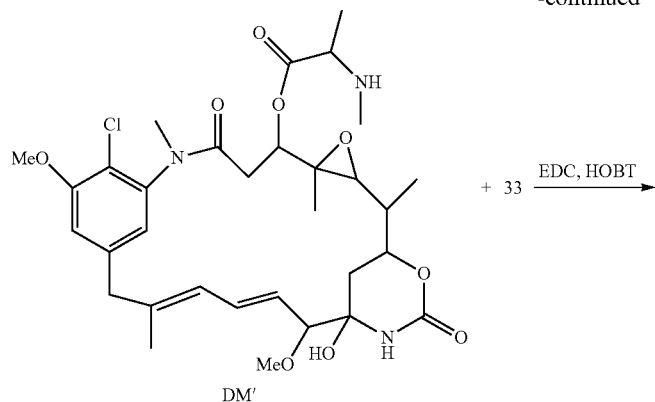

DM'

+ 33 →(EDC, HOBT)

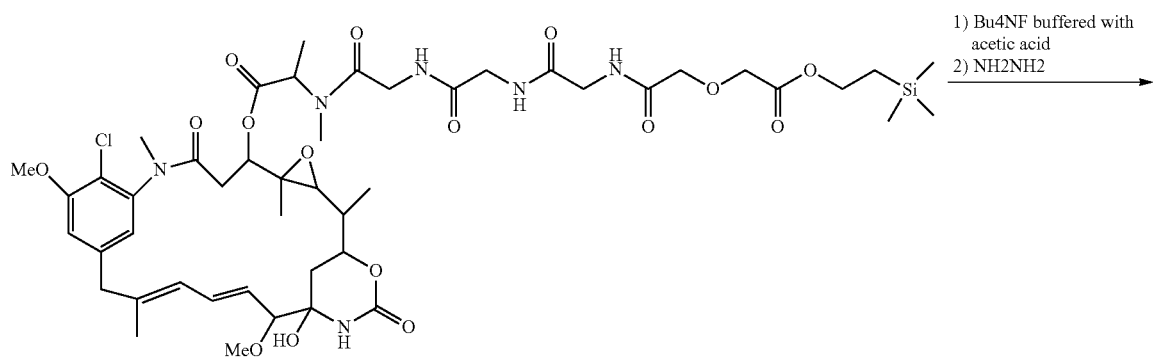

34

1) Bu4NF buffered with acetic acid
2) NH2NH2

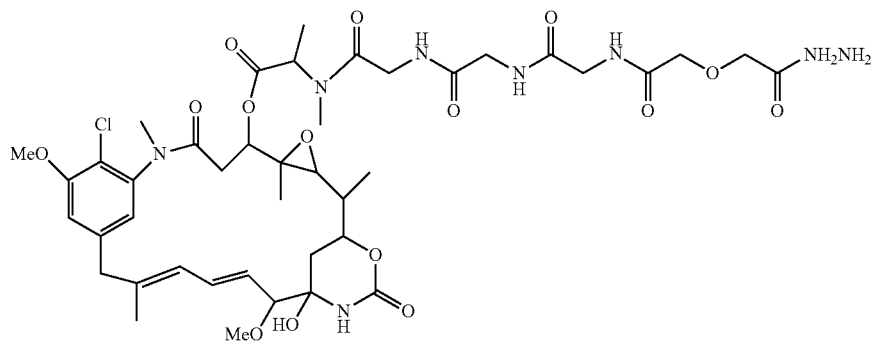

35

Boc protected H-Gly-Gly-Gly-OH (compound 8) can be protected by reaction with a 9-Fluorenemethanol DIC coupling agent and dimethylaminopyridine (DMAP). The resulting compound 30 can be Boc deprotected with trifluoroacetic acid to give compound 31, which can the react with 1,4-Dioxane-2,6-dione followed by protection reaction with trimethylsilylethanol in the presence of DIC and DMAP to yield compound 32. Compound 32 can then be treated with morpholine to deprotect the 9-Fluorenemethane ester to give compound 33. DM' can then be coupled to compound 33 with EDC coupling agent and HOBT to afford compound 34. The trimethyl silylethane ester of compound 34 can be removed by treatment with tetrabutyl ammonium fluoride, followed by reaction with N-hydroxy succinimide to activate the carboxylic acid group and then with hydrazine to give desired compound 35.

The method can be generalized by replacing Boc-Gly-Gly-Gly-OH with a Boc-protected amino acid or peptide of choice. The 1,4-Dioxane-2,6-dione can also be replaced by a different cyclic anhydride or with a mono trimethylsilylethane protected diacid to give other compounds of the present invention having other spacers between the DM' and the peptide moieties.

Example 16
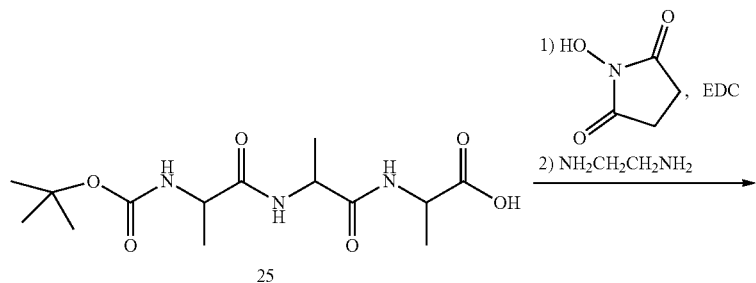
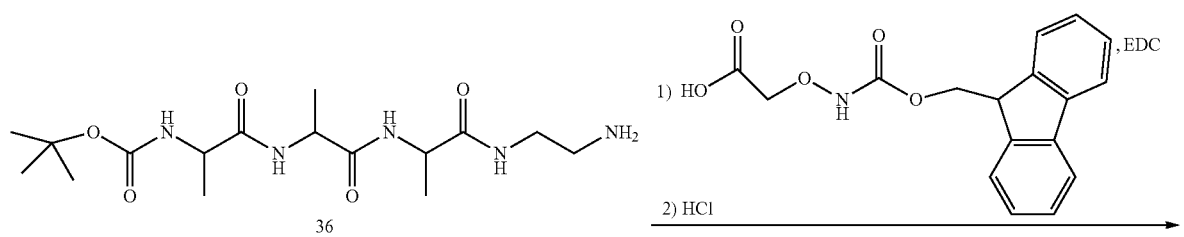
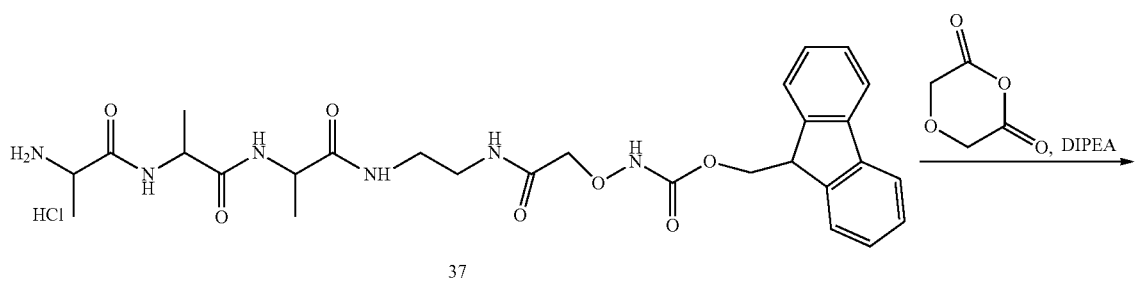
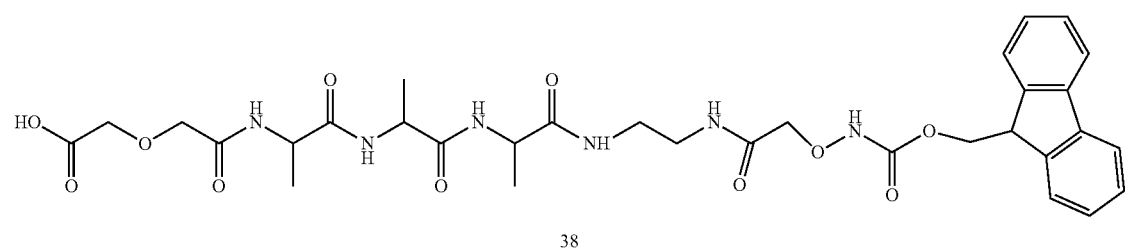
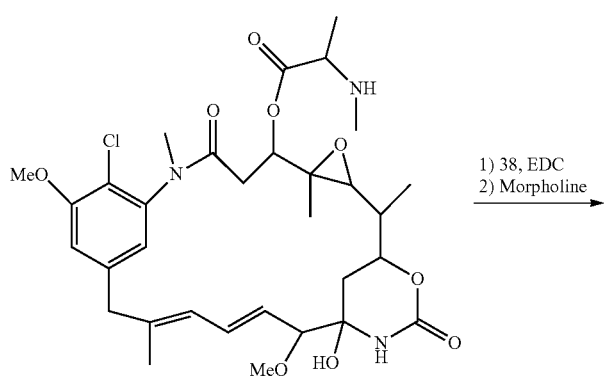

-continued

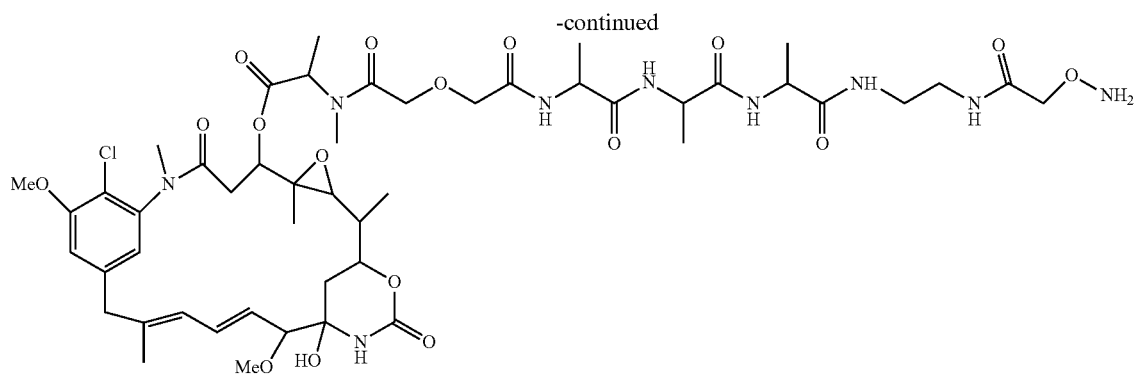

39

Boc protected Ala-Ala-Ala-OH (compound 25) can be activated by reaction with N-hydroxysuccinimide (NHS) and EDC, followed by reaction with 1,2-diaminoethane to give compound 36. Compound 36 can be treated with FMoc-aminoxyacetic acid in the presence EDC coupling agent followed by Boc deprotection with dilute HCl. The resulting compound 37 can react with 1,4-Dioxane-2,6-dione to give compound 38. Coupling of DM' with compound 38 in the presence of EDC followed by hydroxyl amine deprotection with morpholine will give the final product, compound 39.

A similar method can be used with a Boc protected amino acid or a Boc protected peptide to generate compounds of the present invention with different peptide side chains. The 1,4-Dioxane-2,6-dione can also be replaced by a different cyclic anhydride or with a mono protected diacid to give other spacers between the DM' and peptide moieties.

Example 17

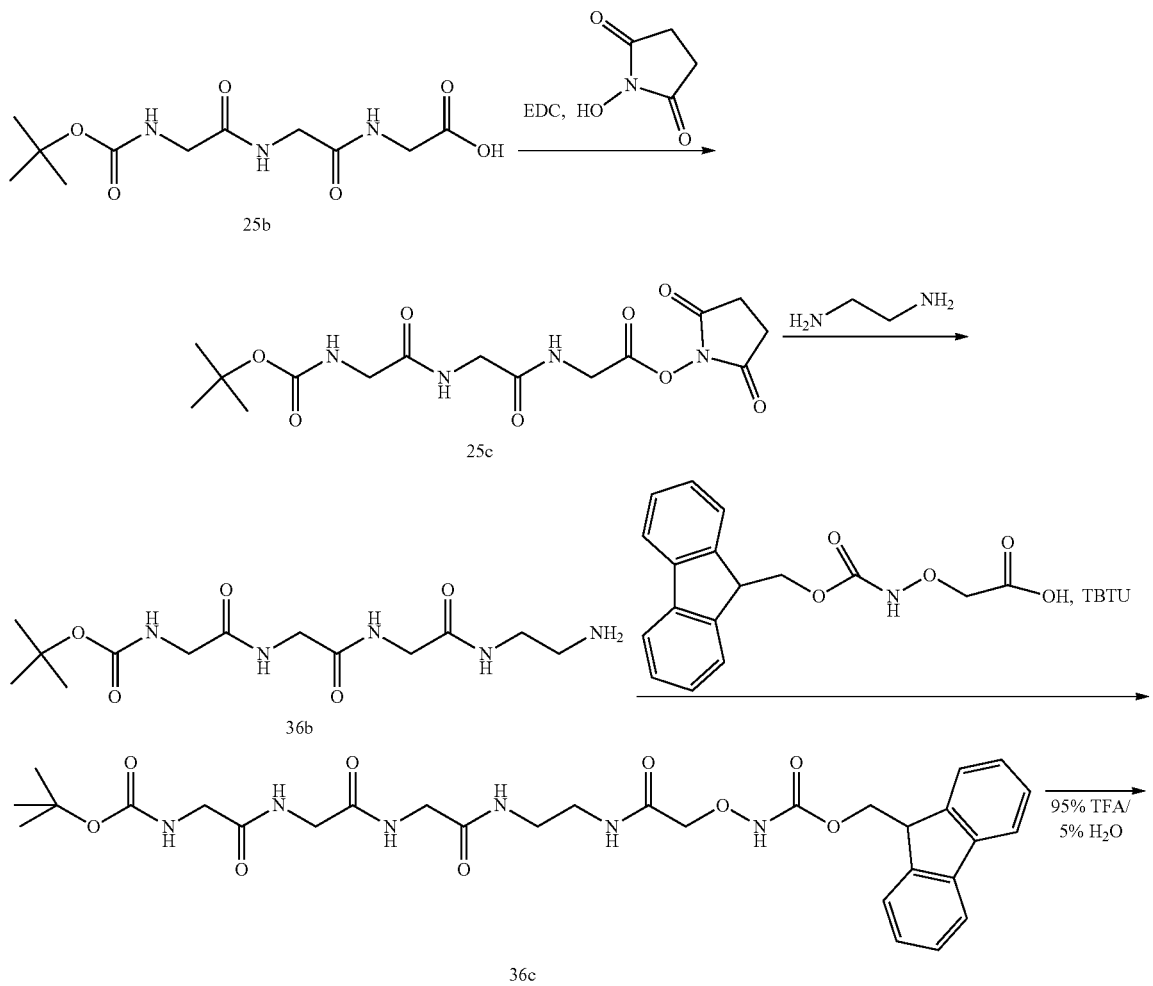

181
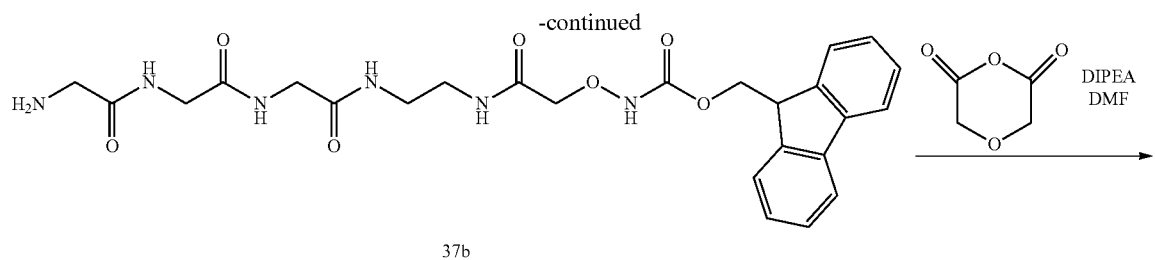
37b
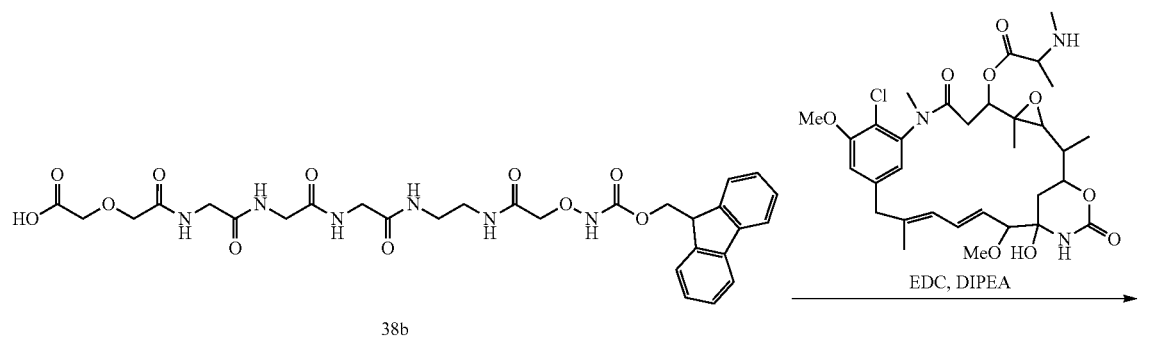
38b
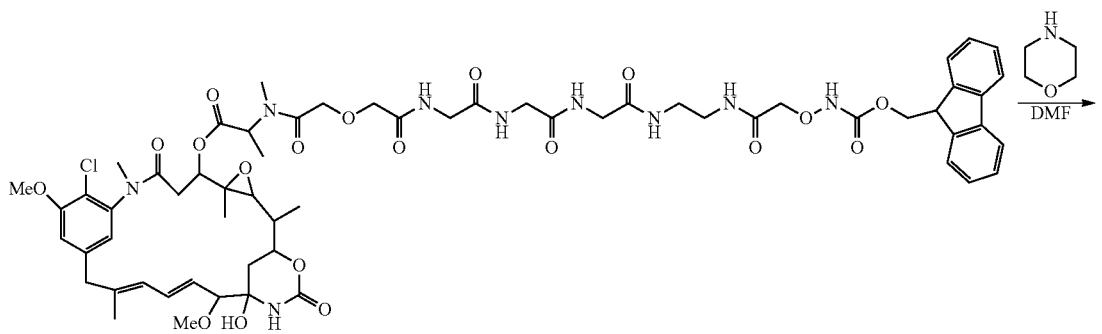
38c
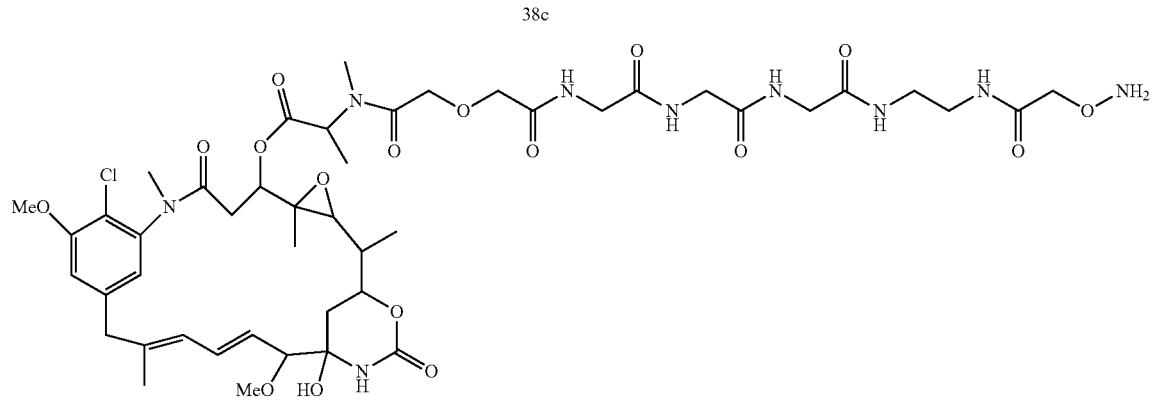
39b
Synthesis of Compound 36b
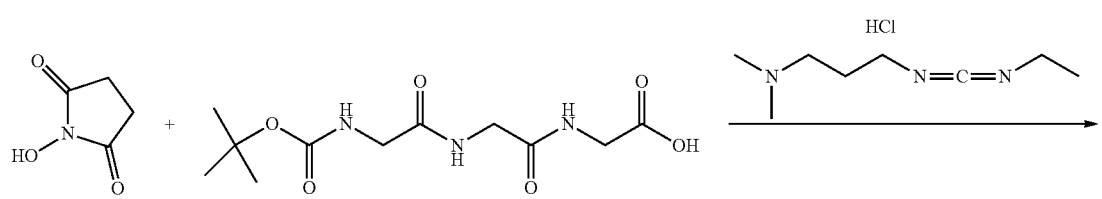

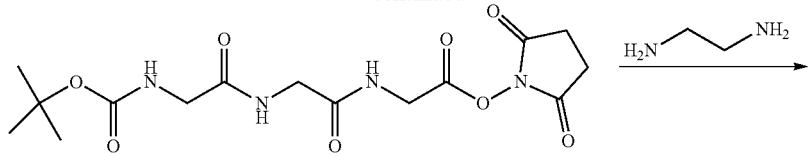

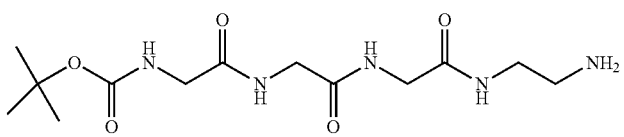

Boc-Gly3-OH (25b, 6 g, 20.7 mmol) was dissolved in DMF (40 mL) to which was added N-hydroxysuccinimide (2.4 g, 20.7 mmol) and EDC (4 g, 20.7 mmol) in a flask containing a magnetic stir bar. The reaction was magnetically stirred for 1 hour then slowly poured into a magnetically stirred solution of ethylene diamine (8 g, 133 mmol) in DMF (20 mL) with vigorous magnetic stirring at room temperature. Diethyl ether (200 mL) was added to precipitate a solid. The flask was then vortexed and placed in a sonication bath for 15 min. The material was vacuum filtered then dried under vacuum at room temperature then dissolved in DMF (20 mL) and purified in three runs using approximately equal injection volumes on a 50 mm×220 mm load and lock C18 column with 220 nm detection eluting at 100 mL/min with deionized water containing 0.2% formic acid and an acetonitrile gradient of 5% acetonitrile for the first 5 min then a linear gradient of 5-95% acetonitrile from 5 to 32 min. Fractions containing pure desired product were combined, frozen and lyophilized to give 4.5 g (65% yield) of desired product 36b.

Synthesis of Compound 36c

Fmoc aminoxyacetic acid (187 mg, 0.60 mmol) was dissolved in anhydrous DMF (1 mL) to which was added TBTU (243 mg, 0.76 mmol) and DIPEA (95 µL, 0.54 mmol) and magnetically stirred for 3 min. A solution of Boc-Gly$_3$NH—(CH$_2$)$_2$—NH$_2$ (200 mg, 0.54 mmol) in anhydrous DMF (1 mL) was then added with magnetic stirring. After 1 h the reaction was directly purified on a 27 mm×220 mm load and lock C18 column 40 mL/min with 254 nm detection eluting with deionized water containing 0.2% formic acid and an acetonitrile gradient of 10% acetonitrile for the first 5 min then a linear gradient of 10%-95% acetonitrile from 5 to 32 min. Fractions containing pure desired product were combined, frozen and lyophilized to give 60 mg (17% yield) of desired product 36c. $^1$H NMR (400 MHz, DMSO-d6) δ 1.37 (s, 9H), 3.15 (dt, J=10.0, 5.6 Hz, 4H), 3.58 (d, J=6.0 Hz, 2H), 3.67 (d, J=5.8 Hz, 2H), 3.74 (d, J=5.6 Hz, 2H), 4.16 (s, 2H), 4.26 (t, J=6.7 Hz, 1H), 4.43 (d, J=6.7 Hz, 2H), 7.01 (t, J=6.0 Hz, 1H), 7.33 (td, J=7.4, 1.2 Hz, 2H), 7.42 (t, J=7.4 Hz, 2H), 7.68 (d, J=7.4 Hz, 2H), 7.85 (d, J=6.0 Hz, 1H), 7.89 (d, J=7.5 Hz, 2H), 7.97 (d, J=5.7 Hz, 1H), 8.05 (t, J=5.6 Hz, 1H), 8.10 (t, J=6.0 Hz, 1H). HRMS calcd. 649.2592, found 649.2588.

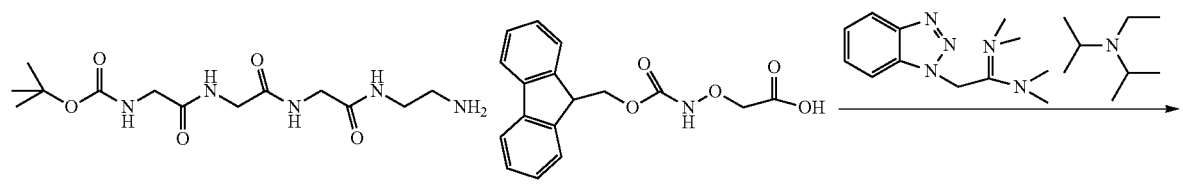

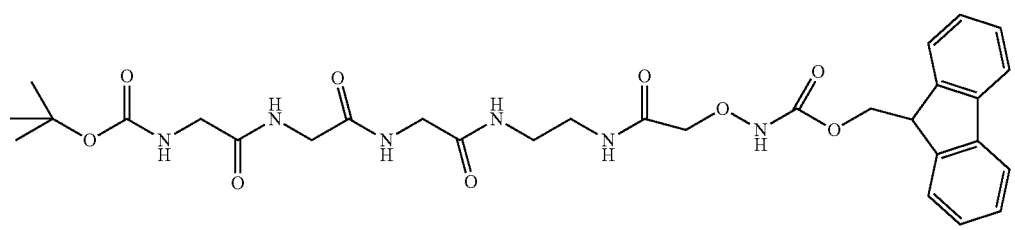

Synthesis of Compound 37b

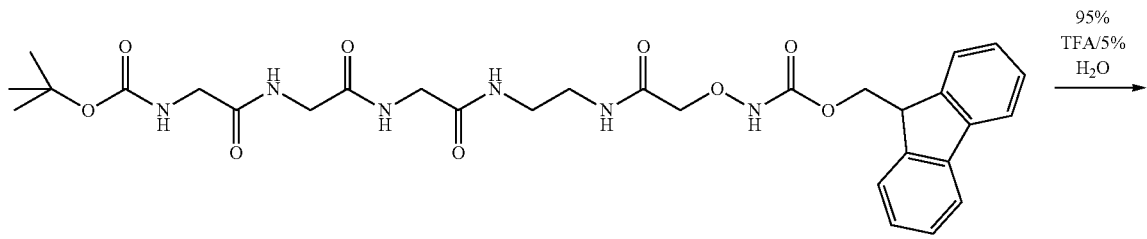

A 25 mL round bottom flask was charged with Boc-Gly₃-NH(CH₂)₂NHCOCH₂—O—NH-FMoc (76 mg, 0.122 mmol) and dissolved in a solution of 95/5 trifluoroacetic acid in water (10 mL). The reaction was magnetically stirred at room temperature for 1 hour. The reaction volume was reduced in vacuo and the crude residue was redissolved in a 1:1 mixture of methylene chloride and toluene (10 mL) then concentrated in vacuo. The coevaporation was repeated three times and the resulting product (37b) was used without further purification. MS (m+H⁺) found: 527.4, calcd. 527.2; (m-1).

Sythesis of Compound 38b

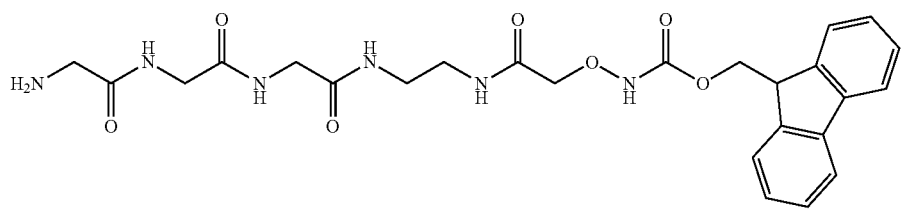

A 10 mL round bottom flask was charged with the t-butyl deprotected H-Gly₃-NH(CH₂)₂NHCOCH₂ONH-Fmoc (64 mg, 0.122 mmol) and DMF (3 mL). The solution was stirred as diglycolic anhydride (15.52 mg, 0.134 mmol) and N,N-diisopropylethylamine (0.042 mL, 0.243 mmol) were sequentially added. The flask was equipped with a septum and magnetically stirred at room temperature for 1 hour. The desired product was isolated by semi-preparative C18 HPLC eluting with deionized water containing 0.1% formic acid and a linear gradient of acetonitrile 5-95% over 25 min. Product containing fractions were combined and concentrated in vacuo to give 40 mg (0.062 mmol, 51.2% yield) of the desired product (38b) as a white residue. MS (m+H+) found: 643.4, calcd. 643.2; (m-1) found: 641.2, calculated: 641.2.

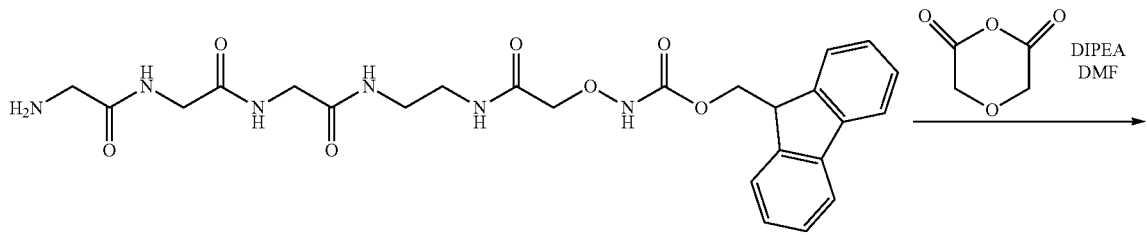

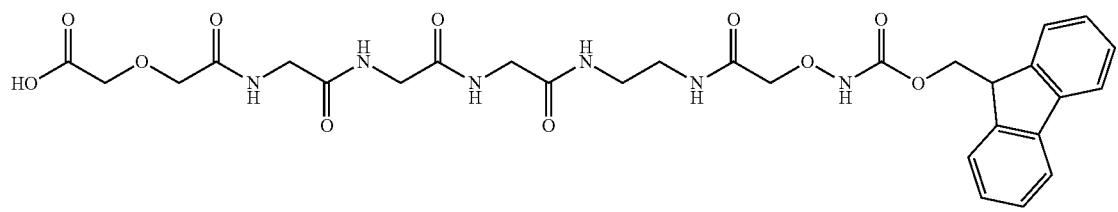

Synthesis of Compound 38c

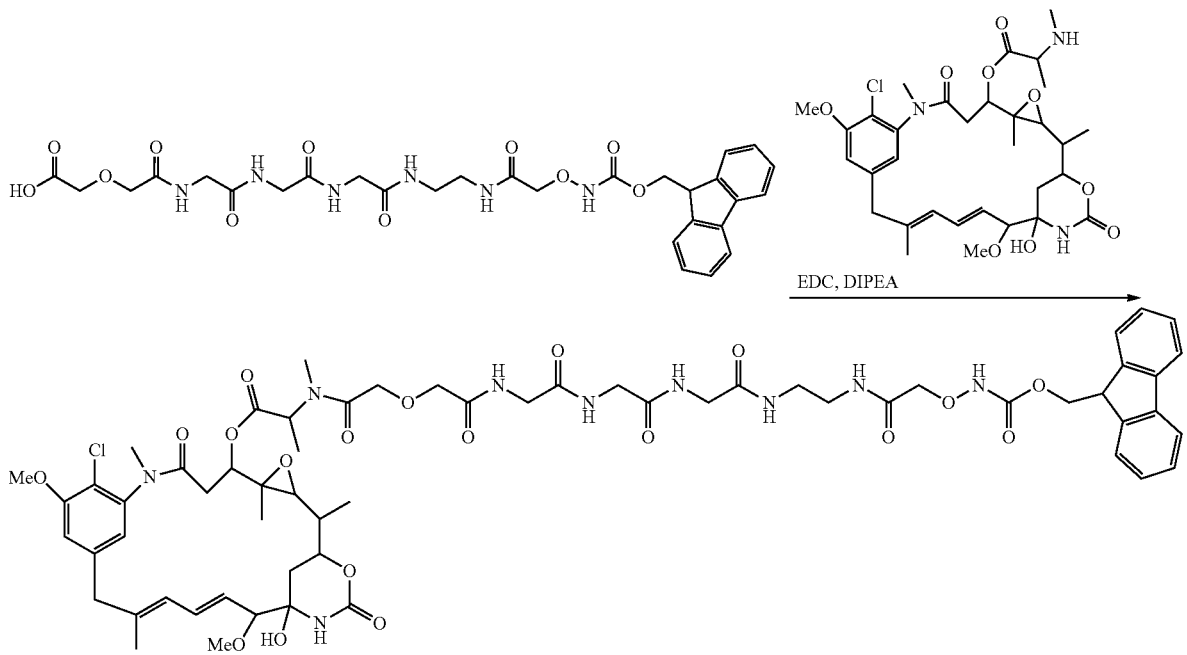

A 10 mL round bottom flask was charged with a solution of May-NMA (5.06 mg, 7.78 µmol) in ethyl acetate (1.500 mL). N-(3-Dimethylaminopropyl)-N'-ethylcarbodiimide hydrochloride (EDC, 3.73 mg, 0.019 mmol) and N,N-diisopropylethylamine (3.39 µl, 0.019 mmol) were then added followed by a solution of HOCOCH$_2$OCH$_2$CO-Gly$_3$NH(CH$_2$)$_2$NHCOCH$_2$ONH-FMoc (10 mg, 0.016 mmol) in N,N-dimethylformamide (1.5 mL). The reaction was stirred for 1 hour at room temperature. The reaction volume was reduced by half in vacuo and the product was isolated by semi-preparative C18 HPLC eluting with deionized water containing 0.1% formic acid and a linear gradient of acetonitrile 5-95% over 25 min. Product containing fractions were combined, frozen and lyophilized to give desired product (38c) 1.4 mg (13% yield) as a white solid. MS (m+Na+) found: 1296.7, calcd: 1296.5.

Synthesis of Compound 39b

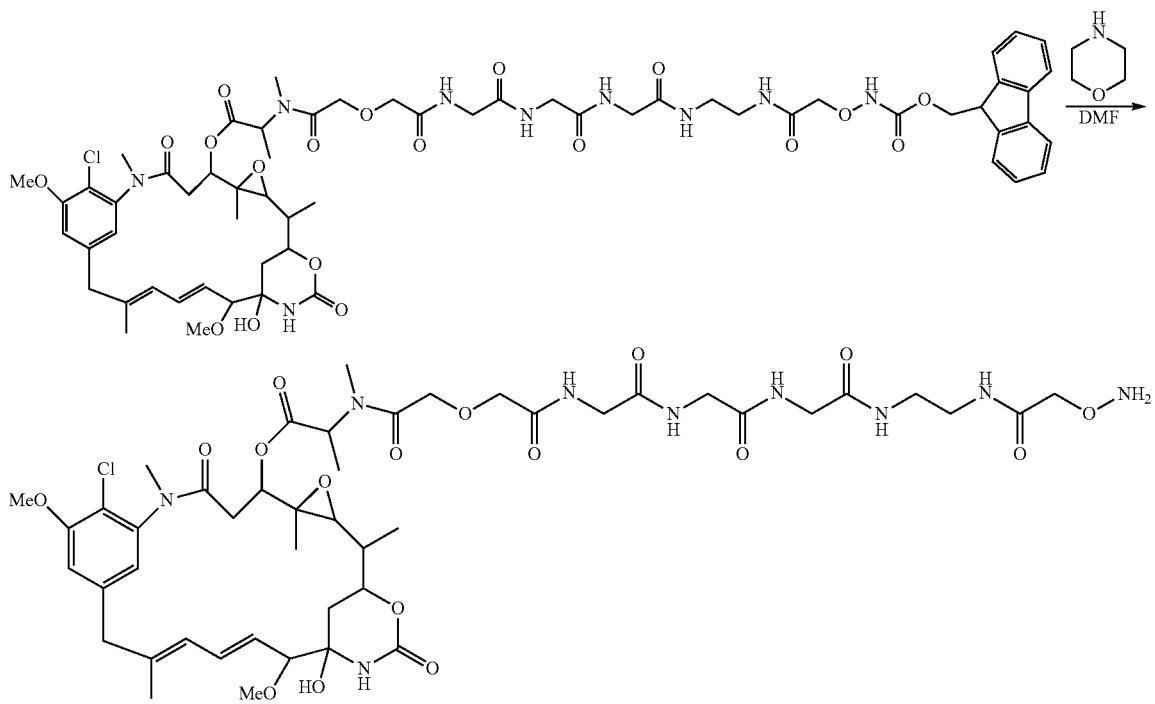

May-NMA-COCH₂OCH₂CO-Gly₃NH(CH₂)₂NHCH₂ONH-Fmoc (1.4 mg, 1.098 μmol) was dissolved in N,N-dimethylformamide (1.5 mL) and transferred to a 3 mL glass vial equipped with a stir bar. The solution was stirred as 20% v/v morpholine (300 μL, 3.44 mmol) was added. The reaction proceeded with stirring at room temperature until determined complete. The crude reaction mixture was purified by semi-preparative C18 HPLC over 3 injections. Product containing fractions were combined, transferred to a scintillation vial, frozen in a bath of dry ice and acetone and lyophilized to give 1.1 mg (95% yield) of desired product (39b). MS (m+Na+) found: 1074.7, calculated: 1074.4; high-resolution MS (m+H)⁺ found: 1052.4331, calculated: 1052.4338; (m+Cl−) found: 1086.5, calculated: 1086.4.

Example 18

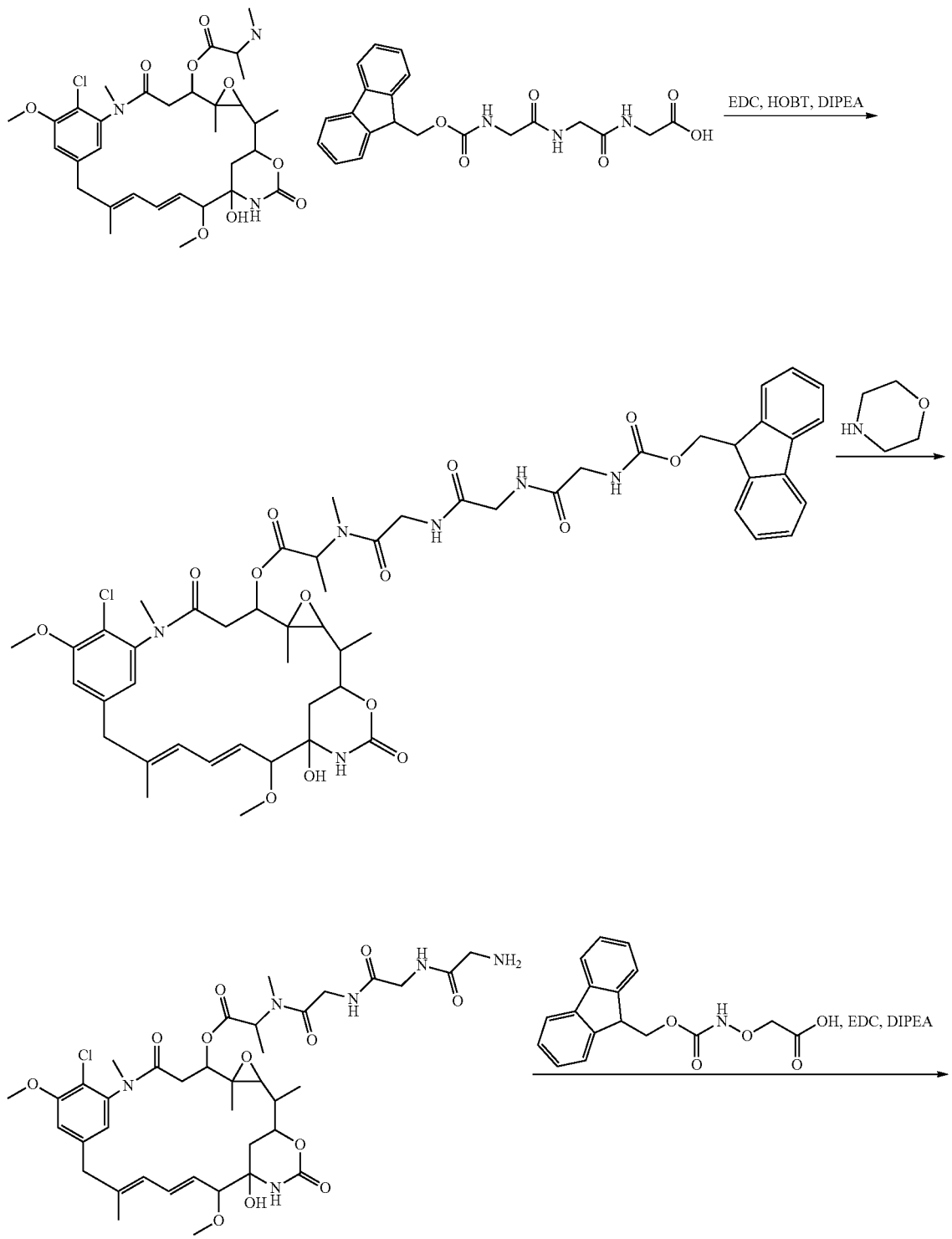

191 192
-continued
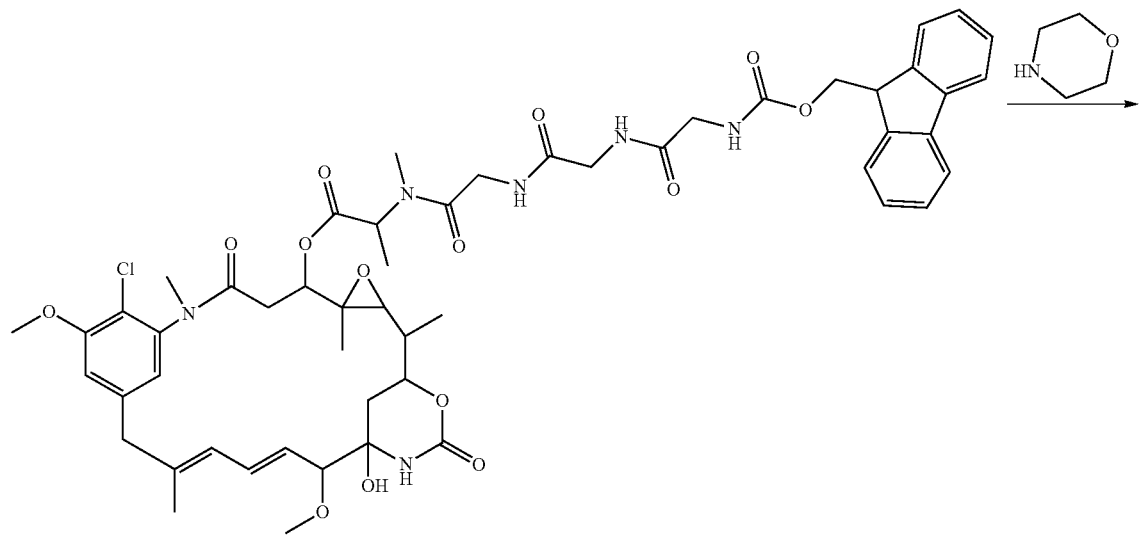
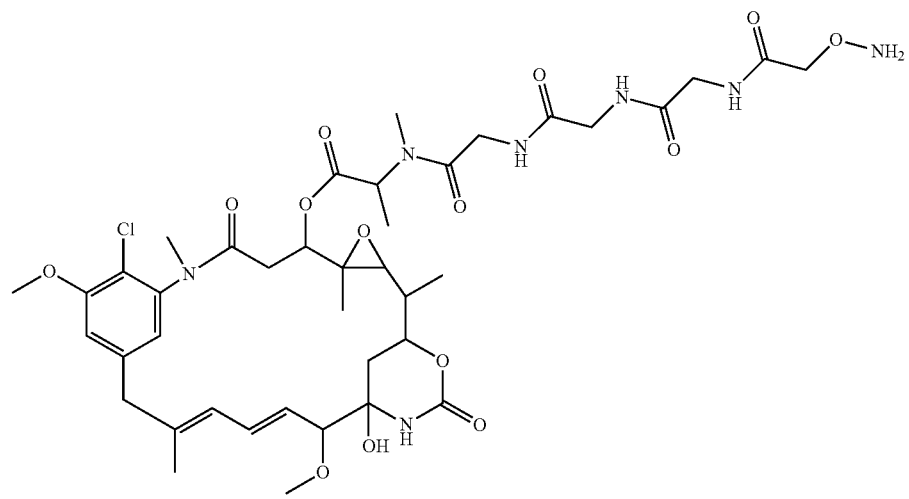
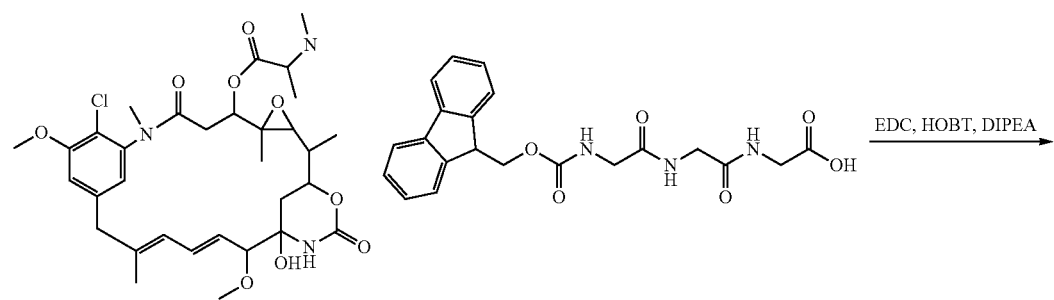

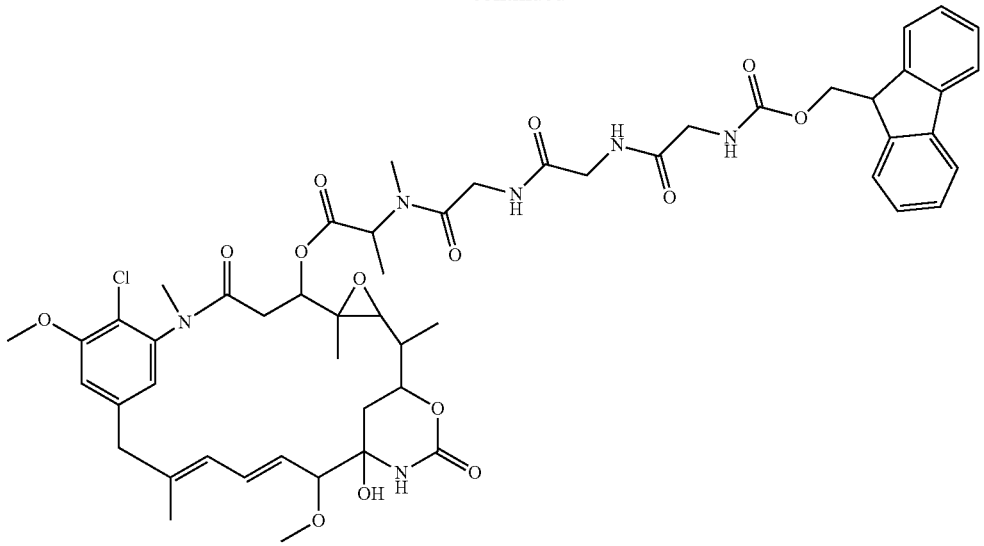 [SMILES: COc1cc2cc(c1Cl)N(C)C(=O)CC(OC(=O)C(C)N(C)C(=O)CNC(=O)CNC(=O)CNC(=O)OCC1c3ccccc3-c3ccccc31)C1(C)OC1C(C)C1CC(O)(NC(=O)O1)C(OC)/C=C/C=C(\C)C2]

Fmoc-Gly₃-MayNMA

A 100 mL flask was charged with a solution of MayNMA (200 mg, 0.308 mmol) in ethyl acetate (19 mL). The reaction flask was concentrated in vacuo to remove EtOAC. The material was re-dissolved in DMSO (10 mL), treated with FMoc-Gly₃-OH (165 mg, 0.400 mmol), HOBT (12.25 mg, 0.080 mmol), EDC (77 mg, 0.400 mmol) and DIPEA (53.7 µL, 0.308 mmol). The reaction was allowed to proceed at room temperature under argon. After 1 hour the reaction was purified using a Combiflash Rf 200i using C18 high performance gold 30 g column, at 35 mL/min. Eluting with deionized water containing 0.1% formic acid and an acetonitrile gradient of 5-95% over 20 min. Fractions containing desired product were combined, frozen and lyophilized to give desired product 296 mg (93% yield). MS (M)⁺ found 1043.4, calcd.: 1043.4

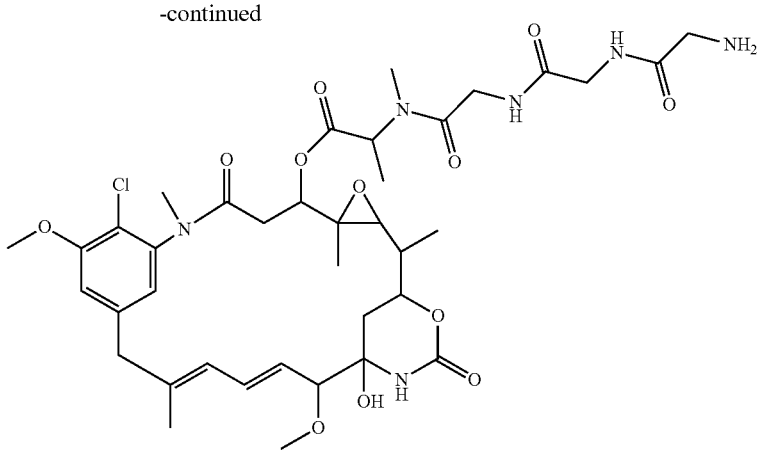

H-Gly₃-MayNMA

FMoc-Gly₃-MayNMA (37.7 mg, 0.036 mmol) was dissolved in 20% morpholine in DMSO (5 mL) and magnetically stirred for 1 hour. The reaction was purified using a Combiflash Rf 200i using C18 high performance gold 30 g column at 35 mL/min. Eluting with deionized water containing 0.1% formic acid with an acetonitrile gradient 2-95% over 25 min. Fractions containing desired product were combined, frozen and lyophilized to desired product 20 mg (75% yield). LRMS (M)⁺ found 821.40, calculated: 821.34

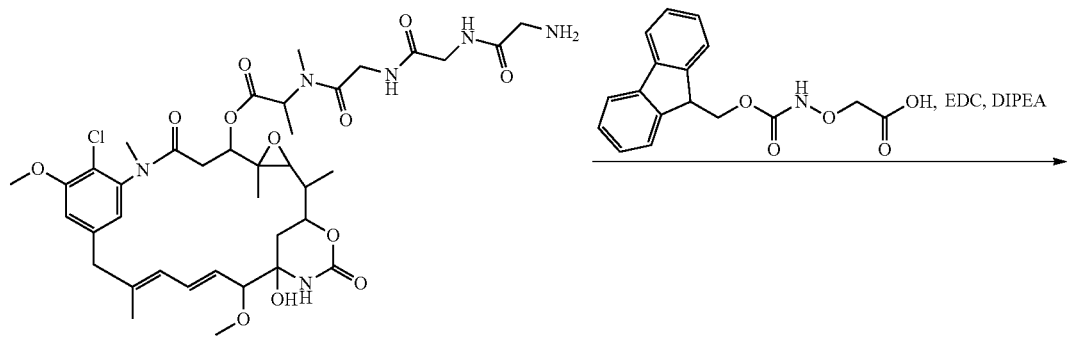

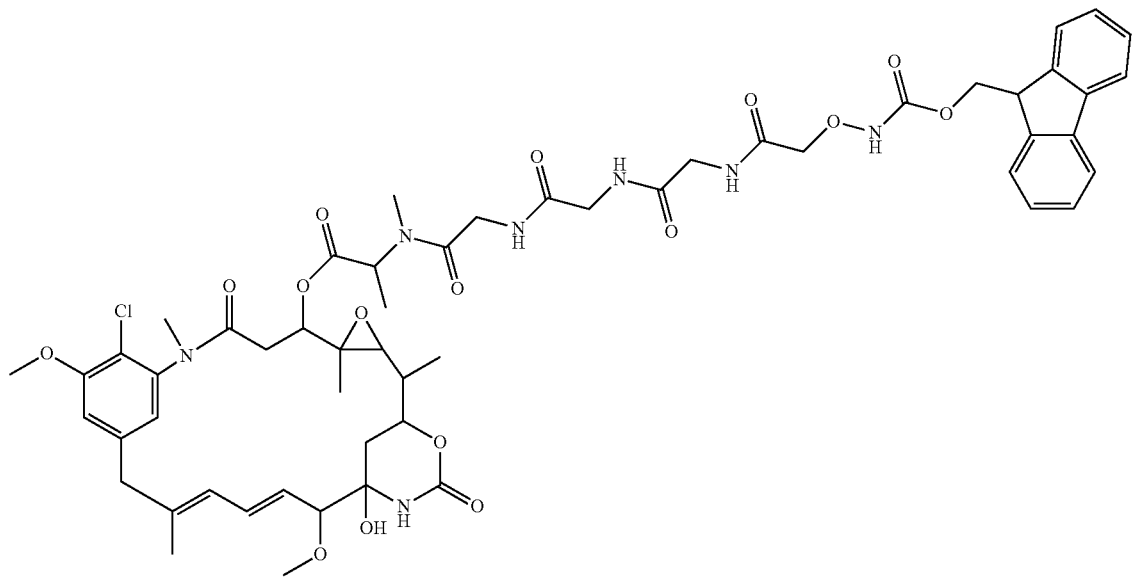

Fmoc-Aminoxy-Gly$_3$-MayNMA

H-Gly$_3$-MayNMA (15 mg, 0.018 mmol) was dissolved in DMSO (2 mL), to which FMoc-aminoxyacetic acid (11.44 mg, 0.037 mmol), DIPEA (3.19 µL, 0.018 mmol) and EDC (7.0 mg, 0.037 mmol) were added. After 1 hour the crude material was purified by semi-preparative C18 HPLC using a XB-C18 21.2×150 mm, 5 µm column with a flow rate of 21.2 mL/min. Eluting with deionized water containing 0.1% formic acid and 5% acetonitrile for 3 min then a linear gradient of 5%-95% acetonitrile from 5-25 min. Fractions containing desired product were combined, frozen and lyophilized to give 2 mg (8% yield) of desired product. MS (M+Na)$^+$ found 1138.6, calculated: 1138.4

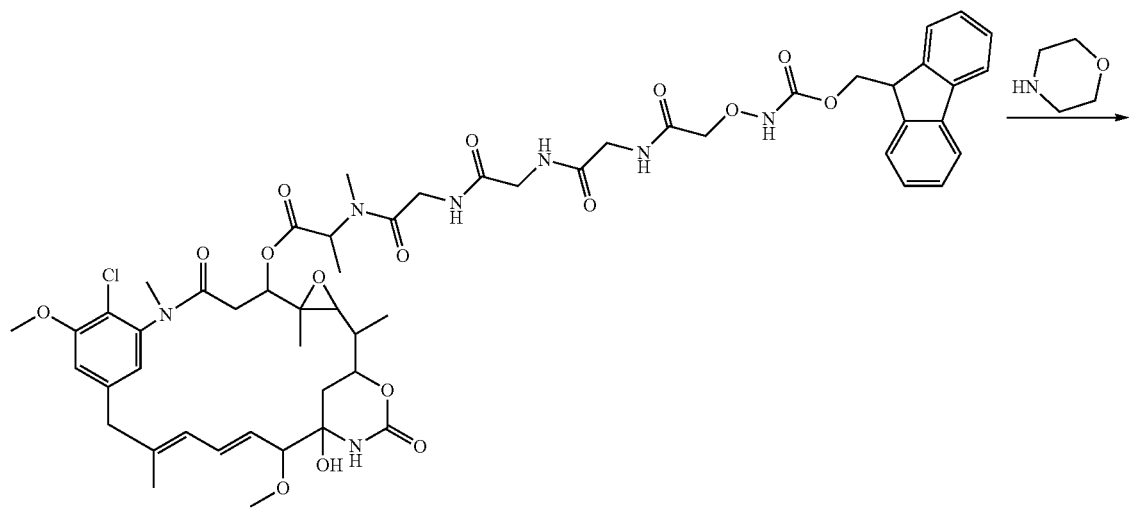

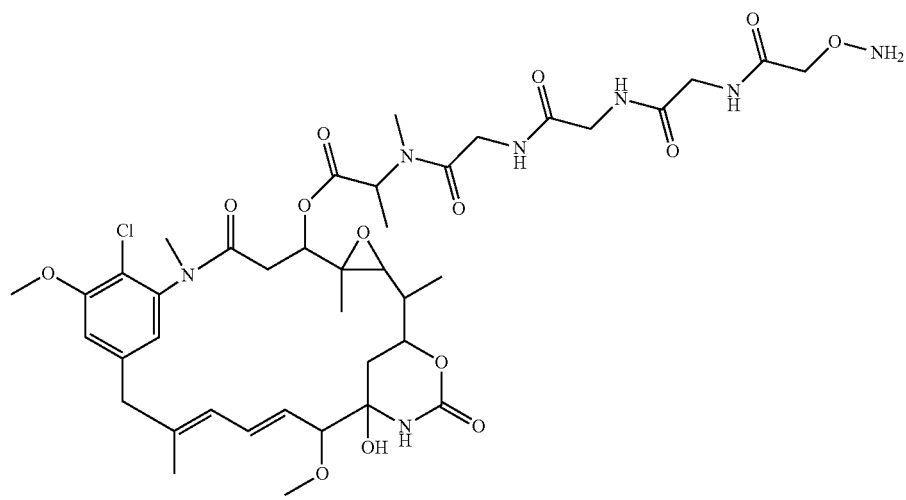

Aminoxy-Gly₃-MayNMA

FMoc-aminoxy-Gly₃-MayNMA (2 mg, 18 μmol) was treated with a solution of 20% morpholine in DMSO (1 mL) with magnetic stirring at room temperature for 2 hours. The reaction was purified by semi-preparative C18 HPLC using a XB-C18 21.2×150 mm, 5 μm column with a flow rate of 21.2 mL/min. Eluting with deionized water containing 0.1% formic acid and 5% acetonitrile for 5 min then a linear gradient of acetonitrile 5%-95% from 5 min-25 min. Fractions containing desired product was immediately collected, frozen and lyophilized to yield aminoxy-Gly₃-MayNMA (0.2 mg, 0.224 μmol). LRMS (M+Na)⁺ found 916.60, calcd: 916.36; HRMS (M+Na)⁺ found: 916.3466; calcd: 916.3466.

Example 19

FMoc Protected Aminoxy MayNMA

A 100 mL flask was charged with MayNMA (150 mg, 0.231 mmol) in ethyl acetate (35 mL). The reaction flask was concentrated in vacuo to remove EtOAC. The material was re-dissolved in DMF (5 mL), treated with FMoc-aminoxy-acetic acid (72.3 mg, 0.231 mmol) followed by EDC (44.2 mg, 0.231 mmol) with magnetic stirring. The reaction was allowed to proceed under argon at room temperature for 4 hours then purified by semi-preparative C18 HPLC using a XB-C18 21.2×150 mm, 5 μm column with a flow rate of 21.2 mL/min. Eluting with deionized water containing 0.1% formic acid and an acetonitrile gradient of 5% for the first 5 min then 5%-95% from 5 min to 25. Fractions containing desired product were combined frozen and lyophilized to give 24.2 mg (11% yield) of desired product. LRMS (M)⁺ found 945.35, calculated: 945.36

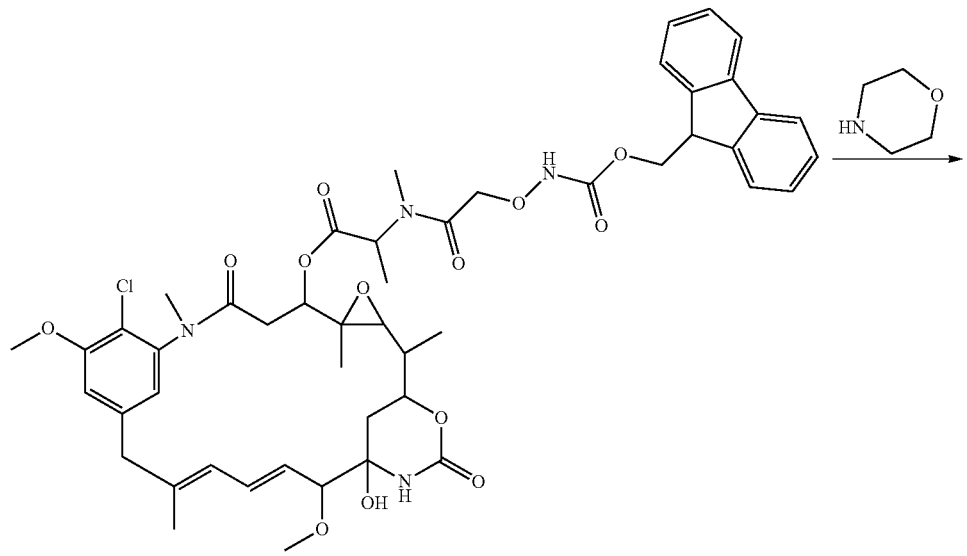

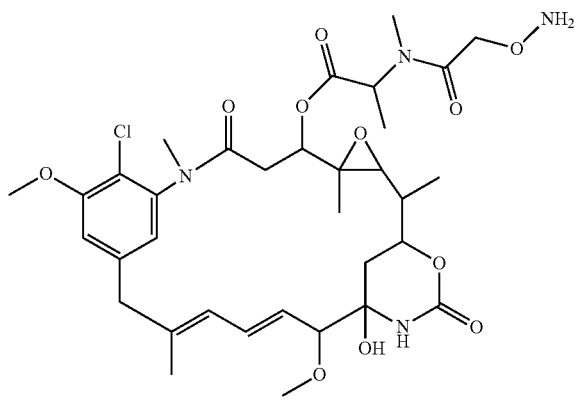

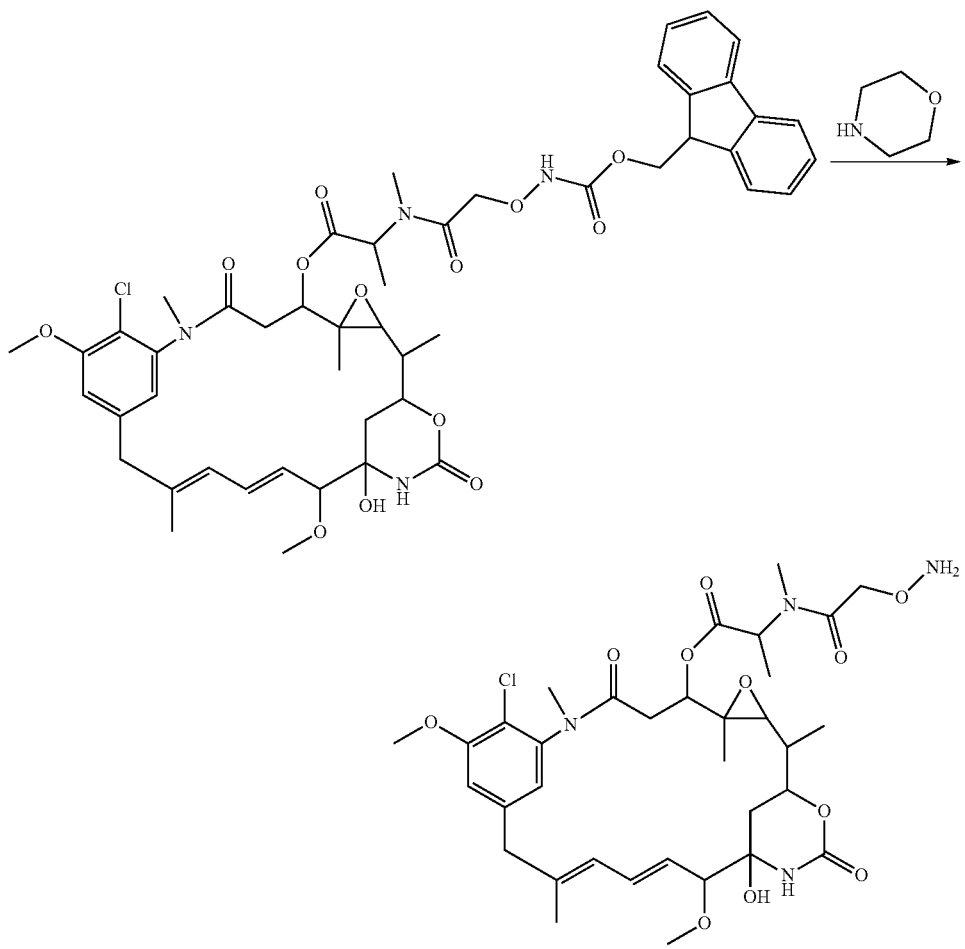

Aminoxy-MayNMA

FMoc protected aminoxy MayNMA (24.2 mg, 0.026 mmol) was treated 20% morpholine in DMF (2 mL). After 1 hour with magnetic stirring the reaction was purified by semi-preparative C18 HPLC using a XB-C18 21.2×150 mm, 5 μm column with a flow rate of 21.2 mL/min. Eluting with deionized water containing 0.1% formic acid and an acetonitrile gradient of 5% for 5 min then a linear gradient of 5%-95% over 25 min. Fractions containing desired product were combined, frozen and lyophilized to give 10 mg (54.0% yield) of desired product. MS (M)⁺ found: 723.3, calculated: 723.3; high-resolution MS found: 723.2995; calculated: 723.3003.

Example 20. Antitumor Activity of Single-Dose SeriMab Site-Specific huMOV19NTS #2-Linker1-Compound a Against NCI-H2110 NSCLC Xenografts in Female SCID Mice Female CB.17 SCID mice, 6 weeks old, were received from Charles River Laboratories. Mice were inoculated with 1×10$^7$ NCI-H2110 tumor cells suspended in 0.1 ml 50% matrigel/serum free medium by subcutaneous injection in the right flank. When tumor volumes reached approximately 100 mm$^3$ (day 7 post inoculation), animals were randomized based on tumor volume into 4 groups of 6 mice each. Mice received a single IV administration of vehicle control (0.2 ml/mouse) or huMOV19NTS #2-Linker1-Compound A ([6], scheme 1) conjugate at 10, 25 or 50 μg/kg based on compound A concentration on day 1 (day 8 post inoculation).

Tumor size was measured twice to three times weekly in three dimensions using a caliper. The tumor volume was expressed in mm$^3$ using the formula V=Length×Width×Height×½. A mouse was considered to have a partial regression (PR) when tumor volume was reduced by 50% or greater, complete tumor regression (CR) when no palpable tumor could be detected. Tumor volume was determined by StudyLog software.

Tumor growth inhibition (T/C Value) was determined using the following formula:

$T/C(\%)$=Median tumor volume of the treated/Median tumor volume of the control×100.

Tumor volume was determined simultaneously for treated (T) and the vehicle control (C) groups when tumor volume of the vehicle control reached predetermined size of 1000 mm$^3$. The daily median tumor volume of each treated group was determined, including tumor-free mice (0 mm$^3$). According to NCI standards, a T/C<42% is the minimum level of anti-tumor activity. A T/C<10% is considered a high anti-tumor activity level.

Figure 13:
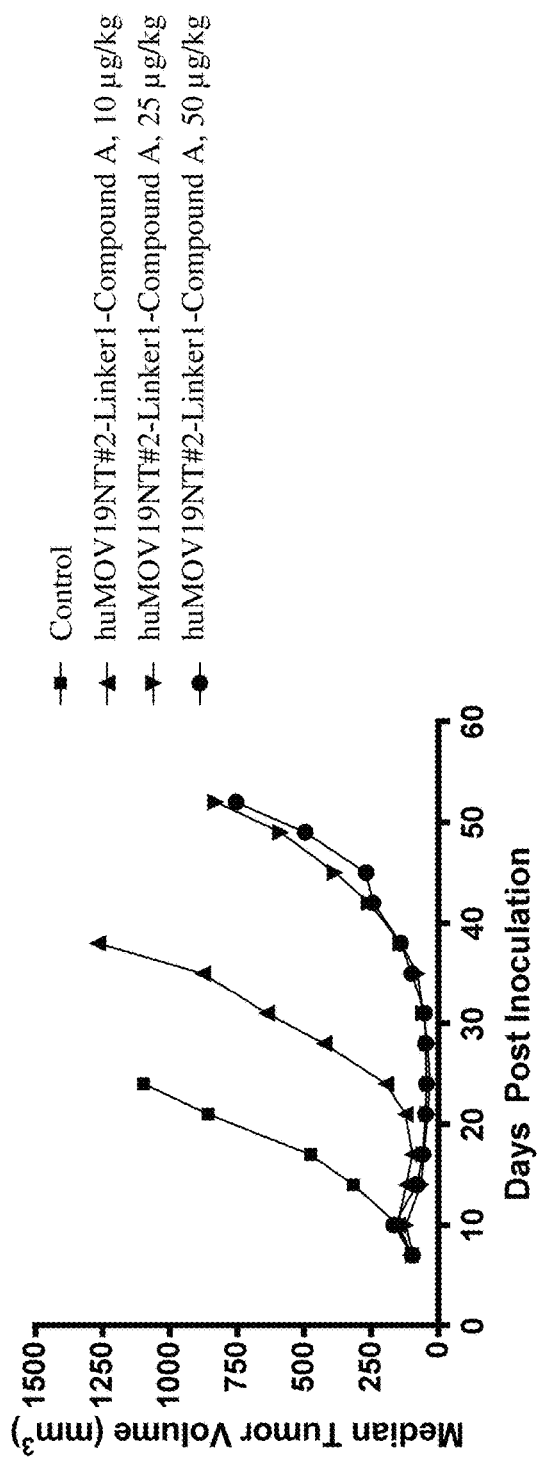
FIG. 13 shows the in vivo efficacy for huMOV19-NTS #2-Linker1-Compound A conjugate in NCI-H2110 bearing SCID mice.
Figure 14A:
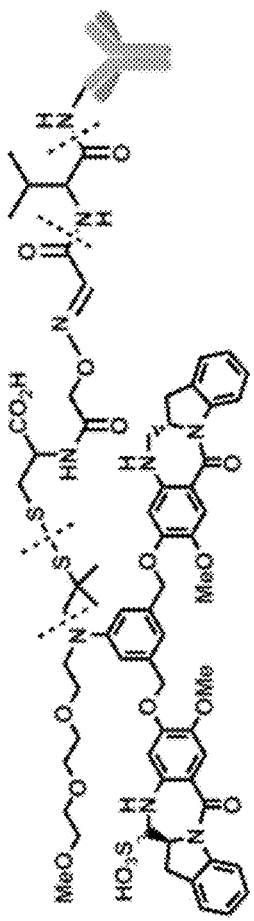
FIG. 14A shows the structure of SeriMab-sDGN462 conjugate with a disulfide linker. Dotted lines indicate the location of cleavage sites which lead to the observed target cell catabolites.
Figure 14B:
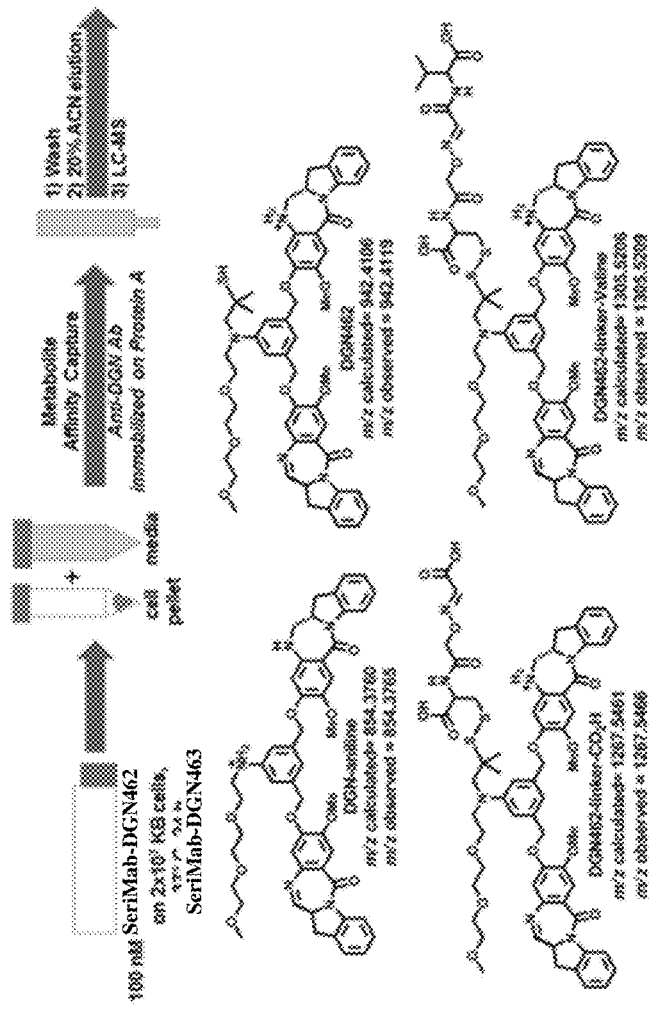
FIG. 14B shows scheme for incubation, purification, and isolation of catabolites from SeriMab-sDGN462 conjugate formed in KB cervical cancer cells in vitro. The four catabolites identified by LC-MS are shown along with the calculated and observed m/z ratios.
Figure 15A:
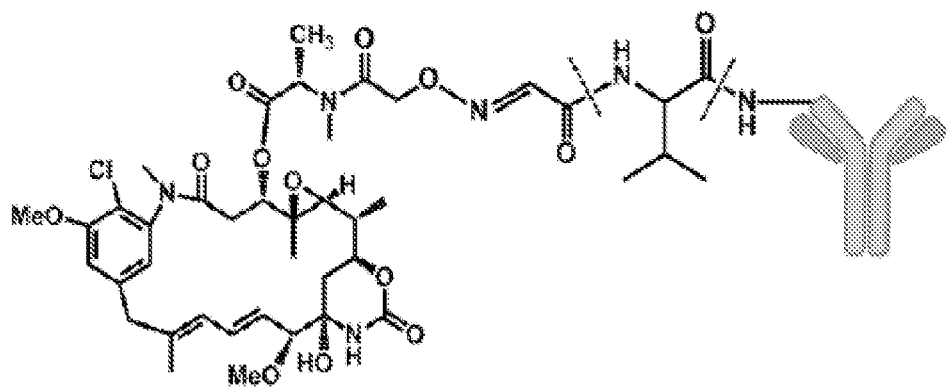
FIG. 15A shows the structure of SeriMab-May conjugate with a non-cleavable linker. Dotted lines indicate the location of cleavage sites which lead to the observed target cell catabolites.
Figure 15B:
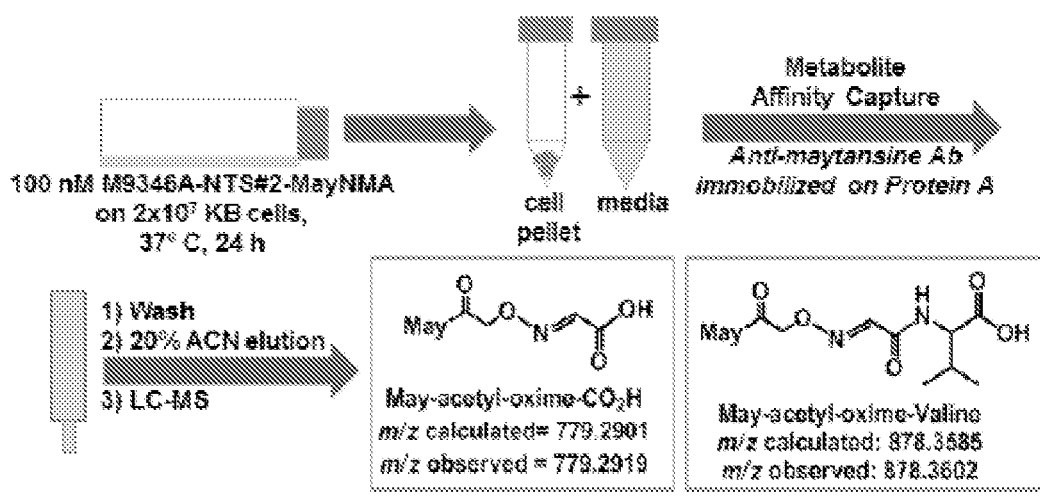
FIG. 15B shows scheme for incubation, purification, and isolation of catabolites from SeriMab-May conjugate formed in KB cervical cancer cells in vitro. The two catabolites identified by LC-MS are shown along with the calculated and observed m/z ratios.

As shown in FIG. 13, the conjugate is highly active at 25 μg/kg and 50 μg/kg doses.

Example 21. Catabolite Enrichment by Affinity Capture with Protein A Resin

KB cells expressing folate receptor α (FRα) were cultured in 5×T150 tissue culture plates. Saturating amount of FRα targeting huMOV19NTS #2-Linker1-Compound A (or SeriMab-sDGN462) conjugate was incubated with KB cells for 24 hours at 37° C. in a humidified incubator buffered with 5% $CO_2$. After 24 hours, the media containing cell-effluxed catabolites were harvested and pooled for the following assay.

Saturating amount of anti-indolinobenzodiazepine compound antibody was bound to a slurry of protein A resin by overnight incubation at 4° C. 1 ml of pre-bound protein A/anti-benzodizepine compound antibody complex was incubated with 25 ml of media on an end-to-end rotator for several hours. The resin was centrifuged gently at 1000 rpm, and the supernatant was decanted. The protein-A/anti-IGN antibody resin bound to IGN catabolites was washed with PBS (5×) to remove media components. The catabolites were released into organic phase by acetone extraction. The catabolites were vacuum-dried overnight until the organic solution was completely evaporated. The catabolites were reconstituted with 20% acetonitrile in water, and analyzed by LC-MS.

KB cells expressing folate receptor α (FRα) were cultured in 5×T150 tissue culture plates. Saturating amount of FRα targeting huMOV19-NTS #2-aminooxy-acetyl-MayNMA (also known as "SeriMab-May") conjugate was incubated with KB cells for 24 hours at 37° C. in a humidified incubator buffered with 5% $CO_2$. After 24 hours, the media containing cell-effluxed catabolites were harvested and pooled for the following assay.

Saturating amount of anti-maytansine antibody was bound to a slurry of protein A resin by overnight incubation at 4° C. 1 ml of pre-bound protein A/anti-maytansine antibody complex was incubated with 20 ml of media on an end-to-end rotator for several hours. The resin was centrifuged gently at 1000 rpm, and the supernatant was decanted. The protein-A/anti-maytansine antibody resin bound to maytansinoid catabolites was washed with PBS (5×) to remove media components. The catabolites were released into organic phase by acetone extraction. The catabolites were vacuum-dried overnight until the organic solution was completely evaporated. The catabolites were reconstituted with 20% acetonitrile in water, and analyzed by LC-MS.

MS Analysis

The drug distribution profile of the huMOV19-NTS #2 conjugates were characterized by intact mass analysis using Waters LCT ESI-TOF. Tryptic peptide mapping of the conjugate was performed by LC/MS/MS using Waters QTOF (samples were reduced, alkylated followed by Trypsin digestion). Cell catabolites were identified by UHPLC/MS/MS using Q-Exactive high resolution mass spec (Thermo). Extracted ion-chromatograms (XIC) were used to identify and characterize the target cell catabolites. All catabolite species containing the characteristic maysine (547 m/z) and DGN (286 m/z) mass signatures were identified.

Both SeriMab-sDGN462 and SeriMab-May conjugates generated catabolites effluxed from the target cell after 24 h processing. The terminal carboxylic acid containing DGN and maytansinoid metabolites are consistent with proteolysis of the N-terminal serine or adjacent valine residue on the antibody heavy chain. These catabolites are unique to SeriMab conjugation platform as the expected metabolites from cysteine or lysine conjugation would be zwitterionic in nature. sDGN462 conjugate generated additional catabolites consistent with disulfide cleavage (sDGN462) and self-immolation of the thiol group (DGN-aniline). These metabolites are also generated from lysine linked DGN462 conjugates.

Example 22. Bystander Activity

50 µl/well of conjugate were each diluted in RPMI-1640 (Life Technologies) supplemented with heat-inactivated 10% FBS (Life Technologies), 0.1 mg/ml gentamycin (Life Technologies) and βME (Life Technologies) in a 96-well plate (Falcon, round bottom) at concentrations of 1 e-10 M and 4 e-10 M in sextuplicate. Both 300.19 cells (mouse) expressing recombinant FOLR1(FR1 #14) or no expression vector (parental) were counted on a hemacytometer. 50 µl/ml of 1000 FR1 #14 cells/well were added to wells containing ADC or media only, 50 µl/ml of 2000 parental cells/well were added to wells containing ADC or media only and both FR1 #14 and parental cells were added together to wells containing ADC or media only. All plates were incubated in a 37° C. incubator with 5% $CO_2$ for 4 days. Total volume was 150 µl/well. After incubation, cell viability was analyzed by addition of 75 µl/well Cell Titer Glo (Promega) and allowed to develop for 30 min. Luminescence was read on a luminometer and background in wells containing media only was subtracted from all values. A bar graph of the average of each cell treatment was graphed using Graph Pad Prism.

Figure 16:
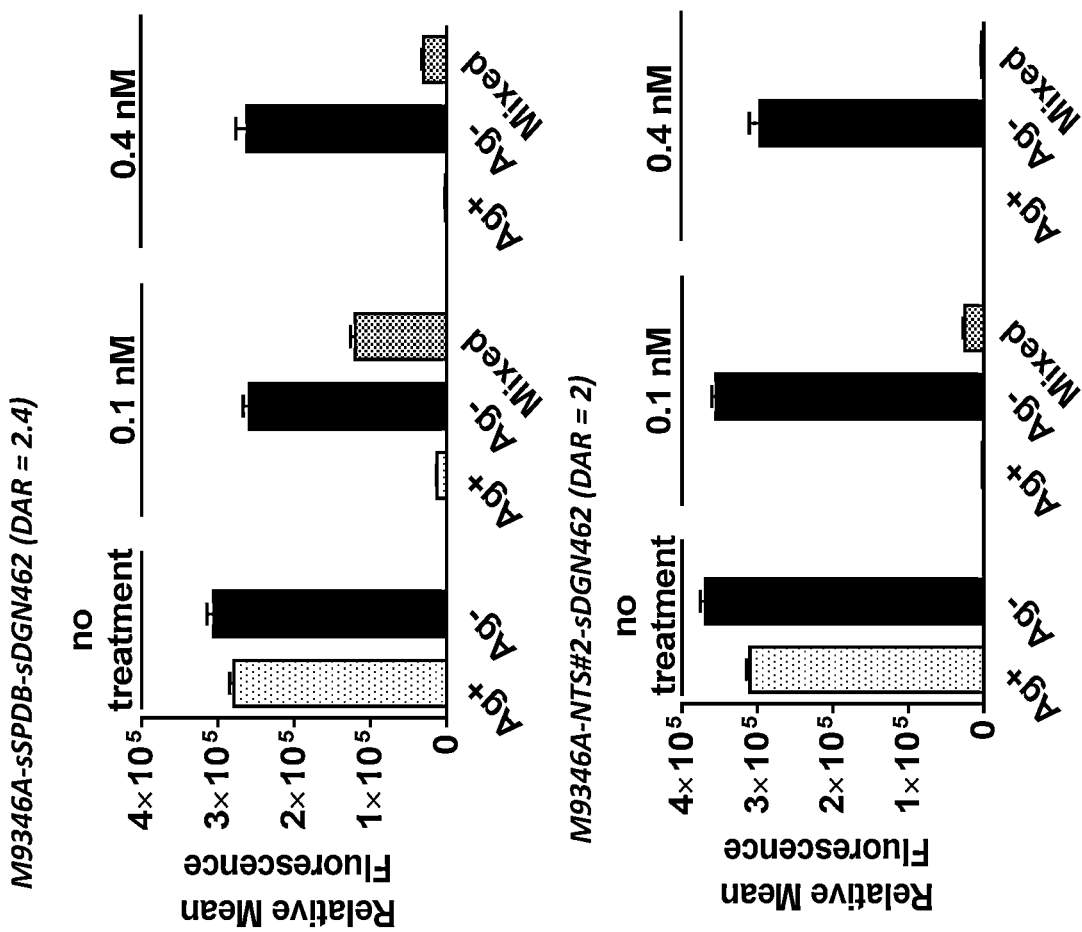
FIG. 16 shows the results of bystander killing assay for SeriMab-sDGN462 and the corresponding Lys-linked conjugated Ab-sSPDB-sDGN462.

As shown in FIG. 16, disulfide linked sDGN462 ADCs conjugated through either lysine or N-terminal serine show potent bystander killing of proximal antigen negative cells.

Figure 27:
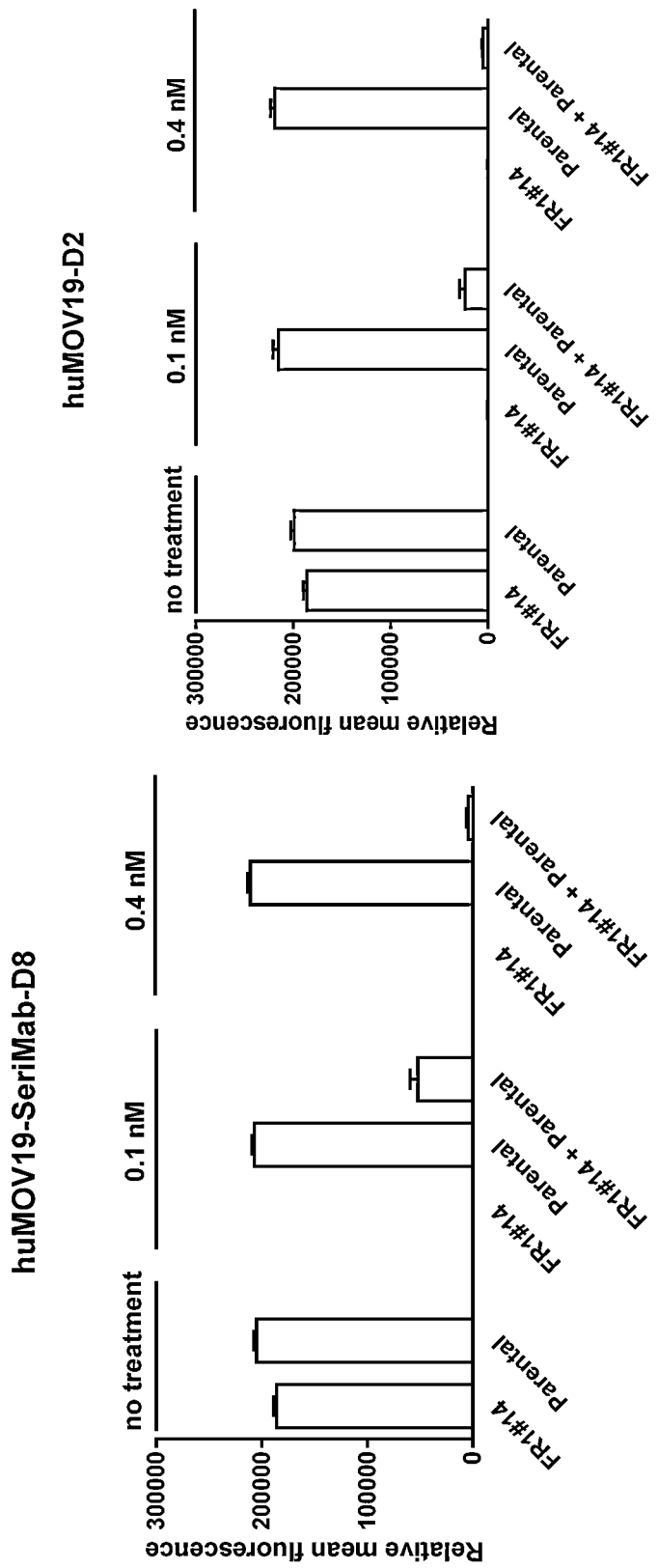
FIG. 27 shows the results of bystander killing assay for huMOV19-SeriMab-D8 and the corresponding Lys-linked conjugated huMOV19-D2.

Similar results are observed for serine-linked D8 conjugates. See FIG. 27.

Example 23. Synthesis of Compound D8

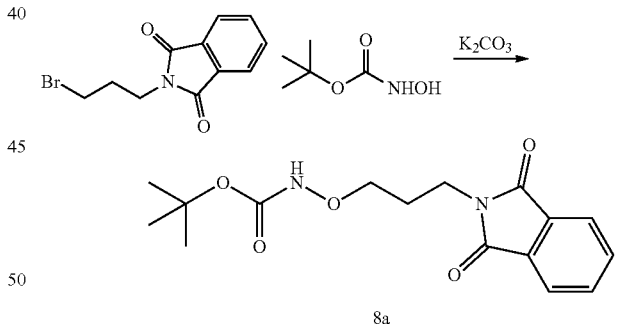

8a

Step 1: Tert-butyl hydroxycarbamate (1.490 g, 11.19 mmol) was dissolved in anhydrous DMF (22.38 mL). 2-(3-bromopropyl)isoindoline-1,3-dione (3 g, 11.19 mmol) and potassium carbonate (3.09 g, 22.38 mmol) were added and the reaction stirred overnight at room temperature. It was diluted with cold water and extracted with EtOAc. The organic was washed with brine, dried over sodium sulfate and the crude residue was purified by silica gel flash chromatography (EtOAc/Hex, gradient, 0% to 45%) to obtain compound 8a as sticky solid (2.41 g, 67% yield). LCMS=4.99 min (8 min method). $^1$H NMR (400 MHz, $CDCl_3$): δ 7.86-7.83 (m, 2H), 7.73-7.77 (m, 2H), 7.28 (bs, 1H), 3.92 (t, 2H, J=6.0 Hz), 3.82 (t, 2H, 6.9 Hz), 2.05-1.98 (m, 2H), 1.47 (s, 9H).

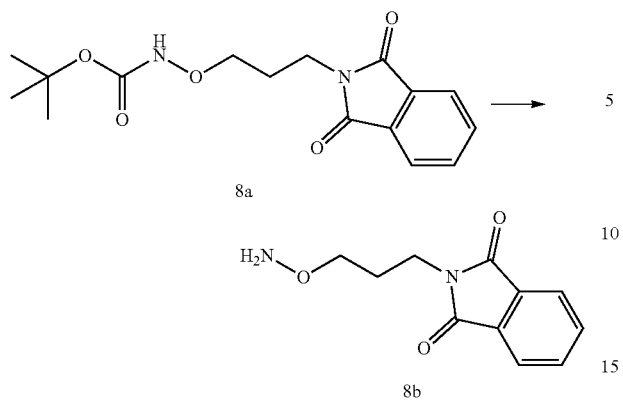

8a

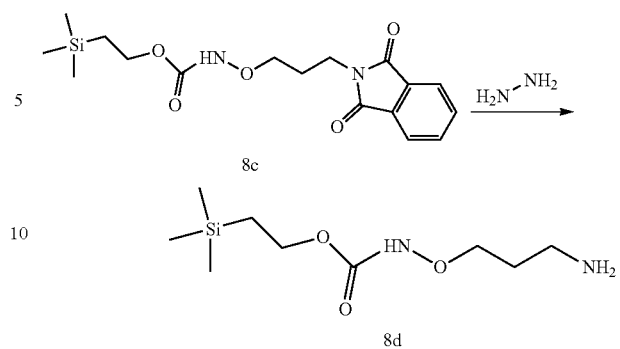

8c

8b

8d

Step 2: Compound 8a (2.41 g, 7.52 mmol) was dissolved in anhydrous DCM (18.81 mL) and cooled to 0° C. in an ice bath. A freshly mixed solution of DCM (9.40 ml) and TFA (9.40 ml) was added and the ice bath was removed. The reaction stirred at room temperature for 1 hour and was diluted with DCM and washed with saturated sodium bicarb. The organic layer was washed with brine, dried, filtered and concentrated to give compound 8b (1.32 g, 80% yield). The crude material was used without further purification. $^1$H NMR (400 MHz, CDCl$_3$): δ 7.85-7.82 (m, 2H), 7.72-7.69 (m, 2H), 3.78 (t, 2H, J=7.0 Hz), 3.72 (t, 2H, 6.0 Hz), 1.99-1.93 (m, 2H).

Step 4: Compound 8c (148 mg, 0.406 mmol) was dissolved in Ethanol (2.7 mL) and stirred until completely soluble. Hydrazine (63.7 μl, 2.030 mmol) was added and the reaction stirred at room temperature until rapid formation of a white precipitate at 1 hour. The reaction was filtered through celite and rinsed with additional ethanol. The filtrate was evaporated and purified by silica gel flash chromatography (A=MeOH, B=EtOAc gradient, 100% to 10%). Product fractions were detected by mass and evaporated to give compound 8d as a sticky solid (67.5 mg, 71% yield). $^1$H NMR (400 MHz, CDCl$_3$): δ 4.27-4.21 (m, 2H), 3.98 (t, 2H, J=5.9 Hz), 2.92-2.87 (m, 2H), 1.85-1.77 (m, 2H), 1.06-0.99 (m, 2H), 0.04 (s, 9H).

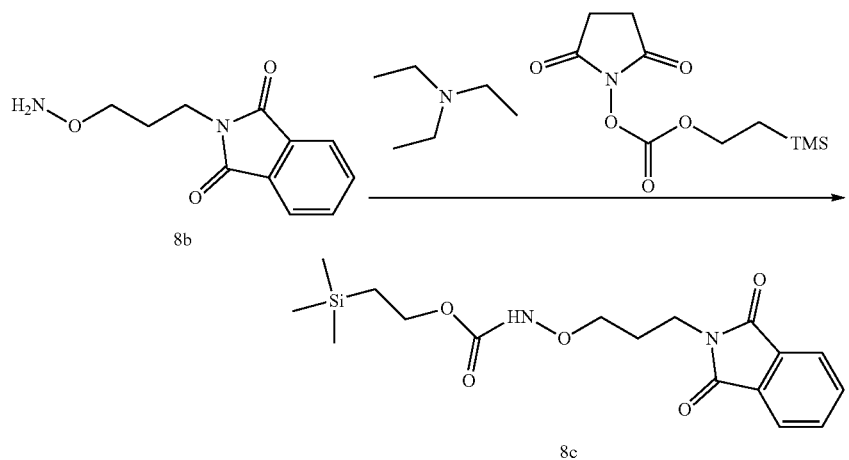

Step 3: Compound 8b (100 mg, 0.454 mmol) was dissolved in anhydrous DCM (4.5 mL) TEA (127 μl, 0.908 mmol) and 2,5-dioxopyrrolidin-1-yl (2-(trimethylsilyl) ethyl) carbonate (177 mg, 0.681 mmol) were added and the reaction stirred at room temperature overnight. The reaction was diluted with DCM, washed with brine, dried, filtered, and evaporated. The crude residue was purified by silica gel flash chromatography (EtOAc/Hex, gradient, 0% to 40%) to obtain compound 8c (148 mg, 89% yield). LCMS=5.91 min (8 min method). $^1$H NMR (400 MHz, CDCl$_3$): δ 7.86-7.83 (m, 2H), 7.73-7.69 (m, 2H), 7.39 (bs, 1H), 4.26-4.20 (m, 2H), 3.94 (t, 2H, J=6.0 Hz), 3.83 (t, 2H, 6.9 Hz), 2.06-1.98 (m, 2H), 1.05-0.98 (m, 2H), 0.04 (s, 9H).

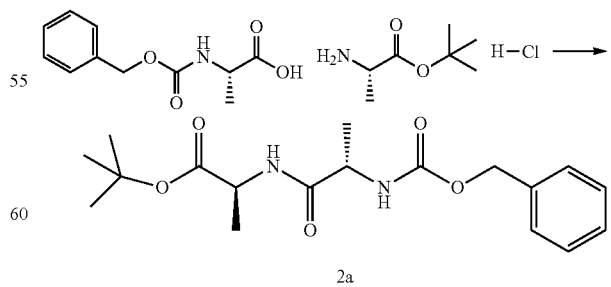

2a

Step 5: (S)-2-(((benzyloxy)carbonyl)amino)propanoic acid (5 g, 22.40 mmol) and (S)-tert-butyl 2-aminopropanoate hydrochloride (4.48 g, 24.64 mmol) were dissolved in anhydrous DMF (44.8 mL). EDC.HCl (4.72 g, 24.64 mmol), HOBt (3.43 g, 22.40 mmol), and DIPEA (9.75 mL, 56.0 mmol) were added. The reaction stirred under argon, at room temperature, overnight. The reaction mixture was diluted with dichloromethane and then washed with saturated ammonium chloride, saturated sodium bicarbonate, water, and brine. The organic layer was dried over sodium sulfate and concentrated. The crude oil was purified via silica gel chromatography (Hexanes/Ethyl Acetate) to yield compound 2a (6.7 g, 85% yield). $^1$H NMR (400 MHz, CDCl$_3$): δ 7.38-7.31 (m, 5H), 6.53-6.42 (m, 1H), 5.42-5.33 (m, 1H), 5.14 (s, 2H), 4.48-4.41 (m, 1H), 4.32-4.20 (m, 1H), 1.49 (s, 9H), 1.42 (d, 3H, J=6.8 Hz), 1.38 (d, 3H, J=7.2 Hz).

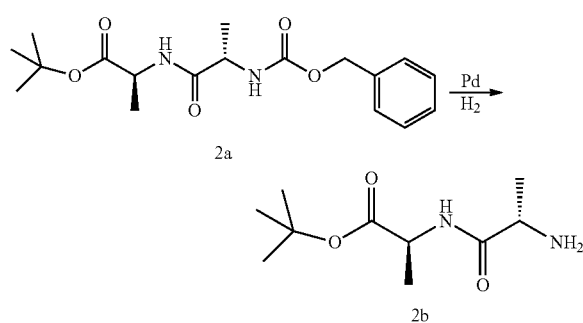

Step 6: Compound 2a (6.7 g, 19.12 mmol) was dissolved in methanol (60.7 mL) and water (3.03 mL). The solution was purged with argon for five minutes. Palladium on carbon (wet, 10%) (1.017 g, 0.956 mmol) was added slowly. The reaction was stirred overnight under an atmosphere of hydrogen. The solution was filtered through Celite, rinsed with methanol and concentrated. It was azeotroped with methanol and acetonitrile and the resulting oil was placed directly on the high vacuum to give compound 2b (4.02 g, 97% yield) which was used directly in the next step. $^1$H NMR (400 MHz, CDCl$_3$): δ 7.78-7.63 (m, 1H), 4.49-4.42 (m, 1H), 3.55-3.50 (m, 1H), 1.73 (s, 2H), 1.48 (s, 9H), 1.39 (d, 3H, J=7.2 Hz), 1.36 (d, 3H, J=6.8 Hz).

Step 7: Compound 2b (4.02 g, 18.59 mmol) and mono methyladipate (3.03 mL, 20.45 mmol) were dissolved in anhydrous DMF (62.0 mL). EDC.HCl (3.92 g, 20.45 mmol), HOBt (2.85 g, 18.59 mmol) and DIPEA (6.49 mL, 37.2 mmol) were added. The mixture was stirred overnight at room temperature. The reaction was diluted with dichloromethane/methanol (150 mL, 5:1) and washed with saturated ammonium chloride, saturated sodium bicarbonate, and brine. It was dried over sodium sulfate, filtered and stripped. The compound was azeotroped with acetonitrile (5×), then pumped on the high vacuum at 35° C. to give compound 2c (6.66 g, 100% yield). The crude material was taken onto next step without purification. $^1$H NMR (400 MHz, CDCl$_3$): δ 6.75 (d, 1H, J=6.8 Hz), 6.44 (d, 1H, J=6.8 Hz), 4.52-4.44 (m, 1H), 4.43-4.36 (m, 1H), 3.65 (s, 3H), 2.35-2.29 (m, 2H), 2.25-2.18 (m, 2H), 1.71-1.60 (m, 4H), 1.45 (s, 9H), 1.36 (t, 6H, J=6.0 Hz).

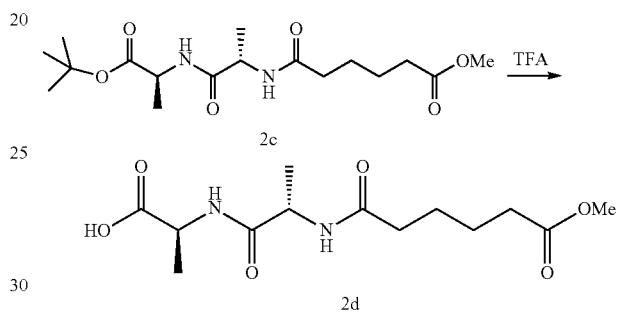

Step 8: Compound 2c (5.91 g, 16.5 mmol) was stirred in TFA (28.6 mL, 372 mmol) and deionized water (1.5 mL) at room temperature for three hours. The reaction mixture was concentrated with acetonitrile and placed on high vacuum to give crude compound 2d as a sticky solid (5.88 g, 100% yield). $^1$H NMR (400 MHz, CDCl$_3$): δ 7.21 (d, 1H, J=6.8 Hz), 6.81 (d, 1H, J=7.6 Hz), 4.69-4.60 (m, 1H), 4.59-4.51 (m, 1H), 3.69 (s, 3H), 2.40-2.33 (m, 2H), 2.31-2.24 (m, 2H), 1.72-1.63 (m, 4H), 1.51-1.45 (m, 3H), 1.42-1.37 (m, 3H).

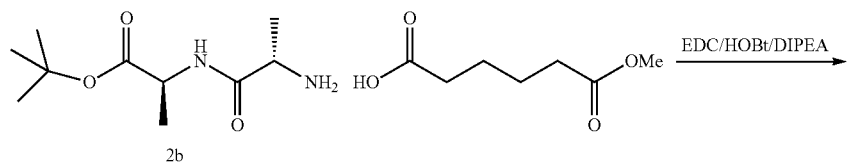

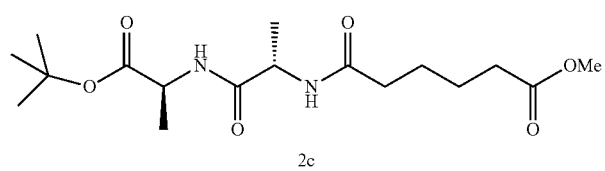

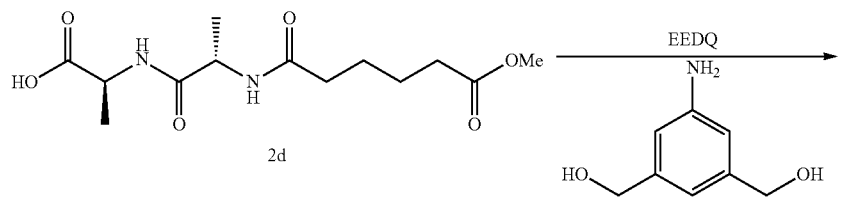

2d

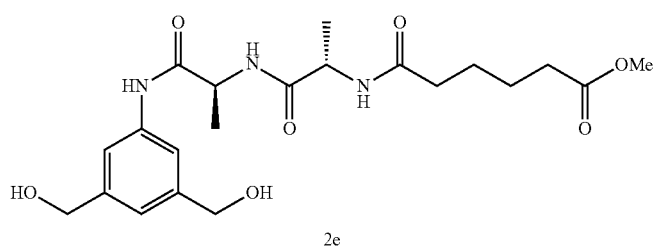

2e

Step 9: Compound 2d (5.6 g, 18.52 mmol) was dissolved in anhydrous dichloromethane (118 mL) and anhydrous methanol (58.8 mL). (5-amino-1,3-phenylene)dimethanol (2.70 g, 17.64 mmol) and EEDQ (8.72 g, 35.3 mmol) were added and the reaction was stirred at room temperature, overnight. The solvent was stripped and ethyl acetate was added. The resulting slurry was filtered, washed with ethyl acetate and dried under vacuum/N2 to give compound 2e (2.79 g, 36% yield). $^1$H NMR (400 MHz, DMSO-d6): δ 9.82 (s, 1H), 8.05, (d, 1H, J=9.2 Hz), 8.01 (d, 1H, J=7.2 Hz), 7.46 (s, 2H), 6.95 (3, 1H), 5.21-5.12 (m, 2H), 4.47-4.42 (m, 4H), 4.40-4.33 (m, 1H), 4.33-4.24 (m, 1H), 3.58 (s, 3H), 2.33-2.26 (m, 2H), 2.16-2.09 (m, 2H), 1.54-1.46 (m, 4H), 1.30 (d, 3H, J=7.2 Hz), 1.22 (d, 3H, J=4.4 Hz).

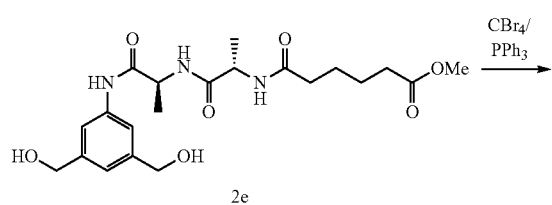

2e

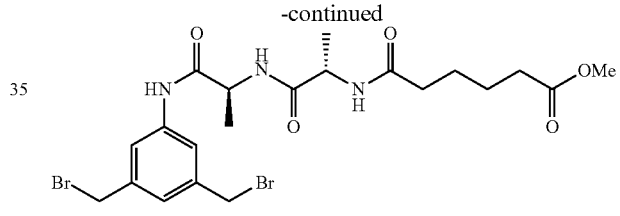

2f

Step 10: Compound 2e (0.52 g, 1.189 mmol) and carbon tetrabromide (1.183 g, 3.57 mmol) were dissolved in anhydrous DMF (11.89 mL). Triphenylphosphine (0.935 g, 3.57 mmol) was added and the reaction stirred under argon for four hours. The reaction mixture was diluted with DCM/MeOH (10:1) and washed with water and brine, dried over sodium sulfate, filtered, and concentrated. The crude material was purified by silica gel chromatography (DCM/MeOH) to give compound 2f (262 mg, 39% yield). $^1$H NMR (400 MHz, DMSO-d6): δ 10.01 (s, 1H), 8.11 (d, 1H, J=6.8 Hz), 8.03 (d, 1H, J=6.8 Hz), 7.67 (s, 2H), 7.21 (s, 1H), 4.70-4.64 (m, 4H), 4.40-4.32 (m, 1H), 4.31-4.23 (m, 1H), 3.58 (s, 3H), 2.34-2.26 (m, 2H), 2.18-2.10 (m, 2H), 1.55-1.45 (m, 4H), 1.31 (d, 3H, J=7.2 Hz), 1.21 (d, 3H, J=7.2 Hz).

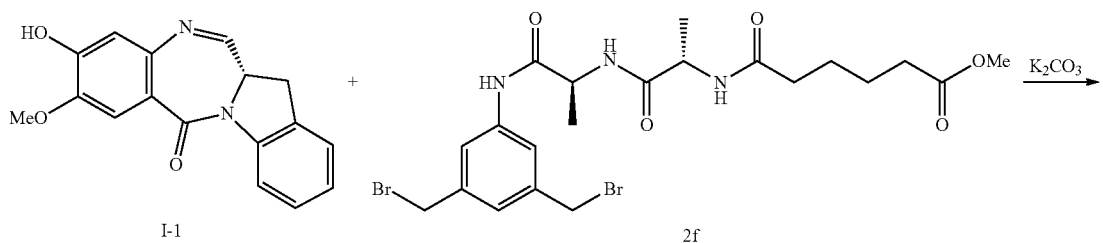

I-1          2f

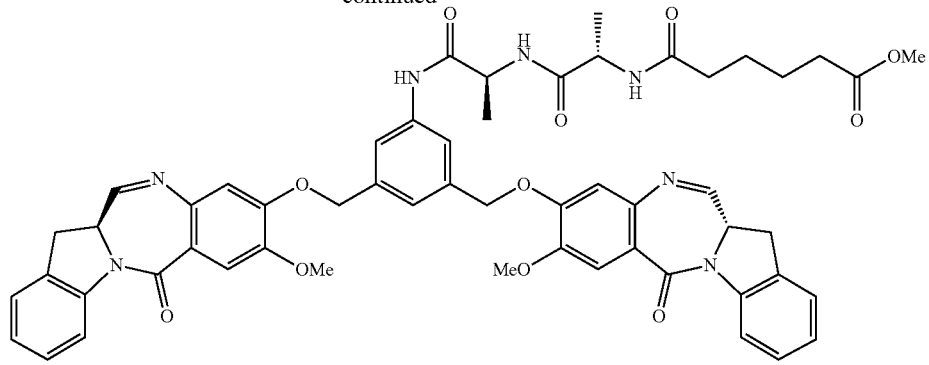

2g

Step 11: Dibromide compound 2f nd IGN monomer compound I-1 were dissolved in DMF. Potassium carbonate was added and was stirred at rt overnight. Water was added to the reaction mixture to precipitate the product. The slurry was stirred at rt for 5 min and was then filtered and dried under vacuum/N2 for 1 h. The crude material was purified by silica gel chromatography (dichloromethane/methanol) to give compound 2g (336 mg, 74% yield). LCMS=5.91 min (15 min method). MS (m/z): 990.6 (M+1)$^+$.

Step 12: Diimine compound 2g was dissolved in 1,2-dichloroethane. NaBH(OAc)$_3$ was added to the reaction mixture and was stirred at rt for 1 h. The reaction was diluted with CH$_2$C12 and was quenched with sat' d aq NH$_4$C1 solution. The layers were separated and was washed with brine, dried over Na$_2$SO$_4$ and concentrated. The crude material was purified via RPHPLC (C18 column, Acetonitrile/Water) to give compound 2h (85.5 mg, 25% yield). LCMS=6.64 min (15 min method). MS (m/z): 992.6 (M+1)$^+$.

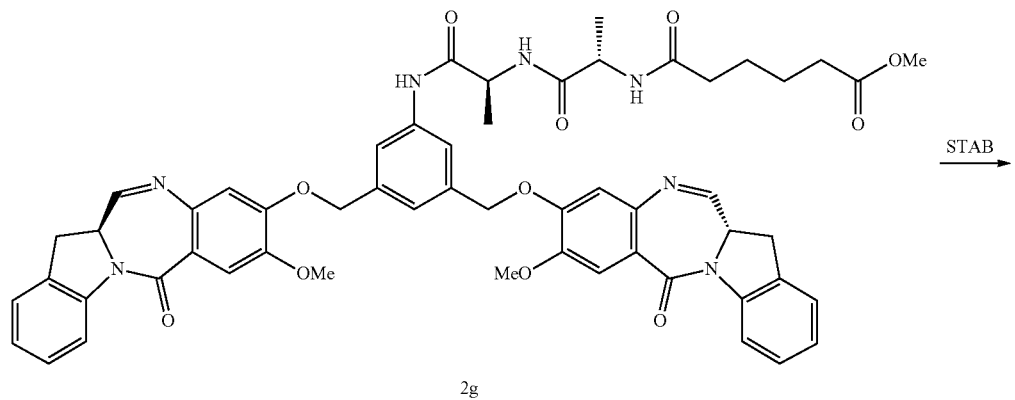

2g

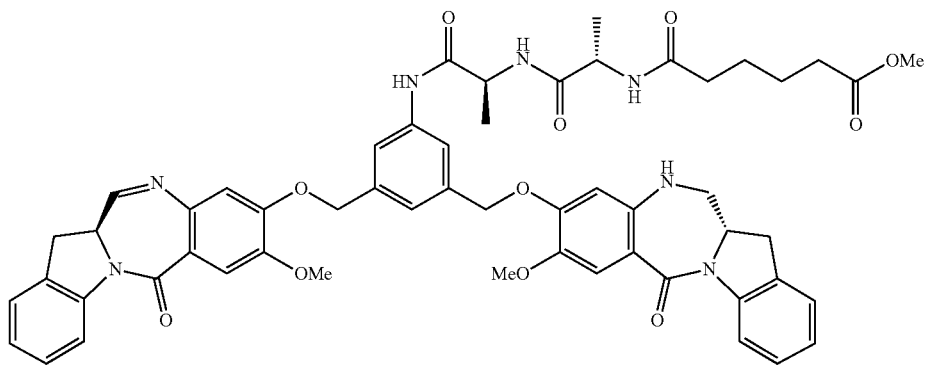

2h

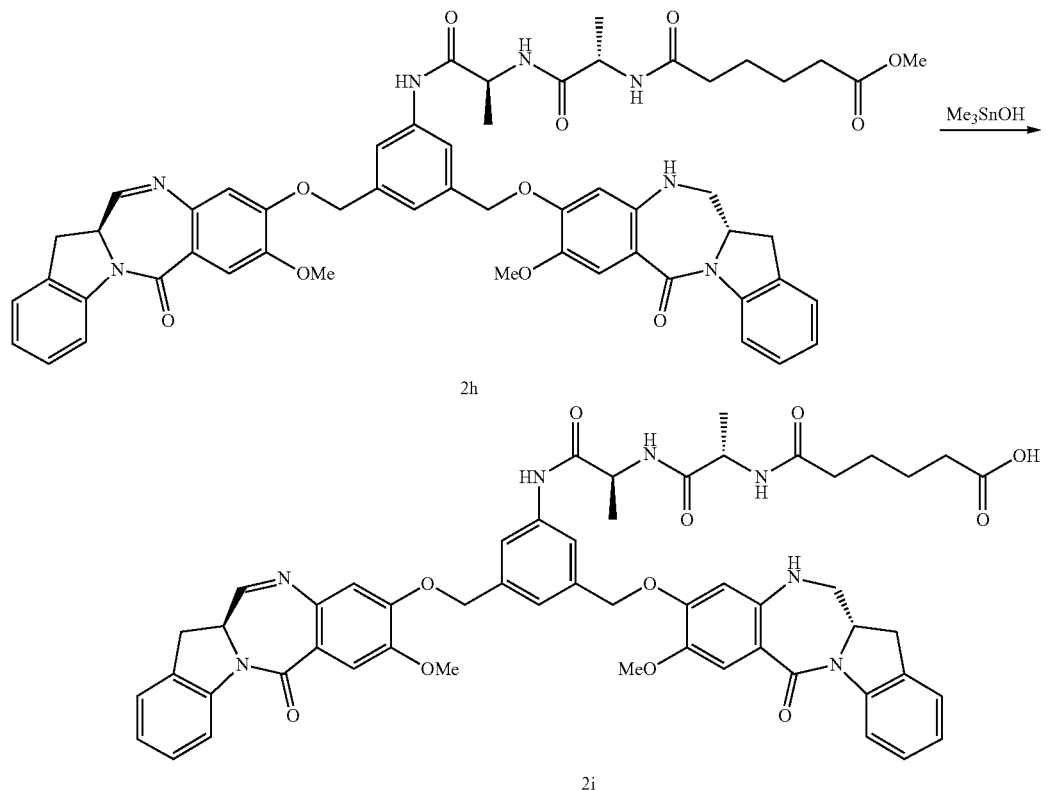

Step 13: Methylester compound 2h was dissolved in 1,2-dichloroethane. Trimethylstannanol was added to the reaction mixture and was heated at 80° C. overnight. The reaction mixture was cooled to rt and was diluted with water. The aqueous layer was acidified to pH~4 with 1 M HCl. The mixture was extracted with CH$_2$Cl$_2$/MeOH (10:1, 3×20 mL). The combined organic layers were washed with brine and was dried over Na$_2$SO$_4$ and concentrated. The crude material was passed through a silica plug to give compound 2i (48.8 mg, 80% yield). LCMS=5.89 min (15 min method). MS (m/z): 978.6 (M+1)$^+$.

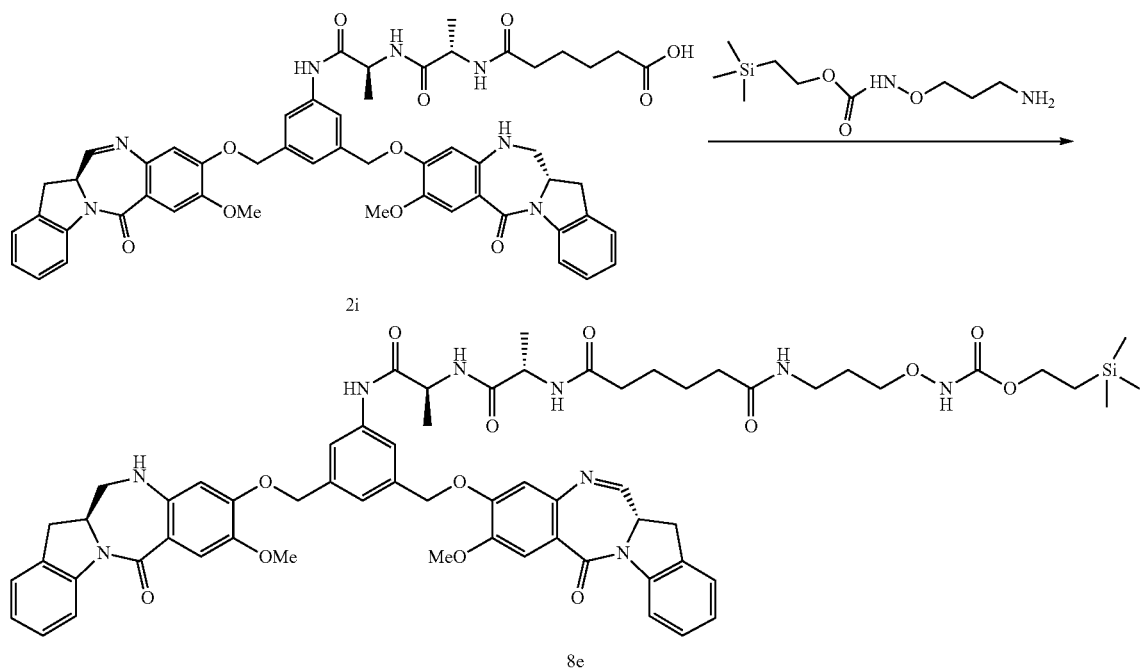

Step 14: Compound 2i (30 mg, 0.031 mmol) was suspended in anhydrous DCM (613 µl). Anhydrous DMF was added dropwise until the solution cleared. Compound 8d (21.57 mg, 0.092 mmol), EDC.HCl (29.4 mg, 0.153 mmol), and DMAP (0.749 mg, 6.13 µmol) were added and the reaction stirred at room temperature for 1 hour. It was diluted with DCM/MeOH 10:1 and then washed with water. The aqueous layer was extracted with DCM/MeOH 10:1 and the combined organic was dried and concentrated to give Compound 8e (49 mg) which was used without further purification. LCMS=5.94 min (8 min method). MS (m/z): 1194.4 (M+1)+.

Step 15: Compound 8e (49 mg, 0.041 mmol) was dissolved in THF (820 µl) and the reaction was cooled to 0° C. in an ice bath. TBAF (205 µl, 0.205 mmol) was added and the reaction stirred for 15 minutes before the ice bath was removed. It was stirred at room temperature until completion. The reaction was cooled to 0° C., quenched with saturated ammonium chloride and extracted with DCM/MeOH 10:1. The organic was washed with brine, dried with sodium sulfate and evaporated. The crude material was purified via RPHPLC (C18 column, Acetonitrile/Water) to give compound D8 (17.6 mg, 54% yield over 2 steps). LCMS=5.1 min (8 min method). MS (m/z): 1050.4 (M+1)+.

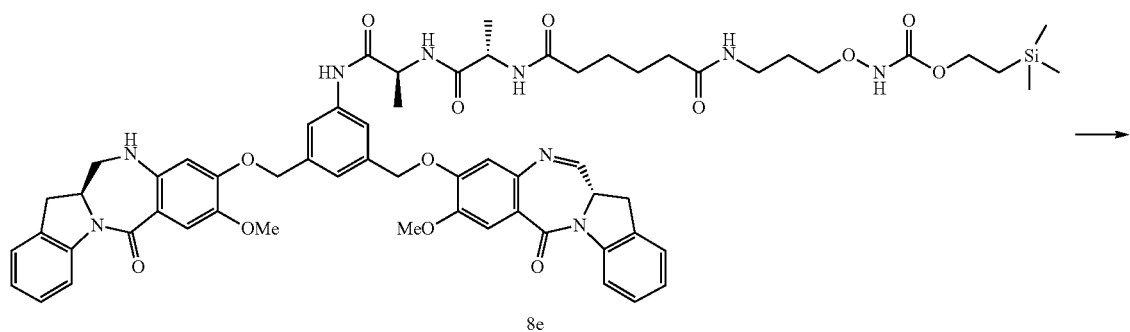

8e

D8

Example 24. Synthesis of Compound D9

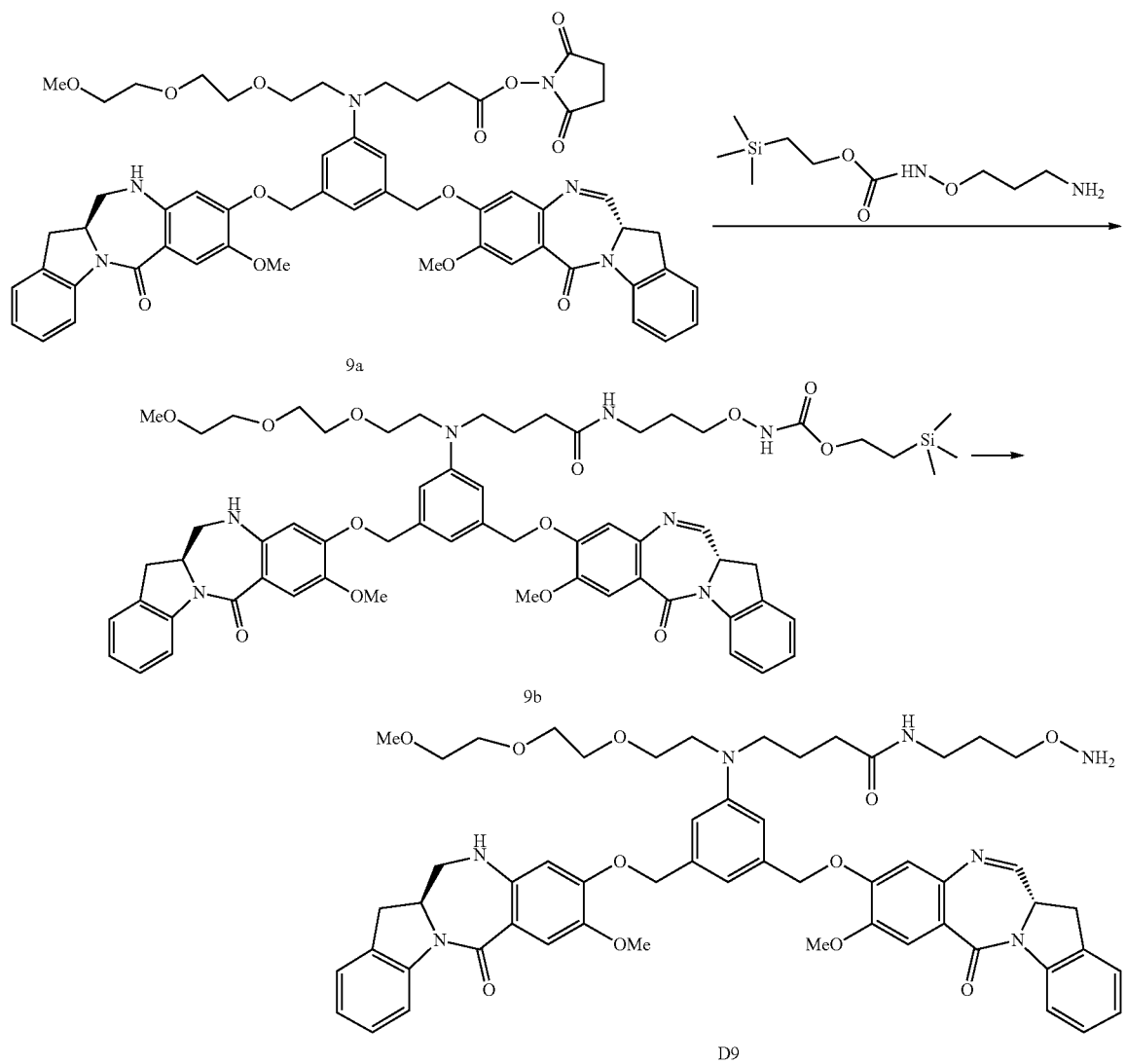

Step 1: Compound 9a (17 mg, 0.016 mmol) was dissolved in DCM (328 μl). Compound 8d (5.76 mg, 0.025 mmol) and DIPEA (5.71 μl, 0.033 mmol) were added at room temperature and the reaction stirred until completion. It was diluted with 10:1 DCM:MeOH and washed with brine. The organic was dried and concentrated to give compound 9b which was used directly.

Step 2: Compound D9 was prepared similarly as compound D8 in Example 23. The crude material was purified via RPHPLC (C18 column, Acetonitrile/Water) to give compound D9 (5 mg, 31% yield over 2 steps). LCMS=5.68 min (8 min method). MS (m/z): 1012.5 (M+1)$^+$.

Figure 5:
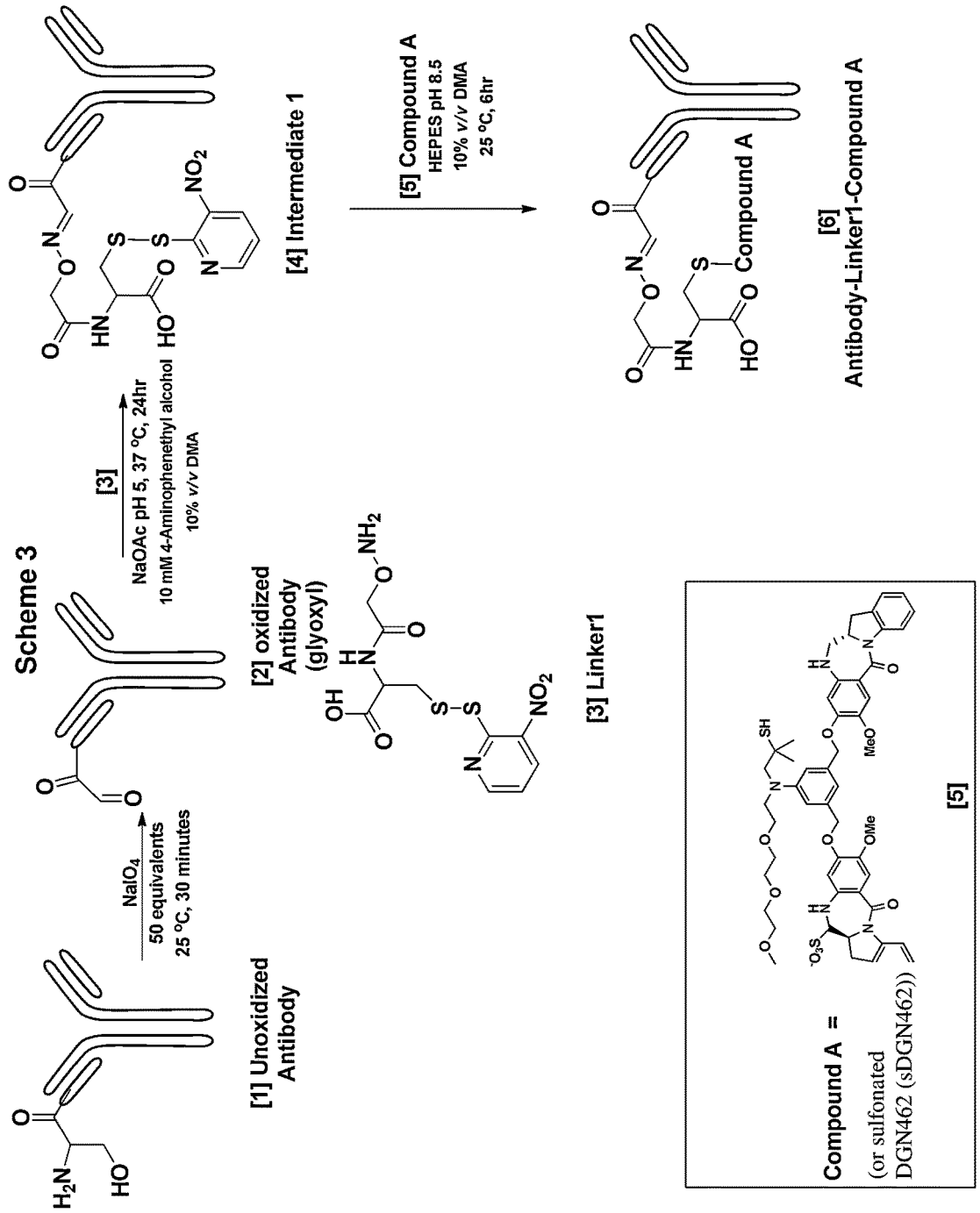
FIG. 5 shows Scheme 3 for synthesizing the Antibody (such as huMOV19-NTS #1)-Linker1-Compound A ADC using engineered N-terminal Ser-containing humanized monoclonal antibody (e.g., huMOV19-NTS #1).

Example 25. Preparation of SeriMab Conjugates of the huCD123-6 Antibody a) N-Terminal Antibody Conjugation—a Two-Step Approach huCD123-6Gv4.6/7S3 antibody Mt in Scheme 3 as shown in FIG. 5; 3 mg/mL in PBS, pH7.4) was treated with 5 mM aqueous sodium periodate (50 equivalents, 25° C., 30 minutes). The mixture was then buffer exchanged through a NAP desalting column (Illustra Sephadex G-25 DNA Grade, GE Healthcare) into sodium acetate buffer, pH5.0.

The resulting solution was treated with 4-Aminophenethyl alcohol (100 mM in DMA [N,N-Dimethylacetamide]) to 10% v/v cosolvent. Heterobifunctional Linker1 ([3] in Scheme 3; 5 equivalents) was subsequently introduced, and the reaction vessel was sealed and incubated at 37° C. for 24 hours.

The mixture was then buffer exchanged through a NAP desalting column (Illustra Sephadex G-25 DNA Grade, GE Healthcare) into HEPES (4-(2-hydroxyethyl)-1-piperazine ethanesulfonic acid), pH8.5 buffer. The solution was then adjusted with DMA (N,N-Dimethylacetamide) cosolvent (10% v/v), and treated with sulfonated DGN462 (sDGN462) ([5], Scheme 3; free thiol; 5 equivalents), at 25° C. for 6 hours.

The resulting conjugate was buffer exchanged into 250 mM Glycine, 10 mM Histidine, 1% sucrose, 0.01% Tween-20, 50 μM sodium bisulfite formulation buffer at pH 6.2 using a NAP filtration column (Illustra Sephadex G-25 DNA Grade, GE Healthcare). Dialysis was performed in the same buffer for 4 hours at 25° C. utilizing Slide-a-Lyzer dialysis cassettes (ThermoScientific 10,000 MWCO).

The purified conjugate ([6], Scheme 3) was found to have a homogenous average of two DGN462 molecules linked per antibody (via Q-ToF Mass Spectrometry), >98% monomer (via Size Exclusion Chromatography), <2% free drug (via acetone precipitated reverse-phase HPLC analysis), and a final protein concentration of 0.18 mg/mL (via UV-Vis using molar extinction coefficients $\varepsilon_{280}$=213320 $M^{-1}$ $cm^{-1}$ for the huCD123-6Gv4.6/7S3 antibody).

b) N-Terminal Antibody Conjugation—IGN Direct Link

The engineered N-terminal Ser-containing huCD123-6Gv4.7S2 antibody, engineered with an N-terminal serine on the heavy chain ([1] in Scheme 4, FIG. 17; 3 mg/mL in PBS, pH7.4) was treated with 5 mM aqueous sodium periodate (50 molar equivalents) at 25° C. for 30 minutes. The mixture was then buffer exchanged through a NAP desalting column (Illustra Sephadex G-25 DNA Grade, GE Healthcare) into sodium acetate buffer, pH5.0.

The resulting solution was treated with p-phenylenediamine (100 mM in DMA [N,N-Dimethylacetamide]) to 10% v/v cosolvent. Then, an in situ sulfonated-D8 (or sD8) ([3], Scheme 4; 5 molar equivalents) was subsequently introduced, and the reaction vessel was sealed and incubated at 37° C. for 24 hours.

The mixture was then buffer exchanged through a NAP desalting column (Illustra Sephadex G-25 DNA Grade, GE Healthcare) into 250 mM Glycine, 10 mM Histidine, 1% sucrose buffer at pH 6.2. Dialysis was performed in the same buffer for 4 hours at 25° C., utilizing Slide-a-Lyzer dialysis cassettes (ThermoScientific 10,000 MWCO).

The purified conjugate ([4], Scheme 4) was found to have a homogenous average of two D8 molecules linked per antibody (via Q-ToF Mass Spectrometry), >96% monomer (via Size Exclusion Chromatography), <3% free drug (via HISEP reverse-phase HPLC analysis), and a final protein concentration of 1.4 mg/mL (via UV-Vis using molar extinction coefficients $\varepsilon_{280}$=213320 $M^{-1}$ $cm^{-1}$ for the huCD123-6Gv4.7S2 antibody).

The in situ sulfonated-D8 (or sD8) described above was prepared according to the following procedure: The D8 reagent, as a lyophilized, white solid, was dissolved in DMA (N,N-Dimethylacetamide) to a 10-20 mM stock concentration solution. Fresh sodium bisulfite (500 mM solution in water, 5 molar equivalents) was added and the resulting solution reacted for 4-6 hours at 25° C. before a 15 hour hold step at 4° C. A further aliquot of fresh sodium bisulfite (500 mM solution in water, 2 molar equivalents) was introduced and allowed to react for 4 hours at 25° C. before storage at −80° C. until further use.

c) N-Terminal Antibody Conjugation—Two-Step Protocol for CD123-6Gv4.7S3 or S2

The huCD123-6Gv4.7S3 (or S2—the schematic drawing of Ab is for S3, but the scheme applies to S2 as well) antibody engineered with an N-terminal serine on the light chain ([1] in Scheme 5, FIG. 18; 3 mg/mL in PBS, pH7.4) was treated with 5 mM aqueous sodium periodate (50 molar equivalents) at 25° C. for 30 minutes. The mixture was then buffer exchanged through a NAP desalting column (Illustra Sephadex G-25 DNA Grade, GE Healthcare) into sodium acetate buffer, pH5.0.

The resulting solution was treated with 4-Aminophenethyl alcohol (100 mM in DMA [N,N-Dimethylacetamide]) to 10% v/v cosolvent. Heterobifunctional Linker1 ([3], Scheme 5; 5 molar equivalents) was subsequently introduced, and the reaction vessel was sealed and incubated at 37° C. for 24 hours.

The mixture was then buffer exchanged through a NAP desalting column (Illustra Sephadex G-25 DNA Grade, GE Healthcare) into HEPES (4-(2-hydroxyethyl)-1-piperazine ethanesulfonic acid) pH8.5 buffer. The solution was then adjusted with DMA (N,N-Dimethylacetamide) cosolvent (10% v/v), and treated with sulfonated-D1 (or sD1) ([5], Scheme 5; free thiol; 5 molar equivalents) at 25° C. for 6 hours.

The resulting conjugate was buffer exchanged into 250 mM Glycine, 10 mM Histidine, 1% sucrose, 0.01% Tween-20, 50 µM sodium bisulfite formulation buffer at pH 6.2, using a NAP filtration column (Illustra Sephadex G-25 DNA Grade, GE Healthcare). Dialysis was performed in the same buffer for 4 hours at 25° C., utilizing Slide-a-Lyzer dialysis cassettes (ThermoScientific 10,000 MWCO).

The purified conjugate ([6], Scheme 5) was found to have an average of 2.0 molecules of sD1 linked per antibody (via Q-ToF Mass Spectrometry), >96% monomer (via Size Exclusion Chromatography), <3% free drug (via acetone precipitated reverse-phase HPLC analysis), and a final protein concentration of 0.4 mg/mL (via UV-Vis using molar extinction coefficients $\varepsilon_{280}$=213320 $M^{-1}$ $cm^{-1}$ for the huCD123-6Gv4.7S3 antibody).

Figure 19:
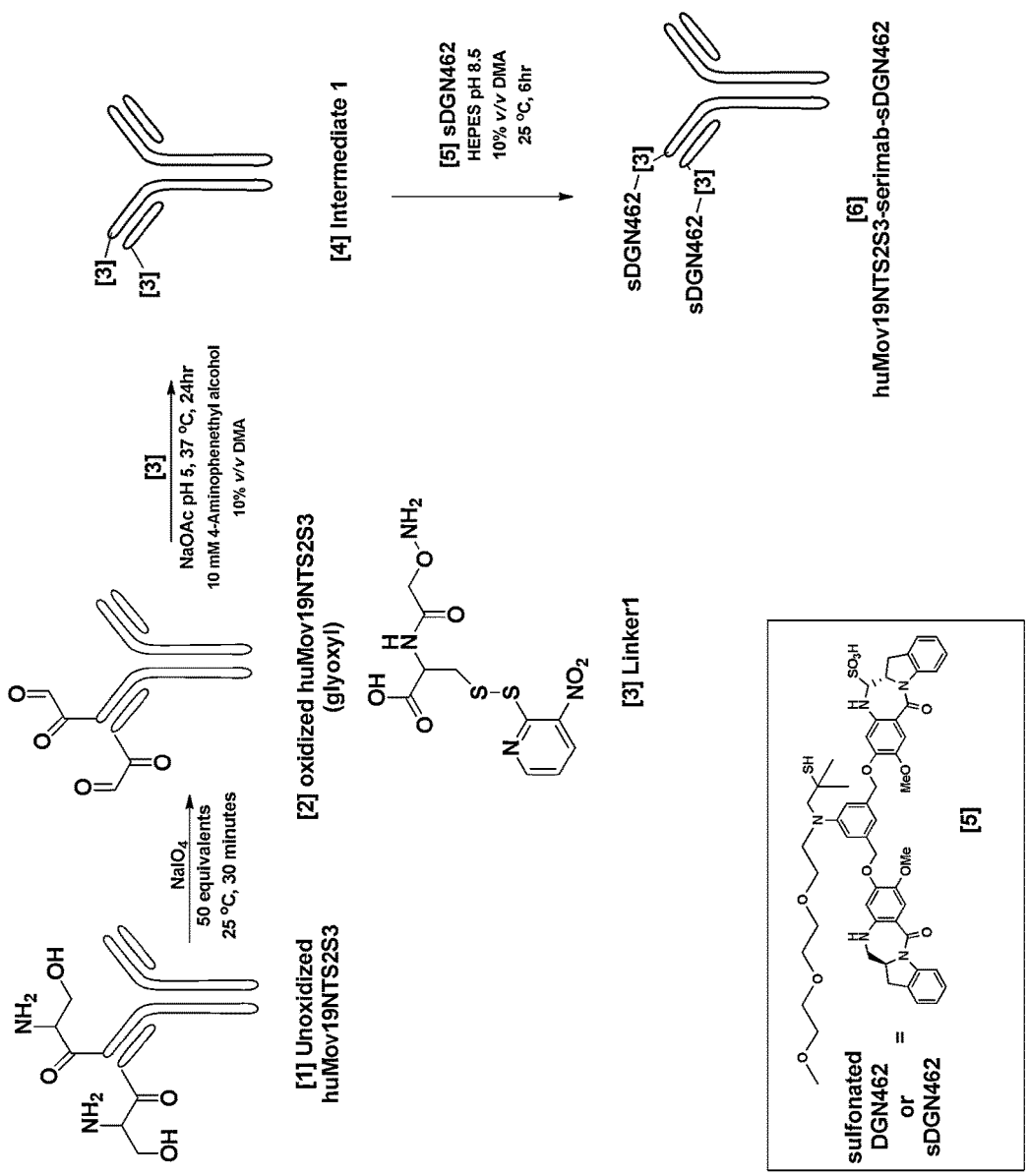
FIG. 19 shows an exemplary scheme for synthesizing the huMOV19NTS2S3-SeriMab-DGN462 or -sDGN462 conjugate with 4 DAR (huMov19NTS2S3-SeriMab-sDGN462), which bears a Linker 1 residue.

Example 26 N-Terminal Antibody Conjugation for Preparing Conjugates with 4 DAR (a) Two-Step Approach huMOV19-NTS2S3 antibody engineered with an N-terminal serine on the heavy chain and the light chain ([1], in Scheme 6 as shown in FIG. 19; 3 mg/mL in PBS, pH7.4) was treated with 5 mM aqueous sodium periodate (50 equivalents, 25° C., 30 minutes). The mixture was then buffer exchanged through a NAP desalting column (Illustra Sephadex G-25 DNA Grade, GE Healthcare) into sodium acetate buffer, pH5.0.

The resulting solution was treated with 4-Aminophenethyl alcohol, to a 10 mM concentration in the reaction vessel, which contained 10% v/v DMA (N,N-Dimethylacetamide) cosolvent. Linker1 ([3] in Scheme 6; 10 equivalents) was subsequently introduced, and the reaction vessel was sealed and incubated at 37° C. for 24 hours.

The mixture was then buffer exchanged through a NAP desalting column (Illustra Sephadex G-25 DNA Grade, GE Healthcare) into HEPES (4-(2-hydroxyethyl)-1-piperazine ethanesulfonic acid), pH8.5 buffer. The solution was then adjusted with DMA (N,N-Dimethylacetamide) cosolvent (10% v/v), and treated with Compound A (or sulfonated DGN462 (sDGN462)) ([5], Scheme 6; free thiol; 10 equivalents), at 25° C. for 6 hours.

The resulting conjugate was buffer exchanged into 250 mM Glycine, 10 mM Histidine, 1% sucrose, 0.01% Tween- 20, 50 μM sodium bisulfite formulation buffer at pH 6.2 using a NAP filtration column (Illustra Sephadex G-25 DNA Grade, GE Healthcare). Dialysis was performed in the same buffer for 4 hours at 25° C. utilizing Slide-a-Lyzer dialysis cassettes (ThermoScientific 10,000 MWCO).

Figure 20:
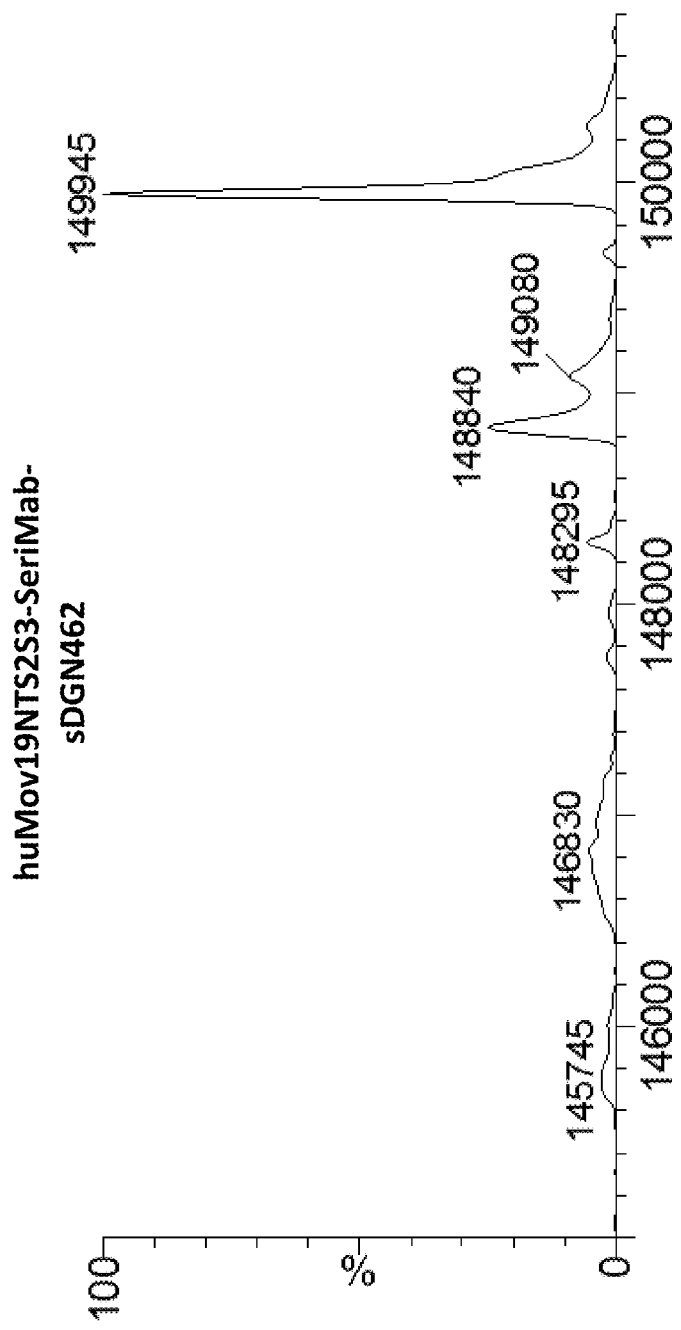
FIG. 20 shows Q-ToF Mass Spectrometry (MS) data of huMOV19NTS2S3-SeriMab-sDGN462 conjugate with 4 DAR (huMov19NTS2S3-SeriMab-sDGN462).

The purified conjugate ([6], Scheme 6) was found to have a homogenous average of four Compound A molecules linked per antibody (via Q-ToF Mass Spectrometry, FIG. 20), >93% monomer (via Size Exclusion Chromatography), <2% free drug (via acetone precipitated reverse-phase HPLC analysis), and a final protein concentration of 0.1 mg/mL (via UV-Vis using molar extinction coefficients $\epsilon_{280}=201400$ $M^{-1}$ $cm^{-1}$ for the huMOV19-NTS2S3 antibody).

(b) DMx Direct Link

Figure 21A:
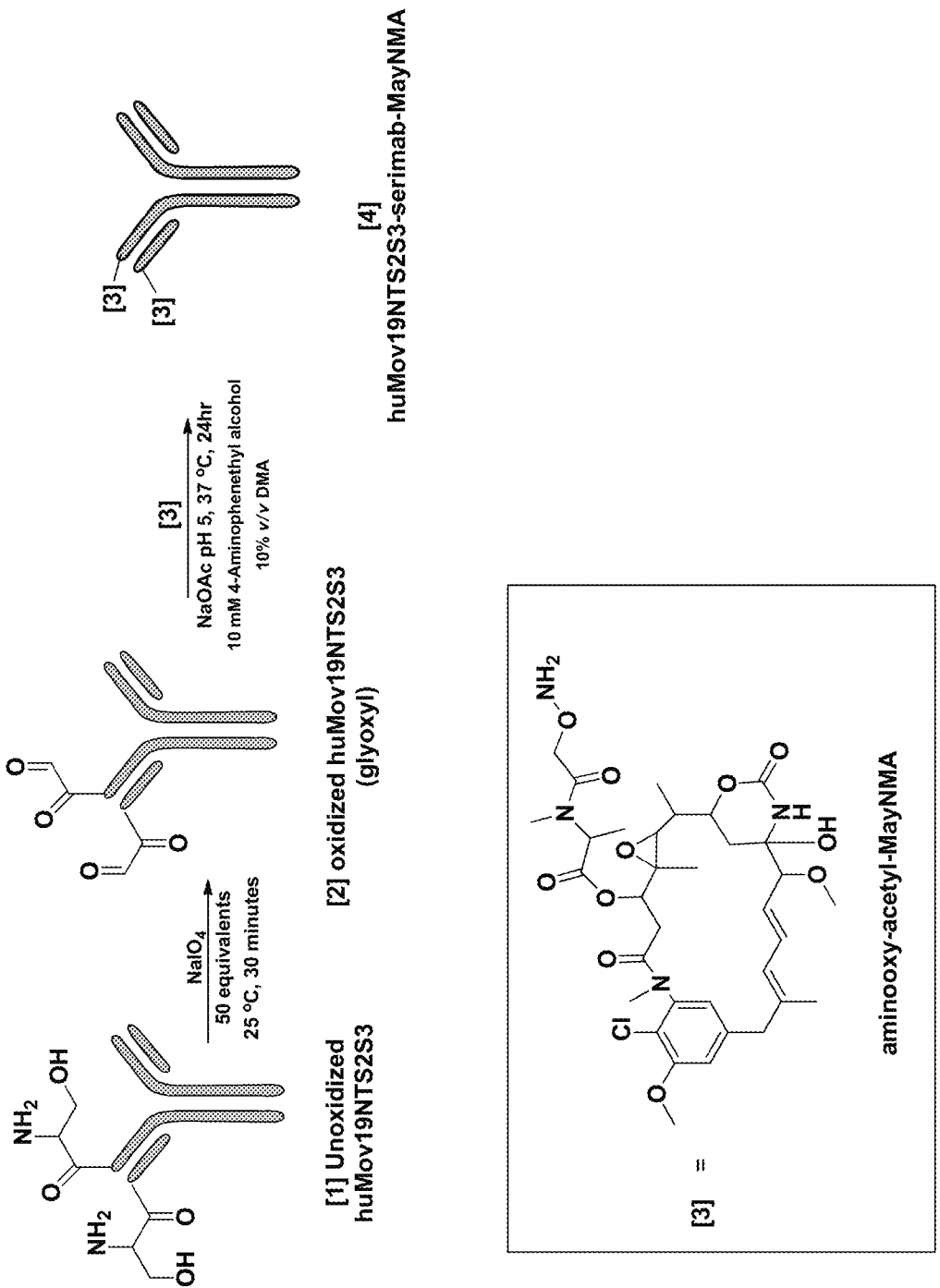
FIG. 21A shows an exemplary scheme for synthesizing the huMOV19NTS2S3-SeriMab-MayNMA conjugate with 4 DAR.

The engineered N-terminal Ser-containing huMOV19-NTS2S3 antibody ([1] in Scheme 7, FIG. 21A; 3 mg/mL in PBS, pH7.4) was treated with 5 mM aqueous sodium periodate (50 molar equivalents) at 25° C. for 30 minutes. The mixture was then buffer exchanged through a NAP desalting column (Illustra Sephadex G-25 DNA Grade, GE Healthcare) into sodium acetate buffer, pH5.0.

The resulting solution was treated with 4-Aminophenethyl alcohol, to a 10 mM concentration in the reaction vessel, which contained 10% v/v DMA (N,N-Dimethylacetamide) cosolvent. Then, aminooxy-acetyl-MayNMA ([3], Scheme 7; 10 molar equivalents) was subsequently introduced, and the reaction vessel was sealed and incubated at 37° C. for 24 hours.

The mixture was then buffer exchanged through a NAP desalting column (Illustra Sephadex G-25 DNA Grade, GE Healthcare) into 250 mM Glycine, 10 mM Histidine, 1% sucrose buffer at pH 6.2. Dialysis was performed in the same buffer for 4 hours at 25° C., utilizing Slide-a-Lyzer dialysis cassettes (ThermoScientific 10,000 MWCO).

Figure 21B:
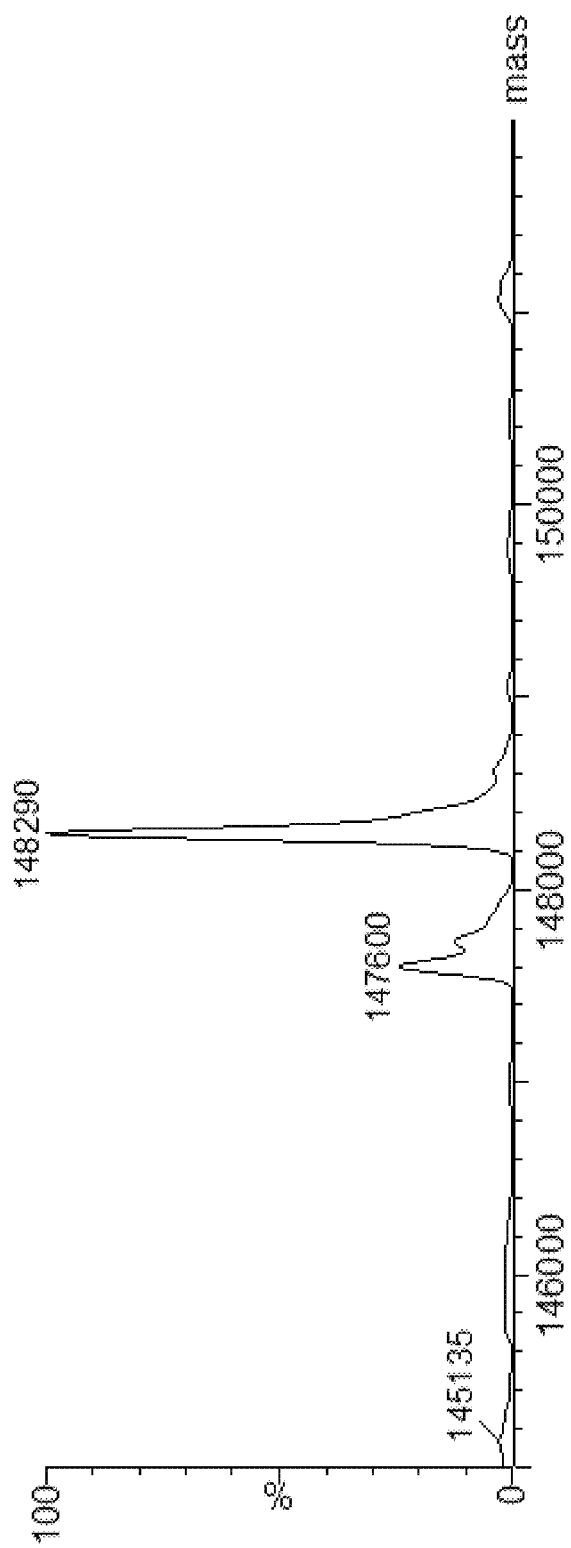
FIG. 21B shows Q-ToF Mass Spectrometry (MS) data of the Ser-linked huMOV19-SeriMab-MayNMA conjugate with 4 DAR.

The purified conjugate ([4], Scheme 7) was found to have a homogenous average of four MayNMA molecules linked per antibody (via Q-ToF Mass Spectrometry, FIG. 21B), >95% monomer (via Size Exclusion Chromatography), <2% free drug (via HISEP reverse-phase HPLC analysis), and a final protein concentration of 0.2 mg/mL (via UV-Vis using molar extinction coefficients $\epsilon_{280}=201400$ $M^{-1}$ $cm^{-1}$ for the huMov19-NTS2S3 antibody).

Example 27 In Vitro Cytotoxicity of Site-Specific Conjugates of the huCD123-6 Antibody The ability of site-specific conjugates of huCD123-6 with the various IGN compounds (huCD123-6Rv1.1S2-SeriMab-D8) to kill cells that express CD123 on their cell surface was compared to that of the lysine-linked conjugates containing the matching antibody and the payload (huCD123-6Rv1.1-D2) using in vitro cytotoxicity assays. The cytotoxicity assays were carried out and analyzed as described below.

The cell lines were cultured in culture medium as recommended by the cell supplier (ATCC or DSMZ). The cells, 2,000 to 10,000 in 100 μL of the culture medium, were added to each well of flat bottom 96-well plates. To block Fc receptors on the cell surface, the culture medium was supplemented with 100 nM chKTI antibody (an antibody of the same isotype). Conjugates were diluted into the culture medium using 3-fold dilution series and 100 μL were added per well. To determine the contribution of CD123-independent cytotoxicity, CD123 blocking antibody (100 nM of chCD123-6 antibody) was added to some wells prior to the testing conjugates. Control wells containing cells and the medium but lacking the conjugates, as well as wells contained medium only, were included in each assay plate. Assays were performed in triplicate for each data point. The plates were incubated at 37° C. in a humidified 6% $CO_2$ incubator for 4 to 7 days. Then the relative number of viable cells in each well was determined using the WST-8 based Cell Counting Kit-8 (Dojindo Molecular Technologies, Inc., Rockville, Md.). The apparent surviving fraction of cells in each well was calculated by first correcting for the medium background absorbance, and then dividing each value by the average of the values in the control wells (non-treated cells). The surviving fraction of cells was plotted against conjugate concentration in semi-log plots.

Figure 22B:
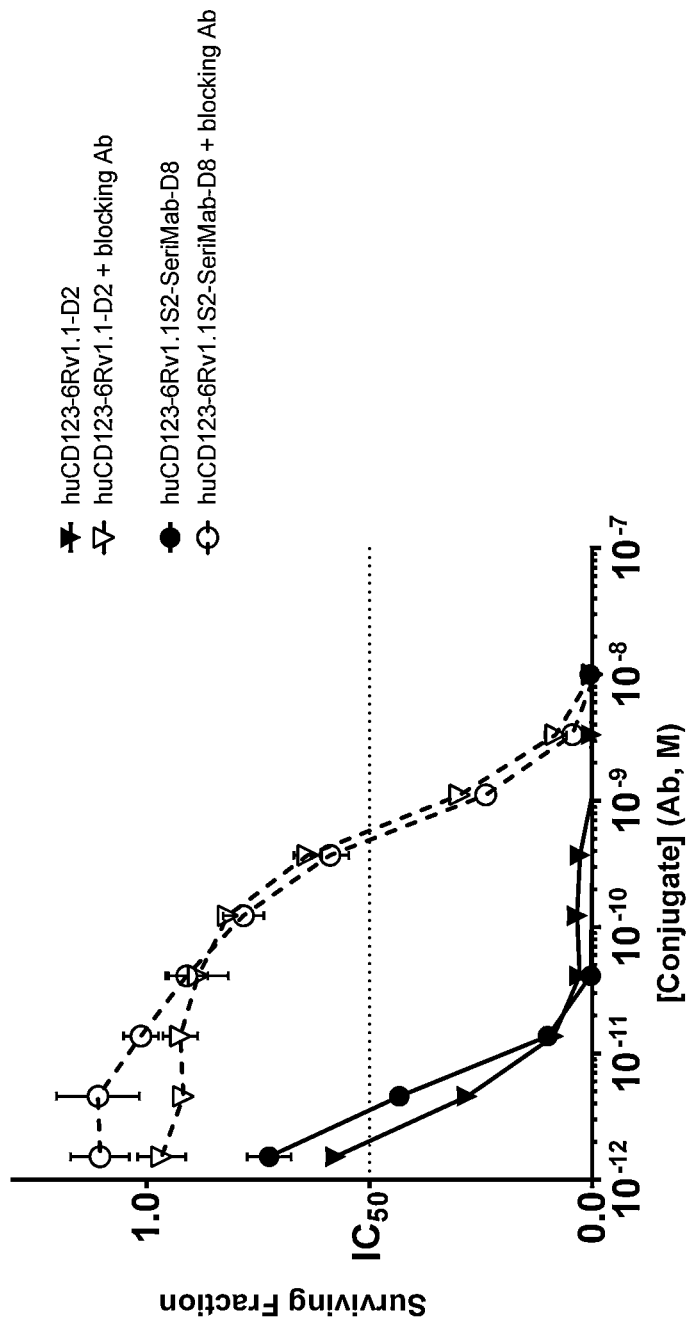

The huCD123-6Rv1.1S2-SeriMab-D8 conjugate maintained target (CD123) binding, and was at least as active as the lysine-linked huCD123-6Rv1.1-D2 conjugate on multiple cell lines. Several examples of the cytotoxicity assay using the AML cell lines SHI-1 and HNT-34, as well as the CML cell line MOLM-1 are shown in FIGS. 22A-22C, respectively. Both conjugates killed the cells in a dose-dependent manner with the $IC_{50}$ values of approximately 0.01 nM, 0.002 nM, and 0.03 nM for SHI-1 cells, HNT-34 cells, and MOLM-1 cells, respectively. The killing was CD123-dependent as the conjugates were at least 100 fold less toxic to the cells when the CD123 antigen was blocked by the unconjugated huCD123-6 antibody.

In another experiment, huCD123-6-Gv4.7S3-SeriMab-sD1 conjugate bearing a Linker 1 residue (See FIG. 18) shows similar potency as the huCD123-6Gv4.7S2 (or S3)-SeriMab-D8 conjugate in EOL-1 cells (FIG. 24).

Figure 25:
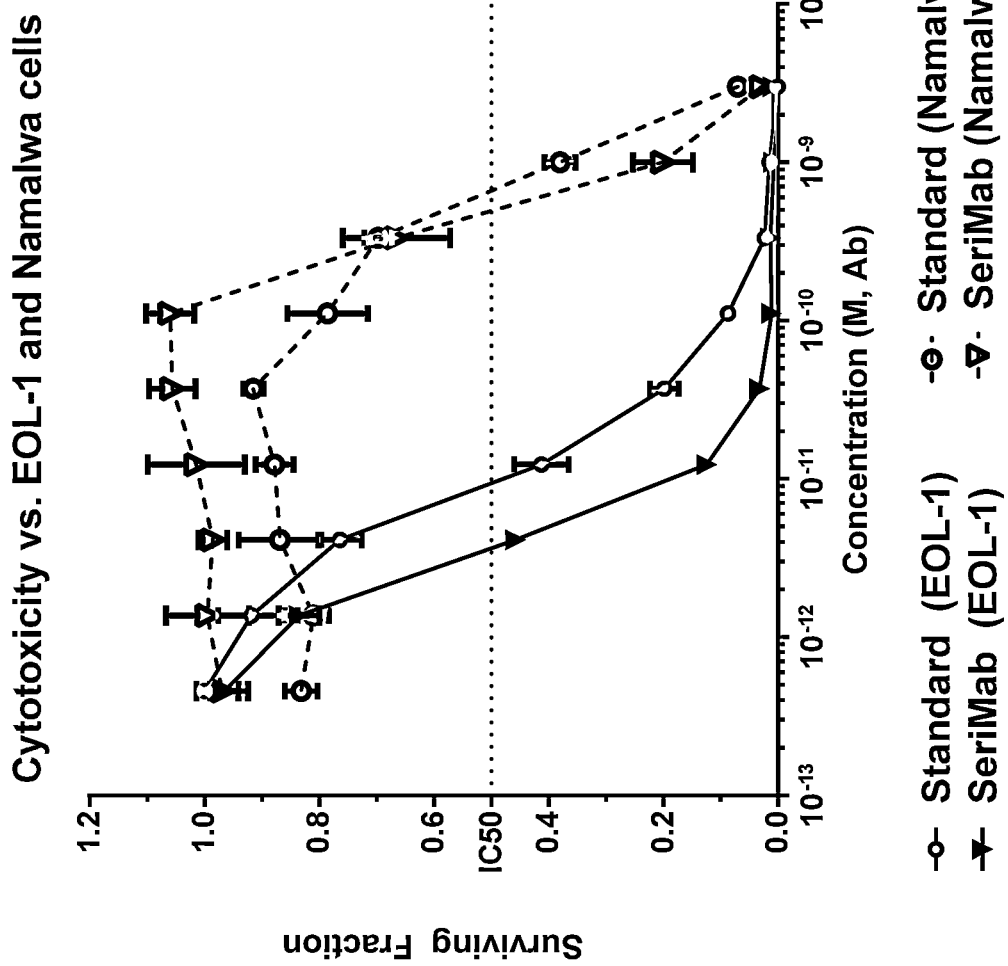
FIG. 25 shows Ser-linked DGN462 compound with huCD123 antibody has 3-fold higher antigen-specific potency against EOL-1 cells than lysine linked version with higher DAR.

In another experiment, it was found that Ser-linked DGN462 compound with huCD123 antibody has 3-fold higher antigen-specific potency than lysine linked version with higher DAR against EOL-1 cells (see FIG. 25). The lysine-linked conjugate has a DAR of 2.9; while the Ser-linked conjugate has a DAR of 2.0. In contrast, when antigen-negative Namalwa cells were used, both the lysine-linked and the serine-linked conjugates exhibit significantly less activity, indicating antigen-specific activity in EOL-1 cells.

Example 28. In Vitro Potency of SeriMab-D8 Conjugate

In vitro potency of SeriMab-D8 conjugate (huMOV19-NTS #2-SeriMab-D8) was tested on KB cells (FIG. 26A), Ishikawa cells (human endometrial adenocarcinoma cells) (FIG. 26B), and HEC-1B cells (human endometrial adenocarcinoma cells) (FIG. 26C) using assay protocols similar to that described in Example 8.

Figure 26B:
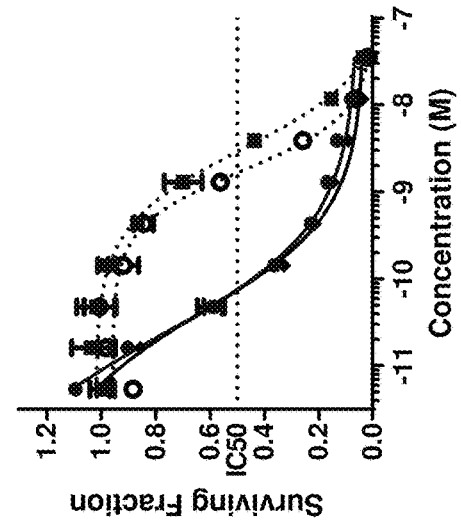
FIGS. 26A-26C show that SeriMab-D8 (huMOV19-NTS #2-SeriMab-D8) conjugate has comparable antigen-specific potency and target binding as the lysine conjugate (huMOV19-D2).
Figure 26A:
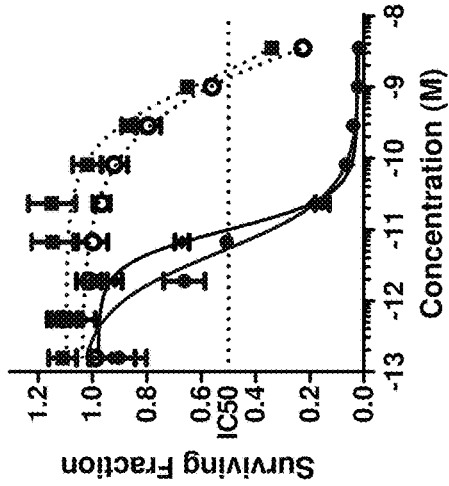
Figure 26C:
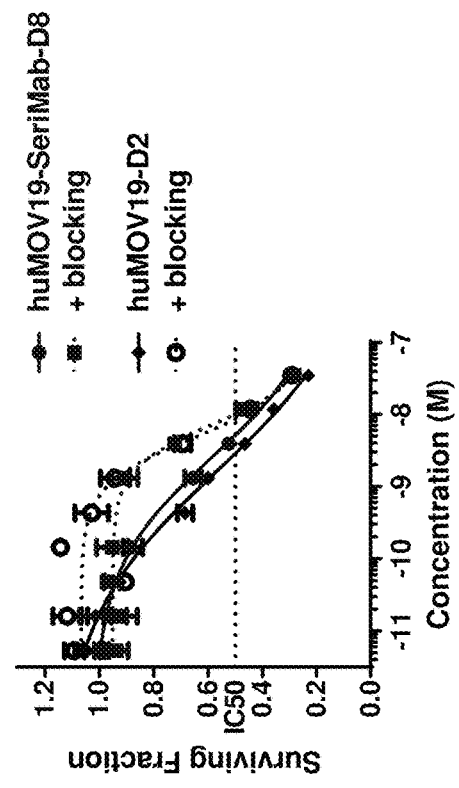

As shown in FIGS. 26A-26C, SeriMab-D8 conjugate has comparable antigen-specific potency and target binding as the lysine conjugate (huMOV19-D2).

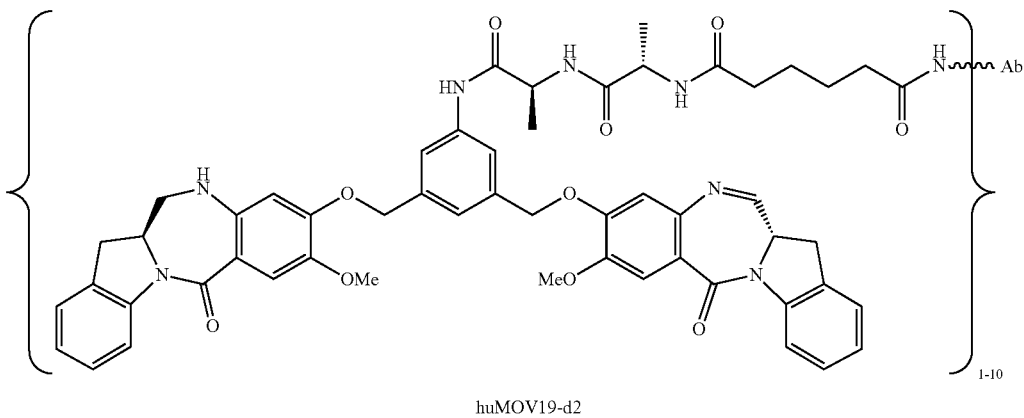

huMOV19-d2

Example 29. In Vivo Stability of SeriMab Conjugate Having Oxime Linkage Affinity Capture LC-MS Commercially available xMag-Streptavidin Microparticles (Biochain, CA) were washed with washing buffer (50 mM Tris.HCl, 0.15 M NaCl, pH 8.0) twice and resuspended in the same buffer to their original volume. Biotinylated Fc-FRα (2.6 Biotin/Fc-FRα; ~114 µg) was then added to the streptavidin particles (200 µL) and rotated at room temperature for 2 h. The beads were washed 3 times with washing buffer and re-suspended to their original volume in washing buffer with 0.4% Tween 20.

Plasma samples were collected from CD-1 mice dosed with 10 mg/kg huMOV19-NTS #2-aminooxy-acetyl-MayNMA conjugate at 2 min, 1 day, and 3 days, and was added to streptavidin-biotin-FRα-Fc particles (200 µL per sample) along with final 20% washing buffer and 0.2% Tween-20. After gentle shaking at room temperature for 2 h, the resin was washed 3 times with 1 mL washing buffer and eluted using 50 µL of 0.1 M citric acid/sodium citrate, pH 3.0, 50% ethylene glycol. The eluent containing purified huMOV19 conjugated species was immediately neutralized with 9 µL of 1 M Tris.HCl, pH 8.5, and then analyzed by SEC or SEC-LC/MS as described previously (Lazar, Wang et al. 2005).

Figure 28:
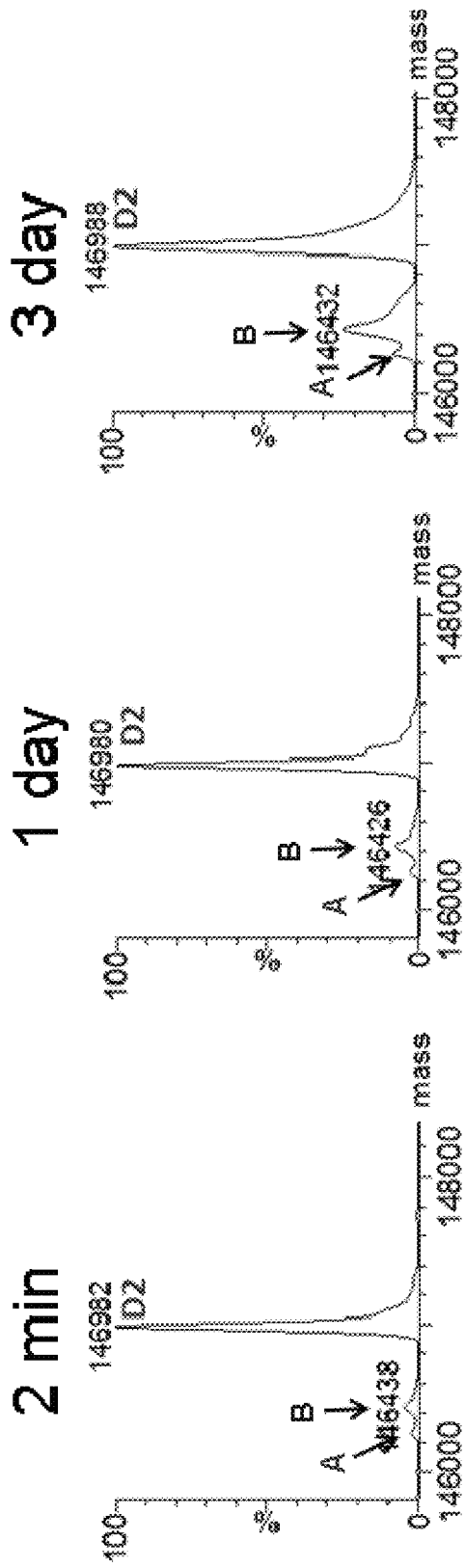
FIG. 28 shows in vivo stability of the oxime linkage in huMOV19-NTS #2-aminooxy-acetyl-MayNMA conjugate.

As shown in FIG. 28, the oxime linkage is stable over 3 days in mouse circulation. The peak labeled D2 corresponds to the intact conjugate. The peaks labeled as A and B are cleavage products from oxime hydrolysis and maysine elimination. Small amount of maytansine elimination was also observed with half-life of approximately 17 days, which has been observed with lysine-linked Ab-SMCC-DM1 conjugate.

Example 30. In Vivo Tolerability Study

Female CD-1 mice (7 weeks of age) were obtained from Charles River Laboratories. Upon receipt, the animals were observed for 8 days prior to study initiation. Animals showed no sign of disease or illness upon arrival, or prior to treatment.

Mice were randomized into three groups by body weight. The body weights ranged from 25.6 to 24.1 grams with an average of 25 grams. Eight mice were dosed with huMOV19-D2 at 100 and 150 µg/kg (D2 drug dose) and 2 mice with huMOV19-SeriMab-D8 at 200 µg/kg (D8 drug dose) based on individual body weight. Administration of all conjugates was carried out intravenously with a 1.0 ml syringe fitted with a 27 gauge, ½ inch needle. Individual body weights were measured at the indicated time points in FIG. 29 and the % change is graphed vs. time (days). Each line represents the body weight changes of one mouse. Animals that were moribund or experienced body weight loss >20% were sacrificed, as this is defined as an intolerable dose.

Figure 29:
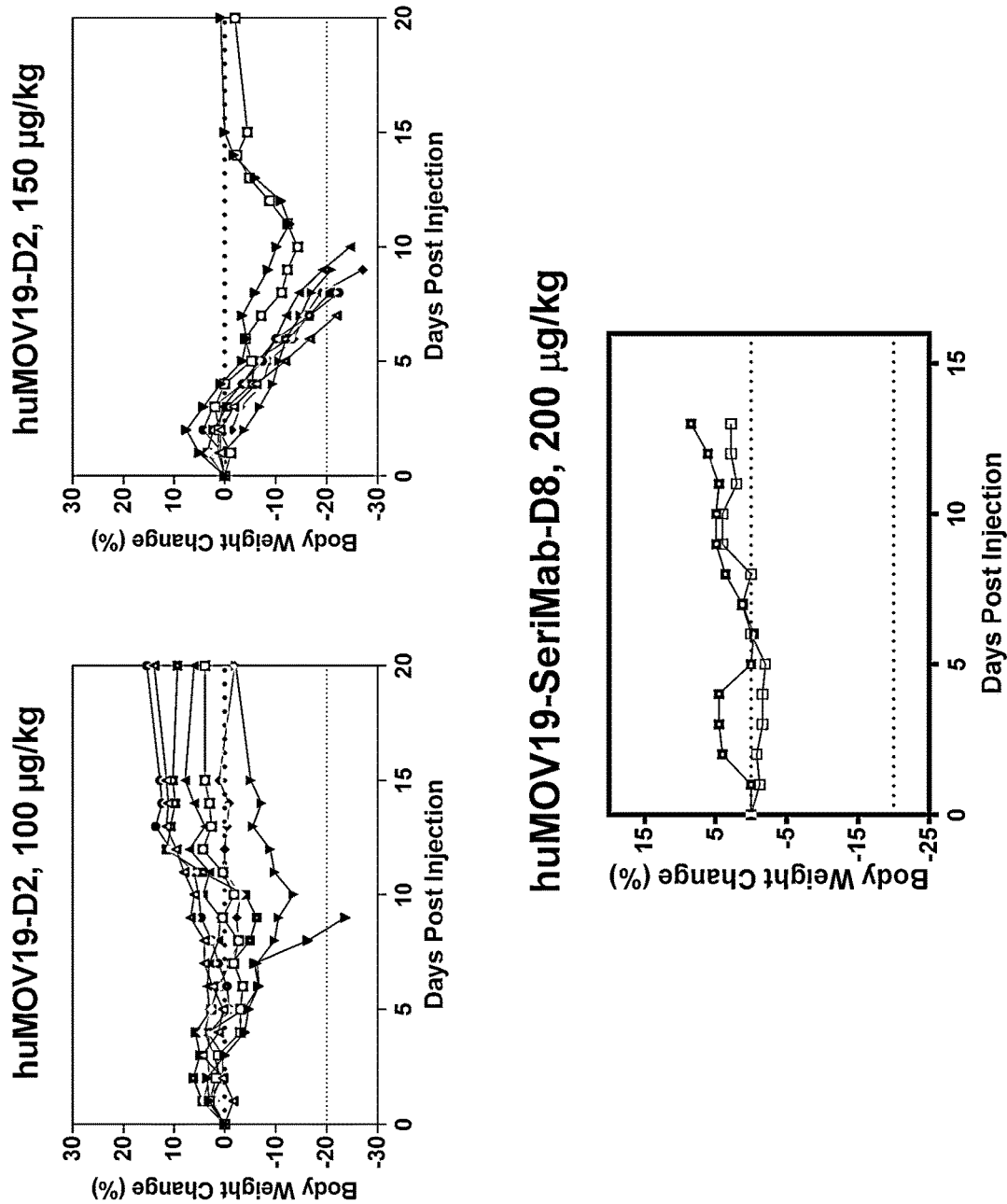
FIG. 29 shows individual body weight percent change of female CD-1 mice treated with 100 μg/kg or 150 μg/kg of lysine-linked huMOV19-D2 conjugate or 200 μg/kg huMOV19-SeriMab-D8.

As shown in FIG. 29, the lysine-linked huMOV19-D2 has maximum tolerated dose (MTD) of ~100 µg/kg; while the serine-linked conjugate huMOV19-SeriMab-D8 is well tolerated at 200 µg/kg with little sign of body weight loss over 2 weeks.

Example 31. Synthesis of Compound D11

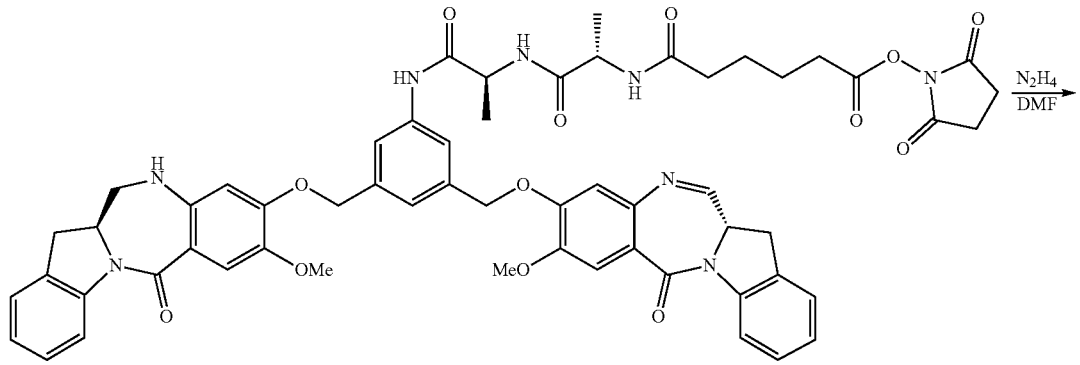

11a

-continued

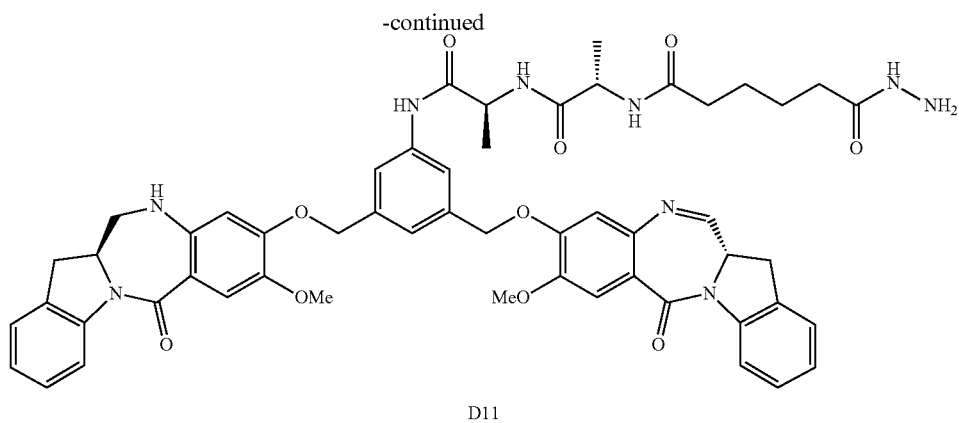

D11

NHS ester 11a (10.5 mg, 9.47 μmol) was dissolved in DMF (0.316 mL). Hydrazine (1.2 μL, 38 μmol) was added to the solution at rt and was stirred for 2 h. The crude reaction mixture was purified directly by RPHPLC (C18 column, CH$_3$CN/H$_2$O, gradient, 40% to 55%) to obtain the hydrazide D11 as a white solid (6.5 mg, 68% yield). LCMS=4.923 min (8 min method). Mass observed (ESI$^+$): 992.70 (M+H).

Example 32

Figure 30:
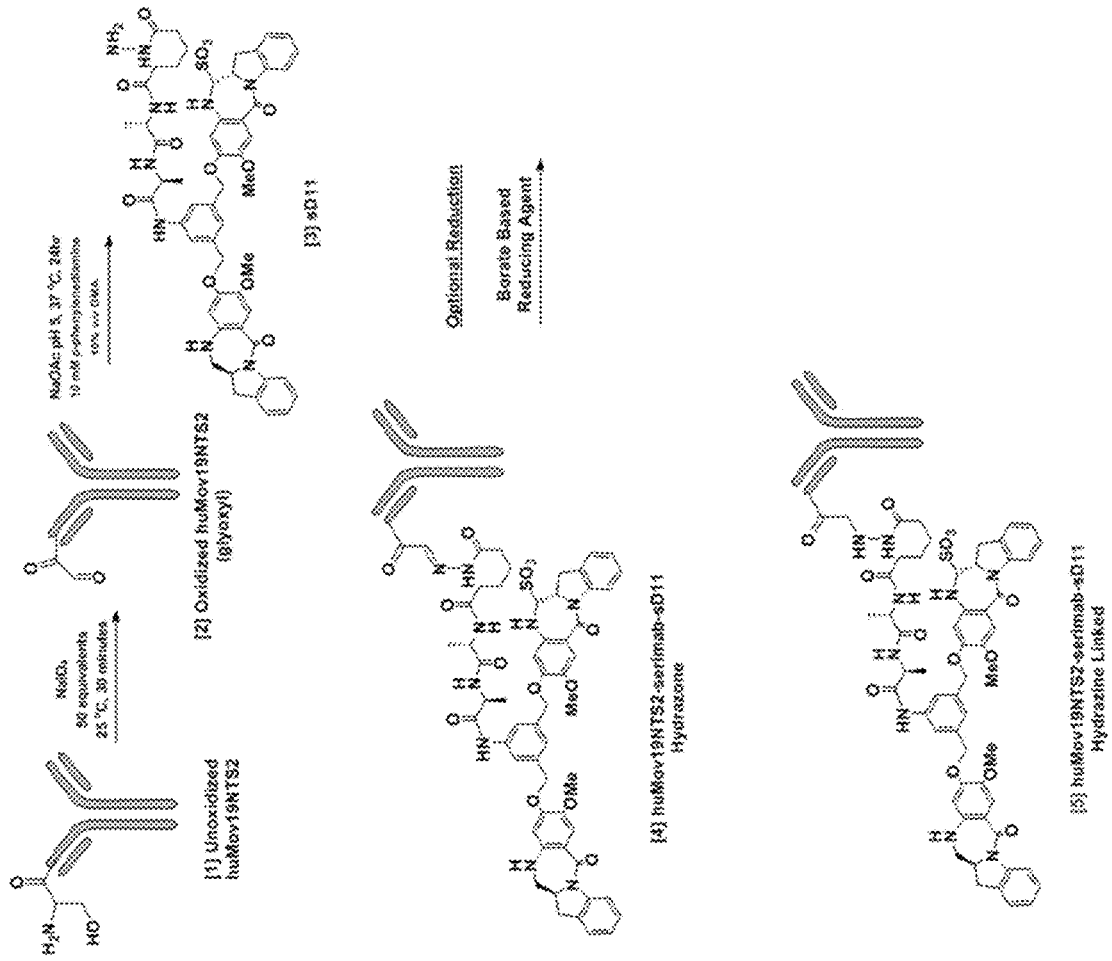
FIG. 30 shows an exemplary scheme for synthesizing the conjugate of the present invention.
Figure 31A:
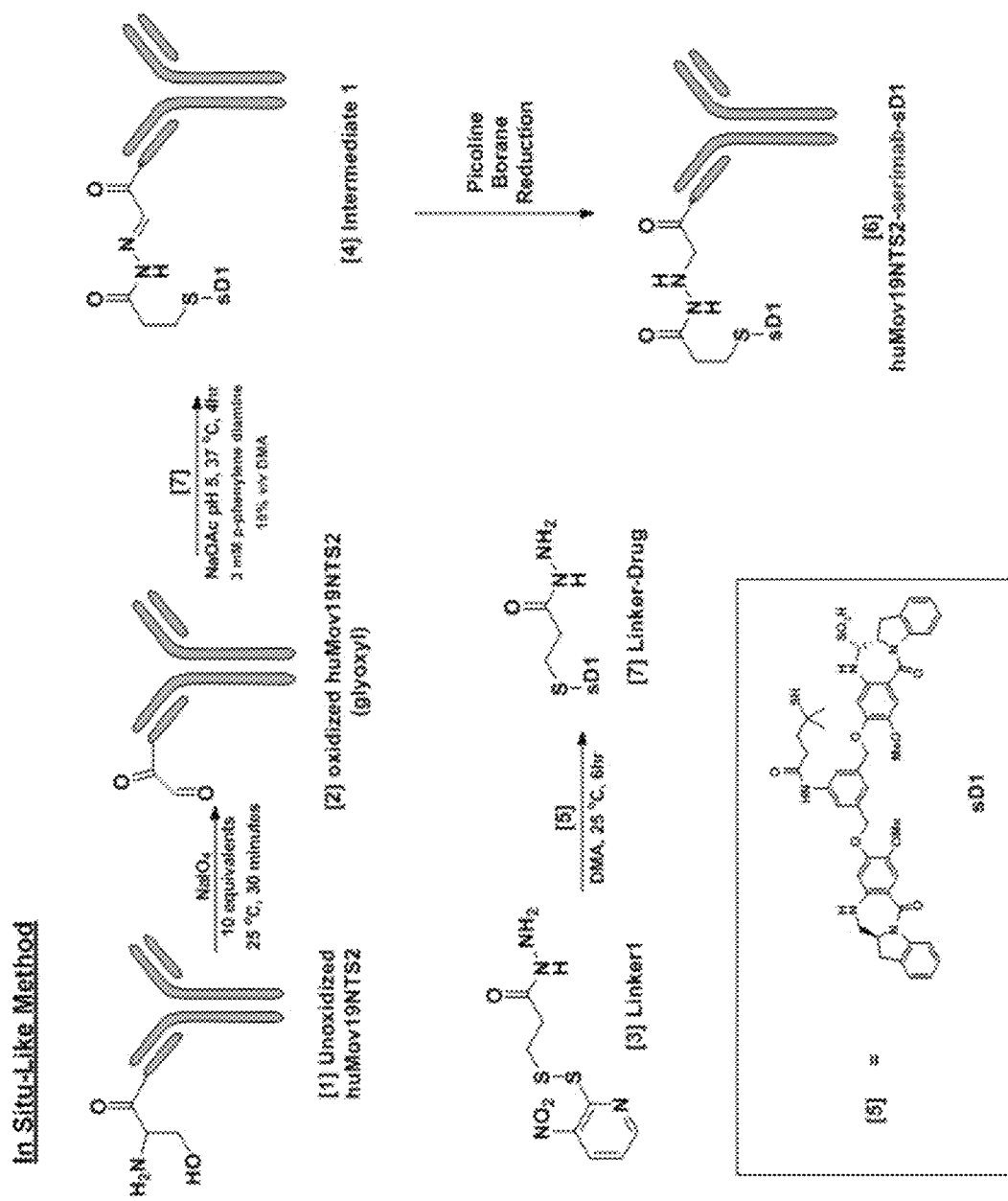
FIGS. 31A and 31B shown exemplary schemes for synthesizing the conjugate of the present invention.
Figure 31B:
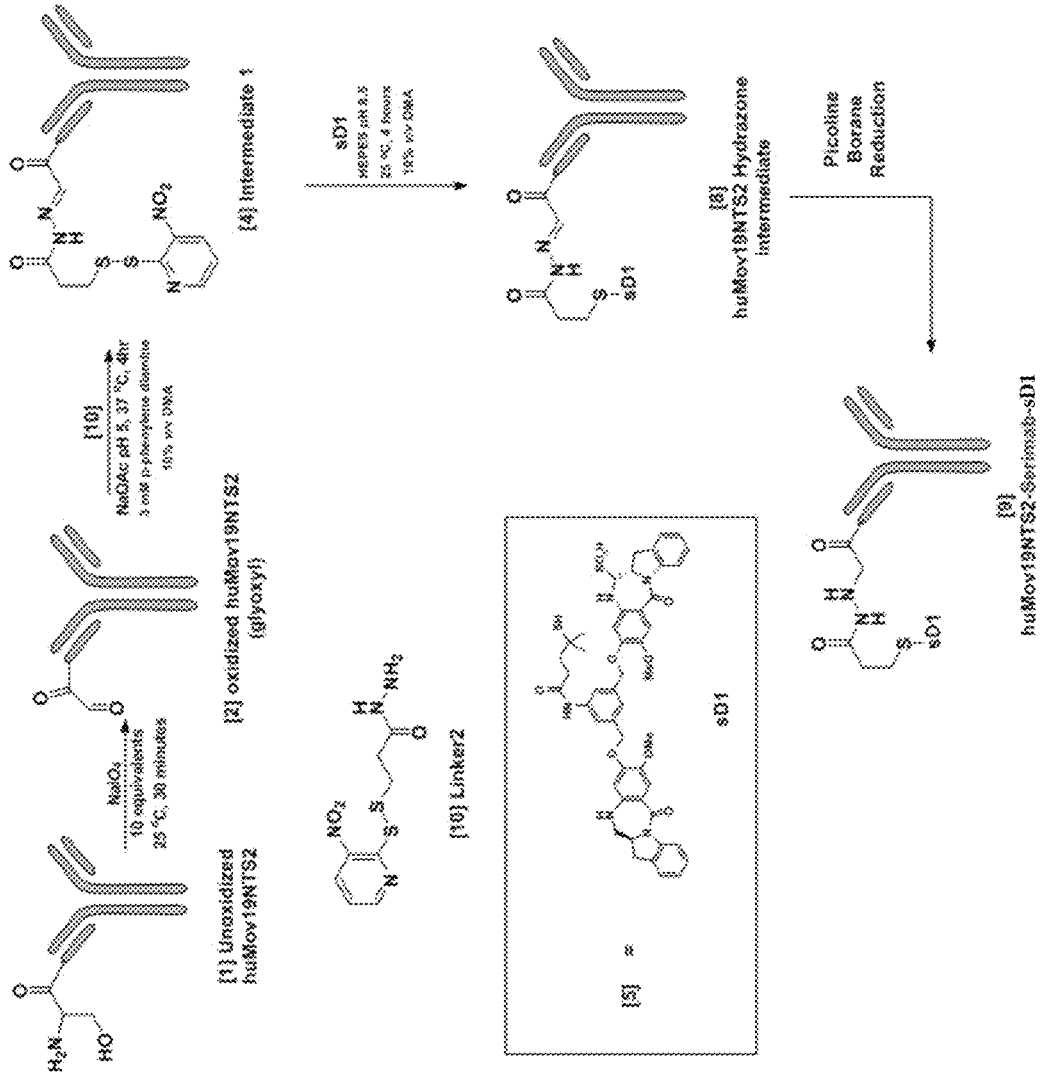

Conjugates of huMOV19NTS2 antibody with sD11 or sD1 can be prepared using similar procedures described in Example 25 (see FIGS. 30, 31A and 31B).

All publications, patents, patent applications, internet sites, and accession numbers/database sequences (including both polynucleotide and polypeptide sequences) cited herein are hereby incorporated by reference in their entirety for all purposes to the same extent as if each individual publication, patent, patent application, internet site, or accession number/database sequence were specifically and individually indicated to be so incorporated by reference.

What is claimed is:

1. A cytotoxic compound represented by the following structural formula:

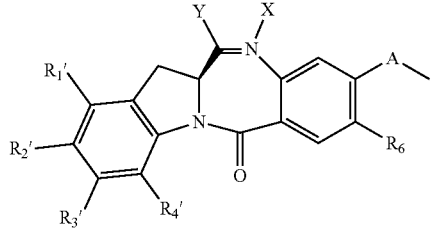

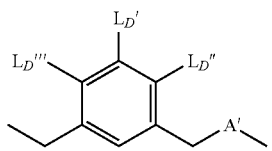

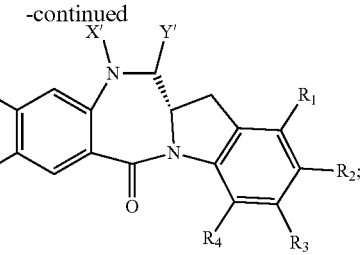

or a pharmaceutically acceptable salt thereof, wherein:

$L_D''$ and $L_D'''$ are both —H;

$L_D'$ is represented by the following formula:

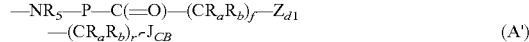

(A')

$Z_{d1}$ is absent, —C(=O)—NR$_9$— or —NR$_9$—C(=O)—;

P is a peptide containing between 2 to 5 amino acid residues;

$R_a$ and $R_b$, for each occurrence, are independently —H, $(C_1-C_3)$alkyl or a charged substituent or an ionizable group Q;

r and r' are independently an integer from 1 to 6;

the double line ═ between N and C represents a single bond or a double bond, provided that when it is a double bond X is absent and Y is —H, and when it is a single bond, X is —H, and Y is —OH or —SO$_3$M, wherein M is H$^+$, Na$^+$ or K$^+$;
X' is —H
Y' is —H
R$_1$, R$_2$, R$_3$, R$_4$, R$_1$', R$_2$', R$_3$' and R$_4$' are each —H;
R$_6$ is —OMe;
A and A' are each —O;
R$_5$ and R$_9$ are each independently —H or Me;
J$_{CB}$ is

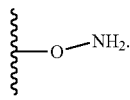

2. The compound of claim 1, wherein R$_a$ and R$_b$ are both H.

3. The compound of claim 1, wherein R$_5$ and R$_9$ are each H.

4. The compound of claim 1, wherein P is elected from Gly-Gly-Gly, Ala-Val, Val-Ala, Val-Cit, Val-Lys, Phe-Lys, Lys-Lys, Ala-Lys, Phe-Cit, Leu-Cit, Lle-Cit, Trp-Cit, Phe-Ala, Phe-N$^9$-tosyl-Arg, Phe-N$^9$-nitro-Arg, Phe-Phe-Lys, D-Phe-Phe-Lys, Gly-Phe-Lys, Leu-Ala-Leu, Ile-Ala-Leu, Val-Ala-Val, Ala-Leu-Ala-Leu (SEQ ID NO: 17), β-Ala-Leu-Ala-Leu (SEQ ID NO: 18) and Gly-Phe-Leu-Gly (SEQ ID NO: 19), Val-Arg, Arg-Val, Arg-Arg, Val-D-Cit, Val-D-Lys, Val-D-Arg, D-Val-Cit, D-Val-Lys, D-Val-Arg, D-Val-D-Cit, D-Val-D-Lys, D-Val-D-Arg, D-Arg-D-Arg, Ala-Ala, Ala-D-Ala, D-Ala-Ala, and D-Ala-D-Ala.

5. The compound of claim 1, wherein the compound is represented by the following structural formula:

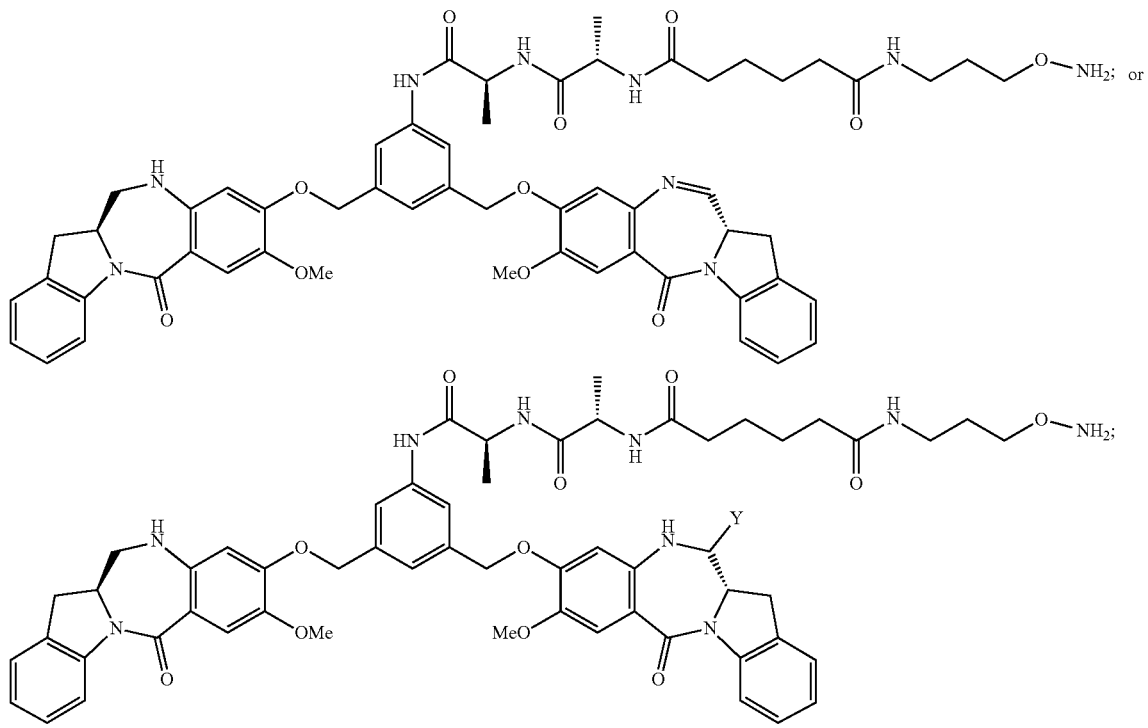

or a pharmaceutically acceptable salt thereof.

6. The conjugate of claim 1, wherein P is Gly-Gly-Gly, Ala-Val, Ala-Ala, Ala-D-Ala, D-Ala-Ala, or D-Ala-D-Ala.

* * * * *

UNITED STATES PATENT AND TRADEMARK OFFICE
CERTIFICATE OF CORRECTION

PATENT NO. : 11,732,038 B2
APPLICATION NO. : 17/174911
DATED : August 22, 2023
INVENTOR(S) : Nathan Elliott Fishkin et al.

It is certified that error appears in the above-identified patent and that said Letters Patent is hereby corrected as shown below:

In the Claims

Column 310, Lines 54-59, Claim 1, should read:
or a pharmaceutically acceptable salt thereof, wherein:
  $L_D''$ and $L_D'''$ are both –H;
  $L_D'$ is represented by the following formula:
    $-NR_5-P-C(=O)-(CR_aR_b)_r-Z_{d1}-(CR_aR_b)_{r'}-J_{CB}$     (A')
    $Z_{d1}$ is absent, $-C(=O)-NR_9-$ or $-NR_9-C(=O)-$;

And

Column 311, Line 8, Claim 1, should read:
A and A' are each –O–;

Signed and Sealed this
Third Day of September, 2024

Katherine Kelly Vidal
*Director of the United States Patent and Trademark Office*